United States Patent
Cusack et al.

(10) Patent No.: US 9,150,592 B2
(45) Date of Patent: Oct. 6, 2015

(54) HETEROCYCLIC NUCLEAR HORMONE RECEPTOR MODULATORS

(71) Applicants: Kevin P. Cusack, Holden, MA (US); Thomas D. Gordon, Medway, MA (US); Michael Z. Hoemann, Shrewsbury, MA (US); David C. Ihle, Worcester, MA (US); Bin Li, Ashland, MA (US); Gloria Y. Lo Schiavo, Shrewsbury, MA (US); Gagandeep K. Somal, Ashland, MA (US); Michael Friedman, Brookline, MA (US); Martin E. Hayes, Lowell, MA (US); Wouter Iwema Bakker, Badhoevedorp (NL)

(72) Inventors: Kevin P. Cusack, Holden, MA (US); Thomas D. Gordon, Medway, MA (US); Michael Z. Hoemann, Shrewsbury, MA (US); David C. Ihle, Worcester, MA (US); Bin Li, Ashland, MA (US); Gloria Y. Lo Schiavo, Shrewsbury, MA (US); Gagandeep K. Somal, Ashland, MA (US); Michael Friedman, Brookline, MA (US); Martin E. Hayes, Lowell, MA (US); Wouter Iwema Bakker, Badhoevedorp (NL)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/135,793

(22) Filed: Dec. 20, 2013

(65) Prior Publication Data
US 2014/0179676 A1    Jun. 26, 2014

Related U.S. Application Data

(60) Provisional application No. 61/740,931, filed on Dec. 21, 2012.

(30) Foreign Application Priority Data

Dec. 5, 2013   (WO) ................ PCT/CN2013/001505

(51) Int. Cl.
| | | |
|---|---|---|
| A61K 31/44 | (2006.01) | |
| C07D 401/14 | (2006.01) | |
| C07D 513/04 | (2006.01) | |
| C07D 401/04 | (2006.01) | |
| C07D 487/04 | (2006.01) | |
| C07D 513/20 | (2006.01) | |
| C07D 513/10 | (2006.01) | |

(52) U.S. Cl.
CPC ............ *C07D 513/04* (2013.01); *C07D 401/04* (2013.01); *C07D 401/14* (2013.01); *C07D 487/04* (2013.01); *C07D 513/10* (2013.01); *C07D 513/20* (2013.01)

(58) Field of Classification Search
CPC ..... A61K 31/44; A61K 31/55; C07D 401/14; C07D 513/04
USPC .................. 540/484, 546, 552; 546/255, 256; 514/211.01, 211.05, 277, 333
See application file for complete search history.

(56) References Cited

U.S. PATENT DOCUMENTS

| | | | |
|---|---|---|---|
| 5,385,947 A | 1/1995 | Godel et al. | |
| 6,380,223 B1 | 4/2002 | Dow et al. | |
| 6,589,947 B1 | 7/2003 | Hamanaka et al. | |
| 6,699,893 B2 | 3/2004 | Dow et al. | |
| 6,777,404 B2 | 8/2004 | Hamanaka et al. | |
| 6,852,719 B2 | 2/2005 | Liu et al. | |
| 7,138,406 B2 | 11/2006 | Chantigny et al. | |
| 7,166,593 B2 | 1/2007 | Dow et al. | |
| 7,547,714 B2 | 6/2009 | Cheng et al. | |
| 7,553,877 B2 | 6/2009 | Chantigny et al. | |
| 7,598,231 B2 | 10/2009 | Cheng et al. | |
| 7,625,937 B2 | 12/2009 | Ali et al. | |
| 7,713,989 B2 | 5/2010 | Dow et al. | |
| 7,786,097 B2 | 8/2010 | Cheng et al. | |
| 8,067,447 B2 | 11/2011 | Sheppeck et al. | |
| 8,093,281 B2 | 1/2012 | Eldred et al. | |
| 8,148,409 B2 | 4/2012 | Rucker | |
| 8,445,520 B2 | 5/2013 | Cheng et al. | |
| 8,658,646 B2 * | 2/2014 | Chen et al. ..................... | 514/249 |
| 2002/0120148 A1 | 8/2002 | Taniguchi et al. | |
| 2002/0147336 A1 | 10/2002 | Dow et al. | |
| 2003/0105081 A1 | 6/2003 | Yohannes et al. | |
| 2003/0199527 A1 | 10/2003 | Hamanaka et al. | |
| 2003/0224349 A1 | 12/2003 | Buckbinder | |
| 2004/0014741 A1 | 1/2004 | Liu et al. | |
| 2004/0110778 A1 | 6/2004 | Yohannes et al. | |
| 2004/0138262 A1 | 7/2004 | Chantigny et al. | |

(Continued)

FOREIGN PATENT DOCUMENTS

| | | |
|---|---|---|
| CN | 102584860 A | 7/2012 |
| EP | 1201649 A1 | 5/2002 |

(Continued)

OTHER PUBLICATIONS

Nathans R., Small-molecule inhibition of HIV-1 Vif. Nature Biotechnology Sep. 2008, vol. 26, No. 10, p. 1188.

(Continued)

*Primary Examiner* — Golam M M Shameem
(74) *Attorney, Agent, or Firm* — McCarter & English, LLP; Elizabeth A. Hanley; Yu Lu

(57) ABSTRACT

The invention provides a compound of Formula (I)

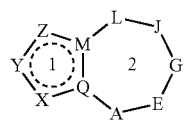

pharmaceutically acceptable salts, pro-drugs, biologically active metabolites, stereoisomers and isomers thereof wherein the variable are defined herein. The compounds of the invention are useful for treating immunological and oncological conditions.

16 Claims, No Drawings

(56) References Cited

U.S. PATENT DOCUMENTS

| | | |
|---|---|---|
| 2004/0176595 A1 | 9/2004 | Dow et al. |
| 2006/0074120 A1 | 4/2006 | Ali et al. |
| 2006/0247264 A1 | 11/2006 | Chantigny et al. |
| 2006/0247266 A1 | 11/2006 | Yamada et al. |
| 2007/0129410 A1 | 6/2007 | Robinson et al. |
| 2008/0188443 A1 | 8/2008 | Cheng et al. |
| 2009/0149445 A1 | 6/2009 | Coghlan et al. |
| 2009/0227548 A1 | 9/2009 | Glossop et al. |
| 2009/0281148 A1 | 11/2009 | Cheng et al. |
| 2010/0069444 A1 | 3/2010 | Rucker |
| 2010/0204239 A1 | 8/2010 | Sui et al. |
| 2010/0286214 A1 | 11/2010 | Cheng et al. |
| 2010/0303758 A1 | 12/2010 | Glossop et al. |
| 2012/0238549 A1 | 9/2012 | Cusack et al. |
| 2014/0162985 A1 | 6/2014 | Burchat et al. |

FOREIGN PATENT DOCUMENTS

| | | |
|---|---|---|
| EP | 1201655 A2 | 5/2002 |
| EP | 1201660 A1 | 5/2002 |
| EP | 2114888 A1 | 11/2009 |
| EP | 2114970 A1 | 11/2009 |
| JP | 2007186480 A | 7/2007 |
| WO | WO-95/18118 A1 | 7/1995 |
| WO | 0020376 A1 | 4/2000 |
| WO | 0066522 A1 | 11/2000 |
| WO | 2004005229 A1 | 1/2004 |
| WO | 2004026248 A2 | 4/2004 |
| WO | 2004052847 A2 | 6/2004 |
| WO | 2005047254 A1 | 5/2005 |
| WO | WO-2006/081659 A1 | 8/2006 |
| WO | 2008093227 A1 | 8/2008 |
| WO | 2008093236 A1 | 8/2008 |
| WO | 2009069032 A2 | 6/2009 |
| WO | WO-2009/110468 A1 | 9/2009 |
| WO | 2009149139 A1 | 12/2009 |
| WO | 2010013158 A1 | 2/2010 |
| WO | 2010040527 A1 | 4/2010 |
| WO | 2011081173 A1 | 7/2011 |

OTHER PUBLICATIONS

Swett R. et al., Pyrazolo[3,4-e][1,4]thiazepines: Synthesis and Structure Proof. Journal of Heterocyclic Chemistry, 1975, vol. 12, No. 6, pp. 1137-1142.

Hudson A et al., "Recent developments in the discovery of the selective glucocorticoid receptor modulators (SGRMs)," 2008, Current Topics in Medicinal Chemistry, 8, 750-765.

Carey, RA. Organic Chemistry 6th Ed. McGraw hill. 2006, chapter 1, pp. 9-10.

Greenwald, RB. et al. Drug Delivery Systems: Water Soluble Taxol 2'-Poly(ethylene glycol) Ester prodrugs—Design and in Vivo Effectiveness. J. Med. Chem. 1996, vol. 39, pp. 425-431.

Jung, M. "A Review of Annulations" Tetrahedron, 1976, vol. 32, pp. 3-31.

Testa, B. et al. Lessons Learned from Marketed and Investigational Prodrugs. J. Med. Chem. 2004, vol. 47(10), pp. 2393-2404.

Akita, H et al., "Diterpeniods. XXXVII. Rearrangement of methyl 13-isopropyl-7-oxo-podocarpa-5,8,11,13-tetraen-15-oate by means of aluminum chloride," Chem. Pharm. Bull. (1975) 23(11):2660-2668.

Bareille, P et al., "Efficacy and safety of once-daily GW870086 a novel selective glucocorticoid in mild-moderate asthmatics: a randomised, two-way crossover, controlled clinical trial," J. Asthma (2013) 50(10):1077-1082.

Bareille, P et al., "Efficacy of a new selective steroid (GW870086) in asthma: an adaptive, randomised, controlled trial," Curr. Drug Therapy (2013) 8(2):69-75.

Barnes, RA et al., "The Stereochemistry of 4a-Methyl-1,2,3,4,4a,9,10,10a-octahydrophenanthrene," J. Am. Chem. Soc. (1955) 77(20):5388-5390.

Brandish, PE et al., "The preclinical efficacy, selectivity and pharmacologic profile of MK-5932, an insulin-sparing selective glucocorticoid receptor modulator," Eur. J. Pharmacology (2014) 724:102-111.

Burnell, RH et al., "The structures of the nellionols. Synthesis of model abieta-8, 11, 13-trien-7-ones. Synthesis of 5-dehydronellionol trimethyl ether," Canadian J. Chem. (1984) 62(12):2822-2829.

Chemical Abstracts Accession No. 1972:448662 & Iresmetov, M et al.: "Synthetic conversions of dehydroabietic acid. II. Synthesis of heterocyclic derivatives of dehydroabietic acid and analogs of D-homo steroids," Sin. Prod. Kanifoli Skipidara (1970) 244-51. From: Ref. Zh., Khim. 1971, Abstr. No. 9Zh546.

CID 11075022 in particular deposit SID 16144193 having a deposit date of Oct. 26, 2006.

CID 11099032 in particular deposit SID 16171282 having a deposit date of Oct. 26, 2006.

Colvin, ES et al., "Glucocorticoid-induced suppression of β-cell proliferation is mediated by Mig6," Endocrinology (2013) 154(3):1039-1046.

Derbenev, AY. et al., "Dexamethasone rapidly increases GABA release in the dorsal motor nucleus of the vagus via retrograde messenger-mediated enhancement of TRPV1 activity," PLoS One (2013) 8(7):e70505.

Erdtman and Malmborg, "Beckmann rearrangement of the oxime of 7-oxodehydroabietate," Acta Chemica Scandinavica (1970) 24(6):2252-2253.

Evans, GB et al., "The Synthesis and Antibacterial Activity of Totarol Derivatives. Part 3: Modification of Ring-B," Bioorg. Med. Chem. (2000) 8:1663-1675.

Fandrick et al., "Zinc Catalyzed and Mediated Propargylations with Propargyl Boronates," Org. Lett., (2010) 12(1):88-91.

Fandrick, DT. et al., "Zinc Catalyzed and Mediated Asymmetric Propargylation of Trifluoromethyl Ketones with a Propargyl Boronate," J. Org. Chem. (2013) 78(8):3592-3615.

Fujita, T et al., "Seven-membered ring compounds. III.Robinson-Mannich reaction to benzocycloheptenones. 3. Synthesis of 3-oxo-11 b-methyl-1 ,2,3,6,7, 11 b-hexahydro-5H-dibenzo-[a,c-]cycloheptatriene," Yakugaku Zasshi (Jan. 1, 1959) pp. 1184-1187.

Fujita, T et al., "Seven-membered ring compounds. IV. Robinson-Mannich reaction to benzocycloheptenones. 4. Synthesis of 3-oxo-11 b-methyl-9 10-dimethoxy- and 9,10,11-trimethoxy-1,2,3,6,7,11 b-hexahydro-5H-dibenzo [a,c]cycloheptatriene," Yakugaku Zasshi (Jan. 1, 1959) pp. 1187-1192.

Fujita, T et al., "Seven-membered ring compounds. VIII. Synthesis of dibenzo[a,c]cyclohepta-1 ,3-diene," Yakugaku Zasshi (1959) 79:1354-1356.

Harris, PWR at al., "Functionalisation of Alkylalkoxysilanes. Studies Towards Annulations of Diterpenoids," Tetrahedron, Elsevier Science Publishers, Amsterdam, NL, (Jun. 9, 2000) 56(24):4001-4015.

Inamochi, Y. et al., "Histone code of genes induced by co-treatment with a glucocorticoid hormone agonist and a p44/42 MAPK inhibitor in human small intestinal Caco-2 cells," Biochimica et Biophysica Acta, General Subjects (2014) 1840(1):693-700.

Krow, GR., "The Baeyer-Villiger oxidation of ketones and aldehydes," Organic Reactions (Hoboken, NJ, United States) (1993) 43:P251-798.

Kuo, Y-H, et al., "New Diterpenes from the Heartwood of Chamaecyparis obtusa var. formosana," J. Nat. Prod. (1998) 61(6):829-831.

Kuzmich, D et al., "Function-regulating pharmacophores in a sulfonamide class of glucocorticoid receptor agonists," Bioorganic & Medicinal Chemistry Letters (2013) 23:6640-6644.

Pelletier, SW, et al., "The Synthesis of Certain 11,14-Dimethoxydeoxypodocarpic Acid Derivatives. An Application to the Synthesis of (+)-Winterin from Drimys Winteri," Tetrahedron, (1977) pp. 1021-1027, URL:http://www.sciencedirect.com/science/article/pii/00404020778022021pdf?md5=80e5526eadf210da5dc578b f28b8b844&pid=1-s2.0-0040402077802202-main.pdf [retrieved on Jul. 4, 2014].

Pettit, GR et al., "Antineoplastic Agents. 529. Isolation and Structure of Nootkastatins 1 and 2 from the Alaskan Yellow Cedar Chamaecyparis nootkatensis," J. Nat. Prod. (2004) 67(9):1476-1482.

(56) References Cited

OTHER PUBLICATIONS

Reeves, JT. et al., "Development of a Large Scale Asymmetric Synthesis of the Glucocorticoid Agonist BI 653048 BS H3PO4," *J. Org. Chem.* (2013) 78(8):3616-3635.

Sanchez and Konopelski, "Phenol Benzylic Epoxide to Quinone Methide Electron Reorganization: Synthesis of (+/−)-Taxodone," *J. Org. Chem.* (1994) 59(18):5445-5452.

Schaffner, K et al., "Triterpenes. CXCI. The stereochemistry of a-onocerin," *Helvetica Chimica Acta* (1956) 39:174-183.

Song, J., "Development of a large scale asymmetric synthesis of the glucocorticoid agonist BI 653048 BS H3PO4," from *Abstracts of Papers, 248th ACS National Meeting & Exposition*, San Francisco, CA, United States, Aug. 10-14, 2014 ORGN-317.

Steiner, JL. et al., "Glucocorticoids Attenuate the Central Sympathoexcitatory Actions of Insulin," *J. Neurophysiol.* (Sep. 3, 2014) pii: jn.00514.2014. [Epub ahead of print] PubMed PMID: 25185805.

Tanis, SP et al., "Furans in synthesis. 5. Furan-terminated cationic cyclizations in the preparation of fused, spirocyclic and bridged ring systems. An application to the synthesis of nakafuran 9," *J. Org. Chem.* (1985) 50(21):3988-3996.

Tashima, T et al., "Design, synthesis, and BK channel-opening activity of hexahydrodibenzazepinone derivatives," *Bioorganic & Medicinal Chemistry* (2006) 14(23):8014-8031.

Uyanik, M et al., "Supporting INformation for Catalytic Diastereoselective Polycyclization of Homo(polyprenyl)arene Analogues Bearing Terminal Siloxyvinyl Groups," General Procedure for the SnCl 4-Promoted Cyclization S23 Determination of the Relative Sterochemistry of Polycyclic Products S35 References and Notes S40, *Organic Letters* (2006) pp. 5649-5652. Retrieved from the Internet:URL:http://pubs.acs.org/doi/suppl/1 0.1 021/ol062378t/ suppl_file/ol062378tsi20061018_123034.pdf [retrieved on Jul. 8, 2014].

Wenkert, E et al., "Condensations of 4-methyl-4-dichloromethyl-2,5-cyclohexadienone," *J. Am. Chem. Soc.* (1969) 91(9):2299-2307.

Wenkert, E et al., "Synthesis of Some Drimanic Sesquiterpenes," *J. Am. Chem. Soc.* (1964) 86(10):2044-2050.

Bungard, et al., "Discovery of selective glucocorticoid receptor modulator MK-5932'", Bioorganic & Medicinal Chemistry, vol. 19, pp. 7374-7386 (2011).

* cited by examiner

HETEROCYCLIC NUCLEAR HORMONE RECEPTOR MODULATORS

CROSS REFERENCE TO PRIOR APPLICATIONS

This application claims, under 35 U.S.C. §365(a), priority to International Application No. PCT/CN2013/001505, filed on Dec. 5, 2013, which designates at least one country other than the U.S. and claims, under 35 U.S.C. §119(e), priority to and the benefit of the filing date of U.S. Provisional Application No. 61/740,931, filed on Dec. 21, 2012. This application also claims, under 35 U.S.C. §119(e), priority to and the benefit of the filing date of U.S. Provisional Application No. 61/740,931, filed on Dec. 21, 2012. The entire contents of both the U.S. provisional and the PCT applications are incorporated herein by reference.

BACKGROUND OF THE INVENTION

The invention provides a novel class of compounds, pharmaceutical compositions comprising such compounds and methods of using such compounds to treat or prevent diseases or disorders associated with modulation of the glucocorticoid receptor. Modulators of the glucocorticoid receptor are useful in the treatment of certain inflammatory related conditions.

Intracellular receptors (IR's) are a class of structurally related proteins involved in the regulation of gene expression. The steroid hormone receptors are a subset of this superfamily whose natural ligands are typically comprised of endogenous steroids such as estradiol, progesterone, and cortisol. Man-made ligands to these receptors play an important role in human health and of these receptors the glucocorticoid receptor (GR) has an essential role in regulating human physiology and immune response.

Steroids which interact with GR have been shown to be potent anti-inflammatory agents. Examples include the glucocorticoid (GC) agonists dexamethasone, prednisone, and prednisolone. The utility of GC agonists in a chronic setting has been limited however due to multiple serious side effects such as osteoporosis, effects on glucose metabolism (diabetogenic), skin thinning, fluid homeostasis and depression for example. (*Expert Opinion on Therapeutic Patents* (2000) 10(1), 117.) These effects are believed to be the result of cross-reactivity with other steroid receptors such as estrogen, progesterone, androgen, and mineralocorticoid receptors which have somewhat homologous ligand binding domains, and/or the inability to selectively modulate downstream signaling. Identification of a selective glucocorticoid receptor modulator (SGRM) that is efficacious with reduced side-effects could fulfill an unmet medical need.

Selective GR modulators (e.g. repressors, agonists, partial agonists and antagonists) of the present disclosure can be used to influence the basic, life-sustaining systems of the body, including carbohydrate, protein and lipid metabolism, and the functions of the cardiovascular, kidney, central nervous, immune, skeletal muscle, and other organ and tissue systems. In this regard, GR modulators have proven useful in the treatment of inflammation, tissue rejection, auto-immunity, various malignancies, such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, and Little's syndrome. GR modulators are especially useful in disease states involving systemic inflammation such as inflammatory bowel disease, systemic lupus erythematosus, polyarteritis nodosa, Wegener's granulomatosis, giant cell arteritis, rheumatoid arthritis, osteoarthritis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, cirrhosis, juvenile rheumatoid arthritis, juvenile idiopathic arthritis, ankylosing spondylitis, psoriasis, plaque psoriasis, and psoriatic arthritis. GR active compounds have also been used as immunostimulants and repressors, and as wound healing and tissue repair agents.

GR modulators have also found use in a variety of topical diseases such as inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, herpes gestationis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitus, erythema nodosum, acne, hirsutism, toxic epidermal necrolysis, erythema multiform, cutaneous T-cell lymphoma and ocular diseases. Selective antagonists of the glucocorticoid receptor have been unsuccessfully pursued for decades. These agents would potentially find application in several disease states associated with Human Immunodeficiency Virus (HIV), cell apoptosis, and cancer including, but not limited to, Kaposi's sarcoma, immune system activation and modulation, desensitization of inflammatory responses, IL-1 expression, anti-retroviral therapy, natural killer cell development, lymphocytic leukemia, and treatment of retinitis pigmentosa. Cogitive and behavioral processes are also susceptible to glucocorticoid therapy where antagonists would potentially be useful in the treatment of processes such as cognitive performance, memory and learning enhancement, depression, addiction, mood disorders, chronic fatigue syndrome, schizophrenia, stroke, sleep disorders, and anxiety.

SUMMARY OF THE INVENTION

In a first embodiment the invention provides a compound represented by the following formula:

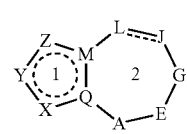

Formula (I)

or a pharmaceutically acceptable salt, pro-drug or solvate thereof, wherein:

Ring 1 is heterocyclic or heteroaromatic;

X is N, N($R^4$), C($R^4$), C($R^4$)($R^4$), S or O;

Y is N, N($R^4$), C($R^4$), S, O or C(=O);

Z is N($R^4$), C($R^4$)C($R^4$) or C($R^4$);

A is, N($R^{3'}$), C($R^3$)($R^3$) or C(=O);

G and J are independently S, S(O), S(O)$_2$, O, C($R^1$)($R^2$), N($R^3$) or C(=O) provided that at least one of G and J are C($R^1$)($R^2$) or C(=O);

E is N($R^4$), S, S(O), S(O)$_2$, O, C($R^1$)($R^2$), or C(=O);

L is $N(R^5)$, $C(R^5)(R^5)$ or $C(R^5)(R^{5'})$; or L is $C(R^5)$ or $C(R^{5'})$ and J is $C(R^1)$ or N;

M and Q are independently N, C or CH;

provided that

X, Y, and Z are not each heteroatoms at the same time;

not more than three of A, E, G, J, L, M and Q are heteroatoms;

M and Q are not both N;

adjacent atoms do not form S—S, S—O, O—O or —C(=O)—C(=O) bonds;

at least one of X, Y and Z is $C(R^4)$ or C(=O);

when Q is N, X is not S or O;

when J is S, O, S(O) or $N(R^3)$, L is not $N(R^5)$;

$R^1$ and $R^2$, for each occurrence, is independently —H, $CF_3$, CN, —C(=O)$NH_2$, OH, an optionally substituted ($C_1$-$C_6$)alkyl, optionally substituted ($C_3$-$C_6$)cycloalkyl, optionally substituted aryl, optionally substituted heteroaryl or optionally substituted heterocyclyl; or $R^1$ and $R^2$, together with the carbon to which they attach, form an optionally substituted ($C_3$-$C_6$)carbocyclic ring spiro to ring 2 or an optionally substituted heterocyclic ring spiro to ring 2;

$R^3$ is independently —H, $CF_3$, CN, OH, —$NR^aR^b$, an optionally substituted ($C_1$-$C_6$)alkyl, optionally substituted ($C_2$-$C_6$)alkenyl, optionally substituted ($C_2$-$C_6$)alkynyl, an optionally substituted aryl, an optionally substituted ($C_3$-$C_6$)cycloalkyl, an optionally substituted heteroaryl, an optionally substituted heterocyclyl, or an optionally substituted benzyl;

$R^{3'}$ is independently —H, an optionally substituted ($C_1$-$C_6$) alkyl, optionally substituted ($C_2$-$C_6$)alkenyl, optionally substituted ($C_2$-$C_6$)alkynyl, an optionally substituted aryl, an optionally substituted ($C_3$-$C_6$)cycloalkyl, an optionally substituted heteroaryl, an optionally substituted heterocyclyl, or an optionally substituted benzyl;

$R^4$ is independently H, —$CF_3$, —CN, —OH, —$NR^aR^b$, an optionally substituted ($C_1$-$C_6$)alkyl, an optionally substituted ($C_2$-$C_6$)alkenyl, an optionally substituted ($C_2$-$C_6$)alkynyl, an optionally substituted ($C_1$-$C_6$)alkoxy, an optionally substituted aryl, an optionally substituted ($C_3$-$C_6$)cycloalkyl, an optionally substituted heteroaryl, or an optionally substituted heterocyclyl;

$R^{4'}$ is independently —H, an optionally substituted ($C_1$-$C_8$)alkyl, an optionally substituted ($C_2$-$C_6$)alkenyl, an optionally substituted ($C_2$-$C_6$)alkynyl, an optionally substituted ($C_3$-$C_6$)cycloalkyl, an optionally substituted heterocyclyl, an optionally substituted aryl, or an optionally substituted heteroaryl;

provided that $R^{4'}$ is not an optionally substituted benzisoxazolyl, an optionally substituted isobenzazolyl, an optionally substituted quinazolinyl, an optionally substituted isoquinolinyl or an optionally substituted phthalazinyl;

$R^5$ is independently —H, OH, F, $CF_3$, CN, optionally substituted ($C_1$-$C_6$)alkyl, optionally substituted ($C_2$-$C_6$)alkenyl, optionally substituted ($C_2$-$C_6$)alkynyl, optionally substituted ($C_3$-$C_6$)cycloalkyl, —$(CH_2)_n$-optionally substituted aryl, —$(CH_2)_n$-optionally substituted heterocyclyl, or —$(CH_2)_n$-optionally substituted heteroaryl;

or both $R^5$, together with the carbon to which they are attached, form a carbocyclic spirocyclic ring;

$R^{5'}$ is —$R^{5'a}$—$R^{5'b}$—$R^{5'c}$ wherein $R^{5'a}$ is attached to the ring and $R^{5'a}$ is optionally substituted phenyl or optionally substituted heteroaryl;

$R^{5'b}$ is a bond or —C(=O)N(H) wherein the —C(=O) is attached to $R^{5'a}$; and $R^{5'c}$ is optionally substituted isoxazolyl, optionally substituted oxazolyl, optionally substituted phenyl, optionally substituted pyrazolyl, optionally substituted pyridazinyl, optionally substituted pyridinyl, optionally substituted pyrimidinyl, optionally substituted pyrido[2,3-b]pyrazinyl, tetrazolyl, optionally substituted 1,3,5-thiadiazolyl, or 1,2,4-triazolyl;

$R^a$ and $R^b$ are independently H and optionally substituted ($C_1$-$C_6$)alkyl; and n, for each occurrence, is independently 0, 1, 2 or 3;

provided that when the compound is

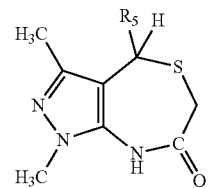

then $R^5$ is not unsubstituted phenyl or phenyl substituted by COOH, Cl, F, OH, $NO_2$ or two $OCH_3$;

provided that when M and Q are both CH or M and Q are both C and Ring 1 contains two nitrogen atoms, Ring 2 is not

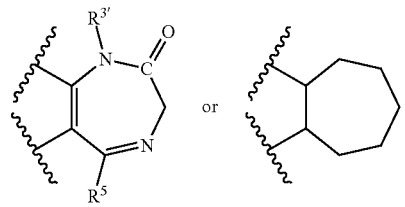

provided that not more than one of X, Y and Z is substituted by phenyl; and provided that the compound is not

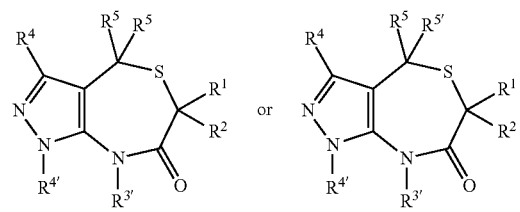

wherein $R^1$ and $R^2$ are independently H or $CH_3$;

$R^{4'}$ is H, optionally substituted ($C_1$-$C_8$)alkyl, —$CH_2C(O)OCH_2CH_3$, optionally substituted ($C_3$-$C_8$)cycloalkyl, optionally substituted benzyl, optionally substituted pyridinyl, optionally substituted pyrimidinyl,

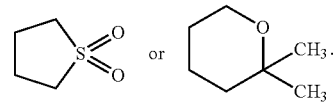

In a second embodiment the invention provides a compound according to the first embodiment wherein Ring 1 is

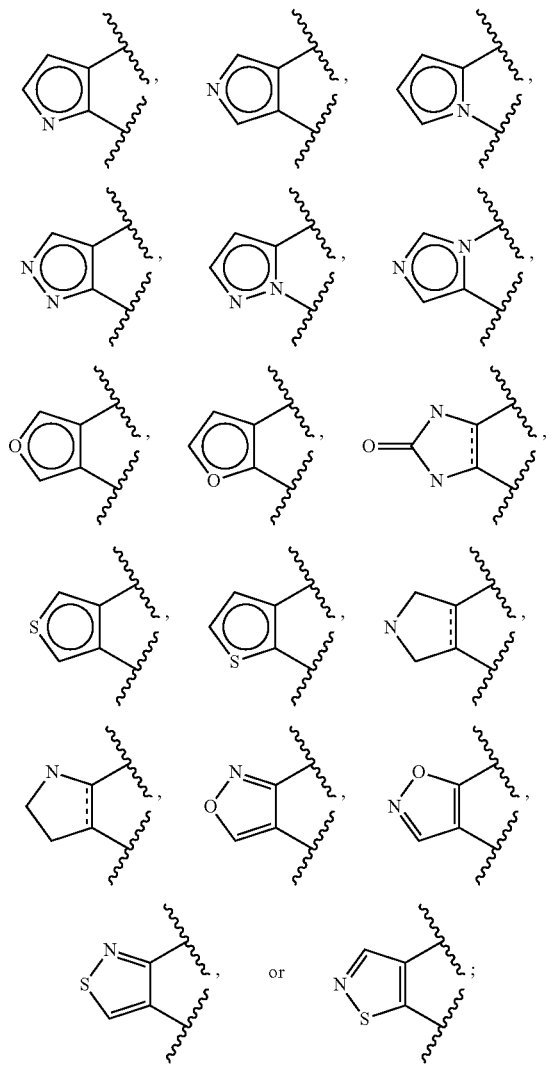

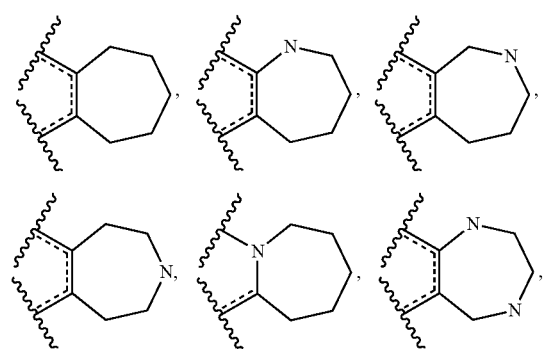

and is optionally substituted by one or more $R^4$ or $R^{4'}$.

In a third embodiment the invention provides a compound according any of the foregoing embodiments wherein Ring 2 is

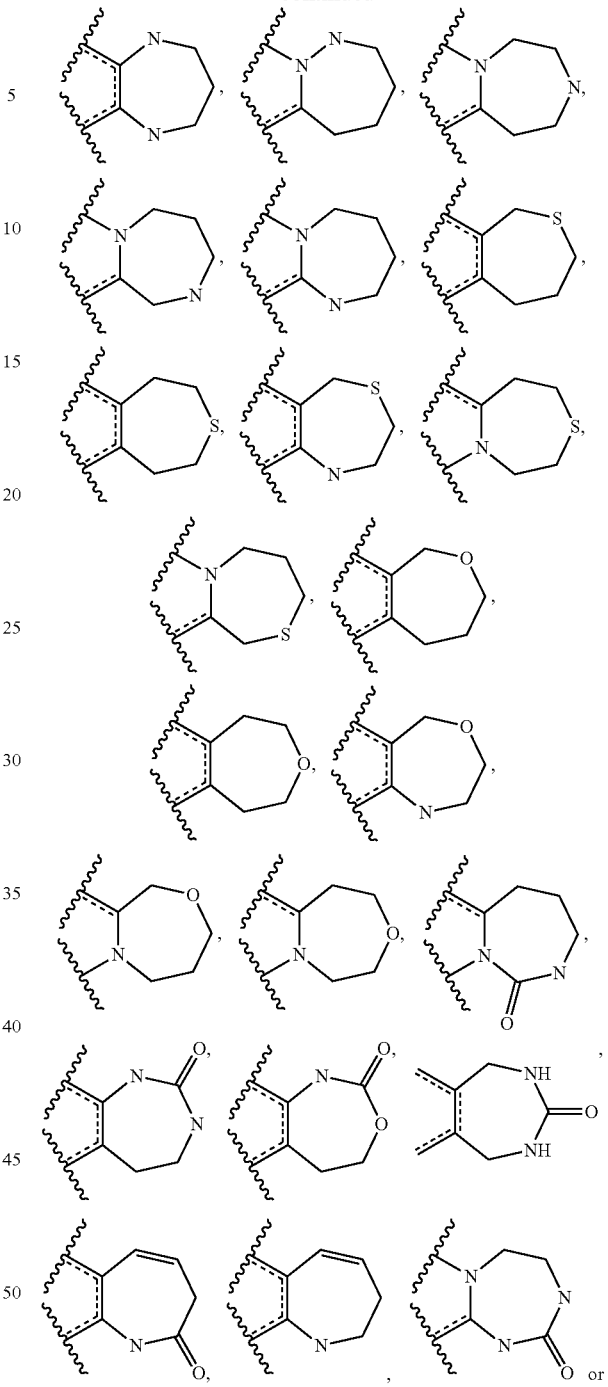

and is optionally substituted by one or more $R^1$, $R^2$, $R^3$, $R^{3'}$, $R^4$, $R^{4'}$, $R^5$ or $R^{5'}$.

In a fourth embodiment the invention provides a compound according to any of the foregoing embodiments wherein Formula (I) is

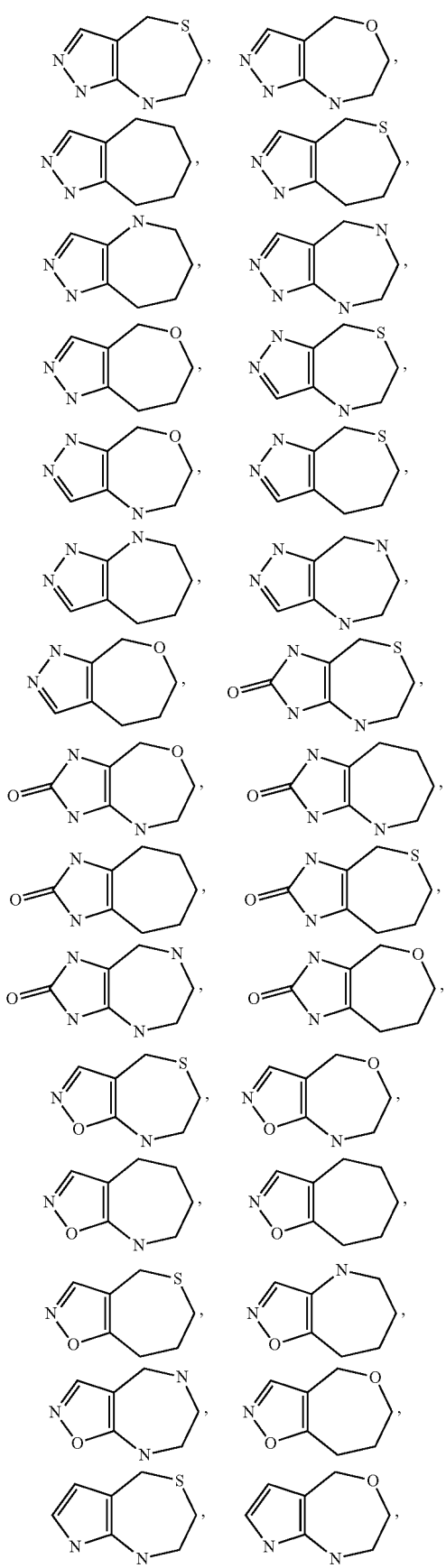

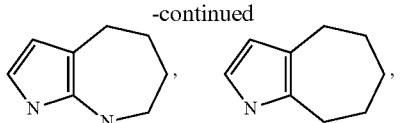
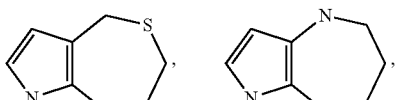
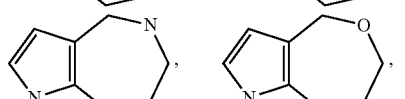
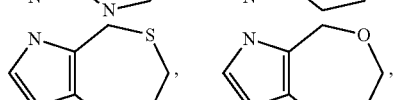
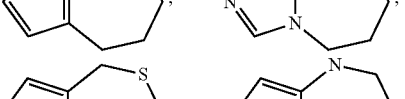

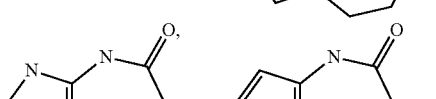

and is optionally substituted by one or more $R^1$, $R^2$, $R^3$, $R^{3'}$, $R^4$, $R^{4'}$, $R^5$ or $R^{5'}$.

In a fifth embodiment the invention provides a compound according to any of the foregoing embodiments wherein $R^1$ and $R^2$, for each occurrence, is independently —H or optionally substituted $(C_1\text{-}C_6)$alkyl; or $R^1$ and $R^2$, together with the carbon to which they attach, form an optionally substituted $(C_3\text{-}C_6)$cycloalkyl spiro to ring 2, or form a tetrahydropyranyl ring 1 spiro to ring 2.

In a sixth embodiment the invention provides a compound according to any of the foregoing embodiments wherein $R^3$ is independently H, optionally substituted phenyl, optionally substituted indazolyl, optionally substituted pyridinyl, optionally substituted pyrazolyl, optionally substituted thiophenyl, optionally substituted piperidinyl, or optionally substituted benzyl.

In a seventh embodiment the invention provides a compound according to any of the foregoing embodiments wherein $R^{3'}$ is H.

In an eighth embodiment the invention provides a compound according to any of the foregoing embodiments wherein $R^4$ is independently H, optionally substituted methyl, optionally substituted ethyl, optionally substituted isopropyl, optionally substituted tert-butyl, optionally substituted isobutyl, optionally substituted cyclopropyl, optionally substituted cyclopentyl, optionally substituted isothiazolidine, optionally substituted 1,2,4-oxadiazolyl, optionally substituted 1,3,4-oxadiazolyl, optionally substituted tetrahydrofuran, optionally substituted phenyl, optionally substituted pyridinyl, optionally substituted pyrimidinyl, optionally substituted thienyl, optionally substituted thiazolyl, optionally substituted pyrazolyl, optionally substituted isoxazolyl, optionally substituted tetrahydropyranyl, —OH, —CH$_2$CF$_3$, or —CF$_3$.

In a ninth embodiment the invention provides a compound according to any of the foregoing embodiments wherein $R^{4'}$ is independently H, optionally substituted methyl, optionally substituted ethyl, optionally substituted propyl, optionally substituted cyclopropyl or optionally substituted cyclopentyl, or optionally substituted pyridinyl.

In a tenth embodiment the invention provides a compound according to any of the foregoing embodiemnts wherein $R^5$ is independently H, optionally substituted methyl, optionally substituted propyl, optionally substituted benzyl, optionally substituted phenyl, optionally substituted piperidinyl, optionally substituted pyrazolyl, optionally substituted pyridinyl, optionally substituted thienyl.

In an eleventh embodiment the invention provides a compound according to any of the foregoing embodiments wherein $R^{5'}$ is —$R^{5'a}$—$R^{5'b}$—$R^{5'c}$ wherein $R^{5'a}$ is attached to the ring and $R^{5'a}$ is optionally substituted phenyl or optionally substituted indazolyl;

$R^{5'b}$ is a bond or —C(═O)N(H) wherein the —C(═O) is attached to $R^{5'a}$; and $R^{5'c}$ is optionally substituted pyrazolyl or optionally substituted pyridinyl.

In a twelfth embodiment the invention provides a compound according to any of the foregoing embodiments wherein n, for each occurrence, is independently 0 or 1.

In a thirteenth embodiment the invention provides a compound according to any of the foregoing embodiments wherein Formula (I) is

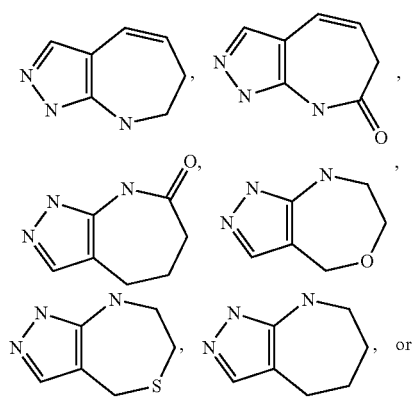

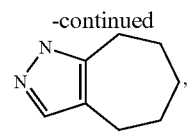

and is optionally substituted by one or more $R^1$, $R^2$, $R^3$, $R^{3'}$, $R^4$, $R^{4'}$, $R^5$ or $R^{5'}$.

In a fourteenth embodiment the invention provides a compound according to any of the foregoing embodiments wherein $R^1$ and $R^2$, for each occurrence, is independently —H, CF$_3$, CH$_3$, CH$_2$OH, CH$_2$CH$_2$OH, OH, optionally substituted phenyl or optionally substituted heteroaryl.

In a fifteenth embodiment the invention provides a compound according to any of the foregoing embodiments wherein $R^4$ is H, optionally substituted methyl, optionally substituted 1,3,4-oxadiazolyl, optionally substituted pyridinyl, or optionally substituted pyrimidinyl.

In a sixteenth embodiment the invention provides the compound 4-(2,6-dichlorophenyl)-1-methyl-3-(pyridin-2-yl)-4,6,7,8-tetrahydro-1H-pyrazolo[3,4-e][1,4]thiazepine;

4-(4-chloro-2-(trifluoromethyl)phenyl)-1-methyl-3-(pyridin-2-yl)-4,6,7,8-tetrahydro-1H-pyrazolo[3,4-e][1,4]thiazepine;

4-(2,4-dichlorophenyl)-1,3,6,6-tetramethyl-4,6,7,8-tetrahydro-1H-pyrazolo[3,4-e][1,4]thiazepine;

4-(4-chloro-2-methoxyphenyl)-1-methyl-3-(pyridin-2-yl)-4,6,7,8-tetrahydro-1H-pyrazolo[3,4-e][1,4]thiazepine;

3-chloro-N,N-dimethyl-4-(1-methyl-3-(pyridin-2-yl)-4,6,7,8-tetrahydro-1H-pyrazolo[3,4-e][1,4]thiazepin-4-yl) aniline;

4-(3-chloropyridin-4-yl)-1-methyl-3-(pyridin-2-yl)-4,6,7,8-tetrahydro-1H-pyrazolo[3,4-e][1,4]thiazepine;

4-(2,4-dichlorophenyl)-1-methyl-3-(pyridin-2-yl)-4,6,7,8-tetrahydro-1H-pyrazolo[3,4-e][1,4]thiazepine;

4-(2,4-dimethylphenyl)-1-methyl-3-(pyridin-2-yl)-4,6,7,8-tetrahydro-1H-pyrazolo[3,4-e][1,4]thiazepine;

4-(4-methoxy-2-methylphenyl)-1-methyl-3-(pyridin-2-yl)-4,6,7,8-tetrahydro-1H-pyrazolo[3,4-e][1,4]thiazepine;

4-(4-fluoro-2-methylphenyl)-1-methyl-3-(pyridin-2-yl)-4,6,7,8-tetrahydro-1H-pyrazolo[3,4-e][1,4]thiazepine;

1-methyl-4-(2-methyl-4-(trifluoromethoxy)phenyl)-3-(pyridin-2-yl)-4,6,7,8-tetrahydro-1H-pyrazolo[3,4-e][1,4]thiazepine;

4-(4-chloro-2-methylphenyl)-2-methyl-3-(pyridin-2-yl)-4,6,7,8-tetrahydro-2H-pyrazolo[3,4-e][1,4]thiazepine;

1-methyl-3-(pyridin-2-yl)-4-o-tolyl-4,6,7,8-tetrahydro-1H-pyrazolo[3,4-e][1,4]thiazepine;

3-(5-bromopyridin-2-yl)-4-(2,4-dichlorophenyl)-1-methyl-4,6,7,8-tetrahydro-1H-pyrazolo[3,4-e][1,4]thiazepine;

4-(2,4-dichlorophenyl)-1-methyl-3-(thiazol-2-yl)-4,6,7,8-tetrahydro-1H-pyrazolo[3,4-e][1,4]thiazepine;

4-(2,4-dichlorophenyl)-1,6,6-trimethyl-3-(thiazol-2-yl)-4,6,7,8-tetrahydro-1H-pyrazolo[3,4-e][1,4]thiazepine;

4-(2,4-dichlorophenyl)-1-methyl-3-(pyridin-4-yl)-4,6,7,8-tetrahydro-1H-pyrazolo[3,4-e][1,4]thiazepine;

3-(4-bromopyridin-2-yl)-4-(4-chloro-2-methylphenyl)-1-methyl-4,6,7,8-tetrahydro-1H-pyrazolo[3,4-e][1,4]thiazepine;

4-(2,5-dimethylphenyl)-1-methyl-3-(pyridin-2-yl)-4,6,7,8-tetrahydro-1H-pyrazolo[3,4-e][1,4]thiazepine;

4-(5-chloro-3-methylpyridin-2-yl)-1-methyl-3-(pyridin-2-yl)-4,6,7,8-tetrahydro-1H-pyrazolo[3,4-e][1,4]thiazepine;

4-(4-chloro-2-methylphenyl)-3-(4-methoxypyridin-2-yl)-1-methyl-4,6,7,8-tetrahydro-1H-pyrazolo[3,4-e][1,4]thiazepine;

4-(4-chlorophenyl)-1-methyl-3-(pyridin-2-yl)-4,6,7,8-tetrahydro-1H-pyrazolo[3,4-e][1,4]thiazepine;

4-(4-chloro-2-methylphenyl)-3-(4-chloropyridin-2-yl)-1-methyl-4,6,7,8-tetrahydro-1H-pyrazolo[3,4-e][1,4]thiazepine;

4-(4-bromophenyl)-1-methyl-3-(pyridin-2-yl)-4,6,7,8-tetrahydro-1H-pyrazolo[3,4-e][1,4]thiazepine;

4-(5-bromo-3-methylthiophen-2-yl)-1-methyl-3-(pyridin-2-yl)-4,6,7,8-tetrahydro-1H-pyrazolo[3,4-e][1,4]thiazepine;

4-(5-bromo-2-methylphenyl)-1-methyl-3-(pyridin-2-yl)-4,6,7,8-tetrahydro-1H-pyrazolo[3,4-e][1,4]thiazepine;

4-(5-methoxy-2-methylphenyl)-1-methyl-3-(pyridin-2-yl)-4,6,7,8-tetrahydro-1H-pyrazolo[3,4-e][1,4]thiazepine;

5-(4-(4-bromo-2-methylphenyl)-1-methyl-4,6,7,8-tetrahydro-1H-pyrazolo[3,4-e][1,4]thiazepin-3-yl)-3-methylisoxazole;

4-(4-bromo-2-methylphenyl)-1-ethyl-3-(pyridin-2-yl)-4,6,7,8-tetrahydro-1H-pyrazolo[3,4-e][1,4]thiazepine;

4-(4-(2,4-dichlorophenyl)-1-methyl-4,6,7,8-tetrahydro-1H-pyrazolo[3,4-e][1,4]thiazepin-3-yl)-N,N-dimethylaniline;

4-(2,4-dichlorophenyl)-1,6,6-trimethyl-3-(pyridin-2-yl)-4,6,7,8-tetrahydro-1H-pyrazolo[3,4-e][1,4]thiazepine;

4-(2,3-dimethylphenyl)-1-methyl-3-(pyridin-2-yl)-4,6,7,8-tetrahydro-1H-pyrazolo[3,4-e][1,4]thiazepine;

4-(5-bromo-2-methylthiophen-3-yl)-1-methyl-3-(pyridin-2-yl)-4,6,7,8-tetrahydro-1H-pyrazolo[3,4-e][1,4]thiazepine;

4-(4-chloro-5-methoxy-2-methylphenyl)-1-methyl-3-(pyridin-2-yl)-4,6,7,8-tetrahydro-1H-pyrazolo[3,4-e][1,4]thiazepine;

4-benzyl-1-methyl-3-(pyridin-2-yl)-4,6,7,8-tetrahydro-1H-pyrazolo[3,4-e][1,4]thiazepine hydrochloride;

4-(2-bromo-4-chlorophenyl)-1-methyl-3-(pyridin-2-yl)-4,6,7,8-tetrahydro-1H-pyrazolo[3,4-e][1,4]thiazepine;

4-(4-chloro-2-cyclopropylphenyl)-1-methyl-3-(pyridin-2-yl)-4,6,7,8-tetrahydro-1H-pyrazolo[3,4-e][1,4]thiazepine;

4-(4-chloro-2-(fluoromethyl)phenyl)-1-methyl-3-(pyridin-2-yl)-4,6,7,8-tetrahydro-1H-pyrazolo[3,4-e][1,4]thiazepine;

4-(5-chloro-2-methylphenyl)-1-methyl-3-(pyridin-2-yl)-4,6,7,8-tetrahydro-1H-pyrazolo[3,4-e][1,4]thiazepine;

1-methyl-4-(2-methyl-4-(trifluoromethyl)phenyl)-3-(pyridin-2-yl)-4,6,7,8-tetrahydro-1H-pyrazolo[3,4-e][1,4]thiazepine;

3-methyl-4-(1-methyl-3-(pyridin-2-yl)-4,6,7,8-tetrahydro-1H-pyrazolo[3,4-e][1,4]thiazepin-4-yl)phenol;

3-(4-(4-chloro-2-methylphenyl)-1-methyl-4,6,7,8-tetrahydro-1H-pyrazolo[3,4-e][1,4]thiazepin-3-yl)-5-methylisoxazole;

4-(4-bromo-2-methylphenyl)-3-(pyridin-2-yl)-4,6,7,8-tetrahydroisoxazolo[5,4-e][1,4]thiazepine;

4-(5-chloro-2-methylphenyl)-3-cyclopropyl-1,6,6-trimethyl-4,6,7,8-tetrahydro-1H-pyrazolo[3,4-e][1,4]thiazepine;

4-(4-chloro-2-methoxyphenyl)-3-cyclopropyl-1,6,6-trimethyl-4,6,7,8-tetrahydro-1H-pyrazolo[3,4-e][1,4]thiazepine hydrochloride;

4-(4-chloro-2-(trifluoromethyl)phenyl)-3-cyclopropyl-1,6,6-trimethyl-4,6,7,8-tetrahydro-1H-pyrazolo[3,4-e][1,4]thiazepine hydrochloride;

3-cyclopropyl-4-(2,5-dimethylphenyl)-1,6,6-trimethyl-4,6,7,8-tetrahydro-1H-pyrazolo[3,4-e][1,4]thiazepine;

4-(5-chloro-3-methylpyridin-2-yl)-3-cyclopropyl-1,6,6-trimethyl-4,6,7,8-tetrahydro-1H-pyrazolo[3,4-e][1,4]thiazepine;

4-(4-bromo-2-methylphenyl)-3-cyclopropyl-1,6-dimethyl-4,6,7,8-tetrahydro-1H-pyrazolo[3,4-e][1,4]thiazepine;

4-(4-bromo-2-methylphenyl)-3-cyclopropyl-1,6-dimethyl-4,6,7,8-tetrahydro-1H-pyrazolo[3,4-e][1,4]thiazepine;

4-(4-chloro-2-fluorophenyl)-3-cyclopropyl-1,6,6-trimethyl-4,6,7,8-tetrahydro-1H-pyrazolo[3,4-e][1,4]thiazepine hydrochloride;

(Z)-4-(5-bromo-2-methylphenyl)-3-cyclopropyl-1,6,6-trimethyl-4,6-dihydro-1H-pyrazolo[3,4-e][1,4]thiazepine;

4-(5-bromo-2-methylphenyl)-3-cyclopropyl-1,6,6-trimethyl-4,6,7,8-tetrahydro-1H-pyrazolo[3,4-e][1,4]thiazepine;

3-cyclopropyl-4-(4-fluoro-2-methylphenyl)-1,6,6-trimethyl-4,6,7,8-tetrahydro-1H-pyrazolo[3,4-e][1,4]thiazepine;

4-(4-chloro-2-methylphenyl)-1,3,6,6-tetramethyl-4,6,7,8-tetrahydro-1H-pyrazolo[3,4-e][1,4]thiazepine;

4-(4-bromo-2-methylphenyl)-1,3,6,6-tetramethyl-4,6,7,8-tetrahydro-1H-pyrazolo[3,4-e][1,4]thiazepine;

4-(4-chloro-2-methylphenyl)-1,3-dimethyl-4,6,7,8-tetrahydro-1H-pyrazolo[3,4-e][1,4]thiazepine;

4-(4-bromo-2-chlorophenyl)-1,3,6,6-tetramethyl-4,6,7,8-tetrahydro-1H-pyrazolo[3,4-e][1,4]thiazepine;

1,3,6,6-tetramethyl-4-(2-methyl-4-(trifluoromethyl)phenyl)-4,6,7,8-tetrahydro-1H-pyrazolo[3,4-e][1,4]thiazepine;

4-(4-bromo-2-methylphenyl)-1,3,6-trimethyl-4,6,7,8-tetrahydro-1H-pyrazolo[3,4-e][1,4]thiazepine;

4-(2,4-dichlorophenyl)-3,6,6-trimethyl-4,6,7,8-tetrahydro-1H-pyrazolo[3,4-e][1,4]thiazepine;

4-(2,4-dichlorophenyl)-3-isopropyl-1,6,6-trimethyl-4,6,7,8-tetrahydro-1H-pyrazolo[3,4-e][1,4]thiazepine hydrochloride;

4'-(2,4-dichlorophenyl)-1',3'-dimethyl-1',4',7',8'-tetrahydrospiro[cyclopentane-1,6'-pyrazolo[3,4-e][1,4]thiazepine];

4'-(2,4-dichlorophenyl)-1',3'-dimethyl-1',4',7',8'-tetrahydrospiro[cyclobutane-1,6'-pyrazolo[3,4-e][1,4]thiazepine];

4'-(2,4-dichlorophenyl)-1',3'-dimethyl-1',2,3,4',5,6,7',8'-octahydrospiro[pyran-4,6'-pyrazolo[3,4-e][1,4]thiazepine];

4-(2,4-dichlorophenyl)-1,3,6,6-tetramethyl-4,6,7,8-tetrahydro-1H-pyrazolo[3,4-e][1,4]thiazepine;

4-(3-bromo-2-methylphenyl)-3-cyclopropyl-1,6,6-trimethyl-4,6,7,8-tetrahydro-1H-pyrazolo[3,4-e][1,4]thiazepine;

4-(4-chloro-2-methylphenyl)-1-cyclopentyl-3,6,6-trimethyl-4,6,7,8-tetrahydro-1H-pyrazolo[3,4-e][1,4]thiazepine;

1,3,6,6-tetramethyl-4-(2-methyl-4-(methylsulfonyl)phenyl)-4,6,7,8-tetrahydro-1H-pyrazolo[3,4-e][1,4]thiazepine;

4-(4-chloro-2-methylphenyl)-1-methyl-3-(tetrahydrofuran-2-yl)-4,6,7,8-tetrahydro-1H-pyrazolo[3,4-e][1,4]thiazepine;

4-(4-chloro-2-methylphenyl)-1-methyl-4,6,7,8-tetrahydro-1H-pyrazolo[3,4-e][1,4]thiazepin-3-ol;

3-cyclopropyl-4-(2,4-dichlorophenyl)-1,6,6-trimethyl-4,6,7,8-tetrahydro-1H-pyrazolo[3,4-e][1,4]thiazepine;

1,3-dimethyl-4-(4-(p-tolyloxy)phenyl)-4,6,7,8-tetrahydro-1H-pyrazolo[3,4-e][1,4]thiazepine2;

4-(1H-indazol-5-yl)-1,3-dimethyl-4,6,7,8-tetrahydro-1H-pyrazolo[3,4-e][1,4]thiazepine;

3-cyclopentyl-4-(2,4-dichlorophenyl)-1-methyl-4,6,7,8-tetrahydro-1H-pyrazolo[3,4-e][1,4]thiazepine;

1,3,6,6-tetramethyl-4-(4-(p-tolyloxy)phenyl)-4,6,7,8-tetrahydro-1H-pyrazolo[3,4-e][1,4]thiazepine;

3-cyclopentyl-4-(2,4-dichlorophenyl)-1,6,6-trimethyl-4,6,7,8-tetrahydro-1H-pyrazolo[3,4-e][1,4]thiazepine;

4-(2,4-dichlorophenyl)-1,3-dimethyl-4,6,7,8-tetrahydro-1H-pyrazolo[3,4-e][1,4]thiazepine;
4-(3-methoxyphenyl)-1,3-dimethyl-4,6,7,8-tetrahydro-1H-pyrazolo[3,4-e][1,4]thiazepine;
3-(4-chlorophenyl)-4-(2,4-dichlorophenyl)-1-methyl-4,6,7,8-tetrahydro-1H-pyrazolo[3,4-e][1,4]thiazepine;
4-(2,4-dichlorophenyl)-1-methyl-3-phenyl-4,6,7,8-tetrahydro-1H-pyrazolo[3,4-e][1,4]thiazepine;
4-(2,4-dichlorophenyl)-3-isopropyl-1-methyl-4,6,7,8-tetrahydro-1H-pyrazolo[3,4-e][1,4]thiazepine;
3-tert-butyl-4-(2,4-dichlorophenyl)-1-methyl-4,6,7,8-tetrahydro-1H-pyrazolo[3,4-e][1,4]thiazepine;
4-(2,4-dichlorophenyl)-1-methyl-3-(pyridin-3-yl)-4,6,7,8-tetrahydro-1H-pyrazolo[3,4-e][1,4]thiazepine;
4-(2,4-dichlorophenyl)-1-methyl-3-p-tolyl-4,6,7,8-tetrahydro-1H-pyrazolo[3,4-e][1,4]thiazepine;
3-(4-tert-butylphenyl)-4-(2,4-dichlorophenyl)-1-methyl-4,6,7,8-tetrahydro-1H-pyrazolo[3,4-e][1,4]thiazepine;
4-(2,4-dichlorophenyl)-3-(3,4-dichlorophenyl)-1-methyl-4,6,7,8-tetrahydro-1H-pyrazolo[3,4-e][1,4]thiazepine;
4-(2,4-dichlorophenyl)-3-(3,5-difluorophenyl)-1-methyl-4,6,7,8-tetrahydro-1H-pyrazolo[3,4-e][1,4]thiazepine;
4-(2,4-dichlorophenyl)-1-methyl-3-(trifluoromethyl)-4,6,7,8-tetrahydro-1H-pyrazolo[3,4-e][1,4]thiazepine;
4-(2,4-dichlorophenyl)-3-isobutyl-1-methyl-4,6,7,8-tetrahydro-1H-pyrazolo[3,4-e][1,4]thiazepine;
4-(2,4-dichlorophenyl)-3-(2,4-difluorophenyl)-1-methyl-4,6,7,8-tetrahydro-1H-pyrazolo[3,4-e][1,4]thiazepine;
4-(2,4-dichlorophenyl)-3-(4-fluorophenyl)-1-methyl-4,6,7,8-tetrahydro-1H-pyrazolo[3,4-e][1,4]thiazepine;
4-(2,4-dichlorophenyl)-1-methyl-3-(4-(trifluoromethoxy)phenyl)-4,6,7,8-tetrahydro-1H-pyrazolo[3,4-e][1,4]thiazepine;
1,3-dimethyl-4-(pyridin-2-yl)-4,6,7,8-tetrahydro-1H-pyrazolo[3,4-e][1,4]thiazepine;
4-(4-methoxyphenyl)-1,3-dimethyl-4,6,7,8-tetrahydro-1H-pyrazolo[3,4-e][1,4]thiazepine;
4-(2-methoxyphenyl)-1,3-dimethyl-4,6,7,8-tetrahydro-1H-pyrazolo[3,4-e][1,4]thiazepine;
1,3-dimethyl-4-(pyridin-3-yl)-4,6,7,8-tetrahydro-1H-pyrazolo[3,4-e][1,4]thiazepine;
2-(4-(4-chlorophenyl)-1,3-dimethyl-4,6,7,8-tetrahydro-1H-pyrazolo[3,4-e][1,4]thiazepin-6-yl)ethanol;
4-(2,4-dichlorophenyl)-1-methyl-3-(thiophen-2-yl)-4,6,7,8-tetrahydro-1H-pyrazolo[3,4-e][1,4]thiazepine;
1,3-dimethyl-4-(1H-pyrazol-3-yl)-4,6,7,8-tetrahydro-1H-pyrazolo[3,4-e][1,4]thiazepine;
4-(4-chloro-2-fluorophenyl)-1-methyl-3-(pyridin-2-yl)-4,6,7,8-tetrahydro-1H-pyrazolo[3,4-e][1,4]thiazepine;
methyl 3-chloro-4-[1-methyl-3-(2-pyridyl)-4,6,7,8-tetrahydropyrazolo[3,4-e][1,4]thiazepin-4-yl]benzoate;
methyl 4-(1-methyl-3-(pyridin-2-yl)-4,6,7,8-tetrahydro-1H-pyrazolo[3,4-e][1,4]thiazepin-4-yl)benzoate;
methyl 3-methyl-4-(1-methyl-3-(pyridin-2-yl)-4,6,7,8-tetrahydro-1H-pyrazolo[3,4-e][1,4]thiazepin-4-yl)benzoate;
methyl 4-(1,3,6,6-tetramethyl-4,6,7,8-tetrahydro-1H-pyrazolo[3,4-e][1,4]thiazepin-4-yl)benzoate;
methyl 5-methyl-4-(1-methyl-3-(pyridin-2-yl)-4,6,7,8-tetrahydro-1H-pyrazolo[3,4-e][1,4]thiazepin-4-yl)thiophene-2-carboxylate;
methyl 6-(4-(2,4-dichlorophenyl)-1-methyl-4,6,7,8-tetrahydro-1H-pyrazolo[3,4-e][1,4]thiazepin-3-yl)nicotinate;
3-chloro-N-(2-methyl-3-pyridyl)-4-[1-methyl-3-(2-pyridyl)-4,6,7,8-tetrahydro-pyrazolo[3,4-e][1,4]thiazepin-4-yl]benzamide;
6-(4-(2,4-dichlorophenyl)-1-methyl-4,6,7,8-tetrahydro-1H-pyrazolo[3,4-e][1,4]thiazepin-3-yl)-N-(2-methylpyridin-3-yl)nicotinamide;
4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide;
4-methyl-5-(1-methyl-3-(pyridin-2-yl)-4,6,7,8-tetrahydro-1H-pyrazolo[3,4-e][1,4]thiazepin-4-yl)-N-(2-methylpyridin-3-yl)thiophene-2-carboxamide;
4-methyl-3-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide;
5-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)thiophene-2-carboxamide;
4-methyl-3-[1-methyl-3-(2-pyridyl)-4,6,7,8-tetrahydropyrazolo[3,4-e][1,4]thiazepin-4-yl]benzonitrile;
3-methyl-4-((4S,6S)-1,3,6-trimethyl-4,6,7,8-tetrahydro-1H-pyrazolo[3,4-e][1,4]thiazepin-4-yl)benzonitrile;
3-methyl-4-((4R,6R)-1,3,6-trimethyl-4,6,7,8-tetrahydro-1H-pyrazolo[3,4-e][1,4]thiazepin-4-yl)benzonitrile;
4-((4R,6S)-3-cyclopropyl-1,6-dimethyl-4,6,7,8-tetrahydro-1H-pyrazolo[3,4-e][1,4]thiazepin-4-yl)-3-methylbenzonitrile;
4-((4S,6R)-3-cyclopropyl-1,6-dimethyl-4,6,7,8-tetrahydro-1H-pyrazolo[3,4-e][1,4]thiazepin-4-yl)-3-methylbenzonitrile;
4-((4S,6S)-3-cyclopropyl-1,6-dimethyl-4,6,7,8-tetrahydro-1H-pyrazolo[3,4-e][1,4]thiazepin-4-yl)-3-methylbenzonitrile;
4-((4R,6R)-3-cyclopropyl-1,6-dimethyl-4,6,7,8-tetrahydro-1H-pyrazolo[3,4-e][1,4]thiazepin-4-yl)-3-methylbenzonitrile;
3-(3-cyclopropyl-1,6,6-trimethyl-4,6,7,8-tetrahydro-1H-pyrazolo[3,4-e][1,4]thiazepin-4-yl)-4-methylbenzonitrile;
3-methyl-4-(1,3,6,6-tetramethyl-4,6,7,8-tetrahydro-1H-pyrazolo[3,4-e][1,4]thiazepin-4-yl)benzonitrile;
4-(1,7-dimethyl-3-(pyridin-2-yl)-4,6,7,8-tetrahydro-1H-pyrazolo[3,4-e][1,4]thiazepin-4-yl)-3-methylbenzonitrile;
3-methyl-4-(1-methyl-3-(pyridin-2-yl)-4,6,7,8-tetrahydro-1H-pyrazolo[3,4-e][1,4]thiazepin-4-yl)benzonitrile;
3-methyl-4-(3-(pyridin-2-yl)-4,6,7,8-tetrahydroisoxazolo[5,4-e][1,4]thiazepin-4-yl)benzonitrile;
4-(1-ethyl-3-(pyridin-2-yl)-4,6,7,8-tetrahydro-1H-pyrazolo[3,4-e][1,4]thiazepin-4-yl)-3-methylbenzonitrile;
3-methyl-4-((4R,6S)-1,3,6-trimethyl-4,6,7,8-tetrahydro-1H-pyrazolo[3,4-e][1,4]thiazepin-4-yl)benzonitrile;
3-methyl-4-((4S,6R)-1,3,6-trimethyl-4,6,7,8-tetrahydro-1H-pyrazolo[3,4-e][1,4]thiazepin-4-yl)benzonitrile;
3-methyl-N-(3-pyridyl)-4-(1,3,6,6-tetramethyl-7,8-dihydro-4H-pyrazolo[3,4-e][1,4]thiazepin-4-yl)benzamide;
3-(3-cyclopropyl-1,6,6-trimethyl-4,6,7,8-tetrahydro-1H-pyrazolo[3,4-e][1,4]thiazepin-4-yl)-4-methyl-N-(2-methylpyridin-3-yl)benzamide;
3-chloro-4-(1-methyl-3-(pyridin-2-yl)-4,6,7,8-tetrahydro-1H-pyrazolo[3,4-e][1,4]thiazepin-4-yl)-N-(pyridin-3-yl)benzamide;
4-(1-ethyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide;
3-methyl-N-(2-methylpyridin-3-yl)-4-(1,3,6,6-tetramethyl-4,6,7,8-tetrahydro-1H-pyrazolo[3,4-e][1,4]thiazepin-4-yl)benzamide;
3-chloro-4-[1-methyl-3-(2-pyridyl)-4,6,7,8-tetrahydropyrazolo[3,4-e][1,4]thiazepin-4-yl]benzamide;

3-chloro-N-methyl-4-(1-methyl-3-(pyridin-2-yl)-4,6,7,8-tetrahydro-1H-pyrazolo[3,4-e][1,4]thiazepin-4-yl)benzamide;

6-(4-(2,4-dichlorophenyl)-1-methyl-4,6,7,8-tetrahydro-1H-pyrazolo[3,4-e][1,4]thiazepin-3-yl)-N-methylnicotinamide;

3-methyl-4-(1,3,6,6-tetramethyl-4,6,7,8-tetrahydro-1H-pyrazolo[3,4-e][1,4]thiazepin-4-yl)benzamide;

6-(4-(2,4-dichlorophenyl)-1-methyl-4,6,7,8-tetrahydro-1H-pyrazolo[3,4-e][1,4]thiazepin-3-yl)nicotinamide;

4-(4-bromo-2-methyl-phenyl)-1,7-dimethyl-3-(2-pyridyl)-4,6,7,8-tetrahydropyrazolo[3,4-e][1,4]thiazepine;

4-(4-bromo-2-methyl-phenyl)-1,7-dimethyl-3-(2-pyridyl)-4,6,7,8-tetrahydropyrazolo[3,4-e][1,4]thiazepine;

(4R,7R)-4-(4-chloro-2-methylphenyl)-1,3,6,6-tetramethyl-7-phenyl-4,6,7,8-tetrahydro-1H-pyrazolo[3,4-e][1,4]thiazepine;

(4S,7S)-4-(4-chloro-2-methylphenyl)-1,3,6,6-tetramethyl-7-phenyl-4,6,7,8-tetrahydro-1H-pyrazolo[3,4-e][1,4]thiazepine;

4-(4-chloro-2-methylphenyl)-7-isopropyl-1-methyl-3-(pyridin-2-yl)-4,6,7,8-tetrahydro-1H-pyrazolo[3,4-e][1,4]thiazepine;

4-(2,4-dichlorophenyl)-1,3,6,6-tetramethyl-7,8-dihydro-4H-pyrazolo[3,4-e][1,4]thiazepine 5-oxide;

4-(2,4-Dichloro-phenyl)-1-methyl-3-pyridin-2-yl-4,6,7,8-tetrahydro-1H-pyrazolo[3,4-e][1,4]thiazepine 5-oxide;

4-(2,4-Dichloro-phenyl)-1-methyl-3-pyridin-2-yl-4,6,7,8-tetrahydro-1H-pyrazolo[3,4-e][1,4]thiazepine 5,5-dioxide;

4-(2,4-Dichloro-phenyl)-1,3,6,6-tetramethyl-4,6,7,8-tetrahydro-1H-pyrazolo[3,4-e][1,4]thiazepine 5,5-dioxide;

(R)-4-(4-Chloro-2-methylphenyl)-1,3,6,6-tetramethyl-4,6,7,8-tetrahydro-1H-pyrazolo[3,4-e][1,4]thiazepine;

(S)-4-(4-Chloro-2-methylphenyl)-1,3,6,6-tetramethyl-4,6,7,8-tetrahydro-1H-pyrazolo[3,4-e][1,4]thiazepine;

(S)-4-(4-bromo-2-chlorophenyl)-1-methyl-3-(pyridin-2-yl)-4,6,7,8-tetrahydro-1H-pyrazolo[3,4-e][1,4]thiazepine;

(R)-4-(4-bromo-2-chlorophenyl)-1-methyl-3-(pyridin-2-yl)-4,6,7,8-tetrahydro-1H-pyrazolo[3,4-e][1,4]thiazepine;

(R)-4-(4-chloro-2-fluorophenyl)-3-cyclopropyl-1,6,6-trimethyl-4,6,7,8-tetrahydro-1H-pyrazolo[3,4-e][1,4]thiazepine;

(S)-4-(4-chloro-2-fluorophenyl)-3-cyclopropyl-1,6,6-trimethyl-4,6,7,8-tetrahydro-1H-pyrazolo[3,4-e][1,4]thiazepine;

3-((S)-4-(2,4-dichlorophenyl)-3,6,6-trimethyl-4,6,7,8-tetrahydro-1H-pyrazolo[3,4-e][1,4]thiazepin-1-yl)-1,1,1-trifluoropropan-2-ol;

(R)-4-(4-chloro-2-methylphenyl)-1,3,6,6-tetramethyl-4,6,7,8-tetrahydro-1H-pyrazolo[3,4-e][1,4]thiazepine;

(S)-4-(4-chloro-2-methylphenyl)-1,3,6,6-tetramethyl-4,6,7,8-tetrahydro-1H-pyrazolo[3,4-e][1,4]thiazepine;

(S)-3-chloro-N-(2-methylpyridin-3-yl)-4-(1,3,6,6-tetramethyl-4,6,7,8-tetrahydro-1H-pyrazolo[3,4-e][1,4]thiazepin-4-yl)benzamide;

(R)-3-chloro-N-(2-methylpyridin-3-yl)-4-(1,3,6,6-tetramethyl-4,6,7,8-tetrahydro-1H-pyrazolo[3,4-e][1,4]thiazepin-4-yl)benzamide;

2-((4R,6S)-4-(4-chloro-2-methylphenyl)-1-methyl-3-(pyridin-2-yl)-4,6,7,8-tetrahydro-1H-pyrazolo[3,4-e][1,4]thiazepin-6-yl)ethanol;

2-((4R,6R)-4-(4-chloro-2-methylphenyl)-1-methyl-3-(pyridin-2-yl)-4,6,7,8-tetrahydro-1H-pyrazolo[3,4-e][1,4]thiazepin-6-yl)ethanol;

2-((4S,6R)-4-(4-chloro-2-methylphenyl)-1-methyl-3-(pyridin-2-yl)-4,6,7,8-tetrahydro-1H-pyrazolo[3,4-e][1,4]thiazepin-6-yl)ethanol;

2-((4S,6S)-4-(4-chloro-2-methylphenyl)-1-methyl-3-(pyridin-2-yl)-4,6,7,8-tetrahydro-1H-pyrazolo[3,4-e][1,4]thiazepin-6-yl)ethanol;

2-((4R,6R)-4-(4-chloro-2-methylphenyl)-1,3-dimethyl-4,6,7,8-tetrahydro-1H-pyrazolo[3,4-e][1,4]thiazepin-6-yl)ethanol;

2-((4R,6S)-4-(4-chloro-2-methylphenyl)-1,3-dimethyl-4,6,7,8-tetrahydro-1H-pyrazolo[3,4-e][1,4]thiazepin-6-yl)ethanol;

2-((4S,6S)-4-(4-chloro-2-methylphenyl)-1,3-dimethyl-4,6,7,8-tetrahydro-1H-pyrazolo[3,4-e][1,4]thiazepin-6-yl)ethanol;

2-((4S,6R)-4-(4-chloro-2-methylphenyl)-1,3-dimethyl-4,6,7,8-tetrahydro-1H-pyrazolo[3,4-e][1,4]thiazepin-6-yl)ethanol;

4-(4-chloro-2-methyl-phenyl)-3-cyclopropyl-1,6,6-trimethyl-7,8-dihydro-4H-pyrazolo[3,4-e][1,4]thiazepine;

(4S)-4-(4-chloro-2-methyl-phenyl)-3-cyclopropyl-1,6,6-trimethyl-7,8-dihydro-4H-pyrazolo[3,4-e][1,4]thiazepine;

(4R)-4-(4-chloro-2-methyl-phenyl)-3-cyclopropyl-1,6,6-trimethyl-7,8-dihydro-4H-pyrazolo[3,4-e][1,4]thiazepine;

4-(4-chloro-2-methyl-phenyl)-1-methyl-3-(2-pyridyl)-4,6,7,8-tetrahydropyrazolo[3,4-e][1,4]thiazepine;

(4R)-4-(4-chloro-2-methylphenyl)-1-methyl-3-(2-pyridyl)-4,6,7,8-tetrahydropyrazolo[3,4-e][1,4]thiazepine;

(4S)-4-(4-chloro-2-methylphenyl)-1-methyl-3-(2-pyridyl)-4,6,7,8-tetrahydropyrazolo[3,4-e][1,4]thiazepine;

3-chloro-N-(2-methyl-3-pyridyl)-4-[1-methyl-3-(2-pyridyl)-4,6,7,8-tetrahydro-pyrazolo[3,4-e][1,4]thiazepin-4-yl]benzamide;

3-chloro-N-(2-methyl-3-pyridyl)-4-[(4R)-1-methyl-3-(2-pyridyl)-4,6,7,8-tetrahydropyrazolo[3,4-e][1,4]thiazepin-4-yl]benzamide;

3-chloro-N-(2-methyl-3-pyridyl)-4-[(4S)-1-methyl-3-(2-pyridyl)-4,6,7,8-tetrahydropyrazolo[3,4-e][1,4]thiazepin-4-yl]benzamide;

3-methyl-N-(2-methyl-3-pyridyl)-4-[1-methyl-3-(2-pyridyl)-4,6,7,8-tetrahydro-pyrazolo[3,4-e][1,4]thiazepin-4-yl]benzamide;

(R)-3-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide;

(S)-3-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide;

(4R,7S)-4-(4-chloro-2-methylphenyl)-1,7-dimethyl-3-(pyridin-2-yl)-4,6,7,8-tetrahydro-1H-pyrazolo[3,4-e][1,4]thiazepine;

(4R,7R)-4-(4-chloro-2-methylphenyl)-1,7-dimethyl-3-(pyridin-2-yl)-4,6,7,8-tetrahydro-1H-pyrazolo[3,4-e][1,4]thiazepine;

(4S,7S)-4-(4-chloro-2-methylphenyl)-1,7-dimethyl-3-(pyridin-2-yl)-4,6,7,8-tetrahydro-1H-pyrazolo[3,4-e][1,4]thiazepine;

(4S,7R)-4-(4-chloro-2-methylphenyl)-1,7-dimethyl-3-(pyridin-2-yl)-4,6,7,8-tetrahydro-1H-pyrazolo[3,4-e][1,4]thiazepine;

4-(4-chloro-2-methyl-phenyl)-1-methyl-3-(1H-pyrazol-5-yl)-4,6,7,8-tetrahydropyrazolo[3,4-e][1,4]thiazepine;

3-chloro-4-[1-methyl-3-(2-pyridyl)-4,6,7,8-tetrahydropyrazolo[3,4-e][1,4]thiazepin-4-yl]benzoic;

6-[4-(2,4-dichlorophenyl)-1-methyl-4,6,7,8-tetrahydropyrazolo[3,4-e][1,4]-thiazepin-3-yl]pyridine-3-carboxylic acid;

1-[4-[1-methyl-3-(2-pyridyl)-4,6,7,8-tetrahydropyrazolo[3,4-e][1,4]thiazepin-4-yl]-1-piperidyl]ethanone;

5: (2-methyl-3-pyridyl)-[4-[1-methyl-3-(2-pyridyl)-4,6,7,8-tetrahydropyrazolo[3,4-e][1,4]thiazepin-4-yl]-1-piperidyl]methanone;

N-(2-methyl-3-pyridyl)-4-[1-methyl-3-(2-pyridyl)-4,6,7,8-tetrahydropyrazolo[3,4-e][1,4]thiazepin-4-yl]piperidine-1-carboxamide;

1-methyl-4-[2-methyl-4-(3-pyridylmethoxy)phenyl]-3-(2-pyridyl)-4,6,7,8-tetrahydropyrazolo[3,4-e][1,4]thiazepine;

1-methyl-4-[2-methyl-4-[(2-methyl-3-pyridyl)methoxy]phenyl]-3-(2-pyridyl)-4,6,7,8-tetrahydropyrazolo[3,4-e][1,4]thiazepine;

2-[4-(2,4-dichlorophenyl)-1-methyl-3-(2-pyridyl)-6,7-dihydro-4H-pyrazolo[3,4-e][1,4]thiazepin-8-yl]acetic acid;

2-[4-(2,4-dichlorophenyl)-1-methyl-3-(2-pyridyl)-6,7-dihydro-4H-pyrazolo[3,4-e][1,4]thiazepin-8-yl]acetamide;

4-(4-chloro-2-methyl-phenyl)-1-methyl-3-(6-methyl-2-pyridyl)-4,6,7,8-tetrahydropyrazolo[3,4-e][1,4]thiazepine;

[4-(4-chloro-2-methyl-phenyl)-1-methyl-4,6,7,8-tetrahydropyrazolo[3,4-e][1,4]thiazepin-3-yl]trifluoromethanesulfonate;

4-(4-chloro-2-vinyl-phenyl)-1-methyl-3-(2-pyridyl)-4,6,7,8-tetrahydropyrazolo-[3,4-e][1,4]thiazepine;

4-(4-chloro-2-ethyl-phenyl)-1-methyl-3-(2-pyridyl)-4,6,7,8-tetrahydropyrazolo-[3,4-e][1,4]thiazepine;

1-methyl-4-(2-methyl-4-methylsulfonyl-phenyl)-3-(2-pyridyl)-4,6,7,8-tetrahydro-pyrazolo[3,4-e][1,4]thiazepine;

4-(2,4-dichlorophenyl)-1-methyl-3-[(2S)-pyrrolidin-2-yl]-4,6,7,8-tetrahydropyrazolo[3,4-e][1,4]thiazepine;

4-(4-chloro-2-methyl-phenyl)-1-methyl-3-[(2S)-pyrrolidin-2-yl]-4,6,7,8-tetrahydropyrazolo[3,4-e][1,4]thiazepine;

2-[3-chloro-4-[1-methyl-3-(2-pyridyl)-4,6,7,8-tetrahydropyrazolo[3,4-e][1,4]thiazepin-4-yl]phenyl]propan-2-ol;

4-(2-chlorophenyl)-1-methyl-3-(2-pyridyl)-4,6,7,8-tetrahydropyrazolo[3,4-e][1,4]thiazepine;

4-(2-chloro-4-methyl-phenyl)-1-methyl-3-(2-pyridyl)-4,6,7,8-tetrahydropyrazolo[3,4-e][1,4]thiazepine;

4-(2,4-dichlorophenyl)-1,3,6,6,8-pentamethyl-4H-pyrazolo[3,4-e][1,4]thiazepin-7-one;

4-(2,4-dichlorophenyl)-1,3,6,6-tetramethyl-4,7-dihydropyrazolo[3,4-e][1,4]thiazepine-8-carbaldehyde;

3-[4-(2,4-dichlorophenyl)-1,3,6,6-tetramethyl-4,7-dihydropyrazolo[3,4-e][1,4]thiazepin-8-yl]-1,1,1-trifluoro-propan-2-ol;

3-[4-(2,4-dichlorophenyl)-3,6,6-trimethyl-7,8-dihydro-4H-pyrazolo[3,4-e][1,4]thiazepin-1-yl]-1,1,1-trifluoro-propan-2-ol;

3-[4-(2,4-dichlorophenyl)-3,6,6-trimethyl-7,8-dihydro-4H-pyrazolo[3,4-e][1,4]thiazepin-2-yl]-1,1,1-trifluoro-propan-2-ol;

4-(2,4-dichlorophenyl)-1,3,6,6,8-pentamethyl-4,7-dihydropyrazolo[3,4-e][1,4]thiazepine hydrochloride;

4-(4-chloro-2-methyl-phenyl)-1-methyl-3-(2-pyridyl)-4,8-dihydropyrazolo[3,4-e][1,4]thiazepin-7-one;

4-(2,4-dichlorophenyl)-1,3,6,6-tetramethyl-4,8-dihydropyrazolo[3,4-e][1,4]thiazepin-7-one;

4-(4-bromo-2-methylphenyl)-1-ethyl-3-(pyrimidin-4-yl)-4,6,7,8-tetrahydro-1H-pyrazolo[3,4-e][1,4]thiazepine;

4-(1-(4-fluorophenyl)-6-methyl-1H-indazol-5-yl)-1-methyl-3-(pyridin-2-yl)-4,6,7,8-tetrahydro-1H-pyrazolo[3,4-e][1,4]thiazepine;

methyl 4-(1,7-dimethyl-3-(pyridin-2-yl)-4,6,7,8-tetrahydro-1H-pyrazolo[3,4-e][1,4]thiazepin-4-yl)-3-methylbenzoate;

3-cyano-4-((4R,7R)-1,7-dimethyl-3-(pyridin-2-yl)-4,6,7,8-tetrahydro-1H-pyrazolo[3,4-e][1,4]thiazepin-4-yl)-N-(2-methylpyridin-3-yl)benzamide;

(R)-3-methyl-4-(1-methyl-3-(pyridin-2-yl)-4,6,7,8-tetrahydro-1H-pyrazolo[3,4-e][1,4]thiazepin-4-yl)benzonitrile;

(S)-3-methyl-4-(1-methyl-3-(pyridin-2-yl)-4,6,7,8-tetrahydro-1H-pyrazolo[3,4-e][1,4]thiazepin-4-yl)benzonitrile;

(S)-4-(1-ethyl-3-(pyridin-2-yl)-4,6,7,8-tetrahydro-1H-pyrazolo[3,4-e][1,4]thiazepin-4-yl)-3-methylbenzonitrile;

2-(4-((4S,7R)-1,7-dimethyl-3-(pyridin-2-yl)-4,6,7,8-tetrahydro-1H-pyrazolo[3,4-e][1,4]thiazepin-4-yl)-3-methylphenoxy)acetonitrile;

2-(4-((4S,7R)-1,7-dimethyl-3-(pyridin-2-yl)-4,6,7,8-tetrahydro-1H-pyrazolo[3,4-e][1,4]thiazepin-4-yl)-3-methylphenoxy)acetamide;

3-(4-((4R,7S)-1-ethyl-7-methyl-3-(pyridin-2-yl)-4,6,7,8-tetrahydro-1H-pyrazolo[3,4-e][1,4]thiazepin-4-yl)-3-methylphenyl)prop-2-yn-1-ol;

3-(4-((4R,7R)-1-ethyl-7-methyl-3-(pyridin-2-yl)-4,6,7,8-tetrahydro-1H-pyrazolo[3,4-e][1,4]thiazepin-4-yl)-3-methylphenyl)prop-2-yn-1-ol;

3-(4-((4S,7R)-1-ethyl-7-methyl-3-(pyridin-2-yl)-4,6,7,8-tetrahydro-1H-pyrazolo[3,4-e][1,4]thiazepin-4-yl)-3-methylphenyl)prop-2-yn-1-ol;

3-(4-((4S,7S)-1-ethyl-7-methyl-3-(pyridin-2-yl)-4,6,7,8-tetrahydro-1H-pyrazolo[3,4-e][1,4]thiazepin-4-yl)-3-methylphenyl)prop-2-yn-1-ol;

4-(4-((4R,7S)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-ol;

4-(4-((4R,7R)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-ol;

4-(4-((4S,7R)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-ol;

4-(4-((4S,7S)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-ol;

3-(4-((4R,7S)-1-ethyl-7-methyl-3-(pyridin-2-yl)-4,6,7,8-tetrahydro-1H-pyrazolo[3,4-e][1,4]thiazepin-4-yl)-3-methylphenyl)propan-1-ol;

3-(4-((4R,7R)-1-ethyl-7-methyl-3-(pyridin-2-yl)-4,6,7,8-tetrahydro-1H-pyrazolo[3,4-e][1,4]thiazepin-4-yl)-3-methylphenyl)propan-1-ol;

3-(4-((4S,7R)-1-ethyl-7-methyl-3-(pyridin-2-yl)-4,6,7,8-tetrahydro-1H-pyrazolo[3,4-e][1,4]thiazepin-4-yl)-3-methylphenyl)propan-1-ol;

3-(4-((4S,7S)-1-ethyl-7-methyl-3-(pyridin-2-yl)-4,6,7,8-tetrahydro-1H-pyrazolo[3,4-e][1,4]thiazepin-4-yl)-3-methylphenyl)propan-1-ol;

4-(4-((4R,7S)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-ol;

4-(4-((4R,7R)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-ol;

4-(4-((4S,7S)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-ol;

4-(4-((4S,7R)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-ol;

4-(4-((4R,7S)-1,7-dimethyl-3-(pyridin-2-yl)-4,6,7,8-tetrahydro-1H-pyrazolo[3,4-e][1,4]thiazepin-4-yl)-3-methylphenyl)-2-methylbutan-2-ol;

4-(4-((4S,7S)-1,7-dimethyl-3-(pyridin-2-yl)-4,6,7,8-tetrahydro-1H-pyrazolo[3,4-e][1,4]thiazepin-4-yl)-3-methylphenyl)-2-methylbutan-2-ol;
4-(4-((4R,7R)-1,7-dimethyl-3-(pyridin-2-yl)-4,6,7,8-tetrahydro-1H-pyrazolo[3,4-e][1,4]thiazepin-4-yl)-3-methylphenyl)-2-methylbutan-2-ol;
4-(4-((4S,7R)-1,7-dimethyl-3-(pyridin-2-yl)-4,6,7,8-tetrahydro-1H-pyrazolo[3,4-e][1,4]thiazepin-4-yl)-3-methylphenyl)-2-methylbutan-2-ol;
4-((4R,7S)-1-ethyl-7-methyl-3-(pyridin-2-yl)-4,6,7,8-tetrahydro-1H-pyrazolo[3,4-e][1,4]thiazepin-4-yl)-3-methylbenzamide;
4-((4S,7R)-1-ethyl-7-methyl-3-(pyridin-2-yl)-4,6,7,8-tetrahydro-1H-pyrazolo[3,4-e][1,4]thiazepin-4-yl)-3-methylbenzamide;
4-((4R,7R)-1-ethyl-7-methyl-3-(pyridin-2-yl)-4,6,7,8-tetrahydro-1H-pyrazolo[3,4-e][1,4]thiazepin-4-yl)-3-methylbenzamide;
4-((4S,7S)-1-ethyl-7-methyl-3-(pyridin-2-yl)-4,6,7,8-tetrahydro-1H-pyrazolo[3,4-e][1,4]thiazepin-4-yl)-3-methylbenzamide;
3-(4-((4R,7S)-1,7-dimethyl-3-(pyridin-2-yl)-4,6,7,8-tetrahydro-1H-pyrazolo[3,4-e][1,4]thiazepin-4-yl)-3-methylphenyl)propan-1-ol;
3-(4-((4R,7R)-1,7-dimethyl-3-(pyridin-2-yl)-4,6,7,8-tetrahydro-1H-pyrazolo[3,4-e][1,4]thiazepin-4-yl)-3-methylphenyl)propan-1-ol;
3-(4-((4S,7R)-1,7-dimethyl-3-(pyridin-2-yl)-4,6,7,8-tetrahydro-1H-pyrazolo[3,4-e][1,4]thiazepin-4-yl)-3-methylphenyl)propan-1-ol;
3-(4-((4S,7S)-1,7-dimethyl-3-(pyridin-2-yl)-4,6,7,8-tetrahydro-1H-pyrazolo[3,4-e][1,4]thiazepin-4-yl)-3-methylphenyl)propan-1-ol;
4-(4-((4R,7S)-1,7-dimethyl-3-(pyridin-2-yl)-4,6,7,8-tetrahydro-1H-pyrazolo[3,4-e][1,4]thiazepin-4-yl)-3-methylphenyl)but-3-yn-1-ol;
4-(4-((4S,7S)-1,7-dimethyl-3-(pyridin-2-yl)-4,6,7,8-tetrahydro-1H-pyrazolo[3,4-e][1,4]thiazepin-4-yl)-3-methylphenyl)but-3-yn-1-ol;
4-(4-((4S,7R)-1,7-dimethyl-3-(pyridin-2-yl)-4,6,7,8-tetrahydro-1H-pyrazolo[3,4-e][1,4]thiazepin-4-yl)-3-methylphenyl)but-3-yn-1-ol;
4-(4-((4R,7R)-1,7-dimethyl-3-(pyridin-2-yl)-4,6,7,8-tetrahydro-1H-pyrazolo[3,4-e][1,4]thiazepin-4-yl)-3-methylphenyl)but-3-yn-1-ol;
4-((4S,7R)-1,7-dimethyl-3-(pyrimidin-4-yl)-4,6,7,8-tetrahydro-1H-pyrazolo[3,4-e][1,4]thiazepin-4-yl)-3-methyl-N-(2-methylpyridin-3-yl)benzamide;
4-((4S,7S)-1,7-dimethyl-3-(pyrimidin-4-yl)-4,6,7,8-tetrahydro-1H-pyrazolo[3,4-e][1,4]thiazepin-4-yl)-3-methyl-N-(2-methylpyridin-3-yl)benzamide;
4-((4R,7S)-1,7-dimethyl-3-(pyrimidin-4-yl)-4,6,7,8-tetrahydro-1H-pyrazolo[3,4-e][1,4]thiazepin-4-yl)-3-methyl-N-(2-methylpyridin-3-yl)benzamide;
4-((4R,7R)-1,7-dimethyl-3-(pyrimidin-4-yl)-4,6,7,8-tetrahydro-1H-pyrazolo[3,4-e][1,4]thiazepin-4-yl)-3-methyl-N-(2-methylpyridin-3-yl)benzamide;
(R)-4-(1-ethyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide;
(S)-4-(1-ethyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide;
2-((4R,7R)-4-(4-bromo-2-methylphenyl)-1,7-dimethyl-4,6,7,8-tetrahydro-1H-pyrazolo[3,4-e][1,4]thiazepin-3-yl)-1,3,4-oxadiazole;
2-((4S,7S)-4-(4-bromo-2-methylphenyl)-1,7-dimethyl-4,6,7,8-tetrahydro-1H-pyrazolo[3,4-e][1,4]thiazepin-3-yl)-1,3,4-oxadiazole;
2-((4R,7R)-4-(4-bromo-2-methylphenyl)-1,7-dimethyl-4,6,7,8-tetrahydro-1H-pyrazolo[3,4-e][1,4]thiazepin-3-yl)-1,3,4-oxadiazole;
2-((4S,7S)-4-(4-bromo-2-methylphenyl)-1,7-dimethyl-4,6,7,8-tetrahydro-1H-pyrazolo[3,4-e][1,4]thiazepin-3-yl)-1,3,4-oxadiazole;
3-(4-((4R,7S)-1-ethyl-7-methyl-3-(pyridin-2-yl)-4,6,7,8-tetrahydro-1H-pyrazolo[3,4-e][1,4]thiazepin-4-yl)-3-methylphenyl)-N,N-dimethylprop-2-yn-1-amine;
3-(4-((4R,7S)-1-ethyl-7-methyl-3-(pyridin-2-yl)-4,6,7,8-tetrahydro-1H-pyrazolo[3,4-e][1,4]thiazepin-4-yl)-3-methylphenyl)-N,N-dimethylprop-2-yn-1-amine;
4-(4-((4S,7S)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-amine;
4-(4-((4S,7R)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-amine;
(R)-4-(1-ethyl-3-(pyridin-2-yl)-4,6,7,8-tetrahydro-1H-pyrazolo[3,4-e][1,4]thiazepin-4-yl)-N-(2-methylpyridin-3-yl)-3-(trifluoromethyl)benzamide;
3-(4-((4R,7R)-1,7-dimethyl-3-(pyridin-2-yl)-4,6,7,8-tetrahydro-1H-pyrazolo[3,4-e][1,4]thiazepin-4-yl)-3-methylphenyl)prop-2-yn-1-ol;
3-(4-((4S,7R)-1,7-dimethyl-3-(pyridin-2-yl)-4,6,7,8-tetrahydro-1H-pyrazolo[3,4-e][1,4]thiazepin-4-yl)-3-methylphenyl)prop-2-yn-1-ol;
3-(4-((4S,7S)-1,7-dimethyl-3-(pyridin-2-yl)-4,6,7,8-tetrahydro-1H-pyrazolo[3,4-e][1,4]thiazepin-4-yl)-3-methylphenyl)prop-2-yn-1-ol;
4-(1,3-dimethyl-7-oxo-1,4,5,6,7,8-hexahydropyrazolo[3,4-b]azepin-4-yl)-3-methyl-N-(2-methylpyridin-3-yl)benzam;
4-(4-((4R,7R)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-amine;
4-(4-((4S,7S)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-amine;
4-(1-ethyl-3-(pyridin-2-yl)-4,6,7,8-tetrahydro-1H-pyrazolo[3,4-e][1,4]thiazepin-4-yl)-3-methyl-N-(3-methylisoxazol-5-yl)benzamide;
4-(1-ethyl-3-(pyridin-2-yl)-4,6,7,8-tetrahydro-1H-pyrazolo[3,4-e][1,4]thiazepin-4-yl)-3-methyl-N-(1-methyl-1H-pyrazol-5-yl)benzamide;
N-(1,3-dimethyl-1H-pyrazol-5-yl)-4-(1-ethyl-3-(pyridin-2-yl)-4,6,7,8-tetrahydro-1H-pyrazolo[3,4-e][1,4]thiazepin-4-yl)-3-methylbenzamide;
4-(1-ethyl-3-(pyridin-2-yl)-4,6,7,8-tetrahydro-1H-pyrazolo[3,4-e][1,4]thiazepin-4-yl)-3-methyl-N-(1,3,4-thiadiazol-2-yl)benzamide;
4-(1-ethyl-3-(pyridin-2-yl)-4,6,7,8-tetrahydro-1H-pyrazolo[3,4-e][1,4]thiazepin-4-yl)-3-methyl-N-(5-methyl-1,3,4-thiadiazol-2-yl)benzamide;
4-(1-ethyl-3-(pyridin-2-yl)-4,6,7,8-tetrahydro-1H-pyrazolo[3,4-e][1,4]thiazepin-4-yl)-3-methyl-N-(4H-1,2,4-triazol-3-yl)benzamide;
4-(1-ethyl-3-(pyridin-2-yl)-4,6,7,8-tetrahydro-1H-pyrazolo[3,4-e][1,4]thiazepin-4-yl)-3-methyl-N-(1H-tetrazol-5-yl)benzamide;
N-(4-cyano-3-methylisoxazol-5-yl)-4-(1-ethyl-3-(pyridin-2-yl)-4,6,7,8-tetrahydro-1H-pyrazolo[3,4-e][1,4]thiazepin-4-yl)-3-methylbenzamide;

N-(4-cyano-1H-pyrazol-3-yl)-4-(1-ethyl-3-(pyridin-2-yl)-4,6,7,8-tetrahydro-1H-pyrazolo[3,4-e][1,4]thiazepin-4-yl)-3-methylbenzamide;

N-(4-cyano-5-methyl-1H-pyrazol-3-yl)-4-(1-ethyl-3-(pyridin-2-yl)-4,6,7,8-tetrahydro-1H-pyrazolo[3,4-e][1,4]thiazepin-4-yl)-3-methylbenzamide;

N-(2-chloropyridin-3-yl)-4-(1-ethyl-3-(pyridin-2-yl)-4,6,7,8-tetrahydro-1H-pyrazolo[3,4-e][1,4]thiazepin-4-yl)-3-methylbenzamide;

4-(2-chloro-4-(5-(methylsulfonyl)pyridin-3-yl)phenyl)-1-methyl-3-(pyridin-2-yl)-4,6,7,8-tetrahydro-1H-pyrazolo[3,4-e][1,4]thiazepine;

4-(2-chloro-4-(pyrimidin-5-yl)phenyl)-1-methyl-3-(pyridin-2-yl)-4,6,7,8-tetrahydro-1H-pyrazolo[3,4-e][1,4]thiazepine;

4-(2-chloro-4-(pyridazin-4-yl)phenyl)-1-methyl-3-(pyridin-2-yl)-4,6,7,8-tetrahydro-1H-pyrazolo[3,4-e][1,4]thiazepine;

5-(3-chloro-4-(1-methyl-3-(pyridin-2-yl)-4,6,7,8-tetrahydro-1H-pyrazolo[3,4-e][1,4]thiazepin-4-yl)phenyl)nicotinonitrile;

(2-(4-(3-chloro-4-(1-methyl-3-(pyridin-2-yl)-4,6,7,8-tetrahydro-1H-pyrazolo[3,4-e][1,4]thiazepin-4-yl)phenyl)-1H-pyrazol-1-yl)ethyl)morpholine;

4-(2-chloro-4-(1-(tetrahydro-2H-pyran-2-yl)-1H-pyrazol-4-yl)phenyl)-1-methyl-3-(pyridin-2-yl)-4,6,7,8-tetrahydro-1H-pyrazolo[3,4-e][1,4]thiazepine;

5-(3-chloro-4-(1-methyl-3-(pyridin-2-yl)-4,6,7,8-tetrahydro-1H-pyrazolo[3,4-e][1,4]thiazepin-4-yl)phenyl)nicotinamide;

5-(3-chloro-4-(1-methyl-3-(pyridin-2-yl)-4,6,7,8-tetrahydro-1H-pyrazolo[3,4-e][1,4]thiazepin-4-yl)phenyl)-N-methylnicotinamide;

4-(3-chloro-4-(1-methyl-3-(pyridin-2-yl)-4,6,7,8-tetrahydro-1H-pyrazolo[3,4-e][1,4]thiazepin-4-yl)phenyl)nicotinonitrile;

3-(3-chloro-4-(1-methyl-3-(pyridin-2-yl)-4,6,7,8-tetrahydro-1H-pyrazolo[3,4-e][1,4]thiazepin-4-yl)phenyl)isonicotinonitrile;

4-(2-chloro-4-(pyrido[2,3-b]pyrazin-7-yl)phenyl)-1-methyl-3-(pyridin-2-yl)-4,6,7,8-tetrahydro-1H-pyrazolo[3,4-e][1,4]thiazepine;

(5-(3-chloro-4-(1-methyl-3-(pyridin-2-yl)-4,6,7,8-tetrahydro-1H-pyrazolo[3,4-e][1,4]thiazepin-4-yl)phenyl)pyridin-3-yl)(morpholino)methanone;

4-(2-chloro-4-(6-(methylsulfonyl)pyridin-3-yl)phenyl)-1-methyl-3-(pyridin-2-yl)-4,6,7,8-tetrahydro-1H-pyrazolo[3,4-e][1,4]thiazepine;

1-(4-(5-(3-chloro-4-(1-methyl-3-(pyridin-2-yl)-4,6,7,8-tetrahydro-1H-pyrazolo[3,4-e][1,4]thiazepin-4-yl)phenyl)pyridin-2-yl)piperazin-1-yl)ethanone;

4-(2-chloro-4-(1-(2-methoxyethyl)-1H-pyrazol-4-yl)phenyl)-1-methyl-3-(pyridin-2-yl)-4,6,7,8-tetrahydro-1H-pyrazolo[3,4-e][1,4]thiazepine;

3-(4-(3-chloro-4-(1-methyl-3-(pyridin-2-yl)-4,6,7,8-tetrahydro-1H-pyrazolo[3,4-e][1,4]thiazepin-4-yl)phenyl)-1H-pyrazol-1-yl)propanenitrile;

2-(4-(3-chloro-4-(1-methyl-3-(pyridin-2-yl)-4,6,7,8-tetrahydro-1H-pyrazolo[3,4-e][1,4]thiazepin-4-yl)phenyl)-1H-pyrazol-1-yl)acetamide;

3-(4-(3-chloro-4-(1-methyl-3-(pyridin-2-yl)-4,6,7,8-tetrahydro-1H-pyrazolo[3,4-e][1,4]thiazepin-4-yl)phenyl)-1H-pyrazol-1-yl)propanamide;

4-(5-(3-chloro-4-(1-methyl-3-(pyridin-2-yl)-4,6,7,8-tetrahydro-1H-pyrazolo[3,4-e][1,4]thiazepin-4-yl)phenyl)pyrimidin-2-yl)morpholine;

4-(4-bromo-2-methylphenyl)-1-ethyl-3-(pyridin-2-yl)-4,5,6,8-tetrahydropyrazolo[3,4-b]azepin-7(1H)-one;

4-(4-bromo-2-methylphenyl)-1,3-dimethyl-4,5,6,8-tetrahydropyrazolo[3,4-b]azepin-7(1H)-one;

4-(4-bromo-2-methylphenyl)-1-ethyl-3-(pyridin-2-yl)-1,4,5,6,7,8-hexahydropyrazolo[3,4-b]azepine;

4-(4-bromophenyl)-1-ethyl-3-(pyridin-2-yl)-1,4,5,6,7,8-hexahydropyrazolo[3,4-b]azepine;

rac-2-((4S,6S,7R)-4-(4-chloro-2-methylphenyl)-1,3,7-trimethyl-4,6,7,8-tetrahydro-1H-pyrazolo[3,4-e][1,4]thiazepin-6-yl)ethanol;

2-((4R,6R,7S)-4-(4-chloro-2-methylphenyl)-1,3,7-trimethyl-4,6,7,8-tetrahydro-1H-pyrazolo[3,4-e][1,4]thiazepin-6-yl)ethanol;

rac-(4R,7R)-4-(4-bromo-2-methylphenyl)-1-methyl-3-(pyridin-2-yl)-7-(trifluoromethyl)-4,6,7,8-tetrahydro-1H-pyrazolo[3,4-e][1,4]thiazepine;

rac-(4R,7S)-4-(4-bromo-2-methylphenyl)-1-methyl-3-(pyridin-2-yl)-7-(trifluoromethyl)-4,6,7,8-tetrahydro-1H-pyrazolo[3,4-e][1,4]thiazepine;

rac-(4R,7S)-4-(4-bromo-2-methylphenyl)-1-methyl-3-(pyridin-2-yl)-4,6,7,8-tetrahydro-1H-pyrazolo[3,4-e][1,4]thiazepine-7-carboxamide;

rac-(4R,7S)-4-(4-bromo-2-methylphenyl)-1-methyl-3-(pyridin-2-yl)-4,6,7,8-tetrahydro-1H-pyrazolo[3,4-e][1,4]thiazepine-7-carbonitrile;

rac-2-((4R,7S)-4-(4-bromo-2-methylphenyl)-1-methyl-3-(pyridin-2-yl)-4,6,7,8-tetrahydro-1H-pyrazolo[3,4-e][1,4]thiazepin-7-yl)acetonitrile;

4-((4S,7R)-7-(hydroxymethyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide;

4-((4R,7S)-7-(hydroxymethyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide;

rac-4-(1-(4-fluorophenyl)-6-methyl-1H-indazol-5-yl)-1-methyl-3-(pyridin-2-yl)-6,8-dihydro-1H-pyrazolo[3,4-e][1,4]thiazepin-7(4H)-one;

1-methyl-4-(6-methyl-1-(2-methylpyridin-4-yl)-1H-indazol-5-yl)-3-(pyridin-2-yl)-6,8-dihydro-1H-pyrazolo[3,4-e][1,4]thiazepin-7(4H)-one;

4-(1-(4-fluorophenyl)-6-methyl-1H-indazol-5-yl)-1-methyl-3-(pyridin-2-yl)-6,8-dihydro-1H-pyrazolo[3,4-e][1,4]thiazepin-7(4H)-one;

4-(6-chloro-1-(2-methylpyridin-4-yl)-1H-indazol-5-yl)-1-methyl-3-(pyridin-2-yl)-6,8-dihydro-1H-pyrazolo[3,4-e][1,4]thiazepin-7(4H)-one;

1-methyl-4-(1-(2-methylpyridin-4-yl)-1H-indazol-5-yl)-3-(pyridin-2-yl)-6,8-dihydro-1H-pyrazolo[3,4-e][1,4]thiazepin-7(4H)-one;

4-(6-chloro-1-(4-fluorophenyl)-1H-indazol-5-yl)-1-methyl-3-(pyridin-2-yl)-6,8-dihydro-1H-pyrazolo[3,4-e][1,4]thiazepin-7(4H)-one;

4-(1-(4-fluorophenyl)-1H-indazol-5-yl)-1-methyl-3-(pyridin-2-yl)-6,8-dihydro-1H-pyrazolo[3,4-e][1,4]thiazepin-7(4H)-one;

4-(6-fluoro-1-(2-methylpyridin-4-yl)-1H-indazol-5-yl)-1-methyl-3-(pyridin-2-yl)-6,8-dihydro-1H-pyrazolo[3,4-e][1,4]thiazepin-7(4H)-one;

4-(6-fluoro-1-(4-fluorophenyl)-1H-indazol-5-yl)-1-methyl-3-(pyridin-2-yl)-6,8-dihydro-1H-pyrazolo[3,4-e][1,4]thiazepin-7(4H)-one;

1-methyl-4-(1-(2-methylpyridin-4-yl)-6-(trifluoromethyl)-1H-indazol-5-yl)-3-(pyridin-2-yl)-6,8-dihydro-1H-pyrazolo[3,4-e][1,4]thiazepin-7(4H)-one;

4-(1-(4-fluorophenyl)-6-(trifluoromethyl)-1H-indazol-5-yl)-1-methyl-3-(pyridin-2-yl)-6,8-dihydro-1H-pyrazolo[3,4-e][1,4]thiazepin-7(4H)-one;

1-ethyl-4-(6-methyl-1-(2-methylpyridin-4-yl)-1H-indazol-5-yl)-3-(pyridin-2-yl)-6,8-dihydro-1H-pyrazolo[3,4-e][1,4]thiazepin-7(4H)-one;

4-(6-chloro-1-(2-methylpyridin-4-yl)-1H-indazol-5-yl)-1-ethyl-3-(pyridin-2-yl)-6,8-dihydro-1H-pyrazolo[3,4-e][1,4]thiazepin-7(4H)-one;

1-ethyl-4-(1-(2-methylpyridin-4-yl)-1H-indazol-5-yl)-3-(pyridin-2-yl)-6,8-dihydro-1H-pyrazolo[3,4-e][1,4]thiazepin-7(4H)-one;

1-ethyl-4-(6-fluoro-1-(2-methylpyridin-4-yl)-1H-indazol-5-yl)-3-(pyridin-2-yl)-6,8-dihydro-1H-pyrazolo[3,4-e][1,4]thiazepin-7(4H)-one;

1-ethyl-4-(1-(2-methylpyridin-4-yl)-6-(trifluoromethyl)-1H-indazol-5-yl)-3-(pyridin-2-yl)-6,8-dihydro-1H-pyrazolo[3,4-e][1,4]thiazepin-7(4H)-one;

1-ethyl-4-(1-(4-fluorophenyl)-6-methyl-1H-indazol-5-yl)-3-(pyridin-2-yl)-6,8-dihydro-1H-pyrazolo[3,4-e][1,4]thiazepin-7(4H)-one;

(Z)-3-(1-aminobuta-1,3-dien-1-yl)-4-(6-chloro-1-(4-fluorophenyl)-1H-indazol-5-yl)-1-ethyl-6,8-dihydro-1H-pyrazolo[3,4-e][1,4]thiazepin-7(4H)-one;

(Z)-3-(1-aminobuta-1,3-dien-1-yl)-1-ethyl-4-(1-(4-fluorophenyl)-1H-indazol-5-yl)-6,8-dihydro-1H-pyrazolo[3,4-e][1,4]thiazepin-7(4H)-one;

1-ethyl-4-(6-fluoro-1-(4-fluorophenyl)-1H-indazol-5-yl)-3-(pyridin-2-yl)-6,8-dihydro-1H-pyrazolo[3,4-e][1,4]thiazepin-7(4H)-one;

1-ethyl-4-(1-(4-fluorophenyl)-6-(trifluoromethyl)-1H-indazol-5-yl)-3-(pyridin-2-yl)-6,8-dihydro-1H-pyrazolo[3,4-e][1,4]thiazepin-7(4H)-one;

rac-4-((4R,7R)-7-hydroxy-1-methyl-3-(pyridin-2-yl)-7-(trifluoromethyl)-1,4,5,6,7,8-hexahydrocyclohepta[c]pyrazol-4-yl)-3-methyl-N-(2-methylpyridin-3-yl)benzamide;

4-(4-chloro-2-methyl-phenyl)-1-methyl-3-(2-pyridyl)-4,8-dihydropyrazolo[3,4-e][1,4]thiazepin-7-one; or rac-4-((4R,7S)-7-hydroxy-1-methyl-3-(pyridin-2-yl)-7-(trifluoromethyl)-1,4,5,6,7,8-hexahydrocyclohepta[c]pyrazol-4-yl)-3-methyl-N-(2-methylpyridin-3-yl)benzamide.

In a seventeenth embodiment the invention provides a pharmaceutical composition comprising a compound according to any of the foregoing embodiments, and a pharmaceutically acceptable carrier or excipient.

In an eighteenth embodiment the invention provides a method of treating a disease or condition comprising administering a therapeutically effective amount of a compound of any of the foregoing embodiments, or a pharmaceutical composition according to the seventeenth embodiment.

In a nineteenth embodiment the invention provides a method of treating a disease or condition comprising administering a pharmaceutical composition according to any of the foregoing embodiments.

In a twentieth embodiment the invention provides a method according to any of the foregoing embodiments, wherein the disease or condition to be treated is acquired immunodeficiency syndrome (AIDS), acute adrenal insufficiency, addiction, Addison's Disease, adrenal function, age-related macular degeneration, allergic rhinitis, allergies, Alzheimer's, anorexia, angioneurotic edema, ankylosing spondylitis, anxiety, asthma, atopic dermatitis, auto-immunity, autoimmune chronic active hepatitis, autoimmune diseases, blepharitis, bursitis, cachexia, cardiovascular disease, cerebral edema, choroidal neovascularization due to age-related macular degeneration, chronic kidney disease, chronic obstructive pulmonary disease, chronic primary adrenal insufficiency, chronic retinal detachment, compulsive behavior, congenital adrenal hyperplasia, cognitive dysfunction, conjunctivitis, cirrhosis, Crohn's disease, Cushing's syndrome, depression, diabetes, diabetes mellitus, diabetic microangiopathy, diabetic neuropathy, diabetic retinopathy, dry eye syndrome, frailty, giant cell arteritis, glaucoma, granulomatous polyarteritis, hay fever, hepatitis, HPA axis suppression and regulation, human immunodeficiency virus (HIV), hypercalcemia, hypercortisolemia, hypergylcemia, hypertension, immune proliferation/apoptosis, immunodeficiency, immunomodulation, inflammation, inflammation of the eye, inflammatory bowel disease, inhibition of myeloid cell lines, insulin dependent diabetes mellitus, insulin-dependent diabetes mellitus glaucoma, insulin resistance, iridocyclitis, juvenile idiopathic arthritis, juvenile rheumatoid arthritis, leukemia, Little's syndrome, lupus, lymphoma, macular degeneration, macular edema, a malignancy, medical catabolism, multi-drug resistance, multiple sclerosis, neurodgeneration, obesity, ocular or macular edema, ocular neovascular disease, organ transplantation, modulation of the Th1/Th2 cytokine balance, optic neuritis, optic pits, neuropathy, osteoarthritis, osteoporosis, Parkinson's, plaque psoriasis, polyarteritis nodosa, polymyalgia rheumatica, post-laser treatment complications, post-surgical bone fracture, post-traumatic stress syndrome, prevention of muscle frailty, psoriasis, psoriatic arthritis, psychosis, regulation of carbohydrate, protein and lipid metabolism, regulation of electrolyte and water balance, regulation of functions of the cardiovascular, kidney, central nervous, immune, or skeletal muscle systems, retinopathy of prematurity, rheumatic fever, rheumatoid arthritis, rhinitis, scleritis, secondary adrenal insufficiency, stroke and spinal cord injury, sympathetic ophthalmia, systemic lupus erythematosus, Syndrome X, tendonitis, thrombocytopenia, tissue rejection, ulcerative colitis, urticaria, uveitis, viral infection, or Wegener's granulomatosis or wound healing.

In a twenty-first embodiment the invention provides a method according to any of the foregoing embodiment, wherein the disease or condition to be treated is age-related macular degeneration, ankylosing spondylitis, atopic dermatitis, Crohn's disease, dry eye syndrome, giant cell arteritis, inflammatory bowel disease, juvenile idiopathic arthritis, juvenile rheumatoid arthritis, lupus, macular edema, plaque psoriasis, psoriasis, polymyalgia rheumatica, psoriatic arthritis, rheumatoid arthritis, ulcerative colitis, or uveitis.

DETAILED DESCRIPTION OF THE INVENTION

The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFK-B. Such interactions result in inhibition of API- and NFK-B-mediated transcription and are believed to be responsible for some of the anti-inflammatory activity of endogenously administered glucocorticoids. In addition, glucocorticoids may also exert physiologic effects independent of nuclear transcription. Biologically relevant glucocorticoid receptor agonists include Cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU486 is an example of a non-selective glucocorticoid receptor antagonist.

Although there are glucocorticoid receptor therapies in the art, there is a continuing need for and a continuing search in this field of art for selective glucocorticoid receptor therapies. Thus, the identification of non-steroidal compounds which have specificity for one or more steroid receptors, but which have reduced or no cross-reactivity for other steroid or intracellular receptors, is of significant value in this field.

Many autoimmune diseases and disease associated with chronic inflammation, as well as acute responses, have been linked to excessive or unregulated production or activity of one or more cytokines.

The compounds of the invention are also useful in the treatment of rheumatoid arthritis, ankylosing spondilitis, a solid tumor, a sarcoma, fibrosarcoma, osteoma, melanoma, retinoblastoma, an ocular disease, a cancer, a rhabdomyosarcoma, glioblastoma, neuroblastoma, teratocarcinoma, hypersensitivity reactions, hyperkinetic movement disorders, hypersensitivity pneumonitis, hypertension, hypokinetic movement disorders, aortic and peripheral aneuryisms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile spinal muscular atrophy, lymphoma, myeloma, leukaemia, malignant ascites, hematopoietic cancers, a diabetic condition such as insulin-dependent diabetes mellitus glaucoma, diabetic retinopathy or microangiopathy, sickle cell anaemia, chronic inflammation, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, progressive supranucleo palsy, primary pulmonary hypertension, radiation therapy, Raynaud's phenomenon, Raynaud's disease, Refsum's disease, regular narrow QRS tachycardia, renovascular hypertension, restrictive cardiomyopathy, sarcoma, senile chorea, senile dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, diabetes, diabetes mellitus, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia greata, seronegative arthropathy, arthropathy, Reiter's disease, psoriatic arthropathy, ulcerative colitic arthropathy, enteropathic synovitis, chlamydia, *yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, His bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, *pneumocystis carinii* pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, post-infectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthritis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Compounds of Formula (I) of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the compounds of this invention. Non-limiting examples of therapeutic agents for rheumatoid arthritis with which a compound of Formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (U.S. Pat. No. 6,090,382, HUMIRA™), CA2 (REMICADE™), SIMPONI™ (golimumab), CIMZIA™, ACTEMRA™, CDP 571, and soluble p55 or p75 TNF receptors, derivatives, thereof, p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I) of the invention may also be combined with agents, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adenssosine agonists, antithrombotic agents, complement inhibitors, adrenergic agents, agents which interfere with signaling by pro-inflammatory cytokines such as TNFα or IL-1 (e.g., NIK, IKK, p38 or MAP kinase inhibitors), IL-1β converting enzyme inhibitors, T-cell signaling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™) and p55TNFRIgG (Lenercept), sIL-1RI, sIL-1RII, sIL-6R), anti-inflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/ misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/ chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as Fingolimod), and Mesopram. Preferred combinations include methotrexate or leflunomide and in moderate or severe rheumatoid arthritis cases, cyclosporin and anti-TNF antibodies as noted above.

Non-limiting examples of therapeutic agents for inflammatory bowel disease with which a compound of Formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signaling by pro-inflammatory cytokines such as TNFα or IL-1 (e.g. NIK, IKK, or MAP kinase inhibitors); IL-1β converting enzyme inhibitors; TNFα converting enzyme inhibitors; T-cell signaling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and anti-inflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (U.S. Pat. No. 6,090,382, HUMIRA™), CA2 (REMICADE™), CDP 571, TNFR-Ig constructs, (p75TNFRIgG (ENBREL™) and p55TNFRIgG (LENERCEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of pro-inflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-1F (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by pro-inflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and anti-inflammatory cytokines (e.g. IL-4, IL-10, IL-13 and TGFβ).

Preferred examples of therapeutic agents for multiple sclerosis in which a compound of Formula (I) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of Formula (I) may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™)

Non-limiting examples of therapeutic agents for psoriasis with which a compound of Formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (U.S. Pat. No. 6,090,382, HUMIRA™), and efalizumab.

Preferred examples of therapeutic agents for SLE (Lupus) with which a compound of Formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of pro-inflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™).

In this invention, the following definitions are applicable:

A "therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, trifluoroacetate, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (I) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula (I) and their salts may exist in more than one crystal form and the present invention includes each crystal form and mixtures thereof.

Certain compounds of Formula (I) and their salts may also exist in the form of solvates, for example hydrates, and the present invention includes each solvate and mixtures thereof.

Certain compounds of Formula (I) may contain one or more chiral centers, and exist in different optically active forms. When compounds of Formula (I) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of Formula (I), and mixtures thereof. Certain compounds of Formula (I) may exist in different tautomeric forms or as different geometric isomers, and the present invention includes each tautomer and/or geometric isomer of compounds of Formula (I) and mixtures thereof. Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof. Certain compounds of Formula (I) may exist in zwitterionic form and the present invention includes each zwitterionic form of compounds of Formula (I) and mixtures thereof.

As used herein the term "pro-drug" refers to an agent which is converted into the parent drug in vivo by some physiological chemical process (e.g., a pro-drug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the pro-drug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to phosphates, phosphate esters, and carboxylic acid substituents wherein the free hydrogen is replaced by $(C_1-C_4)$ alkyl, $(C_1-C_{12})$alkanoyloxymethyl, $(C_4-C_9)$1-(alkanoyloxy) ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$- alkylcarbamoyl-$(C_1-C_2)$alkyl and piperidino-, pyrrolidino- or morpholino$(C_2-C_3)$alkyl.

Other exemplary pro-drugs release an alcohol of Formula (I) wherein the free hydrogen of the hydroxyl substituent is replaced by $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_{12})$ alkoxycarbonyloxymethyl, N—$(C_1-C_6)$alkoxycarbonylamino-methyl, succinoyl, $(C_1-C_6)$alkanoyl, α-amino $(C_1-C_4)$alkanoyl, arylacetyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1-C_6)alkyl)_2$ or glycosyl (the radical resulting from detachment of the hydroxyl of the hemiacetal of a carbohydrate).

Other exemplary pro-drugs release an amine of Formula (I) wherein the free hydrogen of the amine group is replaced by —C(O)alkyl, —C(O)O-alkyl, N-phosphonoxyalkyl, alkyl, cycloalkyl, aryl, heteroaryl or heterocyclyl, wherein the alkyl, cycloalkyl, aryl, heteroaryl or heterocyclyl can be optionally substituted with, for example, halogen and hydroxyl.

As used herein "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

As used herein, "spirocyclic $(C_2-C_{10})$ heterocyclyl" means bicyclic or polycyclic hydrocarbon group having two or three $(C_3-C_{10})$ rings at least one of which contains a heteroatom such as nitrogen, oxygen or sulfur. For purposes of exemplification, which should not be construed as limiting the scope of this invention, spirocyclic $(C_2-C_{10})$ heterocyclyl may include diazaspiro[3.5]nonane and diazaspiro[4.5]decane.

As used herein, "spirocyclic $(C_5-C_{11})$ carbocyclyl" means a saturated or unsaturated, bicyclic or polycyclic hydrocarbon group having two or three $(C_3-C_{10})$ cycloalkyl rings. For purposes of exemplification, which should not be construed as limiting the scope of this invention, spirocyclic $(C_5-C_{11})$ carbocyclyl includes spiro[5.5]undecane, spiro[4.5]decane and spiro[4.4]nonane.

The term "heterocyclic," "heterocyclyl" or "heterocyclylene," as used herein, include non-aromatic ring systems, including, but not limited to, monocyclic, bicyclic, and tricyclic rings, which can be completely saturated or which can contain one or more units of unsaturation. (for the avoidance of doubt, the degree of unsaturation does not result in an aromatic ring system) and have 5 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, indolinyl, isoindolinyl, morpholinyl, piperazinyl, piperidinyl, pyrrolidinyl, quinucludinyl, thiomorpholinyl, tetrahydropyranyl, tetrahydrofuranyl, tetrahydroindolyl, thiomorpholinyl and tropanyl.

The term "heteroaryl" or "heteroarylene" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzoxadiazolyl, 6,7-dihydro-5H-cyclopentapyrimidinyl, furanyl, imidazolyl, imidazopyridinyl, indolyl, indazolyl, isoxazolyl, isothiazolyl, octahydro-pyrrolopyrrolyl, oxadiazolyl, oxazolyl, phthalazinyl, pteridinyl, purinyl, pyranyl, 5,8-dihydro-6H-pyrano[3,4-d]pyridinyl, pyrazinyl, pyrazolyl, pyridinyl, pyrido[2,3-d]pyrimidinyl, pyrido[4,3-d]pyrimidinyl, pyrido[3,4-d]pyrimidinyl, pyrimidinyl, pyrimido[4,5-d] pyrimidinyl, pyrrolyl, pyrrolo[2,3-d]pyrimidinyl, pyrazolo [3,4-d]pyrimidinyl, quinolinyl, quinazolinyl, 5,6,7,8-tetrahydroquinazolinyl, triazolyl, thiazolyl, thieno[2,3-d] pyrimidinyl, thieno[3,2-d]pyrimidinyl, thiophenyl, tetrazolyl, thiadiazolyl, thienyl, [1,3,5]triazinyl, 5,6,7,8-tetrahydro-imidazo[1,5-a]pyrazinyl, and 5,6,7,8-tetrahydrotriazolo[1,2,4]pyrazinyl.

As used herein, "alkyl" and "alkylene" include straight chained or branched hydrocarbons which are completely saturated. For purposes of exemplification, which should not be construed as limiting the scope of this invention, examples of alkyls are methyl, ethyl, propyl, isopropyl, butyl, pentyl, hexyl and isomers thereof.

As used herein, "alkenyl," "alkenylene," "alkynylene" and "alkynyl" mean hydrocarbon moieties containing two to eight carbons and include straight chained or branched hydrocarbons which contain one or more units of unsaturation, one or more double bonds for alkenyl and one or more triple bonds for alkynyl. For purposes of exemplification, which should not be construed as limiting the scope of this invention, examples of alkenyl are ethenyl, propenyl and butenyl, and examples of alkynyl are ethynyl, propynyl and butynyl.

As used herein, "aryl" or "arylene" groups include aromatic carbocyclic ring systems (e.g. phenyl) and fused polycyclic aromatic ring systems. For purposes of exemplification, which should not be construed as limiting the scope of this invention, aryl groups include naphthyl, biphenyl and 1,2,3,4-tetrahydronaphthyl.

As used herein, "cycloalkyl," "cycloalkylene," "carbocycle" or "carbocyclyl" means $C_3$-$C_{12}$ monocyclic or multicyclic (e.g., bicyclic, tricyclic, etc.) hydrocarbons that are completely saturated or have one or more unsaturated bonds but do not amount to an aromatic group. For purposes of exemplification, which should not be construed as limiting the scope of this invention, examples of a cycloalkyl group are cyclopropyl, cyclobutyl, cyclopentyl, cyclopentenyl, cyclohexyl and cyclohexenyl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: deuterium, $CD_3$, optionally substituted ($C_1$-$C_8$)alkyl groups, optionally substituted ($C_2$-$C_8$)alkenyl groups, ($C_2$-$C_8$)alkynyl groups, optionally substituted ($C_3$-$C_{10}$)cycloalkyl groups, halogen (F, Cl, Br or I), halogenated ($C_1$-$C_8$)alkyl groups (for example but not limited to —$CF_3$), —O—($C_1$-$C_8$)alkyl groups, —OH, —S—($C_1$-$C_8$)alkyl groups, —SH, —NH($C_1$-$C_8$)alkyl groups, —N(($C_1$-$C_8$)alkyl)$_2$ groups, —NH$_2$, —NH—($C_1$-$C_6$)alkyl-optionally substituted heterocycle, —NH-heterocycle, —C(O)NH$_2$, —C(O)NH($C_1$-$C_8$)alkyl groups, —C(O)N(($C_1$-$C_8$)alkyl)$_2$, —NHC(O)H, —NHC(O)($C_1$-$C_8$)alkyl groups, —NHC(O)($C_3$-$C_8$)cycloalkyl groups, —N(($C_1$-$C_8$)alkyl)C(O)H, —N(($C_1$-$C_8$)alkyl)C(O)($C_1$-$C_8$)alkyl groups, —NHC(O)NH$_2$, —NHC(O)NH($C_1$-$C_8$)alkyl groups, —N(($C_1$-$C_8$)alkyl)C(O)NH$_2$ groups, —NHC(O)N(($C_1$-$C_8$)alkyl)$_2$ groups, —N(($C_1$-$C_8$)alkyl)C(O)N(($C_1$-$C_8$)alkyl)$_2$ groups, —N(($C_1$-$C_8$)alkyl)C(O)NH(($C_1$-$C_8$)alkyl), —C(O)H, —C(O)($C_1$-$C_8$) alkyl groups, —CN, —NO$_2$, —S(O)($C_1$-$C_8$)alkyl groups, —S(O)$_2$($C_1$-$C_8$)alkyl groups, —S(O)$_2$N(($C_1$-$C_8$)alkyl)$_2$ groups, —S(O)$_2$NH($C_1$-$C_8$)alkyl groups, —S(O)$_2$NH($C_3$-$C_8$)cycloalkyl groups, —S(O)$_2$NH$_2$ groups, —NHS(O)$_2$($C_1$-$C_8$)alkyl groups, —N(($C_1$-$C_8$)alkyl)S(O)$_2$($C_1$-$C_8$)alkyl groups, —($C_1$-$C_8$)alkyl-O—($C_1$-$C_8$)alkyl groups, —O—($C_1$-$C_8$)alkyl-β-($C_1$-$C_8$)alkyl groups, —C(O)OH, —C(O)O($C_1$-$C_8$)alkyl groups, —NHOH, —NHO($C_1$-$C_8$)alkyl groups, —O-halogenated ($C_1$-$C_8$)alkyl groups (for example but not limited to —OCF$_3$), —S(O)$_2$-halogenated ($C_1$-$C_8$) alkyl groups (for example but not limited to —S(O)$_2$CF$_3$), —S-halogenated ($C_1$-$C_8$)alkyl groups (for example but not limited to —SCF$_3$), —($C_1$-$C_6$)alkyl-optionally substituted heterocycle (for example but not limited to azetidine, piperidine, piperazine, pyrrolidine, tetrahydrofuran, pyran or morpholine), —($C_1$-$C_6$)alkyl-heteroaryl (for example but not limited to tetrazole, imidazole, furan, pyrazine or pyrazole), -optionally substituted phenyl, —NHC(O)O—($C_1$-$C_6$)alkyl groups, —N(($C_1$-$C_6$)alkyl)C(O)O—($C_1$-$C_6$)alkyl groups, —C(═NH)—($C_1$-$C_6$)alkyl groups, —C(═NOH)—($C_1$-$C_6$) alkyl groups, or —C(═N—O—($C_1$-$C_6$)alkyl)-($C_1$-$C_6$)alkyl groups.

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, inhaled or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:SW) consists of VPD diluted 1:1 with a 5% dextrose in water solution.

This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few hours up to over several days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see e.g. Fingl et al., 1975, in *The Pharmacological Basis of Therapeutics*, Ch. 1, p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the following Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| Parts by weight | |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of Formula (I) as a medicament.

EXAMPLES

None of the specific conditions and reagents noted herein are to be construed as limiting the scope of the invention and are provided for illustrative purposes only. All starting materials are commercially available from Sigma-Aldrich (including Fluka and Discovery CPR) unless otherwise noted after the chemical name. Reagent/reactant names given are as named on the commercial bottle or as generated by IUPAC conventions, CambridgeSoft® Chemdraw Ultra 9.0.7 or AutoNom 2000. Compounds designated as salts (e.g. hydrochloride, acetate) may contain more than one molar equivalent of the salt.

Compounds of the invention where the absolute stereochemistry has been determined by the use of a commercially available enantiomerically pure starting material or a stereochemically defined or by X-ray diffraction are denoted by an asterisk after the example number.

Purification Methods

Intermediate and final compounds may be purified by any technique or combination of techniques known to one skilled in the art. Some examples that are not limiting include flash chromatography with a solid phase (i.e. silica gel, alumina, etc.) and a solvent (or combination of solvents, i.e. heptane, EtOAc, DCM, MeOH, MeCN, water, etc.) that elutes the desired compounds; preparatory TLC with a solid phase (i.e. silica gel, alumina etc.) and a solvent (or combination of solvents, i.e. heptane, EtOAc, DCM, MeOH, MeCN, water, etc.) that elutes the desired compounds; reverse phase HPLC (see Table 1 for some non-limiting conditions); recrystallization from an appropriate solvent (i.e. MeOH, EtOH, i-PrOH, EtOAc, toluene, etc.) or combination of solvents (i.e. EtOAc/heptane, EtOAc/MeOH, etc.); chiral chromatography with a solid phase and an appropriate solvent (i.e. EtOH/heptane, MeOH/heptane, i-PrOH/heptane, etc. with or without a modifier such as DEA, Tfa, etc.) to elute the desired compound; precipitation from a combination of solvents (i.e. DMF/water, DMSO/DCM, EtOAc/heptane, etc.); trituration with an appropriate solvent (i.e. EtOAc, DCM, MeCN, MeOH, EtOH, i-PrOH, n-PrOH, etc.); extractions by dissolving a compound in a liquid and washing with an appropriately immiscible liquid (i.e. DCM/water, EtOAc/water, DCM/saturated $NaHCO_3$, EtOAc/saturated $NaHCO_3$, DCM/10% aqueous HCl, EtOAc/10% aqueous HCl, etc.); distillation (i.e. simple, fractional, Kugelrohr, etc.); gas chromatography using an appropriate temperature, carrier gas and flow rate; sublimation at an appropriate temperature and pressure; filtration through a media (i.e. Florosil®, alumina, Celite®, silica gel, etc.) with a solvent (i.e. heptane, hexanes, EtOAc, DCM, MeOH, etc.) or combination of solvents; salt formation with solid support (resin based, i.e. ion exchange) or without. Descriptions of these techniques can be found in the following references: Gordon, A. J. and Ford, R. A. "The Chemist's Companion", 1972; Palleros, D. R. "Experimental Organic Chemistry", 2000; Still, W. C., Kahn and M. Mitra, A. *J. Org. Chem.* 1978, 43, 2923; Yan, B. "Analysis and Purification Methods in Combinatorial Chemistry" 2003; Harwood, L. M., Moody, C. J. and Percy, J. M. "Experimental Organic Chemistry: Standard and Microscale, $2^{nd}$ Edition", 1999; Stichlmair, J. G. and Fair, J. R. "Distillation; Principles and Practices" 1998; Beesley T. E. and Scott, R. P. W. "Chiral Chromatography", 1999; Landgrebe, J. A. "Theory and Practice in the Organic Laboratory, $4^{th}$ Ed.", 1993; Skoog, D. A. and Leary, J. J. "Principles of Instrumental Analysis, $4^{th}$ Ed." 1992; G. Subramanian, "Chiral Separation Techniques $3^{rd}$ Edition" 2007; Y. Kazakevich, R. Lobrutto, "HPLC for Pharmaceutical Scientists" 2007.

Degassing Methods

Preparations of intermediate and final compounds obtained via the General Procedures can be optionally degassed using one or more of the Degassing Methods described below. The reaction mixtures may be degassed by a single or multiple applications of any technique or combination of techniques known to one skilled in the art. Some examples that are not limiting include bubbling a continuous stream of an inert gas (e.g. nitrogen, argon, etc.) through a mixture of reagents and a solvent suitable for the transformation (e.g. THF, 1,4-dioxane, EtOAc, DCM, toluene, MeOH, EtOH, DMF, MeCN, water, etc.); freeze-thawing of a mixture of reagents in a solvent (e.g. THF, 1,4-dioxane, EtOAc, DCM, toluene, MeOH, EtOH, DMF, MeCN, water, etc.) where the resulting solution is cooled below its freezing point and evacuated under reduced pressure, then allowed to warm above the freezing point and purged with an atmosphere of inert gas (e.g. nitrogen, argon, etc.); evacuation under reduced pressure of a mixture of reagents with or without a suitable solvent for the transformation (e.g. THF, 1,4-dioxane, EtOAc, DCM, toluene, MeOH, EtOH, DMF, MeCN, water, etc.) followed by purging of the mixture with an inert gas (e.g. nitrogen, argon, etc.); evacuation under reduced pressure of a mixture of reagents in a suitable solvent for the transformation (e.g. THF, 1,4-dioxane, EtOAc, DCM, toluene, MeOH, EtOH, DMF, MeCN, water, etc.) with the aid of mechanical agitation (e.g. stirring, shaking, sonication, etc.) followed by purging of the mixture with an inert gas (e.g. nitrogen, argon, etc.). Some descriptions of these techniques can be found in the following references, Gordon, A. J. and Ford, R. A. "The Chemist's Companion", 1972; Palleros, D. R. "Experimental Organic Chemistry", 2000; Harwood, L. M., Moody, C. J. and Percy, J. M. "Experimental Organic Chemistry Standard and Microscale, $2^{nd}$ Edition", 1999; Landgrebe, J. A. "Theory and Practice in the Organic Laboratory, $4^{th}$ Edition", 1993; Leonard, J., Lygo, B. and Procter, G. "Advanced Practical Organic Chemistry, $2^{nd}$ Edition", 1998; Meyers, A. G.; Dragovich, P. S. *Organic Syntheses,* 1995, 72, 104; Hajos, Z. G., Parrish, D. R. *Organic Syntheses,* 1985, 63, 26.

EXAMPLES

None of the specific conditions and reagents noted herein are to be construed as limiting the scope of the invention and are provided for illustrative purposes only. All starting materials are commercially available from Sigma-Aldrich (including Fluka and Discovery CPR) unless otherwise noted after the chemical name. Reagent/reactant names given are as named on the commercial bottle or as generated by IUPAC conventions, CambridgeSoft® Chemdraw Ultra 9.0.7 or AutoNom 2000. Compounds designated as salts (e.g. hydrochloride, acetate) may contain more than one molar equivalent of the salt.

Abbreviations
aa Amino acids
$Ac_2O$ Acetic anhydride
AcOH Glacial acetic acid
atm Atmospheres
ATP Adenosine triphosphate
b.p. Boiling point
BArF tetrakis-[3,5-bis(trifluoromethyl)phenyl]borate
Bn Benzyl
Boc t-Butoxycarbonyl
BOP-Cl Bis(2-oxo-3-oxazolidinyl)phosphonic chloride
br. Broad
br. d Broad doublet
br., s Broad singlet
bs Broad singlet
BSA Bovine serum albumin
BuOH Butanol
CAN Ceric ammonium nitrate
Cbz Carboxybenzyl
CDI 1,1'-Carbonyldiimidazole
COD 1,5-Cyclooctadiene
concd Concentrated
CT Computed tomography
cym p-cymene (4-isopropyltoluene)
CyPFt-Bu 1-Dicyclohexylphosphino-2-di-tert-butylphosphinoethylferrocene
d Doublet
DAST Diethylaminosulfur trifluoride
dba Dibenzylideneacetone
DBU 1,8-Diazabicyclo[5.4.0]undec-7-ene
DCC Dicyclohexylcarbodiimide
DCE Dichloroethane
DCM Dichloromethane (methylene chloride)
dd Doublet of doublets
DEA Diethylamine
DEAD Diethyl azodicarboxylate
DIBAL-H Diisobutylaluminium hydride
DIAD Diisopropyl azodicarboxylate
DIEA N,N-Diisopropylethylamine
DMA Dimethylacetamide
DMAP N,N-Dimethylaminopyridine
DMC Chlorodimethyllimidazoliniumchloride
DME 1,2-Dimethoxyethane
DMEM Dulbecco's Modified Eagle Medium
DMF N,N-Dimethylformamide
DMS Dimethylsulfide
DMSO Dimethyl sulfoxide
DNP-HSA Dinitrophenyl-human serum albumin
DPPA Diphenyl phosphorazidate
dppf 1,1'-Bis(diphenylphosphino)ferrocene
dq Doublet of quartets
dr Diastereomeric ratio
dt Doublet of triplets
DTT Dithiothreitol
EDC.HCl N-(3-Dimethylaminopropyl)-N'-ethylcarbodiimide hydrochloride
EDTA Ethylene diamine tetraacetic acid
EGTA Ethylene glycol tetraacetic acid
equiv Equivalent(s)
er Enantiomeric ratio
$Et_2NH$ Diethylamine
EtOAc Ethyl acetate
$Et_2O$ Diethyl ether
EtOH Ethanol
FBS Fetal bovine serum
FLAG DYKDDDDK peptide sequence
g Gram(s)
GST Glutathione S-transferase
h Hour(s)
$H_2SO_4$ Sulfuric acid
HATU O-(7-Azabenzotriazol-1-yl)-N,N,N',N'-tetramethyluronium hexafluorophosphate
HEPES N-2-Hydroxyethylpiperazine-N'-2-ethanesulfonic acid
HOBt Hydroxybenzotriazole
HPLC High-pressure liquid chromatography
Hz Hertz
IBCF Isobutylchloroformate
i.d. Intradermal
IFA Incomplete Freunds Adjuvant
IPA Isopropyl alcohol
KHMDS Potassium hexamethyldisilazane
LAH Lithium aluminum hydride
LC Liquid chromatography
LDA Lithium diisopropylamide
LHMDS Lithium bis(trimethylsilyl)amide
$LiBH_4$ Lithium borohydride
LiOH Lithium hydroxide
m Multiplet
M Molar
m-CPBA meta-Chloroperbenzoic acid
MeCN Acetonitrile
MeOH Methyl alcohol
min Minute(s)
mL Milliliter(s)
mmHg Millimeters of mercury
mmol Millimole
MOPS 3-(N-morpholino)-propanesulfonic acid
MOPSO 3-(N-morpholino)-2-hydroxypropanesulfonic acid
MS Mass spectrometry
MTBE Methyl tert-butyl ether
n- Normal (nonbranched)
n-BuLi n-Butyl lithium
N Normal
NaHMDS Sodium bis(trimethylsilyl)amide
NaOAc Sodium acetate
$Na(OAc)_3BH$ Sodium triacetoxyborohydride
$Na(CN)BH_3$ Sodium cyanoborohydride
NaOt-Bu Sodium tert-butoxide
NBS N-Bromosuccinimide
NCS N-Chlorosuccinimide
ND Not determined
$NH_4OAc$ Ammonium acetate
NIS N-Iodosuccinimide
NMM N-Methylmorpholine
NMP N-Methylpyrrolidinone
NMR Nuclear magnetic resonance
OD Optical density
or Optical rotation
OVA Ovalbumin
p- Para p-TSA p-Toluenesulfonic acid monohydrate
PBS Phosphate buffered saline
Pd/C Palladium(0) on carbon
Pd(OAc)$_2$ Palladium(II) acetate
PdCl$_2$(PPh$_3$)$_2$ Bis(triphenylphosphine)palladium(II) chloride
Pd(dppe)Cl$_2$ Dichloro[1,2-bis(diphenylphosphino)ethane] palladium(II)
Pd(dppf)Cl$_2$ [1,1'-Bis(diphenylphosphino)ferrocene]dichloropalladium(II)
Pd(dppp)Cl$_2$ Dichlorobis[(di-tert-butyl)phenylphosphine]palladium(II)
Pd(PPh$_3$)$_4$ Tetrakis(triphenylphosphine)palladium(0)
PFPAA 2,2,3,3,3-Pentafluoropropanoic Anhydride
pH −log [H+]
PMB p-Methoxybenzyl
pNAG Nitrophenyl-N-acetyl-D-glucosaminide
P(n-Bu)$_3$ tri-n-Butyl phosphine
POCl$_3$ Phosphorus oxychloride
PPh$_3$ Triphenylphosphine
ppm Parts per million
PrOH Propanol
psi Pounds per square inch
psig Pounds per square inch gauge
rcf Relative centrifugal force
RP-HPLC Reverse-phase high-pressure liquid chromatography
R$_t$ Retention time
rt Room temperature
s Singlet
SEM 2-(Trimethylsilyl)ethoxymethyl
SEM-Cl 2-(Trimethylsilyl)ethoxymethyl chloride
SFC Supercritical Fluid Chromatography
SLM Standard liters per minute
t Triplet
t- Tertiary
TBDMS tert-Butyldimethylsilyl
TBDMSCl tert-Butyldimethylsilyl chloride
TBAB Tetra-n-butylammonium bromide
TBAF Tetra-n-butylammonium fluoride
TBAI Tetra-n-butylammonium iodide
TBTU O-(Benzotriazol-1-yl)-N,N,N',N'-tetramethyluronium tetrafluoroborate
td Triplet of doublets
TEA Triethylamine
tert- Tertiary
TFA Trifluoroacetic acid
TFAA Trifluoroacetic anhydride
THF Tetrahydrofuran
TIPS Triisopropylsilyl
TLC Thin layer chromatography
TMA Trimethyl aluminium
TMAD N,N,N',N'-Tetramethylazodicarbonamide or 1,1'-azobis(N,N-dimethylformamide) or diamide [Sigma®]
TMOF Trimethyl orthoformate
TMS Trimethylsilyl
TPP 2,4,6-Tripropyl-[1,3,5,2,4,6]trioxatriphosphinane 2,4,6-trioxide
TsCl para-Toluenesulfonyl chloride
TsOH para-Toluenesulfonic acid
USP United States Pharmacopeia
UV Ultraviolet
wt % Weight percent
w/v Weight/volume
Xantphos 4,5-Bis(diphenylphosphino)-9,9-dimethylxanthene Compounds of the invention where the absolute stereochemistry has been determined by the use of a commercially available enantiomerically pure starting material or a stereochemically defined or by X-ray diffraction are denoted by an asterisk after the example number.

GENERAL PROCEDURES AND EXAMPLES

The general synthetic schemes that were utilized to construct the majority of compounds disclosed in this application are described in the schemes below. These schemes are provided for illustrative purposes only and are not to be construed as limiting the scope of the invention.

Scheme 1. Formation of a 3-substituted 3-oxopropanenitrile (General Procedure A)

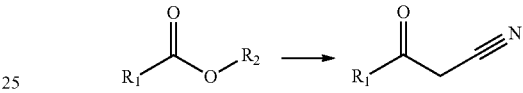

Scheme 2. Preparation of a 3-substituted 5-aminopyrazole (General Procedure B)

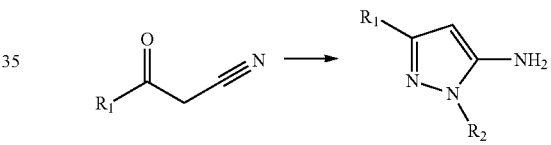

Scheme 3. Cyclization of a 3-substituted 5-aminopyrazole with an aldehyde and thioalkanoic acid to a pyrazolothiazepinone (General Procedure C)

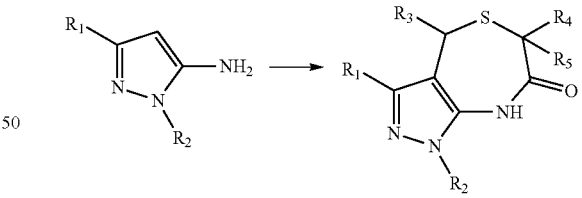

Scheme 4. Reduction of thiazepinone to thiazepine (General Procedure D)

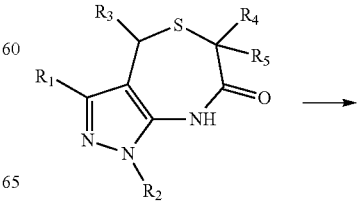

-continued

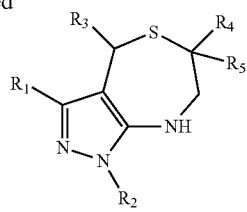

Scheme 5. Conversion of a bromide to a corresponding ester (General Procedure E)

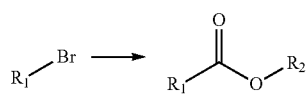

Scheme 6. Conversion of an aromatic or heteoaromatic ester to a corresponding amide (General Procedure F)

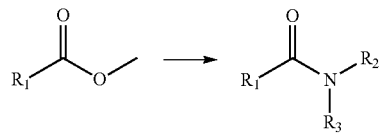

Scheme 7. Conversion of a bromide to a corresponding nitrile (General Procedure G)

Scheme 8. Formation of an amide from an aryl or heteroaryl bromide (General Procedure H)

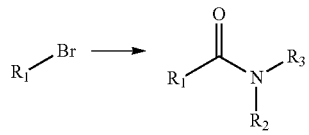

Scheme 9. (General Procedure I) Preparation of an amide from a corresponding ester

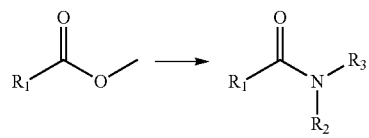

Scheme 10. Formation of pyrazolodihydrothiazepines from ketones (General Procedure J)

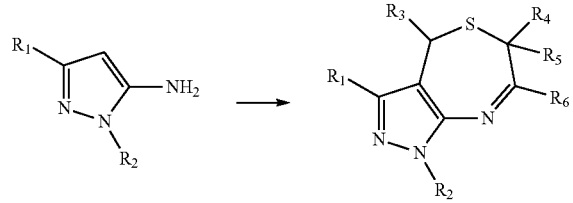

Scheme 11. Reduction of pyrazolodihydrothiazepines to pyrazolotetrahydrothiazepines (General procedure K)

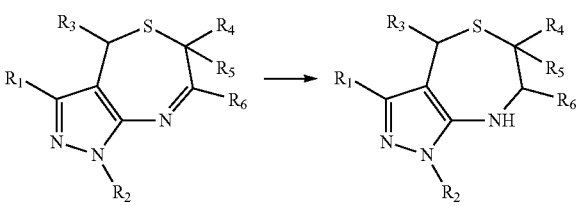

Scheme 12. Preparation of pyrazolothiazepine oxides and/or pyrazolothiazepine dioxides (General Procedure L)

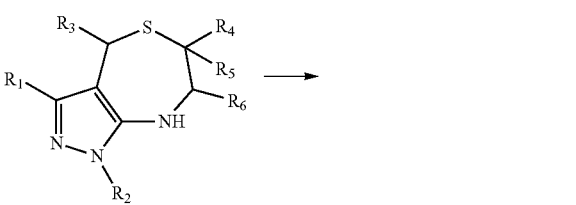

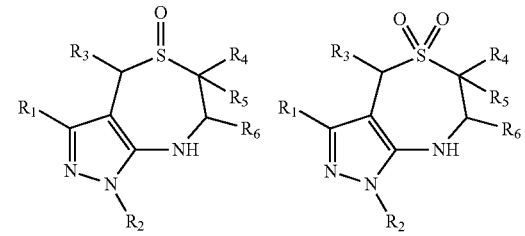

Scheme 13: Chiral preparative HPLC separation of stereoisomers (General Procedure M)

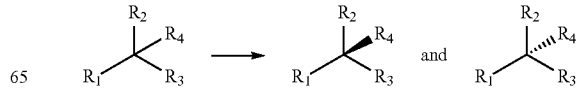

Scheme 14: Halogen-metal exchange on substituted 1,4,5,6,7,8-hexahydropyrazolo[3,4-b]azepin-7(1H)-ones containing an aryl halide (General Procedure N)

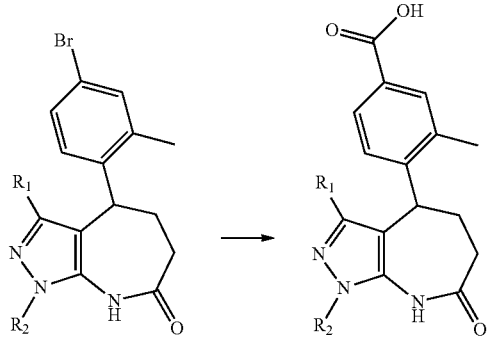

Scheme 15: Amide formation on a substituted 1,4,5,6,7,8-hexahydropyrazolo[3,4-b]azepin-7(1H)-ones containing an aryl carboxylate (General Procedure O)

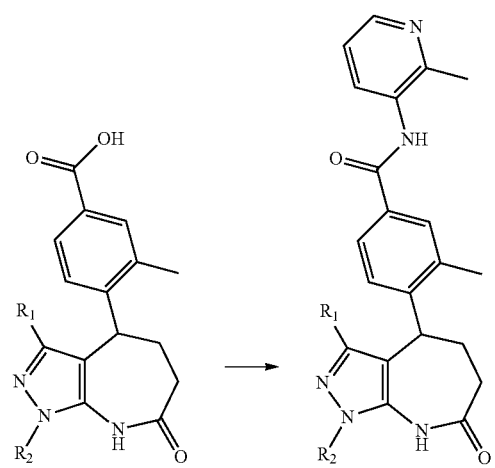

Scheme 16: Sonogashira reaction of an aryl halide with an alkyne (General Procedure P)

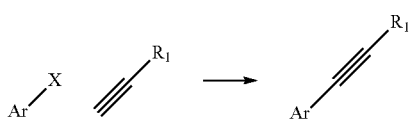

Scheme 17: Hydrogenation of an alkyne to an alkane (General Procedure Q)

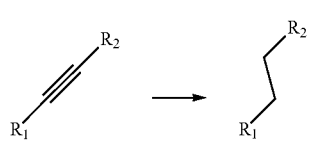

Scheme 18: Formation of an amide from an activated acid and an amine (General Procedure R)

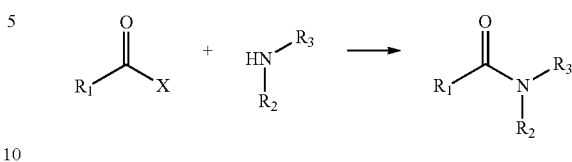

Scheme 19: Formation of an amide from an acid and an amine (General Procedure S)

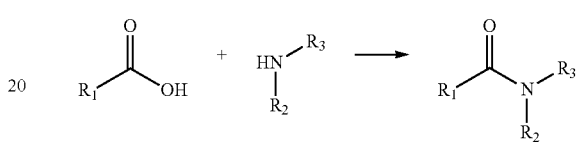

Scheme 20: Formation of an acid chloride (General Procedure T)

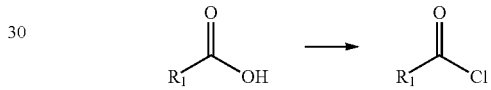

Scheme 21: Suzuki coupling of an aryl halide and aryl boronate or boronic acid (General Procedure U)

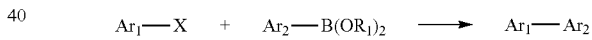

Scheme 22: Hydrolysis of an ester to a carboxylic acid (General Procedure V)

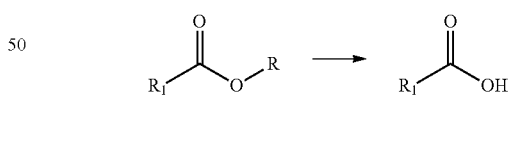

Scheme 23: Formation of a 3-substituted 3-oxopropanenitrile from an ester (General Procedure W)

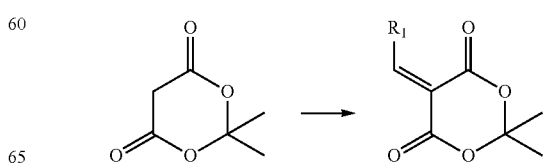

Scheme 24: Formation of
4,5-dihydro-1H-pyrazolo[3,4-b]pyridin-6(7H)-ones (General Procedure X)

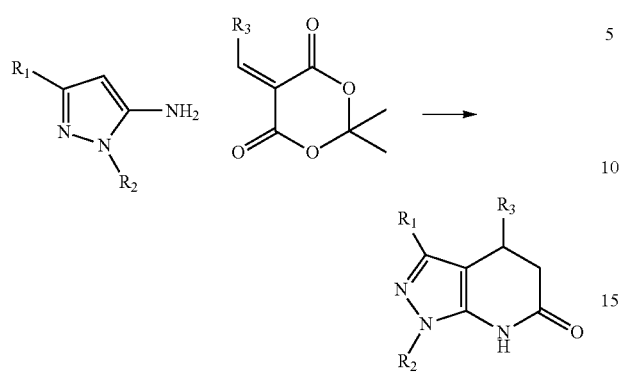

Scheme 25: Ring opening of substituted
4,5-dihydro-1H-pyrazolo[3,4-b]pyridin-6(7H)-ones
(General Procedure Y)

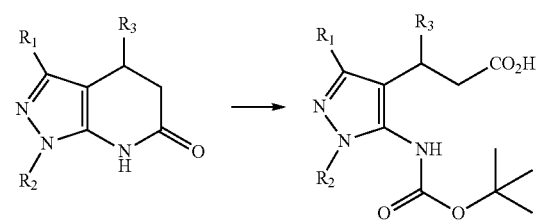

Scheme 26: Arndt-Eistert homologation of ring opened
4,5-dihydro-1H-pyrazolo[3,4-b]pyridin-6(7H)-ones (General Procedure Z)

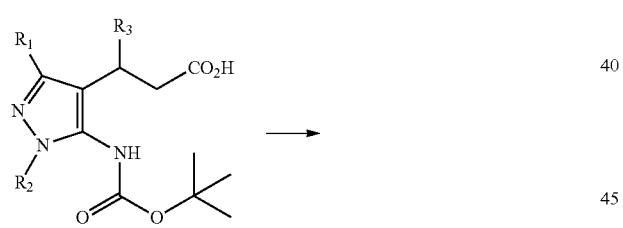

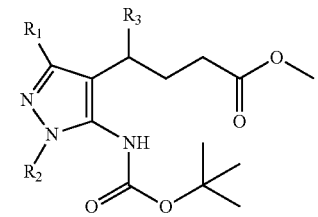

-continued

Scheme 27: Preparation of substituted-4,5,6,8-tetrahydropyrazolo[3,4-b]azepin-7(1H)-ones (General Procedure AA)

Scheme 28: Preparation of substituted 1,4,5,6,7,8-hexahydropyrazolo[3,4-b]azepines (General Procedure BB)

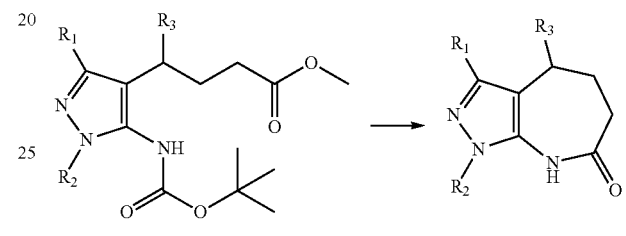

List of General Procedures

| | |
|---|---|
| General Procedure A | Preparation of 3-substituted 3-oxo-propanenitriles |
| General Procedure B | Preparation of 5-substituted 3-amino-pyrazole |
| General Procedure C | Preparation of thiazepinones |
| General Procedure D | Preparation of thiazepines |
| General Procedure E | Preparation of esters from bromides |
| General Procedure F | Preparation of an aromatic or heteoaromatic amides from methyl-esters |
| General Procedure G | Preparation of nitriles from bromides |
| General Procedure H | Preparation of amides from bromides |
| General Procedure I | Preparation of amides from methyl-esters |
| General Procedure J | Preparation of pyrazolodihydrothiazepines from ketones |
| General Procedure K | Reduction of pyrazolodihydrothiazepines to pyrazolotetrahydrothiazepines |
| General Procedure L | Preparation of thiazepine oxide and/or thiazepine dioxide from thiazepine |
| General Procedure M | Chiral preparative HPLC purification |
| General Procedure N | Halogen-metal exchange on substituted 1,4,5,6,7,8-hexahydropyrazolo[3,4-b]azepin-7(1H)-ones containing an aryl halide |
| General Procedure O | Amide formation on a substituted 1,4,5,6,7,8-hexahydropyrazolo[3,4-b]azepin-7(1H)-ones containing an aryl carboxylate |

| | |
|---|---|
| General Procedure P | Sonogashira reaction of an aryl halide with an alkyne |
| General Procedure Q | Hydrogenation of an alkyne to an alkane |
| General Procedure R | Formation of an amide from an activated acid and an amine |
| General Procedure S | Formation of an amide from an acid and an amine |
| General Procedure T | Formation of an acid chloride |
| General Procedure U | Suzuki coupling of an aryl halide with an aryl boronate or boronic acid |
| General Procedure V | Hydrolysis of an ester to a carboxylic acid |
| General Procedure W | Formation of a 3-substituted 3-oxopropanenitrile from an ester |
| General Procedure X | Formation of 4,5-dihydro-1H-pyrazolo[3,4-b]pyridin-6(7H)-ones |
| General Procedure Y | Ring opening of substituted 4,5-dihydro-1H-pyrazolo[3,4-b]pyridin-6(7H)-ones |
| General Procedure Z | Arndt-Eistert homologation of ring opened 4,5-dihydro-1H-pyrazolo[3,4-b]pyridin-6(7H)-ones |
| General Procedure AA | Preparation of substituted-4,5,6,8-tetrahydropyrazolo[3,4-b]azepin-7(1H)-ones |
| General Procedure BB | Preparation of substituted 1,4,5,6,7,8-hexahydropyrazolo[3,4-b]azepines |

General Procedures are designated by their uppercase letter in bold.

Analytical Methods

High-pressure liquid chromatography (HPLC) analytical data are either detailed within the experimental or referenced to the table of HPLC conditions, using the lower case method letter, in Table 1.

TABLE 1

List of HPLC methods

| Method | HPLC Conditions<br>Unless indicated otherwise, mobile phase A was 0.25% formic acid in water, mobile phase B was HPLC grade acetonitrile with 0.25% formic acid. |
|---|---|
| a | 10 min run: The gradient was 5% B for 0.01 min then 5%-100% in 7.5 min with a hold at 100% for 1.5 min (1.5 mL/min) then 1 min from 100%-5% B. The column used for the chromatography is a 3.0 × 30 mm Sunfire C18 (Waters) (2.5 μm particles). Detection methods are diode array (DAD) scanned 240-320 nm and evaporative light scattering detection (ELSD) as well as positive and negative electrospray ionization, scan range 100-900 AMU) |
| b | LC-UV-MS was performed on an Agilent LC series 1100 combined with a Thermo OrbiTrap Mass spectrometer with a 12 min. runtime. The gradient with a flow of 1.5 mL/min. is 5% B at 0.01 min then changed linear to 100% B at 10 min with a hold at 100% for 1.5 min. The column used for the chromatography is a 3.0 × 150 mm Eclipse DXB C18 (Agilent) (3.5 μm particles). Detection methods were diode array (DAD) scanned 240-320 nm and positive electrospray ionization (scan range 100-1000 amu). |
| c | LC-UV-ELSD-MS was performed on a Waters 1525 (LC) 2777 (ALS) 2996 (PDA) 2424 (ELSD) combined with a ZQ 2000 (MS) with a 3 min runtime. The gradient was 10% B for 0.2 min then 10-100% B in 2.5 min with a hold at 100% B for 0.3 min (1.6 mL/min flow rate). The column used for chromatography is a 3.0 × 30 mm Sunfire C18 (Waters) (2.5 μm particles). Detection methods were diode array (DAD) scanned 240-320 nm and evaporative light scattering detection (ELSD) as well as positive electrospray ionization, scan range 117-900 amu) |
| d | LC-UV-ELSD-MS was performed on a Waters 1525 (LC) 2777 (ALS) 2996 (PDA) 2424 (ELSD) combined with a ZQ 2000 (MS) with a 5 min run time. The gradient was 10% B for 0.2 min then 10-100% B in 4.5 min with a hold at 100% B for 0.3 min (1.6 mL/min flow rate). The column used for the chromatography is a 3.0 × 30 mm Sunfire C18 (Waters) (2.5 μm particles). Detection methods are diode array (DAD) scanned 240-320 nm and evaporative light scattering detection (ELSD) as well as positive electrospray ionization, scan range 117-900 amu) |
| e | LC-UV-MS was performed on an Agilent LC series 1100 combined with a Waters Quattro Premier Mass spectrometer with a 12 min run time. The gradient with a flow of 1.5 mL/min. was 5% B at 0.01 min then changed linear to 100% B at 10 min with a hold at 100% for 1.5 min. The column used for the chromatography is a 3.0 × 150 mm Eclipse DXB C18 (Agilent) (3.5 μm particles). Detection methods were diode array (DAD) scanned 240-320 nm and positive electrospray ionization |
| f | LC/MS: The gradient was 30-60% B in 1.50 min then 60-95% B to 2.5 min with a hold at 95% B for 1.2 min (1.3 mL/min flow rate). Mobile phase A was 10 mM ammonium acetate, mobile phase B was HPLC grade MeCN. The column used for the chromatography is a 4.6 × 50 mm MAC-MOD Halo C8 column (2.7 m particles). Detection methods are diode array (DAD) and evaporative light scattering (ELSD) detection as well as pos/neg electrospray ionization. |

TABLE 1-continued

List of HPLC methods

| Method | |
|---|---|
| | HPLC Conditions<br>Unless indicated otherwise, mobile phase A was 0.25% formic acid in water, mobile phase B was HPLC grade acetonitrile with 0.25% formic acid. |
| g | LC/MS: The gradient was 5-60% B in 1.5 min then 60-95% B to 2.5 min with a hold at 95% B for 1.2 min (1.3 mL/min flow rate). Mobile phase A was 10 mM NH$_4$OAc, mobile phase B was HPLC grade MeCN. The column used for the chromatography is a 4.6 × 50 mm MAC-MOD Halo C8 column (2.7 μm particles). Detection methods are diode array (DAD) and evaporative light scattering (ELSD) detection as well as positive/negative electrospray ionization. |
| h | LC/MS: The gradient was 5-60% B in 1.5 min then 60-95% B to 2.5 min with a hold at 95% B for 1.2 min (1.3 mL/min flow rate). Mobile phase A was 10 mM NH$_4$OAc, mobile phase B was HPLC grade MeCN. The column used for the chromatography is a 4.6 × 50 mm MAC-MOD Halo C18 column (2.7 μm particles). Detection methods are diode array (DAD) and evaporative light scattering (ELSD) detection as well as positive/negative electrospray ionization. |
| i | Analytical LC-MS was performed on a Finnigan Navigator mass spectrometer and Agilent 1100 HPLC system running Xcalibur 1.2, Open-Access 1.3, and custom login software. The mass spectrometer was operated under positive APCI ionization conditions. The HPLC system comprised an Agilent Quaternary pump, degasser, column compartment, autosampler and diode-array detector, with a Polymer Labs ELS-2100 evaporative light-scattering detector. The column used was a Phenomenex Luna Combi-HTS C8(2) 5 μm 100 Å (2.1 mm × 50 mm), at a temperature of 55° C. A gradient of 10-100% MeCN (A) and 0.1% TFA in water (B) was used, at a flow rate of 2.0 mL/min (0-0.1 min 10% A, 0.1-2.6 min 10-100% A, 2.6-2.9 min 100% A, 2.9-3.0 min 100-10% A. 0.5 min post-run delay). |
| j | Analytical UPLC-MS was performed on a Waters SQD mass spectrometer and Acquity UPLC system running MassLynx 4.1 and Openlynx 4.1 software. The SQD mass spectrometer was operated under positive APCI ionization conditions. The column used was a Waters BEH C8, 1.7 μm (2.1 mm × 30 mm) at a temperature of 55° C. A gradient of 10-100% MeCN (A) and 0.1% TFA in water (B) was used, at a flow rate of 1.0 mL/min (0-0.1 min 10% A, 0.1-1.1 min 10-100% A, 1.1-1.3 min 100% A, 1.3-1.4 min 100-10% A). |
| k | LC/MS: The gradient was 5% B to 95% B within 1.3 min, then with a hold at 95% B for 1.5 min, back to 5% B within 0.01 min (1.8 mL/min flow rate). Mobile phase A was 10 mM NH$_4$HCO$_3$ in water, and mobile phase B was HPLC grade MeCN. The column used for the chromatography is a 4.6 × 50 mm XBridge C18 column (3.5 μm particles). Column temperature is 50° C. Detection methods are diode array (DAD) and evaporative light scattering (ELSD) detection as well as positive/negative electrospray ionization. |
| l | LC/MS: The gradient was 5% B to 95% B within 1.2 min, then with a hold at 95% B for 1.3 min, back to 5% B within 0.01 min (2.0 mL/min flow rate). Mobile phase A was 0.01% TFA in water, and mobile phase B was 0.01% TFA in HPLC grade MeCN. The column used for the chromatography is a 4.6 × 50 mm XBridge C18 column (3.5 μm particles). Column temperature is 50° C. Detection methods are diode array (DAD) and evaporative light scattering (ELSD) detection as well as positive/negative electrospray ionization. |
| m | LC-UV-MS was performed on an Agilent LC series 1100 combined with a Thermo OrbiTrap Mass spectrometer. A gradient chromotography with a 12 min. runtime was done with mobile phase A: 0.25% formic acid in water, mobile phase B: HPLC grade MeCN with 0.25% formic acid. The gradient with a flow of 1.0 mL/min. is 5% B at 0.01 min then changed linear to 100% B at 10 min with a hold at 100% for 1.5 min. The column used for the chromatography is a 3.0 × 150 mm Intersil C18 (3.5 μm particles). Detection methods were diode array (DAD) scanned 240-320 nm and positive electrospray ionization at unit resolution. |

TABLE 2

List of preparative HPLC methods

| Method | |
|---|---|
| | Equipment: Agilent 1200 series: Prep ALS, Prep pump, DAD, Prep FC, Iso pump, Quadrupole LCMS 6120, splitter 1/1000 Accurate LC packings |
| a | HPLC Conditions:<br>Mobile phase A1: 0.1% formic acid in water (Elix5 quality)<br>Mobile phase B1: 0.1% formic acid in MeCN (HPLC grade)<br>Column 1: Waters, Sunfire Prep C18 OBD 5 μm, 30 × 50 mm<br>Detection methods are UV at 254 nm and ESI pos. scan range 100-1000 amu<br>Injection: sample 50-100 mg dissolved in 4 mL DMSO (HPLC grade)<br>Collection: peak controlled, threshold only (DAD). 12 min run. The gradient was 5% B for 2 min then 5%-100% in 8 min with a hold at 100% for 2 min. then 100%-5% in 0.15 min. Flow 40 mL/min. |
| b | HPLC Conditions:<br>Mobile phase A1: 0.1% formic acid in water (Elix5 quality)<br>Mobile phase B1: 0.1% formic acid in MeCN (HPLC grade)<br>Column 1: Waters, Sunfire Prep C18 OBD 5 μm, 30 × 50 mm |

TABLE 2-continued

List of preparative HPLC methods

| Method | |
|---|---|
| | Equipment: Agilent 1200 series: Prep ALS, Prep pump, DAD, Prep FC, Iso pump, Quadrupole LCMS 6120, splitter 1/1000 Accurate LC packings |
| | Detection methods are UV at 254 nm and ESI pos. scan range 100-1000 amu<br>Injection: sample 50-100 mg dissolved in 4 mL DMSO (HPLC grade)<br>Collection: peak controlled, threshold only (DAD). 15 min. run. The gradient was 5% B for 2 min then 5%-100% in 11 min with a hold at 100% for 2 min. then 100%-5% in 0.15 min. Flow 40 mL/min. |
| c | HPLC Conditions:<br>Mobile phase A1: 0.1% formic acid in water (Elix5 quality)<br>Mobile phase B1: 0.1% formic acid in MeCN (HPLC grade)<br>Column 1: Waters, Sunfire Prep C18 OBD 5 μm, 30 × 50 mm<br>Detection methods are UV at 254 nm and ESI pos. scan range 100-1000 amu<br>Injection: sample 50-100 mg dissolved in 4 mL DMSO (HPLC grade)<br>Collection: peak controlled, threshold only (DAD). 25 min. run. The gradient was 5% B for 0.5 min then 5%-100% in 20 min with a hold at 100% for 5 min. then 100%-5% in 0.15 min. Flow 40 mL/min. |
| d | HPLC conditions:<br>Mobile Phase A: Water (10 mmol $NH_4HCO_3$)<br>Mobile Phase B: MeCN<br>Column: XBridge Prep C18 OBD, 19 × 250 mm, 10 μm<br>Detection methods are UV at 214/254 nm<br>The gradient was 45-55% B in 8.0 min, stop at 14.0. Flow Rate 30.00 mL/min. |
| e | HPLC conditions:<br>Mobile Phase A: Water (10 mmol $NH_4HCO_3$)<br>Mobile Phase B: MeCN<br>Column: XBridge Prep C18 OBD, 19 × 250 mm, 10 μm<br>Detection methods are UV at 214/254 nm<br>The gradient was 30-60% B in 8.0 min, stop at 13.0. Flow Rate 30.00 mL/min. |

TABLE 3

Chiral chromatography methods
HPLC used for prep chiral LC consist of the following modules:
2—Varian 218 LC pumps (25 mL pump heads)
1—Varian CVM 500 with switching valves and heaters for automatic solvent, column and temperature control
1—Varian 701 Fraction collector

| Method | Conditions |
|---|---|
| 1 | The gradient was 35% to 65% A for 9.3 min (20 mL/min flow rate) and then to 75% A over the next 8.7 min.. Mobile phase A was HPLC grade isopropanol, mobile phase B was HPLC grade heptane with 0.12% diethylamine added. The column used for the chromatography was a Daicel IC, 20 × 250 mm column (5 μm particles). Detection methods were evaporative light scattering (ELSD) detection as well as optical rotation. |
| 2 | The gradient was 4-8% A in 30 min (20 mL/min flow rate). Mobile phase A was HPLC grade isopropanol, mobile phase B was HPLC grade heptane with 0.12% diethylamine added. The column used for the chromatography was a Daicel IC, 20 × 250 mm column (5 μm particles). Detection methods were evaporative light scattering (ELSD) detection as well as optical rotation. |
| 3 | Isocratic 10% A for 16 min (20 mL/min flow rate). Mobile phase A was HPLC grade isopropanol, mobile phase B was HPLC grade heptane with 0.12% diethylamine added. The column used for the chromatography was a Daicel IA, 20 × 250 mm column (5 μm particles). Detection methods were evaporative light scattering (ELSD) detection as well as optical rotation. |
| 4 | The gradient was 10-50% A in 20 min with a hold at 50% for 3 min, then to 75% over the next 11 min (20 mL/min flow rate). Mobile phase A was HPLC grade isopropanol, mobile phase B was HPLC grade heptane with 0.12% diethylamine added. The column used for the chromatography was a Daicel IC, 20 × 250 mm column (5 μm particles). Detection methods were evaporative light scattering (ELSD) detection as well as optical rotation. |
| 5 | The gradient was 1% to 6% A in 18 min (20 mL/min flow rate). Mobile phase A was EtOH (200 proof), mobile phase B was HPLC grade heptane with 0.12% diethylamine added. The column used for the chromatography was a Daicel IA, 20 × 250 mm column (5 μm particles). Detection methods were evaporative light scattering (ELSD) detection as well as optical rotation. |
| 6 | The gradient was 15% to 85% A for 24 min (20 mL/min flow rate). Mobile phase A was a 50:50 mixture of HPLC grade MeOH and EtOH (200 proof), mobile phase B was HPLC grade heptane with 0.12% diethylamine added. The column used for the chromatography was a Daicel IC, 20 × 250 mm column (5 μm particles). Detection methods were evaporative light scattering (ELSD) detection as well as optical rotation. |
| 7 | The gradient was 5-15% A in 40 min (20 mL/min flow rate). Mobile phase A was IPA (200 proof), mobile phase B was HPLC grade heptane with 0.12% diethylamine added. The column used for the chromatography was a Daicel IC, 20 × 250 mm column (5 μm |

TABLE 3-continued

Chiral chromatography methods
HPLC used for prep chiral LC consist of the following modules:
2—Varian 218 LC pumps (25 mL pump heads)
1—Varian CVM 500 with switching valves and heaters for automatic solvent,
column and temperature control
1—Varian 701 Fraction collector

| Method | Conditions |
|---|---|
| | particles). Detection methods were evaporative light scattering (ELSD) detection as well as optical rotation. |
| 8 | The gradient was 5-7% A in 50 min (20 mL/min flow rate). Mobile phase A was HPLC grade IPA, mobile phase B was HPLC grade heptane with 0.12% diethylamine added. The column used for the chromatography was a Daicel IC, 20 × 250 mm column (5 μm particles). Detection methods were evaporative light scattering (ELSD) detection as well as optical rotation. |
| 9 | Diastereomers were separated using SFC/MS system. The gradient was isocratic 5% A in 35 min (20 mL/min flow rate). Mobile phase A was EtOH (200 proof), mobile phase B was HPLC grade heptane with 0.12% diethylamine added. The chromatography used a Viridis 2-ethylpyridine OBD 30 × 100 mm column (5 μm particles) from Waters Corporation. The first diastereomer was collected at 21.2 min. and the second at 30.3 min. Enantiomers of the first diastereomer (M.14 and M.16) were separated using the gradient of 2 to 35% A in 40 min. then step to 60% A in 4 min. (20 mL/min flow rate). Mobile phase A was 200 proof EtOH, mobile phase B was HPLC grade heptane with 0.12% diethylamine added. The column used for the chromatography was a Daicel IA 20 × 250 mm column (5 μm particles). Detection methods were evaporative light scattering (ELSD) detection as well as optical rotation. Enantiomers of the second diastereomer (M.15 and M.17) were separated using isocratic 10% A in 22.3 min (20 mL/min flow rate) then step to 60% A for 5 min, then re-equilbrate at 10% A for 4 min. Mobile phase A was HPLC grade isopropanol, mobile phase B was HPLC grade heptane with 0.12% diethylamine added. The column used for the chromatography was a Daicel ID, 20 × 250 mm column (5 μm particles). Detection methods were evaporative light scattering (ELSD) detection as well as optical rotation. |
| 10 | The gradient was 5-20% A in 45 min, then to 65% A over the next 2 min., then hold at 65% A for 9 min. (20 mL/min flow rate). Mobile phase A was HPLC grade i-PrOH, mobile phase B was HPLC grade heptane with 0.12% diethylamine added. The column used for the chromatography was a Daicel IA 20 × 250 mm column (5 μm particles). Detection methods were evaporative light scattering (ELSD) detection as well as optical rotation. |
| 11 | Isocratic 5% A for 12 min (20 mL/min flow rate). Mobile phase A was EtOH (200 proof), mobile phase B was HPLC grade heptane with 0.12% diethylamine added. The column used for the chromatography was a Daicel IA, 20 × 250 mm column (5 μm particles). Detection methods were evaporative light scattering (ELSD) detection as well as optical rotation. |
| 12 | The gradient was 30-70% A in 9.3 min., then to 75% over the next 8.7 min. (20 mL/min flow rate). Mobile phase A was HPLC grade i-PrOH, mobile phase B was HPLC grade heptane with 0.12% diethylamine added. The column used for the chromatography was a Daicel IA 20 × 250 mm column (5 μm particles). Detection methods were evaporative light scattering (ELSD) detection as well as optical rotation. |
| 13 | The gradient was 15% to 85% A for 24 min (20 mL/min flow rate) then to 50% in the next 0.2 min. and hold for 3.8 min. Mobile phase A was a 50:50 mixture of HPLC grade MeOH and EtOH (200 proof), mobile phase B was HPLC grade heptane with 0.12% diethylamine added. The column used for the chromatography was a Daicel IC, 20 × 250 mm column (5 μm particles). Detection methods were evaporative light scattering (ELSD) detection as well as optical rotation. |
| 14 | The gradient was 15% to 29% A for 12.8 min (20 mL/min flow rate) then 29% to 60% A for 0.1 min (20 mL./min flow rate) then held at 60% A for 4.1 min (20 mL/min flow rate). Mobile phase A was HPLC grade i-PrOH, mobile phase B was HPLC grade heptane with 0.12% diethylamine added. The column used for the chromatography was a Daicel IC, 20 × 250 mm column (5 μm particles). Detection method was UV at 252 nm. |
| 15 | The gradient was 10% to 20% A for 10 min (20 mL/min flow rate) then 20% to 45% A for 5 min (20 mL./min flow rate). Mobile phase A was HPLC grade i-PrOH, mobile phase B was HPLC grade heptane with 0.12% diethylamine added. The column used for the chromatography was a Daicel XX, 20 × 250 mm column (5 μm particles). Detection method was UV at 254 nm. |
| 16 | The method was isocratic 30% B for 14 min (20 ml/min flow rate). Mobile phase A was HPLC grade i-PrOH, mobile phase B was HPLC grade heptane with 0.12% diethylamine added. The column used for the chromatography was a Daicel ID, 20 × 250 mm column (5 μm particles). Detection method was UV at 250 nm. |
| 17 | The gradient was 15% to 24% A for 22 min (20 mL/min flow rate) then 24% to 60% A for 0.1 min (20 mL./min flow rate) then held at 60% A for 2.9 min (20 mL/min flow rate). Mobile phase A was HPLC grade i-PrOH, mobile phase B was HPLC grade heptane with 0.12% diethylamine added. The column used for the chromatography was a Daicel IC, 20 × 250 mm column (5 μm particles). Detection method was UV at 247 nm. |
| 18 | The method was isocratic with 20% A for 18 min (20 mL/min flow rate). Mobile phase A was HPLC grade i-PrOH, mobile phase B was HPLC grade heptane with 0.12% diethylamine added. The column used for the chromatography was a Daicel IC, 20 × 250 mm column (5 μm particles). Detection method was UV at 280 nm. |
| 19 | The method was isocratic with 2% A for 40 min (20 mL/min flow rate). Mobile phase A was EtOH, mobile phase B was HPLC grade heptane with 0.2% diethylamine added. |

TABLE 3-continued

Chiral chromatography methods
HPLC used for prep chiral LC consist of the following modules:
2—Varian 218 LC pumps (25 mL pump heads)
1—Varian CVM 500 with switching valves and heaters for automatic solvent,
column and temperature control
1—Varian 701 Fraction collector

| Method | Conditions |
|---|---|
|  | The column used for the chromatography was a Daicel IB, 20 × 250 mm column (5 μm particles). Detection method was UV at 280 nm. |
| 20 | The method was isocratic with 25% A for 20 min (20 mL/min flow rate). Mobile phase A was HPLC grade i-PrOH, mobile phase B was HPLC grade heptane with 0.12% diethylamine added. The column used for the chromatography was a Daicel IC, 20 × 250 mm column (5 μm particles). Detection method was UV at 280 nm. |
| 21 | The method was isocratic with 8% A for 21 min (20 mL/min flow rate). Mobile phase A was EtOH, mobile phase B was HPLC grade heptane with 0.12% diethylamine added. The column used for the chromatography was a Daicel IB, 20 × 250 mm column (5 μm particles). Detection method was UV at 240 nm. |
| 22 | The gradient was 10% to 20% A for 24 min (20 mL/min flow rate). Mobile phase A was EtOH, mobile phase B was HPLC grade heptane with 0.12% diethylamine added. The column used for the chromatography was a Daicel IC, 20 × 250 mm column (5 μm particles). Detection method was UV at 280 nm. |
| 23 | The gradient was 5% to 20% A for 26 min (20 mL/min flow rate). Mobile phase A was EtOH, mobile phase B was HPLC grade heptane with 0.12% diethylamine added. The column used for the chromatography was a Daicel IB, 20 × 250 mm column (5 μm particles). Detection method was UV at 280 nm. |
| 24 | The gradient was 20% to 32% A for 20 min (20 mL/min flow rate). Mobile phase A was HPLC grade i-PrOH, mobile phase B was HPLC grade heptane with 0.12% diethylamine added. The column used for the chromatography was a Daicel IC, 20 × 250 mm column (5 μm particles). Detection method was UV at 280 nm. |
| 25 | The method was isocratic with 15% A for 12 min (20 mL/min flow rate). Mobile phase A was EtOH, mobile phase B was HPLC grade heptane with 0.12% diethylamine added. The column used for the chromatography was a Daicel ID, 20 × 250 mm column (5 μm particles). Detection method was UV at 250 nm. |
| 26 | The gradient was a step gradient of 7% B for 21 min followed by 30% B for 25 min (20 ml/min flow rate). Mobile phase A was EtOH, mobile phase B was HPLC grade heptane with 0.12% diethylamine added. The column used for the chromatography was a Daicel IB, 20 × 250 mm column (5 μm particles). Detection method was UV at 250 nm. |
| 27 | The method was isocratic with 20% A for 9.5 min (20 mL/min flow rate). Mobile phase A was EtOH, mobile phase B was HPLC grade heptane with 0.12% diethylamine added. The column used for the chromatography was a Daicel IC, 20 × 250 mm column (5 μm particles). Detection method was UV at 250 nm. |
| 28 | The gradient was 5-21% B in 33 min (20 mL/min flow rate). Mobile phase B was EtOH (200 proof) and mobile phase A was HPLC grade heptane with 0.20% diethylamine added. The column used for the chromatography was a Daicel IC, 20 × 250 mm column (5 μm particles). Detection method was UV at 263 nm. |
| 29 | The method was isocratic with 20% B for 25 (20 mL/min flow rate). Mobile phase B was IPA (HPLC grade) and mobile phase A was HPLC grade heptane with 0.20% diethylamine added. The column used for the chromatography was a Daicel IC, 20 × 250 mm column (5 μm particles). Detection method was UV at 256 nm. |
| 30 | The gradient was 17-30% B in 25 min then increased to 50% B in 6 min and held at 50% B for 4 min. The method is then equilibrated back down to 17% and held for 5 mins. The flow rate is (20 mL/min). Mobile phase B was HPLC grade isopropanol and mobile phase A was HPLC grade heptane with 0.125% diethylamine added. The column used for the chromatography was a Daicel IC, 20 × 250 mm column (5 μm particles). Detection method was UV (=250 nm) |
| 31 | (LC) Isocratic 10% A for 25 min then step to 30% A for 6 min (20 mL/min flow rate). Mobile phase A was HPLC grade isopropanol, mobile phase B was HPLC grade heptane with 0.1% diethylamine added. The chromatography used a Daicel ID, 21 × 250 mm column (5 μm particles) |
| 32 | The method was isocratic with 13% B for 37 min (23.5 mL/min flow rate). Mobile phase B was EtOH, mobile phase A was HPLC grade heptane with 0.2% diethylamine added. The column used for the chromatography was a Daicel IB, 20 × 250 mm column (5 μm particles). Detection method was UV at 250 nm. |
| 33 | The gradient was 18% B (isocratic) for 40 min then increase to 40% B and hold for 5 min. After 5 min equilibrate to 18% B and hold for 5 min. (20 mL/min flow rate). Mobile phase B was EtOH (200 Proof) and mobile phase A was HPLC grade heptane with 0.20% diethylamine added. The column used for the chromatography was a Daicel IC, 20 × 250 mm column (5 μm particles). Detection method was UV (=280 nm) |
| 34 | The gradient was 30% B (isocratic) for 23 min then increase to 50% B and hold for 9 min. After 9 min equilibrate to 30% B and hold for 3 min. Mobile phase B was EtOH (200 Proof) and mobile phase A was HPLC grade heptane with 0.20% diethylamine added. The column used for the chromatography was a Daicel IB, 20 × 250 mm column (5 μm particles). Detection method was UV (=280 nm) |
| 35 | The gradient was 5% B for 35 min, then 5-6.5% B over 15 min, then decreased to 5% B over 0.1 min and held at 5% B for 3.9 min (20 mL/min flow rate). Mobile phase A was HPLC grade heptane with 0.1% diethylamine added. Mobile phase B was HPLC grade i-PrOH. The column used for the chromatography was a Daicel IA, 20 × 250 mm column (5 μm particles). Detection method was UV (=230 nm). |

TABLE 3-continued

Chiral chromatography methods
HPLC used for prep chiral LC consist of the following modules:
2—Varian 218 LC pumps (25 mL pump heads)
1—Varian CVM 500 with switching valves and heaters for automatic solvent, column and temperature control
1—Varian 701 Fraction collector

| Method | Conditions |
|---|---|
| 36 | The gradient was 30-45% A over 60 min (20 mL/min flow rate). Mobile phase A was HPLC grade i-PrOH, mobile phase B was HPLC grade heptane with 0.2% diethylamine added. The column used for the chromatography was a WhelkO1 RR (Regis technologies) column, 21 × 250 mm (5 μm particles). Detection method was UV (=280 nm). |
| 37 | The gradient was 15% B for 28 min, then 15-50% B over 6 min, then decreased to 15% B over 0.1 min and held at 15% B for 4 min (20 mL/min flow rate). Mobile phase A was HPLC grade heptane with 0.2% diethylamine added. Mobile phase B was EtOH (200 proof). The column used for the chromatography was a Daicel IC column, 20 × 250 mm (5 μm particles). Detection method was UV (=251 nm). |
| 38 | The gradient was 25% A for 28 min (20 mL/min flow rate). Mobile phase A was HPLC grade i-PrOH, mobile phase B was HPLC grade heptane with 0.12% diethylamine added. The column used for the chromatography was a Daicel ID column, 21 × 250 mm (5 μm particles). |
| 39 | Isocratic 13% for 21 min (20 mL/min flow rate). Mobile phase A was EtOH (200 proof), mobile phase B was HPLC grade heptane with 0.1% diethylamine added. The column used for the chromatography was a Daicel IB column, 20 × 250 mm (5 μm particles). |
| 40 | The gradient was 5-65% A for 29.3 min (20 mL/min flow rate) and then hold for 10.7 min. Mobile phase A was ethanol, mobile phase B was HPLC grade heptane with 0.12% diethylamine added. The column used for the chromatography was a Daicel ID, 20 × 250 mm column (5 μm particles). Detection methods were evaporative light scattering (ELSD) detection as well as optical rotation. |
| 41 | The gradient was 5-35% A in 300 min (20 mL/min flow rate) and then hold for 4 min. Mobile phase A was HPLC grade isopropanol with 0.1% diethylamine, mobile phase B was HPLC grade heptane with 0.125% diethylamine added. The column used for the chromatography was a Daicel IA, 20 × 250 mm column (5 μm particles). Detection methods were evaporative light scattering (ELSD) detection as well as optical rotation. |
| 42 | The gradient was 3-24% A in 25 min, then to 50% over 0.1 min and a hold at 50% for 5 min (23.8 mL/min flow rate). Mobile phase A was HPLC grade isopropanol, mobile phase B was HPLC grade heptane with 0.12% diethylamine added. The column used for the chromatography was a Daicel IA, 20 × 250 mm column (5 μm particles). Detection methods were evaporative light scattering (ELSD) detection as well as optical rotation. |
| 43 | The gradient was 3-19.6% A in 40 min, then to 30% over 0.1 min and a hold at 30% for 5 min (23.8 mL/min flow rate). Mobile phase A was HPLC grade isopropanol, mobile phase B was HPLC grade heptane with 0.12% diethylamine added. The column used for the chromatography was a Daicel IA, 20 × 250 mm column (5 μm particles). Detection methods were evaporative light scattering (ELSD) detection as well as optical rotation. |

Assays

Methods:

GR Fluorescence Polarization Assay

Fluorescence polarization assays were carried out using the PolarScreen™ Glucocorticoid Receptor Competitor Assay, Red from Invitrogen (P2893). The assay buffer was prepared according to the manufacturer's protocol and used to dilute the fluorescent glucocorticoid and GR. Compounds were prepared and serial diluted 1:4 in DMSO. Compound, fluorescent glucocorticoid and GR were added in a final volume of 20 μL and incubated overnight at 4° C. Fluorescent polarization was measured on the PerkinElmer Envision®.

A549 Cell Assay to Measure Inflammation Markers

A549 cells were seeded (3E4 cells/well) in 96-well assay plates in culture medium (100 μL/well., F-12 K base media, supplemented with 10% FBS and 100 μg/mL-100 μg/mL Pen-Strep.) After overnight culture in an incubator set to 37° C., 4.9% $CO_2$, and 90% humidity, media was removed from adherent cells by aspiration and replaced with 100 μL/well Assay Medium (F-12 K base media supplemented with 5% charcoal stripped calf sera and 100 U/mL-100 μg/mL Pen-Strep.) Compounds were prepared in DMSO and serial diluted (1:3, 1:4, or 1:5) with DMSO in Dilution Plate(s) to give 10 dilution points for each compound tested. Further dilution (1:250) of compound was made into assay medium and 50 μL/well diluted drug or DMSO/media control was applied to cells. After a 1 h pre-incubation in a temperature, $CO_2$, and humidity controlled incubator, set to 37° C., 50 μL/well of 4 ng/mL IL-1β diluted in assay media, was applied to cultures. Assay plates, with a final volume of 200 μL/well and final concentrations of 0.1% DMSO and 1 ng/mL IL-1β were returned to incubator for a fourth incubation period. Next, plates were spun at 183 g (1000 rpm in Beckman/Coulter Allegra 6KR centrifuge) for 10 min. Cell-free supernatant (150 μL/well) was collected and IL-6 was measured by MSD kit, following protocol of manufacturer, and using MSD SECTOR Imager 6000 instrument. Potency of compounds to inhibit IL-6 was determined using the percent reduction of measured IL-6 in wells with compound compared to control wells without drug, and relative to (100% inhibition) positive control compound of 10 M prednisolone. Results were represented as $IC_{50}$ and Emax values. To verify that viable cell numbers were similar across plate(s), and not confounding compound $IC_{50}$ data interpretation, the remaining 50 μL/well of cells and media (after removal of supernatant) were used to run Cell Titer-Glo Assay per directions of manufacturer.

Preparation #1: methyl 4-bromopyridine-2-carboxylate

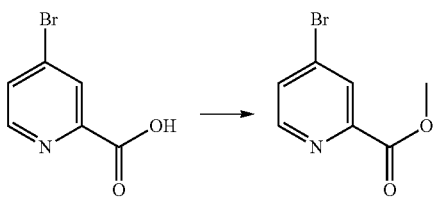

To a solution of 4-bromopyridine-2-carboxylic acid (0.5 g, 2.5 mmol, Apollo Scientific) in a mixture of ethyl acetate (15 mL) and methanol (1.5 mL), was added dropwise a solution of trimethylsilyldiazomethane (3.7 mL, 2 M in diethyl ether, 7.4 mmol), at about 0° C. After the addition was complete the temperature was raised to rt and the mixture stirred for about another 1.5 h at rt. The resulting mixture was concentrated in vacuo and diethyl ether (25 mL) was added to the residue. The resulting mixture was filtered and concentrated in vacuo. The residue was purified by column chromatography (SiO$_2$, diethyl ether/hexanes 1:1) to give methyl 4-bromopyridine-2-carboxylate (0.39 g, 1.8 mmol, 73%) as a pale yellow solid: $^1$H-NMR (CDCl$_3$, Bruker 400 MHz) δ 4.03 (3H, s), 7.67 (1H, dd, J=5.0, 1.6 Hz), 8.31 (1H, d, J=1.6 Hz), 8.57 (1H, d, J=5.0 Hz).

Preparation #2: 4-(4-chloro-2-methyl-phenyl)-1-methyl-3-(1H-pyrazol-5-yl)-4,6,7,8-tetrahydropyrazolo[3,4-e][1,4]thiazepine

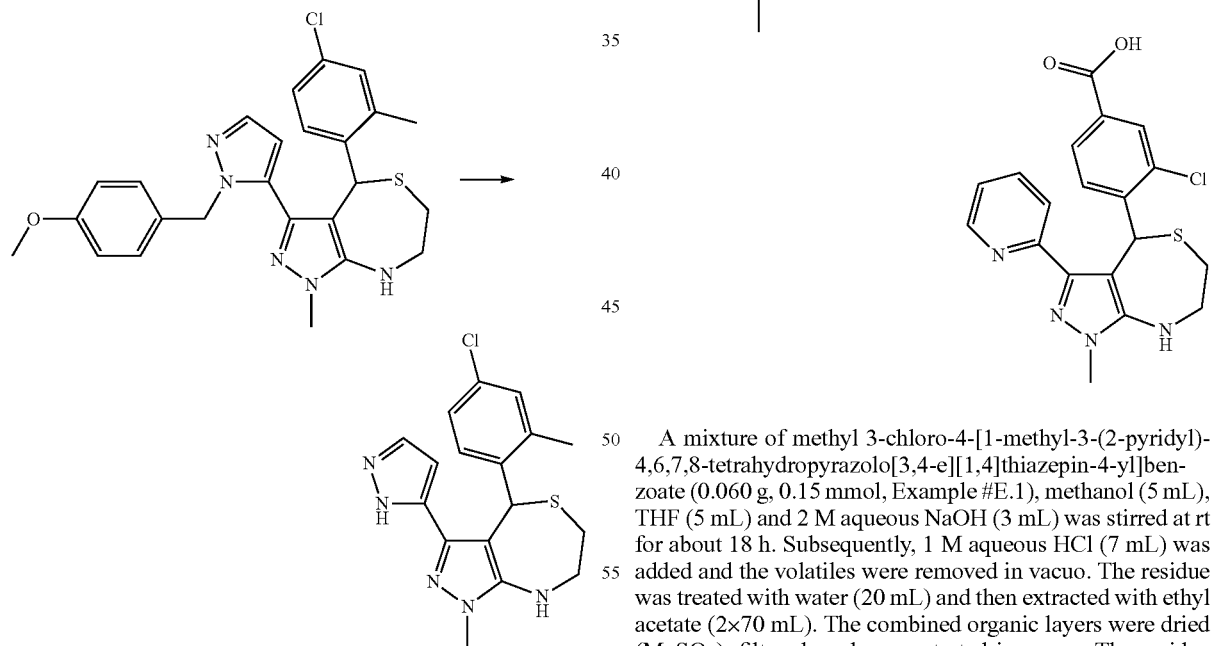

To 4-(4-chloro-2-methyl-phenyl)-3-[2-[(4-methoxyphenyl)methyl]pyrazol-3-yl]-1-methyl-4,6,7,8-tetrahydropyrazolo[3,4-e][1,4]thiazepine (0.32 g, 0.67 mmol, prepared using A with ethyl 1-(4-methoxybenzyl)-1H-pyrazole-5-carboxylate (WO2011079076), B with methylhydrazine, C with thioglycolic acid and 4-chloro-2-methylbenzaldehyde (Fluorochem) and D) was added trifluoroacetic acid (5 mL). The resulting mixture was heated, in a sealed microwave vessel, for about 10 min, at about 140° C., in a microwave. After cooling to rt the mixture was made basic (pH ~8) with 2 M aqueous NaOH and extracted with ethyl acetate. The organic layer was dried (MgSO$_4$), filtered and concentrated in vacuo. The resulting residue was purified by column chromatography (SiO$_2$, ethyl acetate) to give 4-(4-chloro-2-methyl-phenyl)-1-methyl-3-(1H-pyrazol-3 or 5-yl)-4,6,7,8-tetrahydropyrazolo[3,4-e][1,4]thiazepine (0.151 g, 0.42 mmol, 63%) as an off white solid: LC-MS (Table 1, Method e) R$_t$=2.83 min, m/z 360 (M+H)$^+$; $^1$H-NMR (CDCl$_3$, Bruker 400 MHz) 2.54 (3H, s) 2.64-2.72 (1H, m) 2.77-2.86 (1H, m) 3.21-3.31 (1H, m) 3.54-3.63 (1H, m) 3.77-3.83 (1H, br s) 3.81 (3H, s) 5.69 (1H, br. S.) 6.18 (1H, br s) 7.04 (1H, dd, J=8.5, 2.0 Hz) 7.08 (1H, d, J=8.5 Hz) 7.20 (1H, br s) 7.47 (1H, d, J=2.0 Hz) 10.1 (1H, br s).

Preparation #3: 3-chloro-4-[1-methyl-3-(2-pyridyl)-4,6,7,8-tetrahydropyrazolo[3,4-e][1,4]thiazepin-4-yl]benzoic acid

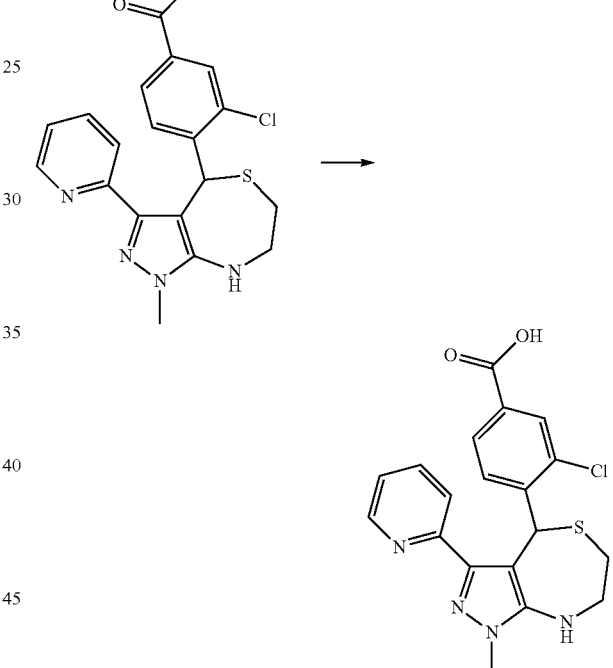

A mixture of methyl 3-chloro-4-[1-methyl-3-(2-pyridyl)-4,6,7,8-tetrahydropyrazolo[3,4-e][1,4]thiazepin-4-yl]benzoate (0.060 g, 0.15 mmol, Example #E.1), methanol (5 mL), THF (5 mL) and 2 M aqueous NaOH (3 mL) was stirred at rt for about 18 h. Subsequently, 1 M aqueous HCl (7 mL) was added and the volatiles were removed in vacuo. The residue was treated with water (20 mL) and then extracted with ethyl acetate (2×70 mL). The combined organic layers were dried (MgSO$_4$), filtered, and concentrated in vacuo. The residue was purified by prep-HPLC (Table 2, Method a) to give 3-chloro-4-[1-methyl-3-(2-pyridyl)-4,6,7,8-tetrahydropyrazolo[3,4-e][1,4]thiazepin-4-yl]benzoic acid (0.016 g, 0.04 mmol, 27%) as an off white solid: LC-MS (Table 1, Method a) R$_t$=3.0 min; m/z 401 (M+H)$^+$; $^1$H-NMR (CDCl$_3$, Bruker 400 MHz) δ 2.58-2.75 (2H, m) 3.06 (1H, t, J=11.8 Hz) 3.68-3.76 (1H, m) 3.77 (3H, s) 5.82 (1H, d) 7.03 (1H, s) 7.14-7.18 (1H, m) 7.42 (1H, d, J=8.0 Hz) 7.66-7.72 (2H, m) 7.79 (1H, d, J=8.0 Hz) 7.89 (1H, d, J=1.7 Hz) 8.43-8.48 (1H, m).

Preparation #3.1: 6-[4-(2,4-dichlorophenyl)-1-methyl-4,6,7,8-tetrahydropyrazolo[3,4-e][1,4]thiazepin-3-yl]pyridine-3-carboxylic acid

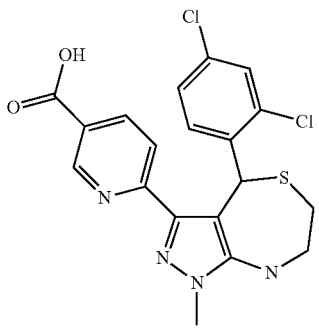 [SMILES: Cn1nc(-c2ccc(C(=O)O)cn2)c2c1NCCSC2c1ccc(Cl)cc1Cl]

The compound was prepared by a similar procedure as Preparation #3 from Example # E.6: LC-MS (Table 1, Method b) $R_t$=3.10 min; m/z 435 (M+H)$^+$; $^1$H-NMR (DMSO-d$_6$, Bruker 400 MHz) δ 2.57-2.78 (2H, m), 3.06 (1H, t, J=11.9 Hz), 3.66-3.76 (1H, m) 3.78 (3H, s) 5.87 (1H, d, J=5.5 Hz) 6.98 (1H, s) 7.21 (1H, dd, J=2.2, 8.4 Hz) 7.30 (1H, d, J=8.5 Hz) 7.48 (1H, d, J=2.2 Hz) 7.92 (1H, d, J=8.3 Hz) 8.16 (1H, dd, J=2.3, 8.3 Hz) 8.95 (1H, br.d, J=1.9 Hz) 13.15 (1H, br s).

Preparation #4: 1-[4-[1-methyl-3-(2-pyridyl)-4,6,7,8-tetrahydropyrazolo[3,4-e][1,4]thiazepin-4-yl]-1-piperidyl]ethanone

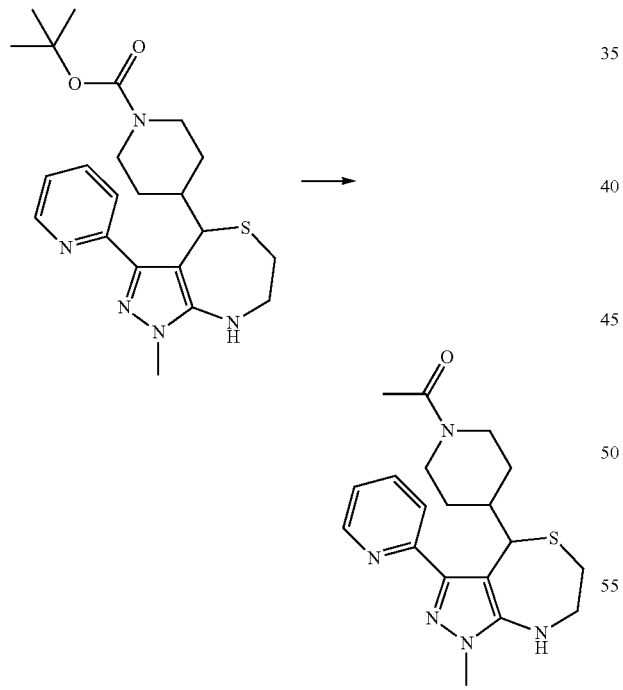

Acetyl chloride (0.3 mL, 4.2 mmol) was added dropwise to methanol (20 mL), at about 0° C. Tert-butyl 4-[1-methyl-3-(2-pyridyl)-4,6,7,8-tetrahydropyrazolo[3,4-e][1,4]thiazepin-4-yl]piperidine-1-carboxylate (0.45 g, 1.1 mmol, prepared using General Procedure C from Example #2 step B with 1-Boc-piperidine-4-carboxaldehyde and thioglycolic acid followed by D) was added in portions and the resulting mixture was stirred at rt overnight. Subsequently, the mixture was concentrated in vacuo to afford 1-methyl-4-(4-piperidyl)-3-(2-pyridyl)-4,6,7,8-tetrahydropyrazolo[3,4-e][1,4]thiazepine dihydrochloride (0.10 g, 0.25 mmol) as a yellow solid which was used as such.

To a mixture of 1-methyl-4-(4-piperidyl)-3-(2-pyridyl)-4,6,7,8-tetrahydropyrazolo[3,4-e][1,4]thiazepine dihydrochloride (0.10 g, 0.25 mmol) and N,N-diisopropylethylamine (0.14 mL, 0.8 mmol) in DCM (20 mL) was added dropwise a solution of acetyl chloride (0.018 mL, 0.25 mmol) in DCM (2 mL), at about −10° C. The resulting mixture was stirred at about −10° C. for about 2 h and about 1 h at rt, then water (10 mL) and DCM (20 mL) were added. The layers were separated and the organic layer was washed with water (10 mL) and brine (10 mL), dried (MgSO$_4$), filtered and concentrated in vacuo. The residue was purified by column chromatography (SiO$_2$, DCM/methanol 95:5) to give 1-[4-[1-methyl-3-(2-pyridyl)-4,6,7,8-tetrahydropyrazolo[3,4-e][1,4]thiazepin-4-yl]-1-piperidyl]ethanone (0.090 g, 97%) as a white solid: LC-MS (Table 1, Method a) $R_t$=1.60 min; m/z 372 (M+H)$^+$; $^1$H-NMR (CDCl$_3$, Bruker 400 MHz) (The spectrum is described as a 1:1 mixture of two compounds ('rotamers'), each contributing 25 protons) δ 1.11 (1H, td, J=12.4, 4.3 Hz) 1.17-1.37 (4H, m) 1.38-1.50 (2H, m) 2.01 (3H, s) 2.07 (3H, s) 2.08-2.28 (4H, m) 2.39 (1H, td, J=12.7, 2.9 Hz) 2.65-2.74 (2H, m) 2.86 (1H, td, J=12.8, 2.9 Hz) 2.96-3.13 (5H, m) 3.39-3.54 (4H, m) 3.65 (1H, br. d, J=13.6 Hz) 3.77 (3H, s) 3.78 (3H, s) 3.84 (1H, br. d, J=13.6 Hz) 4.40 (1H, br. d, J=13.5 Hz) 4.63 (1H, br. d, J=13.7 Hz) 5.04 (1H, d, J=9.5 Hz) 5.06 (1H, d, J=9.9 Hz) 7.11-7.17 (2H, m) 7.63-7.69 (2H, m) 7.84-7.92 (2H, m) 8.50-8.56 (2H, m).

Preparation #5: (2-methyl-3-pyridyl)-[4-[1-methyl-3-(2-pyridyl)-4,6,7,8-tetrahydropyrazolo[3,4-e][1,4]thiazepin-4-yl]-1-piperidyl]methanone

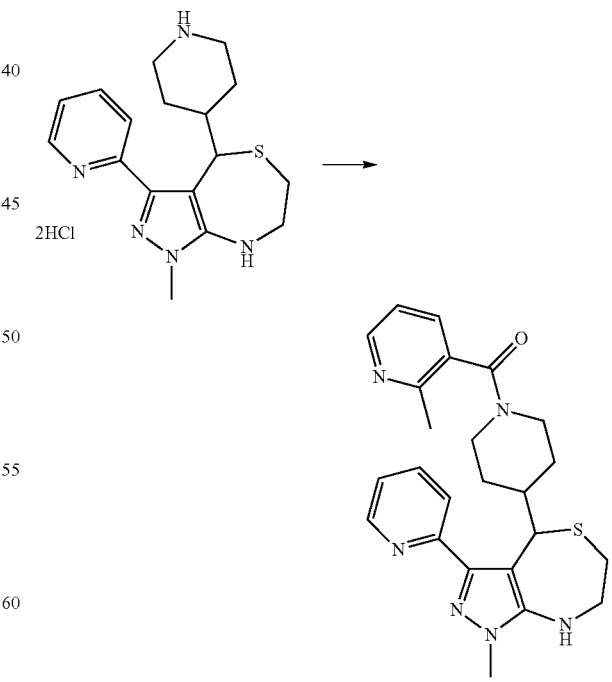

A mixture of 1-methyl-4-(4-piperidyl)-3-(2-pyridyl)-4,6,7,8-tetrahydropyrazolo[3,4-e][1,4]thiazepine dihydrochloride (0.10 g, 0.25 mmol, Preparation #4), 2-methylpyridine- 3-carboxylic acid (0.0341 g, 0.25 mmol), N-(3-Dimethylaminopropyl)-N'-ethylcarbodiimide hydrochloride (0.072 g, 0.37 mmol), 1-hydroxybenzotriazole hydrate (0.0505 g, 0.37 mmol) and N,N-diisopropylethylamine (0.22 mL, 1.25 mmol) in DCM (50 mL) was stirred overnight at rt. Then the mixture was concentrated in vacuo and purified by column chromatography (SiO$_2$, DCM/methanol/ammonium hydroxide 92:7.5:0.5) to give (2-methyl-3-pyridyl)-[4-[1-methyl-3-(2-pyridyl)-4,6,7,8-tetrahydropyrazolo[3,4-e][1,4]thiazepin-4-yl]-1-piperidyl]methanone (0.080 g, 71%) as an off white solid: LC-MS (Table 1, Method a) R$_t$=1.50 min; m/z 449 (M+H)$^+$; $^1$H-NMR (CDCl$_3$, Bruker 400 MHz) 1.17-1.39 (2H, m) 1.44-1.64 (1H, m) 2.08-3.14 (10H, m) 3.22-3.55 (3H, m) 3.74-3.77 (3H, s) 4.58-4.78 (1H, br.d, J=13.0 Hz) 5.06-5.16 (1H, m) 7.05-7.20 (2H, m) 7.36-7.55 (1H, m) 7.62-7.72 (1H, m) 7.89 (1H br.t, J=9.0 Hz) 8.43-8.59 (2H, m).

Preparation #6: N-(2-methyl-3-pyridyl)-4-[1-methyl-3-(2-pyridyl)-4,6,7,8-tetrahydropyrazolo[3,4-e][1,4]thiazepin-4-yl]piperidine-1-carboxamide

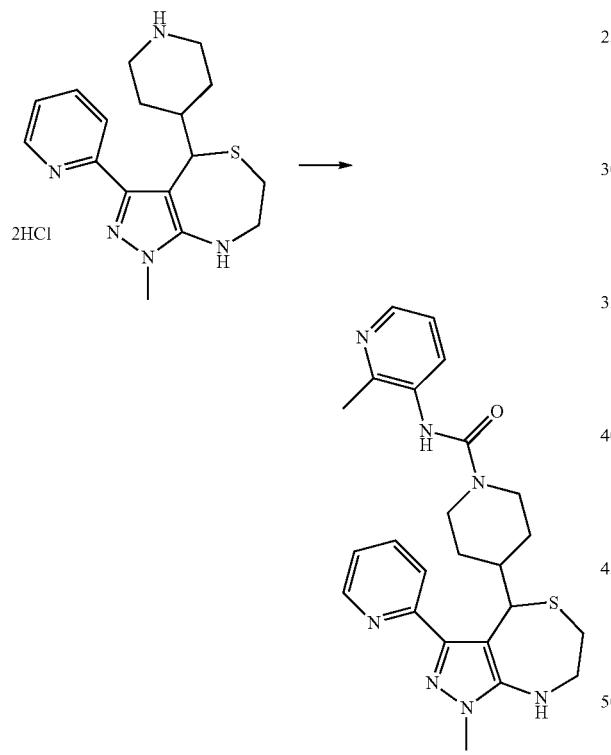

To a mixture of triphosgene (0.017 g, 0.056 mmol) and 3-amino-2-methylpyridine (0.018 g, 0.17 mmol) in anhydrous THF (5 mL) was added dropwise triethylamine (0.14 mL, 1 mmol), at about 0° C. After stirring for about 5 min at about 0° C., 1-methyl-4-(4-piperidyl)-3-(2-pyridyl)-4,6,7,8-tetrahydropyrazolo[3,4-e][1,4]thiazepine dihydrochloride (0.07 g, 0.17 mmol, Preparation #4) was added at about 0° C. Subsequently, the mixture was stirred for about 1 h and allowed to come to rt. Then the mixture was diluted with ethyl acetate (10 mL), washed with water (10 mL) and brine (10 mL), dried (MgSO$_4$), filtered and concentrated in vacuo. The residue was purified by column chromatography (SiO$_2$, DCM/methanol/ammonium hydroxide 92:7.5:0.5) to give N-(2-methyl-3-pyridyl)-4-[1-methyl-3-(2-pyridyl)-4,6,7,8-tetrahydropyrazolo[3,4-e][1,4]thiazepin-4-yl]piperidine-1-carboxamide (0.03 g, 0.065 mmol, 26%) as an off white solid: LC-MS (Table 1, Method b) R$_t$=2.00 min; m/z 464 (M+H)$^+$.

Preparation #7

5-methoxy-2-methyl-benzaldehyde

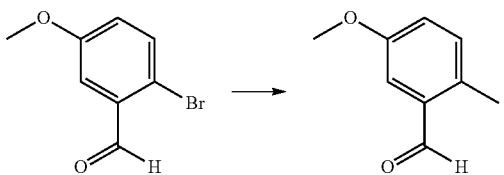

To a degassed solution of 2-bromo-5-methoxybenzaldehyde (1.5 g, 7.04 mmol, Fluorochem) and trimethylboroxine (0.98 mL, 7.04 mmol) in 1,4-dioxane (80 mL) was added potassium carbonate (2.91 g, 21.1 mmol) and tetrakis(triphenylphosphine)palladium(0) (0.813 g, 0.70 mmol). The mixture was heated under reflux for about 20 h, then more tetrakis(triphenylphosphine)palladium(0) (0.200 g, 0.17 mmol) and trimethylboroxine (0.25 mL, 1.8 mmol) were added and the mixture was heated under reflux for about another 3 h. After cooling to rt the mixture was filtered over diatomaceous earth and concentrated in vacuo. The residue was purified by column chromatography (SiO$_2$, diethyl ether/hexanes 1:3) to give 5-methoxy-2-methyl-benzaldehyde (0.97 g, 92%) as a colorless liquid. $^1$H-NMR (CDCl$_3$, Bruker 400 MHz) 2.60 (3 H, s); 3.83 (3 H, s); 7.04 (1 H, dd, J=8.5 Hz, 2.4 Hz); 7.16 (1 H, d, J=8.5 Hz); 7.33 (1 H, d, J=2.4 Hz); 10.2 (1 H, s).

Preparation #8 methyl 3-methylisoxazole-5-carboxylate

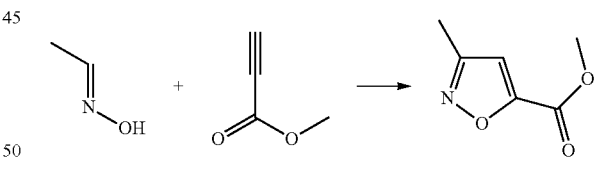

To a solution of N-chlorosuccinimide (2.67 g, 20 mmol) and pyridine (0.1 mL) in chloroform (18 mL), was added, portionwise, acetaldehyde oxime (1.18 g, 20 mmol), at about 5° C. After complete addition the mixture was stirred at rt for about 10 min and then methyl propiolate (2.22 mL, 25 mmol) was added. Subsequently, a solution of triethylamine (2.92 mL, 21 mmol) in chloroform (3 mL) was added dropwise, at such a rate that the temperature was maintained between 15 and 18° C. After complete addition the mixture was stirred at about 18° C. for about 20 min, then water (15 mL) was added. The layers were separated and the organic layer was washed with water (15 mL), dried (MgSO$_4$), filtered, and concentrated in vacuo. The residue was treated with diethyl ether (20 mL) and the formed precipitate was collected by filtration and dried to give methyl 3-methylisoxazole-5-carboxylate (1.75

Preparation #9

Preparation of methyl 2-(4-(2,4-dichlorophenyl)-1-methyl-7-oxo-3-(pyridin-2-yl)-6,7-dihydro-1H-pyrazolo[3,4-e][1,4]thiazepin-8(4H)-yl)acetate

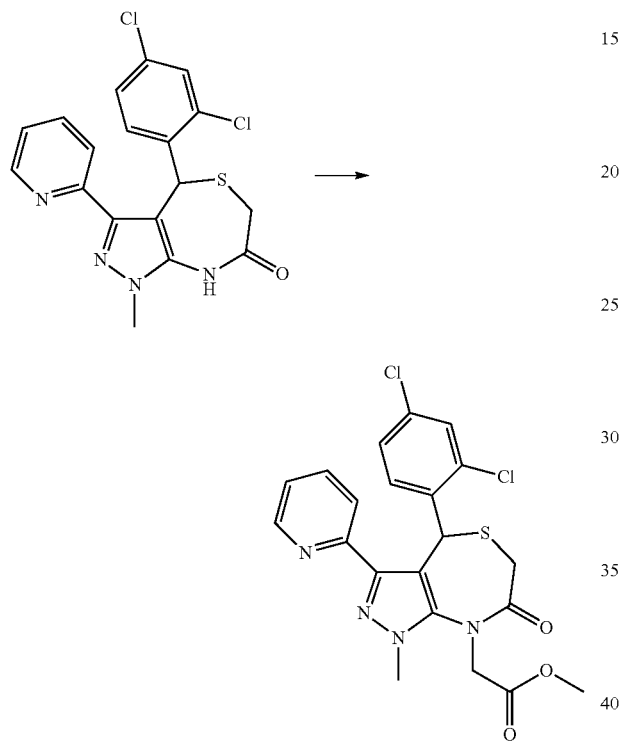

To a solution of 4-(2,4-dichloro-phenyl)-1-methyl-3-(pyridine-2-yl)-6,8-dihydro-1H-pyrazolo[3,4-e][1,4]thiazepin-7-(4H)-one (0.50 g, 1.2 mmol, prepared using C from Example 2 step B with thioglycolic acid and 2,4-dichlorobenzaldehyde) in anhydrous DMF was added cesium carbonate (0.804 g, 2.5 mmol), sodium iodide (0.370 g, 2.5 mmol) and methyl bromoacetate (0.128 mL, 1.4 mmol). The resulting mixture was stirred at rt for about 3 h, and then partitioned between ethyl acetate (50 mL) and water (25 mL). The layers were separated and the organic layer was washed with 5% aqueous sodium bicarbonate (2×25 mL), dried (MgSO$_4$), filtered and concentrated in vacuo. The residue was purified by column chromatography (SiO$_2$, DCM/ethyl acetate 9:1) to give methyl 2-(4-(2,4-dichlorophenyl)-1-methyl-7-oxo-3-(pyridin-2-yl)-6,7-dihydro-1H-pyrazolo[3,4-e][1,4]thiazepin-8(4H)-yl)acetate (0.16 g, 0.34 mmol, 28%) as a white solid: $^1$H-NMR (CDCl$_3$, Bruker 400 MHz) 3.34 (1 H, d, J=17 Hz), 3.46 (1 H, dd, J=17 Hz, 2 Hz), 3.83 (3 H, s), 3.88 (3 H, s), 4.72 (1 H, d, J=15 Hz), 4.87 (1 H, d, J=15 Hz), 6.63 (1 H, d, J=9 Hz), 6.78 (1 H, d, J=2 Hz), 6.96-7.05 (2 H, m), 7.43 (1 H, d, J=2 Hz), 7.57 (1 H, dt, J=8 Hz, 2 Hz), 7.82-7.88 (1 H, m), 8.35 (1 H, m)

Preparation #10

1-methyl-4-[2-methyl-4-(3-pyridylmethoxy)phenyl]-3-(2-pyridyl)-4,6,7,8-tetrahydropyrazolo[3,4-e][1,4]thiazepine To a degassed solution of 3-methyl-4-[1-methyl-3-(2-pyridyl)-4,6,7,8-tetrahydropyrazolo[3,4-e][1,4]thiazepin-4-yl]phenol (0.071 g, 0.2 mmol, Ex. #D.42) in anhydrous THF (10 mL) was added 3-pyridinemethanol (0.033 g, 0.3 mmol) and triphenylphosphine (0.131 g, 0.5 mmol), at rt. After 30 min the mixture was cooled to about 0° C. and diisopropyl azodicarboxylate (0.1 mL, 0.5 mmol) was added dropwise. The resulting mixture was stirred for about 16 h at rt, and then concentrated in vacuo. The residue was purified by column chromatography (SiO$_2$, ethyl acetate/methanol 95:5) followed by trituration with diethyl ether to give 1-methyl-4-[2-methyl-4-(3-pyridylmethoxy)phenyl]-3-(2-pyridyl)-4,6,7,8-tetrahydropyrazolo[3,4-e][1,4]thiazepine (0.012 g, 0.03 mmol, 14%) as a pale yellow solid: LC-MS (Table 1, Method e) R$_t$=5.09 min; m/z 444 (M+H)$^+$; $^1$H-NMR (CDCl$_3$, Bruker 400 MHz) δ 2.59 (3 H, s) 2.70 (1 H, ddd, J=14.9, 6.1, 2.3 Hz) 2.88 (1 H, ddd, J=14.9, 8.8, 2.5 Hz) 3.19-3.29 (1 H, m) 3.53-3.62 (1 H, m) 3.78 (1 H, br s) 3.84 (3 H, s) 5.01 (2 H, s) 6.62 (1 H, s) 6.63 (1 H, dd, J=8.4, 2.6 Hz) 6.82 (1 H, d, J=2.6 Hz) 7.07 (1 H, ddd, J=7.4, 4.9, 1.2 Hz) 7.16 (1 H, d, J=8.4 Hz) 7.30 (1 H, dd, J=7.8, 4.9 Hz) 7.58 (1 H, td, J=7.8, 1.9 Hz) 7.71-7.79 (2 H, m) 8.48 (1 H, d, J=4.9 Hz) 8.56 (1 H, dd, J=4.8, 1.5 Hz) 8.65 (1 H, d, J=1.9 Hz).

Preparation #11

1-methyl-4-[2-methyl-4-[(2-methyl-3-pyridyl)methoxy]phenyl]-3-(2-pyridyl)-4,6,7,8-tetrahydropyrazolo[3,4-e][1,4]thiazepine

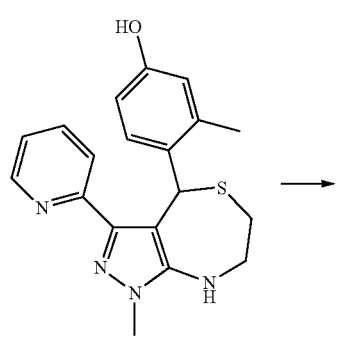

A mixture of 3-methyl-4-[1-methyl-3-(2-pyridyl)-4,6,7,8-tetrahydropyrazolo[3,4-e][1,4]thiazepin-4-yl]phenol (0.078 g, 0.22 mmol, see Ex. #D.42), potassium carbonate (0.061 g, 0.44 mmol), and 2-methyl-3-chloromethylpyridine hydrochloride (0.0356 g, 0.2 mmol, US2005/124586) in acetonitrile (10 mL) was heated at about 60° C., for about 90 h. After cooling to rt the mixture was concentrated in vacuo. The residue was treated with DCM (50 mL) and water (20 mL). The layers were separated and the organic layer was washed with brine, dried (Na$_2$SO$_4$), filtered and concentrated in vacuo. The residue was purified by column chromatography (SiO$_2$, ethyl acetate/methanol 9:1) followed by trituration with diethyl ether to give 1-methyl-4-[2-methyl-4-[(2-methyl-3-pyridyl)methoxy]phenyl]-3-(2-pyridyl)-4,6,7,8-tetrahydropyrazolo[3,4-e][1,4]thiazepine (0.050 g. 0.11 mmol, 50%) as an off white solid: LC-MS (Table 1, Method e) R$_t$=5.00 min; m/z 458 (M+H)$^+$; $^1$H-NMR (CDCl$_3$, Bruker 400 MHz) 2.56 (3 H, s) 2.60 (3 H, s) 2.70 (1 H, ddd, J=14.9, 6.1, 2.2 Hz) 2.88 (1 H, ddd, J=14.9, 8.9, 2.6 Hz) 3.19-3.29 (1 H, m) 3.53-3.62 (1 H, m) 3.78 (1 H, br s) 3.84 (3 H, s) 4.97 (2 H, s) 6.63 (1 H, dd, J=8.4, 2.6 Hz) 6.64 (1 H, s) 6.82 (1 H, d, J=2.6 Hz) 7.07 (1 H, ddd, J=7.4, 4.9, 1.1 Hz) 7.11-7.16 (2 H, m) 7.58 (1 H, td, J=7.8, 1.9 Hz) 7.67 (1 H, dd, J=7.7, 1.1 Hz) 7.77 (1 H, dt, J=8.0, 1.0 Hz) 8.45 (1 H, dd, J=4.9, 1.6 Hz) 8.49 (1 H, d, J=4.9 Hz).

Preparation #12

2-[4-(2,4-dichlorophenyl)-1-methyl-3-(2-pyridyl)-6,7-dihydro-4H-pyrazolo[3,4-e][1,4]thiazepin-8-yl] acetic acid

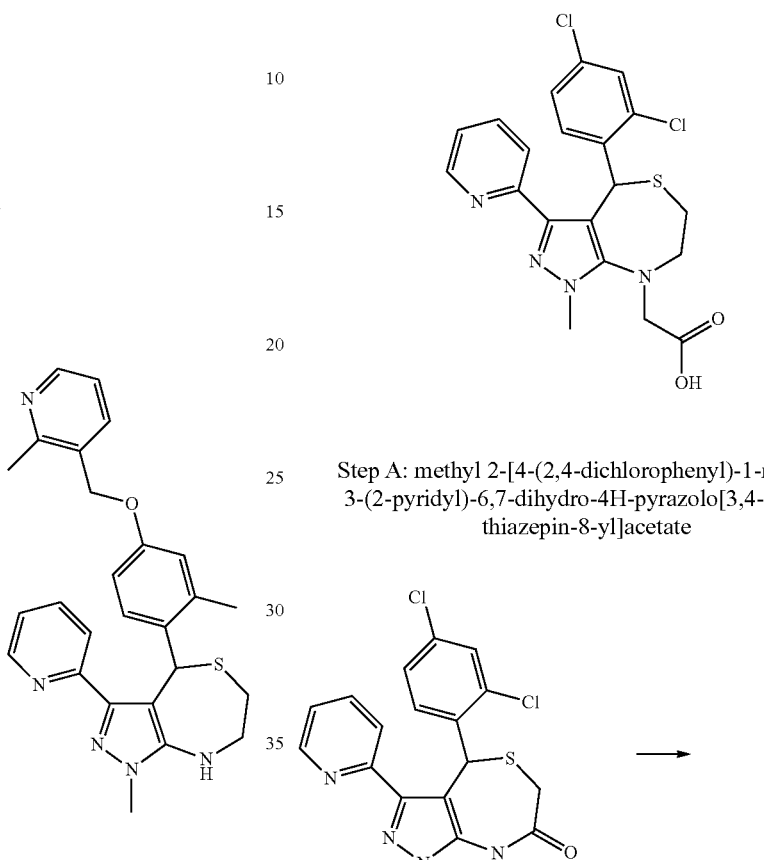

Step A: methyl 2-[4-(2,4-dichlorophenyl)-1-methyl-3-(2-pyridyl)-6,7-dihydro-4H-pyrazolo[3,4-e][1,4]thiazepin-8-yl]acetate To a solution of methyl 2-[4-(2,4-dichlorophenyl)-1-methyl-7-oxo-3-(2-pyridyl)-4H-pyrazolo[3,4-e][1,4]thiazepin-8-yl]acetate (1.18 g, 2.5 mmol, Preparation #9) in anhydrous THF (50 mL) was added a solution of borane THF complex (9.90 mL, 1M in THF, 4 mmol, Acros), the resulting mixture was stirred at rt for about 16 h and then for about 4 h at about 50° C. After cooling to about 4° C., 6 M aqueous HCl (10 mL) was added dropwise and the mixture stirred for about 45 min at rt. Subsequently, the mixture was cooled again to about 4°

C., treated with 2 M aqueous NaOH (35 mL) and extracted with ethyl acetate (75 mL). The organic layer was dried (MgSO₄), filtered and concentrated in vacuo. The residue was purified by column chromatography (SiO₂, ethyl acetate/ DCM 1:1 and ethyl acetate) to give methyl 2-[4-(2,4-dichlorophenyl)-1-methyl-3-(2-pyridyl)-6,7-dihydro-4H-pyrazolo [3,4-e][1,4]thiazepin-8-yl]acetate (0.65 g, 1.4 mmol, 56%) as a white foam, which was used as such: LC-MS (Table 1, Method d) R$_f$=2.90 min; m/z 463 (M+H)⁺

Step B: 2-[4-(2,4-dichlorophenyl)-1-methyl-3-(2-pyridyl)-6,7-dihydro-4H-pyrazolo[3,4-e][1,4]thiazepin-8-yl]acetic acid

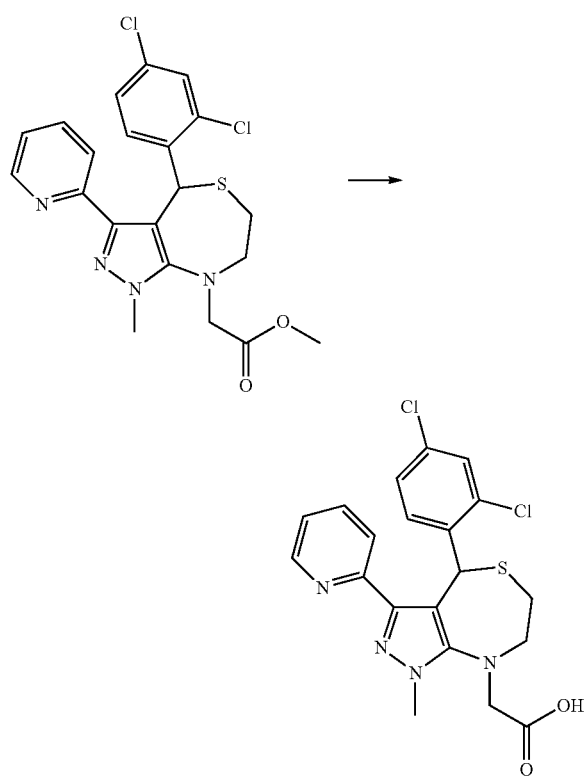

A mixture of methyl 2-[4-(2,4-dichlorophenyl)-1-methyl-3-(2-pyridyl)-6,7-dihydro-4H-pyrazolo[3,4-e][1,4]thiazepin-8-yl]acetate (0.300 g, 0.64 mmol) and lithium hydroxide (0.062 g, 2.6 mmol) in THF (10 mL) and water (5 mL) was stirred at rt for about 2 h. Then 1 M aqueous HCl (15 mL) was added and the mixture was extracted with ethyl acetate (2×25 mL). The combined organic layers were dried (MgSO₄), filtered and concentrated in vacuo. The residue was purified by prep-HPLC (Table 2, Method a) to give 2-[4-(2,4-dichlorophenyl)-1-methyl-3-(2-pyridyl)-6,7-dihydro-4H-pyrazolo [3,4-e][1,4]thiazepin-8-yl]acetic acid (0.160 g, 0.36 mmol, 56%) as a white solid: LC-MS (Table 1, Method b) R$_f$=6.57 min; m/z 449 (M+H)⁺; ¹H-NMR (CDCl₃, Bruker 400 MHz) δ 2.73-2.91 (2 H, m) 3.40-3.63 (2 H, m) 3.92 (3 H, s) 4.12 (1 H, d, J=18.4 Hz) 4.21 (1 H, d, J=18.4 Hz) 5.95 (1 H, br s) 6.46 (1 H, s) 6.94 (1 H, d, J=8.4 Hz) 7.00-7.07 (2H, m) 7.40 (1H, d, J=2.1Hz) 7.58 (1H, td, J=7.5, 1.8 Hz) 7.72 (1H, d, J=7.9 Hz) 8.40 (1H, d, J=5.0 Hz).

Preparation #13

2-[4-(2,4-dichlorophenyl)-1-methyl-3-(2-pyridyl)-6,7-dihydro-4H-pyrazolo[3,4-e][1,4]thiazepin-8-yl] acetamide

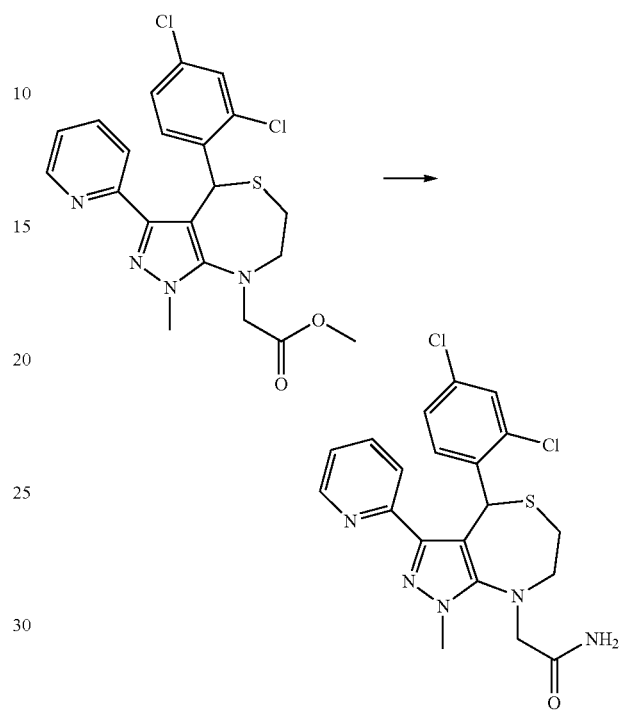

A mixture of methyl 2-[4-(2,4-dichlorophenyl)-1-methyl-3-(2-pyridyl)-6,7-dihydro-4H-pyrazolo[3,4-e][1,4]thiazepin-8-yl]acetate (0.350 g, 0.76 mmol, Preparation #12 step A), KCN (0.050 g, 0.77 mmol), and ammonia (10 mL, 7 M in MeOH, 70 mmol) in methanol (10 mL) was heated, in a sealed flask, for about 50 min at about 140° C. in a microwave. After cooling to rt the mixture was concentrated in vacuo. The residue was purified by column chromatography (SiO₂, ethyl acetate/methanol 95:5) to give 2-[4-(2,4-dichlorophenyl)-1-methyl-3-(2-pyridyl)-6,7-dihydro-4H-pyrazolo[3,4-e][1,4] thiazepin-8-yl]acetamide (0.16 g, 0.36 mmol, 47%) as a beige solid: LC-MS (Table 1, Method b) R$_f$=5.49 min; m/z 448 (M+H)⁺.

Preparation #14

4-(4-chloro-2-methyl-phenyl)-1-methyl-3-(6-methyl-2-pyridyl)-4,6,7,8-tetrahydropyrazolo[3,4-e][1,4] thiazepine

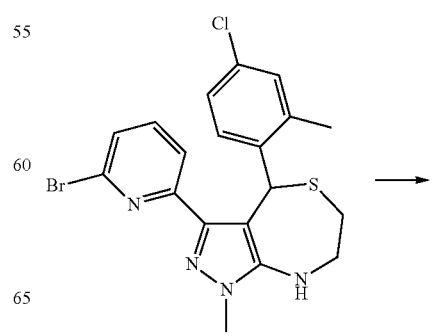

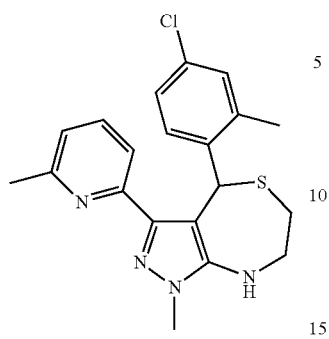

To a degassed mixture of 3-(6-bromo-2-pyridyl)-4-(4-chloro-2-methyl-phenyl)-1-methyl-4,6,7,8-tetrahydropyrazolo[3,4-e][1,4]thiazepine (0.25 g, 0.56 mmol, prepared using C with preparation B.1 with 4-chloro-2-methylbenzaldehyde (Fluorochem) and thioglycolic acid then D) and trimethylboroxine (0.077 mL, 0.56 mmol) in 1,4-dioxane were added potassium carbonate (0.23 g, 1.67 mmol) and tetrakis(triphenylphosphine)palladium(0) (0.064 g, 0.056 mmol). The resulting mixture was heated at about 115° C. for about 28 h. After cooling to rt the mixture was filtered over diatomaceous earth and concentrated in vacuo. The residue was purified by column chromatography twice (SiO$_2$, first column eluted with DCM/methanol 98:2; second column eluted with ethyl acetate/hexanes 2:1) to give: 4-(4-chloro-2-methyl-phenyl)-1-methyl-3-(6-methyl-2-pyridyl)-4,6,7,8-tetrahydropyrazolo[3,4-e][1,4]thiazepine (0.115 g, 0.30 mmol, 53%) as a brown solid: LC-MS (Table 1, Method a) R$_t$=4.37 min; m/z 385 (M+H)$^+$ Preparation #15

5-bromo-2-methylthiophene-3-carbaldehyde

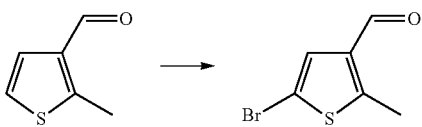

To a solution of 2-methylthiophene-3-carbaldehyde (0.204 g, 1.62 mmol, Comins, D. L.; Killpack, M. O. *J. Org. Chem.* 1987, 52(1), 104-109) in DMF (10 mL) was added N-bromosuccinimide (0.43 g, 2.43 mmol); the resulting mixture was stirred at rt for about 16 h and then water (75 mL) and diethyl ether (25 mL) were added. The layers were separated and the aqueous layer was extracted with diethyl ether (2×30 mL). The combined organic layers were washed with water (15 mL), dried (MgSO$_4$), filtered and concentrated in vacuo. The residue was purified by column chromatography (SiO$_2$, diethyl ether/hexanes 1:9) to give 5-bromo-2-methylthiophene-3-carbaldehyde (0.272 g, 1.33 mmol, 82%) as a yellow oil which crystallized on standing: $^1$H-NMR (CDCl$_3$, Bruker 400 MHz) δ 2.72 (3 H, s), 7.33 (1 H, s), 9.9 (1 H, s).

Preparation #16

4-chloro-5-methoxy-2-methylbenzaldehyde

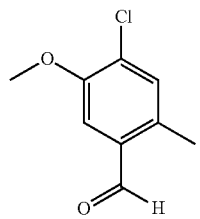

Step A:
(2-bromo-4-chloro-5-methoxy-phenyl)methanol

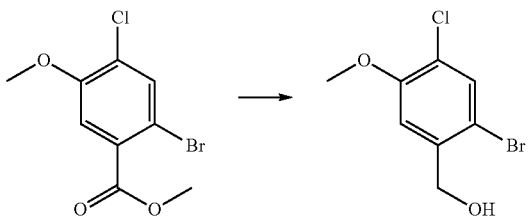

To a solution of methyl 2-bromo-4-chloro-5-methoxybenzoate (1.88 g, 6.7 mmol, Powers, J. J.; Favor, D. A.; Jeganathan, A.; Rankin, T.; Sharma, R.; Pandit, C.; Maiti, S, N. *Tetrahedron Lett.* 2009, 50(12), 1267-1269) in anhydrous THF (20 mL) was added lithium borohydride (0.644 g, 30 mmol). The resulting mixture was heated under reflux for about 72 h. After cooling to rt the mixture was concentrated in vacuo. The residue was partitioned between water (50 mL) and ethyl acetate (90 mL). The layers were separated and the aqueous layer was extracted with ethyl acetate (50 mL). The combined organic layers were washed with water (20 mL), dried (MgSO$_4$), filtered and concentrated in vacuo. The residue was purified by column chromatography (SiO$_2$, diethyl ether/hexanes 1:1) to give (2-bromo-4-chloro-5-methoxyphenyl)methanol (1.57 g, 6.3 mmol, 93%) as a white solid: $^1$H-NMR (CDCl$_3$, Bruker 400 MHz) δ 2.01 (1 H, t, J=6 Hz), 3.92 (3 H, s), 4.71 (2 H, d, J=6 Hz), 7.12 (1 H, s), 7.53 (1 H, s).

Step B: 2-bromo-4-chloro-5-methoxybenzaldehyde

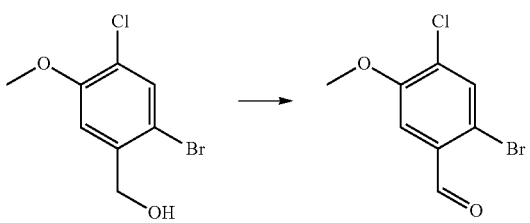

To a solution of oxalyl chloride (0.58 mL, 6.9 mmol) in DCM (20 mL) was added dropwise a solution of dimethylsulfoxide (1.11 mL, 15.6 mmol) in DCM (10 mL), at temperature lower than –65° C. The resulting mixture was stirred for about 20 min at about –70° C. Then a solution of (2-bromo-4-chloro-5-methoxy-phenyl)methanol (1.56 g, 6.2 mmol) in DCM (20 mL) was added dropwise at temperatures lower than −65° C., and the resulting mixture was stirred for about another 20 min. Subsequently, TEA (3.52 mL, 25.2 mmol) was added dropwise at temperatures lower than −70° C., and the mixture was stirred for about 10 min at about −70° C. The mixture was allowed to warm to rt and stirred for about 16 h, treated with 1 M aqueous HCl (100 mL) and DCM (50 mL). The layers were separated and the aqueous layer was extracted with DCM (100 mL). The combined organic layers were washed with water (50 mL), dried (MgSO$_4$), filtered and concentrated in vacuo. The residue was purified by column chromatography (SiO$_2$, diethyl ether/hexanes 5:95) to give 2-bromo-4-chloro-5-methoxybenzaldehyde (1.48 g, 5.9 mmol, 95%) as a white solid: $^1$H-NMR (CDCl$_3$, Bruker 400 MHz) δ 3.96 (3 H, s), 7.46 (1 H, s), 7.68 (1 H, s), 10.3 (1 H, s).

Step C: 4-chloro-5-methoxy-2-methylbenzaldehyde

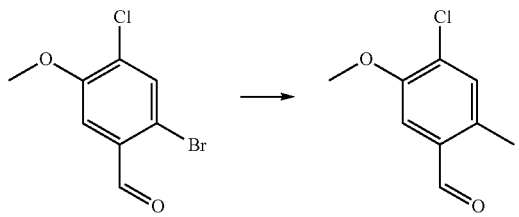

To a degassed solution of 2-bromo-4-chloro-5-methoxybenzaldehyde (1.46 g, 5.9 mmol) and trimethylboroxine (0.82 mL, 5.9 mmol) in 1,4-dioxane (80 mL) was added potassium carbonate (2.43 g, 17.6 mmol) and tetrakis(triphenylphosphine)palladium(0) (0.68 g, 0.6 mmol). The mixture was heated under reflux for about 23 h, then more tetrakis(triphenylphosphine)palladium(0) (0.17 g, 0.15 mmol) and trimethylboroxine (0.2 mL, 1.4 mmol) were added and the mixture was heated under reflux for about another 8 h. After cooling to rt the mixture was filtered over diatomaceous earth and concentrated in vacuo. The residue was purified by column chromatography (SiO$_2$, diethyl ether/hexanes 1:6) to give 4-chloro-5-methoxy-2-methylbenzaldehyde (0.87 g, 4.7 mmol, 81%) as a pale yellow solid: $^1$H-NMR (CDCl$_3$, Bruker 400 MHz) δ 2.60 (3 H, s); 3.95 (3 H, s); 7.29 (1 H, s); 7.37 (1 H, s); 10.3 (1 H, s).

Preparation #17

[4-(4-chloro-2-methyl-phenyl)-1-methyl-4,6,7,8-tetrahydropyrazolo[3,4-e][1,4]thiazepin-3-yl]trifluoromethanesulfonate

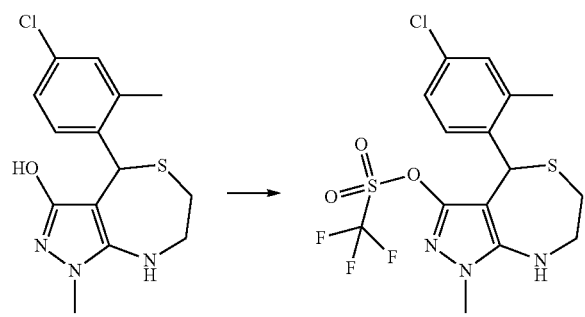 [SMILES: Cc1cc(Cl)ccc1C1SCCNc2c1c(O)nn2C ; Cc1cc(Cl)ccc1C1SCCNc2c1c(OS(=O)(=O)C(F)(F)F)nn2C]

To a solution of 4-(4-chloro-2-methyl-phenyl)-1-methyl-4,6,7,8-tetrahydropyrazolo[3,4-e][1,4]thiazepin-3-ol (0.12 g, 0.39 mmol, Ex. #D.73) in chloroform (15 mL) were added triethylamine (0.078 mL, 0.582 mmol), DMAP (0.005 g, 0.036 mmol) and N-phenyl-bis(trifluoromethanesulfonimide (0.167 g, 0.468 mmol). The resulting mixture was heated for about 18 h at about 75° C. After cooling to about 0° C., 5% aqueous sodium bicarbonate (50 mL) and DCM (100 mL) were added. The layers were separated and the organic layer was washed with water (25 mL), dried (MgSO$_4$), filtered and concentrated in vacuo. The resulting residue was purified by column chromatography (SiO$_2$, ethyl acetate/hexanes (1:2) to give [4-(4-chloro-2-methyl-phenyl)-1-methyl-4,6,7,8-tetrahydropyrazolo[3,4-e][1,4]thiazepin-3-yl]trifluoromethanesulfonate (0.124 g, 0.28 mmol, 72%), as a white solid: LC-MS (Table 1, Method a) R$_t$=5.34 min, m/z 442 (M+H)$^+$; $^1$H NMR (400 MHz, CDCl$_3$) δ ppm 2.46 (3 H, s) 2.66-2.74 (1 H, m) 2.80-2.88 (1 H, m) 3.24-3.35 (1 H, m) 3.57-3.67 (1 H, m) 3.71 (3 H, s) 3.81-3.88 (1 H, m) 5.07 (1 H, s) 6.99 (1 H, d, J=8.5 Hz) 7.06 (1 H, dd, J=8.5, 2.0 Hz) 7.19 (1 H, d, J=2.0 Hz)

Preparation #18

4-(4-chloro-2-vinyl-phenyl)-1-methyl-3-(2-pyridyl)-4,6,7,8-tetrahydropyrazolo[3,4-e][1,4]thiazepine

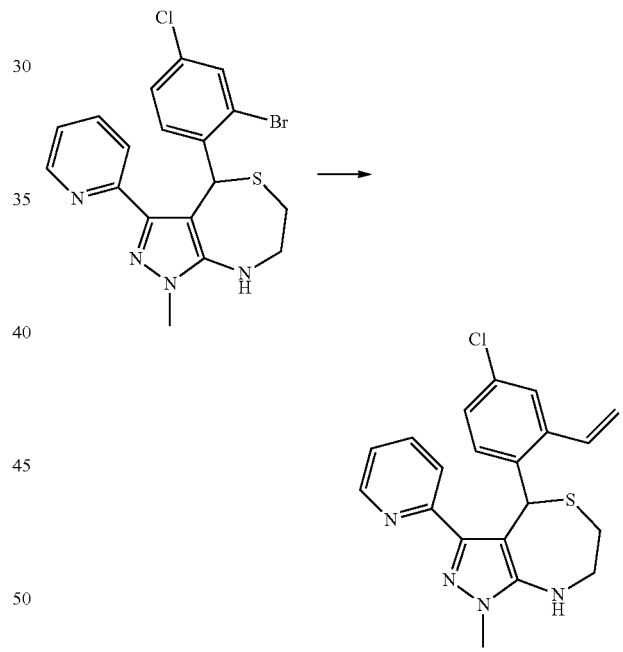

To a degassed mixture of 4-(2-bromo-4-chloro-phenyl)-1-methyl-3-(2-pyridyl)-4,6,7,8-tetrahydropyrazolo[3,4-e][1,4]thiazepine (0.50 g, 1.2 mmol, Example #D.37) and tributyl(vinyl)stannane (0.37 mL, 1.3 mmol) in DMF (5 mL) was added cesium fluoride (0.35 g, 2.3 mmol), copper(I) iodide (0.022 g, 0.12 mmol) and tetrakis(triphenylphosphine)palladium(0) (0.066 g, 0.058 mmol). The resulting mixture was heated at about 45° C. overnight; then diluted with DCM (50 mL), washed with water (20 mL) and brine (20 mL), dried (MgSO$_4$), filtered and concentrated in vacuo. The residue was purified by column chromatography (SiO$_2$, ethyl acetate/hexanes 1:1) to give 4-(4-chloro-2-vinyl-phenyl)-1-methyl-3-(2-pyridyl)-4,6,7,8-tetrahydropyrazolo[3,4-e][1,4]thiazepine (0.28 g, 0.73 mmol, 63%) as an off white solid: LC-MS (Table 1, Method a) $R_t$=4.07 min; m/z 383 (M+H)$^+$; $^1$H-NMR (CDCl$_3$, Bruker 400 MHz) 2.69-2.78 (1 H, m) 2.81-2.89 (1 H, m) 3.19-3.28 (1 H, m) 3.52-3.61 (1 H, m) 3.77-3.86 (1 H, m) 3.84 (3 H, s) 5.47 (1 H, dd, J=11.0, 1.5 Hz) 5.73 (1 H, dd, J=17.5, 1.5 Hz) 6.79 (1 H, s) 7.02-7.08 (2 H, m) 7.14 (1 H, d, J=8.5 Hz) 7.38 (1 H, dd, J=17.5, 11.0 Hz) 7.45 (1 H, d, J=2.0 Hz) 7.58 (1 H, td, J=7.5, 2.0 Hz) 7.77 (1 H, br.d, J=8.0 Hz) 8.42 (1 H, br.d, J=5.0 Hz).

Preparation #19

4-(4-chloro-2-ethyl-phenyl)-1-methyl-3-(2-pyridyl)-4,6,7,8-tetrahydropyrazolo[3,4-e][1,4]thiazepine

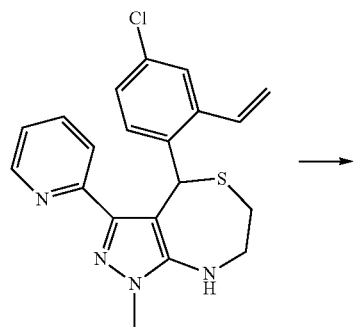

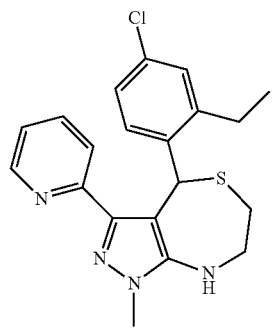

A mixture of 4-(4-chloro-2-vinyl-phenyl)-1-methyl-3-(2-pyridyl)-4,6,7,8-tetrahydropyrazolo-[3,4-e][1,4]thiazepine (0.100 g, 0.26 mmol, Preparation #18) and palladium hydroxide on carbon (0.073 g, 20 wt % on dry basis, ~0.1 mmol), in methanol (5 mL) and DCM (2 mL) was treated with hydrogen (1 atm.), at rt, overnight. Then the mixture was filtered over diatomaceous earth and concentrated in vacuo. The residue was purified by prep-HPLC (Table 2, Method b) to give 4-(4-chloro-2-ethyl-phenyl)-1-methyl-3-(2-pyridyl)-4,6,7,8-tetrahydropyrazolo[3,4-e][1,4]thiazepine as an off white solid: LC-MS (Table 1, Method a) $R_t$=4.03 min; m/z 385 (M+H)$^+$; $^1$H-NMR (CDCl$_3$, Bruker 400 MHz) δ 1.38 (3 H, t, J=7.5 Hz) 2.71 (1 H, ddd, J=15.1, 6.3, 2.7 Hz) 2.83 (1 H, ddd, J=15.1, 8.8, 2.8 Hz) 2.94 (1 H, dq, J=15.1, 7.5 Hz) 3.10 (1 H, dq, J=15.1, 7.5 Hz) 3.18-3.27 (1 H, m) 3.52-3.60 (1 H, m) 3.79 (1 H, br s) 3.84 (3 H, s) 6.78 (1 H, s) 6.99 (1 H, dd, J=8.4, 2.2 Hz) 7.07 (1 H, ddd, J=7.4, 4.9, 0.9 Hz) 7.13 (1 H, d, J=8.4 Hz) 7.20 (1 H, d, J=2.2 Hz) 7.59 (1 H, td, J=7.8, 1.7 Hz) 7.79 (1 H, dt, J=8.0, 0.9 Hz) 8.44 (1 H, ddd, J=4.8, 1.7, 0.9 Hz).

Preparation #20

1-methyl-4-(2-methyl-4-methylsulfonyl-phenyl)-3-(2-pyridyl)-4,6,7,8-tetrahydropyrazolo[3,4-e][1,4]thiazepine

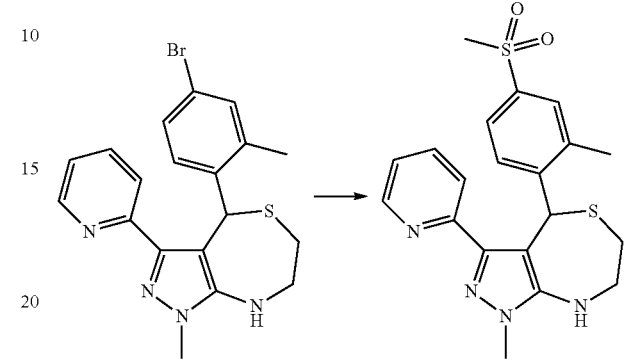

To a degassed solution of 4,5-bis(diphenylphosphino)-9,9-dimethylxanthene (0.057 g, 0.1 mmol) and tris(dibenzylideneacetone)dipalladium(0) (0.045 g, 0.025 mmol) in toluene (6 mL) was added 4-(4-bromo-2-methyl-phenyl)-1-methyl-3-(2-pyridyl)-4,6,7,8-tetrahydropyrazolo[3,4-e][1,4]thiazepine (0.400 g, 0.96 mmol, Example #4 step D), cesium carbonate (0.470 g, 1.5 mmol) and sodium methanesulfinate (0.118 g, 1.2 mmol). The resulting mixture was heated at about 120° C. overnight. After cooling to rt, the mixture was diluted with ethyl acetate (50 mL), washed with water (20 mL) and brine (20 mL), dried (MgSO$_4$), filtered and concentrated in vacuo. The residue was purified by column chromatography (SiO$_2$, DCM/methanol 1:1) followed by prep-HPLC (Table 2, Method b) to give 1-methyl-4-(2-methyl-4-methylsulfonyl-phenyl)-3-(2-pyridyl)-4,6,7,8-tetrahydropyrazolo[3,4-e][1,4]thiazepine (0.015 g, 0.036 mmol, 3%) as an off white solid: LC-MS (Table 1, Method a) $R_t$=2.98 min; m/z 415 (M+H)$^+$; $^1$H-NMR (CDCl$_3$, Bruker 400 MHz) δ 2.65-2.73 (1H, m) 2.70 (3H, s) 2.81 (1H, ddd, J=15.0, 9.3, 2.4 Hz) 3.01 (3H, s) 3.23-3.32 (1H, m) 3.61-3.71 (1H, m) 3.84 (3H, s) 3.86 (1H, br s) 6.79 (1H, s) 7.09 (1H, ddd, J=7.4, 5.1, 1.0 Hz) 7.40 (1H, d, J=8.1 Hz) 7.58-7.64 (2H, m) 7.73 (1H, d, J=1.6 Hz) 7.86 (1H, d, J=8.0 Hz) 8.44 (1H, d, J=4.8 Hz).

Preparation #21

4-chloro-2-cyclopropyl-benzaldehyde

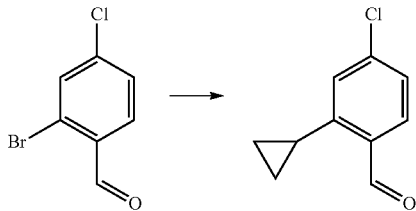 [SMILES: O=Cc1ccc(Cl)cc1Br ; O=Cc1ccc(Cl)cc1C1CC1]

To a degassed mixture of toluene (60 mL) and water (9 mL) was added potassium cyclopropyl-trifluoroborate (0.91 g, 6.2 mmol) and tribasic potassium phosphate (6.37 g, 30 mmol).

The resulting mixture was stirred for 15 min at rt, thereafter, 2-bromo-4-chlorobenzaldehyde (1.50 g, 6.84 mmol, WO2006044454), palladium(II) acetate (0.11 g, 0.5 mmol) and 2-dicyclohexylphosphino-2',6'-diisopropoxybiphenyl (0.48 g, 1.0 mmol) were added and the mixture was heated under reflux, overnight. After cooling to rt, water (50 mL) and ethyl acetate (50 mL) were added and the layers were separated. The organic layer was washed with brine (20 mL), dried (MgSO$_4$), filtered and concentrated in vacuo. The residue was purified by column chromatography (SiO$_2$, DCM/hexanes 1:3) to give 4-chloro-2-cyclopropyl-benzaldehyde (0.48 g, 2.6 mmol, 39%) as a colorless semi solid: $^1$H-NMR (CDCl$_3$, Bruker 400 MHz) δ 0.80 (2 H, m), 1.08-1.17 (2 H, m), 2.58 (1 H, m), 7.10 (1 H, d, J=2 Hz), 7.29 (1 H, dd, J=8 Hz, 2 Hz), 7.75 (1 H, d, J=8 Hz), 10.6 (1 H, s).

Preparation #22

4-chloro-2-(fluoromethyl)benzaldehyde

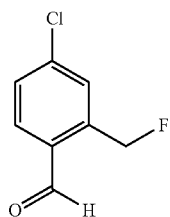 [SMILES: O=Cc1ccc(Cl)cc1CF]

Step A: 1-bromo-4-chloro-2-(fluoromethyl)benzene

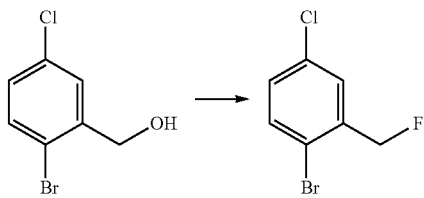 [SMILES: OCc1cc(Cl)ccc1Br ; FCc1cc(Cl)ccc1Br]

To a suspension of 2-bromo-5-chlorobenzyl alcohol (2.0 g, 9.0 mmol, Fluorochem) in anhydrous DCM (30 mL) was added (diethylamino)sulfur trifluoride (1.30 mL, 10 mmol), at about −75° C. After complete addition the mixture was allowed to warm slowly to rt, over about 1 h. Then saturated aqueous sodium bicarbonate (8 mL) was added and the mixture was partitioned between DCM (20 mL) and water (20 mL). The layers were separated and the aqueous layer was extracted twice with DCM (20 mL). The combined organic layers were washed with brine (20 mL), dried (MgSO$_4$), filtered and concentrated in vacuo. The residue was purified by column chromatography (SiO$_2$, DCM/hexanes 1:1) to give 1-bromo-4-chloro-2-(fluoromethyl)benzene (1.31 g, 5.9 mmol, 65%) as a pale yellow oil: $^1$H-NMR (CDCl$_3$, Bruker 400 MHz) δ 5.42 (2 H, d, J=47.0 Hz) 7.19 (1 H, dd, J=8.8, 2.5 Hz) 7.41 (1 H, d, J=2.5 Hz) 7.48 (1 H, d, J=8.8 Hz).

Step B: 4-chloro-2-(fluoromethyl)benzaldehyde

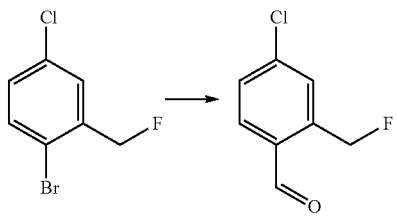 [SMILES: FCc1cc(Cl)ccc1Br ; O=Cc1ccc(Cl)cc1CF]

To a solution of 1-bromo-4-chloro-2-(fluoromethyl)benzene (0.5 g, 2.2 mmol) in anhydrous THF (20 mL) was added a solution of n-butyl lithium (1.0 mL, 2.5 M in hexanes, 2.5 mmol) in anhydrous THF (10 mL), at about −75° C. The resulting mixture was stirred for about 30 min at about −75° C. and then DMF (0.34 mL, 4.5 mmol) was added slowly. Over about 1 h the mixture was warmed to about −55° C. and then saturated aqueous ammonium chloride (10 mL) was added followed by diethyl ether (50 mL). The layers were separated and the organic layer was washed with brine (20 mL), dried (MgSO$_4$), filtered and concentrated in vacuo. The residue was purified by column chromatography (SiO$_2$, diethyl ether/hexanes 1:3) to give 4-chloro-2-(fluoromethyl)benzaldehyde (0.15 g, 0.87 mmol, 39%) as a white solid: $^1$H-NMR (CDCl$_3$, Bruker 400 MHz) δ 5.85 (2 H, d, J=47.8 Hz) 7.52 (1 H, dd, J=8.2, 2.0 Hz) 7.72 (1 H, br s) 7.80 (1 H, dd, J=8.2, 1.4 Hz) 10.04 (1 H, d, J=1.4 Hz).

Preparation #23

4-(2,4-dichlorophenyl)-1-methyl-3-[(2S)-pyrrolidin-2-yl]-4,6,7,8-tetrahydropyrazolo[3,4-e][1,4]thiazepine

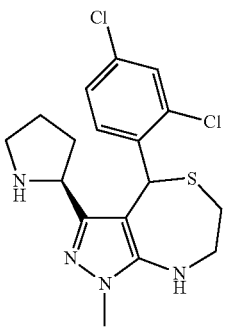 [SMILES: Cn1nc([C@@H]2CCCN2)c2c1NCCSC2c1ccc(Cl)cc1Cl]

Step A: tert-butyl (2S)-2-(2-cyanoacetyl)pyrrolidine-1-carboxylate

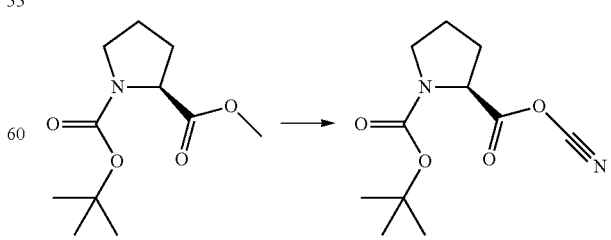

To a solution of acetonitrile (1.5 mL, 29 mmol) in THF (60 mL) was added n-butyl lithium (2.5 M solution in hexane, 10.8 mL, 29 mmol) at −78° C. The solution was stirred at about −78° C. for about 10 min and a solution of 1-tert-butyl 2-methyl (2S)-pyrrolidine-1,2-dicarboxylate (5.64 g, 25 mmol, US2007197506) in 15 mL of THF was added. The mixture was stirred at about −78° C. for about 1 hr and was subsequently allowed to reach rt (overnight). Water was added and the mixture acidified to pH 3 with 1N aqueous hydrochloric acid. The layers were separated and the organic layer was washed with water (10 mL) and brine (10 mL), dried (MgSO$_4$), filtered and concentrated in vacuo to give tert-butyl (2S)-2-(2-cyanoacetyl)pyrrolidine-1-carboxylate (5.8 g, 24.3 mmol, 97%) as a yellow oil.

Step B: tert-butyl (2S)-2-(5-amino-1-methyl-pyrazol-3-yl)pyrrolidine-1-carboxylate

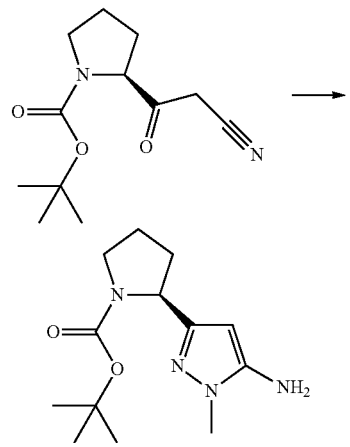

tert-Butyl (2S)-2-(2-cyanoacetyl)pyrrolidine-1-carboxylate (5.8 g, 24.3 mmol), was dissolved in EtOH (100 mL). Methylhydrazine (1.8 mL, 35 mmol) was added and the resulting mixture was heated, for about 12 h, at about 80° C. After cooling to rt, the mixture was concentrated in vacuo. The residue was taken up in toluene (50 mL) and stirred overnight. The precipitated solid was collected by filtration and washed with toluene (2 mL) and diethyl ether to afford tert-butyl (2S)-2-(5-amino-1-methyl-pyrazol-3-yl)pyrrolidine-1-carboxylate (4.43 g, 16.3 mmol, 68%), as white solid: $^1$H-NMR (CDCl$_3$, Bruker 400 MHz, rotamers) δ 1.35 and 1.45 (9 H, br. s), 1.70-2.24 (4 H, m), 3.36-3.53 (4 H, m), 3.60 (3 H, br s), 4.70-4.78 and 4.83-4.90 (1 H, m), 5.35 and 5.41 (1H, br s).

Step C: tert-butyl (2S)-2-[4-(2,4-dichlorophenyl)-1-methyl-4,6,7,8-tetrahydropyrazolo[3,4-e][1,4]thiazepin-3-yl]pyrrolidine-1-carboxylate

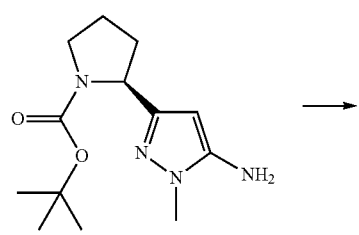

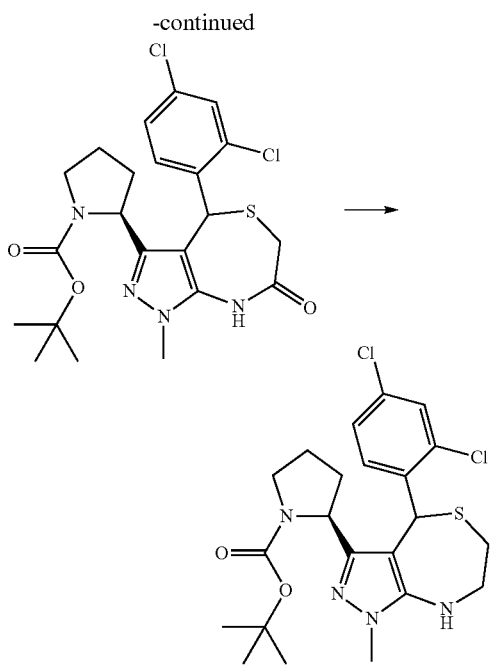

tert-Butyl(2S)-2-[4-(2,4-dichlorophenyl)-1-methyl-4,6,7,8-tetrahydropyrazolo[3,4-e][1,4]thiazepin-3-yl]pyrrolidine-1-carboxylate was prepared according to procedure C using tert-butyl (2S)-2-(5-amino-1-methyl-pyrazol-3-yl)pyrrolidine-1-carboxylate, thioglycolic acid and 2,4-dichlorobenzaldehyde. The resulting amide was reduced according to procedure D and the material was used directly in Step D below.

Step D: 4-(2,4-dichlorophenyl)-1-methyl-3-[(2S)-pyrrolidin-2-yl]-4,6,7,8-tetrahydropyrazolo[3,4-e][1,4]thiazepine

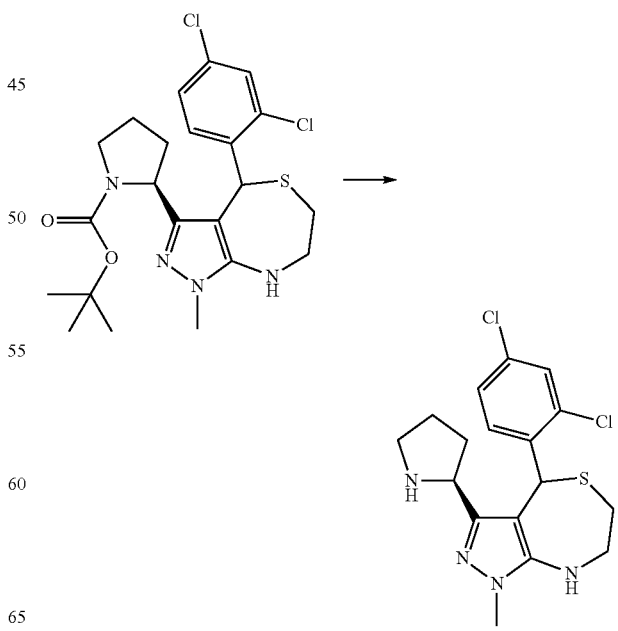

To tert-butyl (2S)-2-[4-(2,4-dichlorophenyl)-1-methyl-4,6,7,8-tetrahydropyrazolo[3,4-e][1,4]thiazepin-3-yl]pyrrolidine-1-carboxylate (0.31 g, 0.64 mmol), was added trifluoroacetic acid in DCM (1:4, 20 mL). The resulting mixture was stirred, for about 18 h, at rt. Subsequently, 5% aqueous sodium bicarbonate (100 mL) and DCM (200 mL) were added. The layers were separated and the organic layer was washed with water (25 mL), dried (MgSO$_4$), filtered and concentrated in vacuo. The resulting residue was purified by column chromatography (SiO$_2$, ethyl acetate/methanol (9:1) followed by 10% methanol in DCM) to afford 4-(2,4-dichlorophenyl)-1-methyl-3-[(2S)-pyrrolidin-2-yl]-4,6,7,8-tetrahydropyrazolo[3,4-e][1,4]thiazepine (38 mg, 0.1 mmol, 32%), as white solid: LC-MS (Table 1, Method a) R$_t$=1.38 min, m/z 383 (M+H)$^+$; Major diastereomer; $^1$H NMR (400 MHz, CDCl$_3$ and two drops of TFA) δ ppm 1.22-1.28 (1H, m) 1.85-2.35 (3H, m) 2.50-2.60 (1H, m) 2.68-2.83 (2H, m) 3.35-3.65 (3H, m) 3.75-3.85 (1H, m) 3.87 (3H, s) 4.60-4.70 (1H, br s) 5.32 (1H, s) 6.97 (1H, d, J=8.0 Hz) 7.16 (1H, dd, J=8.3, 2.2 Hz) 7.47 (1H, d, J=2.1 Hz) 9.65 (1H, br s). Minor diastereomer; $^1$H NMR (400 MHz, CDCl$_3$ and two drops of TFA) δ ppm 1.22-1.28 (1H, m) 1.85-2.35 (4H, m) 2.68-2.83 (2H, m) 3.35-3.65 (3H, m) 3.75-3.85 (1H, m) 3.87 (3H, s) 4.60-4.70 (1H, br s) 5.31 (1H, s) 6.95 (1H, d, J=8.0 Hz) 7.10 (1H, dd, J=8.3, 2.2 Hz) 7.43 (1H, d, J=2.1 Hz) 9.25 (1H, br s).

Preparation #24

4-(4-chloro-2-methyl-phenyl)-1-methyl-3-[(2S)-pyrrolidin-2-yl]-4,6,7,8-tetrahydropyrazolo[3,4-e][1,4]thiazepine

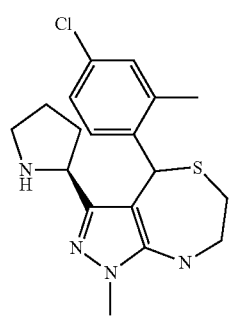 [SMILES: Cc1cc(Cl)ccc1C1SCCNc2c1c([C@@H]1CCCN1)nn2C]

The compound was prepared by a similar procedure to Preparation #23 using 2-methyl-4-chlorobenzaldehyde in step C. LC-MS (Table 1, Method a) R$_t$=1.83 min (minor), 1.98 min (major); m/z 363 (M+H)$^+$, Major diastereomer; $^1$H NMR (400 MHz, CDCl$_3$) δ ppm 1.36-1.46 (1H, m) 1.64-1.82 (3H, m) 2.49 (3H, s) 2.60-3.26 (6H, m) 3.48-3.61 (1H, m) 3.70 (3H, s) 3.79 (1H br.t) 4.12 (1H, t, J=8.0 Hz) 5.26 (1H, s) 6.95-7.06 (2H, m) 7.15-7.19 (1H, m). Minor diastereomer; $^1$H NMR (400 MHz, CDCl$_3$) δ ppm 1.51-1.61 (1H, m) 1.64-1.82 (2H, m) 1.91-2.03 (1H, m) 2.48 (3H, s) 2.60-3.26 (6H, m) 3.48-3.61 (1H, m) 3.69 (3H, s) 3.73 (1H br.t) 3.97 (1H, t, J=8.0 Hz) 5.56 (1H, s) 6.95-7.06 (2H, m) 7.15-7.19 (1H, m)

Preparation #25

2-[3-chloro-4-[1-methyl-3-(2-pyridyl)-4,6,7,8-tetrahydropyrazolo[3,4-e][1,4]thiazepin-4-yl]phenyl]propan-2-ol and 4-(2-chlorophenyl)-1-methyl-3-(2-pyridyl)-4,6,7,8-tetrahydropyrazolo[3,4-e][1,4]thiazepine

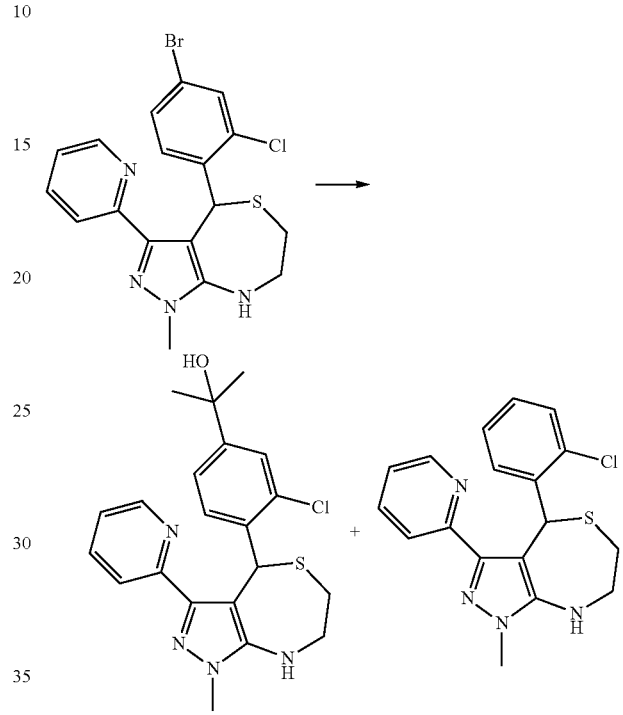

To a degassed solution of 4-(4-bromo-2-chloro-phenyl)-1-methyl-3-(2-pyridyl)-4,6,7,8-tetrahydropyrazolo[3,4-e][1,4]thiazepine (0.255 g, 0.59 mmol, see Ex.#3 step D) in anhydrous THF (2.5 mL) was added dropwise isopropylmagnesium chloride lithium chloride complex solution (2.25 mL, 1.3 M in THF, 2.93 mmol) at about 0° C. After complete addition, the mixture was stirred at rt for about 4 h, then cooled to about −40° C. and acetone (0.3 mL, 4.1 mmol) was added dropwise. Subsequently, the mixture was warmed to rt, treated with methanol (2 mL) and concentrated in vacuo. The residue was dissolved in ethyl acetate (40 mL), washed with saturated aqueous ammonium chloride (10 mL), dried (MgSO$_4$), filtered and concentrated in vacuo. The resulting residue was purified by column chromatography (SiO$_2$, diethyl ether) to give 2-[3-chloro-4-[1-methyl-3-(2-pyridyl)-4,6,7,8-tetrahydropyrazolo[3,4-e][1,4]thiazepin-4-yl]phenyl]propan-2-ol (0.095 g, 0.23 mmol, 39%) as a white foam: LC-MS (Table 1, Method e) R$_t$=6.53 min; m/z 415 (M+H)$^+$; $^1$H-NMR (CDCl$_3$, Bruker 400 MHz) δ 1.52 (3 H, s) 1.53 (3 H, s) 1.69 (1 H, s) 2.71 (1 H, ddd, J=15.0, 5.2, 2.0 Hz) 2.88 (1 H, ddd, J=15.0, 9.3, 2.6 Hz) 3.21-3.29 (1 H, m) 3.57-3.66 (1 H, m) 3.79 (1 H, dd, J=3.8, 5.4 Hz) 3.83 (3 H, s) 6.84 (1 H, s) 7.08 (1 H, ddd, J=7.5, 4.8, 1.1 Hz) 7.20 (1 H, dd, J=8.1, 1.8 Hz) 7.27 (1 H, d, J=8.1 Hz) 7.52 (1 H, d, J=1.8 Hz) 7.59 (1 H, td, J=7.9, 1.8 Hz) 7.73 (1 H, dt, J=7.9, 1.1 Hz) 8.53 (1 H, ddd, J=4.8, 1.8, 1.0 Hz); and 4-(2-chlorophenyl)-1-methyl-3-(2-pyridyl)-4,6,7,8-tetrahydropyrazolo[3,4-e][1,4]thiazepine (0.035 mg, 0.10 mmol, 17%) as a white foam: LC-MS (Table 1, Method e) R$_t$=7.62 min; m/z 357 (M+H)$^+$; $^1$H-NMR (CDCl$_3$, Bruker 400 MHz) δ 2.72 (1 H, ddd, J=15.1, 6.1, 2.2 Hz) 2.87 (1 H, ddd, J=15.1, 9.1, 2.5 Hz) 3.23-3.32 (1 H, m) 3.57-3.66 (1 H, m) 3.81 (1 H, br s) 3.84 (3 H, s) 6.82 (1 H, s) 7.05-7.13 (3 H, m) 7.25-7.31 (1 H, m) 7.36-7.42 (1 H, m) 7.59 (1 H, td, J=7.7, 1.5 Hz) 7.72 (1 H, dt, J=8.0, 1.1 Hz) 8.52 (1 H, ddd, J=4.8, 1.5, 0.8 Hz).

Preparation #26

4-(2-chloro-4-methyl-phenyl)-1-methyl-3-(2-pyridyl)-4,6,7,8-tetrahydro pyrazolo[3,4-e][1,4]thiazepine

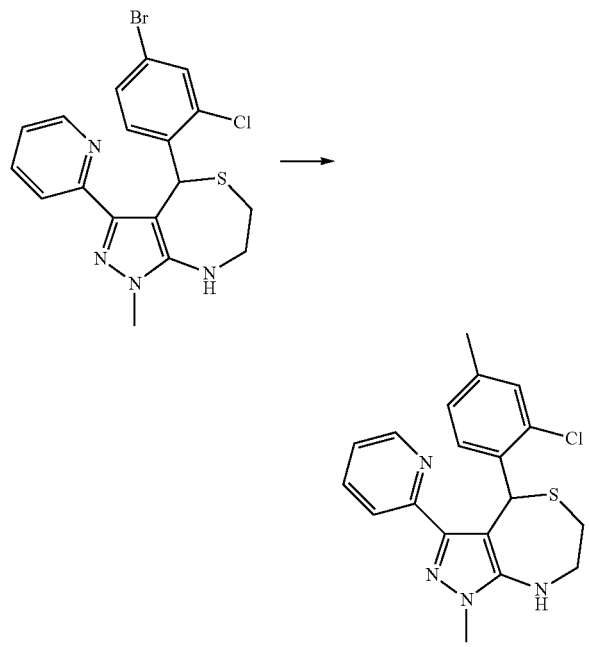

To a degassed solution of 4-(4-bromo-2-chloro-phenyl)-1-methyl-3-(2-pyridyl)-4,6,7,8-tetrahydropyrazolo[3,4-e][1,4] thiazepine (0.4 g, 0.92 mmol, see Ex. #3 step D) in 1,4-dioxane (10 mL) was added potassium carbonate (0.4 g, 2.9 mmol), trimethylboroxine (0.200 g, 1.6 mmol) and tetrakis(triphenylphosphine)palladium(0) (0.2 g, 0.18 mmol). The resulting mixture was heated, in a sealed microwave vessel, for about 1 h at about 100° C. in a microwave. After cooling to rt, the mixture was concentrated in vacuo. The residue was treated with water (25 mL) and ethyl acetate (150 mL). The layers were separated and the aqueous layer was extracted with ethyl acetate (50 mL). The combined organic layers were washed with water (50 mL), dried (MgSO$_4$), filtered and concentrated in vacuo. The resulting residue was purified by column chromatography (SiO$_2$, ethyl acetate/hexanes 1:1) to give 4-(2-chloro-4-methyl-phenyl)-1-methyl-3-(2 pyridyl)-4,6,7,8-tetrahydropyrazolo[3,4-e][1,4]thiazepine (0.055 g, 0.15 mmol, 60%) as an off white solid: LC-MS (Table 1, Method e) R$_t$=8.02 min; m/z 371 (M+H)$^+$; $^1$H-NMR (CDCl$_3$, Bruker 400 MHz) δ 2.27 (3 H, s) 2.72 (1 H, ddd, J=15.0, 6.0, 2.5 Hz) 2.86 (1 H, ddd, J=15.0, 9.0, 2.5 Hz) 3.22-3.29 (1 H, m) 3.54-3.63 (1 H, m) 3.80 (1 H, br s) 3.84 (3 H, s) 6.75 (1 H, s) 6.89 (1 H, br.d, J=7.5 Hz) 7.07 (1 H, ddd, J=7.5, 5.0, 1.0 Hz) 7.16 (1 H, d, J=8.0 Hz) 7.22 (1 H, br.d, J=1.0 Hz) 7.58 (1H, td, J=7.5, 2.0 Hz) 7.70 (1 H, dt, J=8.0, 1.0 Hz) 8.53 (1 H, ddd, J=5.0, 2.0, 1.0 Hz).

Preparation #27

4-(2,4-dichlorophenyl)-1,3,6,6,8-pentamethyl-4H-pyrazolo[3,4-e][1,4]thiazepin-7-one

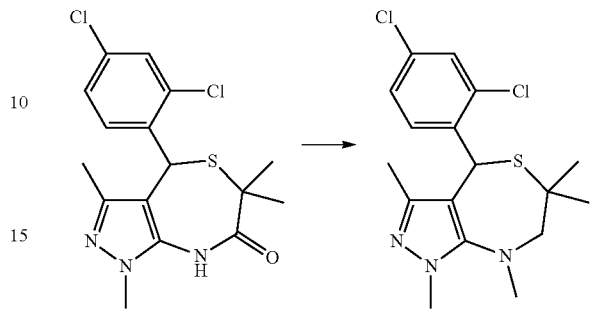

To 4-(2,4-dichlorophenyl)-1,3,6,6-tetramethyl-4,8-dihydropyrazolo[3,4-e][1,4]thiazepin-7-one (0.150 g, 0.4 mmol, made in the same manner as Preparation C.2) dissolved in THF/H$_2$O (1:1, 10 mL), was added NaOH (0.81 mL, 2 M aqueous). The reaction mixture was stirred for about 24 h at rt. Subsequently, dimethylsulfate (0.077 mL, 0.8 mmol) was added, and the reaction mixture was stirred for about 1 hr at rt. To the reaction mixture was added NH$_4$OH (1 mL, 25% aqueous), followed by 5% aqueous sodium bicarbonate (5 mL) and ethyl acetate (25 mL). The layers were separated and the organic layer was washed with water (25 mL), dried (MgSO$_4$), filtered and concentrated in vacuo. The resulting residue was purified by column chromatography (SiO$_2$, ethyl acetate/DCM (1:9)), to afford 4-(2,4-dichlorophenyl)-1,3,6,6,8-pentamethyl-4H-pyrazolo[3,4-e][1,4]thiazepin-7-one (0.110 g, 0.28 mmol, 72%), as a white solid. LC-MS (Table 1, Method a) R$_t$=5.05 min, m/z 384 (M+H)$^+$; $^1$H NMR (400 MHz, CDCl$_3$) δ ppm 1.05 (3 H, br. s.) 1.51 (3 H, br. s.) 2.32 (3 H, br. s.) 2.87 (3 H, br. s.) 3.65 (3 H, br. s.) 5.32 (1 H, br. s.) 7.29 (1 H, dd, J=8.3, 1.9 Hz) 7.34 (1 H, br. s.) 7.72 (1 H, d, J=8.3 Hz).

Preparation #28

4-(2,4-dichlorophenyl)-1,3,6,6-tetramethyl-4,7-dihydropyrazolo[3,4-e][1,4]thiazepine-8-carbaldehyde

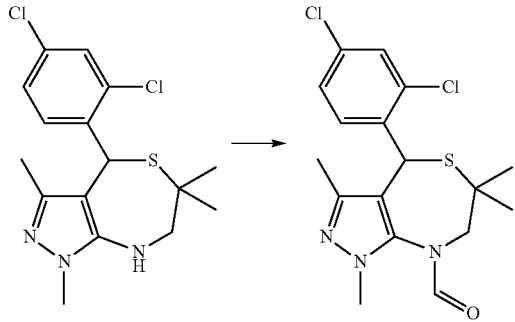

To acetic anhydride (5 mL, 53 mmol), was added formic acid (2.83 mL, 75 mmol). The resulting mixture was heated for about 15 min at about 50° C. To this mixture (after cooling to about 0° C.), was added 4-(2,4-dichlorophenyl)-1,3,6,6-tetramethyl-7,8-dihydro-4H-pyrazolo[3,4-e][1,4]thiazepine (50 mg, 0.14 mmol, Ex. D.4). The reaction mixture was stirred, for about 24 h, at rt. Subsequently, 5% aqueous sodium bicarbonate (25 mL) and ethyl acetate (50 mL) were added. The layers were separated and the organic layer was washed with water (25 mL), dried (MgSO$_4$), filtered and concentrated in vacuo. The resulting residue was purified by column chromatography (SiO₂, ethyl acetate), to afford 4-(2,4-dichlorophenyl)-1,3,6,6-tetramethyl-4,7-dihydropyrazolo[3,4-e][1,4]thiazepine-8-carbaldehyde (35 mg, 0.09 mmol, 65%), as a white solid. LC-MS (Table 1, Method a) R$_t$=4.53/ 4.71 min (rotamers), m/z 384 (M+H)⁺; ¹H NMR (400 MHz, CDCl₃) δ ppm 1.30 (3H, s) 1.49 (3 H, s) 1.65 (3 H, br s) 3.58-3.85 (2 H, br s) 3.73 (3 H, s) 5.48 (1 H, s) 7.11 (1 H, br s) 7.20 (1 H, br s) 7.44 (1 H, br s) 8.45 (1 H, s) (Major) ¹H NMR (400 MHz, CDCl₃) δ ppm 1.17 (3H, br s) 1.34 (3 H, br s) 1.93 (3 H, s) 3.41 (1 H, d, J=14.2 Hz) 3.69 (3 H, s) 3.76 (1 H, d, J=14.2 Hz) 5.54 (1 H, s) 7.12 (1 H, br s) 7.20 (1 H, br s) 7.39 (1 H, br s) 8.23 (1 H, br s) (Minor).

Preparation #29

3-[4-(2,4-dichlorophenyl)-1,3,6,6-tetramethyl-4,7-dihydropyrazolo[3,4-e][1,4]thiazepin-8-yl]-1,1,1-trifluoro-propan-2-ol

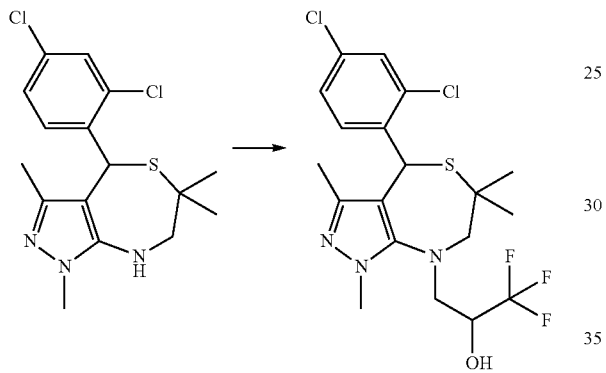

To 4-(2,4-dichlorophenyl)-1,3,6,6-tetramethyl-7,8-dihydro-4H-pyrazolo[3,4-e][1,4]thiazepine (0.1 g, 0.28 mmol, Ex. D.4), dissolved in dry acetonitrile/DMF (4:1, 5 mL), was added 3,3,3-trifluoro-1,2-propenoxide (0.5 mL, 5.45 mmol) and ytterbium triflate (0.05 g, 0.4 mmol). The reaction mixture was stirred, for about 72 h, at about 50° C. After cooling to rt, 5% aqueous sodium bicarbonate (25 mL) and ethyl acetate (25 mL) were added. The layers were separated and the organic layer was washed with water (25 mL), dried (MgSO₄), filtered and concentrated in vacuo. The resulting residue was purified by column chromatography (SiO₂, ethyl acetate/methanol/acetic acid (8:2:0.1) followed by ethyl acetate/methanol/acetic acid (5:5:0.1)), to afford crude product which was purified by prep-HPLC (Table 2, Method c) to yield 3-[4-(2,4-dichlorophenyl)-1,3,6,6-tetramethyl-4,7-dihydropyrazolo[3,4-e][1,4]thiazepin-8-yl]-1,1,1-trifluoro-propan-2-ol (0.077 g, 0.16 mmol, 58%), as a white solid: LC-MS (Table 1, Method a) R$_t$=2.71 min, m/z 468 (M+H)⁺; ¹H NMR (400 MHz, CDCl₃, diastereomer mixture, ratio A:B=54:46) δ ppm 1.04 (3 H, s) 1.38 (3 H, s) 1.87 (3 H, s) 3.43 (1 H, dd, J=14.7, 6.1 Hz) 3.65-3.75 (1 H, m) 4.07 (3 H, s) 4.11-4.28 (2 H, m) 4.41-4.50 (1 H, m) 5.22 (1 H, s) 7.30 (1 H, dd, J=8.3, 2.2 Hz) 7.46 (1 H, d, J=2.2 Hz) 7.50 (1 H, d, J=8.3 Hz) 8.93 (1H, t, J=4.8 Hz) (Isomer A); ¹H NMR (400 MHz, CDCl₃) δ ppm 1.01 (3 H, s) 1.36 (3 H, s) 1.90 (3 H, s) 3.37 (1 H, dd, J=14.6, 7.1 Hz) 3.65-3.75 (1 H, m) 3.98 (3 H, s) 4.11-4.28 (2 H, m) 4.50-4.60 (1 H, m) 5.17 (1 H, s) 7.29 (1 H, dd, J=8.3, 2.2 Hz) 7.44 (1 H, d, J=2.2 Hz) 7559 (1 H, d, J=8.3 Hz) 8.83 (1 H, t, J=4.8 Hz) (Isomer B).

Preparation #30

3-[4-(2,4-dichlorophenyl)-3,6,6-trimethyl-7,8-dihydro-4H-pyrazolo[3,4-e][1,4]thiazepin-1-yl]-1,1,1-trifluoro-propan-2-ol and 3-[4-(2,4-dichlorophenyl)-3,6,6-trimethyl-7,8-dihydro-4H-pyrazolo[3,4-e][1,4]thiazepin-2-yl]-1,1,1-trifluoro-propan-2-ol

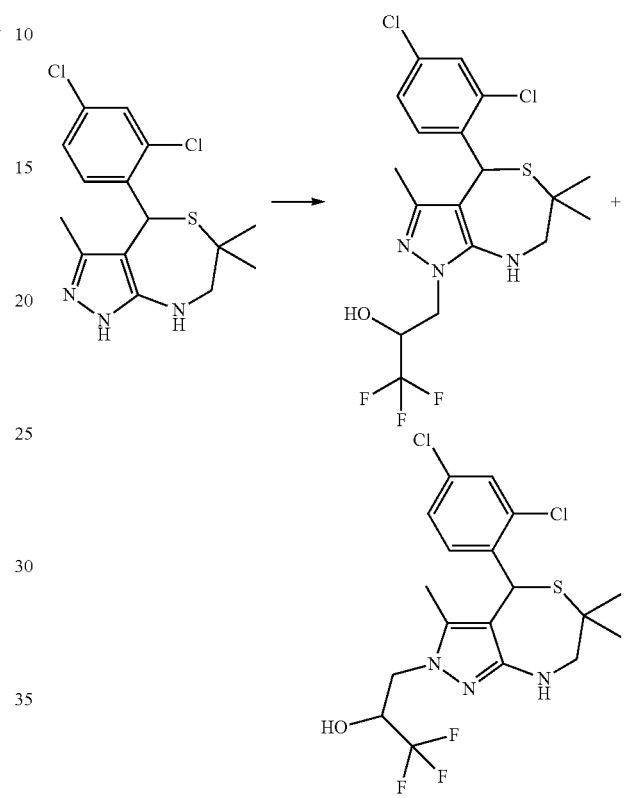

The compound was prepared by a similar procedure as Preparation #29 from Ex. D.63. LC-MS (Table 1, Method d) R$_t$=2.86 min; m/z 454 (M+H)⁺

Preparation #31

4-(2,4-dichlorophenyl)-1,3,6,6,8-pentamethyl-4,7-dihydropyrazolo[3,4-e][1,4]thiazepine hydrochloride

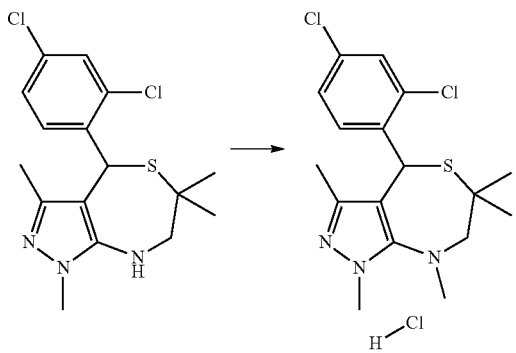

To 4-(2,4-dichlorophenyl)-1,3,6,6-tetramethyl-7,8-dihydro-4H-pyrazolo[3,4-e][1,4]thiazepine (0.12 g, 0.33 mmol, Example #D.4) dissolved in DMF (10 mL), was added NaH (0.133 g, 3.33 mmol, 60% dispersion in mineral oil) and methyl iodide (0.21 mL, 3.33 mmol). The reaction mixture was stirred for about 24 h at rt. To the reaction mixture was added 5% aqueous sodium bicarbonate (30 mL) and ethyl acetate (25 mL). The layers were separated and the organic layer was washed with water (25 mL), dried (MgSO₄), filtered and concentrated in vacuo. The resulting residue was purified by column chromatography (SiO₂, ethyl acetate/DCM (1:9 followed by 1:4)), to 4-(2,4-dichlorophenyl)-1,3,6,6,8-pentamethyl-4,7-dihydropyrazolo[3,4-e]thiazepine (0.07 g, 0.189 mmol, 57%), which was dissolved in ethyl acetate and converted into the HCl salt (using 1M HCl/ethanol). The precipitated solid is collected by filtration and washed with a small amount of diethyl ether to afford 4-(2,4-dichlorophenyl)-1,3,6,6,8-pentamethyl-4,7-dihydropyrazolo[3,4-e][1,4]thiazepine hydrochloride (0.053 g, 0.13 mmol, 39%) as an off white solid. LC-MS (Table 1, Method d) $R_t$=3.05 min, m/z 370 (M+H)⁺

Preparation #32

4-bromo-2,5-dimethylbenzaldehyde

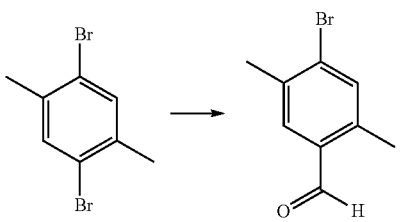

A solution of 1,4-dibromo-2,5-dimethylbenzene (5.0 g, 18.94 mmol, Aldrich) in anhydrous THF (20 mL) was cooled to about −10° C. Isopropyl magnesium chloride (3.95 mL, 2.0 M in THF, 7.9 mmol) was added. The mixture was allowed to stir at about −10° C. for about 0.25 h. Next n-butyl lithium (6.31 mL, 2.5 M in hexanes, 15.8 mmol) was added dropwise keeping the temperature at or below about 0° C. Once the addition was complete the reaction was stirred at about −10° C. for about 1 h. Next a solution of DMF in 10 mL anhydrous THF (20.52 mmol) was added dropwise keeping the temperature at or below about 0° C. The reaction was stirred at ambient temperature for about 3 hours. The reaction was poured into about 50 mL of about 5 M aqueous citric acid solution (exothermic) and stirred at room temperature for about 10 minutes. The layers were separated and the aqueous layer was extracted once with toluene (50 mL). The combined organic layers were washed with water (20 mL), then concentrated in vacuo. The residue was purified by column chromatography (SiO₂, diethyl ether/petroleum ether 5:95) to give 4-bromo-2,5-dimethylbenzaldehyde (3.66 g, 17.18 mmol, 91%) as a pale crystalline solid: ¹H-NMR (CDCl₃, Bruker 400 MHz) δ 2.43 (3 H, s); 2.60 (3 H, s); 7.47 (1 H, s); 7.63 (1 H, s) 10.2 (1 H, s).

Preparation #33

4-(1-Ethyl-7-methyl-3-(pyridin-2-yl)-4,6,7,8-tetrahydro-1H-pyrazolo[3,4-e][1,4]thiazepin-4-yl)-3-methylbenzamide

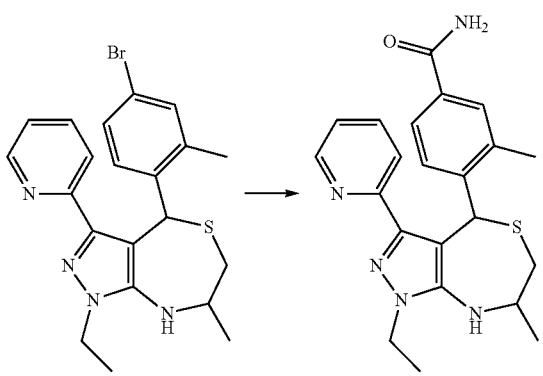 [SMILES: CCn1nc(-c2ccccn2)c2c1NC(C)CSC2c1ccc(Br)cc1C ; CCn1nc(-c2ccccn2)c2c1NC(C)CSC2c1ccc(C(N)=O)cc1C]

A Barney reactor was charged with Pd(OAc)₂ (0.337 mg, 1.50 μmol), Xantphos (0.913 mg, 1.58 μmol) and 4-(4-bromo-2-methylphenyl)-1-ethyl-7-methyl-3-(pyridin-2-yl)-4,6,7,8-tetrahydro-1H-pyrazolo[3,4-e][1,4]thiazepine (33.3 mg, 0.075 mmol, prepared using B from Example #2 step A with ethylhydrazine oxalate, J with 4-bromo-2-methyl-benzaldehyde (AstaTech) and 1-sulfanylpropan-2-one [Enamine] then K with Na(AcO)₃BH). The solids were slurried in 1,4-dioxane (0.15 ml) and then sealed in the reactor. The atmosphere was inerted to N₂ (5×15 psig) then flushed with NH₃ (3×). The reactor was charged with NH₃ (80 psig) (~0.2 g) then with CO (33 psig) for a total pressure of ~113 psig. The reactor was sealed and heated to about 90° C. with stirring at 750 rpm with a pressure of ~150 psig. After about 16 h, the reactor was cooled to rt and purged with N₂. The crude material was purified by flash chromatography (25 g silica gel; heptane/EtOAc 4:1 to 0:1) to give 4-(1-ethyl-7-methyl-3-(pyridin-2-yl)-4,6,7,8-tetrahydro-1H-pyrazolo[3,4-e][1,4]thiazepin-4-yl)-3-methylbenzamide (0.156 g, 85%) as a mixture of stereoisomers: LC-MS (Table 1, Method g) $R_t$=2.00 and 2.02 min.; MS m/z: 408.1 and 408.1 (M+H)⁺.

Preparation #34

Methyl 4-(1-ethyl-3-(pyridin-2-yl)-4,6,7,8-tetrahydro-1H-pyrazolo[3,4-e][1,4]thiazepin-4-yl)-3-methylbenzoate

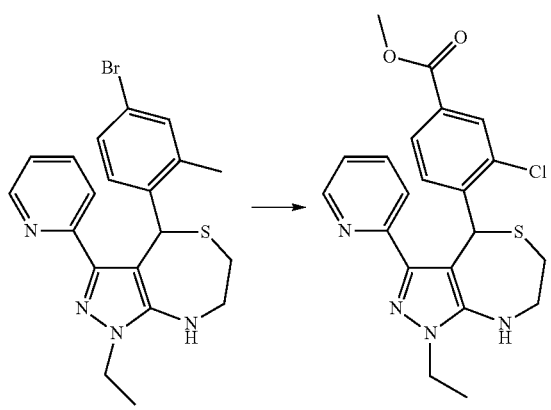 [SMILES: CCn1nc(-c2ccccn2)c2c1NCCSC2c1ccc(Br)cc1C ; CCn1nc(-c2ccccn2)c2c1NCCSC2c1ccc(C(=O)OC)cc1Cl]

A microwave vial was charged with 4-(4-bromo-2-methylphenyl)-1-ethyl-3-(pyridin-2-yl)-4,6,7,8-tetrahydro-1H-pyrazolo[3,4-e][1,4]thiazepine (0.70 g, 1.63 mmol, prepared using B from Example #2, Step A with ethyl hydrazine, C with 4-bromo-2-methylbenzaldehyde (Asta Tech) and 2-mercaptoacetic acid followed by D with borane-THF complex), Pd(OAc)$_2$ (0.04 g, 0.16 mmol), dppf (0.18 g, 0.32 mmol) and DMF (13.5 mL). Nitrogen was bubbled through the reaction mixture for about 10 min. The mixture was evacuated and then back-filled with CO three times. Methanol (3.3 mL) and triethylamine (1.2 mL, 16.3 mmol) were added. The reaction mixture was heated, in a sealed microwave vessel, for about 3 h at about 85° C. After cooling to rt, the mixture was partially concentrated under reduced pressure. The crude product was partitioned between EtOAc (40 mL) and water (10 mL). The organic layer was washed with brine (10 mL), dried over MgSO$_4$, filtered and concentrated under reduced pressure. The crude material was purified by column chromatography (SiO$_2$, EtOAc/heptane 100:0 to 0:100) to afford methyl 4-(1-ethyl-3-(pyridin-2-yl)-4,6,7,8-tetrahydro-1H-pyrazolo[3,4-e][1,4]thiazepin-4-yl)-3-methylbenzoate (0.36 g, 55%): LC-MS (Table 1, Method g) R$_t$=2.38 min, m/z 409 (M+H)$^+$.

Preparation #35

4-(4-Bromo-2-methylphenyl)-1,7-dimethyl-3-(pyrimidin-4-yl)-4,6-dihydro-1H-pyrazolo[3,4-e][1,4]thiazepine

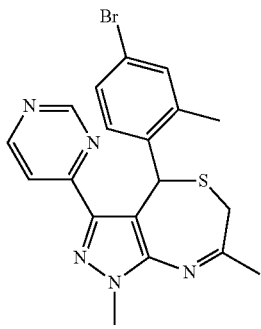 [SMILES: CC1=Nc2c(c(-c3ccncn3)nn2C)C(c2ccc(Br)cc2C)SC1]

Step A: 4-(4-Bromo-2-methylbenzylidene)-1-methyl-3-(pyrimidin-4-yl)-1H-pyrazol-5(4H)-imine

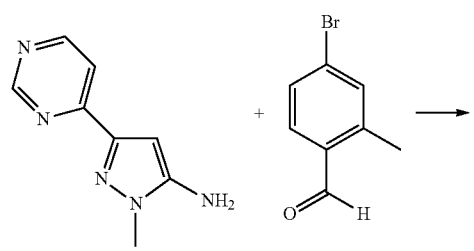

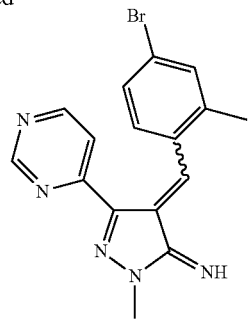

To the suspension of 1-methyl-3-(pyrimidin-4-yl)-1H-pyrazol-5-amine (0.42 g, 2.4 mmol, prepared using A with methylpyrimidine-4-carboxylate (Ark Pharm) with NaH followed by B with methyl hydrazine) and 4-bromo-2-methylbenzaldehyde (0.48 g, 2.40 mmol, Ark Pharm) in acetonitrile (15 mL) was added p-TSA (0.09 g, 0.5 mmol) and heated to about 50° C. for about 5 h. The reaction mixture was cooled to ambient temperature and continued to stir for about 16 h. The precipitate was collected by filtration and dried under reduced pressure to afford 4-(4-bromo-2-methylbenzylidene)-1-methyl-3-(pyrimidin-4-yl)-1H-pyrazol-5(4H)-imine (0.43 g, 51%) as a light brown solid. LC-MS MS (Table 1, Method g) R$_t$=2.48 min, m/z 356, 358 (M+H)$^+$.

Step B: 4-(4-Bromo-2-methylphenyl)-1,7-dimethyl-3-(pyrimidin-4-yl)-4,6-dihydro-1H-pyrazolo[3,4-e][1,4]thiazepine

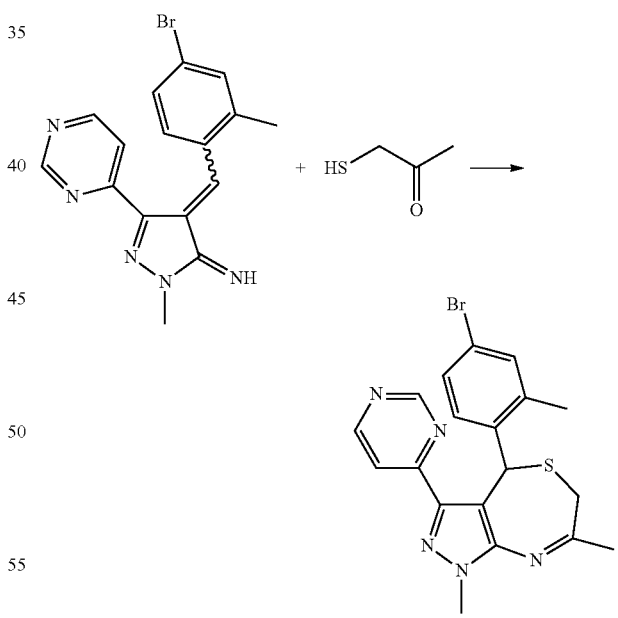

To a suspension of 4-(4-bromo-2-methylbenzylidene)-1-methyl-3-(pyrimidin-4-yl)-1H-pyrazol-5(4H)-imine (0.43 g, 1.21 mmol) in acetonitrile (12 mL) was added 1-mercaptopropan-2-one (0.143 g, 1.26 mmol, Enamine) and p-TSA (0.03 g, 0.18 mmol). The resulting mixture was stirred and heated to about 90° C. for about 16 h. The mixture was cooled to ambient temperature and the solvent was removed under reduced pressure to afford 4-(4-bromo-2-methylphenyl)-1,7-dimethyl-3-(pyrimidin-4-yl)-4,6-dihydro-M-pyrazolo[3,4- e][1,4]thiazepine (0.52 g, 1.21 mmol, 100%, which was used without further purification). LC-MS MS (Table 1, Method g) R$_t$=2.48 min, m/z 428, 430 (M+H)$^+$.

Preparation #36

Methyl 4-(1,7-dimethyl-3-(pyrimidin-4-yl)-4,6,7,8-tetrahydro-1H-pyrazolo[3,4-e][1,4]thiazepin-4-yl)-3-methylbenzoate

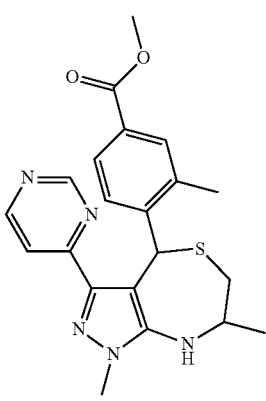 [SMILES: COC(=O)c1ccc(C2SCC(C)Nc3c2c(-c2ccncn2)nn3C)c(C)c1]

The compound was prepared by a similar procedure used to make Preparation #34 from 4-(4-bromo-2-methylphenyl)-1,7-dimethyl-3-(pyrimidin-4-yl)-4,6,7,8-tetrahydro-1H-pyrazolo[3,4-e][1,4]thiazepine (prepared using K with Na(OAc)$_3$BH from Preparation #35) LC-MS (Table 1, Method g) R$_t$=2.30, 2.25 m/z 410 (M+H)$^+$.

Preparation #37

1-Methyl-3-(1,2,4-oxadiazol-3-yl)-1H-pyrazol-5-amine

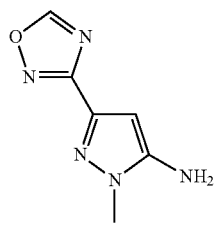

Step A: N'-Hydroxy-1-methyl-5-nitro-1H-pyrazole-3-carboximidamide

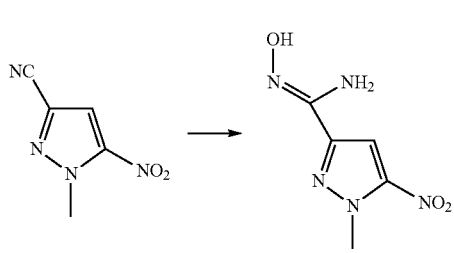

To a solution of 1-methyl-5-nitro-1H-pyrazole-3-carbonitrile (2.4 g, 15.8 mmol, Princeton) and hydroxylamine hydrochloride (3.29 g, 47.3 mmol) in EtOH (0.50 mL) was added potassium carbonate (10.9 g, 79 mmol) and the mixture was refluxed for about 2 h. The reaction mixture was filtered hot and the collected solid was rinsed with EtOH (50 mL) and then MeOH (100 mL). The filtrate was concentrated under reduced pressure. The crude material was partitioned between DCM (40 mL) and water (20 mL). The aqueous layer was acidified to about pH 2 using 1 N HCl and back extracted with DCM (20 mL). The aqueous layer was basified using saturated NaHCO$_3$ and the precipitate was collected by vacuum filtration and dried to afford N'-hydroxy-1-methyl-5-nitro-1H-pyrazole-3-carboximidamide (1.24 g, 4.49 mmol, 67%). LC-MS (Table 1, Method g) R$_t$=1.07 min, m/z 186 (M+H)$^+$. $^1$H-NMR (DMSO-d$_6$, Bruker 400 MHz) δ 9.78 (s, 1H), 7.22 (s, 1H), 5.71 (s, 2H), 4.16 (s, 3H).

Step B: 3-(1-Methyl-5-nitro-1H-pyrazol-3-yl)-1,2,4-oxadiazole

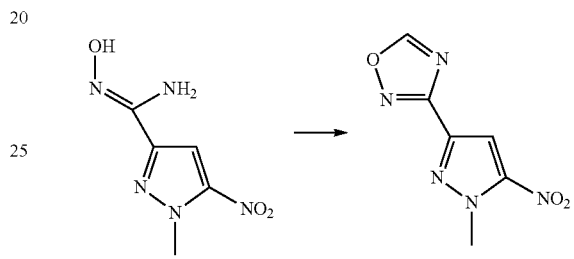

To a solution of N'-hydroxy-1-methyl-5-nitro-1H-pyrazole-3-carboximidamide (1.66 g, 8.97 mmol) and trimethoxymethane (17.6 mL, 161 mmol) in MeOH (2.8 mL) was added 2,2,2-trifluoroacetic acid (0.35 mL, 4.48 mmol) and the mixture was refluxed for about 1 h. The reaction was cooled to ambient temperature and continued to stir for about 16 h. The reaction mixture was concentrated under reduced pressure and the residue was partitioned between DCM (25 mL) and saturated NaHCO$_3$ (10 mL). The aqueous layer was back extracted with DCM (25 mL). The combined organic layers were washed with brine (10 mL), dried over MgSO$_4$, filtered and concentrated under reduced pressure to afford 3-(1-methyl-5-nitro-1H-pyrazol-3-yl)-1,2,4-oxadiazole (1.75 g, 8.97 mmol, 100%, which was used without further purification). LC-MS (Table 1, Method g) R$_t$=1.56 min, m/z 196 (M+H)$^+$. $^1$H-NMR (DMSO-d$_6$, Bruker 400 MHz) 9.79 (s, 1H), 7.72 (s, 1H), 4.27 (s, 3H).

Step C: 1-Methyl-3-(1,2,4-oxadiazol-3-yl)-1H-pyrazol-5-amine

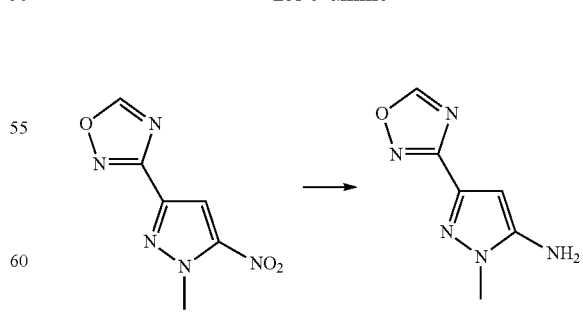

To a mixture of 3-(1-methyl-5-nitro-1H-pyrazol-3-yl)-1,2,4-oxadiazole (2.0 g, 10.3 mmol) and ammonium chloride (7.68 g, 143 mmol) in a 1:1 mixture of THF (32 mL)/MeOH (32 mL) at 0° C. was added zinc dust (9.38 g, 143 mmol)

portionwise. The ice bath was removed after about 10 min and the reaction was stirred at ambient temperature for about 1 h. The reaction mixture was filtered through a pad of Celite® rinsing with MeOH (30 mL) and then concentrated under reduced pressure. The crude material was partitioned between DCM (20 mL) and water (10 mL). The organic layer was separated and the aqueous layer was back extracted with DCM (20 mL). The combined organic layers were dried over MgSO₄, filtered and concentrated under reduced pressure. The aqueous layer was acidified using 1 N HCl to about pH 3 and DCM (50 mL) was added. The organic layer was separated dried over MgSO₄, filtered and concentrated under reduced pressure to provide additional crude material. The aqueous layer was basified using 1 N NaOH to about pH 9. The precipitate was collected by vacuum filtration, combined with the batches collected from the organic layers and dried in a vacuum oven at about 50° C. for about 16 h to afford 1-methyl-3-(1,2,4-oxadiazol-3-yl)-1H-pyrazol-5-amine (1.2 g, 7.27 mmol, 71%, which was used without further purification). LC-MS (Table 1, Method g) $R_t$=0.71 min, m/z 166 (M+H)⁺. ¹H-NMR (DMSO-d₆, Bruker 400 MHz) δ 9.55 (s, 1H), 5.80 (s, 1H), 5.47 (s, 2H), 3.61 (s, 3H).

Preparation #38

1-Methyl-3-(1,3,4-oxadiazol-2-yl)-1H-pyrazol-5-amine

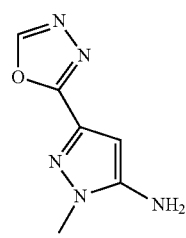

Step A:
1-methyl-5-nitro-1H-pyrazole-3-carbohydrazide

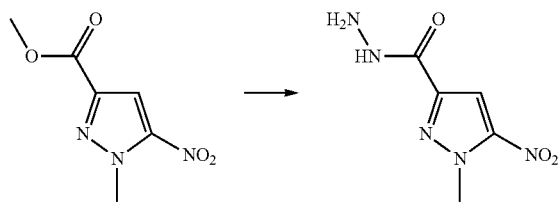

To a solution of 1-methyl-5-nitro-1H-pyrazole-3-carboxylate (3.81 g, 20.6 mmol, Princeton) in MeOH (20 mL) at was added hydrazine (2.0 mL, 35% in water, 41.2 mmol) The reaction mixture was heated to about 60° C. for about 2 h. The reaction was cooled to ambient temperature and concentrated under reduced to afford 1-methyl-5-nitro-1H-pyrazole-3-carbohydrazide (3.81 g, 20.6 mmol, 100%, which was used without further purification). LC-MS (Table 1, Method g) $R_t$=0.90 min, m/z 186 (M+H)⁺.

Step B: 2-(1-methyl-5-nitro-1H-pyrazol-3-yl)-1,3,4-oxadiazole

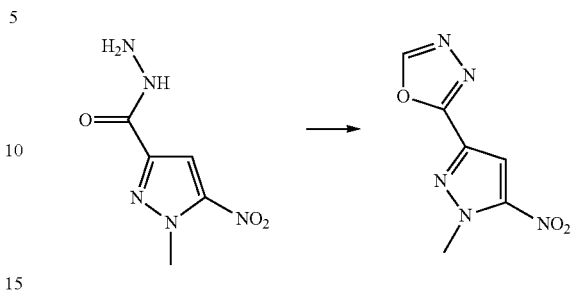

To a solution of 1-methyl-5-nitro-1H-pyrazole-3-carbohydrazide (3.81 g, 20.6 mmol) in DCM (30 mL) was added 2,2,2-trifluoroacetic acid (4 mL, 51.9 mmol). The mixture was stirred for about 2 h then concentrated under reduced pressure. To the residue was added triethoxymethane (31.4 mL, 206 mmol) and the mixture was refluxed for about 24 h. The reaction was cooled to ambient temperature and continued to stir for about 16 h. The reaction mixture was concentrated under reduced pressure and the material was partitioned between DCM (25 mL) and saturated NaHCO₃ (10 mL). The organic layer was separated and the aqueous layer was back extracted with DCM (25 mL). The combined organic layers were washed with brine (10 mL), dried over MgSO₄, filtered and concentrated under reduced pressure and triturated with ether (2×30 mL).

The solid was collected by vacuum filtration and dried under reduced pressure to afford 2-(1-methyl-5-nitro-M-pyrazol-3-yl)-1,3,4-oxadiazole (2.56 g, 13.1 mmol, 64%, which was used without further purification). LC-MS (Table 1, Method g) $R_t$=1.32 min, m/z 196 (M+H)⁺.

Step C: 1-methyl-3-(1,3,4-oxadiazol-2-yl)-1H-pyrazol-5-amine

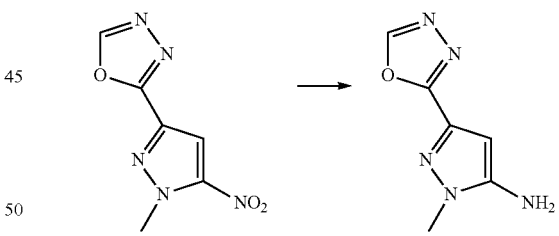

To a mixture of 2-(1-methyl-5-nitro-1H-pyrazol-3-yl)-1,3,4-oxadiazole (2.56 g, 13.1 mmol), ammonium chloride (4.91 g, 92 mmol) in a 1:1 solution of THF/MeOH (82.6 mL) at about 0° C. was added zinc dust (6.0 g, 92 mmol) portionwise. The reaction was stirred for about 10 min at about 0° C. The ice bath was removed and the reaction stirred at ambient temperature for about 16 h. The reaction mixture was filtered through a pad of Celite® rinsing with MeOH (50 mL). The filtrate was concentrated under reduced pressure. The material was partitioned between DCM (50 mL) and water (10 mL). The aqueous layer was back extracted with DCM (2×50 mL). The combined organic layers were dried over MgSO₄, filtered and concentrated under reduced pressure. The aqueous layer was acidified using 1 N HCl to about pH 3 and back extracted with DCM (50 mL). The organic layer was dried over MgSO₄, filtered and concentrated under reduced pressure. The organic layer batches were combined to afford 1-methyl-3-(1,3,4-oxadiazol-2-yl)-1H-pyrazol-5-amine (0.67 g, 4.06 mmol, 31%, which was used without further purification). LC-MS (Table 1, Method g) $R_t$=0.59 min, m/z 166 (M+H)⁺.

Preparation #39 rac-(4R,7S)-Ethyl 4-(4-bromo-2-methylphenyl)-1-methyl-3-(pyridine-2-yl)-4,6,7,8-tetrahydro-1H-pyrazolo[3,4-e][1,4]thiazepine-7-carboxylate

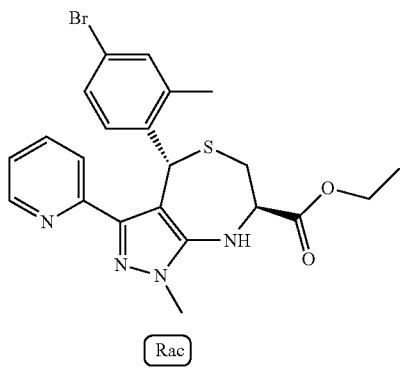 [SMILES: CCOC(=O)[C@@H]1CS[C@@H](c2ccc(Br)cc2C)c2c(-c3ccccn3)nn(C)c2N1]

Step A: 4-(4-bromo-2-methylbenzylidene)-1-methyl-3-(pyridin-2-yl)-1H-pyrazol-5(4H)-imine

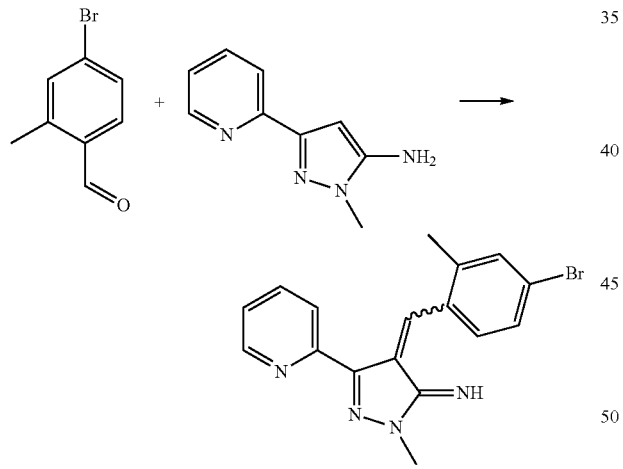

A suspension of 1-methyl-3-(pyridin-2-yl)-1H-pyrazol-5-amine (4.50 g, 25.8 mmol, Example #2 step B), 4-bromo-2-methylbenzaldehyde (5.14 g, 25.8 mmol, Astatech) and 4-methylbenzenesulfonic acid hydrate (0.491 g, 2.58 mmol) in MeCN (36 ml) was warmed up to about 45° C. for about 15 min to give a solution then the reaction was allowed to cool to rt. The precipitate was filtered and washed with MeCN to give 4-(4-bromo-2-methylbenzylidene)-1-methyl-3-(pyridin-2-yl)-1H-pyrazol-5(4H)-imine (5.88 g, 16.55 mmol, 64%) as a beige solid: LC-MS (Table 1, Method g) $R_t$=2.55 min, m/z 355/357 (M+H)⁺; ¹H-NMR (DMSO-d₆, Bruker 400 MHz) δ 9.07 (s, 1H), 8.60-8.57 (m, 1H), 8.02-7.95 (m, 2H), 7.91-7.86 (m, 1H), 7.61-7.50 (m, 2H), 7.40-7.31 (m, 1H), 7.19 (s, 1H), 3.96 (s, 3H), 2.62 (s, 3H).

Step B: Sodium 3-ethoxy-1-mercapto-3-oxoprop-1-en-2-olate

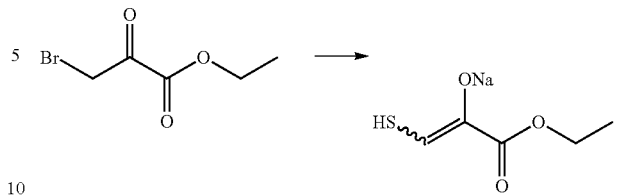

A solution of sodium hydrogensulfide hydrate (17.1 g, 231 mmol) in EtOH (1800 ml) was cooled then ethyl 3-bromo-2-oxopropanoate (29 ml, 231 mmol) was added dropwise at a rate to ensure the reaction temperature did not rise above about 4° C. The reaction was stirred at 0° C. for about 2.5 h. The precipitate that formed was filtered and washed with cold EtOH (50 mL) then Et₂O (50 mL) to give sodium 3-ethoxy-1-mercapto-3-oxoprop-1-en-2-olate (5.51 g, 32.4 mmol, 14%) as a crude white solid which was used as such in the next step. ¹H-NMR (DMSO-d₆, Bruker 400 MHz) δ 7.01-6.87 (m, 1H), 4.22-4.12 (m, 2H), 3.29 (s, 1H), 1.27-1.15 (m, 3H) major, ¹H NMR (DMSO-d₆, Bruker 400 MHz) δ 7.10 (s, 1H), 4.22-4.12 (m, 2H), 3.29 (s, 1H), 1.27-1.15 (m, 3H) minor.

Step C: rac-(4R,7S)-Ethyl 4-(4-bromo-2-methylphenyl)-1-methyl-3-(pyridine-2-yl)-4,6,7,8-tetrahydro-1H-pyrazolo[3,4-e][1,4]thiazepine-7-carboxylate

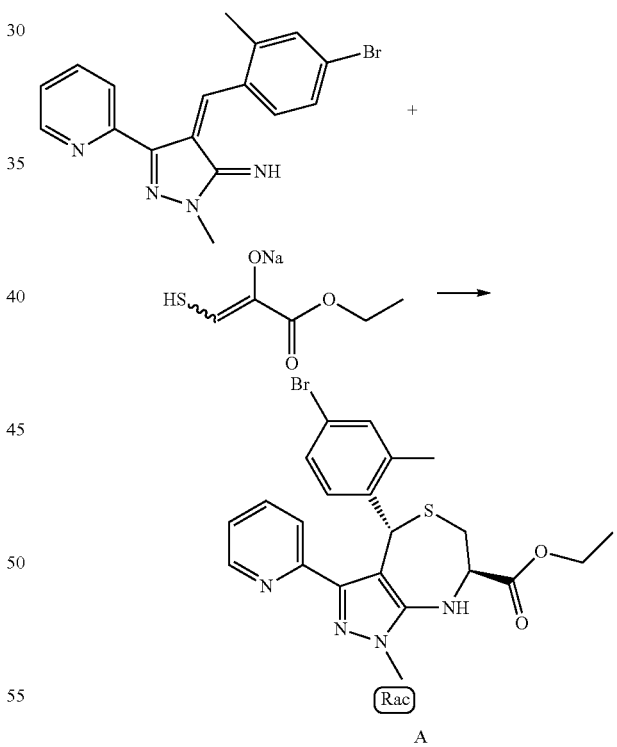

mixture of 4-(4-bromo-2-methylbenzylidene)-1-methyl-3-(pyridin-2-yl)-1H-pyrazol-5 (4H)-imine (5.58 g, 15.7 mmol), sodium 3-ethoxy-1-mercapto-3-oxoprop-1-en-2-olate (2.67 g, 15.7 mmol) and 4-methylbenzenesulfonic acid hydrate (0.299 g, 1.57 mmol) in MeCN (40 mL) was heated at about 85° C. for about 16 h. The reaction was allowed to cool to rt and was concentrated in vacuo. The residue was dissolved in AcOH (100 mL) and NaBH₄ (5.92 g, 94 mmol) was added portionwise. The reaction was heated at about 60° C. for about 16 h. The reaction was allowed to cool to rt. NaBH₄

(5.92 g, 94 mmol) was added to the reaction and the reaction was heated at about 60° C. for about 20 h. The reaction was allowed to cool to rt and was concentrated in vacuo. The residue was partitioned between EtOAc (100 mL) and saturated solution of NaHCO$_3$ (300 mL). The organic layer was washed with brine (30 mL), dried over Na$_2$SO$_4$, filtered and concentrated in vacuo. The residue was purified by column chromatography (SiO$_2$, 10-50% EtOAc/heptane) to give rac-(4R,7S)-Ethyl 4-(4-bromo-2-methylphenyl)-1-methyl-3-(pyridine-2-yl)-4,6,7,8-tetrahydro-M-pyrazolo[3,4-e][1,4]thiazepine-7-carboxylate (0.92 g, 1.89 mmol, 12%) as a white solid: LC-MS (Table 1, Method g) R$_t$=2.66 min, m/z 487/489 (M+H)$^+$; $^1$H-NMR (DMSO-d$_6$, Bruker 400 MHz) δ 8.46-8.43 (m, 1H), 7.83-7.79 (m, 1H), 7.75-7.67 (m, 1H), 7.36 (d, J=1.8 Hz, 1H), 7.26-7.22 (m, 1H), 7.21-7.11 (m, 2H), 6.71 (s, 1H), 4.47.4.43 (m, 1H), 4.15-3.97 (m, 3H), 3.77 (s, 3H), 3.11 (dd, J=15.1, 5.0 Hz, 1H), 2.83 (dd, J=15.1, 2.3 Hz, 1H), 1.98 (s, 3H), 1.21-1.06 (m, 3H).

General Procedure A: Preparation of 3-substituted 3-oxo-propanenitriles

To a suspension of a strong base such as sodium hydride, potassium ethoxide, potassium tert-butoxide or sodium methoxide (preferably sodium hydride) (1-2 equivalents, preferably 1.2 equivalents) in a solvent such as anhydrous toluene or anhydrous THF (preferably anhydrous THF) is added dropwise anhydrous acetonitrile (1-3 equivalents, preferably 1.5 equivalents). The mixture is stirred for about 30 min at rt and then an ester (1 equivalent) in a solvent such as anhydrous toluene or anhydrous THF (preferably anhydrous THF) is added at rt. Subsequently, the resulting mixture is heated under reflux, for 1-24 h (preferably 3 h). Alternatively, an ester (1 equiv) is added to a suspension of a strong base such as sodium hydride, potassium ethoxide, potassium tert-butoxide or sodium methoxide (preferably sodium hydride) (1-2 equivalents, preferably 1.2 equivalents) in a solvent such as anhydrous toluene or anhydrous THF (preferably anhydrous THF). The mixture is heated to about 60-100° C. (preferably about 70-80° C.) and anhydrous acetonitrile (1-8 equivalents, preferably 4-5 equivalents) is added. Subsequently, the resulting mixture is heated at about 60-100° C. (preferably about 80° C.) for 1-24 h (preferably about 3 h). After cooling to rt, the volatiles are removed in vacuo and to the residue is added saturated aqueous ammonium chloride (150 mL) and ethyl acetate (600 mL). The resulting layers are separated, and the aqueous layer is extracted with ethyl acetate (2×125 mL). The combined organic layers are washed with water (2×100 mL), dried (MgSO$_4$), filtered, and concentrated in vacuo to give crude 3-substituted 3-oxo-propanenitrile. If necessary the compound can be purified by column chromatography. Alternatively, the sodium or potassium salt of the 3-substituted 3-oxo-propanenitrile may be isolated by filtration of the suspension that is obtained after cooling to rt.

Illustration of General Procedure A

Preparation #A.1

3-(6-bromo-2-pyridyl)-3-oxo-propanenitrile

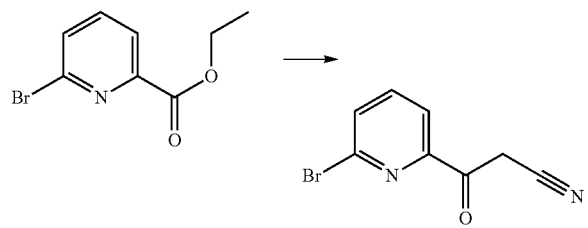

To a suspension of sodium hydride (0.6 g, 60% in oil, 15.7 mmol) in anhydrous THF (70 mL) was added dropwise anhydrous acetonitrile (1.02 mL, 19.6 mmol). The mixture was stirred for about 30 min at rt and then ethyl 6-bromopyridine-2-carboxylate (3.00 g, 13.0 mmol, Apollo Scientific) was added. Subsequently, the resulting mixture was heated under reflux, for about 2 h. After cooling to rt, the volatiles were removed in vacuo and to the residue was added saturated aqueous ammonium chloride (150 mL) and ethyl acetate (600 mL). The resulting layers were separated, and the aqueous layer was extracted with ethyl acetate (2×125 mL). The combined organic layers were washed with water (2×100 mL), dried (MgSO$_4$), filtered, and concentrated in vacuo. The residue was purified by column chromatography (SiO$_2$, ethyl acetate/hexanes 1:3) to give crude 3-(6-bromo-2-pyridyl)-3-oxo-propanenitrile (1.71 g, 7.6 mmol, 58%), as a pale yellow solid: $^1$H-NMR (CDCl$_3$, Bruker 400 MHz) δ 4.38 (2 H, s); 7.74-7.84 (2 H, m); 8.08 (1 H, dd, J=2 Hz, 6.5 Hz).

General Procedure B: Preparation of 3-substituted 5-amino-pyrazole

To a mixture of a 3-oxo-propanenitrile (1 equivalent) or the sodium or potassium salt of the 3-oxo-propanenitrile (1 equivalent) in ethanol is added a hydrazine (1 to 3 equivalents, preferably 1.25 equivalents) at rt. Subsequently the mixture is heated under reflux for 1-24 h (preferably about 5 h). After cooling to rt the mixture is concentrated in vacuo and the residue is purified by trituration with a solvent such as diethyl ether or toluene, or by column chromatography. Alternatively, the sodium or potassium salt of the 3-substituted 3-oxo-propanenitrile may be used, in this case an equivalent of acid, such as hydrochloric acid, sulfuric acid, or oxalic acid (preferably hydrochloric acid) is added to the above mixture.

Illustration of General Procedure B

Preparation #B.1

3-(6-bromo-2-pyridyl)-2-methyl-pyrazol-5-amine

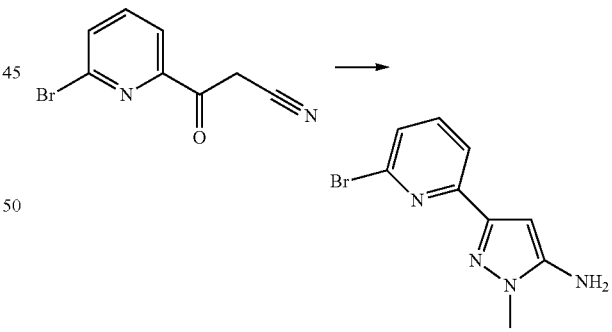

To a solution of 3-(6-bromo-2-pyridyl)-3-oxo-propanenitrile (1.71 g, 7.6 mmol, Preparation A.1) in ethanol (50 mL) was added methyl hydrazine (1.20 mL, 22.8 mmol). The resulting mixture was stirred for about 30 min at rt and then heated under reflux for about 4 h. After cooling to rt the reaction mixture was concentrated in vacuo. The residue was purified by column chromatography (SiO$_2$, ethyl acetate/hexanes 1:2) to give 3-(6-bromo-2-pyridyl)-2-methyl-pyrazol-5-amine (1.56 g, 6.2 mmol, 81%) as an off white solid: $^1$H-NMR (CDCl$_3$, Bruker 400 MHz) δ 3.57 (2 H, br s); 3.75 (3 H, s); 5.90 (1 H, s); 7.34 (1 H, d, J=8 Hz); 7.52 (1 H, t, J=8 Hz); 7.82 (1 H, d, J=8 Hz).

General Procedure C: Preparation of Thiazepinones

A mixture of a 3-aminopyrazole (1-2 equivalents, preferably 1.0 equivalent), an aldehyde (1-2 equivalents, preferably 1.0 equivalent), substituted thioglycolic acid (1-5 equivalents, preferably 3 equivalents) and optionally used p-toluenesulfonic acid (0-3 equivalents) with or without a solvent such as acetonitrile or toluene (preferably acetonitrile) is heated, eventually in a closed vessel in a microwave or an oil bath or a heating block (preferably in a microwave), at temperatures between 90° C. and 250° C. (preferably about 150° C.) for about 5 min to 24 h (preferably about 20 min). After cooling to rt the precipitated solid is collected by filtration and washed with a small amount of solvent. Alternatively, after cooling the mixture is treated with EDC or another coupling agent (preferably EDC) in the presence of DMAP in a solvent like acetonitrile or THF (preferably THF). Subsequently the mixture is stirred for 18-72 h (preferably about 24 h). The crude product can be further purified by column chromatography.

Illustrations of General Procedure C

Preparation #C.1

4-(4-chloro-2-methyl-phenyl)-1-methyl-3-(2-pyridyl)-4,8-dihydropyrazolo[3,4-e][1,4]thiazepin-7-one

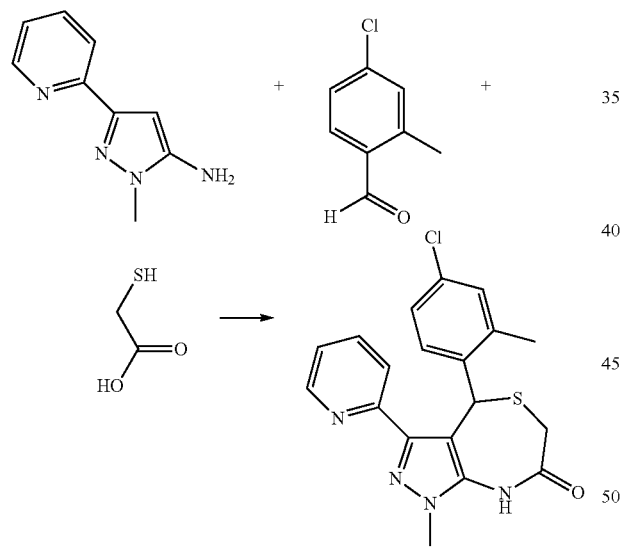

A mixture of 2-methyl-5-(2-pyridyl)pyrazol-3-amine (1.1 g, 6.3 mmol, Example #2, step B), 4-chloro-2-methylbenzaldehyde (1.0 g, 6.5 mmol, Fluorochem), and thioglycolic acid (2.4 g, 26 mmol) in acetonitrile (20 mL) was heated, in a sealed microwave vessel, for about 20 min, at about 150° C., in a microwave. After cooling to rt the precipitated solid was collected by filtration and washed with acetonitrile (2 mL) to afford 4-(4-chloro-2-methyl-phenyl)-1-methyl-3-(2-pyridyl)-4,8-dihydropyrazolo[3,4-e][1,4]thiazepin-7-one (1.16 g, 3.0 mmol, 48%), which was used as such: $^1$H-NMR (CDCl$_3$, Bruker 400 MHz) δ 2.50 (3 H, s); 3.07 (1 H, d, J=12 Hz); 3.50 (1 H, d, J=12 Hz); 3.84 (3 H, s); 6.59 (1 H, s); 6.86 (1 H, d, J=8 Hz); 6.98 (1 H, m); 7.1-7.2 (2 H, m); 7.68 (1 H, m), 7.76 (1 H, d, J=6 Hz); 8.4 (1 H, s); 10.2 (1 H, s).

Preparation #C.2

4-(2,4-dichlorophenyl)-1,3,6,6-tetramethyl-4,8-dihydropyrazolo[3,4-e][1,4]thiazepin-7-one

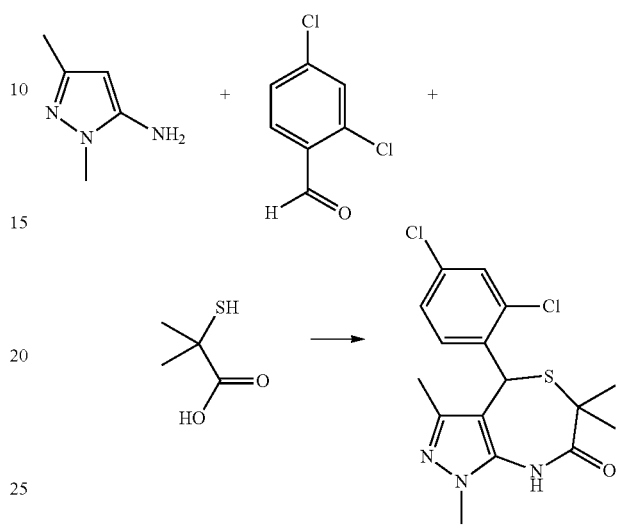

A mixture of 5-amino-1,3-dimethyl-pyrazol (1.87 g, 16.8 mmol), 2,4-dichlorobenzaldehyde (2.95 g, 16.8 mmol, Fluorochem), and 2-mercapto-2-methylpropanoic acid (2.5 g, 20.8 mmol) was heated, in a microwave for about 60 min, at about 100° C. Subsequently, the reaction mixture was sealed and heated, for about 24 h, at about 150° C. After cooling to rt, THF (300 ml) was added, followed by EDC.HCl (4.25 g, 22 mmol) and DMAP (4-dimethylamino-pyridine, 0.2 g, 1.64 mmol). Subsequently, the reaction mixture was stirred for about 24 h, at rt. NaOH (2 M aqueous, 10 mL) and ethyl acetate (200 mL) were added. The layers were separated and the aqueous layer was extracted with ethyl acetate (50 mL). The combined organic layers were washed with water (2×50 mL), dried (MgSO$_4$), filtered and concentrated in vacuo. The residue was purified by column chromatography (SiO$_2$, diethyl ether, followed by ethyl acetate) to afford 4-(2,4-dichlorophenyl)-1,3,6,6-tetramethyl-4,8-dihydropyrazolo[3,4-e][1,4]thiazepin-7-one (3.11 g, 8.4 mmol, 50%) as white solid: $^1$H-NMR (CDCl$_3$, Bruker 400 MHz) δ 1.51 (3 H, s); 1.64 (3 H, s); 1.67 (3H, s); 3.78 (3H, s); 5.77 (1H, s); 7.17 (1H, dd, J=8.4, 2.0 Hz); 7.28 (1 H, d, J=8.4 Hz); 7.41 (1 H, d, J=2.0 Hz); H, m); 8.43 (1 H, bs).

General Procedure D: Preparation of Thiazepines

To a mixture of thiazepinone (0.9-1.2 equivalents, preferably 1.0 equivalents in a suitable anhydrous solvent such as diethyl ether or THF (preferably THF) is added a reducing agent such as lithium aluminum hydride or borane THF complex in THF (preferably borane THF complex) (2 to 12 equivalents, preferably 8 equivalents), at temperatures between about 0° C. and rt (preferably about 0° C.). The resulting mixture is stirred at temperatures between 0° C. and 70° C. (preferably rt) for 1-96 h (preferably about 16 h). Then it is treated with an acid such as aqueous HCl, neutralized with base such as sodium hydroxide or potassium hydroxide (preferably NaOH), and extracted with a suitable organic solvent such as diethyl ether, ethyl acetate or DCM (preferably ethyl acetate). The crude product can be further purified by column chromatography.

Illustration of General Procedure D

Example #D.1

4-(4-chloro-2-methyl-phenyl)-1-methyl-3-(2-pyridyl)-4,6,7,8-tetrahydro-pyrazolo[3,4-e][1,4]thiazepine

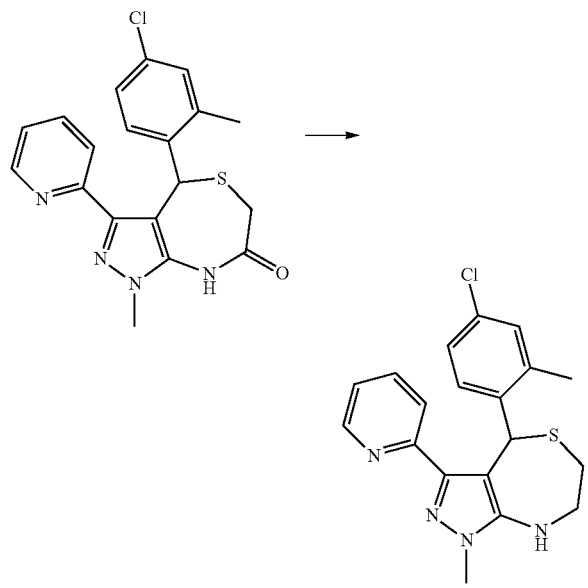

To a solution of 4-(4-chloro-2-methyl-phenyl)-1-methyl-3-(2-pyridyl)-4,8-dihydropyrazolo[3,4-e][1,4]thiazepin-7-one (0.200 g, 0.52 mmol, prepared using C from example #2 step B with thioglycolic acid, and 4-chloro-2-methylbenzaldehyde (Fluorochem)) in THF (6 mL) was added a solution of borane THF complex (4 mL, 1M in THF, 4 mmol, Acros) at rt. Subsequently, the mixture was heated under reflux for about 3 h. After cooling to about 4° C., HCl (5 M aqueous 6 mL) was added dropwise and the mixture was stirred for about 2 h at about 4° C., then NaOH (1 M aqueous, 50 mL) and ethyl acetate (100 mL) were added. The layers were separated and the aqueous layer was extracted with ethyl acetate (50 mL). The combined organic layers were washed with water (2×25 mL), dried (MgSO$_4$), filtered and concentrated in vacuo. The residue was purified by preparative HPLC (Table 2, Method a) to give 4-(4-chloro-2-methyl-phenyl)-1-methyl-3-(2-pyridyl)-4,6,7,8-tetrahydropyrazolo[3,4-e][1,4]thiazepine (0.0917 g, 0.25 mmol, 48%) as white solid: LC-MS (Table 1, Method a) R$_t$=4.23 min, m/z 371 (M+H)$^+$; $^1$H-NMR (CDCl$_3$, Bruker 400 MHz) 2.58 (3H, s) 2.68 (1H, ddd, J=15.0, 6.1, 2.5 Hz) 2.85 (1H, ddd, J=15.0., 9.6, 2.5 Hz) 3.21-3.29 (1 H, m) 3.56-3.65 (1 H, m) 3.79 (1 H, br s) 3.83 (3H, s) 6.66 (1H, s) 6.99 (1 H, dd J=8.3, 2.1 Hz) 7.07 (1 H, ddd J=8.0, 5.0, 1.0 Hz) 7.12 (1 H, d J=8.0 Hz) 7.15 (1 H, d, J=2.0 Hz) 7.59 (1 H, td, J=7.5, 2.0 Hz) 7.79 (1H, d, J=8.0 Hz) 8.46 (1H, d, J=4.5 Hz).

TABLE 4

Examples made using General Procedure D

| Ex. # | Thiazepinone | Product structure | R$_t$ min (Table 1, Method) | m/z ESI+ |
|---|---|---|---|---|
| D.2 | 4-(2,6-dichlorophenyl)-1-methyl-3-(pyridine-2-yl)-6,8-dihydro-1H-pyrazolo[3,4-e][1,4]thiazepin-7-(4H)-one (prepared using C from example #2 step B, thioglycolic acid and 2,6-dichlorobenzaldehyde). | | 1.96 (d) | 391 (M + H)$^+$ |
| D.3 | 4-[4-chloro-2-(trifluoromethyl)phenyl]-1-methyl-3-(pyridine-2-yl)-6,8-dihydro-1H-pyrazolo[3,4-e][1,4]thiazepin-7-(4H)-one (prepared using C from example #2 step B, thioglycolic acid and 4-chloro-2-(trifluoromethyl)benzaldehyde (Apollo Scientific)). | | 2.70 (d) | 425 (M + H)$^+$ |

TABLE 4-continued

Examples made using General Procedure D

| Ex. # | Thiazepinone | Product structure | R, min (Table 1, Method) | m/z ESI+ |
|---|---|---|---|---|
| D.4 | 4-(2,4-dichlorophenyl)-3-methyl-1,3,6,6-tetramethyl-6,8-dihydro-1H-pyrazolo[3,4-e][1,4]thiazepin-7-(4H)-one (prepared using C from 5-amino-1,3-dimethyl-pyrazole, 2-mercapto-2-methylpropanoic acid (Chemwish Technology) and 2,4-dichloro-benzaldehyde (FluoroChem) | | 2.84 (g) | 356 |
| D.5 | 4-(4-chloro-2-methoxy-phenyl)-1-methyl-3-(pyridine-2-yl)-6,8-dihydro-1H-pyrazolo[3,4-e][1,4]thiazepin-7-(4H)-one (prepared using C from example #2 step B, thioglycolic acid and 4-chloro-2-methoxybenzaldehyde (WO09158426)). | | 2.73 (a) | 387 (M + H)+ |
| D.6 | 4-[2-chloro-4-(dimethylamino)phenyl]-1-methyl-3-(2-pyridyl)-4,8-dihydropyrazolo[3,4-e][1,4]thiazepin-7-one (prepared using C from example #2 step B, thioglycolic acid and 2-chloro-4-(dimethylamino)benzaldehyde (ABCR)). | | 2.93 (a) | 400 (M + H)+ |
| D.7 | 4-(3-chloro-4-pyridyl)-1-methyl-3-(pyridine-2-yl)-6,8-dihydro-1H-pyrazolo[3,4-e][1,4]thiazepin-7-(4H)-one (prepared using C from example #2 step B, thioglycolic acid and 3-chloro-4-pyridinecarboxaldehyde). | | 3.01 (a) | 358 (M + H)+ |

TABLE 4-continued

Examples made using General Procedure D

| Ex. # | Thiazepinone | Product structure | R$_t$ min (Table 1, Method) | m/z ESI+ |
|---|---|---|---|---|
| D.8 | 4-(2,4-dichloro-phenyl)-1-methyl-3-(pyridine-2-yl)-6,8-dihydro-1H-pyrazolo[3,4-e][1,4]thiazepin-7-(4H)-one (prepared using C from example #2 step B, thioglycolic acid and 2,4-dichloro-benzaldehyde). | | 4.37 (a) | 391 (M + H)+ |
| D.9 | 4-(2,4-dimethyl-phenyl)-1-methyl-3-(pyridine-2-yl)-6,8-dihydro-1H-pyrazolo[3,4-e][1,4]thiazepin-7-(4H)-one (prepared using C from example #2 step B, thioglycolic acid and 2,4-dimethylbenzaldehyde). | | 5.87 (b) | 351 (M + H)+ |
| D.10 | 4-(4-methoxy-2-methyl-phenyl)-1-methyl-3-(pyridine-2-yl)-6,8-dihydro-1H-pyrazolo[3,4-e][1,4]thiazepin-7-(4H)-one (prepared using C from example #2 step B, thioglycolic acid and 4-methoxy-2-methylbenzaldehyde). | | 5.16 (b) | 367 (M + H)+ |
| D.11 | 4-(4-fluoro-2-methyl-phenyl)-1-methyl-3-(pyridine-2-yl)-6,8-dihydro-1H-pyrazolo[3,4-e][1,4]thiazepin-7-(4H)-one (prepared using C from example #2 step B, thioglycolic acid and 4-fluoro-2-methylbenzaldehyde (Apollo Scientific)) | | 5.81 (b) | 355 (M + H)+ |

TABLE 4-continued

Examples made using General Procedure D

| Ex. # | Thiazepinone | Product structure | R, min (Table 1, Method) | m/z ESI+ |
|---|---|---|---|---|
| D.12 | 1-methyl-4-[2-methyl-4-(trifluoromethoxy)phenyl]-3-(2-pyridyl)-4,8-dihydropyrazolo[3,4-e][1,4]thiazepin-7-one (prepared using C from example #2 step B with thioglycolic acid and 2-methyl-4-trifluoromethoxybenzaldehyde (Apollo Scientific)) | | 7.68 (b) | 421 (M + H)+ |
| D.13 | 4-(4-chloro-2-methyl-phenyl)-2-methyl-4,8-dihydropyrazolo[3,4-e][1,4]thiazepin-7-one (prepared using C from 3-amino-1-methylpyrazole (Maybridge), thioglycolic acid and 4-chloro-2-methylbenzaldehyde (Apollo Scientific)) | | 6.10 (b) | 294 (M + H)+ |
| D.14 | 1-methyl-4-(o-tolyl)-3-(2-pyridyl)-4,8-dihydropyrazolo[3,4-e][1,4]thiazepin-7-one (prepared using C from example #2 step B with thioglycolic acid and o-tolualdehyde). | | 2.52 (a) | 337 (M + H)+ |
| D.15 | 3-(5-bromo-2-pyridyl)-4-(2,4-dichlorophenyl)-1-methyl-4,8-dihydropyrazolo[3,4-e][1,4]thiazepin-7-one (prepared using A from 5-bromopyridine-2-carboxylic acid methyl ester (ABCR), B with methyl hydrazine, and C with 2,4-dichloro-benzaldehyde and thioglycolic acid) | | 5.47 (a) | 469, 471 (M + H)+ |

TABLE 4-continued

Examples made using General Procedure D

| Ex. # | Thiazepinone | Product structure | R, min (Table 1, Method) | m/z ESI+ |
|---|---|---|---|---|
| D.16 | 4-(2,4-dichlorophenyl)-1-methyl-3-thiazol-2-yl-4,8-dihydropyrazolo[3,4-e][1,4]thiazepin-7-one (prepared using A from ethyl 1,3-thiazole-2-carboxylate (see WO2008036579), B with methyl hydrazine, and C with 2,4-dichlorobenzaldehyde and thioglycolic acid) | | 2.37 (c) | 397 (M + H)+ |
| D.17 | 4-(2,4-dichlorophenyl)-1,6,6-trimethyl-3-thiazol-2-yl-4,8-dihydropyrazolo[3,4-e][1,4]thiazepin-7-one (prepared using A from ethyl 1,3-thiazole-2-carboxylate (WO2008036579), B with methyl hydrazine, C with 2,4-dichlorobenzaldehyde and 2-mercapto-2-methylpopanoic acid (Chemwish Technology)) | | 3.01 (d) | 425 (M + H)+ |
| D.18 | 4-(2,4-dichlorophenyl)-1-methyl-3-(4-pyridyl)-4,8-dihydropyrazolo[3,4-e][1,4]thiazepin-7-one (prepared using A from ethyl isonicotinate, B with methyl hydrazine, and C with 2,4-dichlorobenzaldehyde and thioglycolic acid). | | 2.56 (a) | 391 (M + H)+ |
| D.19 | 3-(4-bromo-2-pyridyl)-4-(4-chloro-2-methyl-phenyl)-1-methyl-4,8-dihydro-pyrazolo[3,4-e][1,4]thiazepin-7-one (prepared using A from methyl 4-bromopyridine-2-carboxylate (Preparation #1), B with methyl hydrazine, and C with 4-chloro-2-methylbenzaldehyde (Fluorochem) and thioglycolic acid) | | 5.24 (a) | 449, 451 (M + H)+ |

TABLE 4-continued

Examples made using General Procedure D

| Ex. # | Thiazepinone | Product structure | R$_t$ min (Table 1, Method) | m/z ESI+ |
|---|---|---|---|---|
| D.20 | 4-(2,5-dimethylphenyl)-1-methyl-3-(2-pyridyl)-4,8-dihydropyrazolo[3,4-e][1,4]thiazepin-7-one (prepared using C from example #2 step B with 2,5-dimethylbenzaldehyde(ABCR) and thioglycolic acid). | | 7.32 (e) | 351 (M + H)+ |
| D.21 | 4-(5-chloro-3-methyl-2-pyridyl)-1-methyl-3-(2-pyridyl)-4,8-dihydropyrazolo[3,4-e][1,4]thiazepin-7-one (prepared using C from example #2 step B with 5-chloro-3-methyl-pyridine-2-carbaldehyde (US2004/209921) and thioglycolic acid. | | 7.78 (e) | 372 (M + H)+ |
| D.22 | 4-(4-chloro-2-methyl-phenyl)-3-(4-methoxy-2-pyridyl)-1-methyl-4,8-dihydropyrazolo[3,4-e][1,4]thiazepin-7-one (prepared using A from methyl 4-methoxypyridine-2-carboxylate (Apollo Scientific), B with methyl hydrazine and C with 4-chloro-2-methylbenzaldehyde (Fluorochem) and thioglycolic acid | | 2.88 (a) | 401 (M + H)+ |
| D.23 | 4-(4-chlorophenyl)-1-methyl-3-(2-pyridyl)-4,8-dihydropyrazolo[3,4-e][1,4]thiazepin-7-one (prepared using C from example #2 step B with 4-chloro-benzaldehyde and thioglycolic acid) | | 3.35 (a) | 357 (M + H)+ |

TABLE 4-continued

Examples made using General Procedure D

| Ex. # | Thiazepinone | Product structure | R, min (Table 1, Method) | m/z ESI+ |
|---|---|---|---|---|
| D.24 | 4-(4-chloro-2-methyl-phenyl)-3-(4-chloro-2-pyridyl)-1-methyl-4,8-dihydropyrazolo[3,4-e][1,4]thiazepin-7-one (prepared using A from methyl 4-chloropyridine-2-carboxylate (Apollo Scientific), B with methyl hydrazine, and C with 4-chloro-2-methyl-benzaldehyde (Fluorochem) and thioglycolic acid | | 5.15 (a) | 405 (M + H)+ |
| D.25 | 4-(4-bromophenyl)-1-methyl-3-(2-pyridyl)-4,8-dihydropyrazolo[3,4-e][1,4]thiazepin-7-one (prepared using C from example #2 step B with 4-bromo-benzaldehyde and thioglycolic acid) | | 4.01 (a) | 401, 403 (M + H)+ |
| D.26 | 4-(5-bromo-3-methyl-2-thienyl)-1-methyl-3-(2-pyridyl)-4,8-dihydro-pyrazolo[3,4-e][1,4]thiazepin-7-one (prepared using C from example #2 step B with 5-bromo-3-methyl-thiophene-2-carbaldehyde (see WO2010042674) and thioglycolic acid) | | 4.34 (a) | 421, 423 (M + H)+ |
| D.27 | 4-(5-bromo-2-methylphenyl)-1-methyl-3-(2-pyridyl)-4,8-dihydropyrazolo[3,4-e][1,4]thiazepin-7-one (prepared using C from example #2 step B with 5-bromo-2-methylbenzaldehyde (Fluorochem) and thioglycolic acid | | 9.03 (e) | 415, 417 (M + H)+ |
| D.28 | 4-(5-methoxy-2-methylphenyl)-1-methyl-3-(2-pyridyl)-4,8-dihydropyrazolo[3,4-e][1,4]thiazepin-7-one (prepared using C from example #2 step B with 5-methoxy-2-methylbenzaldehyde (Prep. #7) and thioglycolic acid) | | 7.55 (e) | 367 (M + H)+ |

TABLE 4-continued

Examples made using General Procedure D

| Ex. # | Thiazepinone | Product structure | R$_t$ min (Table 1, Method) | m/z ESI+ |
|---|---|---|---|---|
| D.29 | 4-(4-bromo-2-methyl-phenyl)-1-methyl-3-(3-methylisoxazol-5-yl)-4,8-dihydropyrazolo[3,4-e][1,4]thiazepin-7-one (prepared using A from methyl 3-methylisoxazole-5-carboxylate (Prep. #8), B with methyl hydrazine, and C with 4-bromo-2-methylbenzaldehyde (Ark Pharm) and thioglycolic acid) | | 8.84 (e) | 419, 421 (M + H)+ |
| D.30 | 4-(4-bromo-2-methyl-phenyl)-1-ethyl-3-(2-pyridyl)-4,8-dihydropyrazolo[3,4-e][1,4]thiazepin-7-one (prepared using B from Example #2 step A with ethyl hydrazine oxalate, and C with 4-bromo-2-methylbenzaldehyde (Ark Pharm) and thioglycolic acid) | | 9.53 (e) | 429, 431 (M + H)+ |
| D.31 | 4-(2,4-dichlorophenyl)-3-(4-dimethylaminophenyl)-1-methyl-4,8-dihydropyrazolo[3,4-e][1,4]thiazepin-7-one (prepared using A from ethyl 4-(dimethylamino)benzoate, B with methyl hydrazine, and C with 2,4-dichlorobenzaldehyde and thioglycolic acid) | | 2.63 (d) | 433 (M + H)+ |
| D.32 | 4-(2,4-dichlorophenyl)-1,6,6-trimethyl-3-(pyridin-2-yl)-6,8-dihydro-1H-pyrazolo[3,4-e][1,4]thiazepin-7-(4H)-one (prepared using C from Example #2 step B with 2-mercapto-2-methylpropanoic acid (Chemwish Technology) and 2,4-dichlorobenzaldehyde (Fluorochem)) | | 2.75 (h) | 419 (M + H)+ |

TABLE 4-continued

Examples made using General Procedure D

| Ex. # | Thiazepinone | Product structure | R$_t$ min (Table 1, Method) | m/z ESI+ |
|---|---|---|---|---|
| D.33 | 4-(2,3-dimethylphenyl)-1-methyl-3-(2-pyridyl)-4,8-dihydropyrazolo[3,4-e][1,4]thiazepin-7-one (prepared using C from example #2 step B with 2,3-dimethylbenzaldehyde (Apollo Scientific) and thioglycolic acid | | 3.85 (a) | 351 (M + H)+ |
| D.34 | 4-(5-bromo-2-methyl-3-thienyl)-1-methyl-3-(2-pyridyl)-4,8-dihydro-pyrazolo[3,4-e][1,4]thiazepin-7-one (prepared using C from example #2 step B with 5-bromo-2-methylthiophene-3-carbaldehyde (Prep #15) and thioglycolic acid) | | 8.28 (e) | 423 (M + H)+ |
| D.35 | 4-(4-chloro-5-methoxy-2-methyl-phenyl)-1-methyl-3-(2-pyridyl)-4,8-dihydropyrazolo[3,4-e][1,4]thiazepin-7-one (prepared using C from example #2 step B and 4-chloro-5-methoxy-2-methylbenzaldehyde (Prep.#16) and thioglycolic acid) | | 7.96 (e) | 401 (M + H)+ |
| D.36 | 4-benzyl-1-methyl-3-(2-pyridyl)-4,8-dihydropyrazolo[3,4-e][1,4]thiazepin-7-one (prepared using C from example #2 step B, thioglycolic acid and phenylacetaldehyde) | | 2.45 (a) | 337 (M + H)+ |

TABLE 4-continued

Examples made using General Procedure D

| Ex. # | Thiazepinone | Product structure | R, min (Table 1, Method) | m/z ESI+ |
|---|---|---|---|---|
| D.37 | 4-(2-bromo-4-chloro-phenyl)-1-methyl-3-(2-pyridyl)-4, 8-dihydropyrazolo [3,4-e][1,4]thiazepin-7-one (prepared using C from example #2 step B, thioglycolic acid and 2-bromo-4-chlorobenzaldehyde (see WO2006044454)) | | 4.29 (a) | 435, 437 (M + H)+ |
| D.38 | 4-(4-chloro-2-cyclopropyl-phenyl)-1-methyl-3-(2-pyridyl)-4,8-dihydropyrazolo[3,4-e][1,4]thiazepin-7-one (prepared using C from example #2 step B with thioglycolic acid and 4-chloro-2-cyclopropyl-benzaldehyde (Prep. #21) | | 8.28 (e) | 397 (M + H)+ |
| D.39 | 4-[4-chloro-2-(fluoromethyl)phenyl]-1-methyl-3-(2-pyridyl)-4,8-dihydropyrazolo[3,4-e][1,4]thiazepin-7-one (prepared using C from example #2 step B with thioglycolic acid and 4-chloro-2-(fluoromethyl)-benzaldehyde (Prep. #22)) | | 8.10 (e) | 389 (M + H)+ |
| D.40 | 4-(5-chloro-2-methyl-phenyl)-1-methyl-3-(2-pyridyl)-4,8-dihydro-pyrazolo[3,4-e][1,4]thiazepin-7-one (prepared using C from example #2 step B with thioglycolic acid and 5-chloro-2-methylbenzaldehyde (WO2007088514) | | 8.06 (e) | 371 (M + H)+ |

TABLE 4-continued

Examples made using General Procedure D

| Ex. # | Thiazepinone | Product structure | R, min (Table 1, Method) | m/z ESI+ |
|---|---|---|---|---|
| D.41 | 1-methyl-4-[2-methyl-4-(trifluoromethyl)phenyl]-3-(2-pyridyl)-4,8-dihydropyrazolo[3,4-e][1,4]thiazepin-7-one (prepared using C from example #2 step B with thioglycolic acid and 2-methyl-4-(trifluoromethyl)benzaldehyde (Frontier Scientific) | | 8.67 (e) | 405 (M + H)+ |
| D.42 | 4-(4-hydroxy-2-methyl-phenyl)-1-methyl-3-(2-pyridyl)-4,8-dihydro-pyrazolo[3,4-e][1,4]thiazepin-7-one (prepared using C from example #2 step B with thioglycolic acid and 4-hydroxy-2-methylbenzaldehyde (Ark Pharm)). | | 5.58 (e) | 353 (M + H)+ |
| D.43 | 4-(4-chloro-2-methyl-phenyl)-1-methyl-3-(5-methylisoxazol-3-yl)-4,8-dihydropyrazolo[3,4-e][1,4]thiazepin-7-one (prepared using A from methyl 5-methylisoxazole-3-carboxylate (Apollo Scientific), B with methylhydrazine, and C with thioglycolic acid and 4-chloro-2-methylbenzaldehyde (Apollo Scientific). | | 9.40 (e) | 375 (M + H)+ |
| D.44 | 4-(4-bromo-2-methyl-phenyl)-3-(2-pyridyl)-4,8-dihydroisoxazolo[5,4-e][1,4]thiazepin-7-one (prepared using C from 3-pyridin-2-yl-isoxazol-5-ylamine (U.S. Pat. No. 3,277,105), thioglycolic acid and 4-bromo-2-methylbenzaldehyde (Ark Pharm)) | | 9.86 (e) | 402, 404 (M + H)+ |

TABLE 4-continued

Examples made using General Procedure D

| Ex. # | Thiazepinone | Product structure | R, min (Table 1, Method) | m/z ESI+ |
|---|---|---|---|---|
| D.45 | 4-(4-chloro-2-methyl-phenyl)-3-cyclopropyl-1,6,6-trimethyl-4,8-dihydropyrazolo[3,4-e][1,4]thiazepin-7-one (prepared using C from 3-cyclopropyl-1-methyl-1H-pyrazol-5-amine (Fluorochem), 2-mercapto-2-methylpropanoic acid (Chemwish Technology) and 4-chloro-2-methyl-benzaldehyde (Apollo Scientific) | | 6.76 (b) | 362 (M + H)+ |
| D.46 | 4-(5-chloro-2-methyl-phenyl)-3-cyclopropyl-1,6,6-trimethyl-4,8-dihydropyrazolo[3,4-e][1,4]thiazepin-7-one (prepared using C from 3-cyclopropyl-1-methyl-1H-pyrazol-5-amine (Fluorochem), 2-mercapto-2-methylpropanoic acid (Chemwish Technology) and 5-chloro-2-methylbenzaldehyde (Acros)) | | 7.37 (b) | 362 (M + H)+ |
| D.47 | 4-(4-chloro-2-methoxy-phenyl)-3-cyclopropyl-1,6,6-trimethyl-4,8-dihydropyrazolo[3,4-e][1,4]thiazepin-7-one (prepared using C from 3-cyclopropyl-1-methyl-1H-pyrazol-5-amine (Fluorochem), 2-mercapto-2-methylpropanoic acid (Chemwish Technology) and 4-chloro-2-methoxy-benzaldehyde (See WO09158426)) | | 3.62 (a) | 378 (M + H)+ |
| D.48 | 4-[4-chloro-2-(trifluoromethyl)phenyl]-3-cyclopropyl-1,6,6-trimethyl-4,8-dihydropyrazolo[3,4-e][1,4]thiazepin-7-one (prepared using C from 3-cyclopropyl-1-methyl-1H-pyrazol-5-amine (Fluorochem), 2-mercapto-2-methyl-propanoic acid (Chemwish Technology) and 4-chloro-2-(trifluoromethyl)benzaldehyde (Apollo Scientific)) | | 3.85 (a) | 416 (M + H)+ |
| D.49 | 3-cyclopropyl-4-(2,5-dimethylphenyl)-1,6,6-trimethyl-4,8-dihydro-pyrazolo[3,4-e][1,4]thiazepin-7-one (prepared using C from 3-cyclopropyl-1-methyl-1H-pyrazol-5-amine (Fluorochem), 2-mercapto-2-methyl-propanoic acid (Chemwish Technology) and 2,5-dimethyl-benzaldehyde (ABCR)) | | 7.15 (e) | 342 (M + H)+ |

TABLE 4-continued

Examples made using General Procedure D

| Ex. # | Thiazepinone | Product structure | R$_t$ min (Table 1, Method) | m/z ESI+ |
|---|---|---|---|---|
| D.50 | 4-(5-chloro-3-methyl-2-pyridyl)-3-cyclopropyl-1,6,6-trimethyl-4,8-dihydropyrazolo[3,4-e][1,4]thiazepin-7-one (prepared using C from 3-cyclopropyl-1-methyl-1H-pyrazol-5-amine (Fluorochem), 2-mercapto-2-methylpropanoic acid (Chemwish Technology) and 5-chloro-3-methyl-pyridine-2-carbaldehyde (see US2004/209921)) | | 6.60 (e) | 363 (M + H)+ |
| D.51 | 4-(4-bromo-2-methyl-phenyl)-3-cyclopropyl-1,6-dimethyl-4,8-dihydropyrazolo[3,4-e][1,4]thiazepin-7-one (prepared using C from 3-cyclopropyl-1-methyl-1H-pyrazol-5-amine (Fluorochem), thiolactic acid and 4-bromo-2-methylbenzaldehyde (Ark Pharm)) | | 7.50 (e) | 392, 394 (M + H)+ |
| D.52 | 4-(4-bromo-2-methyl-phenyl)-3-cyclopropyl-1,6-dimethyl-4,8-dihydropyrazolo[3,4-e][1,4]thiazepin-7-one (prepared using C from 3-cyclopropyl-1-methyl-1H-pyrazol-5-amine (Fluorochem), thiolactic acid and 4-bromo-2-methylbenzaldehyde (Ark Pharm)) | | 8.46 (e) | 392, 394 (M + H)+ |
| D.53 | 4-(4-chloro-2-fluoro-phenyl)-3-cyclopropyl-1,6,6-trimethyl-4,8-dihydropyrazolo[3,4-e][1,4]thiazepin-7-one (prepared using C from 3-cyclopropyl-1-methyl-1H-pyrazol-5-amine (Fluorochem), 2-mercapto-2-methylpropanoic acid (Chemwish Technology) and 4-chloro-2-fluoro-benzaldehyde (Acros)) | | 2.34 (c) | 366 (M + H)+ |
| D.54 | 4-(5-bromo-2-methyl-phenyl)-3-cyclopropyl-1,6,6-trimethyl-4,8-dihydropyrazolo[3,4-e][1,4]thiazepin-7-one (prepared using C from 3-cyclopropyl-1-methyl-1H-pyrazol-5-amine (Fluorochem), 2-mercapto-2-methylpropanoic acid (Chemwish Technology) and 5-bromo-2-methyl-benzaldehyde (Fluorochem)) | | 10.82 (e) | 404, 406 (M + H)+ |

TABLE 4-continued

Examples made using General Procedure D

| Ex. # | Thiazepinone | Product structure | R$_t$ min (Table 1, Method) | m/z ESI+ |
|---|---|---|---|---|
| D.55 | 4-(5-bromo-2-methyl-phenyl)-3-cyclopropyl-1,6,6-trimethyl-4,8-dihydropyrazolo[3,4-e][1,4]thiazepin-7-one (prepared using C from 3-cyclopropyl-1-methyl-1H-pyrazol-5-amine (Fluorochem), 2-mercapto-2-methylpropanoic acid (Chemwish Technology) and 5-bromo-2-methylbenzaldehyde (Fluorochem)) | | 7.56 (e) | 406, 408 (M + H)+ |
| D.56 | 3-cyclopropyl-4-(4-fluoro-2-methyl-phenyl)-1,6,6-trimethyl-4,8-dihydropyrazolo[3,4-e][1,4]thiazepin-7-one (prepared using C from 3-cyclopropyl-1-methyl-1H-pyrazol-5-amine (Fluorochem), 2-mercapto-2-methylpropanoic acid (Chemwish Technology) and 4-fluoro-2-methylbenzaldehyde (Apollo Scientific)) | | 7.11 (e) | 346 (M + H)+ |
| D.57 | 4-(4-chloro-2-methyl-phenyl)-1,3,6,6-tetramethyl-4,8-dihydropyrazolo[3,4-e][1,4]thiazepin-7-one (prepared using C from 5-amino-1,3-dimethyl-pyrazole, 2-mercapto-2-methylpropanoic acid (Chemwish Technology) and 4-chloro-2-methylbenzaldehyde (Apollo Scientific)) | | 6.2 (e) | 336 (M + H)+ |
| D.58 | 4-(4-bromo-2-methyl-phenyl)-1,3,6,6-tetramethyl-4,8-dihydropyrazolo[3,4-e][1,4]thiazepin-7-one (prepared using C from 5-amino-1,3-dimethyl-pyrazole, 2-mercapto-2-methylpropanoic acid (Chemwish Technology) and 4-bromo-2-methylbenzaldehyde (Ark Pharm)) | | 3.71 (e) | 380, 382 (M + H)+ |

TABLE 4-continued

Examples made using General Procedure D

| Ex. # | Thiazepinone | Product structure | R<sub>t</sub> min (Table 1, Method) | m/z ESI+ |
|---|---|---|---|---|
| D.59 | 4-(4-chloro-2-methyl-phenyl)-1,3-dimethyl-4,8-dihydropyrazolo[3,4-e][1,4]thiazepin-7-one (prepared using C from 5-amino-1,3-dimethyl-pyrazole, thioglycolic acid and 4-chloro-2-methylbenzaldehyde (Apollo Scientific)) | | 6.09 (e) | 308 (M + H)+ |
| D.60 | 4-(4-bromo-2-chloro-phenyl)-1,3,6,6-tetramethyl-4,8-dihydropyrazolo[3,4-e][1,4]thiazepin-7-one (prepared using C from 5-amino-1,3-dimethyl-pyrazole, 2-mercapto-2-methylpropanoic acid (Chemwish Technology) and 4-bromo-2-chlorobenzaldehyde (Apollo Sceintific)) | | 3.51 (a) | 400, 402 (M + H)+ |
| D.61 | 1,3,6,6-tetramethyl-4-[2-methyl-4-(trifluoromethyl)phenyl]-4,8-dihydropyrazolo[3,4-e][1,4]thiazepin-7-one (prepared using C from 5-amino-1,3-dimethyl-pyrazole, 2-mercapto-2-methylpropanoic acid (Chemwish Technology) and 2-methyl-4-(trifluoromethyl)-benzaldehyde (Frontier)) | | 8.06 (e) | 370 (M + H)+ |
| D.62 | 4-(4-bromo-2-methyl-phenyl)-1,3,6-trimethyl-4,8-dihydropyrazolo[3,4-e][1,4]thiazepin-7-one (prepared using C from 5-amino-1,3-dimethyl-pyrazole, thiolactic acid and 4-bromo-2-methylbenzaldehyde (Ark Pharm)) | | 7.18 major 7.53 Minor (e) | 366, 368 (M + H)+ |

TABLE 4-continued

Examples made using General Procedure D

| Ex. # | Thiazepinone | Product structure | R, min (Table 1, Method) | m/z ESI+ |
|---|---|---|---|---|
| D.63 | 4-(2,4-dichlorophenyl)-3,6,6-trimethyl-4,8-dihydro-1H-pyrazolo[3,4-e][1,4]thiazepin-7-one (prepared using C from 3-methyl-1H-pyrazol-5-amine (Fluorochem), 2-mercapto-2-methylpropanoic acid (Chemwish Technology) and 2,4-dichlorobenzaldehyde (Fluorochem) | 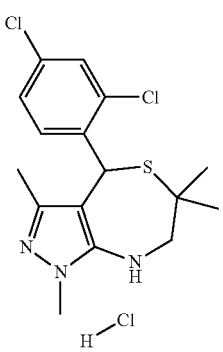 | 2.18 (d) | 342 (M + H)+ |
| D.64 | 4-(2,4-dichlorophenyl)-3-isopropyl-1,6,6-trimethyl-4,8-dihydropyrazolo[3,4-e][1,4]thiazepin-7-one (prepared using C from 3-isopropyl-1-methyl-1H-pyrazol-5-amine (Fluorochem), 2-mercapto-2-methylpropanoic acid (Chemwish Technology) and 2,4-dichlorobenzaldehyde (Fluorochem) | 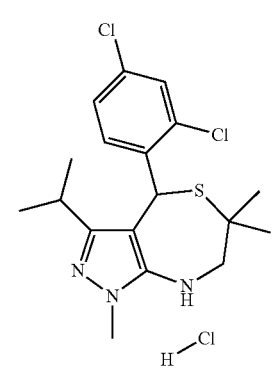 | 2.59 (d) | 384 (M + H)+ |
| D.65 | 4-(2,4-dichlorophenyl)-1,3-dimethyl-spiro[4,8-dihydropyrazolo[3,4-e][1,4]thiazepine-6,1'-cyclopentane]-7-one (prepared using C from 5-amino-1,3-dimethyl-pyrazole, 1-sulfanylcyclopentanecarboxylic acid (Chem. Ber., 109, 1601 (1976)) and 2,4-dichlorobenzaldehyde (Fluorochem)) | 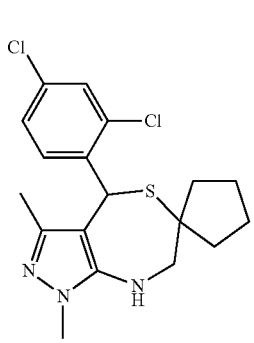 [SMILES: Cc1nn(C)c2c1C(c1ccc(Cl)cc1Cl)SC1(CCCC1)CN2] | 4.14 (a) | 382 (M + H)+ |
| D.66 | 4-(2,4-dichlorophenyl)-1,3-dimethyl-spiro[4,8-dihydropyrazolo[3,4-e][1,4]thiazepine-6,1'-cyclobutane]-7-one (prepared using C from 5-amino-1,3-dimethyl-pyrazole, 1-sulfanylcyclobutanecarboxylic acid (Chem. Ber., 109, 1601 (1976)) and 2,4-dichlorobenzaldehyde (Fluorochem)) | 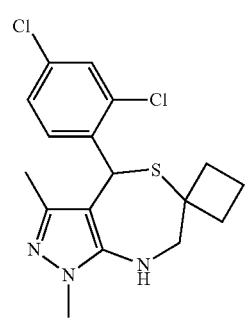 [SMILES: Cc1nn(C)c2c1C(c1ccc(Cl)cc1Cl)SC1(CCC1)CN2] | 4.21 (a) | 368 (M + H)+ |

TABLE 4-continued

Examples made using General Procedure D

| Ex. # | Thiazepinone | Product structure | R$_t$ min (Table 1, Method) | m/z ESI+ |
|---|---|---|---|---|
| D.67 | 4-(2,4-dichlorophenyl)-1,3-dimethyl-spiro[4,8-dihydropyrazolo[3,4-e][1,4]thiazepine-6,4'-tetrahydropyran1-7-one (prepared using C from 5-amino-1,3-dimethyl-pyrazole, 4-sulfanyltetra-hydropyran-4-carboxylic acid (Chem. Ber., 109, 1601 (1976)) and 2,4-dichlorobenzaldehyde (Fluorochem)) | | 3.13 (a) | 398 (M + H)+ |
| D.68 | 2-(4-(4-chlorophenyl)-1,3-dimethyl-4,6,7,8-tetrahydro-1H-pyrazolo[3,4-e][1,4]thiazepin-6-yl)ethanol 2,2,2-trifluoracetate (prepared using C from 5-amino-1,3-dimethyl-pyrazole, 2-mercapto-2-methylpropanoic acid (Chemwish Technology) and 2,4-dichlorobenzaldehyde (Fluorochem) | | 1.82 (g) | 338 (M + H)+ |
| D.69 | 4-(3-bromo-2-methyl-phenyl)-3-cyclopropyl-1,6,6-trimethyl-4,8-dihydropyrazolo[3,4-e][1,4]thiazepin-7-one(prepared using C from from 3-cyclopropyl-1-methyl-1H-pyrazol-5-amine (Fluorochem), 2-mercapto-2-methylpropanoic acid (Chemwish Technology) and 3-bromo-2-methylbenzaldehyde (WO2011134280)) | | 7.80 (e) | 406, 408 (M + H)+ |
| D.70 | 4-(4-chloro-2-methyl-phenyl)-1-cyclopentyl-3,6,6-trimethyl-4,8-dihydropyrazolo[3,4-e][1,4]thiazepin-7-one (prepared using C from 1-cyclopentyl-3-methyl-1H-pyrazol-5-amine (ABCR), 2-mercapto-2-methylpropanoic acid (Chemwish Technology) and 4-chloro-2-methylbenzaldehyde (Apollo Scientific)) | | 7.19 (b) | 390 (M + H)+ |

TABLE 4-continued

Examples made using General Procedure D

| Ex. # | Thiazepinone | Product structure | $R_t$ min (Table 1, Method) | m/z ESI+ |
|---|---|---|---|---|
| D.71 | 1,3,6,6-tetramethyl-4-(2-methyl-4-methylsulfonyl-phenyl)-4,8-dihydropyrazolo[3,4-e][1,4]thiazepin-7-one (prepared using C from 5-amino-1,3-dimethyl-pyrazole, 2-mercapto-2-methylpropanoic acid (Chemwish Technology) and 2-methyl-4-methylsufonyl-benzaldehyde (WO1998047871)) | | 5.81 (e) | 380 (M + H)+ |
| D.72 | 4-(4-chloro-2-methyl-phenyl)-1-methyl-3-tetrahydrofuran-2-yl-4,8-dihydropyrazolo[3,4-e][1,4]thiazepin-7-one (prepared using A from ethyl tetrahydrofuran-2-carboxylate (US2005187266), B with methyl hydrazine and C with thioglycolic acid and 4-chloro-2-methylbenzaldehyde (Apollo Scientific)) | | 3.77 (Minor) 3.87 (Major) (a) | 364 (M + H)+ |
| D.73 | 4-(4-chloro-2-methyl-phenyl)-3-hydroxy-1-methyl-4,8-dihydropyrazolo[3,4-e][1,4]thiazepin-7-one (prepared using C from 5-amino-1-methyl-pyrazol-3-ol (JACS, 1959, 81, 2448-2451), thioglycolic acid and 4-chloro-2-methylbenzaldehyde (Apollo Scientific)) | | 6.55 (e) | 310 (M + H)+ |
| D.74 | 3-cyclopropyl-4-(2,4-dichlorophenyl)-1,6,6-trimethyl-6,8-dihydro-1H-pyrazolo[3,4-e][1,4]thiazepin-7-(4H)-one (prepared using C from 3-cyclopropyl-1-methyl-1H-pyrazol-5-amine (Fluorochem), 2-mercapto-2-methylpropanoic acid (Chemwish Technology) and 2,4-dichlorobenzaldehyde (FluoroChem)) | | 1.72 (i) | 382 (M + H)+ |

143
144

TABLE 4-continued

Examples made using General Procedure D

| Ex. # | Thiazepinone | Product structure | R, min (Table 1, Method) | m/z ESI+ |
|---|---|---|---|---|
| D.75 | 1,3-dimethyl-4-(4-(p-tolyloxy)phenyl)-6,8-dihydro-1H-pyrazolo[3,4-e][1,4]thiazepin-7-(4H)-one (prepared using C with 3-methyl-1-methyl-1H-pyrazole-5-amine, 4-phenoxybenzaldehyde and thioglycolic acid ) | | 2.48 (g) | 366 (M + H)+ |
| D.76 | 4-(1H-indazol-5-yl)-1,3-dimethyl-6,8-dihydro-1H-pyrazolo[3,4-e][1,4]thiazepin-7-(4H)-one (prepared using C with 3-methyl-1-methyl-1H-pyrazole-5-amine, 1H-indazole-5-carboxaldehyde and thioglycolic acid) | | 1.54 (g) | 300 (M + H)+ |
| D.77 | 3-cyclopentyl-4-(2,4-dichlorophenyl)-1-methyl-6,8-dihydro-1H-pyrazolo[3,4-e][1,4]thiazepin-7-(4H)-one (prepared using C with 3-cyclopentyl-1-methyl-1H-pyrazole-5-amine (Ryan Scientific), thioglycolic acid and 2,4-dichlorobenzaldehyde (FluoroChem) | | 2.84 (g) | 382 (M + H)+ |
| D.78 | 1,3,6,6-tetramethyl-4-(4-(p-tolyloxy)phenyl)-6,8-dihydro-1H-pyrazolo[3,4-e][1,4]thiazepin-7-(4H)-one (prepared using C with 3-methyl-1-methyl-1H-pyrazole-5-amine, 4-phenoxybenzaldehyde and 2-mercapto-2-methylpropanoic acid (Chemwish Technology) | | 2.66 (g) | 394 (M + H)+ |

TABLE 4-continued

Examples made using General Procedure D

| Ex. # | Thiazepinone | Product structure | R, min (Table 1, Method) | m/z ESI+ |
|---|---|---|---|---|
| D.79 | 3-cyclopentyl-4-(2,4-dichlorophenyl)-1,6,6-trimethyl-6,8-dihydro-1H-pyrazolo[3,4-e][1,4]thiazepin-7-(4H)-one (prepared using C with 3-cyclopentyl-1-methyl-1H-pyrazole-5-amine (Ryan Scientific), 2-mercapto-2-methylpropanoic acid (Chemwish Technology) and 2,4-dichlorobenzaldehyde (FluoroChem) | 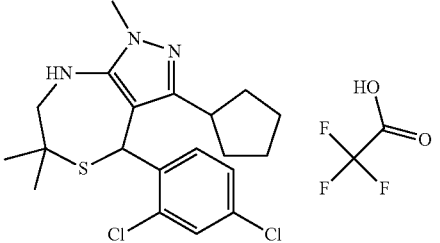 | 2.97 (g) | 410 (M + H)+ |
| D.80 | 4-(2,4-dichlorophenyl)-1,3-dimethyl-6,8-dihydro-1H-pyrazolo[3,4-e][1,4]thiazepin-7-(4H)-one (prepared using C with 3-methyl-1-methyl-1H-pyrazole-5-amine, 2,4-dichlorobenzaldehyde (FluoroChem) and thioglycolic acid) | 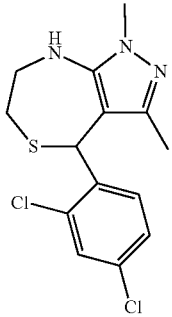 [SMILES: Cc1nn(C)c2c1C(c1ccc(Cl)cc1Cl)SCCN2] | 2.38 (g) | 328 (M + H)+ |
| D.81 | 4-(3-methoxyphenyl)-1,3-dimethyl-6,8-dihydro-1H-pyrazolo[3,4-e][1,4]thiazepin-7(4H)-one (prepared using C with 3-methyl-1-methyl-1H-pyrazole-5-amine, 3-methoxybenzaldehyde and thioglycolic acid) | 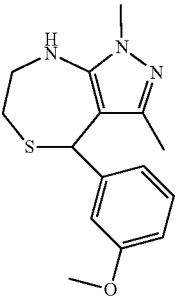 [SMILES: COc1cccc(C2SCCNc3c2c(C)nn3C)c1] | 1.95 (g) | 290 (M + H)+ |
| D.82 | 3-(4-chlorophenyl)-4-(2,4-dichlorophenyl)-1-methyl-6,8-dihydro-1H-pyrazolo[3,4-e][1,4]thiazepin-7-(4H)-one (prepared using C from 3-(4-chlorophenyl)-1-methyl-1H-pyrazole-5-amine and 2,4-dichlorbenzaldehyde (FluoroChem) | 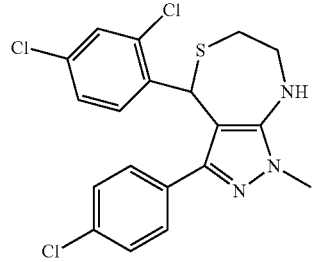 [SMILES: Cn1nc(-c2ccc(Cl)cc2)c2c1NCCSC2c1ccc(Cl)cc1Cl] | 2.89 (g) | 424, 426 (M + H)+ |
| D.83 | 4-(2,4-dichlorophenyl)-1-methyl-3-phenyl-6,8-dihydro-1H-pyrazolo[3,4-e][1,4]thiazepin-7-(4H)-one (prepared using C with 3-phenyl-1-methyl-1H-pyrazole-5-amine, thioglycolic acid and 2,4-dichlorobenzaldehyde (FluoroChem) | 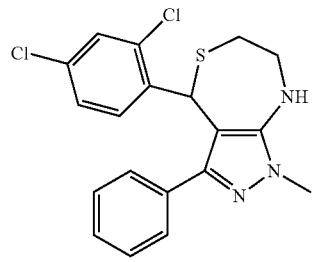 [SMILES: Cn1nc(-c2ccccc2)c2c1NCCSC2c1ccc(Cl)cc1Cl] | 2.69 (g) | 390 (M + H)+ |

TABLE 4-continued

Examples made using General Procedure D

| Ex. # | Thiazepinone | Product structure | R$_t$ min (Table 1, Method) | m/z ESI+ |
|---|---|---|---|---|
| D.84 | 4-(2,4-dichlorophenyl)-3-isopropyl-1-methyl-6,8-dihydro-1H-pyrazolo[3,4-e][1,4]thiazepin-7-(4H)-one (prepared using C with 3-isopropyl-1-methyl-1H-pyrazole-5-amine, thioglycolic acid and 2,4-dichlorobenzaldehyde (FluoroChem) | | 2.56 (g) | 356 (M + H)+ |
| D.85 | 3-tert-butyl-4-(2,4-dichlorophenyl)-1-methyl-6,8-dihydro-1H-pyrazolo[3,4-e][1,4]thiazepin-7-(4H)-one (prepared using C with 3-tert-butyl-1-methyl-1H-pyrazole-5-amine, thioglycolic acid and 2,4-dichlorobenzaldehyde (FluoroChem) | | 2.83 (g) | 370 (M + H)+ |
| D.86 | 4-(2,4-dichlorophenyl)-1-methyl-3-(pyridin-3-yl)-6,8-dihydro-1H-pyrazolo[3,4-e][1,4]thiazepin-7-(4H)-one (prepared using C with 3-pyridyl-1-methyl-1H-pyrazole-5-amine, thioglycolic acid and 2,4-dichlorobenzaldehyde (FluoroChem) | | 2.27 (g) | 391 (M + H)+ |
| D.87 | 4-(2,4-dichlorophenyl)-1-methyl-3-p-tolyl-6,8-dihydro-1H-pyrazolo[3,4-e][1,4]thiazepin-7-(4H)-one (prepared using C with 3-(4-methylphenyl)-1-methyl-1H-pyrazole-5-amine, thioglycolic acid and 2,4-dichlorobenzaldehyde (FluoroChem) | | 2.79 (g) | 404 (M + H)+ |
| D.88 | 3-(4-tert-butylphenyl)-4-(2,4-dichlorophenyl)-1-methyl-6,8-dihydro-1H-pyrazolo[3,4-e][1,4]thiazepin-7-(4H)-one (prepared using C with 3-(4-tert-butylphenyl)-1-methyl-1H-pyrazole-5-amine, thioglycolic acid and 2,4-dichlorobenzaldehyde (FluoroChem) | | 3.07 (g) | 446 (M + H)+ |

TABLE 4-continued

Examples made using General Procedure D

| Ex. # | Thiazepinone | Product structure | R, min (Table 1, Method) | m/z ESI+ |
|---|---|---|---|---|
| D.89 | 4-(2,4-dichlorophenyl)-3-(3,4-dichlorophenyl)-1-methyl-6,8-dihydro-1H-pyrazolo[3,4-e][1,4]thiazepin-7-(4H)-one (prepared using C with 3-(3,4-dichlorophenyl)-1-methyl-1H-pyrazole-5-amine, thioglycolic acid and 2,4-dichlorobenzaldehyde (FluoroChem) | | 3.05 (g) | 357, 359 (M + H)+ |
| D.90 | 4-(2,4-dichlorophenyl)-3-(3,5-difluorophenyl)-1-methyl-6,8-dihydro-1H-pyrazolo[3,4-e][1,4]thiazepin-7-(4H)-one (prepared using C with 3-(3,5-difluorophenyl)-1-methyl-1H-pyrazole-5-amine, thioglycolic acid and 2,4-dichlorobenzaldehyde (FluoroChem) | | 2.82 (g) | 426 (M + H)+ |
| D.91 | 4-(2,4-dichlorophenyl)-1-methyl-3-(trifluoromethyl)-6,8-dihydro-1H-pyrazolo[3,4-e][1,4]thiazepin-7-(4H)-one (prepared using C with 3-trifluororomethyl-1-methyl-1H-pyrazole-5-amine (FluoroChem), thioglycolic acid and 2,4-dichlorobenzaldehyde (FluoroChem) | | 2.89 (g) | 382 (M + H)+ |
| D.92 | 4-(2,4-dichlorophenyl)-3-isobutyl-1-methyl-6,8-dihydro-1H-pyrazolo[3,4-e][1,4]thiazepin-7-(4H)-one (prepared using C with 3-(2-methylpropyl)-1-methyl-1H-pyrazole-5-amine, thioglycolic acid and 2,4-dichlorobenzaldehyde (FluoroChem) | | 2.74 (g) | 370 (M + H)+ |
| D.93 | 4-(2,4-dichlorophenyl)-3-(2,4-difluorophenyl)-1-methyl-6,8-dihydro-1H-pyrazolo[3,4-e][1,4]thiazepin-7-(4H)-one (prepared using C with 3-(2,4-difluorophenyl)-1-methyl-1H-pyrazole-5-amine, thioglycolic acid and 2,4-dichlorobenzaldehyde (FluoroChem) | | 2.70 (g) | 426 (M + H)+ |

TABLE 4-continued

Examples made using General Procedure D

| Ex. # | Thiazepinone | Product structure | R$_t$ min (Table 1, Method) | m/z ESI+ |
|---|---|---|---|---|
| D.94 | 4-(2,4-dichlorophenyl)-3-(4-fluorophenyl)-1-methyl-6,8-dihydro-1H-pyrazolo[3,4-e][1,4]thiazepin-7-(4H)-one (prepared using C with 3-(4-fluorophenyl)-1-methyl-1H-pyrazole-5-amine, thioglycolic acid and 2,4-dichlorobenzaldehyde (FluoroChem) | 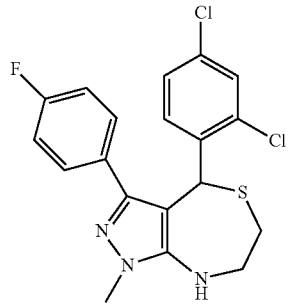 [SMILES: Cn1nc(-c2ccc(F)cc2)c2c1NCCSC2c1ccc(Cl)cc1Cl] | 2.73 (g) | 408 (M + H)+ |
| D.95 | 4-(2,4-dichlorophenyl)-1-methyl-3-(4-(trifluoromethoxy)phenyl)-6,8-dihydro-1H-pyrazolo[3,4-e][1,4]thiazepin-7-(4H)-one (prepared using C with 3-(4-trifluoromethoxyphenyl)-1-methyl-1H-pyrazole-5-amine, thioglycolic acid and 2,4-dichlorobenzaldehyde (FluoroChem) | 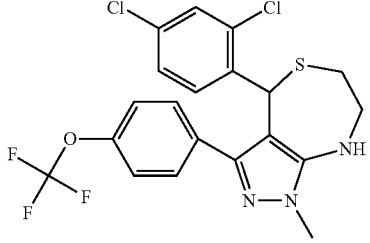 [SMILES: Cn1nc(-c2ccc(OC(F)(F)F)cc2)c2c1NCCSC2c1ccc(Cl)cc1Cl] | 2.95 (g) | 474 (M + H)+ |
| D.96 | 1,3-dimethyl-4-(pyridin-2-yl)-6,8-dihydro-1H-pyrazolo[3,4-e][1,4]thiazepin-7-(4H)-one (prepared using C with 3-methyl-1-methyl-1H-pyrazole-5-amine, 2-pyridinecarboxaldehyde and thioglycolic acid) | 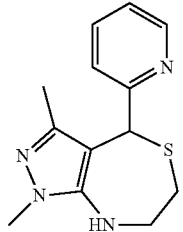 [SMILES: Cc1nn(C)c2c1C(c1ccccn1)SCCN2] | 1.38 (g) | 261 (M + H)+ |
| D.97 | 4-(4-methoxyphenyl)-1,3-dimethyl-6,8-dihydro-1H-pyrazolo[3,4-e][1,4]thiazepin-7-(4H)-one (prepared using C with 3-methyl-1-methyl-1H-pyrazole-5-amine, thioglycolic acid and 4-methoxybenzaldehyde) | 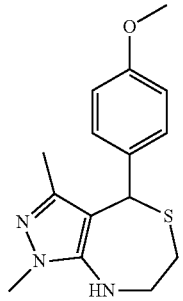 [SMILES: COc1ccc(C2SCCNc3c2c(C)nn3C)cc1] | 1.93 (g) | 290 (M + H)+ |
| D.98 | 4-(2-methoxyphenyl)-1,3-dimethyl-6,8-dihydro-1H-pyrazolo[3,4-e][1,4]thiazepin-7-(4H)-one (prepared using C with 3-methyl-1-methyl-1H-pyrazole-5-amine, thioglycolic acid and 2-methoxybenzaldehyde) | 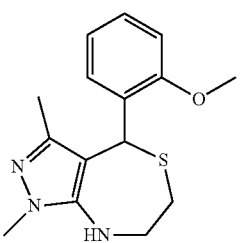 | 1.93 (g) | 290 (M + H)+ |

TABLE 4-continued

Examples made using General Procedure D

| Ex. # | Thiazepinone | Product structure | R, min (Table 1, Method) | m/z ESI+ |
|---|---|---|---|---|
| D.99 | 1,3-dimethyl-4-(pyridin-3-yl)-6,8-dihydro-1H-pyrazolo[3,4-e][1,4]thiazepin-7-(4H)-one (prepared using C with 3-methyl-1-methyl-1H-pyrazole-5-amine, thioglycolic acid and 3-pyridinecarboxaldehyde) | | 1.41 (g) | 261 (M + H)+ |
| D.100 | 4-(4-chlorophenyl)-6-(2-hydroxyethyl)-1,3-dimethyl-6,8-dihydro-1H-pyrazolo[3,4-e][1,4]thiazepin-7(4H)-one (prepared using C with 3-methyl-1-methyl-1H-pyrazole-5-amine, 4-chloro-benzaldehyde and mercaptosuccinic acid). | | 1.86 (g) | 338 (M + H)+ |
| D.101 | 4-(2,4-dichlorophenyl)-1-methyl-3-(thiophen-2-yl)-6,8-dihydro-1H-pyrazolo[3,4-e][1,4]thiazepin-7-(4H)-one (prepared using C with 3-(2-thienyl)-1-methyl-1H-pyrazole-5-amine (Fluka), thioglycolic acid and 2,4-dichlorobenzaldehyde (FluoroChem) | | 2.67 (g) | 396 (M + H)+ |
| D.102 | 1,3-dimethyl-4-(1H-pyrazol-3-yl)-6,8-dihydro-1H-pyrazolo[3,4-e][1,4]thiazepin-7-(4H)-one (prepared using C with 3-methyl-1-methyl-1H-pyrazole-5-amine, thioglycolic acid and 1H-pyrazole-3-carbaldehyde) | | 1.29 (g) | 250 (M + H)+ |
| D.103 | 4-(4-chloro-2-fluorophenyl)-1-methyl-3-(pyridine-2-yl)-6,8-dihydro-1H-pyrazolo[3,4-e][1,4]thiazepin-7-(4H)-one (prepared using C from example #2 step B with thioglycolic acid and 4-chloro-2-fluorobenzaldehyde (Acros)). | | 2.16 (c) | 375 (M + H)+ |

TABLE 4-continued

Examples made using General Procedure D

| Ex. # | Thiazepinone | Product structure | R$_t$ min (Table 1, Method) | m/z ESI+ |
|---|---|---|---|---|
| D.104 | 4-(4-chloro-2-methylphenyl)-3-(pyridin-2-yl)-1-(2,2,2-trifluoroethyl)-6,8-dihydro-1H-pyrazolo [3,4-e][1,4]thiazepin-7(4H)-one (prepared using A from pyridine-2-carboxylic acid methyl ester, B with (2,2,2 trifluoroethyl)hydrazine hydrochloride, and C with 4-chloro-2-methyl-benzaldehyde and thioglycolic acid) | | 10.16 (m) | 439 (M + H)+ |
| D.105 | 4-(4-chloro-2-methylphenyl)-1-isopropyl-3-(pyridin-2-yl)-6,8-dihydro-1H-pyrazolo[3,4-e][1,4]thiazepin-7(4H)-one (prepared using A from pyridine-2-carboxylic acid methyl ester, B with isopropylhydrazine, and C with 4-chloro-2-methyl-benzaldehyde and thioglycolic acid) | | 9.94 (m) | 399 (M + H)+ |
| D.106 | 3-cyclopropyl-4-(5-methoxy-2-methylphenyl)-1,6,6-trimethyl-6,8-dihydro-1H-pyrazolo[3,4-e][1,4]thiazepin-7(4H)-one (prepared using C from 3-cyclopropyl-1-methyl-1H-pyrazol-5-amine, 2-mercapto-2-methylpropanoic acid (Chemwish Technology) and 5-methoxy-2-methyl-benzaldehyde (Preparation #7)) | | 6.76 (m) | 358 (M + H)+ |
| D.107 | 4-(4-chloro-2-methylphenyl)-3-cyclopropyl-1-ethyl-6,6-dimethyl-6,8-dihydro-1H-pyrazolo[3,4-e][1,4]thiazepin-7(4H)-one (prepared using C from 3-cyclopropyl-1-ethyl-4 1H-pyrazol-5-amine (FluoroChem), 2-mercapto-2-methylpropanoic acid (Chemwish Technology) and 4-chloro-2-methylbenzaldehyde (Apollo Scientific)). | | 7.94 (m) | 376 (M + H)+ |

TABLE 4-continued

Examples made using General Procedure D

| Ex. # | Thiazepinone | Product structure | R, min (Table 1, Method) | m/z ESI+ |
|---|---|---|---|---|
| D.108 | 4-(4-bromo-2-methylphenyl)-1-ethyl-3-(pyrimidin-4-yl)-6,8-dihydro-1H-pyrazolo[3,4-e][1,4]thiazepin-7(-4H)-one (prepared using A from methylpyrimidine-4-carboxylate, B with ethylhydrazine and C with 4-bromo-2-methyl-benzaldehyde and thioglycolic acid) | | 2.53 (g) | 430, 432 (M + H)+ |
| D.109 | 4-(1-(4-fluorophenyl)-6-methyl-1H-indazol-5-yl)-1-methyl-3-(pyridin-2-yl)-6,8-dihydro-1H-pyrazolo[3,4-e][1,4]thiazepin-7(4H)-one (Example #14) | | 2.53 (g) | 471 (M + H)+ |

General Procedure E: Preparation of Esters from Bromides

To a mixture of a bromide (1 equivalent), trans-di-MU-acetatobis[2-(di-o-tolylphosphino)benzyl]dipalladium(II) (0.1 equivalent), tri-tert-butylphosphine tetrafluoroborate (0-1 equivalent, preferably 0.2 equivalent), molybdenum-hexacarbonyl (1-3 equivalents, preferably 1 equivalent), and 1,8-diazabicyclo[5.4.0]undec-7-ene (0-2 equivalents, preferably 1.5 equivalents), is added degassed methanol and a degassed solvent such as acetonitrile. The resulting mixture is heated, in a sealed microwave vessel, for about 1 h at about 100° C. in a microwave. After cooling to rt, the mixture is filtered and concentrated in vacuo. The residue is purified by chromatography to afford the methyl ester. Alternatively a reaction vessel is charged with a catalyst (such as Pd(OAc)$_2$, PdCl$_2$(dppf), PdCl$_2$(dppf)-DCM adduct, PdCl$_2$(PPh$_3$)$_2$, Pd(PPh$_3$)$_4$, preferably PdCl$_2$(dppf)-DCM adduct (0.01-0.2 equiv, preferably 0.1 equiv) and optionally a ligand, such as dppf (0.05-0.3 equiv, preferably 0.2 equiv). The reaction flask is then optionally purged with N$_2$ or Ar gas for about 10-30 min followed by the addition of a suitable organic solvent such as DMF, DMA, 1,4-dioxane, toluene, THF (preferably DMF). To the solution is added a base such as TEA or DIEA (preferably TEA, 1-10 equiv, preferably 5 equiv) and MeOH or EtOH (preferably MeOH, 10-100 equiv, preferably 50 equiv) and CO gas is then bubbled through the reaction flask for about 10 min. The mixture is heated to about 60-110° C. (preferably about 90° C.) for about 3-24 h (preferably about 18 h) under CO (between 1 atm and 200 psi). The reaction mixture is cooled to room temperature and an organic solvent such as DCM or EtOAc and water are optionally added. The layers are separated and the organic solution is dried over anhydrous MgSO$_4$ or Na$_2$SO$_4$, filtered and concentrated under reduced pressure. The material can optionally be further purified by trituration, crystallization, or silica gel chromatography to afford the desired product. Alternatively, the crude reaction mixture can be directly concentrated under reduced pressure and purified by silica gel chromatography to afford the desired product.

Illustration of General Procedure E

Example #E.1 methyl 3-chloro-4-[1-methyl-3-(2-pyridyl)-4,6,7,8-tetrahydropyrazolo[3,4-e][1,4]thiazepin-4-yl]benzoate

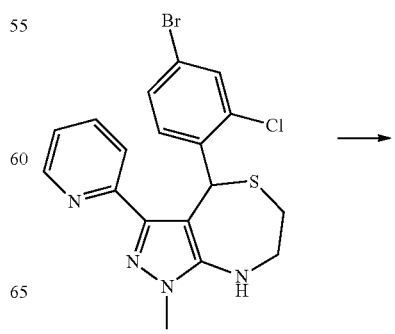

-continued

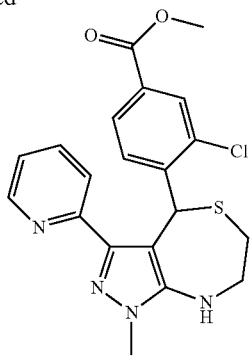

To a mixture of 4-(4-bromo-2-chloro-phenyl)-1-methyl-3-(2-pyridyl)-4,6,7,8-tetrahydropyrazolo[3,4-e][1,4]thiazepine (1.5 g, 3.4 mmol, Example #3 step D), trans-di-MU-acetatobis[2-(di-o-tolylphosphino)benzyl]dipalladium(II) (0.325 g, 0.3 mmol, Alfa Aesar), molybdenumhexacarbonyl (0.91 g, 3.4 mmol, Fluka), and 1,8-diazabicyclo[5.4.0]undec-7-ene (0.798 g, 5.2 mmol), was added a degassed mixture of methanol and acetonitrile (9:3, 14 mL). The resulting mixture was heated, in a sealed microwave vessel, for about 1 h at about 100° C. in a microwave. After cooling to rt, the mixture was filtered and concentrated in vacuo. The resulting oil was purified by column chromatography (SiO$_2$, DCM/ethyl acetate 100:0 to 0:100) to afford methyl 3-chloro-4-[1-methyl-3-(2-pyridyl)-4,6,7,8-tetrahydropyrazolo[3,4-e][1,4]thiazepin-4-yl]benzoate (0.350 g, 24%): LC-MS (Table 1, Method b) R$_t$=6.60 min, m/z 415 (M+H)$^+$; $^1$H-NMR (CDCl$_3$, Bruker 400 MHz) δ 2.72 (1H, ddd, J=15.5, 9.0, 2.0 Hz); 2.83 (1H, ddd, J=15.5, 6.0, 2.0 Hz); 3.24-3.33 (1H, m); 3.59-3.69 (1H, m); 3.80-3.92 (7H, m); 6.88 (1H, s); 7.07 (1H, ddd, J=8.0, 5.0, 1.0 Hz); 7.35 (1H, d, J=8.0 Hz); 7.59 (1H, dt, J=8.0, 2.0 Hz); 7.73-7.79 (2H, m); 8.07 (1H, d, J=2.0 Hz); 8.46-8.50 (1H, m).

TABLE 5

Examples made using General Procedure E

| Ex. # | Bromide | Product structure | R$_t$ min (Table 1, Method) | m/z ESI+ |
|---|---|---|---|---|
| E.2 | 4-(4-bromophenyl)-1-methyl-3-(2-pyridyl)-4,6,7,8-tetrahydropyrazolo[3,4-e][1,4]thiazepine (Ex. D.25) | | 3.15 (a) | 381 (M + H)$^+$ |
| E.3 | 4-(5-bromo-2-methyl-phenyl)-1-methyl-3-(2-pyridyl)-4,6,7,8-tetrahydropyrazolo[3,4-e][1,4]thiazepine (Ex. D.27) | | 7.91 (e) | 395 (M + H)$^+$ |
| E.4 | 4-(4-bromo-2-methyl-phenyl)-1,3,6,6-tetramethyl-7,8-dihydro-4H-pyrazolo[3,4-e][1,4]thiazepine (Ex. D.58) | | 2.71 (a) | 360 (M + H)$^+$ |

TABLE 5-continued

Examples made using General Procedure E

| Ex. # | Bromide | Product structure | R$_t$ min (Table 1, Method) | m/z ESI+ |
|---|---|---|---|---|
| E.5 | 4-(5-bromo-2-methyl-3-thienyl)-1-methyl-3-(2-pyridyl)-4,6,7,8-tetrahydropyrazolo[3,4-e][1,4]thiazepine (Ex D.34) | | 7.14 (e) | 401 (M + H)+ |
| E.6 | 3-(5-bromo-2-pyridyl)-4-(2,4-dichlorophenyl)-1-methyl-4,6,7,8-tetrahydropyrazolo[3,4-e][1,4]thiazepine (Ex D.15) | | 5.12 (b) | 449 (M + H)+ |
| E.7 | 4-(4-bromo-2-methylphenyl)-1,7-dimethyl-3-(pyridin-2-yl)-4,6,7,8-tetrahydro-1H-pyrazolo[3,4-e][1,4]thiazepine (Ex. K.5) | | 2.45 (d) | 409 (M + H)+ |

General Procedure F: Preparation of Aromatic or Heteoaromatic Amides from Esters To a mixture of a ester (1 equivalent) and amine (1-2 equivalents, preferably 1.2 equivalents) in anhydrous THF, dioxane or diethyl ether (preferably THF) is added a lithium bis(trimethylsilyl)amide solution (1 M in THF, 1-4 equivalents, preferably 2 equivalents), at temperatures between −78° C. and −30° C. (preferably −40° C.). The resulting mixture is stirred for about 30 min, at temperatures between −40° C. and 0° C. (preferably −10° C.), and then quenched by the addition of water and ethyl acetate. The layers are separated and the organic layer is washed with water, dried (MgSO$_4$), filtered and concentrated in vacuo. The resulting residue is purified by chromatography. Alternatively a reaction vessel is charged with an amine (1-4 equiv, preferably 3 equiv) in a suitable organic solvent (such as THF, 1,4-dioxane, Et$_2$O, DMF, DMA, preferably THF) and the solution is cooled to about −10-10° C. (preferably about 0° C.) followed by the addition of a base such as LiHMDS, NaHMDS, KHMDS, NaH, (preferably LiHMDS, 1-5 equiv, preferably 4 equiv) as a solution in a suitable organic solvent (preferably THF). The reaction mixture is stirred at about −10-10° C. (preferably about 0° C.) for about 10-60 min (preferably about 20 min) and is then warmed to about 10° C.-room temperature (preferably room temperature) and stirred for about 1-5 h (preferably about 2 h). To the reaction mixture are added saturated aqueous NH$_4$Cl and water and the resulting mixture is extracted with an organic solvent (such as DCM or EtOAc). The combined extracts are dried over MgSO$_4$ or Na$_2$SO$_4$, filtered and concentrated under reduced pressure to give the crude product which is optionally purified further by trituration, crystallization or silica gel chromatography.

Illustration of General Procedure F

Example #F.1

3-chloro-N-(2-methyl-3-pyridyl)-4-[1-methyl-3-(2-pyridyl)-4,6,7,8-tetrahydropyrazolo[3,4-e][1,4]thiazepin-4-yl]benzamide

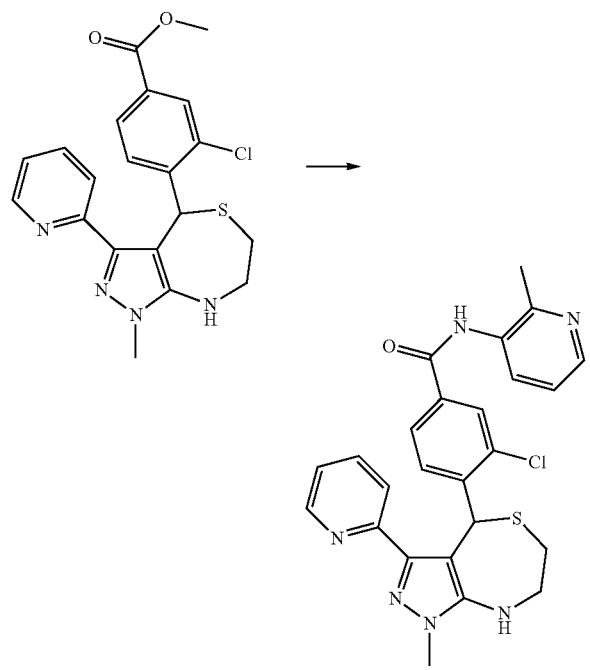

To a mixture of methyl 3-chloro-4-[1-methyl-3-(2-pyridyl)-4,6,7,8-tetrahydropyrazolo[3,4-e][1,4]thiazepin-4-yl]benzoate (0.14 g, 0.34 mmol, Example #E.1) and 3-amino-2-methylpyridine (0.04 g, 0.37 mmol) in anhydrous THF (10 mL), was added lithium bis(trimethylsilyl)amide solution (1.3 mL, 1 M in THF, 1.3 mmol), at about −40° C. The resulting mixture was stirred for about 30 min, at about −40° C., and then quenched by the addition of water (10 mL) and ethyl acetate (130 mL). The layers were separated and the organic layer was washed with water (25 mL), dried ($MgSO_4$), filtered and concentrated in vacuo. The resulting residue was purified by column chromatography ($SiO_2$, ethyl acetate/methanol 100:0 to 0:100) and preparative HPLC (Table 2, Method a) to afford 3-chloro-N-(2-methyl-3-pyridyl)-4-[1-methyl-3-(2-pyridyl)-4,6,7,8-tetrahydro-pyrazolo[3,4-e][1,4]thiazepin-4-yl]benzamide (0.0162 g, 0.03 mmol, 9%): LC-MS (Table 1, Method b) $R_t$=3.70 min, m/z 491 (M+H)$^+$; $^1$H-NMR (CDCl$_3$, Bruker 400 MHz) 2.56 (3H, s), 2.70-2.90 (2H, m), 3.26-3.35 (1H, m), 3.63-3.71 (1H, m) 3.60-4.00 (1H, br s) 3.84 (3H, s) 6.91 (1H, s) 7.09 (1H, ddd, J=1.2, 4.8, 7.9 Hz) 7.21 (1H, dd, J=4.8, 8.2 Hz) 7.44 (1H, d, J=8.0 Hz) 7.58-7.64 (3H, m) 7.80 (1H, d, J=8.0 Hz) 7.92 (1H, d, J=2.0 Hz) 8.28-8.34 (2H, m) 8.48-8.51 (1H, m).

TABLE 6

Examples made using General Procedure F with 3-amino-2-methylpyridine

| Ex. # | Ester | Product structure | $R_t$ min (Table 1, Method) | m/z ESI+ |
|---|---|---|---|---|
| F.2 | methyl 6-[4-(2,4-dichlorophenyl)-1-methyl-4,6,7,8-tetrahydropyrazolo[3,4-e][1,4]thiazepin-3-yl]pyridine-3-carboxylate (Ex. E.6) | | 2.72 (a) | 525 (M + H)$^+$ |

TABLE 6-continued

Examples made using General Procedure F with 3-amino-2-methylpyridine

| Ex. # | Ester | Product structure | R, min (Table 1, Method) | m/z ESI+ |
|---|---|---|---|---|
| F.3 | methyl 4-[1-methyl-3-(2-pyridyl)-4,6,7,8-tetrahydropyrazolo[3,4-e][1,4]thiazepin-4-yl]benzoate (Ex. E.2). | | 4.23 (e) | 457 (M + H)+ |
| F.4 | methyl 4-methyl-5-[1-methyl-3-(2-pyridyl)-4,6,7,8-tetrahydropyrazolo[3,4-e][1,4]thiazepin-4-yl]thiophene-2-carboxylate (prepared using E from 4-(5-bromo-3-methyl-2-thienyl)-1-methyl-3-(2-pyridyl)-4,6,7,8-tetrahydropyrazolo[3,4-e][1,4]thiazepine (Ex. D.26)) | | 4.69 (e) | 477 (M + H)+ |
| F.5 | methyl 4-methyl-3-[1-methyl-3-(2-pyridyl)-4,6,7,8-tetrahydropyrazolo[3,4-e][1,4]thiazepin-4-yl]benzoate (Ex. E.3) | | 5.44 (e) | 417 (M + H)+ |

TABLE 6-continued

Examples made using General Procedure F with 3-amino-2-methylpyridine

| Ex. # | Ester | Product structure | $R_t$ min (Table 1, Method) | m/z ESI+ |
|---|---|---|---|---|
| F.6 | methyl 5-methyl-4-[1-methyl-3-(2-pyridyl)-4,6,7,8-tetrahydropyrazolo[3,4-e][1,4]thiazepin-4-yl]thiophene-2-carboxylate (prepared using E from 4-(5-bromo-2-methyl-3-thienyl)-1-methyl-3-(2-pyridyl)-4,6,7,8-tetrahydropyrazolo[3,4-e][1,4]thiazepine (Ex. #D.34)). | | 5.27 (e) | 477 (M + H)+ |

TABLE 6a

Examples prepared from methyl 4-(1-ethyl-3-(pyridin-2-yl)-1,4,5,6,7,8-hexahydropyrazolo[3,4-b]azepin-4-yl)-3-methylbenzoate (prepared using E from 4-(4-bromo-2-methylphenyl)-1-ethyl-3-(pyridin-2-yl)-1,4,5,6,7,8-hexahydropyrazolo[3,4-b]azepine (Prepared using E from Example #BB.1) using General Procedure F

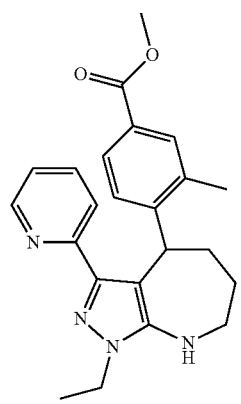

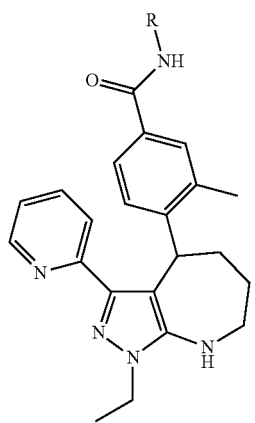

TABLE 6a-continued

| Ex. # | Amine | Product structure | $R_t$ min (Table 1, Method) | m/z ESI+ |
|---|---|---|---|---|
| F.7 | 3-amino-2-methyl-pyridine (Apollo) | | 1.98 (h) | 457 (M + H)+ |

General Procedure G: Preparation of Nitriles from Bromides

To a degassed solution of a bromide (1 equivalent) in anhydrous DMF is added zinc cyanide (0.5-1 equivalent, preferably 0.7 equivalents) and tetrakis(triphenylphosphine)palladium(0) (0.01-0.1 equivalents, preferably 0.05 equivalent). The resulting mixture is heated, in a sealed microwave vessel, for about 1 h, at about 120° C. in a microwave. After cooling to rt, ethyl acetate and water are added, and the mixture is filtered over diatomaceous earth. The layers are separated and the aqueous layer is extracted with ethyl acetate. The combined organic layers are dried (MgSO$_4$), filtered, and concentrated in vacuo. The residue can be purified by column chromatography.

Illustration of General Procedure G

Example #G.1

4-methyl-3-[1-methyl-3-(2-pyridyl)-4,6,7,8-tetrahydropyrazolo[3,4-e][1,4]thiazepin-4-yl]benzonitrile

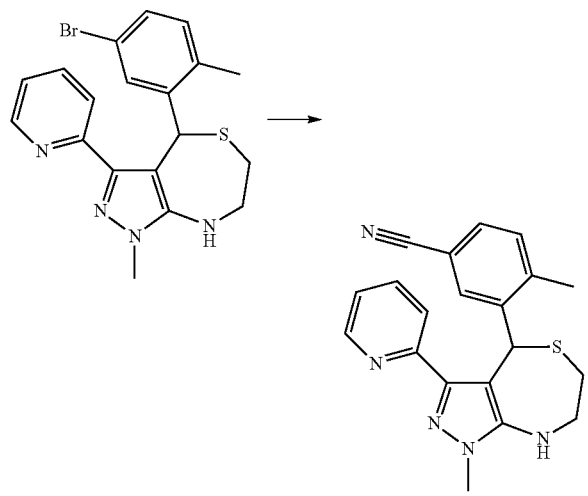

To a degassed solution of 4-(5-bromo-2-methyl-phenyl)-1-methyl-3-(2-pyridyl)-4,6,7,8-tetrahydropyrazolo[3,4-e][1,4]thiazepine (0.250 g, 0.6 mmol, Example D.27) in anhydrous DMF (3 mL) was added zinc cyanide (0.0511 g, 0.43 mmol) and tetrakis(triphenylphosphine)-palladium(0) (0.0346 g, 0.03 mmol). The resulting mixture was heated, in a sealed microwave vessel, for about 1 h, at about 120° C. in a microwave. After cooling to rt, ethyl acetate (50 mL) and water (50 mL) were added, and the mixture was filtered through a pad of Celite®. The layers were separated and the aqueous layer was extracted with ethyl acetate (2×100 mL). The combined organic layers were dried (MgSO$_4$), filtered, and concentrated in vacuo. The residue was purified by column chromatography (SiO$_2$, hexanes/ethyl acetate 1:1) followed by trituration with diethyl ether to give 4-methyl-3-[1-methyl-3-(2-pyridyl)-4,6,7,8-tetrahydropyrazolo[3,4-e][1,4]thiazepin-4-yl]benzonitrile (0.042 g, 0.117 mmol, 20%). LC-MS (Table 1, Method e) R$_t$=8.10 min, m/z 362 (M+H)$^+$; $^1$H-NMR (DMSO-d$_6$, Bruker 400 MHz) δ 2.57-2.66 (1 H, m) 2.63 (3 H, s) 2.70 (1 H, dd, J=14.7, 4.4 Hz) 3.04 (1 H, ddt, J=13.1, 10.6, 1.6 Hz) 3.68-3.77 (1 H, m) 3.79 (3 H, s) 5.87 (1 H, d, J=5.5 Hz) 6.87 (1 H, s) 7.17 (1 H, ddd, J=7.4, 4.9, 1.3 Hz) 7.34 (1 H, d, J=8.0 Hz) 7.46 (1 H, dd, J=7.8, 1.8 Hz) 7.54 (1 H, d, J=1.8 Hz) 7.70 (1 H, ddd, J=9.4, 7.3, 1.8 Hz) 7.86 (1 H, dt, J=8.0, 1.0 Hz) 8.46 (1 H, ddd, J=4.9, 1.9, 0.9 Hz).

TABLE 7

Examples made using General Procedure G

| Ex. # | Bromide | Product structure | R$_t$ min (Table 1, Method) | m/z ESI+ |
|---|---|---|---|---|
| G.2 | 4-(4-bromo-2-methyl-phenyl)-1,3,6-trimethyl-4,6,7,8-tetrahydropyrazolo[3,4-e][1,4]thiazepine (Example D.62) | | 6.84 (e) | 313 (M + H)$^+$ |

TABLE 7-continued

Examples made using General Procedure G

| Ex. # | Bromide | Product structure | R$_t$ min (Table 1, Method) | m/z ESI+ |
|---|---|---|---|---|
| G.3 | 4-(4-bromo-2-methyl-phenyl)-3-cyclopropyl-1,6-dimethyl-4,6,7,8-tetrahydropyrazolo[3,4-e][1,4]thiazepine (Example D.51) | | 7.18 (e) | 339 (M + H)$^+$ |
| G.4 | 4-(4-bromo-2-methyl-phenyl)-3-cyclopropyl-1,6-dimethyl-4,6,7,8-tetrahydropyrazolo[3,4-e][1,4]thiazepine (Example D.51) | | 7.68 (e) | 339 (M + H)$^+$ |

TABLE 7-continued

Examples made using General Procedure G

| Ex. # | Bromide | Product structure | R$_t$ min (Table 1, Method) | m/z ESI+ |
|---|---|---|---|---|
| G.5 | 4-(5-bromo-2-methyl-phenyl)-3-cyclopropyl-1,6,6-trimethyl-7,8-dihydro-4H-pyrazolo[3,4-e][1,4]thiazepine (Example D.55) | | 6.67 (e) | 353 (M + H)+ |
| G.6 | 4-(4-bromo-2-methyl-phenyl)-1,3,6,6-tetramethyl-7,8-dihydro-4H-pyrazolo[3,4-e][1,4]thiazepine (Example D.58) | | 6.47 (e) | 327 (M + H)+ |
| G.7 | 4-(4-bromo-2-methyl-phenyl)-1,7-dimethyl-3-(2-pyridyl)-4,6,7,8-tetrahydropyrazolo[3,4-e][1,4]thiazepine (Example #K.1) | | 8.48 (minor) and 8.65 (major); (e) | 376 (M + H)+ |
| G.8 | 4-(4-bromo-2-methyl-phenyl)-1-pyridyl)-4,6,7,8-tetrahydropyrazolo[3,4-e][1,4]thiazepine (Example 4 step D). | | 7.64 (e) | 362 (M + H)+ |

TABLE 7-continued

Examples made using General Procedure G

| Ex. # | Bromide | Product structure | R$_t$ min (Table 1, Method) | m/z ESI+ |
|---|---|---|---|---|
| G.9 | 4-(4-bromo-2-methyl-phenyl)-3-(2-pyridyl)-4,6,7,8-tetra-hydroisoxazolo-[5,4-e][1,4]thiazepine (Example D.44) | | 8.67 (e) | 349 (M + H)+ |
| G.10 | 4-(4-bromo-2-methyl-phenyl)-1-ethyl-3-(2-pyridyl)-4,6,7,8-tetra-hydropyrazolo[3,4-e][1,4]-thiazepine (Example D.30) | | 8.63 (e) | 376 (M + H)+ |
| G.11 | 4-(4-bromo-2-methyl-phenyl)-1,3,6-trimethyl-4,6,7,8-tetrahydropyrazolo[3,4-e][1,4]thiazepine (Example D.62) | | 6.61 (e) | 313 (M + H)+ |

General Procedure H: Preparation of Amides from Bromides

To a mixture of a bromide (1 equivalent) and the amine (1-4 equivalents, preferably 2 equivalent) in degassed THF, is added (1-3, trans-di-MU-acetatobis[2-(di-o-tolylphosphino)benzyl]dipalladium(II) (0.05-0.15 equivalent, preferably 0.1 equivalent), tri-tert-butylphosphine tetrafluoroborate (0-1 equivalent, preferably 0.2 equivalent), molybdenumhexacarbonyl (1-3 equivalents, preferably 1 equivalent), and a base such as $K_2CO_3$ or 1,8-diazabicyclo[5.4.0]undec-7-ene, preferably $K_2CO_3$ (0-3 equivalents, preferably 2 equivalents). The resulting mixture is heated, in a sealed microwave vessel, for about 1 h at about 120° C. in a microwave. After cooling to rt, the mixture is filtered and concentrated in vacuo. The residue is purified by column chromatography to afford the methyl ester.

Illustration of General Procedure H

Example #H.1

3-methyl-N-(3-pyridyl)-4-(1,3,6,6-tetramethyl-7,8-dihydro-4H-pyrazolo[3,4-e][1,4]thiazepin-4-yl)benzamide

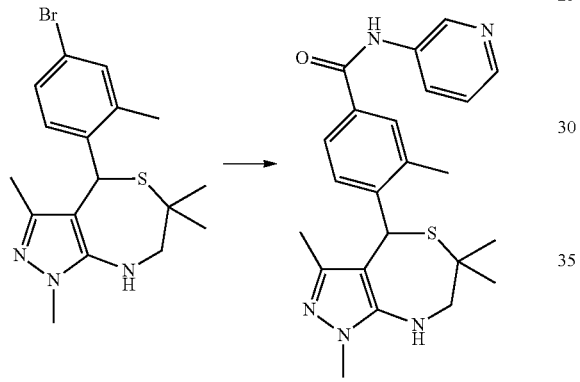

To THF (5 mL) was added 4-(4-bromo-2-methyl-phenyl)-1,3,6,6-tetramethyl-7,8-dihydro-4H-pyrazolo[3,4-e][1,4]thiazepine (0.1 g, 0.26 mmol, Example D.58), trans-di-MU-acetatobis[2-(di-o-tolylphosphino)benzyl]dipalladium(II) (0.025 g, 0.026 mmol, Alfa Aesar), molybdenumhexacarbonyl (0.072 g, 0.26 mmol, Fluka), tri-tert-butylphosphonium tetrafluoroboronate (0.016 g, 0.052 mmol), 1,8-diazabicyclo[5.4.0]undec-7-ene (0.061 g, 0.052 mmol) and 3-aminopyridine (0.075 g, 0.78 mmol). The resulting mixture was heated, in a sealed microwave vessel, for about 1 h at about 120° C. in a microwave. After cooling to rt, the mixture was filtered and partitioned between ethyl acetate (50 mL) and 5% aqueous sodium bicarbonate (25 mL). The layers were separated and the organic layer was washed with 5% aqueous sodium bicarbonate (10 mL), dried ($MgSO_4$), filtered and concentrated in vacuo. The resulting oil was purified by column chromatography ($SiO_2$, ethyl acetate followed by 2% MeOH/ethyl acetate to 5% MeOH/ethyl acetate) to afford 3-methyl-N-(3-pyridyl)-4-(1,3,6,6-tetramethyl-7,8-dihydro-4H-pyrazolo[3,4-e][1,4]thiazepin-4-yl)benzamide (0.071 g, 64%) as white solid: LC-MS (Table 1, Method e) $R_t$=4.87 min, m/z 422 $(M+H)^+$

TABLE 8

Examples made using General Procedure H

| Ex. # | Bromide | Product structure | $R_t$ min (Table 1, Method) | m/z ESI+ |
|---|---|---|---|---|
| H.2 | 4-(5-bromo-2-methyl-phenyl)-3-cyclopropyl-1,6,6-trimethyl-7,8-dihydro-4H-pyrazolo[3,4-e][1,4]thiazepine (Example D.55) | | 4.46 (e) | 462 $(M + H)^+$ |

TABLE 8-continued

Examples made using General Procedure H

| Ex. # | Bromide | Product structure | $R_t$ min (Table 1, Method) | m/z ESI+ |
|---|---|---|---|---|
| H.3 | 4-(4-bromo-2-chloro-phenyl)-1-methyl-3-(2-pyridyl)-4,6,7,8-tetra-hydropyrazolo[3,4-e][1,4]thiazepine (Example #3 step D) | | 5.56 (e) | 477 (M + H)+ |
| H.4 | 4-(4-bromo-2-methyl-phenyl)-1-ethyl-3-(2-pyridyl)-4,6,7,8-tetrahydropyrazolo[3,4-e][1,4]thiazepine (Example D.30) | | 4.96 (e) | 485 (M + H)+ |
| H.5 | 4-(4-bromo-2-methyl-phenyl)-1,3,6,6-tetramethyl-7,8-dihydro-4H-pyrazolo[3,4-e][1,4]thiazepine (Example D.58) | | 5.15 (e) | 436 (M + H)+ |

TABLE 8-continued

Examples made using General Procedure H

| Ex. # | Bromide | Product structure | R$_t$ min (Table 1, Method) | m/z ESI+ |
|---|---|---|---|---|
| H.6 | 4-(4-bromo-2-methylphenyl)-1,7-dimethyl-3-(pyridin-2-yl)-4,6,7,8-tetrahydro-1H-pyrazolo[3,4-e][1,4]thiazepine (Example K.5) | | 5.38 (m) | 485 (M + H)+ |

General Procedure I: Preparation of Amides from Methyl-Esters

To the ester in a suitable anhydrous solvent such as EtOH or MeOH (preferably MeOH) and KCN (0.5-1.5 equivalents, preferably 1 equivalent), is added an amine (100-300 equivalents, preferably 200 equivalents). The resulting mixture is heated, in a sealed vessel, for about 18 h at temperatures between 90 and 150° C. (preferably 110° C.). After cooling to rt, the mixture is concentrated in vacuo. The residue can be purified by column chromatography to afford the amide.

Illustration of General Procedure I

Example #I.1

3-chloro-4-[1-methyl-3-(2-pyridyl)-4,6,7,8-tetrahydropyrazolo[3,4-e][1,4]thiazepin-4-yl]benzamide

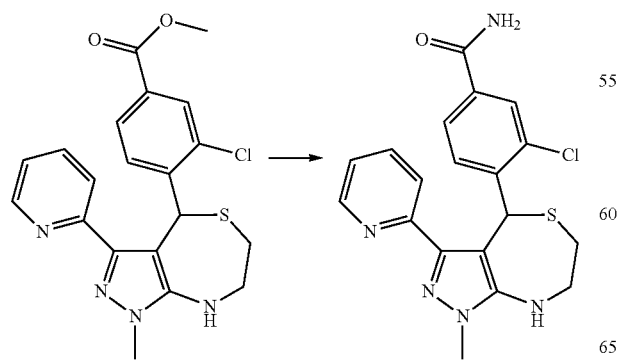

A mixture of methyl 3-chloro-4-[1-methyl-3-(2-pyridyl)-4,6,7,8-tetrahydropyrazolo[3,4-e][1,4]thiazepin-4-yl]benzoate (0.14 g, 0.32 mmol, Example #E.1), methanol (15 mL), potassium cyanide (0.02 g, 0.3 mmol), and ammonia (10 mL, 7 M in MeOH, 70 mmol) was heated, in a sealed flask, for about 18 h at about 110° C. After cooling to rt the mixture was concentrated in vacuo. The residue was dissolved in DCM (100 mL) and washed with water (2×40 mL). The organic layer was dried (MgSO$_4$), filtered, and concentrated in vacuo. The residue was purified by prep-HPLC (Table 2, Method a,) to give 3-chloro-4-[1-methyl-3-(2-pyridyl)-4,6,7,8-tetrahydropyrazolo[3,4-e][1,4]thiazepin-4-yl]benzamide as an off white solid (0.018 g, 0.05 mmol, 16%): LC-MS (Table 1, Method b) R$_t$=4.5 min; m/z 400 (M+H)+; $^1$H-NMR (CDCl$_3$, Bruker 400 MHz) δ 2.63-2.72 (1H, m) 2.75-2.86 (1H, m) 3.18-3.28 (1H, m) 3.75-3.75 (1H, m) 3.83 (3H, s) 4.78 (1H, br.d, J=5.5 Hz) 6.23 (1H, br. s) 6.91 (1H, s) 7.08 (1H, ddd, J=8.0, 5.0, 1.0 Hz) 7.32-7.49 (2H, m) 7.56-7.65 (2H, m) 7.77 (1H, d, J=8.5 Hz) 7.94 (1H, d, J=1.5 Hz) 8.46-8.51 (1H, m).

TABLE 9

Examples made using General Procedure I

| Ex. # | Methyl ester | Amine | Product structure | R, min (Table 1, Method) | m/z ESI+ |
|---|---|---|---|---|---|
| I.2 | methyl 3-chloro-4-[1-methyl-3-(2-pyridyl)-4,6,7,8-tetrahydropyrazolo[3,4-e][1,4]thiazepin-4-yl]benzoate (Example #3 step E) | Methyl amine | | 4.7 (b) | 414 (M + H)+ |
| I.3 | methyl 6-[4-(2,4-dichlorophenyl)-1-methyl-4,6,7,8-tetrahydropyrazolo[3,4-e][1,4]thiazepin-3-yl]pyridine-3-carboxylate (Example E.6) | Methyl amine | | 2.99 (b) | 448 (M + H)+ |
| I.4 | methyl 3-methyl-4-(1,3,6,6-tetramethyl-7,8-dihydro-4H-pyrazolo[3,4-e][1,4]thiazepin-4-yl)benzoate (Example E.4) | Ammonia | | 5.03 (e) | 345 (M + H)+ |
| I.5 | methyl 6-[4-(2,4-dichlorophenyl)-1-methyl-4,6,7,8-tetrahydropyrazolo[3,4-e][1,4]thiazepin-3-yl]pyridine-3-carboxylate (Example E.6) | Ammonia | | 2.75 (b) | 434 (M + H)+ |

General Procedure J: Preparation of Pyrazolodihydrothiazepines from Ketones

A mixture of a 5-aminopyrazole (1-2 equivalents, preferably 1.0 equivalent), an aldehyde (1-2 equivalents, preferably 1.0 equivalent), an α-sulfanylketone (1-5 equivalents, preferably 2 equivalents) and p-toluenesulfonic acid monohydrate (0-3 equivalents, preferably 0.3 equivalent) with a solvent such as acetonitrile or toluene (preferably acetonitrile) is heated, eventually in a closed vessel in a microwave or an oil bath (preferably in a microwave), at temperatures between 90° C. and 250° C. (preferably about 150° C.) for about 5 min to 24 h (preferably about 40 min). After cooling to rt the mixture is concentrated in vacuo. The residue is dissolved in a solvent such as ethyl acetate/methanol mixture to obtain a clear solution, and washed with 5% aqueous sodium bicarbonate. The aqueous layer is extracted with a solvent such as ethyl acetate. The combined organic layers are washed with water, dried (MgSO$_4$), filtered and concentrated in vacuo. The residue can be purified by column chromatography.

Illustration of General Procedure J

Preparation #J.1

4-(4-bromo-2-methylphenyl)-1,7-dimethyl-3-(pyridin-2-yl)-4,6-dihydro-1H-pyrazolo[3,4-e][1,4]thiazepine

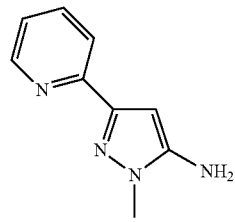

A mixture of 1-methyl-3-(2-pyridyl)pyrazol-5-amine (0.30 g, 1.72 mmol, Example #2, step B), 4-bromo-2-methylbenzaldehyde (0.34 g, 1.72 mmol, Ark Pharm), 1-sulfanylpropan-2-one (0.31 g, 3.44 mmol, Enamine), and p-toluenesulfonic acid monohydrate (0.098 g, 0.52 mmol) in acetonitrile (3 mL) was heated, in a sealed microwave vessel, for about 40 min, at about 150° C., in a microwave. After cooling to rt the mixture was concentrated in vacuo. The residue was dissolved in ethyl acetate (40 mL) and methanol (2 mL), and washed with 5% aqueous sodium bicarbonate (20 mL). The aqueous layer was extracted with ethyl acetate (40 mL). The combined organic layers were washed with water (10 mL), dried (MgSO$_4$), filtered and concentrated in vacuo. The residue was purified by column chromatography (SiO2, ethyl acetate/hexanes 1:4) to afford 4-(4-bromo-2-methylphenyl)-1,7-dimethyl-3-(pyridin-2-yl)-4,6-dihydro-M-pyrazolo[3,4-e][1,4]thiazepine (0.507 g, 1.19 mmol, 69%), as a yellow oil: $^1$H-NMR (CDCl$_3$, Bruker 400 MHz) δ 2.36 (3 H, s) 2.60 (3 H, s) 3.15 (1 H, d, J=16 Hz) 3.29 (1 H, dd, J=16, 2 Hz) 4.03 (3 H, s) 6.44 (1 H, d, J=9 Hz) 6.59 (1 H, d, J=1.5 Hz) 6.98-7.06 (2 H, m) 7.29 (1 H, d, J=2 Hz) 7.56 (1 H, td, J=8, 2 Hz) 7.86 (1 H, d, J=8 Hz) 8.34 (1 H, d, J=4 Hz).

General Procedure K: Reduction of Pyrazolodihydrothiazepines to Pyrazolotetrahydrothiazepines To a mixture of the pyrazolodihydrothiazepine in a suitable anhydrous solvent such as diethyl ether or THF (preferably THF) is added a reducing agent such as borane THF complex in THF (preferably borane THF complex) (2 to 6 equivalents, preferably 4 equivalents), at temperatures between about 0° C. and rt (preferably about 0° C.). The resulting mixture is stirred at temperatures between 0° C. and 70° C. (preferably rt) for 1-96 h (preferably about 16 h). Then it is treated with an acid such as aqueous HCl, neutralized with a base such as sodium hydroxide or potassium hydroxide (preferably NaOH), and extracted with a suitable organic solvent such as diethyl ether, ethyl acetate or DCM (preferably ethyl acetate). The crude product can be further purified by column chromatography.

Alternatively, to a mixture of the (dihydro)thiazepine in a suitable anhydrous solvent such as DCE or a mixture of MeOH and DCM, is added a reducing agent such as Na(AcO)$_3$BH or sodium cyanoborohydride (2 to 6 equivalents, preferably 4 equivalents), in the presence of an acid such as acetic acid. The resulting mixture is stirred at temperatures between 0° C. and 70° C. (preferably rt) for 1-96 h (preferably about 16 h). Then it is treated with a base such as aqueous NaHCO$_3$, and extracted with a suitable organic solvent such as diethyl ether, ethyl acetate or DCM (preferably ethyl acetate). The crude product can be further purified by column chromatography.

Illustration of General Procedure K

Example #K.1

4-(4-bromo-2-methyl-phenyl)-1,7-dimethyl-3-(2-pyridyl)-4,6,7,8-tetrahydropyrazolo[3,4-e][1,4]thiazepine

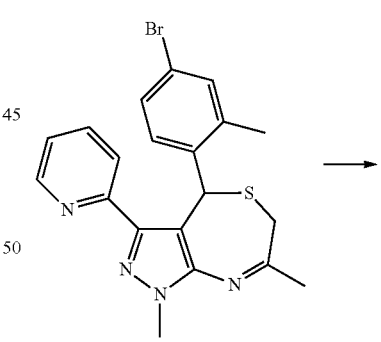

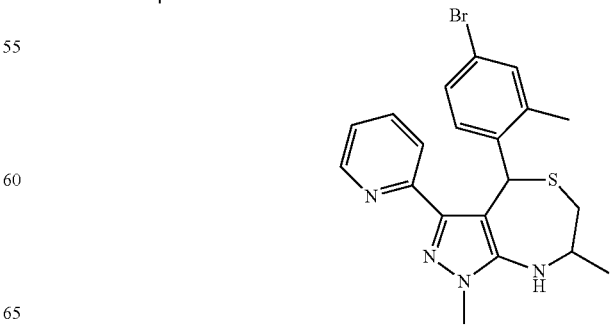

A mixture of 4-(4-bromo-2-methyl-phenyl)-1,7-dimethyl-3-(2-pyridyl)-4,6-dihydropyrazolo[3,4-e][1,4]thiazepine (0.48 g, 1.13 mmol., Preparation J.1), acetic acid (0.194 mL, 3.40 mmol) and Na(AcO)$_3$BH (0.29 g, 1.36 mmol) in DCE (30 mL) was stirred at rt for about 16 h. Additional acetic acid (0.194 mL, 3.4 mmol) and Na(AcO)$_3$BH (0.29 g, 1.36 mmol) were added and stirring was continued for about another 24 h, at rt. The resulting mixture was concentrated in vacuo and partitioned between 5% aq sodium bicarbonate (60 mL) and ethyl acetate (35 mL). The layers were separated and the aqueous layer was extracted with ethyl acetate (35 mL). The combined organic layers were washed with water (20 mL), dried (MgSO$_4$), filtered and concentrated in vacuo. The residue was purified by column chromatography (SiO$_2$, ethyl acetate/hexanes 1:1) to give 4-(4-bromo-2-methyl-phenyl)-1,7-dimethyl-3-(2-pyridyl)-4,6,7,8-tetrahydropyrazolo[3,4-e][1,4]thiazepine (0.413 g, 0.96 mmol, 85%) as a pale yellow oil as a racemic mixture of two diastereomers (ratio 63:37). LC-MS (Table 1, Method g) R$_t$=2.75 and 2.79 min; m/z 429, 431 (M+H)$^+$

TABLE 10

Examples made using General Procedure K

| Ex. # | Imine | Reducing agent | Product structure | R$_t$ min (Table 1, Method) | m/z ESI+ |
|---|---|---|---|---|---|
| K.2 | 4-(4-chloro-2-methyl-phenyl)-1,3,6,6-tetramethyl-7-phenyl-4H-pyrazolo[3,4-e][1,4]thiazepine (prepared using J from 5-amino-1,3-dimethyl-pyrazole with 2-methyl-1-phenyl-2-sulfanyl-propan-1-one (J. Org. Chem., 1995, 60(13), 4153) and 4-chloro-2-methylbenzaldehyde (Apollo Scientific)) | BH$_3$•THF | | 8.66 (e) | 412 (M + H)$^+$ |
| K.3 | 4-(4-chloro-2-methyl-phenyl)-7-isopropyl-1-methyl-3-(2-pyridyl)-4,6-dihydropyrazolo[3,4-e][1,4]thiazepine (prepared using J from Example #2 step B with 3-methyl-1-sulfanyl-butan-2-one (Liebigs Ann. Chem., 1958, 611, 131) and 4-chloro-2-methyl-benzaldehyde (Apollo Scientific)). | BH$_3$•THF | | 10.54 (minor) and 10.79 (Major) (e) (16:84) | 413 (M + H)$^+$ |

TABLE 10-continued

Examples made using General Procedure K

| Ex. # | Imine | Reducing agent | Product structure | R$_t$ min (Table 1, Method) | m/z ESI+ |
|---|---|---|---|---|---|
| K.4 | 4-(4-bromo-2,5-dimethylphenyl)-1,7-dimethyl-3-(pyridin-2-yl)-4,6-dihydro-1H-pyrazolo[3,4-e][1,4]thiazepine (prepared using J from Example #2 step B with 1-sulfanyl-propan-2-one (Enamine Building Blocks) and 4-bromo-2,5-dimethylbenzaldehyde (Preparation #32)) | NaBH(OAc)$_3$ | 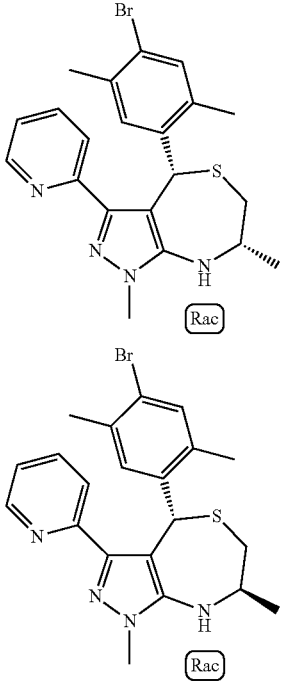 | 10.24 (m) | 443 (M + H)$^+$ |
| K.5 | 4-(4-bromo-2-methylphenyl)-1,7-dimethyl-3-(pyridin-2-yl)-4,6-dihydro-1H-pyrazolo[3,4-e][1,4]thiazepine (prepared using J from Example #2 step B with 1-sulfanyl-propan-2-one (Enamine Building Blocks) and 4-bromo-2-methylbenzaldehyde (Ark Pharm. Inc.)) | NaBH(OAc)$_3$ | 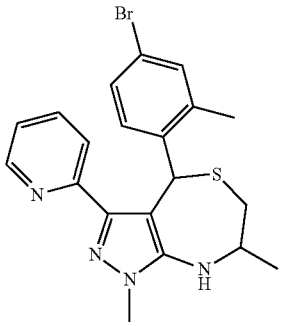 [SMILES: Cc1cc(Br)ccc1C1SCC(C)Nc2c1c(-c1ccccn1)nn2C] | 2.88 (d) | 431 (M + H)$^+$ |
| K.6 | 4-(4-chloro-2-methylphenyl)-1,3,7-trimethyl-4,6-dihydro-1H-pyrazolo[3,4-e][1,4]thiazepine (prepared using J from 5-amino-1,3-dimethyl-pyrazole with 1-sulfanylpropan-2-one (Enamine) and 4-chloro-2-methylbenzaldehyde (Asta Tech)) | Na(OAc)$_3$BH | 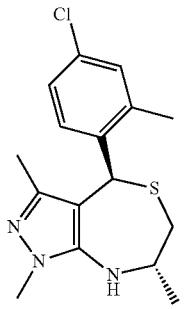 | 2.41 (g) | 322 (M + H)$^+$ |

TABLE 10-continued

Examples made using General Procedure K

| Ex. # | Imine | Reducing agent | Product structure | R$_t$ min (Table 1, Method) | m/z ESI+ |
|---|---|---|---|---|---|
| K.7 | 4-(4-chloro-2-methylphenyl)-1,3,7-trimethyl-4,6-dihydro-1H-pyrazolo[3,4-e][1,4]thiazepine (prepared using J from 5-amino-1,3-dimethyl-pyrazole with 1-sulfanylpropan-2-one (Enamine) and 4-chloro-2-methylbenzaldehyde (Asta Tech)) | Na(OAc)$_3$BH | | 2.44 (g) | 322 (M + H)$^+$ |
| K.8 | 3-(4-(4-bromo-2-methylphenyl)-1,7-dimethyl-4,6-dihydro-1H-pyrazolo[3,4-e][1,4]thiazepin-3-yl)-1,2,4-oxadiazole (prepared using J from Preparation #37 with 1-sulfanylpropan-2-one (Enamine) and 4-bromo-2-methylbenzaldehyde (Ark Pharm)) | Na(OAc)$_3$BH | | 2.48 (g) | 420, 422 (M + H)$^+$ |

TABLE 10-continued

Examples made using General Procedure K

| Ex. # | Imine | Reducing agent | Product structure | R$_t$ min (Table 1, Method) | m/z ESI+ |
|---|---|---|---|---|---|
| K.9 | rac-4-(4-bromo-2-methylphenyl)-1-methyl-3-(pyridin-2-yl)-4,6-dihydro-1H-pyrazolo[3,4-e][1,4]thiazepin-7-yl)methanol (prepared using J from 1-methyl-3-(pyridin-2-yl)-1H-pyrazol-5-amine (Example #2, step B), sodium 3-ethoxy-1-mercapto-3-oxoprop-1-en-2-olate (Preparation #39, step B) and 4-bromo-2-methyl-benzaldehyde (Astatech); similar to Example #7, step E with DIBAL-H | NaBH$_4$ | 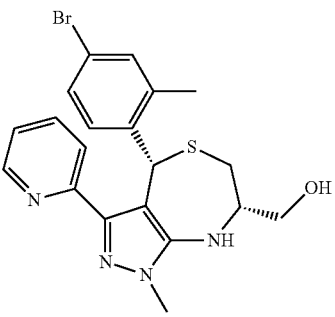 | 2.39 (g) | 445/447 (M + H)+ |
| K.10 | rac-(4-(4-bromo-2-methylphenyl)-1-methyl-3-(pyridin-2-yl)-4,6-dihydro-1H-pyrazolo[3,4-e][1,4]thiazepin-7-yl)methanol (prepared using J from Example #2 step B with sodium 3-ethoxy-1-mercapto-3-oxoprop-1-en-2-olate (Preparation #39 step B) and 4-bromo-2-methyl-benzaldehyde (Astatech); similar to Example #7, step E with DIBAL-H | NaBH$_4$ | 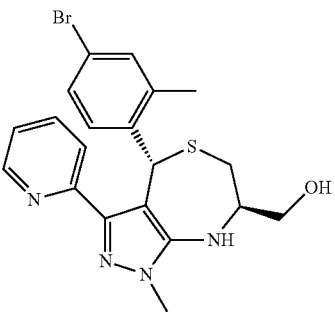 | 2.32 (g) | 445/447 (M + H)+ |

TABLE 10-continued

Examples made using General Procedure K

| Ex. # | Imine | Reducing agent | Product structure | R$_t$ min (Table 1, Method) | m/z ESI+ |
|---|---|---|---|---|---|
| K.11 | 4-(4-bromo-2-(trifluoromethyl)phenyl)-1,7-dimethyl-3-(pyridin-2-yl)-4,6-dihydro-1H-pyrazolo[3,4-e][1,4]thiazepine (prepared using J from Example #2 step B with 4-bromo-2-(trifluoromethyl)benzaldehyde [Combi-Blocks] and 2-oxopropane-1-thiolate) | Na(CN)BH$_3$ | | 2.85 290 (g) | 481, 483 (M + H)+ |

General Procedure L: Preparation of Thiazepine Oxide and/or Thiazepine Dioxide from Thiazepine To a thiazepine, dissolved in a suitable anhydrous solvent such as diethyl ether, chloroform or DCM (preferably DCM) at −25° to rt (preferably at 0° C.), is added m-CPBA (0.9-1.5 equivalents, preferably 1 equivalent for the oxide) or (1.8-3.0 equivalents, preferably 2.1 equivalent for the dioxide) dissolved in DCM. The resulting mixture is stirred for about 5-45 min (preferably 10 min) at rt and subsequently concentrated in vacuo. The residue is purified by column chromatography to afford the oxide and/or dioxide.

Illustration of General Procedure L

Example #L.1

4-(2,4-dichlorophenyl)-1,3,6,6-tetramethyl-7,8-dihydro-4H-pyrazolo[3,4-e][1,4]thiazepine 5-oxide

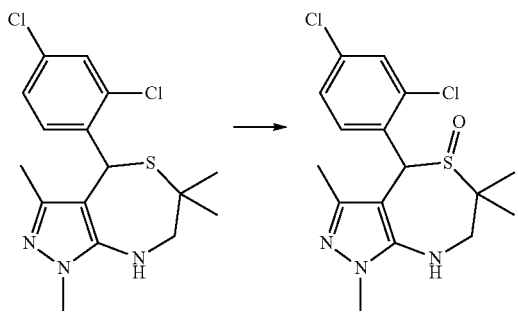

To 4-(2,4-dichlorophenyl)-1,3,6,6-tetramethyl-7,8-dihydro-4H-pyrazolo[3,4-e][1,4]thiazepine (0.1 g, 0.28 mmol), Example D.4) in DCM (5 mL) at 0° C., was added m-CPBA (48.5 mg, 0.28 mmol) dissolved in 3 mL DCM (dropwise in 10 min). The resulting mixture was stirred for about 10 min at rt. Subsequently, 5% aqueous sodium bicarbonate (10 mL) and DCM (20 mL) were added. The layers were separated and the organic layer was washed with water (25 mL), dried (MgSO$_4$), filtered and concentrated in vacuo. The resulting residue was purified by column chromatography (SiO$_2$, ethyl acetate followed by 10% MeOH in ethyl acetate) to afford 4-(2,4-dichlorophenyl)-1,3,6,6-tetramethyl-7,8-dihydro-4H-pyrazolo[3,4-e][1,4]thiazepine 5-oxide (65 mg, 0.175 mmol, 62%), as white solid: LC-MS (Table 1, Method a) R$_t$=2.72 (major) and 2.97 (minor), diastereomeric ratio (64:36); m/z 372 (M+H)+; Isomer A: $^1$H NMR (400 MHz, CDCl$_3$) δ ppm 1.08 (3 H, s) 1.35 (3 H, s) 1.74 (3 H, s) 3.05 (1 H, dd, J=14.7, 6.1 Hz) 3.55 (1 H, dd, J=14.7, 3.8 Hz) 3.66 (3H, s) 3.65-3.69 (1 H, m) 5.67 (1 H, s) 7.17-7.23 (2 H, m) 7.18-7.23 (1 H, m); Isomer B: $^1$H NMR (400 MHz, CDCl$_3$) δ ppm 1.37 (3 H, s) 1.38 (3 H, s) 1.39 (3 H, s) 3.02 (1 H, dd, J=14.6, 7.1 Hz) 3.51 (1 H, dd, J=14.6, 2.8 Hz) 3.61 (1 H, dd, J=2.8 Hz) 3.64 (3 H, s) 5.50 (1 H, s) 7.34 (1 H, dd, J=8.6, 2.2 Hz) 7.47 (1 H, d, J=2.2 Hz) 7.89 (1 H, d, J=8.6 Hz).

TABLE 11

Examples made using General Procedure L

| Ex. # | Thiazepine | Product structure | R, min (Table 1, Method) | m/z ESI+ |
|---|---|---|---|---|
| L.2 | 4-(2,4-dichlorophenyl)-1-methyl-3-(2-pyridyl)-4,6,7,8-tetrahydro-pyrazolo[3,4-e][1,4]thiazepine (Example D.8) | | 2.66 (a) (Major) 3.09 (a) (Minor) | 407 (M + H)+ |
| L.3 | 4-(2,4-dichlorophenyl)-1-methyl-3-(2-pyridyl)-4,6,7,8-tetrahydro-pyrazolo[3,4-e][1,4]thiazepine (Example D.8) | | 3.51 (a) | 423 (M + H)+ |
| L.4 | 4-(2,4-dichlorophenyl)-1,3,6,6-tetramethyl-7,8-dihydro-4H-pyrazolo[3,4-e][1,4]thiazepine (Example D.4) | | 3.26 (a) | 388 (M + H)+ |

General Procedure M: Chiral Preparative HPLC Purification

Chiral purification is performed using Varian 218 LC pumps, a Varian CVM 500 with switching valves and heaters for automatic solvent, column and temperature control and a Varian 701 Fraction collector. Detection methods include a Varian 210 variable wavelength detector, an in-line polarimeter (PDR-chiral advanced laser polarimeter, model ALP2002) used to measure qualitative optical rotation (+/−) and an evaporative light scattering detector (ELSD) (a PS-ELS 2100 (Polymer Laboratories)) using a 100:1 split flow. ELSD settings are as follows: evaporator: 46° C., nebulizer: 24° C. and gas flow: 1.1 SLM. The absolute stereochemistry of the purified compounds was assigned arbitrarily and is drawn as such. Compounds of the invention where the absolute stereochemistry has been determined by the use of a commercially available enantiomerically pure starting material, or a stereochemically defined intermediate, or X-ray diffraction are denoted by an asterisk after the example number.

Illustration of General Procedure M

Examples # M.6 and #M.7

(R)-4-(4-Chloro-2-methylphenyl)-1,3,6,6-tetramethyl-4,6,7,8-tetrahydro-1H-pyrazolo[3,4-e][1,4]thiazepine and (S)-4-(4-Chloro-2-methylphenyl)-1,3,6,6-tetramethyl-4,6,7,8-tetrahydro-1H-pyrazolo[3,4-e][1,4]thiazepine

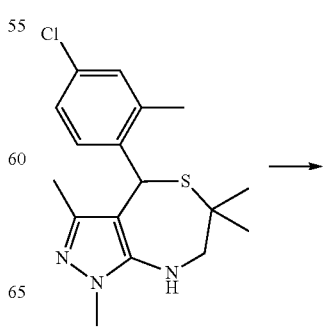

-continued

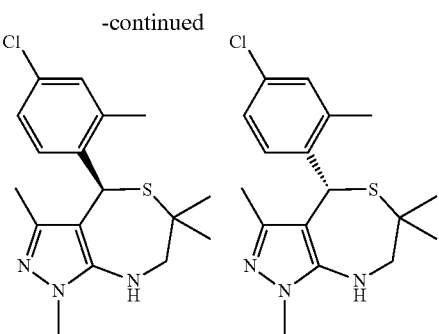

rac-4-(4-Chloro-2-methylphenyl)-1,3,6,6-tetramethyl-4,6,7,8-tetrahydro-1H-pyrazolo[3,4-e][1,4]thiazepine (0.100 g, 0.298 mmol, prepared using C from 1,3-dimethyl-1H-pyrazol-5-amine with 2-methyl-4-chlorobenzaldehyde (Apollo Scientific), and 2-mercapto-2-methylpropanoic acid followed by D with borane-THF complex) was dissolved in MeOH:DCM (1:2, 3 mL). The mixture was separated using Varian 218 LC pumps, a Varian CVM 500 with switching valves and heaters for automatic solvent, column and temperature control and a Varian 701 Fraction collector using Method 5 (Table 3) to give (R)-4-(4-Chloro-2-methylphenyl)-1,3,6,6-tetramethyl-4,6,7,8-tetrahydro-M-pyrazolo[3,4-e][1,4]thiazepine ($R_t$=15.88 min, or =positive) (0.0415 g, 41.5%) [M.6] and (S)-4-(4-Chloro-2-methylphenyl)-1,3,6,6-tetramethyl-4,6,7,8-tetrahydro-M-pyrazolo[3,4-e][1,4]thiazepine ($R_t$=12.65 min, or =negative) (0.032 g, 32%) [M.7]: LC/MS (Table 1, Method g) $R_t$=2.46 min; MS m/z: 336 (M+H)$^+$.

TABLE 12

Compounds prepared using general procedure M

| Ex. # | Compound | Product structure | $R_t$ min (Table 1, Method) | m/z ESI+ |
|---|---|---|---|---|
| M.1* | 4-(4-bromo-2-chlorophenyl)-1-methyl-3-(pyridin-2-yl)-4,6,7,8-tetrahydro-1H-pyrazolo[3,4-e][1,4]thiazepine (prepared using C from Example 2 step B with thioglycolic acid and 4-bromo-2-chlorobenzaldehyde (Apollo Scientific) followed by D with borane-THF complex) [Table 3, Method 1, $R_t$ = 5.29 min, or = positive] | | 2.60 (g) | 435, 437 (M + H)$^+$ |
| M.2* | 4-(4-bromo-2-chlorophenyl)-1-methyl-3-(pyridin-2-yl)-4,6,7,8-tetrahydro-1H-pyrazolo[3,4-e][1,4]thiazepine (prepared using prepared using C from Example 2 step B with thioglycolic acid and 4-bromo-2-chlorobenzaldehyde (Apollo Scientific) followed by D with borane-THF complex) [Table 3, Method 1, $R_t$ = 7.28 min, or = negative] | | 2.60 (g) | 435, 437 (M + H)$^+$ |
| M.3 | 4-(4-chloro-2-fluorophenyl)-3-cyclopropyl-1,6,6-trimethyl-4,6,7,8-tetrahydro-1H-pyrazolo[3,4-e][1,4]thiazepine (prepared using C with 3-cyclopropyl-1-methyl-1H-pyrazol-5-amine (Fluorochem), 2-mercapto-2-methylpropanoic acid (Chemwish Technology) and 4-chloro-2-fluorobenzaldehyde (Acros) followed by D with borane-THF complex) [Table 3, Method 3, $R_t$ = 4.9 min, or = negative] | | 2.62 (g) | 366 (M + H)$^+$ |

TABLE 12-continued

Compounds prepared using general procedure M

| Ex. # | Compound | Product structure | $R_t$ min (Table 1, Method) | m/z ESI+ |
|---|---|---|---|---|
| M.4 | 4-(4-chloro-2-fluorophenyl)-3-cyclopropyl-1,6,6-trimethyl-4,6,7,8-tetrahydro-1H-pyrazolo[3,4-e][1,4]thiazepine (prepared using C with 3-cyclopropyl-1-methyl-1H-pyrazol-5-amine (Fluorochem), 2-mercapto-2-methylpropanoic acid (Chemwish Technology) and 4-chloro-2-fluorobenzaldehyde (Acros) followed by D with borane-THF complex) [Table 3, Method 3, $R_t$ = 13.67 min, or = positive] | | 2.62 (g) | 366 (M + H)+ |
| M.5 | 3-(4-(2,4-dichlorophenyl)-3,6,6-trimethyl-4,6,7,8-tetrahydro-1H-pyrazolo[3,4-e][1,4]thiazepin-1-yl)-1,1,1-trifluoropropan-2-ol (Preparation #30) [Table 3, Method 4, $R_t$ = 13.2 min, or = positive] | | 2.58 (g) | 454 (M + H)+ |
| M.6 | 4-(4-chloro-2-methylphenyl)-1,3,6,6-tetramethyl-4,6,7,8-tetrahydro-1H-pyrazolo[3,4-e][1,4]thiazepine (prepared using C from 1,3-dimethyl-1H-pyrazol-5-amine with 2-methyl-4-chlorobenzaldehyde (Apollo Scientific) and 2-mercapto-2-methylpropanoic acid (Chemwish Technology) followed by D with borane-THF complex) [Table 3, Method 5, $R_t$ = 15.88 min, or = positive] | | 2.46 (g) | 336 (M + H)+ |
| M.7 | 4-(4-chloro-2-methylphenyl)-1,3,6,6-tetramethyl-4,6,7,8-tetrahydro-1H-pyrazolo[3,4-e][1,4]thiazepine (prepared using C from 1,3-dimethyl-1H-pyrazol-5-amine with 2-methyl-4-chlorobenzaldehyde (Apollo Scientific), and 2-mercapto-2-methylpropanoic acid (Chemwish Technology) followed by D with borane-THF complex) [Table 3, Method 5, $R_t$ = 12.65 min, or = negative] | | 2.46 (g) | 336 (M + H)+ |

TABLE 12-continued

Compounds prepared using general procedure M

| Ex. # | Compound | Product structure | R$_t$ min (Table 1, Method) | m/z ESI+ |
|---|---|---|---|---|
| M.8 | 3-chloro-N-(2-methylpyridin-3-yl)-4-(1,3,6,6-tetramethyl-4,6,7,8-tetrahydro-1H-pyrazolo[3,4-e][1,4]thiazepin-4-yl)benzamide (prepared using C from 5-amino-1,3-dimethyl-pyrazole with 2-mercapto-2-methylpropanoic acid (Chemwish Technology) and 4-bromo-2-chlorobenzaldehyde (Apollo Sceintific), D with borane THF complex, E, followed by F with 2-methyl-3-aminopyridine) [Table 3, Method 6, R$_t$ = 20.08 min, or = negative] | | 1.85 (g) | 456 (M + H)+ |
| M.9 | 3-chloro-N-(2-methylpyridin-3-yl)-4-(1,3,6,6-tetramethyl-4,6,7,8-tetrahydro-1H-pyrazolo[3,4-e][1,4]thiazepin-4-yl)benzamide (prepared using C from 5-amino-1,3-dimethyl-pyrazole with 2-mercapto-2-methylpropanoic acid (Chemwish Technology) and 4-bromo-2-chlorobenzaldehyde (Apollo Scientific), D with borane-THF complex, E, followed by F with 2-methyl-3-aminopyridine) [Table 3, Method 6, R$_t$ =20.08 min, or = negative] | | 1.85 (g) | 456 (M + H)+ |
| M.10 | 2-(4-(4-chloro-2-methylphenyl)-1-methyl-3-(pyridin-2-yl)-4,6,7,8-tetrahydro-1H-pyrazolo[3,4-e][1,4]thiazepin-6-yl)ethanol (prepared using C from Example #2 step B with 4-chloro-2-methyl- N benzaldehyde and mercaptosuccinic acid (Apollo Scientific) followed by D with borane-THF complex) [Table 3, Method 7 followed by 8, R$_t$ = 30.61 min, or = positive] | | 1.35 (f) | 415 (M + H)+ |
| M.11 | 2-(4-(4-chloro-2-methylphenyl)-1-methyl-3-(pyridin-2-yl)-4,6,7,8-tetrahydro-1H-pyrazolo[3,4-e][1,4]thiazepin-6-yl)ethanol (prepared using C from Example #2 step B with 4-chloro-2-methyl-benzaldehyde and mercaptosuccinic acid (Apollo Scientific) followed by D with borane-THF complex) [Table 3, Method 7 followed by 8, R$_t$ = 39.76 min, or = positive] | | 1.38 (f) | 415 (M + H)+ |

TABLE 12-continued

Compounds prepared using general procedure M

| Ex. # | Compound | Product structure | R, min (Table 1, Method) | m/z ESI+ |
|---|---|---|---|---|
| M.12 | 2-(4-(4-chloro-2-methylphenyl)-1-methyl-3-(pyridin-2-yl)-4,6,7,8-tetrahydro-1H-pyrazolo[3,4-e][1,4]thiazepin-6-yl)ethanol (prepared using C from Example #2 step B with 4-chloro-2-methyl-benzaldehyde and mercaptosuccinic acid (Apollo Scientific) followed by D with borane-THF complex) [Table 3, Method 7, $R_t$ = 16.52 min, or = negative] | | 1.35 (f) | 415 (M + H)+ |
| M.13 | 2-(4-(4-chloro-2-methylphenyl)-1-methyl-3-(pyridin-2-yl)-4,6,7,8-tetrahydro-1H-pyrazolo[3,4-e][1,4]thiazepin-6-yl)ethanol (prepared using C from Example #2 step B with 4-chloro-2-methyl-benzaldehyde and mercaptosuccinic acid (Apollo Scientific) followed by D with borane-THF complex) [Table 3, Method 7, $R_t$ = 21.45 min, or = negative] | | 1.38 (f) | 415 (M + H)+ |
| M.14 | 2-[4-(4-chloro-2-methyl-phenyl)-1,3-dimethyl-4,6,7,8-tetrahydro-1H-pyrazolo[3,4-e][1,4]thiazepin-6-yl]-ethanol (prepared using C from 5-amino-1,3-dimethyl-pyrazole with 4-chloro-2-methyl-benzaldehyde and mercaptosuccinic acid (Apollo Scientific) followed by D with borane-THF complex) [Table 3, Method 9, $R_t$ = 29.35 min, or = negative] | | 1.19 (f) | 352 (M + H)+ |
| M.15 | 2-[4-(4-chloro-2-methyl-phenyl)-1,3-dimethyl-4,6,7,8-tetrahydro-1H-pyrazolo[3,4-e][1,4]thiazepin-6-yl]-ethanol (prepared using C from 5-amino-1,3-dimethyl-pyrazole with 4-chloro-2-methyl-benzaldehyde and mercaptosuccinic acid (Apollo Scientific) followed by D with borane-THF complex) [Table 3, Method 9, $R_t$ = 21.9 min, or = negative] | | 1.18 (f) | 352 (M + H)+ |

TABLE 12-continued

Compounds prepared using general procedure M

| Ex. # | Compound | Product structure | R$_t$ min (Table 1, Method) | m/z ESI+ |
|---|---|---|---|---|
| M.16 | 2-[4-(4-chloro-2-methyl-phenyl)-1,3-dimethyl-4,6,7,8-tetrahydro-1H-pyrazolo[3,4-e][1,4]thiazepin-6-yl]-ethanol (prepared using C from 5-amino-1,3-dimethyl-pyrazole with 4-chloro-2-methyl-benzaldehyde and mercaptosuccinic acid (Apollo Scientific) followed by D with borane-THF complex) [Table 3, Method 9, R$_t$ = 34.24 min, or = positive] | | 1.19 (f) | 352 (M + H)+ |
| M.17 | 2-[4-(4-chloro-2-methyl-phenyl)-1,3-dimethyl-4,6,7,8-tetrahydro-1H-pyrazolo[3,4-e][1,4]thiazepin-6-yl]-ethanol (prepared using C from 5-amino-1,3-dimethyl-pyrazole with 4-chloro-2-methyl-benzaldehyde and mercaptosuccinic acid (Apollo Scientific) followed by D with borane-THF complex)[Table 3, Method 9, R$_t$ = 26.2 min, or = positive] | | 1.18 (f) | 352 (M + H)+ |
| M.18 | 3-cyano-4-(1,7-dimethyl-3-(pyridin-2-yl)-4,6,7,8-tetrahydro-1H-pyrazolo[3,4-e][1,4]thiazepin-4-yl)-N-(2-methylpyridin-3-yl)benzamide (prepared using J from Example #2, Step B with 5-bromo-2-formylbenzonitrile [Milestone]and 1-mercaptopropan-2-one [Enamine], K with Na(AcO)$_3$BH and AcOH, E, F with 2-methylpyridin-3-amine) [Table 3, Method 33, R$_t$ = 35.20 min, followed by Method 34, R$_t$ = 19.88 min, or = ND] | | 1.95 (g) | 496 (M + H)+ |
| M.19 | 3-cyano-4-(1,7-dimethyl-3-(pyridin-2-yl)-4,6,7,8-tetrahydro-1H-pyrazolo[3,4-e][1,4]thiazepin-4-yl)-N-(2-methylpyridin-3-yl)benzamide (prepared using J from Example #2, Step B with 5-bromo-2-formylbenzonitrile [Milestone]and 1-mercaptopropan-2-one [Enamine], K with Na(AcO)$_3$BH and AcOH, E, F with 2-methylpyridin-3-amine) [Table 3, Method 34, R$_t$ = 43.66 min, or = ND] | | 2.60 (g) | 496 (M + H)+ |

TABLE 12-continued

Compounds prepared using general procedure M

| Ex. # | Compound | Product structure | R$_t$ min (Table 1, Method) | m/z ESI+ |
|---|---|---|---|---|
| M.20 | 3-methyl-4-(1-methyl-3-(pyridin-2-yl)-4,6,7,8-tetrahydro-1H-pyrazolo[3,4-e][1,4]thiazepin-4-yl)benzonitrile (Example G.8) [Table 3, Method 40, R$_t$ = 33.8 min, or = positive] | | 2.30 (g) | 362 (M + H)+ |
| M.21 | 3-methyl-4-(1-methyl-3-(pyridin-2-yl)-4,6,7,8-tetrahydro-1H-pyrazolo[3,4-e][1,4]thiazepin-4-yl)benzonitrile (Example G.8) [Table 3, Method 40, R$_t$ = 26.6 min, or = negative] | | 2.30 (g) | 362 (M + H)+ |
| M.22 | 3-methyl-4-(1-ethyl-3-(pyridin-2-yl)-4,6,7,8-tetrahydro-1H-pyrazolo[3,4-e][1,4]thiazepin-4-yl)benzonitrile (Example G.10) [Table 3, Method 41, R$_t$ = 15.9 min, or = negative] | | 2.41 (g) | 376 (M + H)+ |

TABLE 12-continued

Compounds prepared using general procedure M

| Ex. # | Compound | Product structure | $R_t$ min (Table 1, Method) | m/z ESI+ |
|---|---|---|---|---|
| M.23 | 2-(4-(1,7-dimethyl-3-(pyridin-2-yl)-4,6,7,8-tetrahydro-1H-pyrazolo[3,4-e][1,4]thiazepin-4-yl)-3-methylphenoxy)acetonitrile (prepared using J with Example #2 step B with 4-hydroxy-2-methylbenzaldehyde and 1-sulfanyl-Na(AcO)₃BH and then a similar procedure described in Preparation #9 with bromoacetonitrile) [Table 3, Method 42, $R_t$ = 23.3 min, or = negative] | | 2.47 (g) | 420 (M + H)⁺ |
| M.24 | 2-(4-(1,7-dimethyl-3-(pyridin-2-yl)-4,6,7,8-tetrahydro-1H-pyrazolo[3,4-e][1,4]thiazepin-4-yl)-3-methylphenoxy)acetamide (prepared using J with Example #2 step B with 4-hydroxy-2-methylbenzaldehyde and 1-sulfanyl-propan-2-one (Enamine), K with Na(AcO)₃ BH and then a similar procedure described in Preparation #9 with bromoacetamide) [Table 3, Method 43, $R_t$ = 33.0 min, or = negative] | | 2.06 (g) | 438 (M + H)⁺ |
| M.25 | 3-(4-(1-ethyl-7-methyl-3-(pyridin-2-yl)-4,6,7,8-tetrahydro-1H-pyrazolo[3,4-e][1,4]thiazepin-4-yl)-3-methylphenyl)prop-2-yn-1-ol (prepared using B from Example#2, step A with ethyl hydrazine oxalate, J with 4-bromo-2-methylbenzaldehyde and 1-sulfanylpropan-2-one [Enamine], K with Na(AcO)₃BH and P with prop-2-yn-1-ol) [Table 3, Method 14, $R_t$ = 8.4 min, or = positive] | | 2.39 (h) | 419.1 (M + H)⁺ |

TABLE 12-continued

Compounds prepared using general procedure M

| Ex. # | Compound | Product structure | R$_t$ min (Table 1, Method) | m/z ESI+ |
|---|---|---|---|---|
| M.26 | 3-(4-(1-ethyl-7-methyl-3-(pyridin-2-yl)-4,6,7,8-tetrahydro-1H-pyrazolo[3,4-e][1,4]thiazepin-4-yl)-3-methylphenyl)prop-2-yn-1-ol (prepared using B from Example#2, step A with ethyl hydrazine oxalate, J with 4-bromo-2-methylbenzaldehyde and 1-sulfanylpropan-2-one [Enamine], K with Na(AcO)$_3$BH and P with prop-2-yn-1-ol) [Table 3, Method 14, R$_t$ = 10.3 min, or = positive] | | 2.42 (h) | 419.1 (M + H)+ |
| M.27 | 3-(4-(1-ethyl-7-methyl-3-(pyridin-2-yl)-4,6,7,8-tetrahydro-1H-pyrazolo[3,4-e][1,4]thiazepin-4-yl)-3-methylphenyl)prop-2-yn-1-ol prepared using B from Example#2, step A with ethyl hydrazine oxalate, J with 4-bromo-2-methylbenzaldehyde and 1-sulfanylpropan-2-one [Enamine], K with Na(AcO)$_3$BH and P with prop-2-yn-1-ol) [Table 3, Method 14, R$_t$ = 13 min, or = negative] | | 2.39 (h) | 419.1 (M + H)+ |
| M.28 | 3-(4-(1-ethyl-7-methyl-3-(pyridin-2-yl)-4,6,7,8-tetrahydro-1H-pyrazolo[3,4-e][1,4]thiazepin-4-yl)-3-methylphenyl)prop-2-yn-1-ol (prepared using B from Example #2, step A with ethyl hydrazine oxalate, J with 4-bromo-2-methylbenzaldehyde and 1-sulfanylpropan-2-one [Enamine], K with Na(AcO)$_3$BH and P with prop-2-yn-1-ol) [Table 3, Method 14, R$_t$ = 16 min, or = negative] | | 2.42 (h) | 419.1 (M + H)+ |

TABLE 12-continued

Compounds prepared using general procedure M

| Ex. # | Compound | Product structure | R$_t$ min (Table 1, Method) | m/z ESI+ |
|---|---|---|---|---|
| M.29 | 4-(4-(1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-ol (Preparation #P.1) [Table 3, Method 15, R$_t$ = 8.5 min, or = positive] | | 2.52 (g) | 447.1 (M + H)+ |
| M.30 | 4-(4-(1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-ol (Preparation #P.1) [Table 3, Method 15, R$_t$ = 10.4 min, or = positive] | | 2.55 (g) | 447.2 (M + H)+ |
| M.31 | 4-(4-(1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-ol (Preparation #P.1) [Table 3, Method 15, R$_t$ = 14.1 followed by Method 16, R$_t$ = 6.6 min, or = negative] | | 2.52 (g) | 447.1 (M + H)+ |

TABLE 12-continued

Compounds prepared using general procedure M

| Ex. # | Compound | Product structure | R$_t$ min (Table 1, Method) | m/z ESI+ |
|---|---|---|---|---|
| M.32 | 4-(4-(1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-ol (Preparation #P.1) [Table 3, Method 15, R$_t$ = 14.1 followed by Method 16, R$_t$ = 9.4 min, or = negative] | | 2.55 (g) | 447.1 (M + H)+ |
| M.33 | 3-(4-(1-ethyl-7-methyl-3-(pyridin-2-yl)-4,6,7,8-tetrahydro-1H-pyrazolo[3,4-e][1,4]thiazepin-4-yl)-3-methylphenyl)propan-1-ol (prepared using B from Example #2, step A with ethyl hydrazine oxalate, J with 4-bromo-2-methylbenzaldehyde and 1-sulfanylpropan-2-one [Enamine], K with Na(AcO)$_3$BH, P with prop-2-yn-1-ol and Q) [Table 3, Method 17, R$_t$ = 9.7 min, or = positive] | | 2.29 (g) | 423.1 (M + H)+ |
| M.34 | 3-(4-(1-ethyl-7-methyl-3-(pyridin-2-yl)-4,6,7,8-tetrahydro-1H-pyrazolo[3,4-e][1,4]thiazepin-4-yl)-3-methylphenyl)propan-1-ol (prepared using B from Example #2, step A with ethyl hydrazine oxalate, J with 4-bromo-2-methylbenzaldehyde and 1-sulfanylpropan-2-one [Enamine], K with Na(AcO)$_3$BH, P with prop-2-yn-1-ol and Q) [Table 3, Method 17, R$_t$ = 13.2 min, or = positive] | | 2.32 (g) | 423.1 (M + H)+ |

TABLE 12-continued

Compounds prepared using general procedure M

| Ex. # | Compound | Product structure | R$_t$ min (Table 1, Method) | m/z ESI+ |
|---|---|---|---|---|
| M.35 | 3-(4-(1-ethyl-7-methyl-3-(pyridin-2-yl)-4,6,7,8-tetrahydro-1H-pyrazolo[3,4-e][1,4]thiazepin-4-yl)-3-methylphenyl)propan-1-ol (prepared using B from Example #2, step A with ethyl hydrazine oxalate, J with 4-bromo-2-methylbenzaldehyde and 1-sulfanylpropan-2-one [Enamine], K with Na(AcO)$_3$BH, P with prop-2-yn-1-ol and Q) [Table 3, Method 17, R$_t$ = 16.7 min, or = negative] | | 2.29 (g) | 423.1 (M + H)+ |
| M.36 | 3-(4-(1-ethyl-7-methyl-3-(pyridin-2-yl)-4,6,7,8-tetrahydro-1H-pyrazolo[3,4-e][1,4]thiazepin-4-yl)-3-methylphenyl)propan-1-ol (prepared using B from Example #2, step A with ethyl hydrazine oxalate, J with 4-bromo-2-methylbenzaldehyde and 1-sulfanylpropan-2-one [Enamine], K with Na(AcO)$_3$BH, P with prop-2-yn-1-ol and Q) [Table 3, Method 17, R$_t$ = 18.1 min, or = negative] | | 2.32 (g) | 423.1 (M + H)+ |
| M.37 | 4-(4-(1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-ol (prepared using B from Example #2, step A with ethyl hydrazine oxalate, J with 4-bromo-2-methylbenzaldehyde and 1-sulfanylpropan-2-one [Enamine], K with Na(AcO)$_3$BH, P with 2-methylbut-3-yn-2-ol) and Q) [Table 3, Method 18, R$_t$ = 7.5 min, or = positive] | | 2.59 (h) | 451.2 (M + H)+ |

TABLE 12-continued

Compounds prepared using general procedure M

| Ex. # | Compound | Product structure | R$_t$ min (Table 1, Method) | m/z ESI+ |
|---|---|---|---|---|
| M.38 | 4-(4-(1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-ol (prepared using B from Example #2, step A with ethyl hydrazine oxalate, J with 4-bromo-2-methylbenzaldehyde and 1-sulfanylpropan-2-one [Enamine], K with Na(AcO)$_3$BH, P with 2-methylbut-3-yn-2-ol) and Q) [Table 3, Method 18, R$_t$ = 10.2 min, or = positive] | | 2.62 (h) | 451.3 (M + H)+ |
| M.39 | 4-(4-(1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-ol (prepared using B from Example #2, step A with ethyl hydrazine oxalate, J with 4-bromo-2-methylbenzaldehyde and 1-sulfanylpropan-2-one [Enamine], K with Na(AcO)$_3$BH, P with 2-methylbut-3-yn-2-ol) and Q) [Table 3, Method 18, R$_t$ = 12.6 min followed by Method 19, R$_t$ = 29.7min, or = negative] | | 2.62 (h) | 451.3 (M + H)+ |
| M.40 | 4-(4-(1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-ol (prepared using B from Example #2, step A with ethyl hydrazine oxalate, J with 4-bromo-2-methylbenzaldehyde and 1-sulfanylpropan-2-one [Enamine], K with Na(AcO)$_3$BH, P with 2-methylbut-3-yn-2-ol) and Q) [Table 3, Method 18, R$_t$ = 12.6 min followed by Method 19, R$_t$ = 35.8 min, or = negative] | | 2.58 (h) | 451.2 (M + H)+ |

TABLE 12-continued

Compounds prepared using general procedure M

| Ex. # | Compound | Product structure | R$_t$ min (Table 1, Method) | m/z ESI+ |
|---|---|---|---|---|
| M.41 | 4-(4-(1,7-dimethyl-3-(pyridin-2-yl)-4,6,7,8-tetrahydro-1H-pyrazolo[3,4-e][1,4]thiazepin-4-yl)-3-methylphenyl)-2-methylbutan-2-ol (Prepared using P from Example #K.1 with 2-methylbut-3-yn-2-ol and Q) [Table 3, Method 20, R$_t$ = 9.5 min, or = positive] | | 2.45 (h) | 437.1 (M + H)$^+$ |
| M.42 | 4-(4-(1,7-dimethyl-3-(pyridin-2-yl)-4,6,7,8-tetrahydro-1H-pyrazolo[3,4-e][1,4]thiazepin-4-yl)-3-methylphenyl)-2-methylbutan-2-ol (Prepared using P from Example #K.1 with 2-methylbut-3-yn-2-ol and Q) [Table 3, Method 20, R$_t$ = 12.9 min followed by Method 21, R$_t$ = 9.9 min, or = negative] | | 2.47 (h) | 437.2 (M + H)$^+$ |
| M.43 | 4-(4-(1,7-dimethyl-3-(pyridin-2-yl)-4,6,7,8-tetrahydro-1H-pyrazolo[3,4-e][1,4]thiazepin-4-yl)-3-methylphenyl)-2-methylbutan-2-ol (Prepared using P from Example #K.1 with 2-methylbut-3-yn-2-ol and Q) [Table 3, Method 20, R$_t$ = 12.9 min followed by Method 21, R$_t$ = 16.6 min, or = positive] | | 2.47 (h) | 437.1 (M + H)$^+$ |

TABLE 12-continued

Compounds prepared using general procedure M

| Ex. # | Compound | Product structure | R, min (Table 1, Method) | m/z ESI+ |
|---|---|---|---|---|
| M.44 | 4-(4-(1,7-dimethyl-3-(pyridin-2-yl)-4,6,7,8-tetrahydro-1H-pyrazolo[3,4-e][1,4]thiazepin-4-yl)-3-methylphenyl)-2-methylbutan-2-ol (Prepared using P from Example #K.1 with 2-methylbut-3-yn-2-ol and Q) [Table 3, Method 20, R, = 16.2 min, or = negative] | 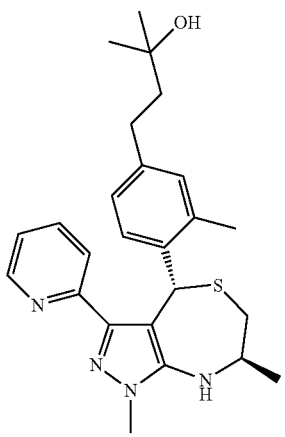 [SMILES: Cc1cc(CCC(C)(C)O)ccc1[C@@H]1SC[C@@H](C)Nc2c1c(-c1ccccn1)nn2C] | 2.44 (h) | 437.1 (M + H)+ |
| M.45 | 4-(1-ethyl-7-methyl-3-(pyridin-2-yl)-4,6,7,8-tetrahydro-1H-pyrazolo[3,4-e][1,4]thiazepin-4-yl)-3-methylbenzamide (Preparation #33) [Table 3, Method 22, R, = 17.1 min, or = positive] | 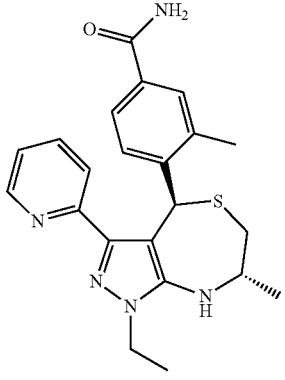 [SMILES: CCn1nc(-c2ccccn2)c2c1N[C@@H](C)CS[C@@H]2c1ccc(C(N)=O)cc1C] | 2.04 (h) | 408.1 (M + H)+ |
| M.46 | 4-(1-ethyl-7-methyl-3-(pyridin-2-yl)-4,6,7,8-tetrahydro-1H-pyrazolo[3,4-e][1,4]thiazepin-4-yl)-3-methylbenzamide (Preparation #33) [Table 3, Method 22, R, = 19.9 followed by Method 23, R, = 17.8, min, or = negative] | 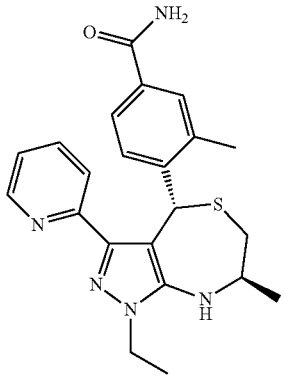 [SMILES: CCn1nc(-c2ccccn2)c2c1N[C@H](C)CS[C@H]2c1ccc(C(N)=O)cc1C] | 2.04 (h) | 408.1 (M + H)+ |

TABLE 12-continued

Compounds prepared using general procedure M

| Ex. # | Compound | Product structure | R<sub>t</sub> min (Table 1, Method) | m/z ESI+ |
|---|---|---|---|---|
| M.47 | 4-(1-ethyl-7-methyl-3-(pyridin-2-yl)-4,6,7,8-tetrahydro-1H-pyrazolo[3,4-e][1,4]thiazepin-4-yl)-3-methylbenzamide (Preparation #33) [Table 3, Method 22, $R_t$ = 19.9 followed by Method 23, $R_t$ = 20.2, min, or = positive] | | 2.07 (h) | 408.1 (M + H)+ |
| M.48 | 4-(1-ethyl-7-methyl-3-(pyridin-2-yl)-4,6,7,8-tetrahydro-1H-pyrazolo[3,4-e][1,4]thiazepin-4-yl)-3-methylbenzamide (Preparation #33) [Table 3, Method 22, $R_t$ = 22.2 min, or = negative] | | 2.06 (h) | 408.1 (M + H)+ |
| M.49 | 3-(4-(1,7-dimethyl-3-(pyridin-2-yl)-4,6,7,8-tetrahydro-1H-pyrazolo[3,4-e][1,4]thiazepin-4-yl)-3-methylphenyl)propan-1-ol (Preparation #Q.1) [Table 3, Method 24, $R_t$ = 10.5 min, or = positive] | | 2.22 (h) | 409.1 (M + H)+ |

TABLE 12-continued

Compounds prepared using general procedure M

| Ex. # | Compound | Product structure | R$_t$ min (Table 1, Method) | m/z ESI+ |
|---|---|---|---|---|
| M.50 | 3-(4-(1,7-dimethyl-3-(pyridin-2-yl)-4,6,7,8-tetrahydro-1H-pyrazolo[3,4-e][1,4]thiazepin-4-yl)-3-methylphenyl)propan-1-ol (Preparation #Q.1) [Table 3, Method 24, R$_t$ = 14 min, or = positive] | | 2.25 (h) | 409.2 (M + H)+ |
| M.51 | 3-(4-(1,7-dimethyl-3-(pyridin-2-yl)-4,6,7,8-tetrahydro-1H-pyrazolo[3,4-e][1,4]thiazepin-4-yl)-3-methylphenyl)propan-1-ol (Preparation #Q.1) [Table 3, Method 24, R$_t$ = 16 min followed by Method 25, R$_t$ = 8.4 min, or = negative] | | 2.22 (h) | 409.1 (M + H)+ |
| M.52 | 3-(4-(1,7-dimethyl-3-(pyridin-2-yl)-4,6,7,8-tetrahydro-1H-pyrazolo[3,4-e][1,4]thiazepin-4-yl)-3-methylphenyl)propan-1-ol (Preparation #Q.1) [Table 3, Method 24, R$_t$ = 16 min followed by Method 25, R$_t$ = 10 min, or = negative] | | 2.25 (h) | 409.1 (M + H)+ |

TABLE 12-continued

Compounds prepared using general procedure M

| Ex. # | Compound | Product structure | R$_t$ min (Table 1, Method) | m/z ESI+ |
|---|---|---|---|---|
| M.53 | 4-(4-(1,7-dimethyl-3-(pyridin-2-yl)-4,6,7,8-tetrahydro-1H-pyrazolo[3,4-e][1,4]thiazepin-4-yl)-3-methylphenyl)but-3-yn-1-ol (Prepared using P from Example #K.1 with but-3-yn-1-ol) [Table 3, Method 26, R$_t$ = 17.7 min followed by Method 27, R$_t$ = 6.1 min, or = positive] | | 2.24 (g) | 419.1 (M + H)$^+$ |
| M.54 | 4-(4-(1,7-dimethyl-3-(pyridin-2-yl)-4,6,7,8-tetrahydro-1H-pyrazolo[3,4-e][1,4]thiazepin-4-yl)-3-methylphenyl)but-3-yn-1-ol (Prepared using P from Example #K.1 with but-3-yn-1-ol) [Table 3, Method 26, R$_t$ = 17.7 min followed by Method 27, R$_t$ = 7.6 min, or = negative] | | 2.26 (g) | 419.1 (M + H)$^+$ |
| M.55 | 4-(4-(1,7-dimethyl-3-(pyridin-2-yl)-4,6,7,8-tetrahydro-1H-pyrazolo[3,4-e][1,4]thiazepin-4-yl)-3-methylphenyl)but-3-yn-1-ol (Prepared using P from Example #K.1 with but-3-yn-1-ol) [Table 3, Method 26, R$_t$ = 21.3 min, or = negative] | | 2.24 (g) | 419.1 (M + H)$^+$ |

TABLE 12-continued

Compounds prepared using general procedure M

| Ex. # | Compound | Product structure | R$_t$ min (Table 1, Method) | m/z ESI+ |
|---|---|---|---|---|
| M.56 | 4-(4-(1,7-dimethyl-3-(pyridin-2-yl)-4,6,7,8-tetrahydro-1H-pyrazolo[3,4-e][1,4]thiazepin-4-yl)-3-methylphenyl)but-3-yn-1-ol (Prepared using P from Example #K.1 with but-3-yn-1-ol) [Table 3, Method 26, R$_t$ = 24.4 min, R$_t$ = 7.6 min, or = positive] | | 2.26 (g) | 419.1 (M + H)$^+$ |
| M.57 | 4-(1,7-dimethyl-3-(pyrimidin-4-yl)-4,6,7,8-tetrahydro-1H-pyrazolo[3,4-e][1,4]thiazepin-4-yl)-3-methyl-N-(2-methylpyridin-3-yl)benzamide (prepared using F with Preparation #36 and 2-methyl-3-pyridinamine). [Table 3, Method 36, R$_t$ = 37.2 min, or = negative] | | 1.85 (g) | 486 (M + H)$^+$ |
| M.58 | 4-(1,7-dimethyl-3-(pyrimidin-4-yl)-4,6,7,8-tetrahydro-1H-pyrazolo[3,4-e][1,4]thiazepin-4-yl)-3-methyl-N-(2-methylpyridin-3-yl)benzamide (prepared using F with Preparation #36 and 2-methyl-3-pyridinamine). [Table 3, Method 36, R$_t$ = 41.3 min then Method 38, R$_t$ = 20.3 min, or = negative] | | 1.88 (g) | 486 (M + H)$^+$ |

TABLE 12-continued

Compounds prepared using general procedure M

| Ex. # | Compound | Product structure | R$_t$ min (Table 1, Method) | m/z ESI+ |
|---|---|---|---|---|
| M.59 | 4-(1,7-dimethyl-3-(pyrimidin-4-yl)-4,6,7,8-tetrahydro-1H-pyrazolo[3,4-e][1,4]thiazepin-4-yl)-3-methyl-N-(2-methylpyridin-3-yl)benzamide (prepared using F with Preparation #36 and 2-methyl-3-pyridinamine). [Table 3, Method 36, R$_t$ = 45.4 min then Method 38 R$_t$ = 16.1 min, or = positive] | | 1.85 (g) | 486 (M + H)+ |
| M.60 | 4-(1,7-dimethyl-3-(pyrimidin-4-yl)-4,6,7,8-tetrahydro-1H-pyrazolo[3,4-e][1,4]thiazepin-4-yl)-3-methyl-N-(2-methylpyridin-3-yl)benzamide (prepared using F with Preparation #36 and 2-methyl-3-pyridinamine). [Table 3, Method 36, R$_t$ = 48 min then Method 38 R$_t$ = 23.7 min, or = positive] | | 1.88 (g) | 486 (M + H)+ |
| M.61 | 4-(1-ethyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide (prepared using F with Preparation #34 and 2-methyl-3-pyridinamine). [Table 3, Method 37, R$_t$ = 25.8 min, or = positive] | | 1.95 (g) | 485 (M + H)+ |

TABLE 12-continued

Compounds prepared using general procedure M

| Ex. # | Compound | Product structure | R, min (Table 1, Method) | m/z ESI+ |
|---|---|---|---|---|
| M.62 | 4-(1-ethyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide (prepared using F with Preparation #34 and 2-methyl-3-pyridinamine). [Table 3, Method 37, R$_t$ = 31 min, or = negative] | | 1.95 (g) | 485 (M + H)+ |
| M.63 | 2-(4-(4-bromo-2-methylphenyl)-1,7-dimethyl-4,6,7,8-tetrahydro-1H-pyrazolo[3,4-e][1,4]thiazepin-3-yl)-1,3,4-oxadiazole (prepared using J with Preparation #38 Step C, 1-sulfanylpropan-2-one (Enamine) and 4-bromo-2-methylbenzaldehyde (Ark Pharm) followed by K with Na(OAc)3BH). [Table 3, Method 39, R$_t$ = 18.9 min] | | 2.30 (g) | 420, 422 (M + H)+ |

TABLE 12-continued

Compounds prepared using general procedure M

| Ex. # | Compound | Product structure | R, min (Table 1, Method) | m/z ESI+ |
|---|---|---|---|---|
| M.64 | 3-(4-(1-ethyl-7-methyl-3-(pyridin-2-yl)-4,6,7,8-tetrahydro-1H-pyrazolo[3,4-e][1,4]thiazepin-4-yl)-3-methylphenyl)-N,N-dimethylprop-2-yn-1-amine (prepared using B from Example#2, step A with ethyl hydrazine oxalate, J with 4-bromo-2-methylbenzaldehyde and 1-sulfanylpropan-2-one, K with Na(AcO)$_3$BH, P with N,N-dimethylprop-2-yn-1-amine) [Table 3, Method 31, R$_t$ = 14.6 min, or = positive] | | 1.93 (g) | 446 (M + H)+ |
| M.65 | 3-(4-(1-ethyl-7-methyl-3-(pyridin-2-yl)-4,6,7,8-tetrahydro-1H-pyrazolo[3,4-e][1,4]thiazepin-4-yl)-3-methylphenyl)-N,N-dimethylprop-2-yn-1-amine (prepared using B from Example#2, step A with ethyl hydrazine oxalate, J with 4-bromo-2-methylbenzaldehyde and 1-sulfanylpropan-2-one, K with Na(AcO)$_3$BH, P with 2-methylbut-3-yn-2-amine) [Table 3, Method 30, R$_t$ = 12.23 min, or = positive] | | 2.10 (g) | 446 (M + H)+ |
| M.66 | 3-(4-(1-ethyl-7-methyl-3-(pyridin-2-yl)-4,6,7,8-tetrahydro-1H-pyrazolo[3,4-e][1,4]thiazepin-4-yl)-3-methylphenyl)-N,N-dimethylprop-2-yn-1-amine (prepared using B from Example#2, step A with ethyl hydrazine oxalate, J with 4-bromo-2-methylbenzaldehyde and 1-sulfanylpropan-2-one, K with Na(AcO)$_3$BH, P with 2-methylbut-3-yn-2-amine) [Table 3, Method 30, R$_t$ = 22.82 min, or = negative] | | 2.11 (g) | 446 (M + H)+ |

TABLE 12-continued

Compounds prepared using general procedure M

| Ex. # | Compound | Product structure | R, min (Table 1, Method) | m/z ESI+ |
|---|---|---|---|---|
| M.67 | 3-(4-(1-ethyl-7-methyl-3-(pyridin-2-yl)-4,6,7,8-tetrahydro-1H-pyrazolo[3,4-e][1,4]thiazepin-4-yl)-3-methylphenyl)-N,N-dimethylprop-2-yn-1-amine (prepared using B from Example#2, step A with ethyl hydrazine oxalate, J with 4-bromo-2-methylbenzaldehyde and 1-sulfanylpropan-2-one, K with Na(AcO)₃BH, P with 2-methylbut-3-yn-2-amine) [Table 3, Method 30, R, = 17.26 min, or = positive] | | 2.10 (g) | 446 (M + H)+ |
| M.68 | 4-(1-ethyl-3-(pyridin-2-yl)-4,6,7,8-tetrahydro-1H-pyrazolo[3,4-e][1,4]thiazepin-4-yl)-N-(2-methylpyridin-3-yl)-3-(trifluoromethyl)benzamide (prepared using B from Example#2, step A with ethyl hydrazine oxalate, C with 4-bromo-2-(trifluoromethyl)benzaldehyde [Combi-Blocks]and thioglycolic acid, D, E, F with 2-methylpyridin-3-amine) [Table 3, Method 28, R, = 30.20 min, or = positive] | | 2.12 (h) | 539 (M + H)+ |
| M.69 | 3-(4-(1,7-dimethyl-3-(pyridin-2-yl)-4,6,7,8-tetrahydro-1H-pyrazolo[3,4-e][1,4]thiazepin-4-yl)-3-methylphenyl)prop-2-yn-1-ol (prepared using P from Example #K.1 with prop-2-yn-1-ol) [Table 3, Method 29, R, = 14.85 min, or = positive] | | 2.29 (h) | 405 (M + H)+ |

TABLE 12-continued

Compounds prepared using general procedure M

| Ex. # | Compound | Product structure | R$_t$ min (Table 1, Method) | m/z ESI+ |
|---|---|---|---|---|
| M.70 | 3-(4-(1,7-dimethyl-3-(pyridin-2-yl)-4,6,7,8-tetrahydro-1H-pyrazolo[3,4-e][1,4]thiazepin-4-yl)-3-methylphenyl)prop-2-yn-1-ol (prepared using P from Example #K.1 with prop-2-yn-1-ol) [Table 3, Method 29, R$_t$ = 20.58 min, or = negative] | | 2.21 (h) | 405 (M + H)+ |
| M.71 | 3-(4-(1,7-dimethyl-3-(pyridin-2-yl)-4,6,7,8-tetrahydro-1H-pyrazolo[3,4-e][1,4]thiazepin-4-yl)-3-methylphenyl)prop-2-yn-1-ol (prepared using P from Example #K.1 with prop-2-yn-1-ol) [Table 3, Method 29, R$_t$ = 24.02 min, or = negative] | | 2.22 (h) | 405 (M + H)+ |

General Procedure N: Preparation of substituted 1,4,5,6,7,8-hexahydropyrazolo[3,4-b]azepin-7(1H)-ones containing an aryl carboxylate A solution of a substituted 1,4,5,6,7,8-hexahydropyrazolo[3,4-b]azepine-7(1H)-one (1 equivalent) is dissolved in a suitable solvent such as THF or DME (preferably THF) and the reaction is cooled to −50 to −100° C. (preferably about −78° C.) under nitrogen. The reaction is treated at a rapid dropwise rate with an alkyl lithium reagent (preferably n-butyl lithium). The reaction is allowed to stir at for 5-60 min (preferably about 10 min) at about −78° C. and then the anion is quenched by addition of CO$_2$ gas until the reaction is essentially complete. Alternatively, the lactam can be deprotonated using a base such as NaH or LiHMDS (preferably NaH) prior to metal-halogen exchange with alkyl lithium reagent and quenching with CO$_2$. On completion, the reaction is quenched with an acid such as HOAc, citric acid or aqueous HCl (preferably HCl) and concentrated. The product is isolated by dilution with a small amount of water and extracted into a suitable organic solvent such as EtOAc, DCM or toluene (preferably DCM), dried, filtered and concentrated in vacuo. The product can be used crude, purified by crystallization or purified by silica gel column chromatography.

Illustration of General Procedure N

Preparation #N.1

4-(1,3-Dimethyl-1,4,5,6,7,8-hexahydropyrazolo[3,4-b]azepin-4-yl)-3-methylbenzoic acid

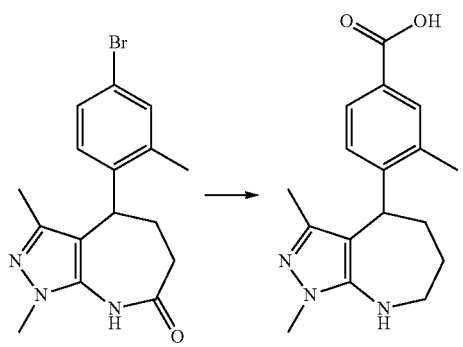 [SMILES: Cc1cc(Br)ccc1C1CCC(=O)Nc2c1c(C)nn2C ; Cc1cc(C(=O)O)ccc1C1CCCNc2c1c(C)nn2C]

A solution of 4-(4-bromo-2-methylphenyl)-1,3-dimethyl-4,5,6,8-tetrahydropyrazolo[3,4-b]azepin-7(1H)-one (0.143 g, 0.41 mmol, prepared using W from 4-bromo-2-methylbenzaldehyde (Ark Pharm, Inc), X from 1,3-dimethyl-1H-pyrazol-5-amine, Y, Z, then AA) in dry THF (20 mL) was cooled to about −78° C. under nitrogen. A solution of n-BuLi (0.66 mL, 1.64 mmol) (2.5M in THF) was added dropwise maintaining the reaction temperature below about −70° C. The mixture was stirred for about an additional 10 min at about −78° C. and then a stream of $CO_2$ generated from dry ice was bubbled through the solution for about 15 min. Cooling was removed and the reaction was allowed to warm to rt. The reaction was concentrated to solids and then acidified with 2N HCl (2 mL) and extracted with EtOAc (2×10 mL). The EtOAc extracts were dried over $Na_2SO_4$, filtered and concentrated in vacuo. The residue was purified on silica gel using a gradient of 0-10% MeOH in DCM. Product fractions were combined and concentrated in vacuo and dried on vacuum pump to yield 4-(1,3-dimethyl-1,4,5,6,7,8-hexahydropyrazolo[3,4-b]azepin-4-yl)-3-methylbenzoic acid as an off white solid (0.055 g, 0.18 mmol, 53%); LC-MS (Table 1, Method g) $R_t$=1.37 min, m/z 312 (M−H)⁻. The carboxylate was used in the next step without further manipulation.

General Procedure O: Preparation of substituted 1,4,5,6,7,8-hexahydropyrazolo[3,4-b]azepin-7(1H)-ones containing an aryl carboxamide A solution of carboxylic acid (1 equivalent) in a suitable solvent such as THF, 1,4-dioxane or toluene (preferably THF) is treated with a tertiary amine base (1-2 equivalents, preferably 1 equivalent) such as DIEA, TEA or NMM (preferably DIEA) and an activating reagent such as BTFFH or 2-chloro-4,6-dimethoxy-1,3,5-triazine (preferably BTFFH) and the reaction is stirred for 1-30 min (preferably about 5 min). The amine component (1-5 equivalents, preferably 2 equivalents) of the coupling reaction is added and the reaction is heated at 30-100° C. (preferably about 60° C.) until the reaction is essentially complete. Solvents are removed and the residue is acidified with a suitable solvent such as HOAc, citric acid or HCl (preferably citric acid) and the product extracted with a suitable solvent such as EtOAc, toluene or DCM (preferably DCM). The organic extracts are dried over $Na_2SO_4$, filtered and concentrated in vacuo. The crude product may be further purified by crystallization from a suitable solvent or by silica gel column chromatography.

Illustration of General Procedure O

Example #O.1

4-(1,3-Dimethyl-7-oxo-1,4,5,6,7,8-hexahydropyrazolo[3,4-b]azepin-4-yl)-3-methyl-N-(2-methylpyridin-3-yl)benzamide

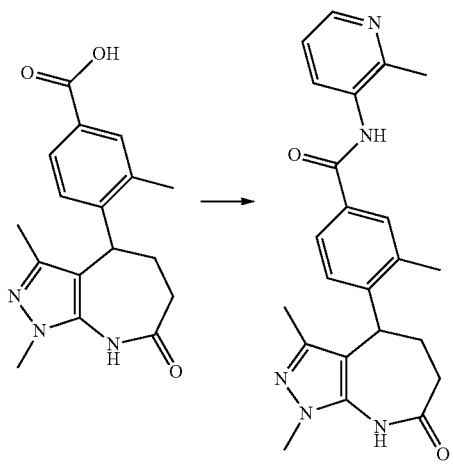 [SMILES: Cc1cc(C(=O)O)ccc1C1CCC(=O)Nc2c1c(C)nn2C ; Cc1cc(C(=O)Nc2cccnc2C)ccc1C1CCC(=O)Nc2c1c(C)nn2C]

To a solution of 4-(1,3-dimethyl-7-oxo-1,4,5,6,7,8-hexahydropyrazolo[3,4-b]azepin-4-yl)-3-methylbenzoic acid (0.047 g, 0.15 mmol, prepared using W from 4-bromo-2-methylbenzaldehyde (Ark Pharm, Inc), X from 1,3-dimethyl-1H-pyrazol-5-amine, Y, Z, AA, then N) and DIEA (0.026 mL, 0.15 mmol) in THF (1 mL) was added BTFFH (0.047 g, 0.15 mmol) and the reaction was stirred for about 5 min at rt. 2-Methylpyridin-3-amine (0.032 g, 0.30 mmol) was added and the mixture was heated to 60° C. for about 24 h. The reaction was cooled to rt and concentrated in vacuo. The residue was purified on silica gel using a gradient from 0-10% MeOH in DCM. Product fractions were combined and concentrated. The residue was triturated with EtOAc (about 2 mL) and the product was filtered off and dried under vacuum at about 50° C. to yield 4-(1,3-dimethyl-7-oxo-1,4,5,6,7,8-hexahydropyrazolo[3,4-b]azepin-4-yl)-3-methyl-N-(2-methylpyridin-3-yl)benzamide (0.021 g, 0.052 mmol, 35%) as an off-white solid; LC-MS (Table 1, Method g) $R_t$=1.44 min, m/z 404 (M+H)⁺; ¹H NMR (400 MHz, DMSO-$d_6$) δ 9.92 (s, 2H), 8.31 (d, J=3.9 Hz, 1H), 7.82-7.75 (m, 1H), 7.73-7.65 (m, 2H), 7.28-7.22 (m, 1H), 7.00-6.95 (m, 1H), 4.31 (dd, J=9.5, 6.7 Hz, 1H), 3.63 (s, 3H), 2.47-2.42 (m, 5H), 2.41 (s, 3H), 2.34-2.21 (m, 1H), 1.74-2.61 (m, 1H), 1.50 (s, 3H).

TABLE 12A

Examples made using General Procedure O

| Ex. # | Aryl carboxylate | Product structure | $R_f$ min (Table 1, Method) | m/z ESI+ |
|---|---|---|---|---|
| O.2 | 4-(1-Ethyl-7-oxo-3-(pyridin-2-yl)-1,4,5,6,7,8-hexahydropyrazolo[3,4-b]azepin-4-yl)-3-methylbenzoic acid (prepared from Ex. #AA.3 using N | 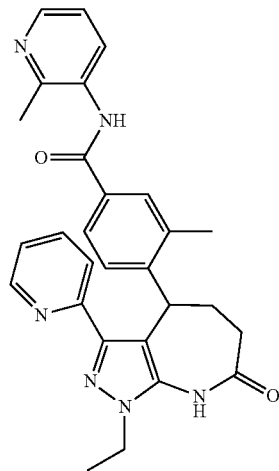 [SMILES: CCn1nc(-c2ccccn2)c2c1NC(=O)CCC2c1ccc(C(=O)Nc2cccnc2C)cc1C] | 164 (d) | 481 (M + H)+ |

General Procedure P: Sonogashira Reaction of an Aryl Halide with an Alkyne

To a microwave vial in no particular order is added a copper salt such as CuBr or CuI (preferably CuI) (0.01 to 0.05 equivalents, preferably 0.02 equivalents), a Pd catalyst such as $PdCl_2(PPh_3)_2$, $Pd(PPh_3)_4$, $Pd(dppe)Cl_2$, $Pd(dppp)Cl_2$ and $Pd(dppf)Cl_2$ (preferably $PdCl_2(PPh_3)_2$ (0.02 to 0.1 equivalents, preferably 0.2 equivalents), $PPh_3$, (0.1 to 0.5 equivalents, preferably 0.2 equivalents), a base such as TEA, DEA, $K_2CO_3$ or $Cs_2CO_3$ (preferably TEA) (5 to 25 equivalents, preferably 10 to 15 equivalents), an aryl halide (1.0 equivalent), an alkyne (1.0 to 4.0 equivalents, preferably 2.0 equivalents) and an organic solvent (such as DMF, DME, 1,4-dioxane and THF; preferably DMF). The vial is sealed and sparged with $N_2$ for about 5 to 30 min (preferably 15 min). The mixture is heated in a microwave at 100 to 175° C. (preferably 150° C.) for about 1 to 12 h (preferably 3 to 6 h). The reaction mixture can be worked up using standard aqueous washes and/or concentrated in vacuo. The crude material can be optionally purified by flash chromatography.

Illustration of General Procedure P

Preparation #P.1

4-(4-(1-Ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-ol

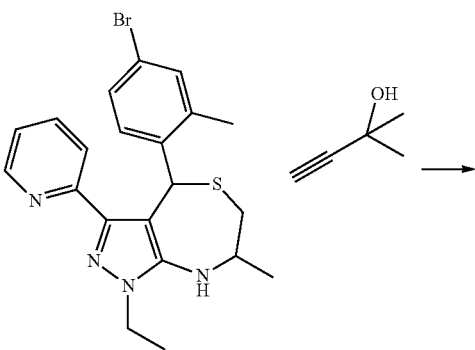

-continued

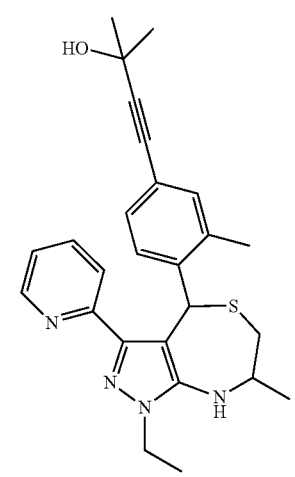

To a microwave vial was added CuI (2.7 mg, 0.014 mmol), PdCl$_2$(PPh$_3$)$_2$ (0.040 g, 0.056 mmol), PPh$_3$ (0.059 g, 0.23 mmol), 4-(4-bromo-2-methylphenyl)-1-ethyl-7-methyl-3-(pyridin-2-yl)-4,6,7,8-tetrahydro-1H-pyrazolo[3,4-e][1,4]thiazepine (0.500 g, 1.13 mmol, prepared using B from Example #2, step A with ethyl hydrazine oxalate, J with 4-bromobenzaldehyde and 1-sulfanylpropan-2-one [Enamine] and K with Na(OAc)$_3$BH) as a solution in DMF (3.76 ml), 2-methylbut-3-yn-2-ol (0.197 ml, 2.26 mmol) and TEA (2.36 ml, 16.9 mmol). The vial was sealed and the solution was sparged with N$_2$ for about 15 min. The mixture was heated in a microwave (300 W, pressure limit 250 atm) at 150° C. for 6 h. The mixture was diluted with water (25 mL) and extracted with EtOAc (2×25 mL). The organic layer was washed with water (25 mL), brine (25 mL), dried with MgSO$_4$, filtered and concentrated in vacuo. The crude material was purified by flash chromatography (silica gel; heptane/EtOAc 1:0 to 0:1) to give 4-(4-(1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-ol (0.3 g, 59% yield); LC-MS (Table 1, Method g) R$_t$=2.52 and 2.55 min.; MS m/z: 447.17 and 447.17 (M+H)$^+$.

General Procedure Q: Hydrogenation of an Alkyne to an Alkane

To a flask is added an alkyne (1.0 equivalent) and an organic solvent or mixture of solvents (such as THF, MeOH, EtOH, iPrOH, 1,4-dioxane, THF/MeOH, THF/EtOH; preferably THF/MeOH or THF/EtOH). The solution can then be treated with the H-Cube (Pd/C 10 wt %, Manual Control, 20 to 60 bar, 1 to 2 mL/min, rt) for about 1 to 96 h (preferably about 2 to 24 h) at about rt to 60° C. (preferably rt to 50° C.). The reaction mixture can be concentrated in vacuo and purified by flash chromatography.

Illustration of General Procedure Q

Preparation #Q.1

3-(4-(1,7-Dimethyl-3-(pyridin-2-yl)-4,6,7,8-tetrahydro-1H-pyrazolo[3,4-e][1,4]thiazepin-4-yl)-3-methylphenyl)propan-1-ol

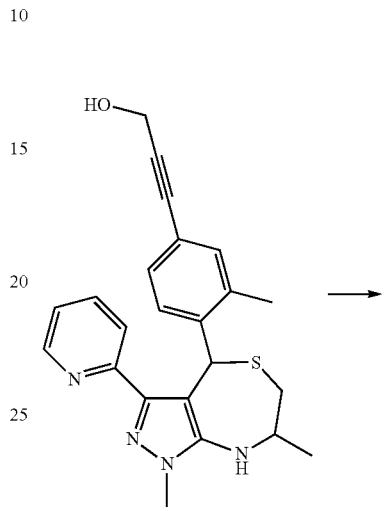

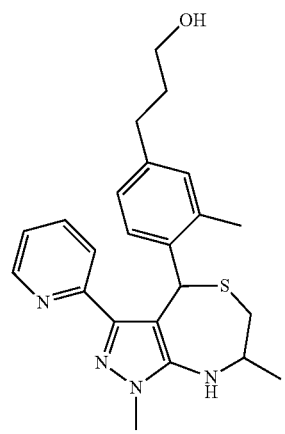

To a flask was added 3-(4-(1-ethyl-7-methyl-3-(pyridin-2-yl)-4,6,7,8-tetrahydro-1H-pyrazolo[3,4-e][1,4]thiazepin-4-yl)-3-methylphenyl)prop-2-yn-1-ol (0.126 g, 0.301 mmol, prepared from P with Example #K.1 and prop-2-yn-1-ol), MeOH (7.53 ml) and THF (7.53 ml). The solution was treated with the H-Cube (Pd/C 10 wt %, Manual Control, 20 bar, 1 mL/min, rt) for about 2 h. The mixture was concentrated in vacuo and purified by flash chromatography (25 g silica gel; DCM/MeOH 1:0 to 9:1) to give 3-(4-(1-ethyl-7-methyl-3-(pyridin-2-yl)-4,6,7,8-tetrahydro-1H-pyrazolo[3,4-e][1,4]thiazepin-4-yl)-3-methylphenyl)propan-1-ol (0.110 g, 86%); LC-MS (Table 1, Method g) R$_t$=2.29 and 2.32 min.; MS m/z: 423.14 and 423.14 (M+H)$^+$.

TABLE 13

Examples made using General Procedure Q

| Ex. # | Alkyne | Product structure | $R_t$ min (Table 1, Method) | m/z ESI+ |
|---|---|---|---|---|
| Q.1 | 3-(4-(1-Ethyl-7-methyl-3-(pyridin-2-yl)-4,6,7,8-tetrahydro-1H-pyrazolo[3,4-e][1,4]thiazepin-4-yl)-3-methylphenyl)-N,N-dimethylprop-2-yn-1-amine (prepared using B from Example # 2, step A with ethyl hydrazine oxalate, J with 4-bromo-2-methylbenzaldehyde and 2-oxopropane-1-thiolate, K with Na(OAc)$_3$BH, P with 2-methylbut-3-yn-2-amine) | 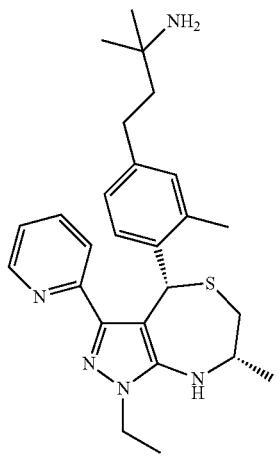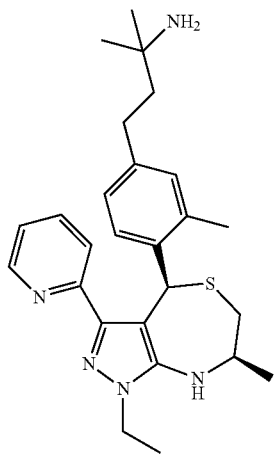 | 1.83 (g) | 450 (M + H)+ |

General Procedure R: Formation of an Amide from an Activated Acid and an Amine

To a round-bottomed flask containing an amine or an HCl salt of an amine (preferably 1 equiv) in an organic solvent (such as DCM, DMF, or 1,4-dioxane, preferably DCM or DMF) is added a base such as (DIEA, TEA or K$_2$CO$_3$, preferably DIEA, 0-10 equiv, preferably 2 equiv). The reaction mixture is optionally made homogeneous by heating or sonicating (preferably by sonicating). To the reaction mixture is added an activated acid (such as a perfluorophenyl ester derivative or an acid chloride, preferably an acid chloride). The resulting mixture is stirred for about 1-24 h (preferably about 16 h) with the optional addition of base and amine as needed.

The reaction mixture may be directly purified by chromatography. Alternatively, the solvent is concentrated under reduced pressure or a suitable organic solvent (such as EtOAc or DCM) is added and the solution is washed with water or brine. The layers are separated and the organic solution is optionally dried over Na$_2$SO$_4$ or MgSO$_4$, filtered or decanted, and concentrated to dryness under reduced pressure. The crude material is optionally purified by precipitation, crystallization, and/or trituration from an appropriate solvent or solvents and/or by chromatography to give the target compound.

Illustration of General Procedure R

Example #R.1

4-(1-ethyl-3-(pyridin-2-yl)-4,6,7,8-tetrahydro-1H-pyrazolo[3,4-e][1,4]thiazepin-4-yl)-3-methyl-N-(3-methylisoxazol-5-yl)benzamide

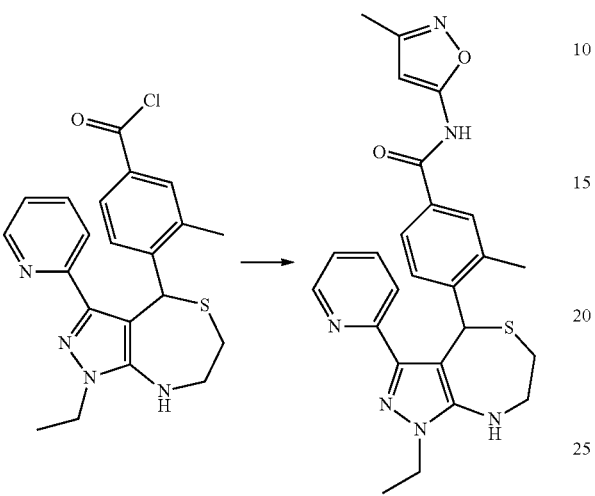

A mixture of 3-methylisoxazol-5-amine (0.2 g, 2.04 mmol, Alfa Aesar), K$_2$CO$_3$ (0.35 g, 2.55 mmol), 4-(1-ethyl-3-(pyridin-2-yl)-4,6,7,8-tetrahydro-1H-pyrazolo[3,4-e][1,4]thiazepin-4-yl)-3-methylbenzoyl chloride (0.7 g, 1.69 mmol, Preparation # T.1) was stirred at room temperature for 5 h. To the mixture was added K$_2$CO$_3$ (0.51 g, 8.49 mmol) and 3-methylisoxazol-5-amine (0.83 g, 8.49 mmol, Alfa Aesar) and the reaction was stirred overnight. The reaction was purified by RP-HPLC (Table 2, Method d) to give 4-(1-ethyl-3-(pyridin-2-yl)-4,6,7,8-tetrahydro-M-pyrazolo[3,4-e][1,4]thiazepin-4-yl)-3-methyl-N-(3-methylisoxazol-5-yl)benzamide (0.28 g, 0.59 mmol, 35%) as a white solid. LC-MS (Table 1, Method g) R$_t$=2.29 min, m/z 475 (M+H)$^+$; $^1$H NMR (DMSO-d$_6$) δ 11.67 (s, 1H), 8.50-8.46 (m, 1H), 7.86-7.81 (m, 1H), 7.80-7.76 (m, 1H), 7.74-7.60 (m, 2H), 7.31 (d, J=8.1 Hz, 1H), 7.23-7.17 (m, 1H), 6.87 (s, 1H), 6.25 (s, 1H), 5.82 (d, J=5.3 Hz, 1H), 4.24-4.01 (m, 2H), 3.77-3.63 (m, 1H), 3.04-2.94 (m, 1H), 2.77-2.61 (m, 2H), 2.58 (s, 3H), 2.18 (s, 3H), 1.32 (t, J=7.1 Hz, 3H).

General Procedure S: Formation of an Amide from an Acid and an Amine

To a solution or suspension of a carboxylic acid (1-5 equiv, preferably 1.0 equiv) and an amine (1-5 equiv, preferably 1-3 equiv) in an organic solvent (such as DCM, DCE, THF, DMF, or 1,4-dioxane, preferably DMF) is added a peptide coupling reagent (such as BOP-Cl, IBCF, HATU, TBTU, DMC, or EDC.HCl, preferably HATU, 1-10 equiv, preferably 1-10 equiv), a base (such as TEA, DIEA, or pyridine, preferably DIEA, 0-20 equiv, preferably 2-5 equiv). The reaction mixture is then stirred at ambient temperature for about 15 min to 24 h (preferably about 16 h). The reaction mixture is then purified by one of the following methods. Method 1. The solvent is concentrated under reduced pressure or a suitable organic solvent (such as EtOAc or DCM) is added and the solution is washed with water, saturated aqueous NaHCO$_3$ or brine. The layers are separated and the organic solution is optionally dried over Na$_2$SO$_4$ or MgSO$_4$, filtered or decanted, and concentrated to dryness under reduced pressure. Method 2. The reaction mixture optionally concentrated under reduced pressure is diluted with water or saturated aqueous NaHCO$_3$. The layers are separated. The aqueous layer is optionally extracted with an organic solvent such as EtOAc or DCM. The organic layer is (or combined layers are) optionally washed with water, saturated aqueous NaHCO$_3$ and/or brine, dried over MgSO$_4$ or Na$_2$SO$_4$, filtered or decanted, and concentrated under reduced pressure. Method 3. The crude reaction mixture is directly purified by chromatography. In all cases, the crude material is optionally purified by precipitation, crystallization, and/or trituration from an appropriate solvent or solvents and/or by chromatography to give the target compound.

Illustration of General Procedure S

Example #S.1

4-(1-ethyl-3-(pyridin-2-yl)-4,6,7,8-tetrahydro-1H-pyrazolo[3,4-e][1,4]thiazepin-4-yl)-3-methyl-N-(1-methyl-1H-pyrazol-5-yl)benzamide

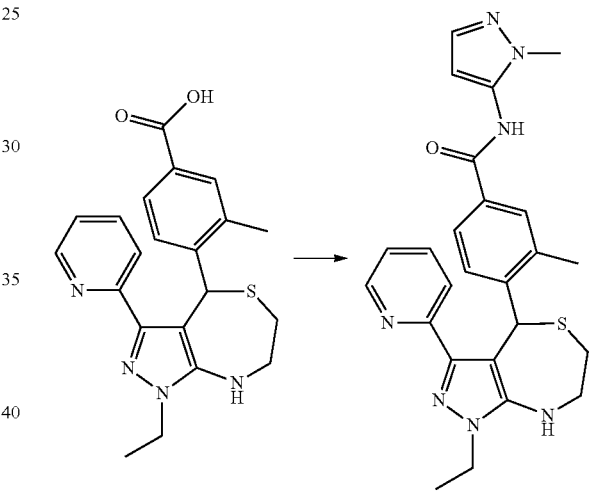

To a solution of 4-(1-ethyl-3-(pyridin-2-yl)-4,6,7,8-tetrahydro-1H-pyrazolo[3,4-e][1,4]thiazepin-4-yl)-3-methylbenzoic acid (0.60 g, 1.521 mmol, Preparation # V.1) and DIEA (0.80 mL, 4.56 mmol), in DMF was added HATU (0.64 g, 1.67 mmol). The reaction mixture was stirred for about 30 min and 1-methyl-1H-pyrazol-5-amine (0.22 g, 2.28 mmol, Aldrich) was added. The reaction mixture stirred for about 5 h and was concentrated under reduced pressure. The residue was dissolved in DCM (15 mL) and washed with saturated NaHCO$_3$ (5 mL). The organic layer was separated and dried over MgSO$_4$, filtered and concentrated under reduced pressure. The residue was purified by RP-HPLC (Table 2, Method e), to afford 4-(1-ethyl-3-(pyridin-2-yl)-4,6,7,8-tetrahydro-1H-pyrazolo[3,4-e][1,4]thiazepin-4-yl)-3-methyl-N-(1-methyl-1H-pyrazol-5-yl)benzamide (0.30 g, 0.64 mmol, 42%) as a white solid. LC-MS (Table 1, Method g) R$_t$=2.01 min, m/z 474 (M+H)$^+$; $^1$H NMR (DMSO-d$_6$) δ 10.11 (s, 1H), 8.52-8.48 (m, 1H), 7.87-7.81 (m, 1H), 7.76-7.70 (m, 2H), 7.62 (dd, J=8.1, 1.8 Hz, 1H), 7.36 (d, J=1.9 Hz, 1H), 7.33 (d, J=8.1 Hz, 1H), 7.24-7.18 (m, 1H), 6.89 (s, 1H), 6.19 (d, J=1.9 Hz, 1H), 5.83 (d, J=4.6 Hz, 1H), 4.31-4.00 (m, 2H), 3.76-3.68 (m, 1H), 3.65 (s, 3H), 3.06-2.95 (m, 1H), 2.77-2.62 (m, 2H), 2.60 (s, 3H), 1.34 (t, J=7.1 Hz, 3H).

TABLE 14
Examples prepared from 4-(1-ethyl-3-(pyridin-2-yl)-4,6,7,8-tetrahydro-1H-pyrazolo[3,4-e][1,4]thiazepin-4-yl)-3-methylbenzoic acid (Preparation #V.1) using General Procedure S
| Example # | Amine | Peptide Coupling Reagent/ Solvent | Product | R, min (method) | m/z ESI+ (M + H)+ |
|---|---|---|---|---|---|
| S.2 | 5-Amino-1,3-dimethyl-1H-pyrazole (Alfa Aesar) | HATU/DMF | 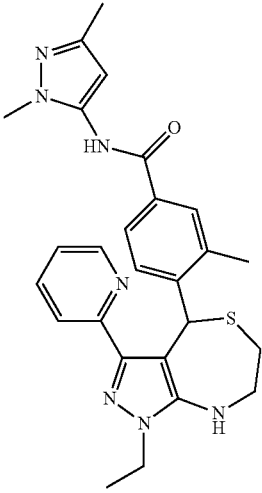 [SMILES: CCn1nc(-c2ccccn2)c2c1NCCSC2c1ccc(C(=O)Nc2cc(C)nn2C)cc1C] | 2.06 (g) | 488 |
| S.3 | 2-Amino-1,3,4-thiadiazole (Alfa Aesar) | HATU/DMF | 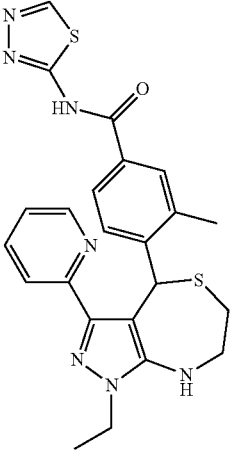 [SMILES: CCn1nc(-c2ccccn2)c2c1NCCSC2c1ccc(C(=O)Nc2nncs2)cc1C] | 2.12 (g) | 478 |
| S.4 | 2-Amino-5-methyl-1,3,4-thiadiazole | HATU/DMF | 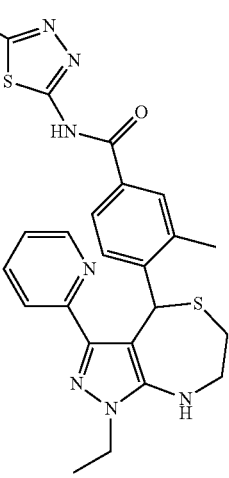 | 2.18 (g) | 492 |

TABLE 14-continued

Examples prepared from 4-(1-ethyl-3-(pyridin-2-yl)-4,6,7,8-tetrahydro-1H-pyrazolo[3,4-e][1,4]thiazepin-4-yl)-3-methylbenzoic acid (Preparation #V.1) using General Procedure S

| Example # | Amine | Peptide Coupling Reagent/ Solvent | Product | $R_t$ min (method) | m/z ESI+ (M + H)+ |
|---|---|---|---|---|---|
| S.5 | 3-Amino-1H-1,2,4-triazole (Alfa Aesar) | HATU/DMF | | 1.85 (g) | 461 |
| S.6 | 5-Aminotetrazole | TBTU/DMF | | 1.82 (g) | 462 |
| S.7 | 5-Amino-3-methyl-4-isoxazolecarbonitrile | TBTU/DMF | | 2.28 (g) | 500 |

TABLE 14-continued

Examples prepared from 4-(1-ethyl-3-(pyridin-2-yl)-4,6,7,8-tetrahydro-1H-pyrazolo[3,4-e][1,4]thiazepin-4-yl)-3-methylbenzoic acid (Preparation #V.1) using General Procedure S

| Example # | Amine | Peptide Coupling Reagent/ Solvent | Product | R, min (method) | m/z ESI+ (M + H)+ |
|---|---|---|---|---|---|
| S.8 | 3-Aminopyrazole-4-carbonitrile | TBTU/DMF | 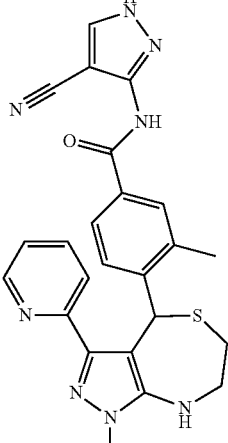 | 1.95 (g) | 485 |
| S.9 | 5-Amino-3-methyl-1H-pyrazole-4-carbonitrile | TBTU/DMF | 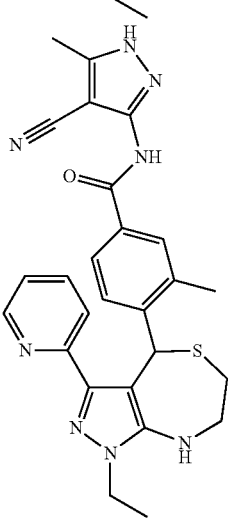 | 2.00 (g) | 499 |
| S.10 | 3-Amino-2-chloropyridine (Alfa Aesar) | DMC/DCM | 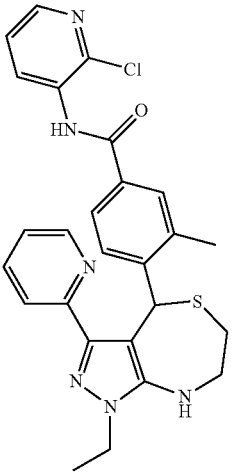 [SMILES: CCn1nc(-c2ccccn2)c2c1NCCSC2c1ccc(C(=O)Nc2cccnc2Cl)cc1C] | 2.42 (g) | 505 |

General Procedure T: Formation of an Acid Chloride

To a solution of the carboxylic acid (preferably 1 equiv.) in an organic solvent (preferably DCM) is added oxalyl chloride or thionyl chloride (preferably thionyl chloride, 1.2-5.0 equiv, preferably 2-5 equiv.) followed by DMF (0.01-0.10 equiv, preferably about 0.10 equiv.). The reaction is stirred at about 25-50° C. (preferably 50° C.) for about 3-6 h (preferably 2-3 h) before it is concentrated under reduced pressure to a constant weight to give the target compound.

Illustration of General Procedure T

Preparation #T.1

4-(1-ethyl-3-(pyridin-2-yl)-4,6,7,8-tetrahydro-1H-pyrazolo[3,4-e][1,4]thiazepin-4-yl)-3-methylbenzoyl chloride

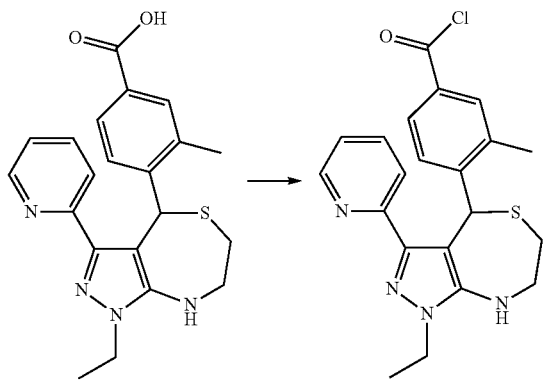 [SMILES: CCn1nc(-c2ccccn2)c2c1NCCSC2c1ccc(C(=O)O)cc1C ; CCn1nc(-c2ccccn2)c2c1NCCSC2c1ccc(C(=O)Cl)cc1C]

To a mixture of 4-(1-ethyl-3-(pyridin-2-yl)-4,6,7,8-tetrahydro-1H-pyrazolo[3,4-e][1,4]thiazepin-4-yl)-3-methylbenzoic acid (2.0 g, 5.07 mmol, Preparation #V.1) and thionyl chloride (1.8 mL, 25.3 mmol) in DCM (20 mL) was added DMF (0.04 mL, 0.51 mmol) and stirred at about 50° C. for about 2 h. The reaction was cooled to ambient temperature and the solvent was removed under reduced pressure to give 4-(1-ethyl-3-(pyridin-2-yl)-4,6,7,8-tetrahydro-1H-pyrazolo[3,4-e][1,4]thiazepin-4-yl)-3-methylbenzoyl chloride (2.1 g, 5.09 mmol, 100%) as a brown solid. LC-MS (Table 1, Method k) $R_t$=1.97 min, m/z 409 (M+H)$^+$ for MeOH quench.

General Procedure U: Suzuki Coupling of an Aryl Halide with an Aryl Boronate or Boronic Acid To a mixture of an aryl halide (1 equiv) in a solvent mixture (such as EtOH, 1,4-dioxane/water, EtOH/water or acetonitrile/water, preferably EtOH) is added a boronic acid or ester (1 to 3 equiv, preferably 1.3 to 1.6 equiv), a palladium catalyst (such as Siliacat-DPP-Pd resin, Pd(PPh$_3$)$_4$, PdCl$_2$(PPh$_3$)$_2$, Pd$_2$dba$_3$, Pd(OAc)$_2$, PdCl$_2$(dppf)-CH$_2$Cl$_2$, preferably Siliacat-DPP-Pd resin; 0.02 to 1.0 equiv, preferably 0.1 to 0.2 equiv) and a base or an aqueous solution of base (such as Na$_2$CO$_3$, Cs$_2$CO$_3$, K$_3$PO$_4$, NaOt-Bu, KOt-Bu, KOAc, preferably and aqueous solution of Cs$_2$CO$_3$; 1 to 5 equiv, preferably 2 to 3 equiv). The reaction mixture is heated to about 60 to 150° C. (preferably about 110 to 130° C.) for about 15 min to 24 h (preferably about 15 min to 1 h), or optionally heated in a microwave at about 100 to 200° C. for about 5 min to 2 h. The mixture is optionally concentrated in vacuo to give final compound. Alternatively, the reaction mixture is optionally filtered through a media (such as silica gel or Celite®) which is rinsed with an appropriate solvent (such as EtOAc, 1,4-dioxane, THF, acetonitrile, DCM, Et$_2$O, MeOH, EtOH) and then optionally concentrated to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated to give the targeted compound. Intermediates and final compounds prepared via this General Procedure can be optionally purified using one or more of the Purification Methods described above.

Illustration of General Procedure U

Preparation #U.1

4-(2-Chloro-4-(5-(methylsulfonyl)pyridin-3-yl)phenyl)-1-methyl-3-(pyridin-2-yl)-4,6,7,8-tetrahydro-1H-pyrazolo[3,4-e][1,4]thiazepine tris(trifluoroacetate)

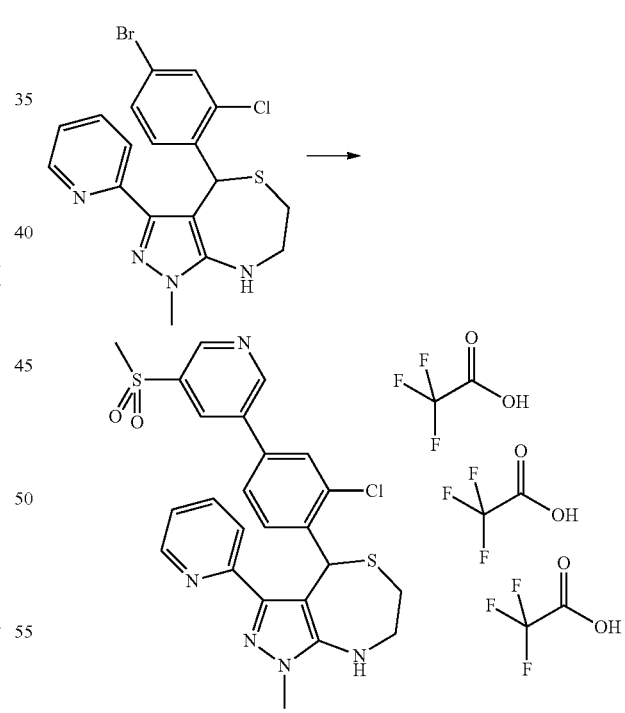

A vial with stir bar was charged with a solution of 4-(4-bromo-2-chlorophenyl)-1-methyl-3-(pyridin-2-yl)-4,6,7,8-tetrahydro-1H-pyrazolo[3,4-e][1,4]thiazepine (0.038 g, 0.087 mmol, Example #3, step D) in EtOH (1 mL), a solution of (5-(methylsulfonyl)pyridin-3-yl)boronic acid (0.026 g, 0.130 mmol) in EtOH (0.43 mL), Siliacat-DPP-Pd resin (0.06 g, 0.25 mmol/g loading), and 1M aqueous solution of Cs$_2$CO$_3$ (0.191 mmol, 0.19 mL). The vial was capped then heated for about 25 min at about 120° C. The mixture was filtered and concentrated to dryness. The mixture was re-dissolved in DMSO/MeOH (1:1 v/v, 1.4 mL) then purified by reverse phase HPLC to give 4-(2-chloro-4-(5-(methylsulfonyl)pyridin-3-yl)phenyl)-1-methyl-3-(pyridin-2-yl)-4,6,7,8-tetrahydro-1H-pyrazolo[3,4-e][1,4]thiazepine tris(trifluoroacetate) (0.019 g, 26%): LC-MS (Table 1, Method j) R$_t$=0.64 min, m/z 512 (M+H)$^+$; $^1$H NMR (500 MHz, DMSO-d$_6$/D$_2$O) δ ppm 2.63-2.70 (m, 1H), 2.80 (dd, J=14.8, 5.1 Hz, 1H), 3.03-3.09 (m, 1H), 3.37 (s, 3H), 3.73 (d, J=5.2 Hz, 2H), 3.77 (s, 3H), 6.98 (s, 1H), 7.27-7.31 (m, 1H), 7.49 (d, J=8.1 Hz, 1H), 7.67 (dd, J=8.1, 1.9 Hz, 1H), 7.77 (d, J=7.9 Hz, 1H), 7.79-7.84 (m, 1H), 7.94 (d, J=1.9 Hz, 1H), 8.51-8.54 (m, 2H), 9.03 (d, J=2.1 Hz, 1H), 9.19 (d, J=2.1 Hz, 1H).

TABLE 15

Examples prepared from 4-(4-bromo-2-chlorophenyl)-1-methyl-3-(pyridin-2-yl)-4,6,7,8-tetrahydro-1H-pyrazolo[3,4-e][1,4]thiazepine (Example # 3, step D) using General Procedure U

| Ex. # | Boronate or boronic acid | Product structure | Rt min (Table 1, Method) | m/z ESI+ |
|---|---|---|---|---|
| U.2 | 5-(4,4,5,5-tetramethyl-1,3,2-dioxaborolan-2-yl)pyrimidine | | 0.62 (j) | 435 (M + H)$^+$ |
| U.3 | 4-(4,4,5,5-tetramethyl-1,3,2-dioxaborolan-2-yl)pyridazine | | 0.59 (j) | 435 (M + H)$^+$ |
| U.4 | 5-(4,4,5,5-tetramethyl-1,3,2-dioxaborolan-2-yl)nicotinonitrile | | 0.68 (j) | 459 (M + H)$^+$ |

TABLE 15-continued

Examples prepared from 4-(4-bromo-2-chlorophenyl)-1-methyl-3-(pyridin-2-yl)-4,6,7,8-tetrahydro-1H-pyrazolo[3,4-e][1,4]thiazepine (Example # 3, step D) using General Procedure U

| Ex. # | Boronate or boronic acid | Product structure | Rt min (Table 1, Method) | m/z ESI+ |
|---|---|---|---|---|
| U.5 | 4-(2-(4-(4,4,5,5-tetramethyl-1,3,2-dioxaborolan-2-yl)-1H-pyrazol-1-yl)ethyl)morpholine | | 0.55 (j) | 536 (M + H)+ |
| U.6 | 4-(5,5-dimethyl-1,3,2-dioxaborinan-2-yl)-1-(tetrahydro-2H-pyran-2-yl)-1H-pyrazole | | 0.70 (j) | 507 (M + H)+ |
| U.7 | 5-(4,4,5,5-tetramethyl-1,3,2-dioxaborolan-2-yl)nicotinamide | | 0.56 (j) | 477 (M + H)+ |

TABLE 15-continued

Examples prepared from 4-(4-bromo-2-chlorophenyl)-1-methyl-3-(pyridin-2-yl)-
4,6,7,8-tetrahydro-1H-pyrazolo[3,4-e][1,4]thiazepine (Example # 3, step D) using General
Procedure U

| Ex. # | Boronate or boronic acid | Product structure | Rt min (Table 1, Method) | m/z ESI+ |
|---|---|---|---|---|
| U.8 | N-methyl-5-(4,4,5,5-tetramethyl-1,3,2-dioxaborolan-2-yl)nicotinamide | | 0.58 (j) | 491 (M + H)+ |
| U.9 | 4-(4,4,5,5-tetramethyl-1,3,2-dioxaborolan-2-yl)nicotinonitrile | | 0.67 (j) | 459 (M + H)+ |
| U.10 | 3-(5,5-dimethyl-1,3,2-dioxaborinan-2-yl)isonicotinonitrile | | 0.67 (j) | 459 (M + H)+ |

TABLE 15-continued

Examples prepared from 4-(4-bromo-2-chlorophenyl)-1-methyl-3-(pyridin-2-yl)-4,6,7,8-tetrahydro-1H-pyrazolo[3,4-e][1,4]thiazepine (Example # 3, step D) using General Procedure U

| Ex. # | Boronate or boronic acid | Product structure | Rt min (Table 1, Method) | m/z ESI+ |
|---|---|---|---|---|
| U.11 | 7-(4,4,5,5-tetramethyl-1,3,2-dioxaborolan-2-yl)pyrido[2,3-b]pyrazine | 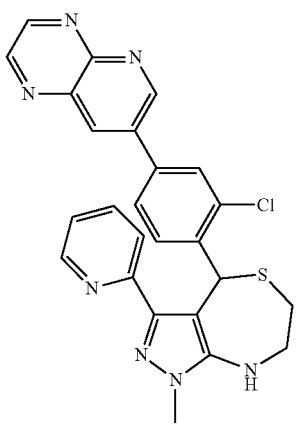 | 0.63 (j) | 486 (M + H)+ |
| U.12 | morpholino(5-(4,4,5,5-tetramethyl-1,3,2-dioxaborolan-2-yl)pyridin-3-yl)methanone | 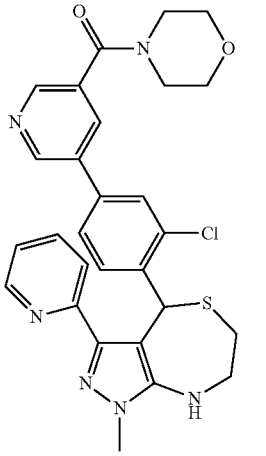 | 0.61 (j) | 547 (M + H)+ |
| U.13 | (6-(methylsulfonyl)pyridin-3-yl)boronic acid | 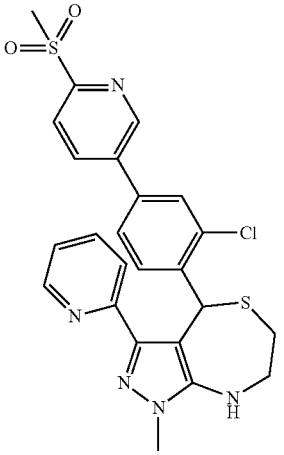 | 0.65 (j) | 512 (M + H)+ |

TABLE 15-continued

Examples prepared from 4-(4-bromo-2-chlorophenyl)-1-methyl-3-(pyridin-2-yl)-
4,6,7,8-tetrahydro-1H-pyrazolo[3,4-e][1,4]thiazepine (Example # 3, step D) using General Procedure U

| Ex. # | Boronate or boronic acid | Product structure | Rt min (Table 1, Method) | m/z ESI+ |
|---|---|---|---|---|
| U.14 | 1-(4-(5-(4,4,5,5-tetramethyl-1,3,2-dioxaborolan-2-yl)pyridin-2-yl)piperazin-1-yl)ethanone | 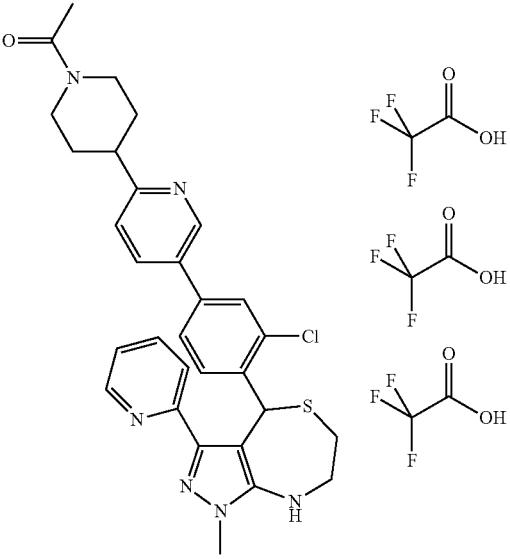 | 0.56 (j) | 560 (M + H)+ |
| U.15 | 1-(2-methoxyethyl)-4-(4,4,5,5-tetramethyl-1,3,2-dioxaborolan-2-yl)-1H-pyrazole | 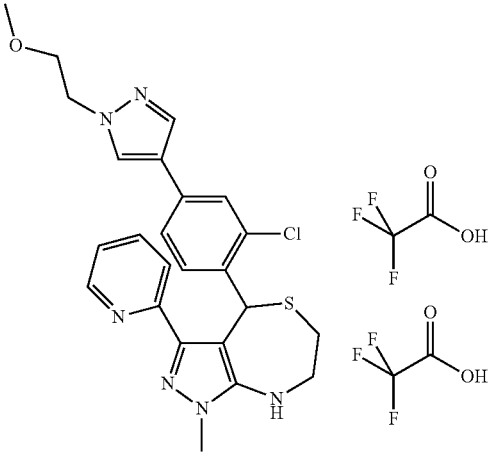 | 0.65 (j) | 481 (M + H)+ |
| U.16 | 3-(4-(4,4,5,5-tetramethyl-1,3,2-dioxaborolan-2-yl)-1H-pyrazol-1-yl)propanenitrile | 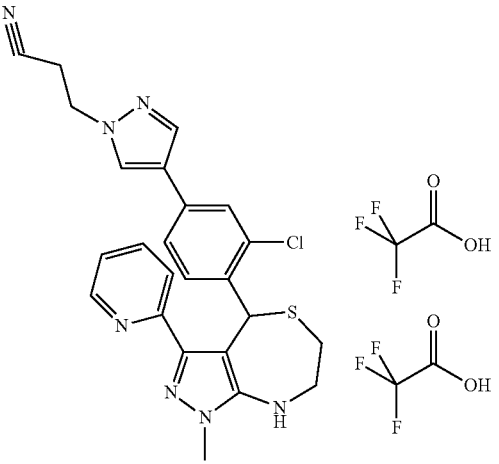 | 0.63 (j) | 476 (M + H)+ |

TABLE 15-continued

Examples prepared from 4-(4-bromo-2-chlorophenyl)-1-methyl-3-(pyridin-2-yl)-
4,6,7,8-tetrahydro-1H-pyrazolo[3,4-e][1,4]thiazepine (Example # 3, step D) using General
Procedure U

| Ex. # | Boronate or boronic acid | Product structure | Rt min (Table 1, Method) | m/z ESI+ |
|---|---|---|---|---|
| U.17 | 2-(4-(4,4,5,5-tetramethyl-1,3,2-dioxaborolan-2-yl)-1H-pyrazol-1-yl)acetamide | | 0.56 (j) | 480 (M + H)+ |
| U.18 | 3-(4-(4,4,5,5-tetramethyl-1,3,2-dioxaborolan-2-yl)-1H-pyrazol-1-yl)propanamide | | 0.57 (j) | 494 (M + H)+ |
| U.19 | 4-(5-(4,4,5,5-tetramethyl-1,3,2-dioxaborolan-2-yl)pyrimidin-2-yl)morpholine | | 0.69 (j) | 520 (M + H)+ |

General Procedure V: Hydrolysis of an Ester to a Carboxylic Acid

A mixture of an ester (preferably 1 equivalent) and an inorganic hydroxide base such as LiOH, NaOH, Ba(OH)$_2$ or NaOH (preferably NaOH; 1 to 10 equivalents, preferably 2-5 equivalents) in an organic solvent or mixture of solvents such as EtOH, 1,4-dioxane/water, THF/water or MeOH (preferably MeOH) is stirred at about 20-60° C. (preferably about 20° C.) for about 0.5 to 60 h (preferably about 2-16 h). The reaction mixture is concentrated in vacuo and the residue partitioned between water and Et$_2$O. The aqueous portion is separated, acidified by the addition of aqueous acid (preferably 1N aqueous HCl), and extracted with an organic solvent (preferably EtOAc). The combined organic portions are washed with brine, dried over an inorganic drying agent (preferably MgSO$_4$), filtered, and dried in vacuo. Alternatively, the product can be obtained by concentration of the crude reaction mixture then dissolving the crude product in water and collecting by vacuum filtration after neutralization or acidification the aqueous solution with a mineral acid such as HCl or H2SO4, preferably HCl. The product can then be further purified by trituration, crystallization or chromatography.

Illustration of General Procedure V

Preparation #V.1

4-(1-ethyl-3-(pyridin-2-yl)-4,6,7,8-tetrahydro-1H-pyrazolo[3,4-e][1,4]thiazepin-4-yl)-3-methylbenzoic acid

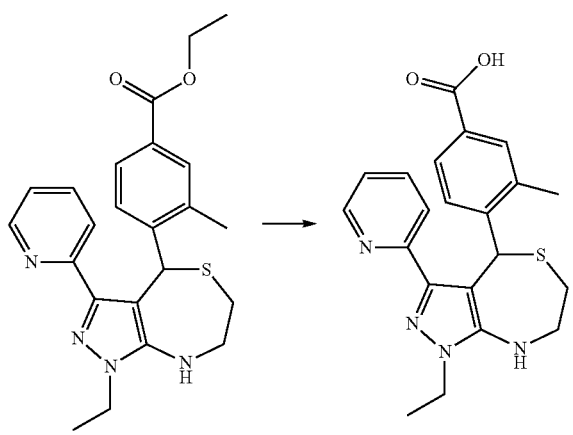 [SMILES: CCOC(=O)c1ccc(C2SCCNc3c2c(-c2ccccn2)nn3CC)c(C)c1 ; CCn1nc(-c2ccccn2)c2c1NCCSC2c1ccc(C(=O)O)cc1C]

A mixture of ethyl 4-(1-ethyl-3-(pyridin-2-yl)-4,6,7,8-tetrahydro-1H-pyrazolo[3,4-e][1,4]thiazepin-4-yl)-3-methylbenzoate (5.0 g, 11.8 mmol, prepared using B from Example #2, Step A with ethyl hydrazine oxalate, C with 4-bromo-2-methylbenzaldehyde (Asta Tech) and 2-mercaptoacetic, D with borane-THF complex, E with PdCl$_2$(dppf), TEA, DMF and EtOH), NaOH (0.95 g, 23.6 mmol), THF (30 mL), MeOH (30 mL) and water (15 mL) was stirred at rt for about 3 h. The organic volatiles were removed under reduced pressure. The aqueous layer was adjusted to about pH 6 by the addition of 1N aqueous HCl. The precipitate was collected by filtration and dried under reduced pressure to afford 4-(1-ethyl-3-(pyridin-2-yl)-4,6,7,8-tetrahydro-1H-pyrazolo[3,4-e][1,4]thiazepin-4-yl)-3-methylbenzoic acid (4.5 g, 11.4 mmol, 96%) as a white solid. LC-MS (Table 1, Method 1) R$_t$=1.15 min, m/z 395 (M+H)$^+$.

General Procedure W: Preparation of 5-(substituted-benzylidene)-2,2-dimethyl-1,3-dioxane-4,6-diones The title compounds are prepared in a manner similar to that described in Franca Bigi, et. al., Tet. Lett., (2001), 42, 5203-5205. To a solution/suspension of a substituted benzaldehyde (1 equivalent) in water with an optional co-solvent such as THF, 1,4-dioxane, DMF or DME (preferably 1,4-dioxane) is added 2,2-dimethyl-1,3-dioxane-4,6-dione (1-2 equivalents, preferably 1.5 equivalents). The mixture is stirred and heated at about 30-100° C. (preferably about 75° C.) for about 1-2 h. Additional portions of 2,2-dimethyl-1,3-dioxane-4,6-dione may be added to consume remaining aldehyde. When the aldehyde is essentially consumed, the reaction is cooled to rt and the product is filtered off, rinsed with water and dried in vacuo. In the event that product does not precipitate from the reaction mixture, solvents may be removed in vacuo and the residue purified by silica gel column chromatography.

Illustration of General Procedure W

Preparation #W.1

5-(4-bromo-2-methylbenzylidene)-2,2-dimethyl-1,3-dioxane-4,6-dione

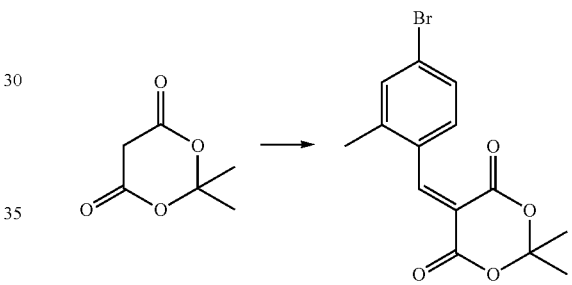

A mixture of 4-bromo-2-methylbenzaldehyde (1.99 g, 10.00 mmol) and 2,2-dimethyl-1,3-dioxane-4,6-dione (2.16 g, 15.0 mmol) in water (20 mL) and 1-4-dioxane (2 mL) was heated at about 75° C. for about 2 h. Additional 2,2-dimethyl-1,3-dioxane-4,6-dione (0.72 g, 5.0 mmol) was added and heating at about 75° C. was continued for about 2 h. The reaction was cooled to rt and solids were filtered off and rinsed with water (25 mL). The resulting solid was air dried on the funnel and then triturated with Et$_2$O (about 20 mL) and filtered. The product was dried overnight in the vacuum oven at about 50° C. to yield 5-(4-bromo-2-methylbenzylidene)-2,2-dimethyl-1,3-dioxane-4,6-dione (2.75 g, 8.46 mmol, 85%) as a pale yellow solid: LC-MS (Table 1, Method g) R$_t$=2.43 min, m/z 341/343 (M−H+NH$_3$)$^−$; $^1$H NMR (400 MHz, DMSO-d$_6$) δ 8.49 (s, 1H), 7.58 (d, J=1.8 Hz, 1H), 7.51-7.42 (m, 2H), 2.33 (s, 3H), 1.77 (s, 6H).

General Procedure X: Preparation of substituted-4,5-dihydro-1H-pyrazolo[3,4-b]pyridin-6(7H)-ones The title compounds are prepared in a manner similar to that described in Jairo Quiroga, et. al., J. Het. Chem., vol. 35, #2, pp. 409-412. A mixture of a substituted 5-amino-pyrazole (1 equivalent) and a 5-(substituted-benzylidene)-2,2-dimethyl-1,3-dioxane-4,6-dione (1-1.5 equivalents, preferably 1 equivalent) in a suitable solvent such as DMF, 1,4-dioxane, THF, DME or NMP (preferably DMF) is heated at rt to 150° C. (preferably about 60° C.) for about 10 min to 6 h (preferably about 30 min). The reaction is cooled to rt and then diluted with 1-20 volumes of water (preferably about 4 vol-

277 umes), and the product is filtered off. Alternatively, the DMF can be removed in vacuo and the residue purified by silica gel column chromatography.

Illustration of General Procedure X

Preparation #X.1

4-(4-Bromo-2-methylphenyl)-1-ethyl-3-(pyridin-2-yl)-4,5-dihydro-1H-pyrazolo[3,4-b]pyridin-6(7H)-one

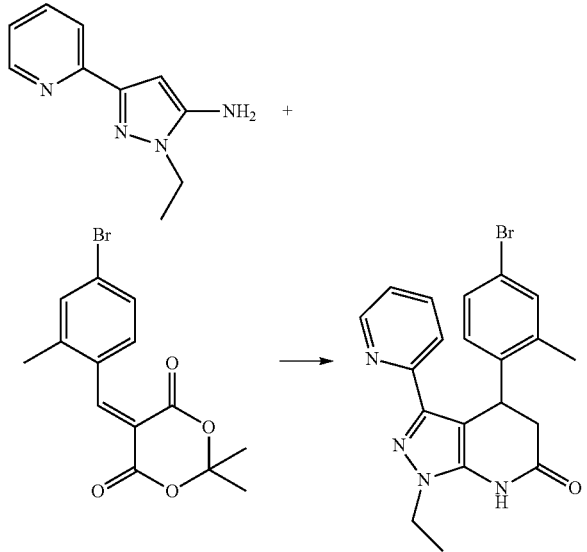

A mixture of 5-(4-bromobenzylidene)-2,2-dimethyl-1,3-dioxane-4,6-dione (1.1 g, 3.54 mmol, Preparation W.1) and 1-ethyl-3-(pyridin-2-yl)-1H-pyrazol-5-amine (0.67 g, 3.54 mmol, prepared using B from Example #2, step A with ethyl hydrazine oxalate) in DMF (5 mL) was heated under nitrogen at about 60° C. for about 30 min. The reaction was cooled to rt, diluted with water (20 mL) and then the product was filtered off and rinsed with water (~20 mL). The product was dried under vacuum at about 50° C. for about 16 h to yield 4-(4-bromo-2-methylphenyl)-1-ethyl-3-(pyridin-2-yl)-4,5-dihydro-1H-pyrazolo[3,4-b]pyridin-6(7H)-one as a tan solid (1.41 g, 3.54 mmol, 80%). LC-MS (Table 1, Method g) $R_t$=2.11 min, m/z 397/399 (M+H)$^+$; $^1$H NMR (400 MHz, DMSO-$d_6$) δ 10.88 (s, 1H), 8.44-8.41 (m, 1H), 7.84 (dt, J=8.0, 1.1 Hz, 1H), 7.77-7.69 (m, 1H), 7.43-7.36 (m, 2H), 7.21-7.17 (m, 1H), 7.10-7.04 (m, 2H), 6.63 (d, J=6.6 Hz, 1H), 4.22-4.03 (m, 2H), 3.14 (dd, J=16.0, 7.8 Hz, 1H), 2.53 (d, J=26.1 Hz, 1H), 1.33 (t, J=7.2 Hz, 3H).

General Procedure Y: Ring opening of substituted-4,5-dihydro-1H-pyrazolo[3,4-b]pyridin-6(7H)-ones A solution of substituted-4,5-dihydro-1H-pyrazolo[3,4-b]pyridin-6(7H)-one (1 equivalent) in a suitable organic solvent such as THF, DME, DMF, or 1,4-dioxane (preferably 1,4-dioxane) is treated with Boc-anhydride (1-2 equivalents, preferably 1.2 equivalents) and DMAP (0.01-1 equivalents, preferably 0.1 equivalents) in a suitable solvent such as THF, DMF, 1,4-dioxane or DCM (preferably DCM) and the reaction is stirred for 1-18 h at 0-50° C. (preferably about rt). The intermediate can be concentrated in vacuo and taken into the hydrolysis crude, or optionally purified by silica gel column chromatography before the hydrolysis. The intermediate is dissolved in a suitable solvent such as THF, 1,4-dioxane,

278

DME or ethanol (preferably THF), treated with aqueous solutions of LiOH, NaOH or KOH (preferably NaOH) and heated at 30-100° C. (preferably about 75° C.) for 1-24 h (preferably 3 h). The solution is concentrated in vacuo. The residue is dissolved in water and washed with a suitable organic solvent such as toluene, DCM, EtOAc or Et$_2$O (preferably Et$_2$O). The aqueous layer is acidified with an acid such as HOAc or citric acid (preferably citric acid) and the product is extracted into a suitable organic acid such as DCM, toluene, EtOAc or Et$_2$O (preferably EtOAc). The organic layer is dried over Na$_2$SO$_4$, filtered and concentrated in vacuo. Product can be used crude, or optionally purified by silica gel column chromatography.

Illustration of General Procedure Y

Preparation #Y.1

3-(4-Bromo-2-methylphenyl)-3-(5-((tert-butoxycarbonyl)amino)-1-ethyl-3-(pyridin-2-yl)-1H-pyrazol-4-yl)propanoic acid

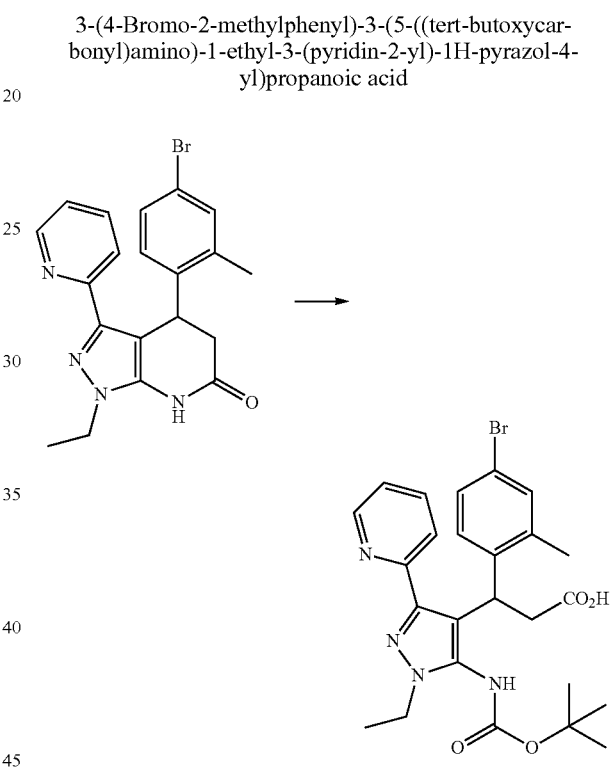

A slurry of 4-(4-bromo-2-methylphenyl)-1-ethyl-3-(pyridin-2-yl)-4,5-dihydro-1H-pyrazolo[3,4-b]pyridin-6(7H)-one (10.0 g, 24.3 mmol, Preparation X.1) and Boc-anhydride (7.1 mL, 30.4 mmol) in DCM (100 mL) was treated with DMAP (0.30 g, 2.43 mmol) and the mixture was stirred at rt for about 16 h. The reaction was concentrated in vacuo and the intermediate was purified on silica gel (220 g) using a gradient of 25-40% EtOAc in heptane. The product fractions were combined and concentrated in vacuo. The residue was taken up in THF (80 mL) and then sodium hydroxide (3.89 g, 97 mmol) and water (10 mL) were added. The reaction was heated at reflux for about 3 h. The reaction was cooled to rt and concentrated in vacuo. The residue was dissolved in water (120 mL) and washed with Et$_2$O (50 mL). The aqueous layer was acidified to pH=5 with HOAc and the product was extracted with EtOAc (2×75 mL). The combined extracts were washed with sat. aq. NH$_4$Cl solution (50 mL), dried over Na$_2$SO$_4$, filtered and concentrated in vacuo to yield 3-(4-bromo-2-methylphenyl)-3-(5-((tert-butoxycarbonyl)amino)-1-ethyl-3-(pyridin-2-yl)-1H-pyrazol-4-yl)propanoic acid as an off-white foam (12.9 g, 15.6 mmol, 64%); LC-MS (Table 1, Method g) $R_t$=2.42 min, m/z 529/531 (M+H)$^+$; $^1$H NMR (400 MHz, DMSO-$d_6$) δ 11.95 (s, 1H), 8.68-8.46 (m, 2H), 7.91-7.73 (m, 2H), 7.34-7.09 (m, 4H), 5.40-5.30 (m, 1H), 3.85 (q, J=7.2 Hz, 2H), 3.27-3.15 (m, 1H), 2.92-2.80 (m, 1H), 1.97 (s, 3H), 1.37 (s, 9H), 1.28 (t, J=6.9 Hz, 3H).

General Procedure Z: Arndt-Eistert homologation of ring opened 4,5-dihydro-1H-pyrazolo[3,4-b]pyridin-6(7H)-ones A solution of substituted Boc protected, ring opened 4,5-dihydro-1H-pyrazolo[3,4-b]pyridin-6(7H)-one (1 equivalent) in a suitable solvent such as DCM, THF, DMF or NMP (preferably DCM) is cooled to −30° C. to 10° C. (preferably about 0° C.) and treated with an activating agent such as isobutyl carbonochloridate, BTFFH or 2-chloro-4,6-dimethoxy-1,3,5-triazine (preferably 2-chloro-4,6-dimethoxy-1,3,5-triazine) and an organic base such as TEA, DIEA, or NMM (preferably NMM). The reaction is allowed to run until activation is essentially complete. Separately, diazomethane (1-20 equivalents, preferably about 10 equivalents) is generated in new glassware. An aqueous, 45% solution of KOH and Et$_2$O are cooled in an ice bath and 1-methyl-3-nitro-1-nitrosoguanidine is added in portions. The reaction is allowed to stir for 10-30 min (preferably about 20 min) and then poured into a diazomethane separatory funnel. The aqueous layer is removed and the Et$_2$O layer decanted. The Et$_2$O layer can optionally be decanted a second time to ensure removal of residual water. The salts are removed from the activated carboxylate at about 0° C. and the filtrate is added slowly to the ethereal solution of diazomethane. The reaction is allowed to warm to rt and stirred for 1-4 h (preferably about 1.5 h). Solvents and excess diazomethane are removed with a stream of nitrogen and the residue is taken up in methanol, cooled to about 0° C. with sonication and treated with silver benzoate or silver trifluoroacetate (preferably silver trifluoroacetate) in TEA for 5-60 min (preferably about 30 min). Solvents are removed in vacuo and the residue is taken up in a suitable solvent such as DCM, EtOAc or toluene (preferably EtOAc), washed with water, dried over Na$_2$SO$_4$, filtered and concentrated in vacuo. The residue is purified by silica gel column chromatography.

Illustration of General Procedure Z

Preparation #Z.1

Methyl 4-(4-bromo-2-methylphenyl)-4-(5-((tert-butoxycarbonyl)amino)-1,3-dimethyl-1H-pyrazol-4-yl)butanoate

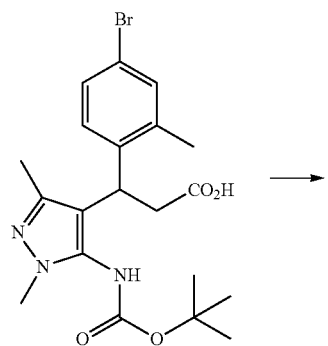

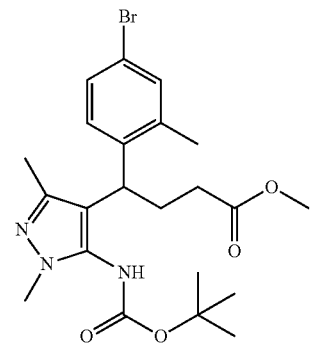

A solution of 3-(4-bromo-2-methylphenyl)-3-(5-((tert-butoxycarbonyl)amino)-1,3-dimethyl-1H-pyrazol-4-yl)propanoic acid (0.452 g, 1.0 mmol, Prepared using W from 4-bromo-2-methylbenzaldehyde (Ark Pharm, Inc), X from 1,3-dimethyl-1H-pyrazol-5-amine then Y).) and 2-chloro-4,6-dimethoxy-1,3,5-triazine (0.175 g, 1.0 mmol) in DCM (5 mL) was cooled to about 0° C. and treated with NMM (0.11 mL, 1.0 mmol) dropwise. The mixture was stirred under nitrogen at about 0° C. for about 3 h. Separately, into a new 50 mL Ehrlenmeyer flask, 1-methyl-3-nitro-1-nitrosoguanidine (2.94 g, 10 mmol) was added in portions to a stirred mixture of Et$_2$O (27 mL) and 45% aq. KOH (12 mL) cooled to about 0° C. The mixture was stirred for about an additional 20 min after the reagent was added. The mixture was poured into a diazomethane separatory funnel and the aqueous layer was removed. The Et$_2$O layer was poured into a new 50 mL Ehrlenmyer flask. The Et$_2$O layer was decanted again to remove any residual water. The solids were filtered away from the acid chloride and the acid chloride was added to the stirring diazomethane solution. The reaction was allowed to warm to rt for about 90 min and then the solvents and excess diazomethane were removed with a stream of nitrogen. The residue was dissolved in MeOH (20 mL) and cooled at about 0° C. in sonic bath. A mixture of silver benzoate (0.069 g, 0.300 mmol) in TEA (0.98 mL, 7.0 mmol) was added dropwise. Sonication was continued for about 30 min, then let stand for about 16 h. The reaction was concentrated in vacuo, diluted with sat NaHCO$_3$ solution (25 mL) and extracted with EtOAc (2×25 mL). The organic layer was washed with sat. aq. NaCl solution (25 mL), dried over Na$_2$SO$_4$, filtered and concentrated in vacuo. The residue was purified on silica gel using a gradient of 25-70% EtOAc in heptane. Product fractions were combined and concentrated to yield methyl 4-(4-Bromo-2-methylphenyl)-4-(5-((tert-butoxycarbonyl)amino)-1,3-dimethyl-1H-pyrazol-4-yl)butanoate as a tan foam (0.060 g, 0.13 mmol, 13%); LC-MS (Table 1, Method g) R$_f$=2.56 min, m/z 580/582 (M+H)$^+$; $^1$H NMR (400 MHz, DMSO-d$_6$) δ 8.70 (s, 1H), 7.35-7.13 (m, 3H), 3.84 (t, J=7.4 Hz, 1H), 3.54 (s, 3H), 3.42 (s, 3H), 2.26-2.19 (m, 2H), 2.16 (s, 3H), 2.14-2.02 (m, 2H), 1.92 (s, 3H), 1.39 (s, 9H).

General Procedure AA: Preparation of substituted 4,5,6,8-tetrahydropyrazolo[3,4-b]azepin-7(1H)-ones A solution of a substituted (5-((tert-butoxycarbonyl)amino)-1H-pyrazol-4-yl)butanoate (1 equivalent) is dissolved in a suitable solvent such as DCM and treated with an excess of TFA and the reaction is stirred at rt for 5-60 min (preferably about 20 min). The reaction is concentrated in vacuo and diluted with a suitable solvent such as toluene, xylenes or Dowtherm® (preferably toluene), treated with a 0.01-4 equivalents (preferably about 0.1 equivalents) of a strong acid such as p-toluenesulphonic acid or benzenesulphonic acid (preferably p-toluenesulphonic acid) and the reaction is heated at 50-200° C. (preferably about 110° C.) until the reaction is essentially complete. The reaction is cooled, washed with aqueous solutions, dried, filtered and concentrated. Products can be isolated by crystallization from a suitable solvent or purified by silica gel column chromatography.

Illustration of General Procedure AA

Example #AA.1

4-(4-Bromo-2-methylphenyl)-1-ethyl-3-(pyridin-2-yl)-4,5,6,8-tetrahydropyrazolo[3,4-b]azepin-7(1H)-one

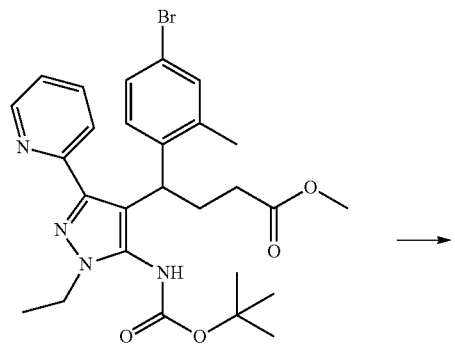

→

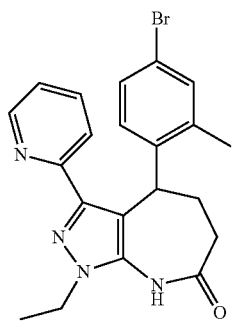

A solution of methyl 4-(4-bromo-2-methylphenyl)-4-(5-((tert-butoxycarbonyl)amino)-1-ethyl-3-(pyridin-2-yl)-1H-pyrazol-4-yl)butanoate (0.072 g, 0.129 mmol, Prepared using W from 4-bromobenzaldehyde, X from 1-ethyl-3-(pyridin-2-yl)-1H-pyrazol-5-amine, Y then Z) in DCM (3 mL) was treated with TFA (3 mL) and the reaction was stirred for about 20 min at rt. Solvents were removed in vacuo and the residue was taken up in toluene (5 mL) containing p-TSA (0.049 g, 0.26 mmol) and the reaction was heated at about 100° C. for about 3 h. The reaction was cooled to rt, diluted with EtOAc (5 mL) to solubilize the product and washed with sat. aq. $NaHCO_3$ (5 mL), then water (5 mL). The organic layer was dried over $Na_2SO_4$, filtered and concentrated in vacuo. Crude product was further purified on silica gel (4 g) using a gradient of 60-90% EtOAc in heptane. Product fractions were combined and concentrated to solids and dried in the vacuum oven overnight to yield 4-(4-bromo-2-methylphenyl)-1-ethyl-3-(pyridin-2-yl)-4,5,6,8-tetrahydropyrazolo[3,4-b]azepin-7(1H)-one as an off-white solid (0.037 g, 0.087 mmol, 67%); LC-MS (Table 1, Method g) $R_t$=2.31 min, m/z 425/427 $(M+H)^+$; $^1$H NMR (400 MHz, $CDCl_3$) δ 8.37-8.30 (m, 1H), 7.84 (br. s, 1H), 7.63 (d, J=8.1 Hz, 1H), 7.58-7.48 (m, 1H), 7.14 (s, 1H), 7.06-6.94 (m, 2H), 6.61 (d, J=8.3 Hz, 1H), 5.30-5.20 (m, 1H), 4.20 (q, J=7.3 Hz, 2H), 2.74-2.66 (m, 2H), 2.47 (s, 3H), 2.41-2.30 (m, 1H), 1.94-1.83 (m, 1H), 1.50 (t, J=7.2 Hz, 3H).

TABLE 16

Examples made using General Procedure AA

| Ex. # | Methyl 4-(5-((tert-butoxycarbonyl)amino)-1H-pyrazol-4-yl)butanoate | Product structure | $R_t$ min (Table 1, Method) | m/z ESI+ |
|---|---|---|---|---|
| AA.2 | Methyl 4-(4-bromo-2-methylphenyl)-4-(5-((tert-butoxycarbonyl)amino)-1,3-dimethyl-1H-pyrazol-4-yl)butanoate (prepared using W from 4-bromo-2-methylbenzaldehyde (Ark Pharm, Inc), X from 1,3-dimethyl-1H-pyrazol-5-amine (Aldrich), Y then Z) | | 2.01 (d) | 348/350 $(M + H)^+$ |

TABLE 16-continued

Examples made using General Procedure AA

| Ex. # | Methyl 4-(5-((tert-butoxycarbonyl)amino)-1H-pyrazol-4-yl)butanoate | Product structure | R$_t$ min (Table 1, Method) | m/z ESI+ |
|---|---|---|---|---|
| AA.3 | Methyl 4-(4-bromo-2-methylphenyl)-4-(5-((tert-butoxycarbonyl)amino)-1-ethyl-3-(pyridin-2-yl)-1H-pyrazol-4-yl)butanoate (prepared using W from 4-bromo-2-methylbenzaldehyde (Ark Pharm, Inc), X from Example # 2, step A with ethylhydrazine oxalate, Y then Z) | 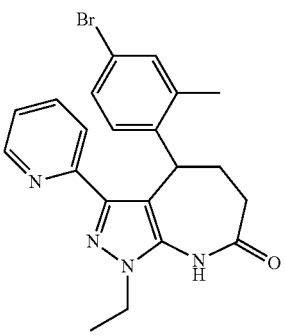 [SMILES: CCn1nc(-c2ccccn2)c2c1NC(=O)CCC2c1ccc(Br)cc1C] | 2.31 (d) | 425/427 (M + H)+ |

General Procedure BB: Preparation of substituted 1,4,5,6,7,8-hexahydropyrazolo[3,4-b]azepines To a mixture of substituted 1,4,5,6,7,8-hexahydropyrazolo[3,4-b]azepine (1 equivalent) in a suitable anhydrous solvent such as Et$_2$O or THF (preferably THF) is added a reducing agent such as lithium aluminum hydride or borane THF complex in THF (preferably borane THF complex) (2 to 12 equivalents, preferably about 8 equivalents), at a temperature between about 0° C. and rt (preferably 0° C.). The resulting mixture is stirred at a temperature between 0° C. and 70° C. (preferably rt) for 1-96 h (preferably 16 h). The mixture is treated with an acid such as aqueous HCl, neutralized with a base such as sodium NaOH, LiOH or KOH (preferably NaOH), and extracted with a suitable organic solvent such as Et$_2$O, EtOAc or DCM (preferably EtOAc). The crude product can be further purified by column chromatography.

Illustration of General Procedure BB

Example #BB.1

4-(4-Bromo-2-methylphenyl)-1-ethyl-3-(pyridin-2-yl)-1,4,5,6,7,8-hexahydropyrazolo[3,4-b]azepine

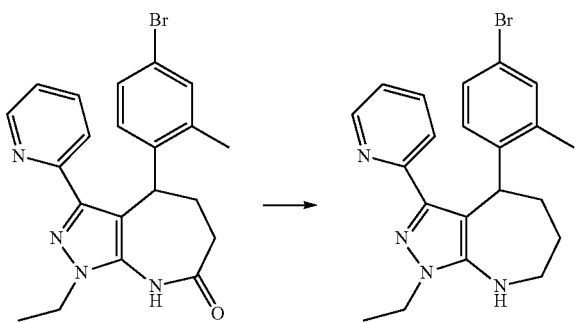 [SMILES: CCn1nc(-c2ccccn2)c2c1NC(=O)CCC2c1ccc(Br)cc1C ; CCn1nc(-c2ccccn2)c2c1NCCCC2c1ccc(Br)cc1C]

To a solution of 4-(4-bromo-2-methylphenyl)-1-ethyl-3-(pyridin-2-yl)-4,5,6,8-tetrahydropyrazolo[3,4-b]azepin-7(1H)-one (0.045 g, 0.11 mmol, Example #AA.1) in THF (2 mL) was added borane tetrahydrofuran complex (1M in THF, 0.74 mL, 0.74 mmol) and the reaction was stirred at rt for about 2 h. The reaction was cooled to 0° C. and carefully quenched with 5M HCl (1 mL) and then stirred about 30 min at rt. The organic solvents were removed in vacuo and the aqueous layer was neutralized with solid Na$_2$CO$_3$ and extracted with EtOAc (2×10 mL). The combined extracts were dried over Na$_2$SO$_4$, filtered and concentrated in vacuo. The crude product was further purified by silica gel column chromatography using a gradient of 65-85% EtOAc in heptane. Product fractions were combined and concentrated in vacuo. The residue was dissolved in ACN (2 mL) and the product was precipitated by addition of water. The product was filtered off and dried in the vacuum oven at about 50° C. to yield 4-(4-bromo-2-methylphenyl)-1-ethyl-3-(pyridin-2-yl)-1,4,5,6,7,8-hexahydropyrazolo[3,4-b]azepine as an off-white solid (0.030 g, 0.073 mmol, 69%); LC-MS (Table 1, Method g) R$_t$=2.72 min, m/z 411/413 (M+H)+; $^1$H NMR (400 MHz, DMSO-d$_6$) δ 8.44-8.39 (m, 1H), 7.77-7.72 (m, 1H), 7.68-7.61 (m, 1H), 7.24 (d, J=2.1 Hz, 1H), 7.16-7.09 (m, 2H), 6.92 (d, J=8.3 Hz, 1H), 5.70 (t, J=3.9 Hz, 1H), 5.66-5.58 (m, 1H), 4.13-3.97 (m, 2H), 3.40-3.30 (m, 1H), 2.84-2.74 (m, 1H), 2.45 (s, 3H), 1.92-1.82 (m, 1H), 1.81-1.70 (m, 1H), 1.68-1.57 (m, 1H), 1.57-1.45 (m, 1H), 1.28 (t, J=7.1 Hz, 3H).

Example #1

4-(4-chloro-2-methyl-phenyl)-3-cyclopropyl-1,6,6-trimethyl-7,8-dihydro-4H-pyrazolo[3,4-e][1,4]thiazepine, (4S)-4-(4-chloro-2-methyl-phenyl)-3-cyclopropyl-1,6,6-trimethyl-7,8-dihydro-4H-pyrazolo[3,4-e][1,4]thiazepine* and (4R)-4-(4-chloro-2-methyl-phenyl)-3-cyclopropyl-1,6,6-trimethyl-7,8-dihydro-4H-pyrazolo[3,4-e][1,4]thiazepine*

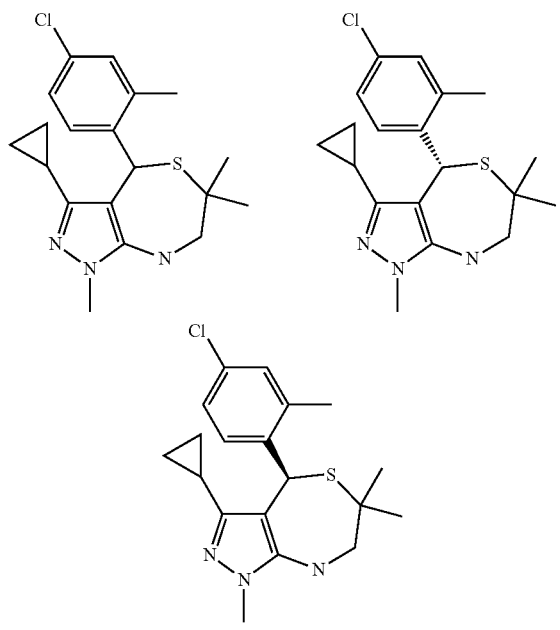

Step A: 4-(4-chloro-2-methyl-phenyl)-3-cyclopropyl-1,6,6-trimethyl-4,8-dihydropyrazolo[3,4-e][1,4]thiazepin-7-one

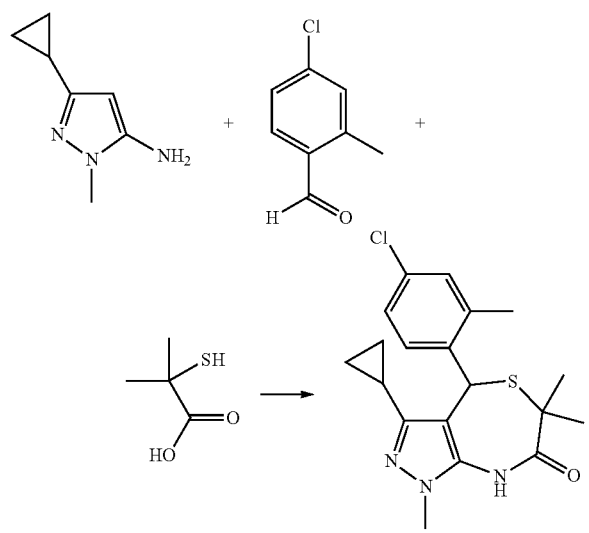

A mixture of 3-cyclopropyl-1-methyl-1H-pyrazol-5-amine (3 g, 22 mmol, Fluorochem), 4-chloro-2-methylbenzaldehyde (3.1 g, 22 mmol, Fluorochem), and 2-mercapto-2-methylpropanoic acid (3.5 g, 33 mmol, Chemwish) was heated, in a sealed microwave vessel, for about 60 min, at about 80° C. Subsequently, the reaction mixture was heated, for about 24 h, at about 150° C. After cooling to rt, acetonitrile (20 mL) was added and the reaction mixture was stirred for about 2 h, at about 40° C. After cooling to about 0° C., the precipitated solid was collected by filtration and washed with acetonitrile (2 mL) to afford 4-(4-chloro-2-methyl-phenyl)-3-cyclopropyl-1,6,6-trimethyl-4,8-dihydropyrazolo[3,4-e][1,4]thiazepin-7-one as white solid (1.25 g, 3.3 mmol, 15%). $^1$H-NMR (CDCl$_3$, Bruker 400 MHz) δ 0.30-0.39 (1H, s); 0.46-0.67 (3H, m); 0.83-0.93 (1H, m); 1.50 (3H, s); 1.66 (3H, s); 2.48 (3H, s); 3.75 (3H, s); 5.58 (1H, s); 7.09 (1H, dd, J=8.5, 2.5 Hz); 7.14 (1H, d, J=2.5 Hz); 7.21 (1H, d, J=8.5 Hz); H, m); 8.65 (1H, s).

Step B: 4-(4-chloro-2-methyl-phenyl)-3-cyclopropyl-1,6,6-trimethyl-7,8-dihydro-4H-pyrazolo[3,4-e][1,4]thiazepine

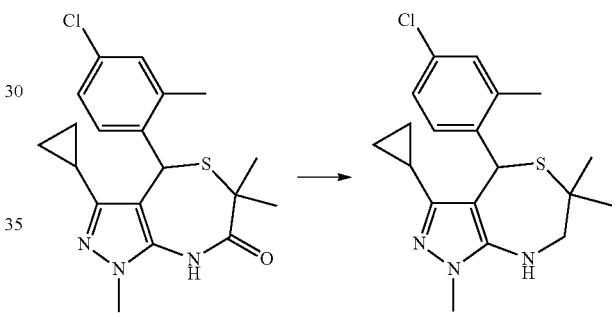

To a solution of 4-(4-chloro-2-methyl-phenyl)-3-cyclopropyl-1,6,6-trimethyl-4,8-dihydropyrazolo[3,4-e][1,4]thiazepin-7-one (1.2 g, 3.19 mmol) in THF (20 mL) was added a solution of borane tetrahydro-furan complex (14 mL, 1M in THF, 4 mmol, Acros) at about 4° C. Subsequently, the mixture was stirred for about 18 h at rt. After cooling to about 4° C., HCl (5 M aqueous, 12 mL) was added dropwise and the mixture was stirred for about 2 h at about 4° C., then NaOH (1 M aq, 60 mL) and ethyl acetate (200 mL) were added. The layers were separated and the aqueous layer was extracted with ethyl acetate (50 mL). The combined organic layers were washed with water (2×25 mL), dried (MgSO$_4$), filtered and concentrated in vacuo. The residue was purified by column chromatography (SiO$_2$, ethyl acetate/hexanes 1:1 to 100:0) to give 4-(4-chloro-2-methyl-phenyl)-3-cyclopropyl-1,6,6-trimethyl-7,8-dihydro-4H-pyrazolo[3,4-e][1,4]thiazepine as white solid (0.75 g, 2.1 mmol, 65%). LC-MS (Table 1, Method e) R$_f$=7.48 min, m/z: 362 (M+H)$^+$; $^1$H-NMR (CDCl$_3$, Bruker 400 MHz) δ 0.38-0.65 (4H, m) 0.91-0.99 (1H, m) 1.01 (3H, s) 1.35 (3H, s) 2.52 (3H, s) 3.09 (1H, dd, J=14.5, 5.5 Hz) 3.40 (1H, dd, J=14.5, 5.0 Hz) 3.62 (3H, s) 3.65 (1H br.t.) 5.17 (1H, s) 7.07 (1H, dd, J=8.5, 2.0 Hz) 7.16 (1H, d, J=2.0 Hz) 7.21 (1H, d, J=8.5 Hz).

287

Step C: (4S)-4-(4-chloro-2-methyl-phenyl)-3-cyclopropyl-1,6,6-trimethyl-7,8-dihydro-4H-pyrazolo[3,4-e][1,4]thiazepine and (4R)-4-(4-chloro-2-methyl-phenyl)-3-cyclopropyl-1,6,6-trimethyl-7,8-dihydro-4H-pyrazolo[3,4-e][1,4]thiazepine

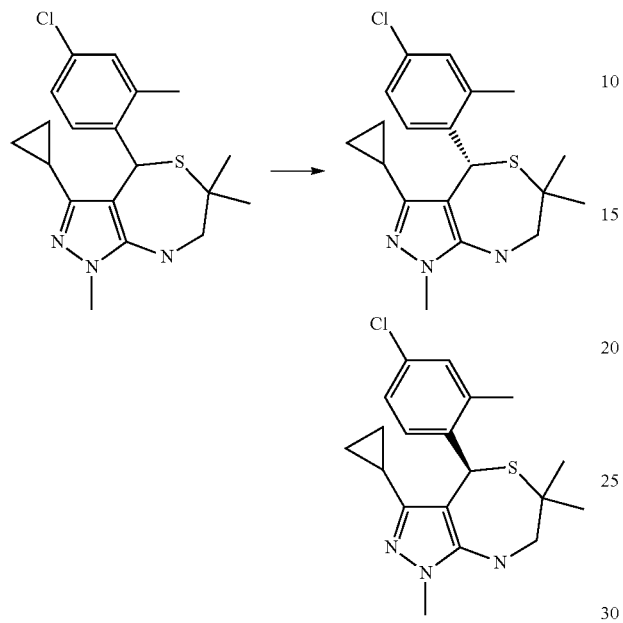

The enantiomers of 4-(4-chloro-2-methyl-phenyl)-3-cyclopropyl-1,6,6-trimethyl-7,8-dihydro-4H-pyrazolo[3,4-e][1,4]thiazepine (0.35 g, 0.966 mmol) were separated using chiral chromatography (Table 3, Method 11) to yield (4S)-4-(4-chloro-2-methyl-phenyl)-3-cyclopropyl-1,6,6-trimethyl-7,8-dihydro-4H-pyrazolo[3,4-e][1,4]thiazepine* (0.107 g, 0.296 mmol) as a white solid (Table 3, Method 11, $R_t$=5.56 min, or =negative. LC-MS (Table 1, Method b) $R_t$=2.64 min. m/z: 362 (M+H)$^+$) and (4R)-4-(4-chloro-2-methyl-phenyl)-3-cyclopropyl-1,6,6-trimethyl-7,8-dihydro-4H-pyrazolo[3,4-e][1,4]thiazepine* (0.125 g, 0.345 mmol) as a white solid (Table 3, Method 11, $R_t$=8.18 min, or =positive. LC-MS (Table 1, Method b) $R_t$=2.64 min. m/z: 362 (M+H)$^+$)

Example #2

4-(4-chloro-2-methyl-phenyl)-1-methyl-3-(2-pyridyl)-4,6,7,8-tetrahydropyrazolo[3,4-e][1,4]thiazepine, (4R)-4-(4-chloro-2-methyl-phenyl)-1-methyl-3-(2-pyridyl)-4,6,7,8-tetrahydropyrazolo[3,4-e][1,4]thiazepine and (4S)-4-(4-chloro-2-methyl-phenyl)-1-methyl-3-(2-pyridyl)-4,6,7,8-tetrahydropyrazolo[3,4-e][1,4]thiazepine

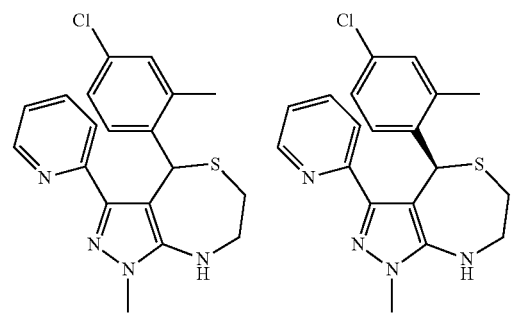

288

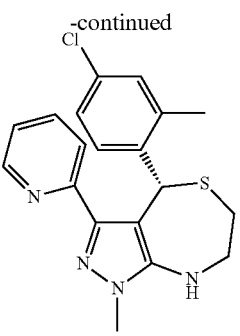

Step A: 3-oxo-3-(2-pyridyl)propanenitrile

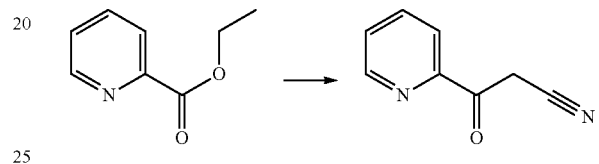

To a mixture of sodium hydride (15 g, 60% in oil, 375 mmol) and ethyl 2-picolinate (50 g, 331 mmol) in anhydrous THF (250 mL) was added dropwise a solution of anhydrous acetonitrile (20 g, 487 mmol) in anhydrous THF (200 mL), at about 65° C. After complete addition the reaction mixture was heated at about 65° C., for about 5 h. After cooling to rt, ethyl acetate (500 mL) was added, followed by 1 M aqueous HCl (360 mL). The resulting layers were separated, and the aqueous layer was extracted with ethyl acetate (250 mL). The combined organic layers were washed with water (2×100 mL), dried (MgSO$_4$), filtered, and concentrated in vacuo to give crude 3-oxo-3-(2-pyridyl)propanenitrile (48.6 g, 331 mmol, 100%), which was used as such in the next step. $^1$H-NMR (CDCl$_3$, Bruker 400 MHz) 4.39 (2H, s); 7.58 (1H, m); 7.91 (1H, dt, J=2 Hz, 10 Hz); 8.11 (1H, dt, J=2 Hz, 10 Hz); 8.70 (1H, s).

Step B: 1-Methyl-3-(2-pyridyl)pyrazol-5-amine

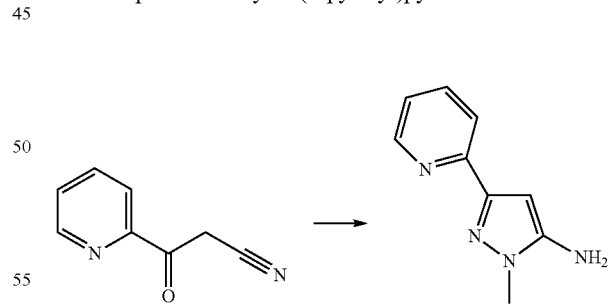

To a solution of crude 3-oxo-3-(2-pyridyl)propanenitrile (48.6 g, 331 mmol) in ethanol (500 mL) was added methyl hydrazine (25 g, 543 mmol). The resulting mixture was stirred for about 30 min at rt and then heated at about 75° C. for about 18 h. After cooling to rt the reaction mixture was concentrated in vacuo. The residue was treated with toluene (300 mL). The formed solid was collected by filtration and washed with toluene (150 mL). The solid was dried under vacuum to give 1-methyl-3-(2-pyridyl)pyrazol-5-amine (36.2 g, 208 mmol, 63%). $^1$H-NMR (CDCl$_3$, Bruker 400

MHz) δ 3.62 (3H, s); 5.34 (2H, br s); 5.90 (1H, s); 7.21 (1H, m); 7.73 (1H, dt, J=10 Hz, 2 Hz); 7.83 (1H, dt, J=10 Hz, 1 Hz); 8.51 (1H, dt, J=6 Hz, 2 Hz).

Step C: 4-(4-chloro-2-methyl-phenyl)-1-methyl-3-(2-pyridyl)-4,8-dihydropyrazolo[3,4-e][1,4]thiazepin-7-one

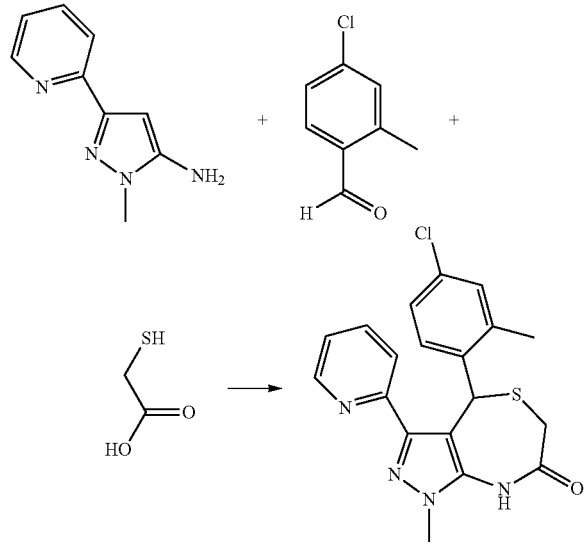

A mixture of 1-methyl-3-(2-pyridyl)pyrazol-5-amine (1.1 g, 6.3 mmol), 4-chloro-2-methylbenzaldehyde (1.0 g, 6.5 mmol, Fluorochem), and thioglycolic acid (2.4 g, 26 mmol) in acetonitrile (20 mL) was heated, in a sealed microwave vessel, for about 20 min, at about 150° C., in a microwave. After cooling to rt the precipitated solid was collected by filtration and washed with acetonitrile (2 mL) to afford 4-(4-chloro-2-methyl-phenyl)-1-methyl-3-(2-pyridyl)-4,8-dihydropyrazolo[3,4-e][1,4]thiazepin-7-one (1.16 g, 3.0 mmol, 48%), which was used as such. ¹H-NMR (CDCl₃, Bruker 400 MHz) δ 2.50 (3H, s); 3.07 (1H, d, J=12 Hz); 3.50 (1H, d, J=12 Hz); 3.84 (3H, s); 6.59 (1H, s); 6.86 (1H, d, J=8 Hz); 6.98 (1H, m); 7.1-7.2 (2H, m); 7.68 (1H, m), 7.76 (1H, d, J=6 Hz); 8.4 (1H, s), 10.2 (1H, s).

Step D: 4-(4-chloro-2-methyl-phenyl)-1-methyl-3-(2-pyridyl)-4,6,7,8-tetrahydropyrazolo[3,4-e][1,4]thiazepine

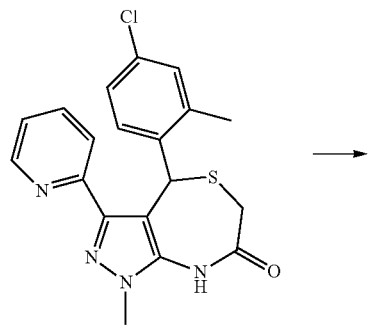

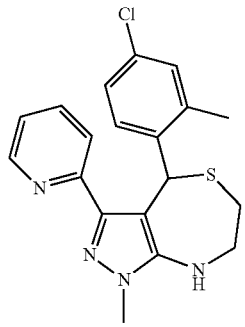

To a solution of 4-(4-chloro-2-methyl-phenyl)-1-methyl-3-(2-pyridyl)-4,8-dihydropyrazolo[3,4-e][1,4]thiazepin-7-one (0.200 g, 0.52 mmol) in THF (6 mL) was added a solution of borane THF complex (4 mL, 1M in THF, 4 mmol, Acros) at rt. Subsequently, the mixture was heated under reflux for about 3 h. After cooling to about 4° C., HCl (5 M aqueous, 6 mL) was added dropwise and the mixture was stirred for about 2 h at about 4° C., then NaOH (1 M aqueous, 50 mL) and ethyl acetate (100 mL) were added. The layers were separated and the aqueous layer was extracted with ethyl acetate (50 mL). The combined organic layers were washed with water (2×25 mL), dried (MgSO₄), filtered and concentrated in vacuo. The residue was purified by prep-HPLC (Method a, Table 2) to give 4-(4-chloro-2-methyl-phenyl)-1-methyl-3-(2-pyridyl)-4,6,7,8-tetrahydropyrazolo[3,4-e][1,4]thiazepine (0.0917 g, 0.25 mmol, 48%). LC-MS (Table 1, Method a) $R_t$=4.23 min, m/z 371 (M+H)⁺; ¹H-NMR (CDCl₃, Bruker 400 MHz) δ 2.58 (3H, s) 2.68 (1H, ddd, J=15.0, 6.1, 2.5 Hz) 2.85 (1H, ddd, J=15.0., 9.6, 2.5 Hz) 3.21-3.29 (1H, m) 3.56-3.65 (1H, m) 3.79 (1H, br s) 3.83 (3H, s) 6.66 (1H, s) 6.99 (1H, dd J=8.3, 2.1 Hz) 7.07 (1H, ddd J=8.0, 5.0, 1.0 Hz) 7.12 (1H, d J=8.0 Hz) 7.15 (1H, d, J=2.0 Hz) 7.59 (1H, td, J=7.5, 2.0 Hz) 7.79 (1H, d, J=8.0 Hz) 8.46 (1H, d, J=4.5 Hz).

Step E: (4R)-4-(4-chloro-2-methyl-phenyl)-1-methyl-3-(2-pyridyl)-4,6,7,8-tetrahydro pyrazolo[3,4-e][1,4]thiazepine and (4S)-4-(4-chloro-2-methyl-phenyl)-1-methyl-3-(2-pyridyl)-4,6,7,8-tetrahydropyrazolo[3,4-e][1,4]thiazepine

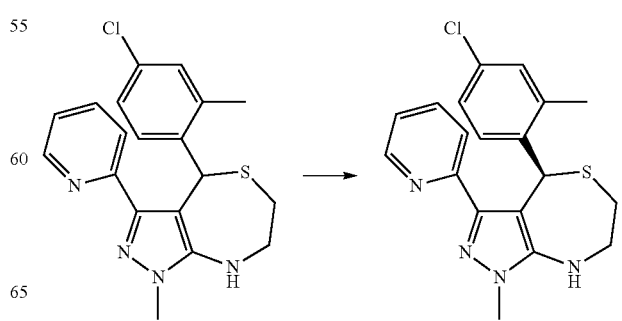

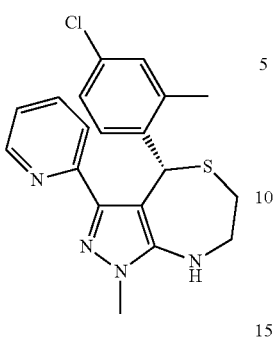

The enantiomers of (4-chloro-2-methyl-phenyl)-1-methyl-3-(2-pyridyl)-4,6,7,8-tetrahydropyrazolo[3,4-e][1,4]thiazepine (0.07 g, 0.189 mmol) were separated using chiral chromatography (Table 3, Method 12) to yield (4R)-4-(4-chloro-2-methyl-phenyl)-1-methyl-3-(2-pyridyl)-4,6,7,8-tetrahydropyrazolo[3,4-e][1,4]thiazepine (0.02 g, 0.055 mmol) as a white solid (Table 3, Method 12, $R_t$=4.48 min, or =positive. LC-MS (Table 1, Method b) $R_t$=2.67 min. m/z: 370 (M+H)$^+$) and (4S)-4-(4-chloro-2-methyl-phenyl)-1-methyl-3-(2-pyridyl)-4,6,7,8-tetrahydropyrazolo[3,4-e][1,4]thiazepine (0.02 g, 0.055 mmol) as a white solid (Table 3, Method 12, $R_t$=7.04 min, or =negative. LC-MS (Table 1, Method b) $R_t$=2.67 min. m/z: 370 (M+H)$^+$)

Example #3

3-chloro-N-(2-methyl-3-pyridyl)-4-[1-methyl-3-(2-pyridyl)-4,6,7,8-tetrahydro-pyrazolo[3,4-e][1,4]thiazepin-4-yl]benzamide, 3-chloro-N-(2-methyl-3-pyridyl)-4-((R)-1-methyl-3-(2-pyridyl)-4,6,7,8-tetrahydropyrazolo[3,4-e][1,4]thiazepin-4-yl)benzamide, 3-chloro-N-(2-methyl-3-pyridyl)-4-((S)-1-methyl-3-(2-pyridyl)-4,6,7,8-tetrahydropyrazolo[3,4-e][1,4]thiazepin-4-yl)benzamide

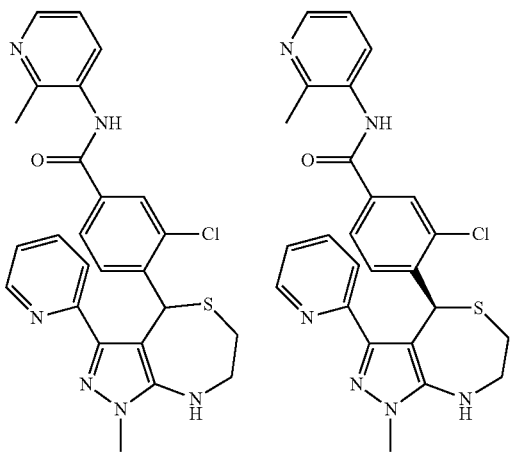

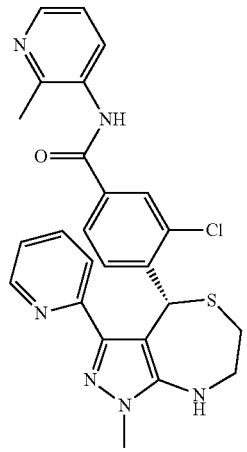

Step A: 3-oxo-3-(2-pyridyl)propanenitrile

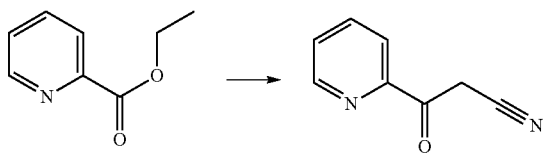

To a mixture of sodium hydride (15 g, 60% in oil, 375 mmol) and ethyl 2-picolinate (50 g. 331 mmol) in anhydrous THF (250 mL) was added dropwise a solution of anhydrous acetonitrile (20 g, 487 mmol) in anhydrous THF (200 mL), at about 65° C. After complete addition the reaction mixture was heated at about 65° C., for about 5 h. After cooling to rt, ethyl acetate (500 mL) was added, followed by 1 M aqueous HCl (360 mL). The resulting layers were separated, and the aqueous layer was extracted with ethyl acetate (250 mL). The combined organic layers were washed with water (2×100 mL), dried (MgSO$_4$), filtered, and concentrated in vacuo to give crude 3-oxo-3-(2-pyridyl)propanenitrile (48.6 g, 331 mmol, 100%), which was used as such in the next step. $^1$H-NMR (CDCl$_3$, Bruker 400 MHz) δ 4.39 (2H, s); 7.58 (1H, m); 7.91 (1H, dt, J=2 Hz, 10 Hz); 8.11 (1H, dt, J=2 Hz, 10 Hz); 8.70 (1H, s).

Step B: 1-methyl-3-(2-pyridyl)pyrazol-5-amine

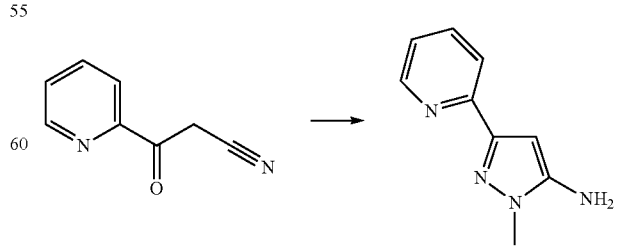

To a solution of crude 3-oxo-3-(2-pyridyl)propanenitrile (48.6 g, 331 mmol) in ethanol (500 mL) was added methyl hydrazine (25 g, 543 mmol). The resulting mixture was stirred for about 30 min at rt and then heated at about 75° C. for about 18 h. After cooling to rt the reaction mixture was concentrated in vacuo. The residue was treated with toluene (300 mL). The formed solid was collected by filtration and washed with toluene (150 mL). The solid was dried under vacuum to give 2-methyl-5-(2-pyridyl)pyrazol-3-amine (36.2 g, 208 mmol, 63%). $^1$H-NMR (CDCl$_3$, Bruker 400 MHz) δ 3.62 (3H, s); 5.34 (2H, br s); 5.90 (1H, s); 7.21 (1H, m); 7.73 (1H, dt, J=10 Hz, 2 Hz); 7.83 (1H, dt, J=10 Hz, 1 Hz); 8.51 (1H, dt, J=6 Hz, 2 Hz).

Step C: Preparation C.2: 4-(4-bromo-2-chloro-phenyl)-1-methyl-3-(2-pyridyl)-4,8-dihydropyrazolo[3,4-e][1,4]thiazepin-7-one

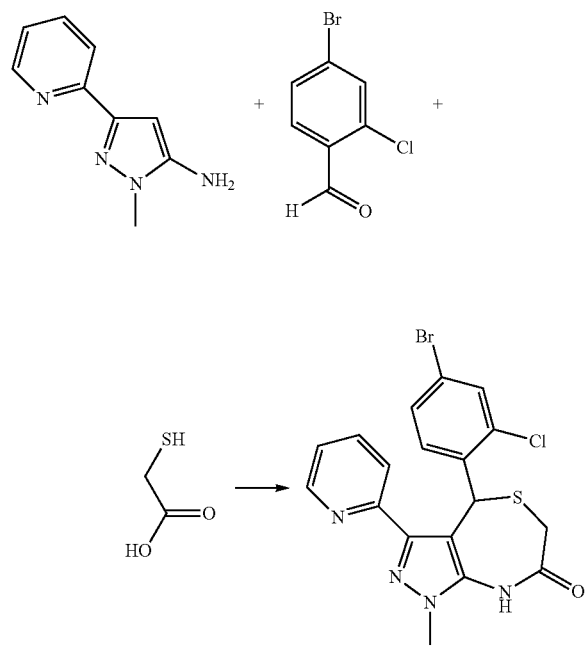

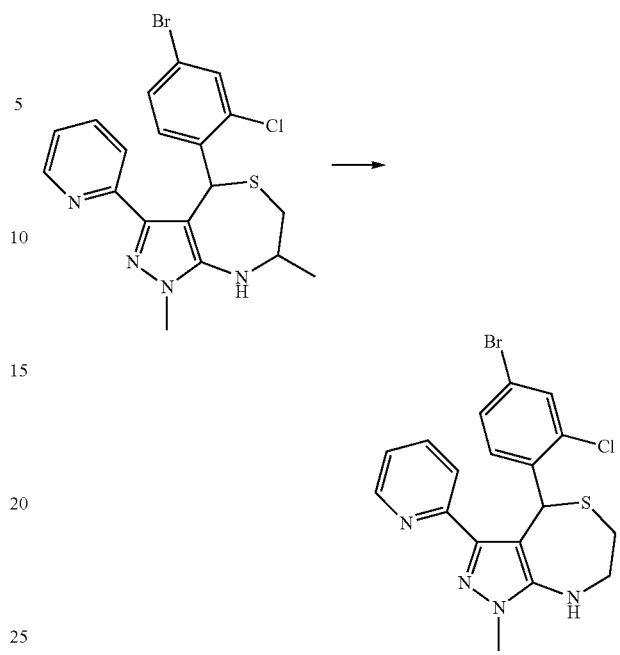

A mixture of 1-methyl-3-(2-pyridyl)pyrazol-5-amine (1.6 g, 9.2 mmol), 4-bromo-2-chloro-benzaldehyde (2.0 g, 9.1 mmol, Apollo Scientific), and thioglycolic acid (3.4 g, 37 mmol) in acetonitrile (20 mL) was heated, in a sealed microwave vessel, for about 20 min, at about 150° C., in a microwave. After cooling to rt the precipitated solid was collected by filtration and washed with acetonitrile (4 mL) to afford 4-(4-bromo-2-chloro-phenyl)-1-methyl-3-(2-pyridyl)-4,8-dihydropyrazolo[3,4-e][1,4]thiazepin-7-one (2.86 g, 6.4 mmol, 70%), which was used as such. $^1$H-NMR (CDCl$_3$, Bruker 400 MHz) δ 3.10 (1H, d, J=12 Hz); 3.43 (1H, d, J=12 Hz); 3.86 (3H, s); 6.68 (1H, s); 6.93 (1H, d, J=8 Hz); 7.15 (1H, m); 7.28 (1H, dd, J=2 Hz, 8 Hz); 7.65 (1H, d, J=2 Hz); 7.70 (1H, dd, J=2 Hz, 8 Hz), 7.78 (1H, d, J=8 Hz); 8.34 (1H, d, J=4 Hz); 10.2 (1H, s).

Step D: 4-(4-bromo-2-chloro-phenyl)-1-methyl-3-(2-pyridyl)-4,6,7,8-tetrahydropyrazolo[3,4-e]-[1,4]thiazepine To a solution of 4-(4-bromo-2-chloro-phenyl)-1-methyl-3-(2-pyridyl)-4,8-dihydropyrazolo[3,4-e][1,4]thiazepin-7-one (5.83 g, 13.0 mmol) in THF (50 mL) was added a solution of borane THF complex (40 mL, 1M in THF, 40 mmol, Acros) at rt. Subsequently, the mixture was heated under reflux for about 2 h. After cooling to about 4° C., HCl (5 M aq, 40 mL) was added dropwise and the mixture was stirred for about 18 h at rt, then NaOH (2 M aq, 110 mL) and ethyl acetate (200 mL) were added. The layers were separated and the aqueous layer was extracted with ethyl acetate (50 mL). The combined organic layers were washed with water (2×50 mL), dried (MgSO$_4$), filtered and concentrated in vacuo. The residue was purified by column chromatography (SiO$_2$, ethyl acetate) to give 4-(4-bromo-2-chloro-phenyl)-1-methyl-3-(2-pyridyl)-4,6,7,8-tetrahydropyrazolo[3,4-e][1,4]thiazepine (4.86 g, 11.1 mmol, 86%). LC-MS (Table 1, Method a) R$_t$=4.54 min, m/z 435, 437 (M+H)$^+$ Step E: methyl 3-chloro-4-[1-methyl-3-(2-pyridyl)-4,6,7,8-tetrahydropyrazolo[3,4-e][1,4]thiazepin-4-yl]benzoate

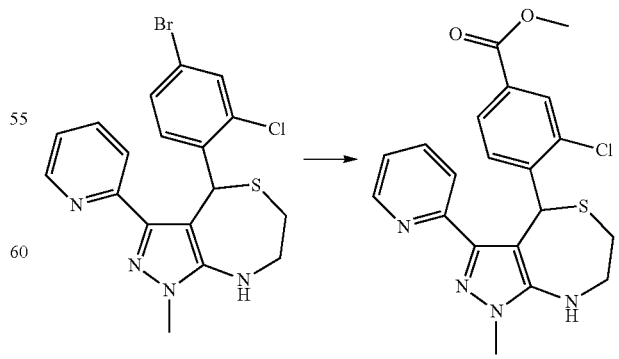

To a mixture of 4-(4-bromo-2-chloro-phenyl)-1-methyl-3-(2-pyridyl)-4,6,7,8-tetrahydropyrazolo[3,4-e][1,4]thiazepine (1.5 g, 3.4 mmol, prep D.2), trans-di-MU-acetatobis[2-(di-o-tolylphosphino)benzyl]dipalladium(II) (0.325 g, 0.3 mmol, Alfa Aesar), molybdenumhexacarbonyl (0.91 g, 3.4 mmol, Fluka), and 1,8-diazabicyclo[5.4.0]undec-7-ene (0.798 g, 5.2 mmol), was added a degassed mixture of methanol and acetonitrile (9:3, 14 mL). The resulting mixture was heated, in a sealed microwave vessel, for about 1 h at about 100° C. in a microwave. After cooling to rt, the mixture was filtered and concentrated in vacuo. The resulting oil was purified by column chromatography (SiO$_2$, DCM/ethyl acetate 100:0 to 0:100) to afford methyl 3-chloro-4-[1-methyl-3-(2-pyridyl)-4,6,7,8-tetrahydropyrazolo[3,4-e][1,4]thiazepin-4-yl]benzoate (0.350 g, 24%). LC-MS (Table 1, Method b) R$_t$=6.60 min, m/z 415 (M+H)$^+$; $^1$H-NMR (CDCl$_3$, Bruker 400 MHz) δ 2.72 (1H, ddd, J=15.5, 9.0, 2.0 Hz); 2.83 (1H, ddd, J=15.5, 6.0, 2.0 Hz); 3.24-3.33 (1H, m); 3.59-3.69 (1H, m); 3.80-3.92 (7H, m); 6.88 (1H, s); 7.07 (1H, ddd, J=8.0, 5.0, 1.0 Hz); 7.35 (1H, d, J=8.0 Hz); 7.59 (1H, dt, J=8.0, 2.0 Hz); 7.73-7.79 (2H, m); 8.07 (1H, d, J=2.0 Hz); 8.46-8.50 (1H, m)

Step F: 3-chloro-N-(2-methyl-3-pyridyl)-4-[1-methyl-3-(2-pyridyl)-4,6,7,8-tetrahydro-pyrazolo[3,4-e][1,4]thiazepin-4-yl]benzamide in vacuo. The resulting residue was purified by column chromatography (SiO2, ethyl acetate/methanol 100:0 to 0:100) and prep-HPLC (Table 2, Method a) to afford 3-chloro-N-(2-methyl-3-pyridyl)-4-[1-methyl-3-(2-pyridyl)-4,6,7,8-tetrahydro¬pyrazolo[3,4-e][1,4]thiazepin-4-yl]benzamide (0.0162 g, 0.03 mmol, 9%). LC-MS (Table 1, Method b) R$_t$=3.70 min, m/z 491 (M+H)$^+$; $^1$H-NMR (CDCl$_3$, Bruker 400 MHz) δ 2.56 (3H, s), 2.70-2.90 (2H, m), 3.26-3.35 (1H, m), 3.63-3.71 (1H, m) 3.60-4.00 (1H, br s) 3.84 (3H, s) 6.91 (1H, s) 7.09 (1H, ddd, J=1.2, 4.8, 7.9 Hz) 7.21 (1H, dd, J=4.8, 8.2 Hz) 7.44 (1H, d, J=8.0 Hz) 7.58-7.64 (3H, m) 7.80 (1H, d, J=8.0 Hz) 7.92 (1H, d, J=2.0 Hz) 8.28-8.34 (2H, m) 8.48-8.51 (1H, m).

Step G: 3-chloro-N-(2-methyl-3-pyridyl)-4-((R)-1-methyl-3-(2-pyridyl)-4,6,7,8-tetrahydropyrazolo[3,4-e][1,4]thiazepin-4-yl)benzamide and 3-chloro-N-(2-methyl-3-pyridyl)-4-((S)-1-methyl-3-(2-pyridyl)-4,6,7,8-tetrahydropyrazolo[3,4-e][1,4]thiazepin-4-yl)benzamide

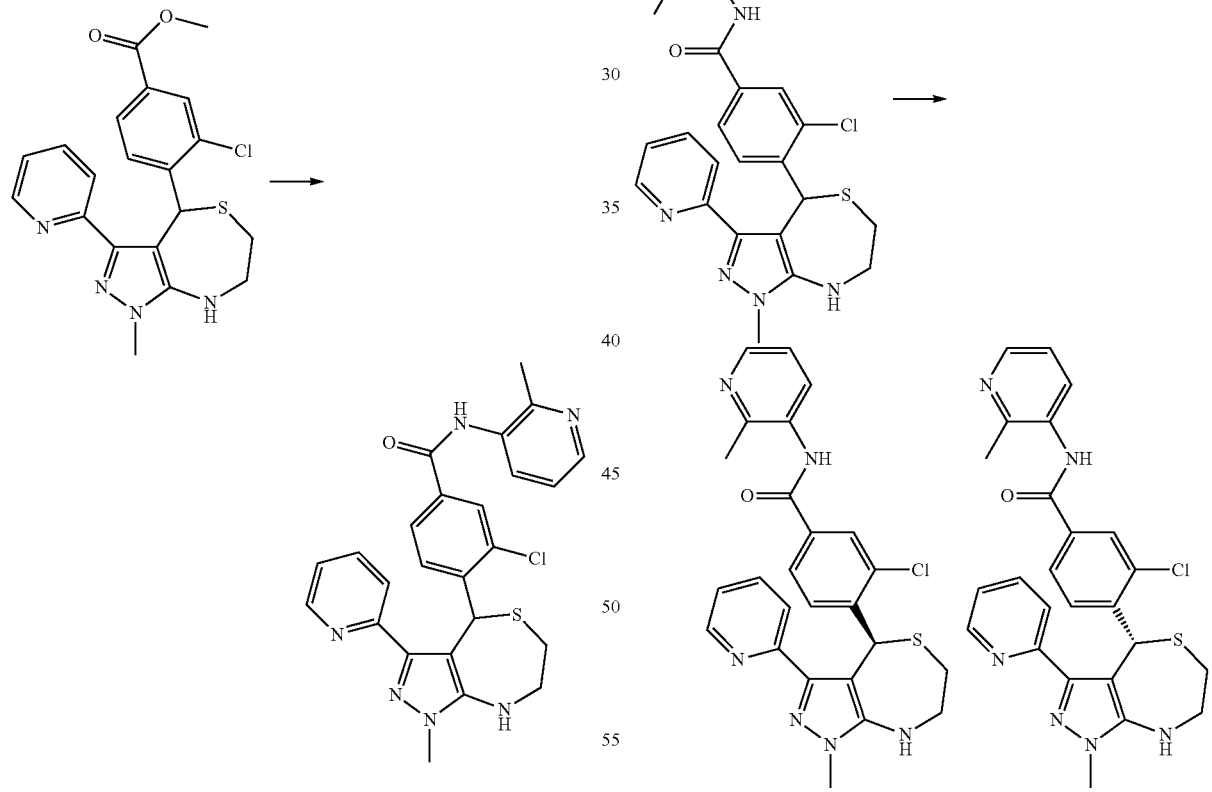

To a mixture of methyl 3-chloro-4-[1-methyl-3-(2-pyridyl)-4,6,7,8-tetrahydropyrazolo[3,4-e][1,4]thiazepin-4-yl]benzoate (0.14 g, 0.34 mmol) and 3-amino-2-methylpyridine (0.04 g, 0.37 mmol) in anhydrous THF (10 mL), was added lithium bis(trimethylsilyl)amide solution (1.3 mL, 1 M in THF, 1.3 mmol), at about −40° C. The resulting mixture was stirred for about 30 min, at about −40° C., and then quenched by the addition of water (10 mL) and ethyl acetate (130 mL). The layers were separated and the organic layer was washed with water (25 mL), dried (MgSO$_4$), filtered and concentrated The enantiomers of 3-chloro-N-(2-methyl-3-pyridyl)-4-[1-methyl-3-(2-pyridyl)-4,6,7,8-tetrahydropyrazolo[3,4-e][1,4]thiazepin-4-yl]benzamide (0.07 g, 0.189 mmol) were separated using chiral chromatography (Table 3, Method 13) to yield 3-chloro-N-(2-methyl-3-pyridyl)-4-((R)-1-methyl-3-(2-pyridyl)-4,6,7,8-tetrahydropyrazolo[3,4-e][1,4]thiazepin-4-yl)benzamide (0.02 g, 0.055 mmol) as a white solid (Table 3, Method 13, R$_t$=22.45 min, or =positive. LC-MS (Table 1, Method b) R$_t$=2.00 min. m/z: 491 (M+H)$^+$) and 3-chloro-N-(2-methyl-3-pyridyl)-4-((S)-1-methyl-3-(2-pyridyl)-4,6,7,8-tetrahydropyrazolo[3,4-e][1,4]thiazepin-4-yl)benzamide (0.02 g, 0.055 mmol) as a white solid (Table 3, Method 13, R$_t$=24.35 min, or =negative. LC-MS (Table 1, Method b) R$_t$=2.00 min. m/z: 491 (M+H)$^+$)

Example #4

3-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide, (R)-3-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide, (S)-3-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide

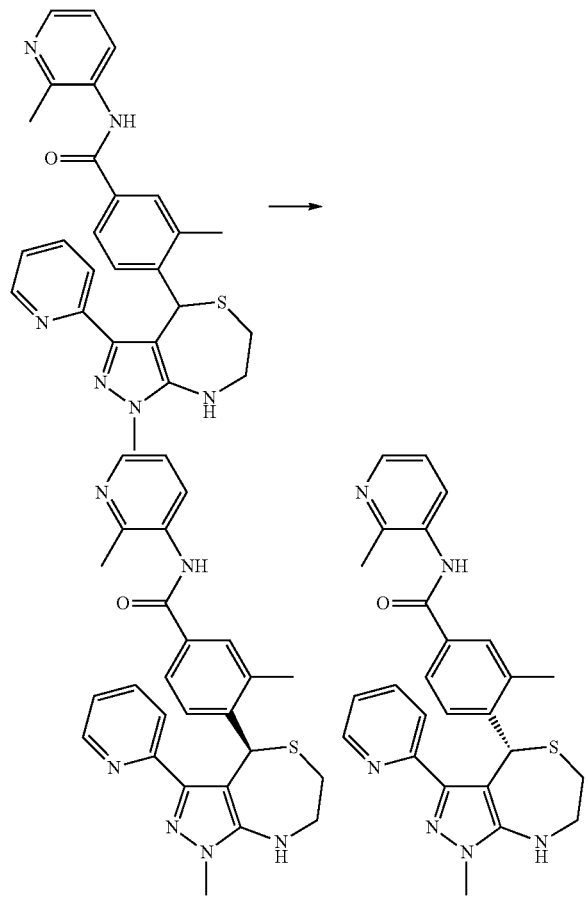

Step A: 3-oxo-3-(2-pyridyl)propanenitrile

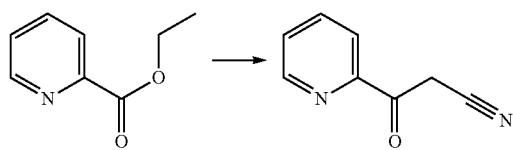

To a mixture of sodium hydride (15 g, 60% in oil, 375 mmol) and ethyl 2-picolinate (50 g. 331 mmol) in anhydrous THF (250 mL) was added dropwise a solution of anhydrous acetonitrile (20 g, 487 mmol) in anhydrous THF (200 mL), at about 65° C. After complete addition the reaction mixture was heated at about 65° C., for about 5 h. After cooling to rt, ethyl acetate (500 mL) was added, followed by 1 M aq HCl (360 mL). The resulting layers were separated, and the aqueous layer was extracted with ethyl acetate (250 mL). The combined organic layers were washed with water (2×100 mL), dried (MgSO$_4$), filtered, and concentrated in vacuo to give crude 3-oxo-3-(2-pyridyl)propanenitrile (48.6 g, 331 mmol, 100%), which was used as such in the next step. $^1$H-NMR (CDCl$_3$, Bruker 400 MHz) δ 4.39 (2H, s); 7.58 (1H, m); 7.91 (1H, dt, J=2 Hz, 10 Hz); 8.11 (1H, dt, J=2 Hz, 10 Hz); 8.70 (1H, s).

Step B: 1-methyl-3-(2-pyridyl)pyrazol-5-amine

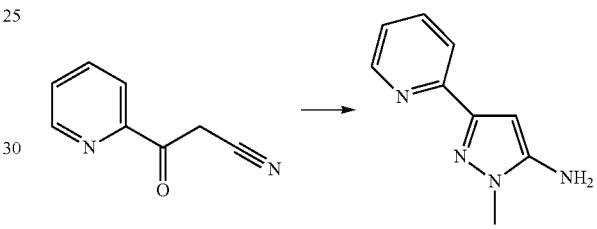

To a solution of crude 3-oxo-3-(2-pyridyl)propanenitrile (48.6 g, 331 mmol) in ethanol (500 mL) was added methyl hydrazine (25 g, 543 mmol). The resulting mixture was stirred for about 30 min at rt and then heated at about 75° C. for about 18 h. After cooling to rt the reaction mixture was concentrated in vacuo. The residue was treated with toluene (300 mL). The formed solid was collected by filtration and washed with toluene (150 mL). The solid was dried under vacuum to give 1-methyl-3-(2-pyridyl)pyrazol-5-amine (36.2 g, 208 mmol, 63%). $^1$H-NMR (CDCl$_3$, Bruker 400 MHz) δ 3.62 (3H, s); 5.34 (2H, br s); 5.90 (1H, s); 7.21 (1H, m); 7.73 (1H, dt, J=10 Hz, 2 Hz); 7.83 (1H, dt, J=10 Hz, 1 Hz); 8.51 (1H, dt, J=6 Hz, 2 Hz).

Step C: 4-(4-bromo-2-methyl-phenyl)-1-methyl-3-(2-pyridyl)-4,8-dihydropyrazolo[3,4-e][1,4]thiazepin-7-one

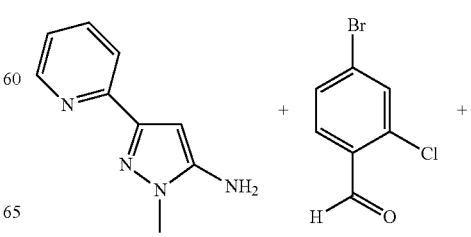

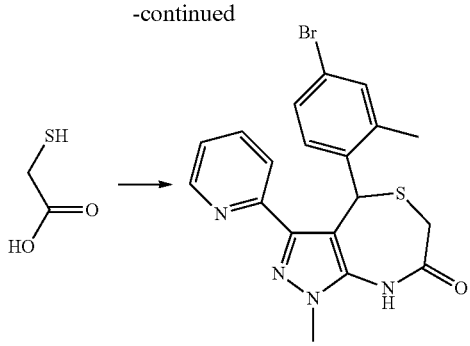

A mixture of 1-methyl-3-(2-pyridyl)pyrazol-5-amine (1.74 g, 10 mmol), 4-bromo-2-methylbenzaldehyde (2.0 g, 10 mmol, Ark Pharm Inc.), and thioglycolic acid (3.90 g, 32 mmol) in acetonitrile (15 mL) was heated, in a sealed microwave vessel, for about 25 min, at about 150° C., in a microwave. After cooling to rt the precipitated solid was collected by filtration and washed with acetonitrile and diethyl ether to afford 4-(4-bromo-2-methyl-phenyl)-1-methyl-3-(2-pyridyl)-4,8-dihydropyrazolo[3,4-e][1,4]thiazepin-7-one (2.92 g, 6.8 mmol, 68%), which was used as such. $^1$H-NMR (CDCl$_3$, Bruker 400 MHz) δ 2.56 (3H, s), 3.29 (1H, d, J=15 Hz); 3.37 (1H, d, J=15 Hz); 3.95 (3H, s); 6.58 (1H, s); 6.66 (1H, d, J=8 Hz); 7.03 (2H, m); 7.24 (1H, d, J=11 Hz); 7.56 (1H, dt, J=8 Hz, 2 Hz); 7.75 (1H, m), 8.30 (1H, d, J=4 Hz).

Step D: 4-(4-bromo-2-methyl-phenyl)-1-methyl-3-(2-pyridyl)-4,6,7,8-tetrahydropyrazolo[3,4-e][1,4]thiazepine

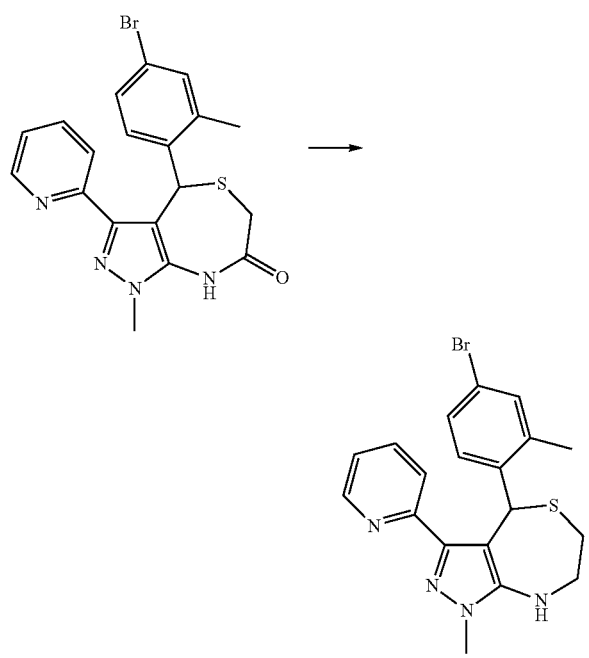

To a solution of 4-(4-bromo-2-methyl-phenyl)-1-methyl-3-(2-pyridyl)-4,8-dihydropyrazolo[3,4-e][1,4]thiazepin-7-one (2.92 g, 6.8 mmol) in anhydrous THF (50 mL) was added a solution of borane THF complex (27.2 mL, 1M in THF, 27.2 mmol, Acros) at about 0° C. Subsequently, the mixture was stirred at rt, overnight. After cooling to about 0° C., HCl (5 M aq, 20 mL) was added dropwise and the mixture was stirred for about 30 min at rt, then the solution was brought to about pH=7 with 2 M aq NaOH, at about 0° C. The resulting mixture was extracted with ethyl acetate (200 mL). The organic layer was washed with brine (50 mL), dried (MgSO$_4$), filtered and concentrated in vacuo. The residue was purified by column chromatography (SiO2, ethyl acetate) to give 4-(4-bromo-2-methyl-phenyl)-1-methyl-3-(2-pyridyl)-4,6,7,8-tetrahydropyrazolo[3,4-e]-[1,4]thiazepine (2.1 g, 5.0 mmol, 74%) as an off white solid: LC-MS (Table 1, Method e) R$_t$=8.32 min, m/z 415 (M+H)$^+$; $^1$H-NMR (CDCl$_3$, Bruker 400 MHz) δ 2.58 (3H, s) 2.69 (1H, ddd, J=15.0, 6.0, 2.0 Hz) 2.86 (1H, ddd, J=15.0, 9.0, 2.5 Hz) 3.21-3.31 (1H, m) 3.57-3.65 (1H, m) 3.79 (1H, br s) 3.83 (3H, s) 6.65 (1H, s) 7.04-7.09 (2H, m) 7.14 (1H, dd, J=8.5, 2.0 Hz) 7.31 (1H, d, J=2.0 Hz) 7.59 (1H, td, J=7.5, 2.0 Hz) 7.80 (1H, br.d, J=8.0 Hz) 8.45 (1H, br.d, J=5.0 Hz).

Step E: methyl 3-methyl-4-[1-methyl-3-(2-pyridyl)-4,6,7,8-tetrahydropyrazolo[3,4-e][1,4]thiazepin-4-yl] benzoate

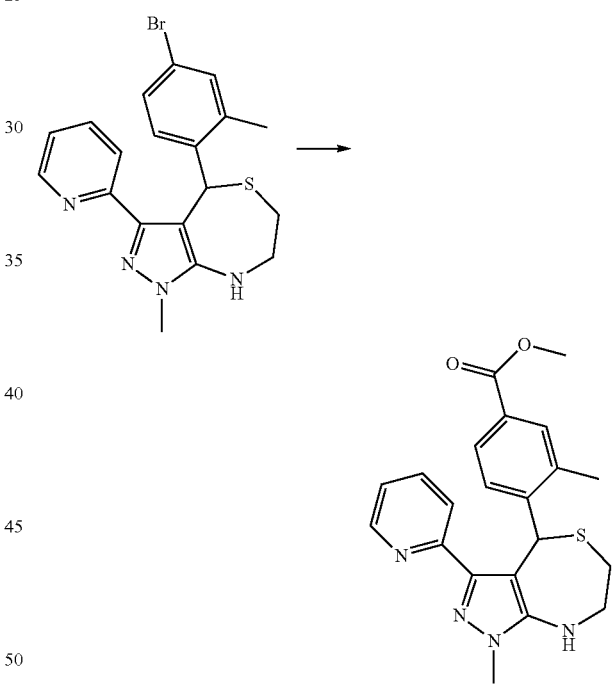

To a mixture of 4-(4-bromo-2-methyl-phenyl)-1-methyl-3-(2-pyridyl)-4,6,7,8-tetrahydropyrazolo[3,4-e][1,4]thiazepine (0.40 g, 0.96 mmol), trans-di-MU-acetatobis[2-(di-o-tolylphosphino)benzyl]dipalladium(II) (0.0904 g, 0.096 mmol, Alfa Aesar), Molybdenumhexacarbonyl (0.25 g, 0.96 mmol, Fluka), tri(tert-butyl)phosphonium tetrafluoroborate (0.571 g, 0.2 mmol) and 1,8-diazabicyclo[5.4.0]undec-7-ene (0.22 mL, 1.5 mmol), was added a degassed mixture of methanol and acetonitrile (6:2, 8 mL). The resulting mixture was heated, in a sealed microwave vessel, for about 1 h at about 100° C. in a microwave. After cooling to rt, the mixture was filtered and concentrated in vacuo. The residue was purified by column chromatography (SiO$_2$, ethyl acetate/hexanes 8:2 to 10:0) to afford methyl 3-methyl-4-[1-methyl-3-(2-pyridyl)-4,6,7,8-tetrahydropyrazolo[3,4-e][1,4]thiazepin-4-yl]

benzoate (0.20 g, 52%) as an beige foam: ¹H-NMR (CDCl₃, Bruker 400 MHz) δ 2.65 (3H, s), 2.66-2.72 (1H, m); 2.80-2.89 (1H, m); 3.22-3.31 (1H, m); 3.57-3.68 (1H, m); 3.79-3.83 (1H, m); 3.84 (3H, s), 3.87 (3H, s), 6.72 (1H, s); 7.04-7.08 (1H, m); 7.55-7.61 (1H, dt, J=8 Hz, 2 Hz); 7.68-7.72 (1H, dd, J=9, 2 Hz); 7.78-7.82 (1H, m); 7.85 (1H, s); 8.43-8.46 (1H, m).

Step F: 3-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide

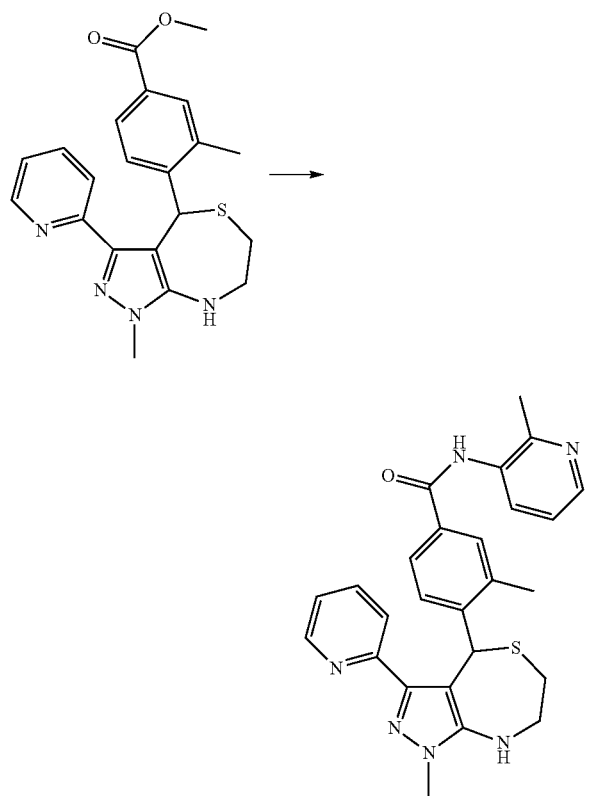

To a mixture of methyl 3-methyl-4-[1-methyl-3-(2-pyridyl)-4,6,7,8-tetrahydropyrazolo[3,4-e][1,4]thiazepin-4-yl]benzoate (0.20 g, 0.51 mmol) and 3-amino-2-methylpyridine (0.066 g, 0.61 mmol) in anhydrous THF (20 mL), was added lithium bis(trimethylsilyl)amide solution (1.01 mL, 1 M in THF, 1.01 mmol), at about −60° C. The resulting mixture was stirred for about 30 min, during which time the temperature was allowed to rise from about −60° C. to about 0° C., and then quenched by the addition of water (20 mL), while keeping the temperature below 0° C. The resulting mixture was extracted with ethyl acetate (60 mL). The organic layer was washed with brine (20 mL), dried (MgSO₄), filtered and concentrated in vacuo. The resulting residue was purified by column chromatography (SiO₂, ethyl acetate) to afford 3-methyl-N-(2-methyl-3-pyridyl)-4-[1-methyl-3-(2-pyridyl)-4,6,7,8-tetrahydropyrazolo[3,4-e][1,4]thiazepin-4-yl]benzamide (0.10 g, 0.21 mmol, 42%) as a beige foam: LC-MS (Table 1, Method a) R$_t$=1.85 min, m/z 471 (M+H)⁺; ¹H-NMR (CDCl₃, Bruker 400 MHz) δ 2.56 (3H, s) 2.72 (3H, s) 2.67-2.75 (1H, m) 2.87 (1H, ddd, J=15.0, 9.3, 2.6 Hz) 3.29 (1H, ddd, J=13.3, 9.3, 2.5 Hz) 3.65 (1H, ddd, J=13.3, 6.2, 2.3 Hz) 3.85 (3H, s) 3.87 (1H, br s) 6.76 (1H, s) 7.08 (1H, ddd, J=7.4, 4.9, 1.1 Hz) 7.20 (1H, dd, J=8.1, 4.7 Hz) 7.35 (1H, t, J=8.0 Hz) 7.55 (1H, dd, J=8.0, 2.0 Hz) 7.60 (1H, td, J=7.8, 1.8 Hz) 7.62 (1H, d, J=1.8 Hz) 7.69 (1H, br s) 7.84 (1H, dt, J=8.0, 1.0 Hz) 8.30 (1H, dd, J=4.8, 1.6 Hz) 8.35 (1H, dd, J=8.1, 1.4 Hz) 8.47 (1H, ddd, J=4.8, 1.7, 0.8 Hz).

Step G: (R)-3-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide, (S)-3-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide

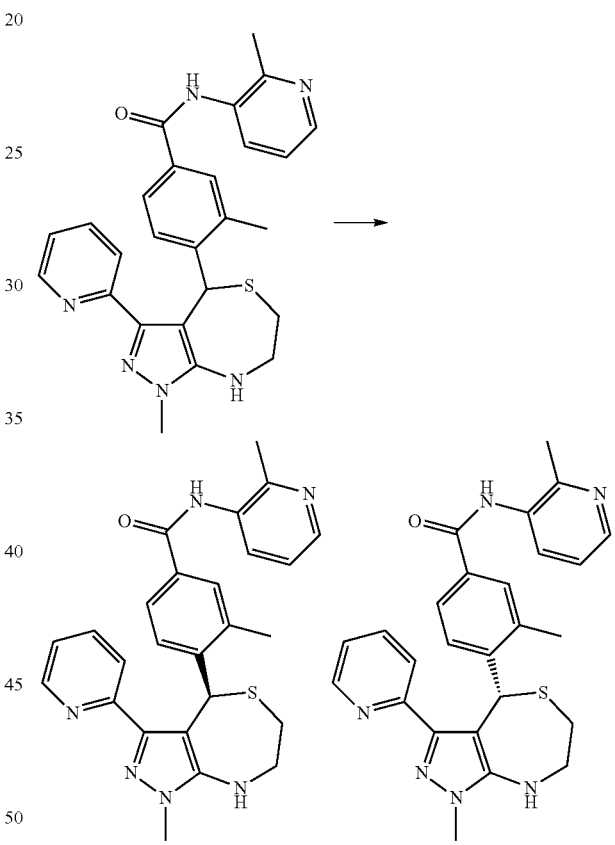

The enantiomers of 3-methyl-N-(2-methyl-3-pyridyl)-4-[1-methyl-3-(2-pyridyl)-4,6,7,8-tetrahydropyrazolo[3,4-e][1,4]thiazepin-4-yl]benzamide (0.07 g, 0.189 mmol) were separated using chiral chromatography (Table 2, Method 10) to yield (R)-3-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide (0.02 g, 0.055 mmol) as a white solid (Table 3, Method 10, R$_t$=39.75 min, or =positive. LC-MS (Table 1, Method a) R$_t$=1.16 min. m/z: 471 (M+H)⁺) and (S)-3-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide (0.02 g, 0.055 mmol) as a white solid (Table 3, Method 10, R$_t$=51.2 min, or =negative. LC-MS (Table 1, Method a) R$_t$=1.16 min. m/z: 471 (M+H)⁺)

Example 5

(4R,7S)-4-(4-chloro-2-methylphenyl)-1,7-dimethyl-3-(pyridin-2-yl)-4,6,7,8-tetrahydro-1H-pyrazolo[3,4-e][1,4]thiazepine*, (4R,7R)-4-(4-chloro-2-methylphenyl)-1,7-dimethyl-3-(pyridin-2-yl)-4,6,7,8-tetrahydro-1H-pyrazolo[3,4-e][1,4]thiazepine, (4S,7S)-4-(4-chloro-2-methylphenyl)-1,7-dimethyl-3-(pyridin-2-yl)-4,6,7,8-tetrahydro-1H-pyrazolo[3,4-e][1,4]thiazepine, (4S,7R)-4-(4-chloro-2-methylphenyl)-1,7-dimethyl-3-(pyridin-2-yl)-4,6,7,8-tetrahydro-1H-pyrazolo[3,4-e][1,4]thiazepine*

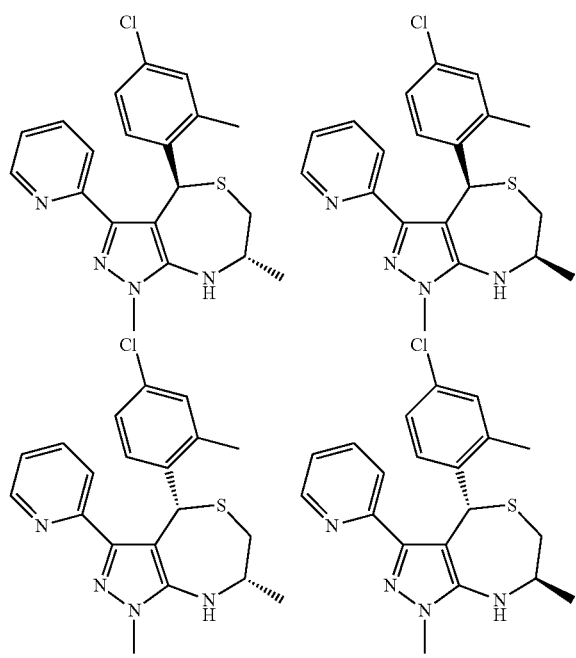

Step A: 3-oxo-3-(2-pyridyl)propanenitrile

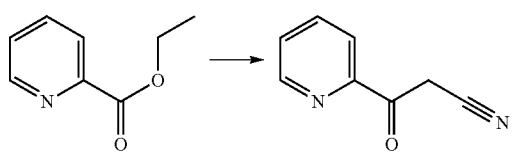

To a mixture of sodium hydride (15 g, 60% in oil, 375 mmol) and ethyl 2-picolinate (50 g. 331 mmol) in anhydrous THF (250 mL) was added dropwise a solution of anhydrous acetonitrile (20 g, 487 mmol) in anhydrous THF (200 mL), at about 65° C. After complete addition the reaction mixture was heated at about 65° C., for about 5 h. After cooling to rt, ethyl acetate (500 mL) was added, followed by 1 M aqueous HCl (360 mL). The resulting layers were separated, and the aqueous layer was extracted with ethyl acetate (250 mL). The combined organic layers were washed with water (2×100 mL), dried (MgSO$_4$), filtered, and concentrated in vacuo to give crude 3-oxo-3-(2-pyridyl)propanenitrile (48.6 g, 331 mmol, 100%), which was used as such in the next step.

$^1$H-NMR (CDCl$_3$, Bruker 400 MHz) δ 4.39 (2H, s); 7.58 (1H, m); 7.91 (1H, dt, J=2 Hz, 10 Hz); 8.11 (1H, dt, J=2 Hz, 10 Hz); 8.70 (1H, s).

Step B: 1-methyl-3-(2-pyridyl)pyrazol-5-amine

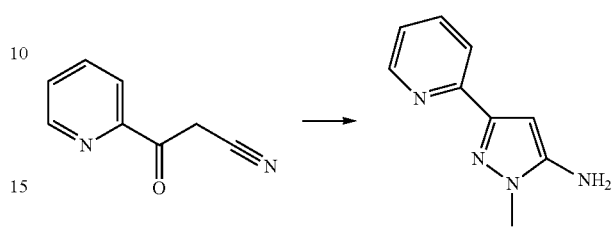

To a solution of crude 3-oxo-3-(2-pyridyl)propanenitrile (48.6 g, 331 mmol) in ethanol (500 mL) was added methyl hydrazine (25 g, 543 mmol). The resulting mixture was stirred for about 30 min at rt and then heated at about 75° C. for about 18 h. After cooling to rt the reaction mixture was concentrated in vacuo. The residue was treated with toluene (300 mL). The formed solid was collected by filtration and washed with toluene (150 mL). The solid was dried under vacuum to give 1-methyl-3-(2-pyridyl)pyrazol-5-amine (36.2 g, 208 mmol, 63%). $^1$H-NMR (CDCl$_3$, Bruker 400 MHz) δ 3.62 (3H, s); 5.34 (2H, br s); 5.90 (1H, s); 7.21 (1H, m); 7.73 (1H, dt, J=10 Hz, 2 Hz); 7.83 (1H, dt, J=10 Hz, 1 Hz); 8.51 (1H, dt, J=6 Hz, 2 Hz).

Step C: 4-(4-chloro-2-methyl-phenyl)-1,7-dimethyl-3-(2-pyridyl)-4,6-dihydropyrazolo[3,4-e][1,4]thiazepine

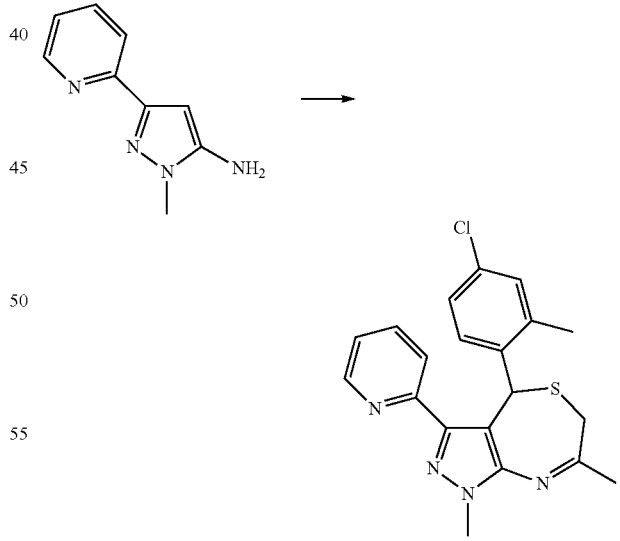

A mixture of 1-methyl-3-(2-pyridyl)pyrazol-5-amine (0.215 g, 1.23 mmol), 4-chloro-2-methyl-benzaldehyde (0.1906 g, 1.23 mmol, Fluorochem), 1-sulfanylpropan-2-one (0.45 g, 4.93 mmol, Enamine), and p-toluenesulfonic acid (0.070 g, 0.37 mmol) in acetonitrile (3 mL) was heated, in a sealed microwave vessel, for about 30 min, at about 150° C., in a microwave. After cooling to rt the mixture was concentrated under reduced pressure. The residue was dissolved in ethyl acetate (70 mL) and methanol (10 mL), and washed with 5% aqueous sodium bicarbonate (20 mL). The aqueous layer was extracted with ethyl acetate (20 mL). The combined organic layers were washed with water (40 mL), dried (MgSO$_4$), filtered and concentrated in vacuo. The residue was purified by column chromatography (SiO2, ethyl acetate/hexanes 1:4) to afford 4-(4-chloro-2-methyl-phenyl)-1,7-dimethyl-3-(2-pyridyl)-4,6-dihydropyrazolo[3,4-e][1,4]thiazepine (0.36 g, 0.94 mmol, 76%), as a yellow oil: LC-MS (Table 1, Method a) R$_t$=5.41 min, m/z 383 (M+H)$^+$; $^1$H-NMR (CDCl$_3$, Bruker 400 MHz) δ 2.36 (3H, s) 2.60 (3H, s) 3.16 (1H, d, J=16.3 Hz) 3.29 (1H, dd, J=16.3, 1.5 Hz) 4.03 (3H, s) 6.50 (1H, d, J=8.2 Hz) 6.60 (1H, d, J=1.5 Hz) 6.88 (1H, dd, J=8.2, 2.1 Hz) 7.01 (1H, ddd, J=7.4, 4.9, 1.1 Hz) 7.16 (1H, d, J=2.1 Hz) 7.56 (1H, td, J=7.8, 1.7 Hz) 7.86 (1H, dt, J=8.1, 1.0 Hz) 8.35 (1H, ddd, J=4.8, 1.8, 0.8 Hz).

Step D: 4-(4-chloro-2-methyl-phenyl)-1,7-dimethyl-3-(2-pyridyl)-4,6,7,8-tetrahydro pyrazolo[3,4-e][1,4]thiazepine

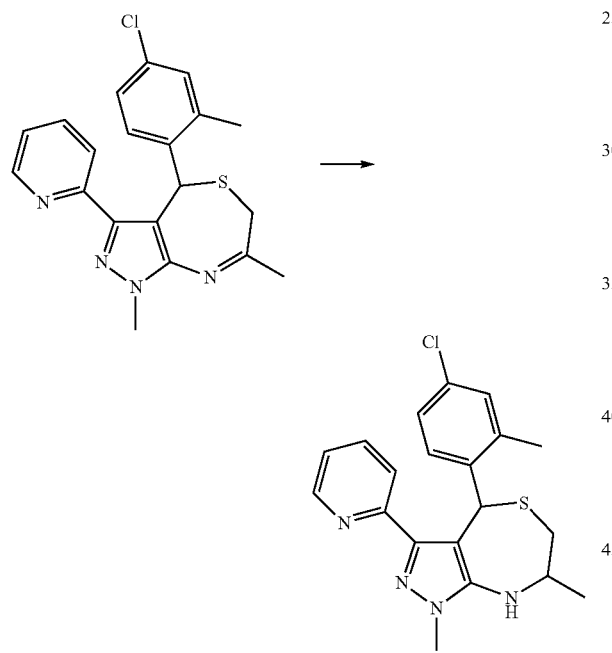

A mixture of 4-(4-chloro-2-methyl-phenyl)-1,7-dimethyl-3-(2-pyridyl)-4,6-dihydropyrazolo[3,4-e][1,4]thiazepine (0.120 g, 0.31 mmol), acetic acid (0.054 mL, 0.94 mmol) and sodium triacetoxyborohydride (0.080 g, 0.38 mmol) in DCE (10 mL) was stirred at rt for about 16 h. Then more acetic acid (0.054 mL, 0.94 mmol) and sodium triacetoxyborohydride (0.080 g, 0.38 mmol) were added and stirring was continued for another 24 h. The resulting mixture was concentrated in vacuo and partitioned between 5% aqueous sodium bicarbonate (40 mL) and ethyl acetate (40 mL). The layers were separated and the aqueous layer was extracted with ethyl acetate (40 mL). The combined organic layers were washed with water (15 mL), dried (MgSO$_4$), filtered and concentrated in vacuo. The residue was purified by column chromatography (SiO$_2$, ethyl acetate/hexanes 1:1) to give 4-(4-chloro-2-methyl-phenyl)-1,7-dimethyl-3-(2-pyridyl)-4,6,7,8-tetrahydropyrazolo[3,4-e][1,4]thiazepine (0.100 g, 0.26 mmol, 84%) as a pale yellow solid as a mixture of two diasereomers (ratio 61:39): LC-MS (Table 1, Method e) R$_t$=8.51 min and 8.76 min, m/z 385 (M+H)$^+$; Major isomer $^1$H-NMR (CDCl$_3$, Bruker 400 MHz) δ 1.33 (3H, d, J=6.4 Hz) 2.58 (3H, s) 2.62-2.72 (2H, m) 3.43-3.53 (1H, m) 3.84 (3H, s) 4.06 (1H, br s) 6.59 (1H, s) 6.99 (1H, dd, J=8.3, 2.1 Hz) 7.01-7.09 (1H, m) 7.11 (1H, d, J=8.3 Hz) 7.14 (1H, d, J=2.1 Hz) 7.58 (1H, td, J=7.9, 1.9 Hz) 7.77 (1H, d, J=8.0 Hz) 8.44 (1H, d, J=4.6 Hz); Minor diastereomer: $^1$H-NMR (CDCl$_3$, Bruker 400 MHz) δ 1.21 (3H, d, J=6.6 Hz) 2.55 (1H, dd, J=15.0, 8.0 Hz) 2.61 (3H, s) 2.95 (1H, dd, J=15.0, 4.3 Hz) 3.36-3.43 (1H, m) 3.86 (3H, s) 4.06 (1H, br s) 6.44 (1H, s) 6.96 (1H, dd, J=8.3, 2.1 Hz) 7.01-7.09 (1H, m) 7.06 (1H, d, J=8.0 Hz) 7.12 (1H, d, J=2.1 Hz) 7.56 (1H, td, J=7.9, 1.9 Hz) 7.76 (1H, d, J=8.0 Hz) 8.40 (1H, d, J=4.6 Hz).

Step E: (4R,7S)-4-(4-chloro-2-methylphenyl)-1,7-dimethyl-3-(pyridin-2-yl)-4,6,7,8-tetrahydro-1H-pyrazolo[3,4-e][1,4]thiazepine*, (4R,7R)-4-(4-chloro-2-methylphenyl)-1,7-dimethyl-3-(pyridin-2-yl)-4,6,7,8-tetrahydro-1H-pyrazolo[3,4-e][1,4]thiazepine, (4S,7S)-4-(4-chloro-2-methylphenyl)-1,7-dimethyl-3-(pyridin-2-yl)-4,6,7,8-tetrahydro-1H-pyrazolo[3,4-e][1,4]thiazepine, (4S,7R)-4-(4-chloro-2-methylphenyl)-1,7-dimethyl-3-(pyridin-2-yl)-4,6,7,8-tetrahydro-1H-pyrazolo[3,4-e][1,4]thiazepine*

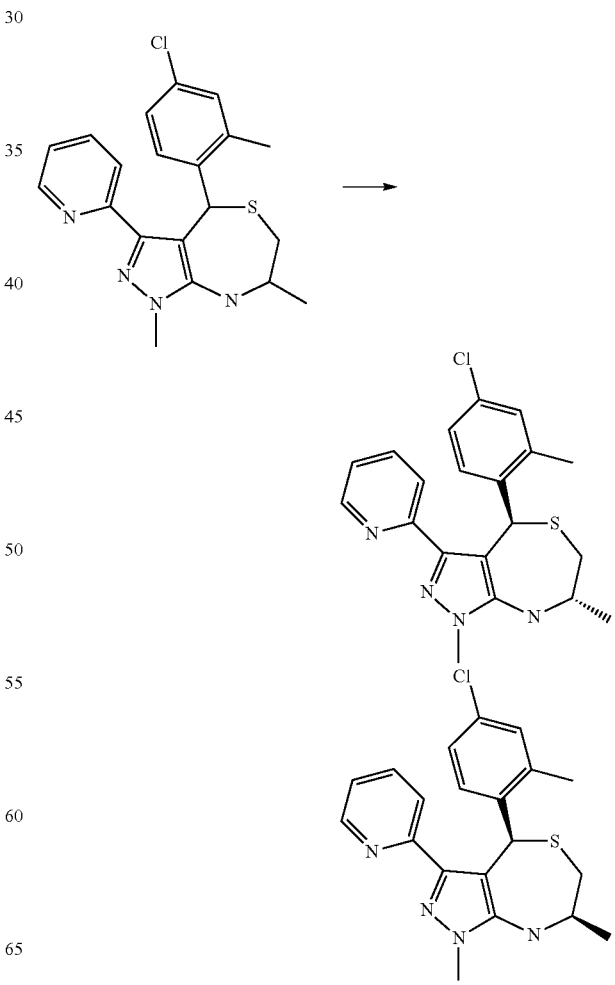

307
-continued

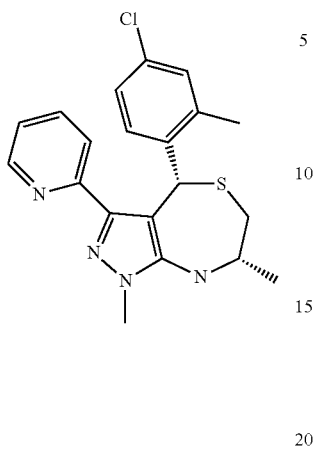

Two pairs of enantiomers of 4-(4-chloro-2-methyl-phenyl)-1,7-dimethyl-3-(2-pyridyl)-4,6,7,8-tetrahydropyrazolo[3,4-e][1,4]thiazepine (0.8 g, 2.78 mmol) were separated using chiral chromatography (Table 2, Method 2) to yield (4R,7S)-4-(4-chloro-2-methylphenyl)-1,7-dimethyl-3-(pyridin-2-yl)-4,6,7,8-tetrahydro-1H-pyrazolo[3,4-e][1,4]thiazepine (0.103 g, 0.268 mmol) as a white solid (Table 3, Method 2, $R_t$=12.8 min, or =positive. LC-MS (Table 1, Method b) $R_t$=1.84 min. m/z: 385 (M+H)$^+$), (4R,7R)-4-(4-chloro-2-methylphenyl)-1,7-dimethyl-3-(pyridin-2-yl)-4,6,7,8-tetrahydro-1H-pyrazolo[3,4-e][1,4]thiazepine (0.166 g, 0.431 mmol) as a white solid (Table 3, Method 2 $R_t$=20.34 min., or =positive. LC-MS (Table 1, Method b) $R_t$=1.87 min. m/z: 385 (M+H)$^+$), (4S,7S)-4-(4-chloro-2-methylphenyl)-1,7-dimethyl-3-(pyridin-2-yl)-4,6,7,8-tetrahydro-M-pyrazolo[3,4-e][1,4]thiazepine (0.095 g, 0.247 mmol) as a white solid (Table 3, Method 2 $R_t$=26.13 min., or =negative. LC-MS (Table 1, Method b) $R_t$=1.87 min. m/z: 385 (M+H)$^+$), (4S,7R)-4-(4-chloro-2-methylphenyl)-1,7-dimethyl-3-(pyridin-2-yl)-4,6,7,8-tetrahydro-M-pyrazolo[3,4-e][1,4]thiazepine (0.18 g, 0.468 mmol) as a white solid (Table 3, Method 2, $R_t$=28.6 min, or =negative. LC-MS (Table 1, Method b) $R_t$=1.84 min. m/z: 385 (M+H)$^+$).

308

Example #6

4-(4-bromophenyl)-1-ethyl-3-(pyridin-2-yl)-1,4,5,6,7,8-hexahydropyrazolo[3,4-b]azepine

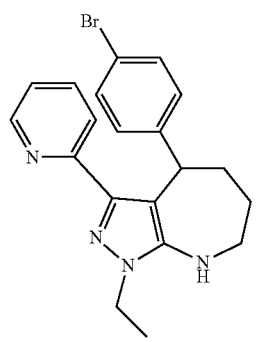 [SMILES: CCn1nc(-c2ccccn2)c2c1NCCCC2c1ccc(Br)cc1]

Step A: tert-butyl (4-(1-(4-bromophenyl)-3-hydroxypropyl)-1-ethyl-3-(pyridin-2-yl)-1H-pyrazol-5-yl)carbamate

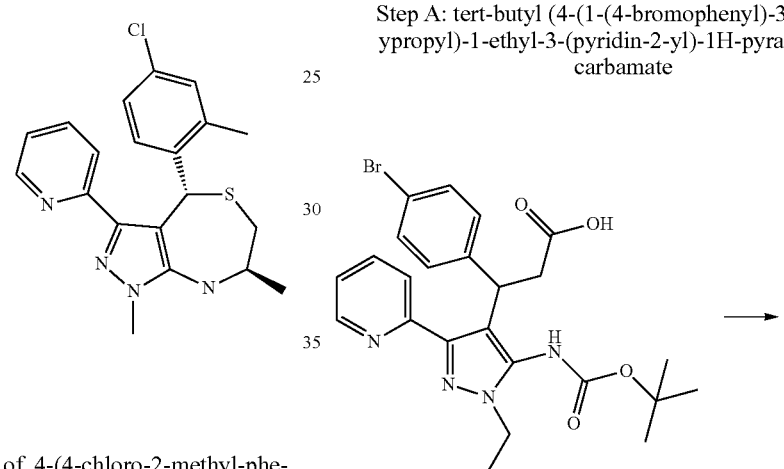

3-(4-Bromophenyl)-3-(5-((tert-butoxycarbonyl)amino)-1-ethyl-3-(pyridin-2-yl)-1H-pyrazol-4-yl)propanoic acid (0.786 g, 1.525 mmol, prepared using W from 4-bromobenzaldehyde, X from 1-ethyl-3-(pyridin-2-yl)-1H-pyrazol-5-amine then Y) was added in one portion to a mixture of LAH (0.232 g, 6.10 mmol) and Et$_2$O (15.0 mL) under N$_2$ at about 0° C. After about 1 h, the ice bath was removed. After stirring at rt for about 3 h, LAH (0.116 g, 3.05 mmol) was added in one portion. After about 2 h, the mixture was cooled to about 0° C. Sodium sulfate decahydrate was slowly added over about 15 min. After about 15 min, the ice bath was removed, the mixture was diluted with Et$_2$O (20 mL), and then the mixture was left to vigorously stir for about 63 h. The mixture was filtered rinsing with Et$_2$O (100 mL). The organic volatiles were removed under reduced pressure. The residue was purified on silica gel using a gradient of 50-75% EtOAc in heptane. The fractions containing product were combined and concentrated under reduced pressure to afford tert-butyl (4-(1-(4-bromophenyl)-3-hydroxypropyl)-1-ethyl-3-(pyridin-2-yl)-1H-pyrazol-5-yl)carbamate (0.359 g, 0.715 mmol, 47%) as a very pale yellow film. LC-MS (Table 1, Method g) $R_t$=2.45 min; m/z 501 and 503 (M+H)$^+$; $^1$H NMR (400 MHz, DMSO) 8.82 (s, 1H), 8.59-8.52 (m, 1H), 7.89-7.72 (m, 2H), 7.39-7.18 (m, 5H), 5.02-4.87 (m, 1H), 4.61-4.45 (m, 1H), 3.97-3.86 (m, 2H), 3.36-3.22 (m, 1H), 2.36-2.04 (m, 2H), 1.43 (s, 9H), 1.43-1.21 (m, 3H).

Step B: tert-butyl (4-(1-(4-bromophenyl)-3-oxopropyl)-1-ethyl-3-(pyridin-2-yl)-1H-pyrazol-5-yl)carbamate

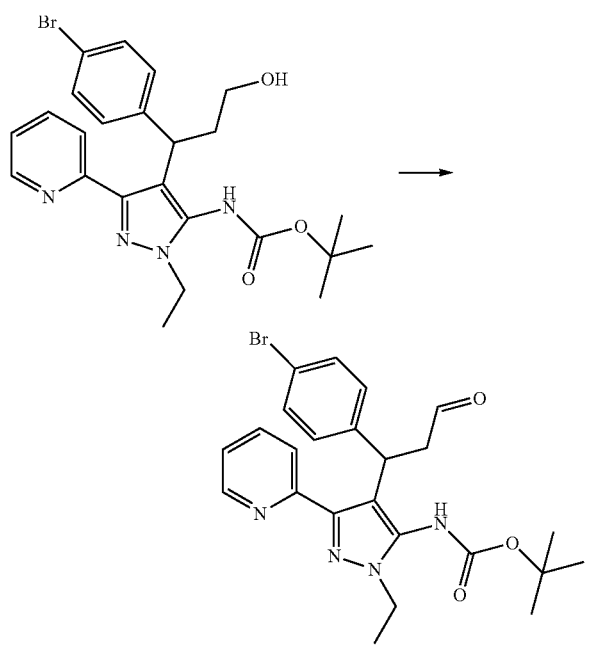

Dess-Martin periodinane (0.203 g, 0.480 mmol) was added in one portion to a solution of tert-butyl (4-(1-(4-bromophenyl)-3-hydroxypropyl)-1-ethyl-3-(pyridin-2-yl)-1H-pyrazol-5-yl)carbamate (0.334 g, 0.480 mmol) and DCM (5.00 mL) under N$_2$ at about 0° C. After about 5 min, the ice bath was removed. After about 30 min, Dess-Martin periodinane (0.203 g, 0.480 mmol) was added in one portion. After about 30 min, the reaction mixture was cooled to 0° C. then saturated aqueous NaHCO$_3$ (5 mL), water (5 mL), 10% aqueous sodium thiosulfate (5 mL), and DCM (10 mL) were added. After stirring vigorously for about 15 min, the layers were separated and the aqueous layer was extracted with DCM (10 mL). The combined organics were dried over Na$_2$SO$_4$, filtered and concentrated under reduced pressure. The residue was purified on silica gel using a gradient of 20-75% EtOAc in heptane. The fractions containing product were combined and concentrated under reduced pressure to afford tert-butyl (4-(1-(4-bromophenyl)-3-oxopropyl)-1-ethyl-3-(pyridin-2-yl)-1H-pyrazol-5-yl)carbamate (0.0848 g, 0.170 mmol, 35%) as a pale yellow solid. LC-MS (Table 1, Method g) $R_t$=2.61 min; m/z 499 and 501 (M+H)$^+$.

Step C: tert-butyl (4-(1-(4-bromophenyl)-4-methoxybut-3-en-1-yl)-1-ethyl-3-(pyridin-2-yl)-1H-pyrazol-5-yl)carbamate

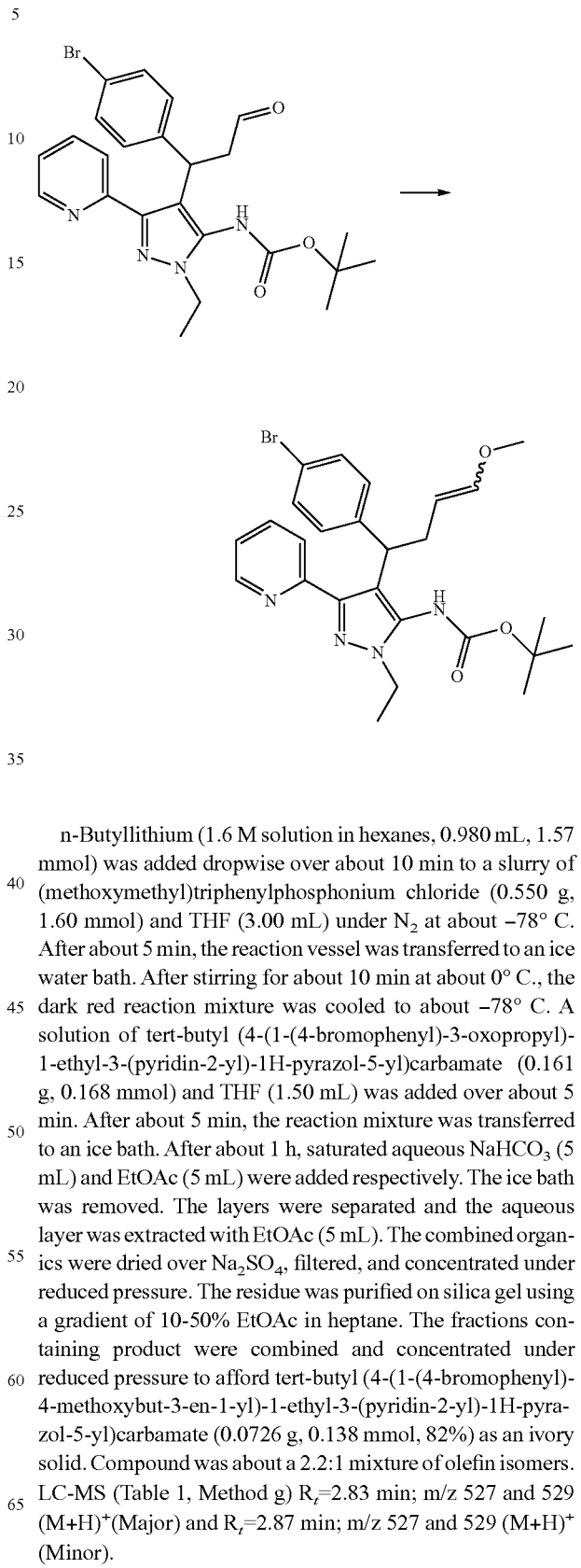

n-Butyllithium (1.6 M solution in hexanes, 0.980 mL, 1.57 mmol) was added dropwise over about 10 min to a slurry of (methoxymethyl)triphenylphosphonium chloride (0.550 g, 1.60 mmol) and THF (3.00 mL) under N$_2$ at about -78° C. After about 5 min, the reaction vessel was transferred to an ice water bath. After stirring for about 10 min at about 0° C., the dark red reaction mixture was cooled to about -78° C. A solution of tert-butyl (4-(1-(4-bromophenyl)-3-oxopropyl)-1-ethyl-3-(pyridin-2-yl)-1H-pyrazol-5-yl)carbamate (0.161 g, 0.168 mmol) and THF (1.50 mL) was added over about 5 min. After about 5 min, the reaction mixture was transferred to an ice bath. After about 1 h, saturated aqueous NaHCO$_3$ (5 mL) and EtOAc (5 mL) were added respectively. The ice bath was removed. The layers were separated and the aqueous layer was extracted with EtOAc (5 mL). The combined organics were dried over Na$_2$SO$_4$, filtered, and concentrated under reduced pressure. The residue was purified on silica gel using a gradient of 10-50% EtOAc in heptane. The fractions containing product were combined and concentrated under reduced pressure to afford tert-butyl (4-(1-(4-bromophenyl)-4-methoxybut-3-en-1-yl)-1-ethyl-3-(pyridin-2-yl)-1H-pyrazol-5-yl)carbamate (0.0726 g, 0.138 mmol, 82%) as an ivory solid. Compound was about a 2.2:1 mixture of olefin isomers. LC-MS (Table 1, Method g) $R_t$=2.83 min; m/z 527 and 529 (M+H)$^+$(Major) and $R_t$=2.87 min; m/z 527 and 529 (M+H)$^+$ (Minor).

Step D: tert-butyl (4-(1-(4-bromophenyl)-4-oxobutyl)-1-ethyl-3-(pyridin-2-yl)-1H-pyrazol-5-yl)carbamate

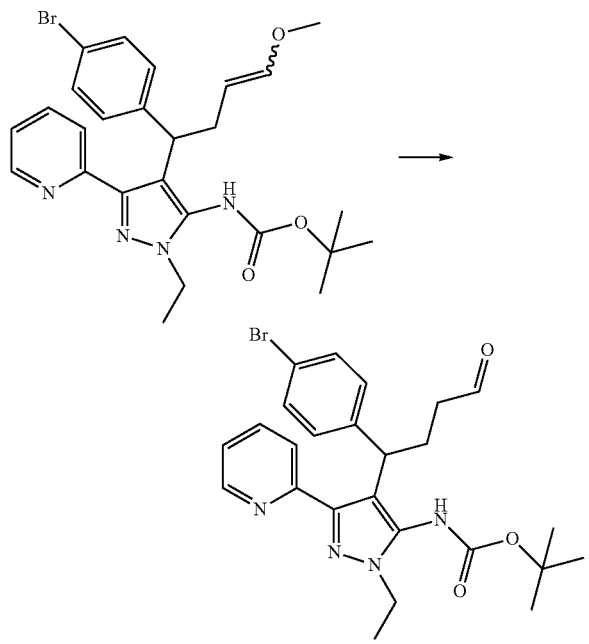

A solution of 2 M aqueous hydrogen chloride (1.00 mL, 2.00 mmol) was added in one portion to a solution of tert-butyl (4-(1-(4-bromophenyl)-4-methoxybut-3-en-1-yl)-1-ethyl-3-(pyridin-2-yl)-1H-pyrazol-5-yl)carbamate (0.0708 g, 0.118 mmol) and THF (2.00 mL) under air. After about 45 min, 5 mL saturated aqueous NaHCO$_3$ (5 mL) was added. The mixture was extracted with EtOAc (2×5 mL). The combined organics were dried over Na$_2$SO$_4$, filtered, and concentrated under reduced pressure. The residue was purified on silica gel using a gradient of 0-50% EtOAc in heptane. The fractions containing product were combined and concentrated under reduced pressure to afford tert-butyl (4-(1-(4-bromophenyl)-4-oxobutyl)-1-ethyl-3-(pyridin-2-yl)-1H-pyrazol-5-yl)carbamate (0.0450 g, 0.0880 mmol, 74%) as a sticky, pale yellow solid. LC-MS (Table 1, Method g) R$_t$=2.72 min; m/z 513 and 515 (M+H)$^+$.

Step E: 4-(4-bromophenyl)-1-ethyl-3-(pyridin-2-yl)-1,4,5,6,7,8-hexahydropyrazolo[3,4-b]azepine

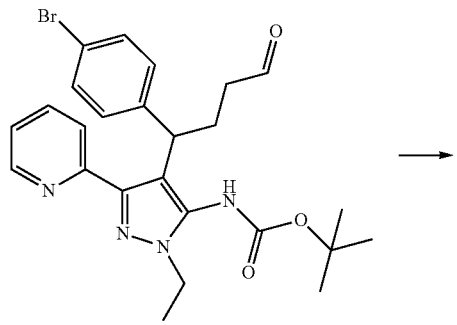

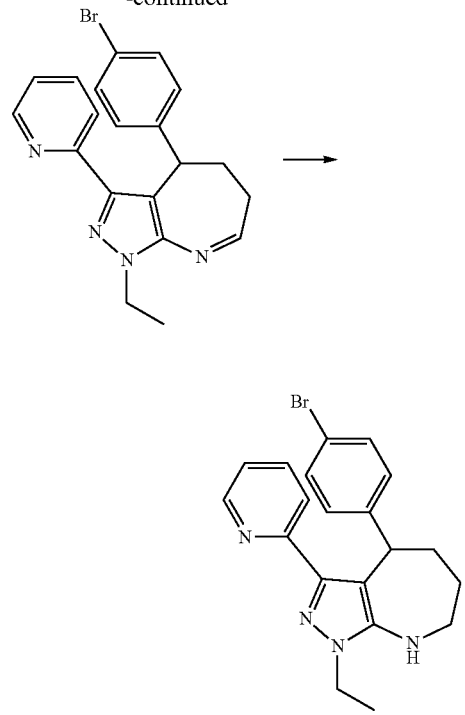

TFA (0.800 mL) was added to a solution of tert-butyl (4-(1-(4-bromophenyl)-4-oxobutyl)-1-ethyl-3-(pyridin-2-yl)-1H-pyrazol-5-yl)carbamate (0.0400 g, 0.0780 mmol) and DCM (0.800 mL). After about 40 min, reaction monitor by LC-MS (Table 1, Method g) R$_t$=2.68 min; m/z 395 and 397 (M+H)$^+$ indicated conversion to 4-(4-bromophenyl)-1-ethyl-3-(pyridin-2-yl)-1,4,5,6-tetrahydropyrazolo[3,4-b]azepine. Sodium triacetoxyhydroborate (0.083 g, 0.390 mmol) was added in one portion. After about 45 min, the volatiles were removed under reduced pressure. THF (0.8 mL) and 2 M aqueous HCl (0.8 mL) were added. After about 15 min, saturated aqueous NaHCO$_3$ (5 mL) was added. The solution was extracted with EtOAc (2×5 mL). The combined organics were dried over Na$_2$SO$_4$, filtered, and concentrated under reduced pressure. The residue was purified on silica gel (4 g) using a gradient of 50-100% EtOAc in heptane. The fractions containing product were combined and concentrated under reduced pressure to afford an ivory solid. Acetonitrile (0.5 mL) was added. The slurry was diluted with water (4 mL) then sonicated for about 2 min. The organic volatiles were removed under reduced pressure. The mixture was frozen then lyophilized to afford 4-(4-bromophenyl)-1-ethyl-3-(pyridin-2-yl)-1,4,5,6,7,8-hexahydropyrazolo[3,4-b]azepine (0.0239 g, 0.0600 mmol, 77%) as an ivory solid. LC-MS (Table 1, Method h) R$_t$=2.61 min; m/z 397 and 399 (M+H)$^+$; $^1$H NMR (400 MHz, DMSO) δ 8.44-8.34 (m, 1H), 7.79-7.75 (m, 1H), 7.70-7.63 (m, 1H), 7.35 (d, J=8.4 Hz, 2H), 7.17-7.11 (m, 1H), 7.05 (d, J=8.4 Hz, 2H), 5.56-5.47 (m, 2H), 4.16-3.94 (m, 2H), 3.33-3.20 (m, 1H), 2.81-2.70 (m, 1H), 2.18-2.07 (m, 1H), 1.92-1.80 (m, 1H), 1.71-1.59 (m, 1H), 1.49-1.35 (m, 1H), 1.30 (t, J=7.1 Hz, 3H).

Example #7 rac-2-((4S,6S,7R)-4-(4-chloro-2-methylphenyl)-1,3,7-trimethyl-4,6,7,8-tetra hydro-1H-pyrazolo[3,4-e][1,4]thiazepin-6-yl)ethanol and Example #8: 24(4R,6R,7S)-4-(4-chloro-2-methylphenyl)-1,3,7-trimethyl-4,6,7,8-tetrahydro-1H-pyrazolo[3,4-e][1,4]thiazepin-6-yl)ethanol

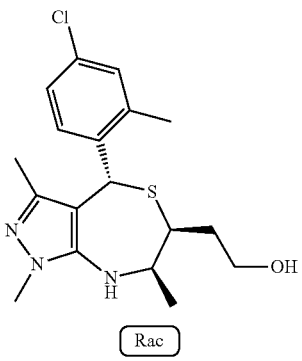

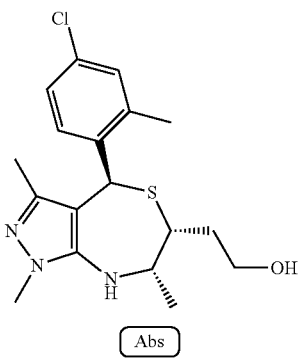

Step A: ethyl 3-bromo-4-oxopentanoate

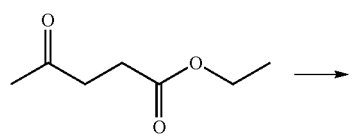

To a solution of ethyl 4-oxopentanoate (4.92 mL, 34.7 mmol) in Et$_2$O (180 mL) at about 0° C. was added bromine (1.8 mL, 34.7 mmol) in Et$_2$O (10 mL) and the reaction was stirred for about 3 h. To the reaction mixture was added saturated aqueous sodium thiosulfate (50 mL) and stirred for about 10 min. The reaction was warmed to ambient temperature. The organic layer was separated and the aqueous layer was back extracted with Et$_2$O (30 mL). The combined organic layers were washed with water (20 mL), dried over MgSO$_4$, filtered and concentrated under reduced pressure. The resulting oil was purified by column chromatography (SiO$_2$, EtOAc/heptane 100:0 to 0:20) to afford ethyl 3-bromo-4-oxopentanoate (3.29 g, 14.6 mmol, 43%). $^1$H NMR (CDCl$_3$) δ 4.67-4.33 (m, 1H), 4.15 (q, J=7.1 Hz, 2H), 3.29-3.22 (m, 1H), 2.90-2.86 (m, 1H), 2.42 (s, 3H), 1.26 (t, J=7.1 Hz, 3H).

Step B: ethyl 3-mercapto-4-oxopentanoate

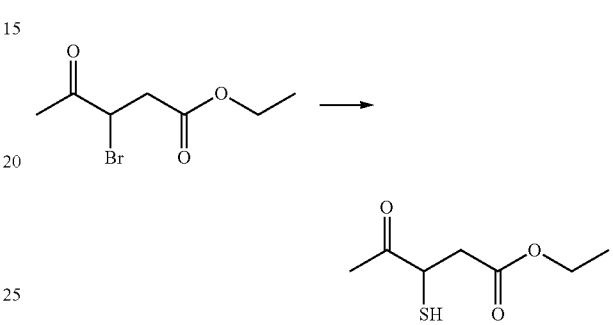

A round bottom flask was charged with sodium hydrogensulfide hydrate (1.23 g, 16.9 mmol) in water (14.2 mL). The solution was cooled to about 0° C. followed by the addition of ethyl 3-bromo-4-oxopentanoate (3.79 g, 16.9 mmol) dropwise over about 30 min. The mixture was stirred at about 0° C. for about 3 h. To the reaction mixture was added Et$_2$O (40 mL) and the reaction was warmed to ambient temperature. The crude product was partitioned between Et$_2$O (15 mL) and water (15 mL). The layers were separated and the aqueous layer was back extracted with Et$_2$O (10 mL). The combined organic layers were dried over MgSO$_4$, filtered and concentrated under reduced pressure to afford ethyl 3-mercapto-4-oxopentanoate (1.74 g, 9.87 mmol, 58%, which was used without further purification). LC-MS (Table 1, Method g) R$_t$=2.24 min, m/z 177 (M+H)$^+$.

Step C: ethyl 2-(4-(4-chloro-2-methylphenyl)-1,3,7-trimethyl-4,6-dihydro-1H-pyrazolo[3,4-e][1,4]thiazepin-6-yl)acetate

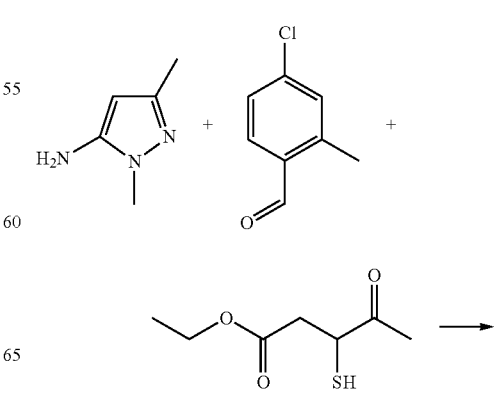

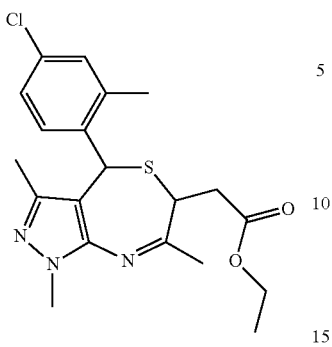

To a solution of 1,3-dimethyl-1H-pyrazol-5-amine (0.58 g, 5.22 mmol, Oakwood Chemicals), 4-chloro-2-methylbenzaldehyde (0.81 g, 5.22 mmol, Ark Pharm) and p-TSA (0.10 g, 0.52 mmol) in acetonitrile (10.5 mL) was added ethyl 3-mercapto-4-oxopentanoate (1.74 g, 9.87 mmol) and stirred at about 90° C. for about 18 h. The reaction mixture was cooled to ambient temperature and saturated NaHCO$_3$ (15 mL) and DCM (20 mL) were added. The organic layer was separated and the aqueous layer was back extracted using DCM (20 mL). The combined organic layers were dried over MgSO$_4$, filtered and concentrated under reduced pressure. The crude material was purified by column chromatography (SiO$_2$, EtOAc/heptane 100:0 to 0:50) to afford ethyl 2-(4-(4-chloro-2-methylphenyl)-1,3,7-trimethyl-4,6-dihydro-1H-pyrazolo[3,4-e][1,4]thiazepin-6-yl)acetate (0.85 g, 1.97 mmol, 37%). LC-MS (Table 1, Method g) R$_t$=2.66, 2.63 min, m/z 406 (M+H)$^+$.

Step D: rac-ethyl 2-((4R,6S,7R)-4-(4-chloro-2-methylphenyl)-1,3,7-trimethyl-4,6,7,8-tetrahydro-1H-pyrazolo[3,4-e][1,4]thiazepin-6-yl)acetate and rac-ethyl 2-((4S,6S,7R)-4-(4-chloro-2-methylphenyl)-1,3,7-trimethyl-4,6,7,8-tetrahydro-1H-pyrazolo[3,4-e][1,4]thiazepin-6-yl)acetate

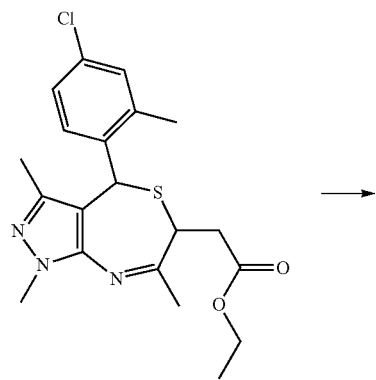

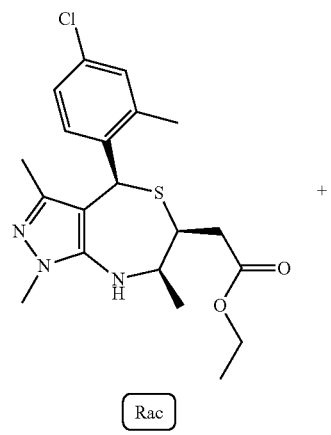

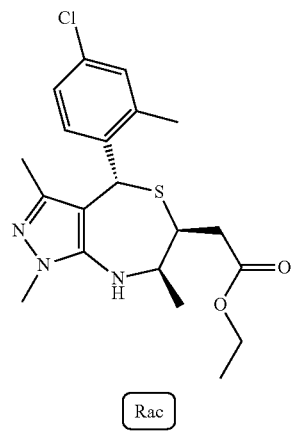

A solution of ethyl 2-(4-(4-chloro-2-methylphenyl)-1,3,7-trimethyl-4,6-dihydro-1H-pyrazolo[3,4-e][1,4]thiazepin-6-yl)acetate (0.85 g, 1.97 mmol) in MeOH (3.94 mL) was cooled to about 0° C. To the reaction mixture was added sodium tetrahydroborate (0.298 g, 7.88 mmol) portionwise. The reaction mixture was allowed to slowly warm to ambient temperature and stirred for about 16 h. The reaction mixture was cooled to about 0° C. and then saturated aqueous NH$_4$Cl (10 mL) was added. The mixture was partially concentrated under reduced pressure and EtOAc (20 mL) was added. The layers were separated and the aqueous layer was back extracted with EtOAc (10 mL). The combined organic layers were dried over MgSO$_4$, filtered and concentrated under reduced pressure. The crude material was purified by column chromatography (SiO$_2$, EtOAc/DCM 100:0 to 0:50) to afford rac-ethyl 2-((4R,6S,7R)-4-(4-chloro-2-methylphenyl)-1,3,7-trimethyl-4,6,7,8-tetrahydro-1H-pyrazolo[3,4-e][1,4]thiazepin-6-yl)acetate (0.15 g, 0.37 mmol, 19%) LC-MS (Table 1, Method g) R$_t$=2.58, m/z 408 (M+H)$^+$ and rac-ethyl 2-((4S,6S,7R)-4-(4-chloro-2-methylphenyl)-1,3,7-trimethyl-4,6,7,8-tetrahydro-1H-pyrazolo[3,4-e][1,4]thiazepin-6-yl)acetate (0.39 g, 0.97 mmol, 49%) LC-MS (Table 1, Method g) R$_t$=2.48, m/z 408 (M+H)$^+$.

Step E: rac-2-((4S,6S,7R)-4-(4-chloro-2-methylphenyl)-1,3,7-trimethyl-4,6,7,8-tetrahydro-1H-pyrazolo[3,4-e][1,4]thiazepin-6-yl)ethanol

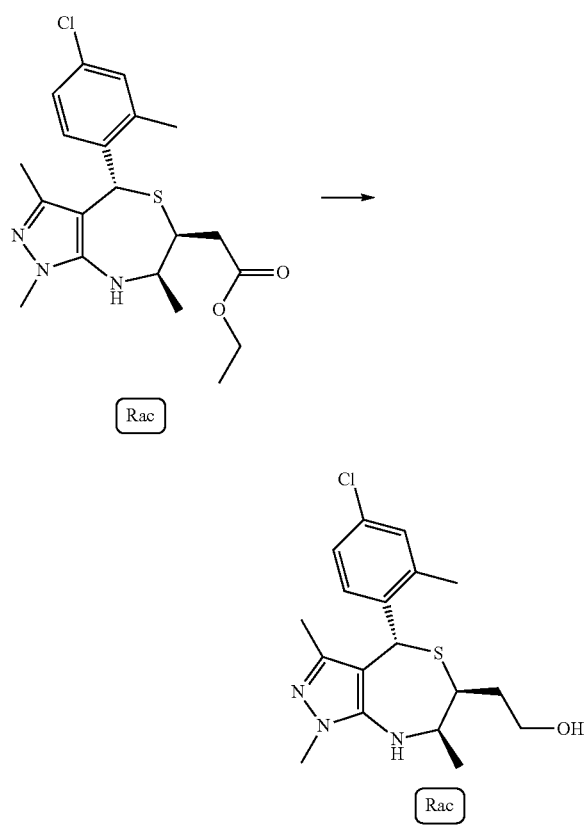

To a solution of rac-ethyl 2-((4S,6S,7R)-4-(4-chloro-2-methylphenyl)-1,3,7-trimethyl-4,6,7,8-tetrahydro-1H-pyrazolo[3,4-e][1,4]thiazepin-6-yl)acetate (0.39 g, 0.97 mmol) in THF (9 mL) at about 0° C. was added DIBAL-H (2.6 mL, 2.6 mmol). After about 30 min the reaction mixture was warmed to ambient temperature and stirred for about 4 h. To the reaction mixture was added EtOAc (10 mL) and 10% aqueous Rochelle's salt (15 mL) and stirred for about 16 h. The layers were separated and the aqueous layer was back extracted with EtOAc (2×10 mL). The combined organic layers were dried over MgSO4, filtered and concentrated under reduced pressure. The residue was dissolved in THF (9 mL) and cooled to about 0° C. and LAH (1 M solution in Et$_2$O, 1.3 mL, 1.3 mmol) was added dropwise. The ice bath was removed and the reaction was stirred for about 30 min. The reaction was cooled to 0° C. and aqueous NH$_4$Cl (10 mL) was added to the reaction mixture. Ethyl acetate (20 mL) was added and the mixture was stirred at rt for about 1 h. The layers were separated and the aqueous layer was back extracted with EtOAc (10 mL). The combined organic layers were washed with brine (10 mL), dried over MgSO$_4$, filtered and concentrated under reduced pressure. The crude material was purified by column chromatography (SiO$_2$, DCM/MeOH 100:0 to 95:5) to afford rac-2-((4S,6S,7R)-4-(4-chloro-2-methylphenyl)-1,3,7-trimethyl-4,6,7,8-tetrahydro-1H-pyrazolo[3,4-e][1,4]thiazepin-6-yl)ethanol (0.09 g, 0.24 mmol, 18%). LC-MS (Table 1, Method g) R$_t$=1.98, m/z 366 (M+H)$^+$. $^1$H-NMR (DMSO-d$_6$, Bruker 400 MHz) δ 7.24 (s, 1H), 7.13-7.08 (m, 2H), 5.55-5.50 (m, 1H), 4.86 (s, 1H), 4.334-4.26 (m, 1H), 3.54 (s, 3H), 3.50-3.42 (m, 1H), 3.42-3.34 (m, 1H), 3.22-3.08 (m, 2H), 2.45 (s, 3H), 1.81 (s, 3H), 1.54-1.42 (m, 1H), 1.38-1.28 (m, 1H), 1.01 (d, J=6.4 Hz, 3H).

Step F: 2-((4R,6R,7S)-4-(4-chloro-2-methylphenyl)-1,3,7-trimethyl-4,6,7,8-tetrahydro-1H-pyrazolo[3,4-e][1,4]thiazepin-6-yl)ethanol

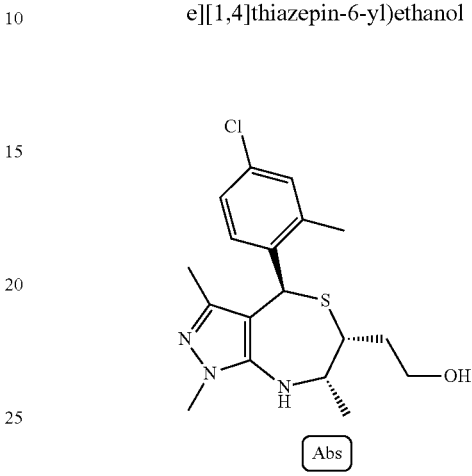

The rac-2-((4S,6S,7R)-4-(4-chloro-2-methylphenyl)-1,3,7-trimethyl-4,6,7,8-tetrahydro-1H-pyrazolo[3,4-e][1,4]thiazepin-6-yl)ethanol (0.09 g, 0.24 mmol,) mixture was separated using chiral chromatography (Table 3, Method 35) to give 2-((4R,6R,7S)-4-(4-chloro-2-methylphenyl)-1,3,7-trimethyl-4,6,7,8-tetrahydro-1H-pyrazolo[3,4-e][1,4]thiazepin-6-yl)ethanol (0.01 g, 0.03 mmol) (Table 3, Method 35, R$_t$=44.90 min, or =positive. LC-MS (Table 1, Method g) R$_t$=1.97 min. m/z: 366 (M+H)$^+$).

Example #9 rac-(4R,7R)-4-(4-bromo-2-methylphenyl)-1-methyl-3-(pyridin-2-yl)-7-(trifluoromethyl)-4,6,7,8-tetrahydro-1H-pyrazolo[3,4-e][1,4]thiazepine and rac-(4R,7S)-4-(4-bromo-2-methylphenyl)-1-methyl-3-(pyridin-2-yl)-7-(trifluoromethyl)-4,6,7,8-tetrahydro-1H-pyrazolo[3,4-e][1,4]thiazepine

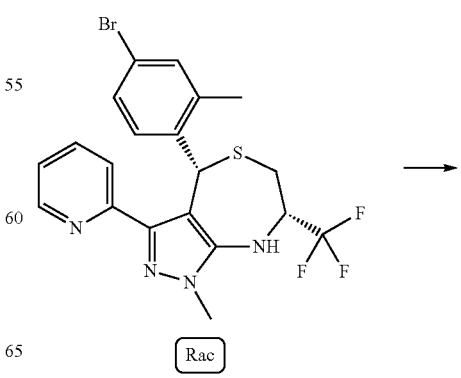

-continued

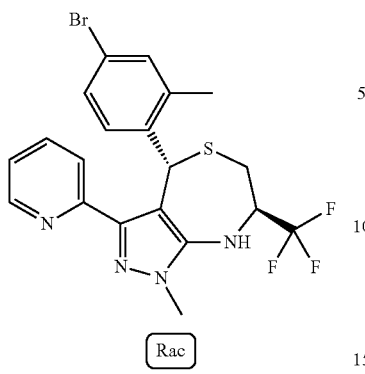

Step A: 2,2-diethoxy-3,3,3-trifluoropropane-1-thiol

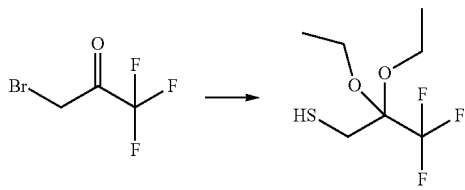

A solution of sodium hydrogen sulfide hydrate (1.94 g, 26.2 mmol) in EtOH (220 mL) was cooled in an icebath. 3-Bromo-1,1,1-trifluoropropan-2-one (5.00 g, 26.2 mmol) was added dropwise at a rate to ensure the reaction temperature does not rise above 4° C. The reaction stirred at 0° C. for about 3 h then allowed to warm up to rt. Approximately 50% of the EtOH was removed in vacuo and the cloudy reaction was stirred at 0° C. for about 1 h. The resulting precipitate was filtered and the filtrate was left standing at rt for about 16 h. The resulting precipitate was filtered and the filtrate was concentrated in vacuo. The residue was triturated with DCM and filtered. The resulting filtrate was concentrated in vacuo to give 2,2-diethoxy-3,3,3-trifluoropropane-1-thiol (1.3 g, 5.96 mmol, 23%) as a crude oily solid which was used as such in the next step.

Step B: rac-(4R,7R)-4-(4-bromo-2-methylphenyl)-1-methyl-3-(pyridin-2-yl)-7-(trifluoromethyl)-4,6,7,8-tetrahydro-1H-pyrazolo[3,4-e][1,4]thiazepine and rac-(4R,7S)-4-(4-bromo-2-methylphenyl)-1-methyl-3-(pyridin-2-yl)-7-(trifluoromethyl)-4,6,7,8-tetrahydro-1H-pyrazolo[3,4-e][1,4]thiazepine

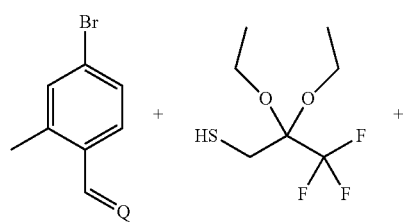

-continued

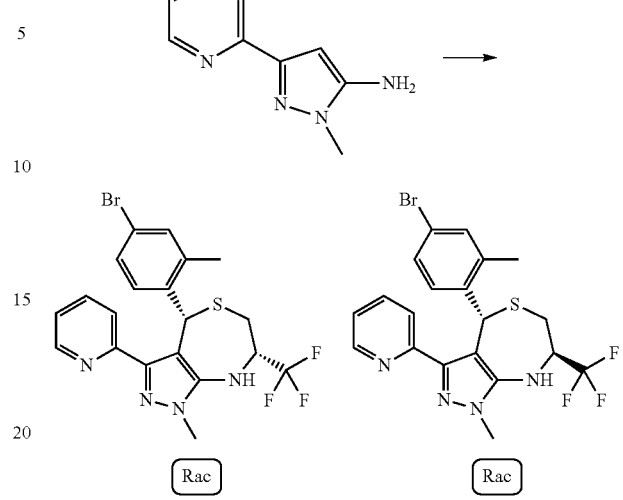

A solution of 1-methyl-3-(pyridin-2-yl)-1H-pyrazol-5-amine (0.300 g, 1.72 mmol, Example #2, step B), 4-bromo-2-methylbenzaldehyde (0.343 g, 1.72 mmol, Astatech) and 4-methylbenzenesulfonic acid hydrate (0.033 g, 0.172 mmol) in MeCN (4 mL) was stirred at rt for about 2 h. 2,2-Diethoxy-3,3,3-trifluoropropane-1-thiol (1.139 g, 1.72 mmol) was added to the reaction and was heated at about 90° C. for about 20 h. The reaction was allowed to cool to rt and was concentrated in vacuo. The residue was dissolved in MeOH (20 mL), cooled to 0° C. and sodium tetrahydroborate (0.130 g, 3.44 mmol) was added. The reaction was stirred at rt for about 2 h. Sodium tetrahydroborate (0.130 g, 3.44 mmol) was added to the reaction. The reaction was stirred at rt for about 2 h. The reaction was quenched with $NH_4Cl$ (10 mL) and extracted with EtOAc (10 mL). The organic layer was washed with brine (10 mL), dried over $Na_2SO_4$, filtered and concentrated in vacuo. The residue was purified by column chromatography ($SiO_2$, 0-2.5% MeOH/DCM) and column chromatography ($SiO_2$, 0-20% EtOAc/heptanes) to give rac-(4R,7R)-4-(4-bromo-2-methylphenyl)-1-methyl-3-(pyridin-2-yl)-7-(trifluoromethyl)-4,6,7,8-tetrahydro-M-pyrazolo[3,4-e][1,4]thiazepine compound (0.204 g, 0.422 mmol, 24%) as a white solid: LC-MS (Table 1, Method g) $R_t$=2.80 min, m/z 483/485 (M+H)$^+$; $^1$H-NMR (CDCl$_3$, Bruker 400 MHz) δ 8.37 (d, J=4.3 Hz, 1H), 7.82 (d, J=8.0 Hz, 1H), 7.66-7.57 (m, 1H), 7.31-7.25 (m, 1H), 7.14-7.03 (m, 2H), 6.83 (d, J=8.3 Hz, 1H), 6.51 (s, 1H), 4.04 (d, J=7.7 Hz, 1H), 3.94 (s, 3H), 3.75-3.60 (m, 1H), 3.05-2.94 (m, 2H), 2.65 (s, 3H) and rac-(4R,7S)-4-(4-bromo-2-methylphenyl)-1-methyl-3-(pyridin-2-yl)-7-(trifluoromethyl)-4,6,7,8-tetrahydro-1H-pyrazolo[3,4-e][1,4]thiazepine compound (0.192 g, 0.397 mmol, 23%) as a white solid: LC-MS (Table 1, Method g) $R_t$=2.87 min, m/z 483/485 (M+H)$^+$; $^1$H-NMR (CDCl$_3$, Bruker 400 MHz) δ 8.39-8.37 (m, 1H), 7.83-7.80 (m, 1H), 7.64-7.62 (m, 1H), 7.32 (d, J=1.8, 1H), 7.15-7.03 (m, 2H), 6.76 (d, J=8.2 Hz, 1H), 6.52 (s, 1H), 3.93 (s, 3H), 3.83-3.75 (m, 2H), 3.00-2.89 (m, 2H), 2.61 (s, 3H).

Example #10 rac-(4R,7S)-4-(4-bromo-2-methylphenyl)-1-methyl-3-(pyridin-2-yl)-4,6,7,8-tetrahydro-1H-pyrazolo[3,4-e][1,4]thiazepine-7-carboxamide

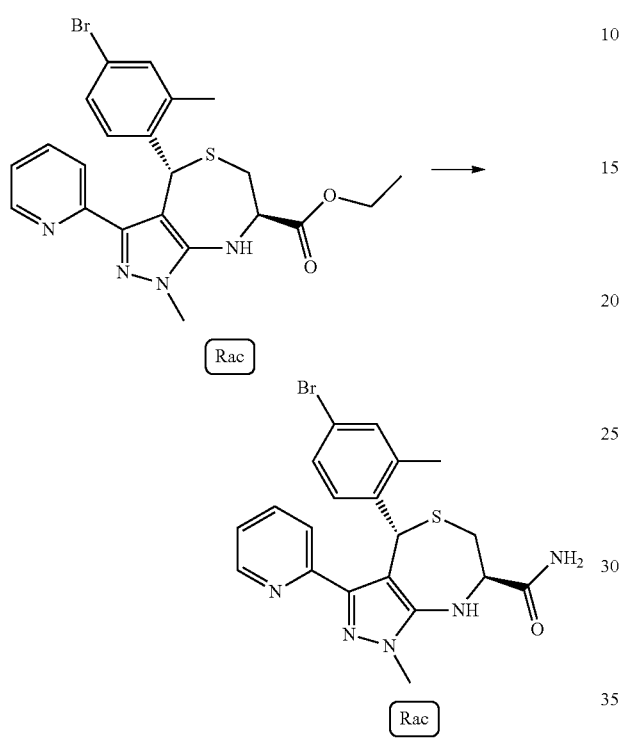

A mixture of rac-(4R,7S)-ethyl 4-(4-bromo-2-methylphenyl)-1-methyl-3-(pyridin-2-yl)-4,6,7,8-tetrahydro-1H-pyrazolo[3,4-e][1,4]thiazepine-7-carboxylate (0.170 g, 0.174 mmol, Preparation #39) and 2 M NaOH (1 mL, 2.00 mmol) in 1,4-dioxane (2 mL) was stirred at rt for about 2 h. The reaction was partitioned between 1 M HCl (40 mL) and EtOAc (50 mL). The organic layer was washed with brine (50 mL), dried with $Na_2SO_4$, filtered and was concentrated in vacuo. The residue was suspended in THF (4 ml) and di(1H-imidazol-1-yl)methanone (0.085 g, 0.52 mmol) was added followed by DMAP (0.026 g, 0.21 mmol). The reaction was stirred at rt for about 1 h. The reaction was quenched with $NH_4OH$ (5.0 mL) and extracted with EtOAc (50 mL). The organic layer was washed with brine (50 mL), dried with $Na_2SO_4$, filtered and was concentrated in vacuo. The residue was recrystallized from DCM/$Et_2O$ to give rac-(4R,7S)-4-(4-bromo-2-methylphenyl)-1-methyl-3-(pyridin-2-yl)-4,6,7,8-tetrahydro-1H-pyrazolo[3,4-e][1,4]thiazepine-7-carboxamide (0.080 g, 0.087 mmol, 50%), as a white solid: LC-MS (Table 1, Method g) $R_t$=2.12 min, m/z 458/460 (M+H)+; 1H-NMR (DMSO-$d_6$, Bruker 400 MHz) δ 8.43-8.40 (m, 1H), 7.81-7.77 (m, 1H), 7.73-7.65 (m, 1H), 7.34 (d, J=1.8 Hz, 1H), 7.23-7.19 (m, 1H), 7.17-7.12 (m, 1H), 7.11-7.08 (m, 2H), 6.99 (s, 1H), 6.61 (s, 1H), 5.82 (d, J=5.0 Hz, 1H), 4.11-4.07 (m, 1H), 3.77 (s, 3H), 3.20 (dd, J=15.2, 5.5 Hz, 1H), 2.83 (dd, J=15.3, 2.8 Hz, 1H), 2.48 (s, 3H).

Example #11 rac-(4R,7S)-4-(4-bromo-2-methylphenyl)-1-methyl-3-(pyridin-2-yl)-4,6,7,8-tetrahydro-1H-pyrazolo[3,4-e][1,4]thiazepine-7-carbonitrile

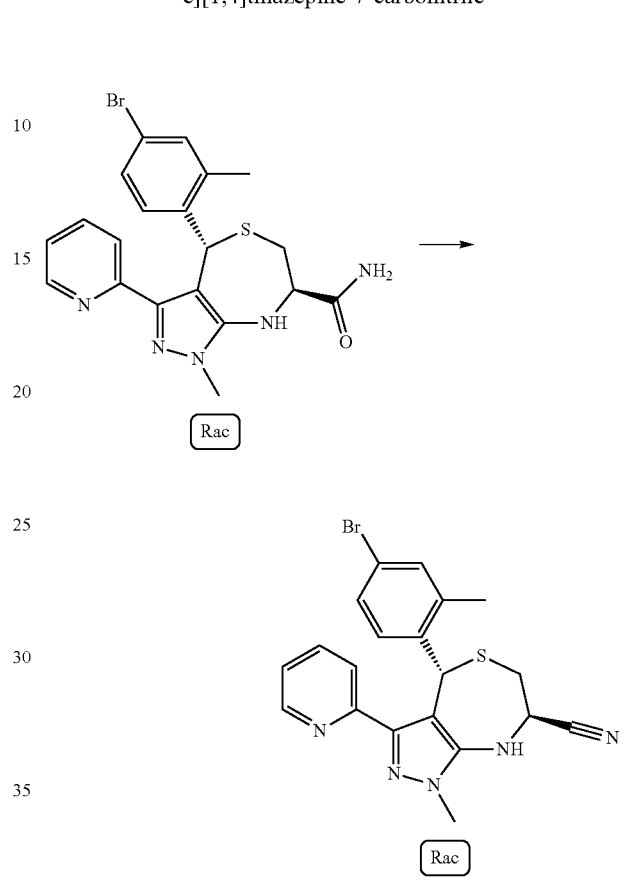

To a solution of rac-(4R,7S)-4-(4-bromo-2-methylphenyl)-1-methyl-3-(pyridin-2-yl)-4,6,7,8-tetrahydro-1H-pyrazolo[3,4-e][1,4]thiazepine-7-carboxamide (0.050 g, 0.055 mmol, Example #10) in DCE (0.5 ml)/pyridine (0.2 ml) at 0° C. was added $POCl_3$ (0.051 ml, 0.545 mmol) dropwise. The icebath was removed about 5 min after the complete addition. The reaction was stirred at rt for about 16 h. The reaction was quenched by adding it dropwise to stirring $H_2O$ (20 mL). A saturated solution of $NaHCO_3$ was added slowly until gas evolution had stopped. The reaction was extracted with DCM (50 mL). The organic layer was washed with brine (50 mL), dried over $Na_2SO_4$, filtered and was concentrated in vacuo. The residue was purified by column chromatography ($SiO_2$, 0-50% EtOAc/heptane) to give rac-(4R,7S)-4-(4-bromo-2-methylphenyl)-1-methyl-3-(pyridin-2-yl)-4,6,7,8-tetrahydro-1H-pyrazolo[3,4-e][1,4]thiazepine-7-carbonitrile (0.026 g, 0.028 mmol, 52%) as a white solid: LC-MS (Table 1, Method g): LC-MS (Table 1, Method g) $R_t$=2.52 min, m/z 440/442 (M+H)+; 1H-NMR (DMSO-$d_6$, Bruker 400 MHz) δ 8.50-8.47 (m, 1H), 7.85-7.82 (m, 1H), 7.79-7.71 (m, 1H), 7.39 (d, J=2.1 Hz, 1H), 7.26-7.19 (m, 2H), 7.08 (d, J=8.3 Hz, 1H), 6.82 (s, 1H), 6.62 (d, J=5.5 Hz, 1H), 5.02-4.98 (m, 1H), 3.79 (s, 3H), 3.04 (dd, J=15.3, 4.9 Hz, 1H), 2.80 (dd, J=15.4, 2.2 Hz, 1H), 2.51 (s, 3H).

Example #12 rac-2-((4R,7S)-4-(4-bromo-2-methylphenyl)-1-methyl-3-(pyridin-2-yl)-4,6,7,8-tetrahydro-1H-pyrazolo[3,4-e][1,4]thiazepin-7-yl)acetonitrile

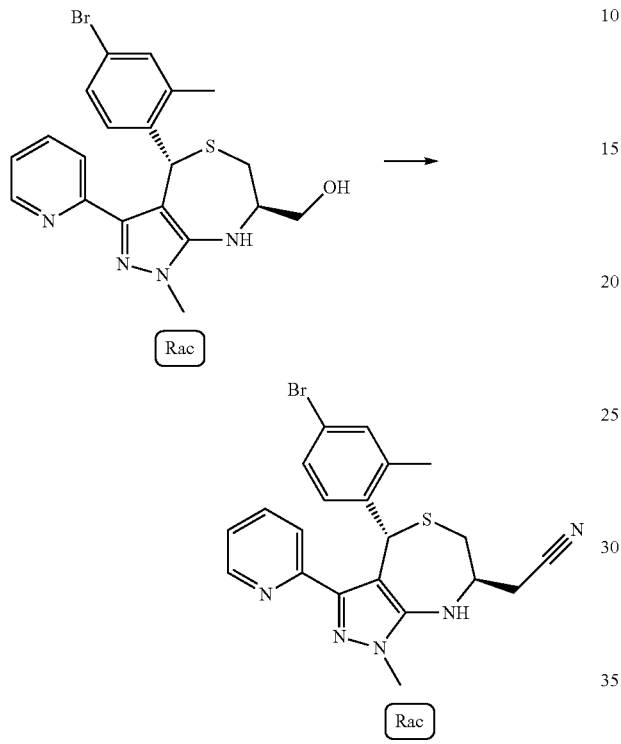

To a solution of rac-((4R,7S)-4-(4-bromo-2-methylphenyl)-1-methyl-3-(pyridin-2-yl)-4,6,7,8-tetrahydro-1H-pyrazolo[3,4-e][1,4]thiazepin-7-yl)methanol (0.070 g, 0.16 mmol, Example #K.10) and triphenylphosphine (0.041 g, 0.16 mmol) in DCM (5 ml)/DMF (0.5 ml) at 0° C. was added 1-bromopyrrolidine-2,5-dione (0.028 g, 0.16 mmol). The reaction was stirred at 0° C. for about 2 h. The reaction was partitioned between DCM (25 mL) and saturated solution of NaHCO$_3$ (40 mL). The organic layer was dried with Na$_2$SO$_4$, filtered and was concentrated in vacuo. The resulting residue was dissolved in DMF (1.5 ml) and cyanosodium (0.077 g, 1.57 mmol) was added. The reaction was heated at about 100° C. for about 1 h. The reaction was partitioned between EtOAc (25 mL) and brine (25 mL). The organic layer was washed with brine (25 mL), dried with Na$_2$SO$_4$, filtered and concentrated in vacuo. The residue was purified by column chromatography (SiO$_2$, 0-50% EtOAc/heptane) to give rac-2-((4R,7S)-4-(4-bromo-2-methylphenyl)-1-methyl-3-(pyridin-2-yl)-4,6,7,8-tetrahydro-1H-pyrazolo[3,4-e][1,4]thiazepin-7-yl)acetonitrile (0.005 g, 0.005 mmol, 3%) as a white solid: LC-MS (Table 1, Method g): LC-MS (Table 1, Method g) R$_t$=2.57 min, m/z 454/456 (M+H)$^+$; $^1$H-NMR (DMSO-d$_6$, Bruker 400 MHz) δ 8.48-8.45 (m, 1H), 7.83-7.80 (m, 1H), 7.75-7.70 (m, 1H), 7.36 (d, J=2.0 Hz, 1H), 7.26-7.17 (m, 2H), 7.09 (d, J=8.3 Hz, 1H), 6.74 (s, 1H), 6.19 (d, J=5.7 Hz, 1H), 4.03-3.92 (m, 1H), 3.77 (s, 3H), 2.95-2.85 (m, 2H), 2.79-2.74 (m, 1H), 2.71-2.63 (m, 1H), 2.50 (s, 3H).

Example #13

4-((4S,7R)-7-(hydroxymethyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide and 4-((4R,7S)-7-(hydroxymethyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide

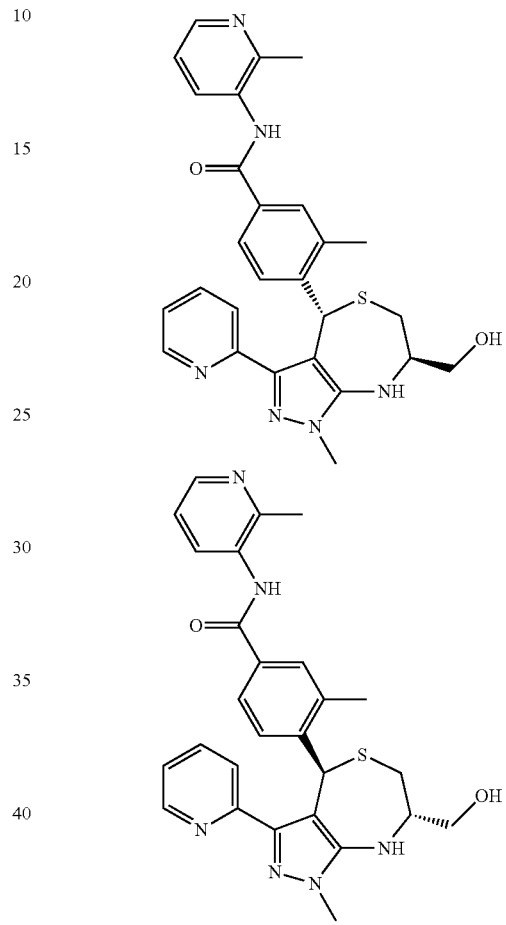

Step A: rac-(4R,7S)-4-(4-bromo-2-methylphenyl)-7-(((tert-butyldimethylsilyl)oxy)methyl)-1-methyl-3-(pyridin-2-yl)-4,6,7,8-tetrahydro-1H-pyrazolo[3,4-e][1,4]thiazepine

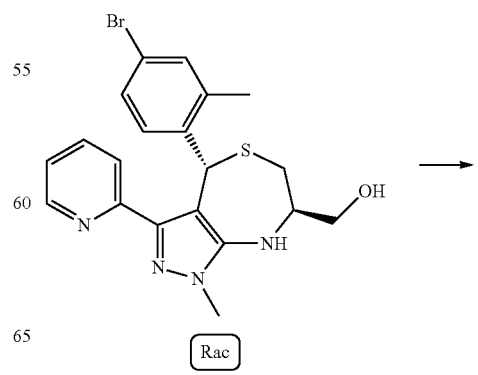

325

-continued

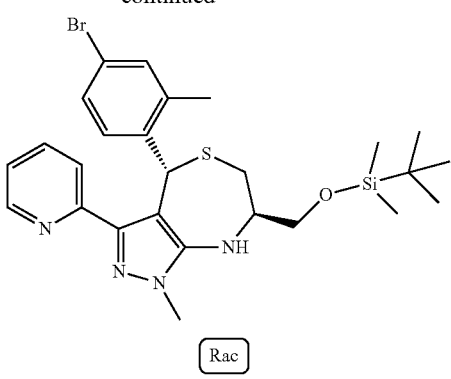

Rac

326

-continued

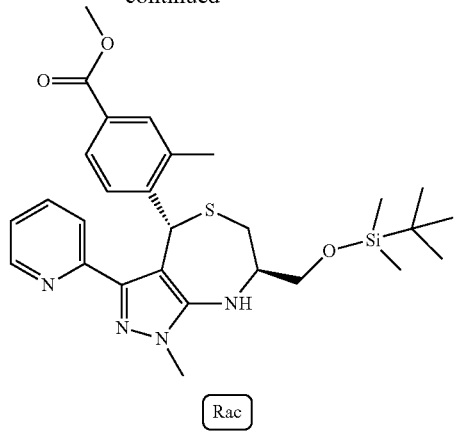

Rac

To a solution of rac-((4R,7S)-4-(4-bromo-2-methylphenyl)-1-methyl-3-(pyridin-2-yl)-4,6,7,8-tetrahydro-1H-pyrazolo[3,4-e][1,4]thiazepin-7-yl)methanol (0.67 g, 1.50 mmol, Example # K.10) and 1H-imidazole (0.205 g, 3.01 mmol) in DMF (15 ml) at 0° C. was added tert-butylchlorodimethylsilane (0.272 g, 1.81 mmol). The reaction was allowed to warm to rt. After about 3 h, 1H-imidazole (0.205 g, 3.01 mmol) and tert-butylchlorodimethylsilane (0.091 g, 0.602 mmol) were added to the reaction. The reaction was stirred at rt for about 16 h. The reaction was partitioned between EtOAc (100 mL) and brine (200 mL). The organic layer was washed with brine (100 mL), dried over $Na_2SO_4$, filtered and concentrated in vacuo. The residue was purified by column chromatography ($SiO_2$, 0-30% EtOAc/heptane) to give rac-(4R,7S)-4-(4-bromo-2-methylphenyl)-7-(((tert-butyldimethylsilyl)oxy)methyl)-1-methyl-3-(pyridin-2-yl)-4,6,7,8-tetrahydro-M-pyrazolo[3,4-e][1,4]thiazepine (0.54 g, 0.97 mmol, 64%) as a white solid: LC-MS (Table 1, Method g): LC-MS (Table 1, Method g) $R_t$=3.35 min, m/z 559/561 (M+H)$^+$; $^1$H-NMR (DMSO-$d_6$, Bruker 400 MHz) δ 8.47-8.44 (m, 1H), 7.81-7.78 (m, 1H), 7.76-7.66 (m, 1H), 7.35 (d, J=1.9 Hz, 1H), 7.26-7.13 (m, 3H), 6.69 (s, 1H), 5.82-5.79 (m, 1H), 3.80-3.59 (m, 5H), 3.50-3.44 (m, 1H), 2.83-2.80 (m, 2H), 2.50 (s, 3H), 0.84 (s, 9H), 0.04--0.02 (m, 6H).

Step B: rac-methyl 4-((4R,7S)-(7-(((tert-butyldimethylsilyl)oxy)methyl)-1-methyl-3-(pyridin-2-yl)-4,6,7,8-tetrahydro-1H-pyrazolo[3,4-e][1,4]thiazepin-4-yl)-3-methylbenzoate

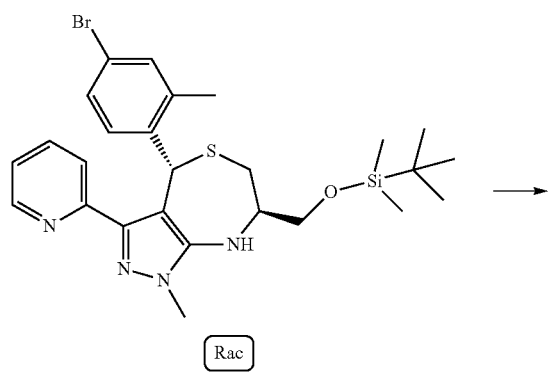

Rac

A microwave vial charged with rac-(4R,7S)-4-(4-bromo-2-methylphenyl)-7-(((tert-butyldimethylsilyl)oxy)methyl)-1-methyl-3-(pyridin-2-yl)-4,6,7,8-tetrahydro-1H-pyrazolo[3,4-e][1,4]thiazepine (0.54 g, 0.965 mmol), diacetoxypalladium (0.022 g, 0.096 mmol) and dppf (0.107 g, 0.193 mmol) was evacuated and back-filled with $N_2$ 3 times. DMF (8 mL) was added. The vial was degassed and filled with CO. MeOH (1.9 mL, 48.2 mmol) and TEA (0.67 mL, 4.8 mmol) were added. The mixture was heated at about 85° C. for about 2 h. The reaction was partitioned between EtOAc (100 mL) and brine (200 mL). The aqueous layer was further extracted with EtOAc (50 ml). Organic layers were combined, washed with brine (100 mL), dried over $Na_2SO_4$, filtered and concentrated in vacuo. The residue was purified by column chromatography ($SiO_2$, 0-30% EtOAc/heptane) to give rac-methyl 4-((4R,7S)-(7-(((tert-butyldimethylsilyl)oxy)methyl)-1-methyl-3-(pyridin-2-yl)-4,6,7,8-tetrahydro-1H-pyrazolo[3,4-e][1,4]thiazepin-4-yl)-3-methylbenzoate (0.30 g, 0.56 mmol, 58% yield) as an off-white foam: LC-MS (Table 1, Method g) $R_t$=3.17 min, m/z 539 (M+H)$^+$; $^1$H-NMR (DMSO-$d_6$, Bruker 400 MHz) δ 8.47-8.44 (m, 1H), 7.81-7.78 (m, 1H), 7.74 (d, J=1.5 Hz, 1H), 7.73-7.66 (m, 1H), 7.64-7.60 (m, 1H), 7.39-7.36 (m, 1H), 7.20-7.16 (m, 1H), 6.77 (s, 1H), 5.84 (d, J=5.2 Hz, 1H), 3.80 (s, 3H), 3.77-3.57 (m, 5H), 3.52-3.46 (m, 1H), 2.87-2.74 (m, 2H), 2.56 (s, 3H), 0.84 (s, 9H), 0.03-0.00 (m, 6H).

Step C: rac-4-((4R,7S)(7-(((tert-butyldimethylsilyl)oxy)methyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide

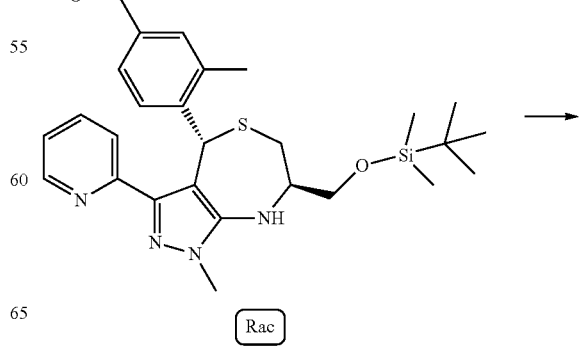

Rac

327
-continued

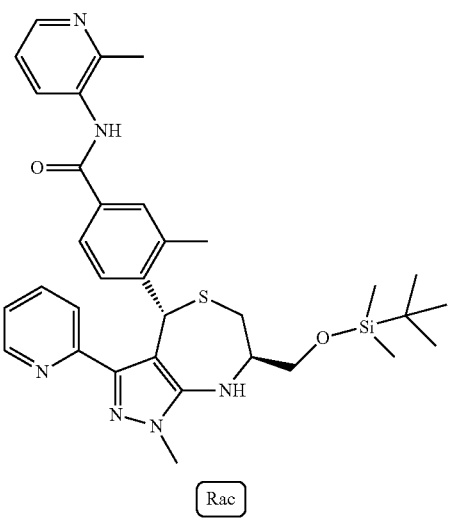

To a solution of rac-methyl 4-((4R,7S)-(7-(((tert-butyldimethylsilyl)oxy)methyl)-1-methyl-3-(pyridin-2-yl)-4,6,7,8-tetrahydro-1H-pyrazolo[3,4-e][1,4]thiazepin-4-yl)-3-methylbenzoate (0.300 g, 0.56 mmol) and 2-methylpyridin-3-amine (0.181 g, 1.67 mmol, Appollo) in THF (6 ml) at about 0° C. was added 1 M lithium bis(trimethylsilyl)amide in hexane (2.78 ml, 2.78 mmol). About 5 min after the complete addition, the cold bath was removed and the reaction was stirred for about 2 h at rt. The reaction was quenched with saturated NH$_4$Cl (50 mL) and extracted with EtOAc (50 mL). The organic layer was washed with brine (50 mL), dried over Na$_2$SO$_4$, filtered and was concentrated in vacuo. The residue was purified by column chromatography (SiO$_2$, 50-100% EtOAc/heptane) to give rac-4-((4R,7S)(7-(((tert-butyldimethylsilyl)oxy)methyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide (0.29 g, 0.47 mmol, 85%) as a pale yellow film: LC-MS (Table 1, Method g) R$_t$=2.83 min, m/z 615 (M+H)$^+$; $^1$H-NMR (DMSO-d$_6$, Bruker 400 MHz) δ 9.84 (s, 1H), 8.48-8.44 (m, 1H), 8.30 (d, J=4.6 Hz, 1H), 7.81-7.78 (m, 1H), 7.73-7.66 (m, 2H), 7.64-7.60 (m, 1H), 7.39-7.36 (m, 1H), 7.28-7.16 (m, 2H), 6.87 (d, J=3.1 Hz, 1H), 6.80 (s, 1H), 5.86 (d, J=5.2 Hz, 1H), 4.96 (s, 1H), 3.78-3.61 (m, 4H), 3.52 (s, 1H), 2.87-2.74 (m, 2H), 2.57 (s, 3H), 2.40 (s, 3H), 0.83 (s, 9H), 0.12--0.15 (m, 6H).

328
Step D: rac-4-((4R,7S)-7-(hydroxymethyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide

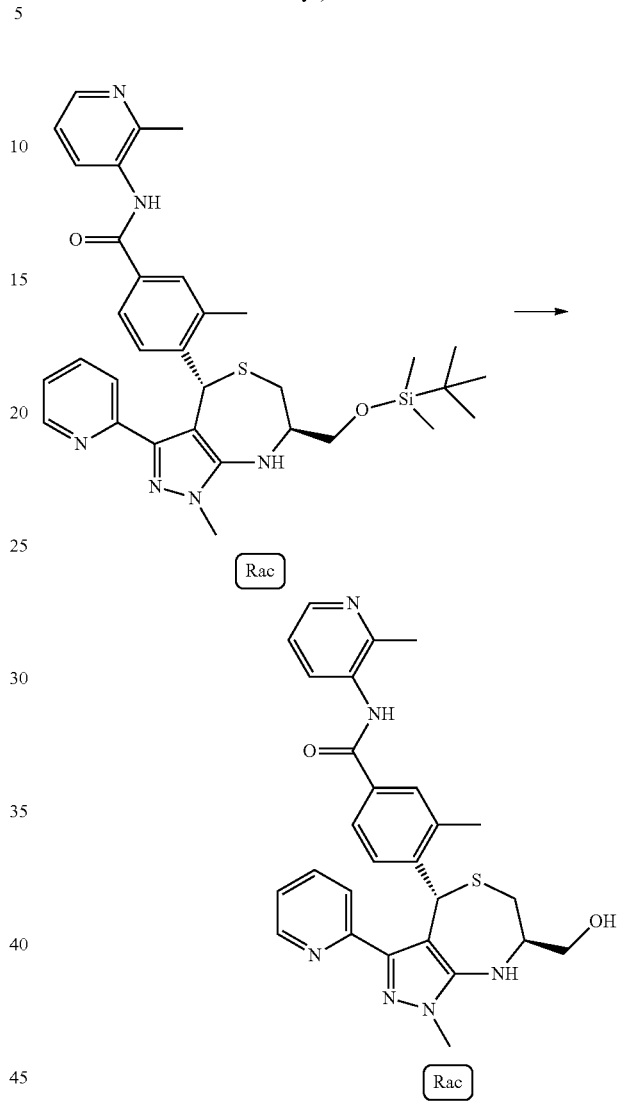

To a solution of rac-4-((4R,7S)(7-(((tert-butyldimethylsilyl)oxy)methyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide (0.29 g, 0.47 mmol) in THF (5 ml) was added 1 M tetrabutylammonium fluoride in THF (0.47 ml, 0.47 mmol). The reaction was stirred at rt for about 2 h. The reaction was partitioned between EtOAc (50 mL) and brine (50 mL). The organic layer was washed with brine (50 mL), dried with Na$_2$SO$_4$, filtered and concentrated in vacuo. The residue was purified by column chromatography (SiO$_2$, 0-5% MeOH/DCM) and the concentrated fractions were dissolved in DCM (3 mL) and the resulting precipitate was collected by filtration to give rac-4-((4R,7S)-7-(hydroxymethyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide (0.200 g, 0.399 mmol, 85%) as a white solid: LC-MS (Table 1, Method g) R$_t$=1.63 min, m/z 501 (M+H)$^+$; $^1$H-NMR (DMSO-d$_6$, Bruker 400 MHz) δ 9.84 (s, 1H), 8.49-8.46 (m, 1H), 8.31-8.28 (m, 1H), 7.86-7.67 (m, 4H), 7.65-7.61 (m, 1H), 7.44 (d, J=8.0 Hz, 1H), 7.26-7.17 (m, 2H), 6.76 (s, 1H), 5.80 (d, J=4.7 Hz, 1H), 4.75-4.71 (m, 1H), 3.75 (s, 3H), 3.54-3.44 (m, 3H), 2.89-2.77 (m, 2H), 2.60 (s, 3H), 2.40 (s, 3H).

Step E: 4-((4S,7R)-7-(hydroxymethyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide and 4-((4R,7S)-7-(hydroxymethyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide

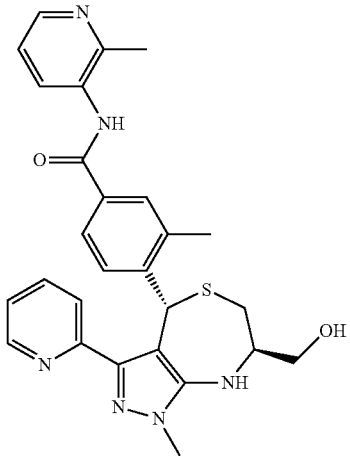

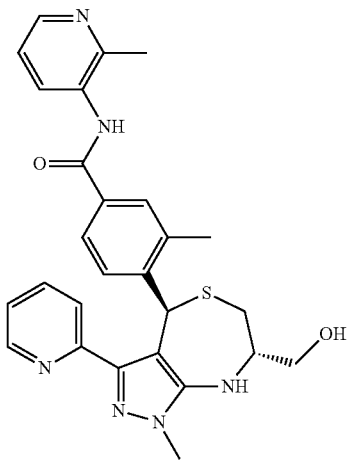

rac-4-((4R,7S)-7-(hydroxymethyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide (0.200 g, 0.399 mmol) was separated using chiral chromatography (Table 3, Method 32) to yield 4-((4S,7R)-7-(hydroxymethyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide (0.050 g, 0.100 mmol, 21%) as a white solid (Table 3, Method 32, $R_t$=23.44 min, or =negative. LC-MS (Table 1, Method g) $R_t$=1.63 min. m/z: 501 (M+H)$^+$) and 4-((4R,7S)-7-(hydroxymethyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide (0.050 g, 0.100 mmol, 21%)) as a white solid (Table 3, Method 32, $R_t$=31.53 min, or =positive. LC-MS (Table 1, Method g) $R_t$=1.63 min. m/z: 501 (M+H)$^+$)

Example #14 rac-4-(1-(4-fluorophenyl)-6-methyl-1H-indazol-5-yl)-1-methyl-3-(pyridin-2-yl)-6,8-dihydro-1H-pyrazolo[3,4-e][1,4]thiazepin-7(4H)-one

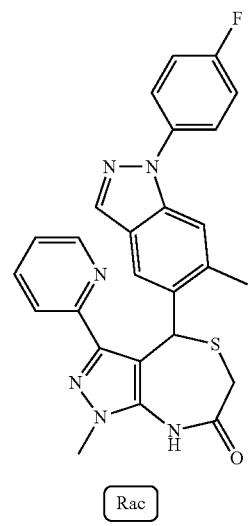 [SMILES: Cc1cc2c(cnn2-c2ccc(F)cc2)cc1C1SCC(=O)Nc2c1c(-c1ccccn1)nn2C]

Step A:
5-bromo-1-(4-fluorophenyl)-6-methyl-1H-indazole

To a solution of 5-bromo-6-methyl-1H-indazole (2.89 g, 13.69 mmol,) in DCM (137 mL) was added 4-fluorophenylboronic acid (3.83 g, 27.4 mmol), diacetoxycopper (2.48 g, 13.7 mmol), pyridine (2.2 mL, 27.4 mmol) and 4 Å molecular sieves. The reaction was stirred open to air for about 4 h. The reaction mixture was filtered through a pad of Celite® rinsing with EtOAc (80 mL) and then concentrated to about (60 mL) under reduced pressure. Water was added (40 mL) and the layers were separated. The aqueous layer was back extracted with EtOAc (20 mL). The combined organic layers were dried over MgSO$_4$, filtered and concentrated under reduced pressure. The resulting residue was purified by column chromatography (SiO$_2$, EtOAc/heptane 100:0 to 0:20) to afford 5-bromo-1-(4-fluorophenyl)-6-methyl-1H-indazole (2.68 g, 8.78 mmol, 64%). LC-MS (Table 1, Method g) R$_t$=2.75 min, m/z 305, 307 (M+H)$^+$. $^1$H NMR (CDCl$_3$) δ 8.07 (s, 1H), 7.98 (s, 1H), 7.69-7.59 (m, 2H), 7.52 (s, 1H), 7.28-7.18 (m, 2H), 2.53 (s, 3H).

Step B: methyl 1-(4-fluorophenyl)-6-methyl-1H-indazole-5-carboxylate

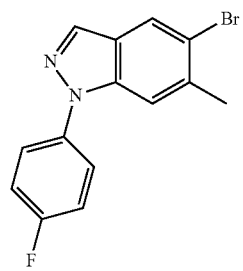

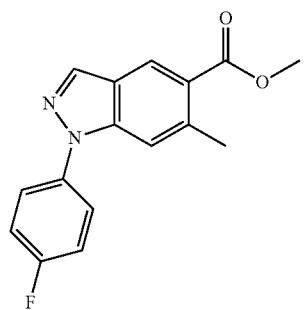

A microwave vial was charged with 5-bromo-1-(4-fluorophenyl)-6-methyl-1H-indazole (0.29 g, 0.94 mmol), Pd(OAc)$_2$ (0.02 g, 0.09 mmol), dppf (0.10 g, 0.19 mmol) and DMF (5.4 mL). Nitrogen was bubbled through the reaction mixture for about 10 min. The mixture was evacuated and then back-filled with CO three times. Methanol (1.9 mL, 46.9 mmol) and triethylamine (0.65 mL, 4.69 mmol) were added. The reaction mixture was heated, in a sealed microwave vessel, for about 24 h at about 90° C. After cooling to rt, the mixture was partially concentrated under reduced pressure. The residue was partitioned between EtOAc (40 mL) and water (10 mL). The organic layer was washed with brine (10 mL), dried over MgSO$_4$, filtered and concentrated under reduced pressure. The residue was purified by column chromatography (SiO$_2$, EtOAc/heptane 100:0 to 0:50) to afford methyl 1-(4-fluorophenyl)-6-methyl-1H-indazole-5-carboxylate (0.25 g, 0.87 mmol, 93%). LC-MS (Table 1, Method g) R$_t$=2.48 min, m/z 285 (M+H)$^+$. $^1$H NMR (CDCl$_3$) δ 8.48 (s, 1H), 8.20 (s, 1H), 7.71-7.63 (m, 2H), 7.47 (s, 1H), 7.30-7.20 (m, 2H), 3.93 (s, 3H), 2.74 (s, 3H).

Step C: (1-(4-fluorophenyl)-6-methyl-1H-indazol-5-yl)methanol

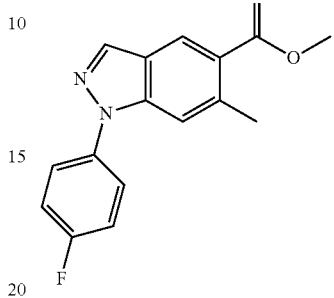

A solution of methyl 1-(4-fluorophenyl)-6-methyl-1H-indazole-5-carboxylate (1.52 g, 5.35 mmol) and THF (36 mL) was cooled to about 0° C. and to it was added DIBAL-H (1 M solution in toluene, 11.2 mL, 11.2 mmol) and stirred for about 2 h. To the reaction mixture was added DIBAL-H (1 M solution in toluene, 6.0 mL, 6.0 mmol) and stirring was continued for 2 h. The reaction was quenched with EtOAc (~20 mL) and allowed to warm to ambient temperature. To the reaction mixture was added 10% aqueous Rochelle's salt (40 mL) and stirred for about 16 h. The reaction mixture was partially concentrated under reduced pressure and partitioned between EtOAc (60 mL) and water (20 mL). The aqueous layer was back extracted with EtOAc (30 mL). The combined organic layers were dried over MgSO4, filtered and concentrated under reduced pressure. The residue was purified by column chromatography (SiO$_2$, DCM/MeOH 100:0 to 0:10) to afford (1-(4-fluorophenyl)-6-methyl-1H-indazol-5-yl)methanol (1.14 g, 4.45 mmol, 83%). LC-MS (Table 1, Method g) R$_t$=2.01 min, m/z 257 (M+H)$^+$.

Step D: 1-(4-fluorophenyl)-6-methyl-1H-indazole-5-carbaldehyde

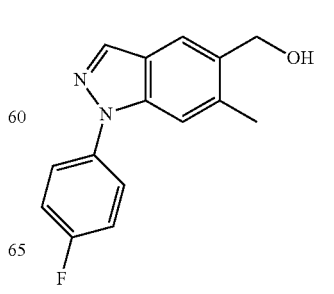

-continued

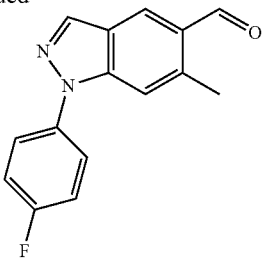

A solution of (1-(4-fluorophenyl)-6-methyl-1H-indazol-5-yl)methanol (1.14 g, 4.45 mmol) was dissolved in DCM (46 mL) and treated with Dess-Martin periodinane (1.87 g, 4.45 mmol). The reaction was stirred at ambient temperature for about 1 h and filtered over a plug of $SiO_2$ rinsing with DCM (50 mL). The filtrate was partially concentrated under reduced pressure and then filtered over a second plug of $SiO_2$ rinsing with DCM (40 mL). The filtrate was concentrated under reduced pressure and the crude material was purified by column chromatography (EtOAc/heptane 100:0 to 0:60) to afford 1-(4-fluorophenyl)-6-methyl-1H-indazole-5-carbaldehyde (1.09 g, 4.29 mmol, 96%). LC-MS (Table 1, Method g) $R_t$=2.01 min, m/z 257 (M+H)$^+$. $^1$H NMR (CDCl$_3$) δ 10.27 (s, 1H), 8.29 (bs, 2H), 7.72-7.63 (m, 2H), 7.45 (s, 1H), 7.32-7.23 (m, 2H), 2.80 (s, 3H).

Step E: rac-4-(1-(4-fluorophenyl)-6-methyl-1H-indazol-5-yl)-1-methyl-3-(pyridin-2-yl)-6,8-dihydro-1H-pyrazolo[3,4-e][1,4]thiazepin-7(4H)-one A reaction vial was charged with 1-methyl-3-(pyridin-2-yl)-1H-pyrazol-5-amine (0.07 g, 0.39 mmol, Example #2, step B), 1-(4-fluorophenyl)-6-methyl-1H-indazole-5-carbaldehyde (0.10 g, 0.39 mmol) and water (0.4 mL). The mixture was stirred for about 1 min then 2-mercaptoacetic acid (0.03 mL, 0.39 mmol) was added and the vial was sealed and warmed in a preheated bath to about 110° C. After stirring for 30 min, 2-mercaptoacetic acid (0.014 mL, 0.20 mmol) was added and continued heating for about 90 min. The vial was cooled to ambient temperature and the water was decanted. The solid was sonicated in Et$_2$O (30 mL) and collected by vacuum filtration. The solid was then rinsed with heptane (30 mL) then dissolve in DCM and purified by column chromatography (EtOAc/heptane 100:0 to 0:100) to afford rac-4-(1-(4-fluorophenyl)-6-methyl-1H-indazol-5-yl)-1-methyl-3-(pyridin-2-yl)-6,8-dihydro-1H-pyrazolo[3,4-e][1,4]thiazepin-7(4H)-one (0.06 g, 0.12 mmol, 29%). LC-MS (Table 1, Method g) $R_t$=2.32 min, m/z 485 (M+H)$^+$. $^1$H NMR (DMSO-d$_6$, 400 MHz) δ 10.11 (s, 1H), 8.36-8.30 (m, 1H), 8.10 (s, 1H), 7.79-7.69 (m, 3H), 7.64-7.60 (m, 1H), 7.54 (s, 1H), 7.40-7.36 (m, 2H), 7.27 (s, 1H), 7.12-7.04 (m, 1H), 6.74 (s, 1H), 3.90 (s, 3H), 3.42-3.38 (m, 1H), 3.18-3.14 (m, 1H), 2.70 (s, 3H).

Example #15 rac-4-((4R,7R)-7-hydroxy-1-methyl-3-(pyridin-2-yl)-7-(trifluoromethyl)-1,4,5,6,7,8-hexahydrocyclohepta[c]pyrazol-4-yl)-3-methyl-N-(2-methylpyridin-3-yl)benzamide and rac-4-((4R,7S)-7-hydroxy-1-methyl-3-(pyridin-2-yl)-7-(trifluoromethyl)-1,4,5,6,7,8-hexahydrocyclohepta[c]pyrazol-4-yl)-3-methyl-N-(2-methylpyridin-3-yl)benzamide

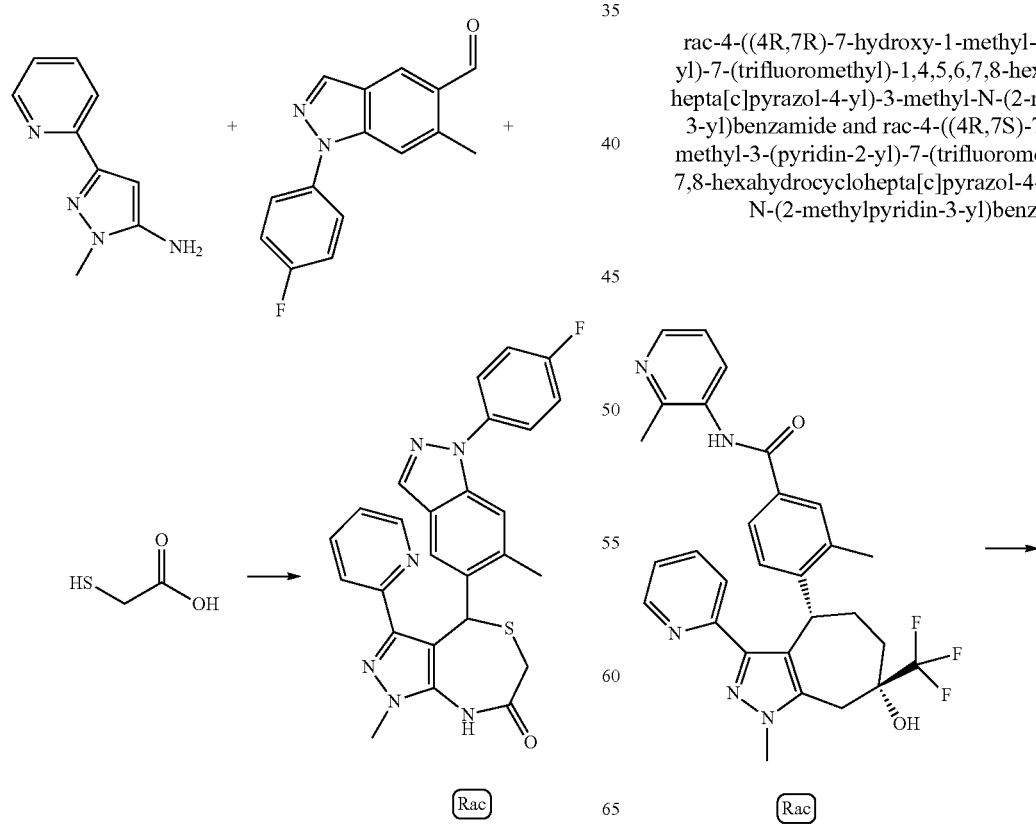

-continued

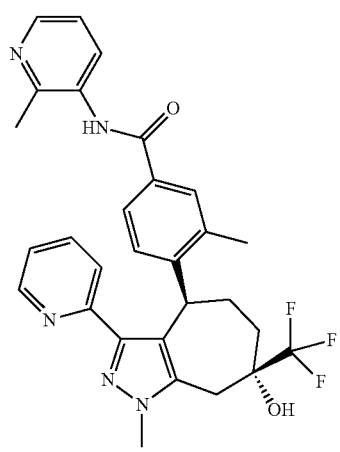

Step A: 1-methyl-3-(pyridin-2-yl)-1H-pyrazol-5-ol

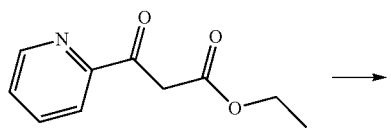

To a solution of ethyl 3-oxo-3-(pyridin-2-yl)propanoate (25.00 g, 129 mmol, Matrix Scientific) in EtOH (60 mL) was added methylhydrazine (6.81 mL, 129 mmol). The mixture was heated at about 85° C. for about 3 h then cooled to rt and concentrated at rt under reduced pressure. The material was triturated with Et$_2$O (40 mL). The solids were collected by filtration then washed with Et$_2$O to give 1-methyl-3-(pyridin-2-yl)-1H-pyrazol-5-ol (17.80 g, 79%). The filtrate was concentrated under reduced pressure then the material was triturated with 1:1 DCM/Et$_2$O. The solids were collected by filtration and washed with Et$_2$O to give a second crop of 1-methyl-3-(pyridin-2-yl)-1H-pyrazol-5-ol (1.20 g, 5%): LC-MS (Table 1, Method g) R$_t$=1.05 min, m/z 176 (M+H)$^+$; $^1$H-NMR (DMSO, Bruker 400 MHz) δ 11.05 (s, 1H), 8.50-8.47 (m, 1H), 7.83-7.80 (m, 1H), 7.78-7.69 (m, 1H), 7.24-7.19 (m, 1H), 5.90 (s, 1H), 3.57 (s, 3H).

Step B: 5-chloro-1-methyl-3-(pyridin-2-yl)-1H-pyrazole-4-carbaldehyde

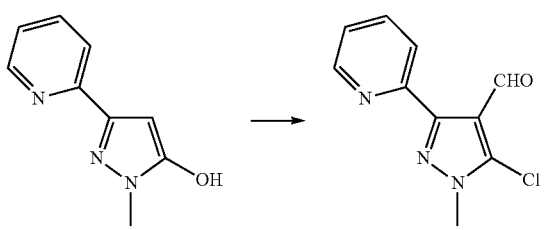

DMF (35 mL) was cooled to 0° C. in an ice bath. POCl$_3$ (99 mL, 1059 mmol) was added dropwise followed by addition of 1-methyl-3-(pyridin-2-yl)-1H-pyrazol-5-ol (26.5 g, 151 mmol). The resulting suspension was heated at about 80° C. for about 18 h. The mixture was allowed to cool to rt then added to ice-water (2000 mL). Saturated aqueous Na$_2$CO$_3$ was slowly added until the solution reached a pH>7. The resulting suspension was filtered and the solids washed with H$_2$O (200 mL). The filter cake was dissolved in DCM (500 mL), dried over Na$_2$SO$_4$, filtered and concentrated in vacuo to give 5-chloro-1-methyl-3-(pyridin-2-yl)-1H-pyrazole-4-carbaldehyde (21.38 g, 64%) as a yellow solid: LC-MS (Table 1, Method g) R$_t$=1.72 min, m/z 222 (M+H)$^+$; $^1$H-NMR (DMSO, Bruker 400 MHz) δ 10.58 (s, 1H), 8.68-8.64 (m, 1H), 8.01-7.87 (m, 2H), 7.49-7.40 (m, 1H), 3.91 (s, 3H).

Step C: (5-chloro-1-methyl-3-(pyridin-2-yl)-1H-pyrazol-4-yl)(4-chloro-2-methylphenyl)methanol

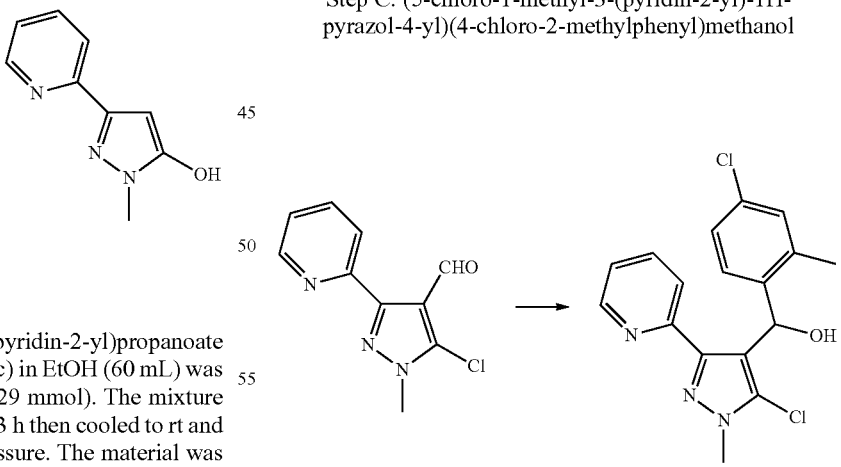

5-chloro-1-methyl-3-(pyridin-2-yl)-1H-pyrazole-4-carbaldehyde (16.38 g, 73.9 mmol) in THF (350 mL) was cooled to about −40 to −50° C. then 0.5 M (4-chloro-2-methylphenyl)magnesium bromide in THF (163 mL, 81 mmol) was added dropwise over about 15 min. The mixture was allowed to warm to rt then cooled in an ice bath. Saturated aqueous NH₄Cl (400 mL) was added then the mixture was extracted with EtOAc (2×300 mL). The organic layer was washed by brine (400 mL), dried over Na₂SO₄, filtered and concentrated in vacuo to give (5-chloro-1-methyl-3-(pyridin-2-yl)-1H-pyrazol-4-yl)(4-chloro-2-methylphenyl)methanol (25.7 g, 100%): LC-MS (Table 1, Method g) R$_f$=2.49 min, m/z 348/350 (M+H)⁺; ¹H-NMR (DMSO, Bruker 400 MHz) δ 8.56 (d, J=5.0 Hz, 1H), 8.03 (d, J=8.1 Hz, 1H), 7.96-7.90 (m, 1H), 7.40-7.36 (m, 1H), 7.22-7.16 (m, 3H), 7.09-7.05 (m, 1H), 6.23 (d, J=7.8 Hz, 1H), 3.87 (s, 3H), 2.26 (s, 3H).

Step D: (5-chloro-1-methyl-3-(pyridin-2-yl)-1H-pyrazol-4-yl)(4-chloro-2-methylphenyl)methanone

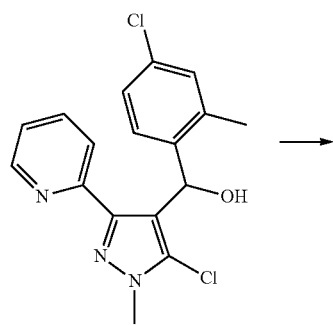

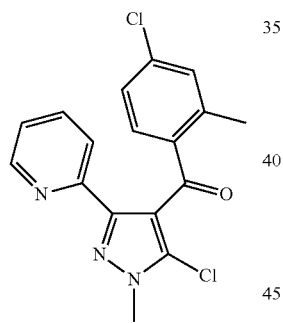

To a solution of (5-chloro-1-methyl-3-(pyridin-2-yl)-1H-pyrazol-4-yl)(4-chloro-2-methylphenyl)methanol (31.6 g, 91 mmol) in DCM (500 mL) at about 0° C. was added Dess-Martin periodinane (42.3 g, 100 mmol). The cold bath was removed and the mixture was allowed to warm to rt. After about 3 h additional Dess-Martin periodinane (1.92 g, 4.54 mmol) was added and the mixture was stirred for about 30 min. A saturated aqueous NaHCO₃ solution (500 mL) was added then the mixture was filtered. The solvent layers of the filtrate were separated. The filter cake was triturated with DCM then filtered. The combined organic layers were washed with brine (500 mL), dried over Na₂SO₄, filtered and concentrated in vacuo. The residue was heated in EtOAc (300 mL) to just below the boiling point then filtered. The filtrate was allowed to cool to rt and the precipitate was collected by filtration. Additional crops of desired product were obtained by concentration of the filtrate followed by precipitation with Et₂O/heptane. The crops were combined to give (5-chloro-1-methyl-3-(pyridin-2-yl)-1H-pyrazol-4-yl)(4-chloro-2-methylphenyl)methanone (23.47 g, 75%): LC-MS (Table 1, Method g) R$_f$=2.43 min, m/z 346/348 (M+H)⁺; ¹H-NMR (DMSO, Bruker 400 MHz) δ 8.20-8.15 (m, 1H), 7.77-7.67 (m, 2H), 7.33-7.28 (m, 1H), 7.21-7.13 (m, 2H), 7.08-7.01 (m, 1H), 3.96-3.89 (s, 3H), 2.50 (s, 3H).

Step E: 2-(5-chloro-4-(1-(4-chloro-2-methylphenyl)-2-methoxyvinyl)-1-methyl-1H-pyrazol-3-yl)pyridine

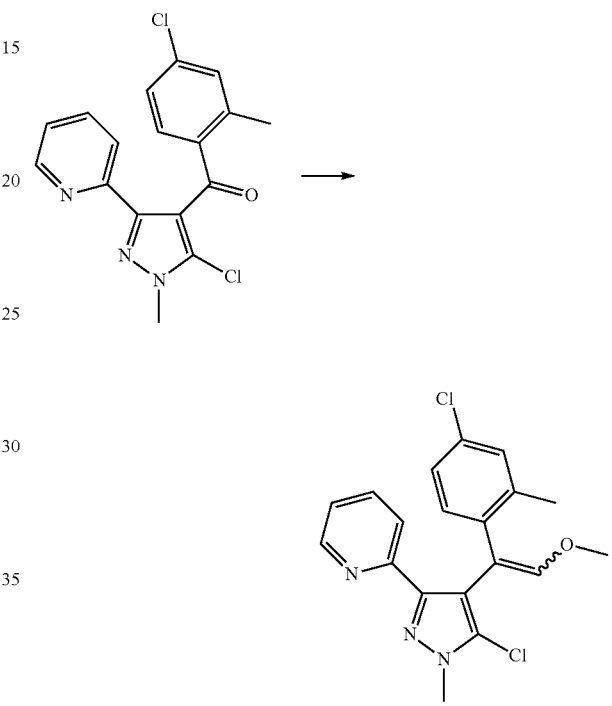

To a solution of (methoxymethyl)triphenylphosphonium chloride (91 g, 265 mmol) in THF (330 mL) at about −10° C. was added 1.6 M butyllithium in hexanes (161 mL, 258 mmol) dropwise. The mixture was stirred at about −10° C. for about 1 h. A solution of (5-chloro-1-methyl-3-(pyridin-2-yl)-1H-pyrazol-4-yl)(4-chloro-2-methylphenyl)methanone (22.35 g, 64.6 mmol) in THF (220 mL) was added to the mixture in a dropwise manner. The mixture was stirred at about −10° C. for about 16 h then treated with a saturated aqueous NH₄Cl solution (1000 mL). The mixture was extracted with EtOAc (2×700 mL). The combined organic layers were washed with brine (500 mL), dried with Na₂SO₄, filtered and concentrated in vacuo. The residue was purified by column chromatography (SiO₂, 0-25% EtOAc/heptanes) to give 2-(5-chloro-4-(1-(4-chloro-2-methylphenyl)-2-methoxyvinyl)-1-methyl-1H-pyrazol-3-yl)pyridine (16.65 g, 69%): LC-MS (Table 1, Method g) R$_f$=2.56 min, m/z 374/376 (M+H)⁺; ¹H-NMR (CDCl₃, Bruker 400 MHz) δ 8.44-8.39 (m, 1H), 7.70-7.58 (m, 2H), 7.21-6.93 (m, 4H), 6.39 (s, 1H), 3.90 (s, 3H), 3.64 (s, 3H), 2.28 (2s, 3H) major; ¹H-NMR (CDCl₃, Bruker 400 MHz) δ 8.44-8.39 (m, 1H), 7.70-7.58 (m, 2H), 7.21-6.93 (m, 4H), 6.38 (s, 1H), 3.88 (s, 3H), 3.52 (s, 3H), 2.20 (s, 3H) minor.

339

Step F: 2-(5-chloro-1-methyl-3-(pyridin-2-yl)-1H-pyrazol-4-yl)-2-(4-chloro-2-methylphenyl)acetaldehyde

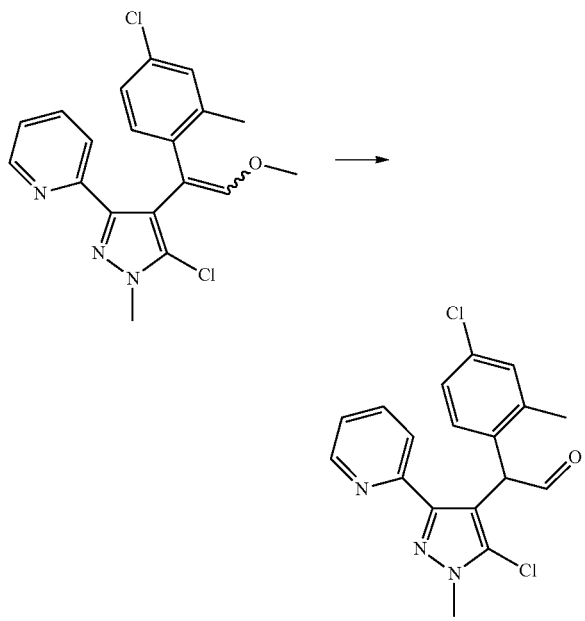

To a solution of 2-(5-chloro-4-(1-(4-chloro-2-methylphenyl)-2-methoxyvinyl)-1-methyl-1H-pyrazol-3-yl)pyridine (16.6 g, 44.4 mmol) in dioxane (80 mL) was added 6 N HCl (340 mL, 2040 mmol). The mixture was heated at about 70° C. for about 10 h then allowed to cool to rt. The mixture was neutralized with a saturated aqueous NaHCO₃ solution then extracted with EtOAc (2×500 mL). The combined organic layers were washed with brine (500 mL), dried with Na₂SO₄, filtered and concentrated in vacuo to give 2-(5-chloro-1-methyl-3-(pyridin-2-yl)-1H-pyrazol-4-yl)-2-(4-chloro-2-methylphenyl)acetaldehyde (15.98 g, 100%): LC-MS (Table 1, Method g) $R_t$=2.48 min, m/z 360/362 (M+H)⁺; ¹H-NMR (CDCl₃, Bruker 400 MHz) δ 9.83 (s, 1H), 8.41-8.37 (m, 1H), 8.02-7.98 (m, 1H), 7.74-7.68 (m, 1H), 7.23-7.13 (m, 2H), 7.05-6.97 (m, 1H), 6.93 (d, J=8.4 Hz, 1H), 5.75 (s, 1H), 3.94 (s, 3H), 2.37 (s, 3H).

Step G: (Z)-methyl 4-(5-chloro-1-methyl-3-(pyridin-2-yl)-1H-pyrazol-4-yl)-4-(4-chloro-2-methylphenyl)but-3-enoate

340

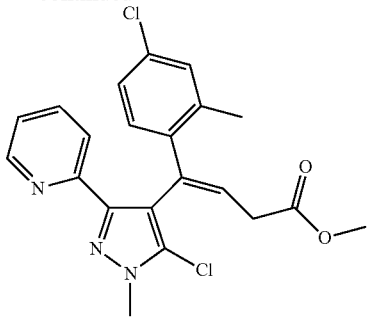

To a solution of 2-(5-chloro-1-methyl-3-(pyridin-2-yl)-1H-pyrazol-4-yl)-2-(4-chloro-2-methylphenyl)acetaldehyde (13 g, 36.1 mmol) in THF (200 mL) was added methyl (triphenylphosphoranylidene)acetate (24.13 g, 72.2 mmol). The mixture was stirred at about 60° C. for about 16 h then cooled in an ice bath. The solids were removed by filtration then filtrate was concentrated in vacuo. The residue was purified by column chromatography (SiO₂, 0-20% EtOAc/heptanes) to give (Z)-methyl 4-(5-chloro-1-methyl-3-(pyridin-2-yl)-1H-pyrazol-4-yl)-4-(4-chloro-2-methylphenyl)but-3-enoate (13.34 g, 89%): LC-MS (Table 1, Method g) $R_t$=2.62 min, m/z 416/418 (M+H)⁺; ¹H-NMR (DMSO, Bruker 400 MHz) δ 8.41-8.38 (m, 1H), 7.81-7.70 (m, 2H), 7.27-7.20 (m, 1H), 7.19-7.17 (m, 1H), 7.09-7.05 (m, 1H), 7.02-6.99 (m, 1H), 5.91 (t, J=7.3 Hz, 1H), 3.91 (s, 3H), 3.52 (s, 3H), 3.11-2.96 (m, 2H), 2.34 (s, 3H).

Step H: 2-methylpropan-2-aminium (Z)-4-(5-chloro-1-methyl-3-(pyridin-2-yl)-1H-pyrazol-4-yl)-4-(4-chloro-2-methylphenyl)but-3-enoate

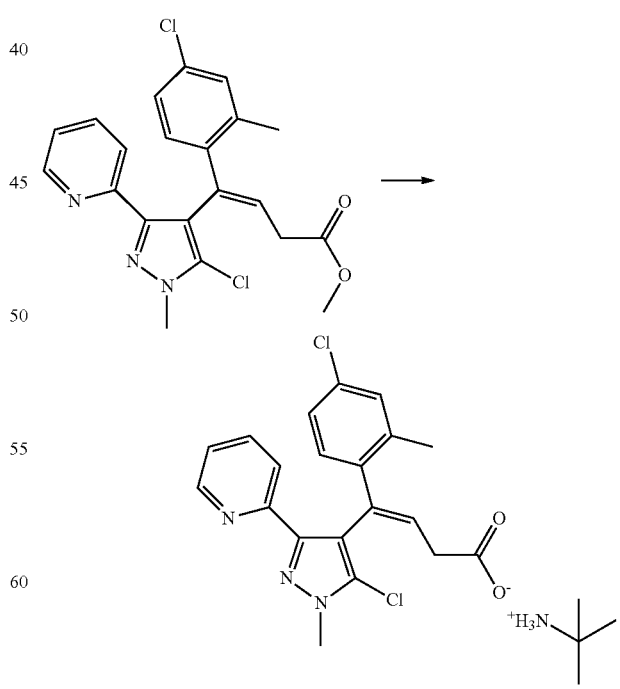

To a solution of (Z)-methyl 4-(5-chloro-1-methyl-3-(pyridin-2-yl)-1H-pyrazol-4-yl)-4-(4-chloro-2-methylphenyl)

but-3-enoate (13.34 g, 32.0 mmol) in dioxane (150 mL) was added 2 N aqueous NaOH (32 mL, 64 mmol). The mixture was stirred at rt for about 16 h then partitioned between EtOAc (300 mL) and 10% citric acid (200 mL). The layers were separated and the aqueous layer was extracted with EtOAc (300 mL). The combined organic layers were washed with water (300 mL) followed by brine (300 mL) then concentrated in vacuo. The residue was triturated in Et$_2$O to give (Z)-4-(5-chloro-1-methyl-3-(pyridin-2-yl)-1H-pyrazol-4-yl)-4-(4-chloro-2-methylphenyl)but-3-enoic acid (12.31 g, 95%) as an off-white solid: LC-MS (Table 1, Method g) R$_t$=2.20 min, m/z 402/404 (M+H)$^+$; $^1$H-NMR (DMSO, Bruker 400 MHz) δ 12.18 (s, 1H), 8.42-8.39 (m, 1H), 7.80-7.68 (m, 2H), 7.26-7.19 (m, 1H), 7.16 (d, J=2.2 Hz, 1H), 7.08-7.04 (m, 1H), 7.01-6.97 (m, 1H), 5.91 (t, J=7.2 Hz, 1H), 3.92 (s, 3H), 2.95 (s, 2H), 2.34 (s, 3H). To a suspension of (Z)-4-(5-chloro-1-methyl-3-(pyridin-2-yl)-1H-pyrazol-4-yl)-4-(4-chloro-2-methylphenyl)but-3-enoic acid (12.31 g, 30.6 mmol) in THF (50 mL) was added 2-methylpropan-2-amine (6.46 mL, 61.2 mmol). The mixture was stirred at rt for about 10 min then concentrated in vacuo to give 2-methylpropan-2-aminium (Z)-4-(5-chloro-1-methyl-3-(pyridin-2-yl)-1H-pyrazol-4-yl)-4-(4-chloro-2-methylphenyl)but-3-enoate (14.40 g, 95%): LC-MS (Table 1, Method g) R$_t$=2.20 min, m/z 402/404 (M+H)$^+$; $^1$H-NMR (DMSO, Bruker 400 MHz) δ 8.41-8.38 (m, 1H), 7.78-7.67 (m, 2H), 7.24-7.17 (m, 1H), 7.13 (d, J=2.1 Hz, 1H), 7.05-7.01 (m, 1H), 6.99-6.96 (m, 1H), 6.01 (t, J=7.1 Hz, 1H), 3.91 (s, 3H), 2.81-2.59 (m, 2H), 2.32 (s, 3H), 1.16 (s, 9H).

Step I: 4-(5-chloro-1-methyl-3-(pyridin-2-yl)-1H-pyrazol-4-yl)-4-(4-chloro-2-methylphenyl)butanoic acid

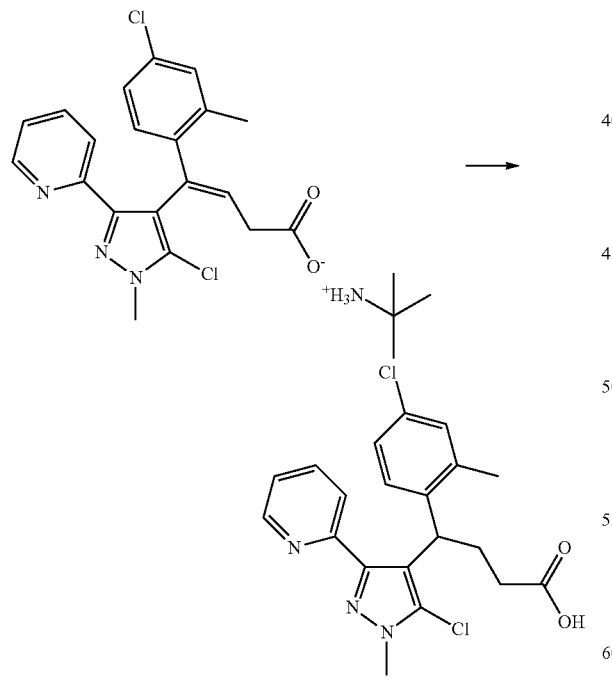

Chloro(1,5-cyclooctadiene)rhodium(I) dimer (0.068 g, 0.277 mmol), (S)-1-[(R$_P$)-2-[Bis(4-methoxy-3,5-dimethylphenyl)phosphino]ferrocenyl}ethyldi-tert-butylphosphine (0.182 g, 0.277 mmol), and 2-methylpropan-2-aminium (Z)-4-(5-chloro-1-methyl-3-(pyridin-2-yl)-1H-pyrazol-4-yl)-4-(4-chloro-2-methylphenyl)but-3-enoate (13.17 g, 27.7 mmol) were combined in a 250 mL stainless steel pressure bottle. A stir bar was added, and the system was degassed with 20 psi argon, and then vented. Argon-degassed MeOH (131 mL) was added against an argon stream by cannula, and the vessel was again sealed and degassed with argon. The system was shaken for about 30 min at about 50° C. The reactor was pressurized to 55 psi with hydrogen shaken at about 70° C. for about 14.5 h. The mixture was filtered through glass wool and concentrated in vacuo to give 2-methylpropan-2-aminium 4-(5-chloro-1-methyl-3-(pyridin-2-yl)-1H-pyrazol-4-yl)-4-(4-chloro-2-methylphenyl)butanoate (13.2 g, 100%) as a foam. 4-(5-Chloro-1-methyl-3-(pyridin-2-yl)-1H-pyrazol-4-yl)-4-(4-chloro-2-methylphenyl)butanoate (14.4 g, 30.2 mmol) in DCM (250 mL) and was washed with 20% citric acid (2×300 mL). The combined aqueous layers were extracted with DCM (250 mL). The combined organic layers were washed with H$_2$O (400 mL). The aqueous layer was extracted with EtOAc (250 mL). The combined organic layers were concentrated in vacuo. The residue was dissolved in THF (150 mL) and loaded on a silica gel pad (600 g) then eluted with THF. The product containing fractions were concentrated in vacuo. The material was dissolved in 2-methyltetrahydrofuran (500 mL) then washed with 20% citric acid (400 mL), H$_2$O (3×400 mL) and brine (400 mL). The organic layer was dried over Na$_2$SO$_4$, filtered and concentrated in vacuo to give 4-(5-chloro-1-methyl-3-(pyridin-2-yl)-1H-pyrazol-4-yl)-4-(4-chloro-2-methylphenyl)butanoic acid (12.2 g, 100%): LC-MS (Table 1, Method g) R$_t$=2.37 min, m/z 404/406 (M+H)$^+$; $^1$H-NMR (DMSO, Bruker 400 MHz) δ 11.98 (s, 1H), 8.60-8.56 (m, 1H), 7.86-7.79 (m, 2H), 7.39 (d, J=8.4 Hz, 1H), 7.36-7.28 (m, 1H), 7.19-7.14 (m, 1H), 7.13-7.11 (m, 1H), 5.30-5.24 (m, 1H), 3.83 (s, 3H), 2.45-2.32 (m, 1H), 2.29-2.14 (m, 3H), 2.08 (s, 3H).

Step J: 4-(3-carboxy-1-(5-chloro-1-methyl-3-(pyridin-2-yl)-1H-pyrazol-4-yl)propyl)-3-methylbenzoic acid

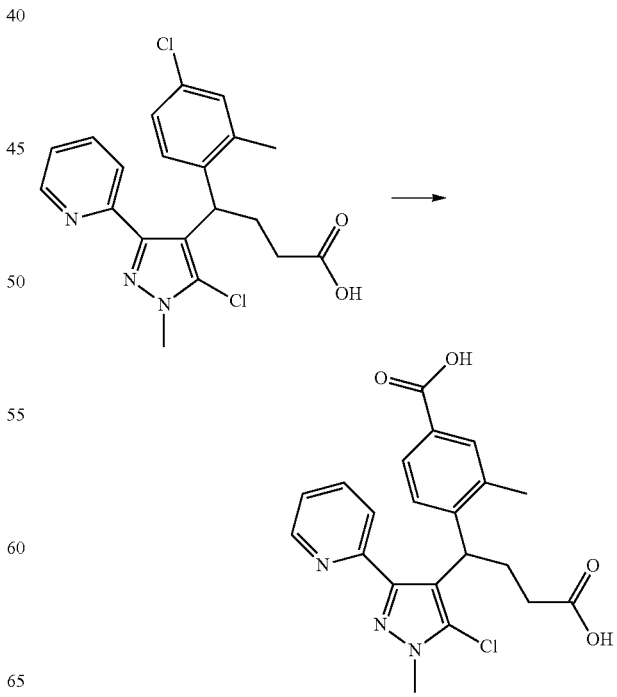

A microwave vial was charged with 4-(5-chloro-1-methyl-3-(pyridin-2-yl)-1H-pyrazol-4-yl)-4-(4-chloro-2-methylphenyl)butanoic acid (2.00 g, 4.94 mmol), potassium ferrocyanide trihydrate (3.14 g, 7.42 mmol), diacetoxypalladium (0.112 g, 0.494 mmol), dicyclohexyl(2',4',6'-triisopropyl-[1,1'-biphenyl]-2-yl)phosphine (0.472 g, 0.990 mmol) and potassium carbonate (1.71 g, 12.36 mmol). The vial was evacuated and backfilled with argon. 1,4-Dioxane (10 mL) and H₂O (10 mL) were added then argon was bubbled through the mixture for about 15 min. The mixture was heated at about 120° C. for about 40 h then cooled to rt and partitioned between EtOAc (600 mL) and 20% citric acid (400 mL). The insoluble material was removed by filtration then the filtrate layers were separated. The collected solids were triturated with EtOAc (200 mL) and 20% citric acid (200 mL). The insoluble material was removed by filtration then the filtrate layers were separated. The combined organic layers were washed with H₂O (600 mL) and brine (600 mL), dried over Na₂SO₄, filtered and concentrated in vacuo. The residue was treated with potassium ferrocyanide trihydrate (1.31 g, 3.09 mmol), diacetoxypalladium (0.056 g, 0.247 mmol), dicyclohexyl(2',4',6'-triisopropyl-[1,1'-biphenyl]-2-yl)phosphine (0.236 g, 0.495 mmol) and potassium carbonate (0.769 g, 5.57 mmol). The flask was evacuated and backfilled with argon. 1,4-Dioxane (5 mL) and H₂O (5 mL) were added and argon was bubbled through the reaction for about 15 min. The mixture was heated at about 120° C. for about 8 h then cooled to rt and partitioned between EtOAc (300 mL) and 20% citric acid (200 mL). The insoluble material was removed by filtration then the filtrate layers were separated. The collected solids were triturated with EtOAc (100 mL) and 20% citric acid (100 mL), filtered then the filtrate layers were separated. The combined organic layers were washed with H₂O (300 mL) and brine (300 mL), dried over Na₂SO₄, filtered and concentrated u in vacuo. The residue was semipurified by column chromatography (SiO₂, 0-2% MeOH/DCM) and the product-containing fractions were concentrated in vacuo. The residue was dissolved in dioxane (30 mL) then 4 N aqueous NaOH (40 mL, 160 mmol) was added. The mixture was heated at about 100° C. for about 16 h then allowed to cool to rt. The mixture was neutralized by the dropwise addition of concentrated hydrochloric acid (4.85 mL, 160 mmol). The layers were separated and the organic layer was washed with 20% citric acid (300 mL), H₂O (2×300 mL) and brine (300 mL) dried with Na₂SO₄, filtered and concentrated in vacuo. The residue was purified by column chromatography (SiO₂, 0-5% MeOH/DCM) and the product containing fractions were concentrated in vacuo. The residue was dissolved in 2-Me THF (300 mL) and washed with H₂O (3×400 mL) and brine (300 mL), dried with Na₂SO₄, filtered and concentrated in vacuo to give 4-(3-carboxy-1-(5-chloro-1-methyl-3-(pyridin-2-yl)-1H-pyrazol-4-yl)propyl)-3-methylbenzoic acid (1.11 g, 2.68 mmol, 54%): LC-MS (Table 1, Method g) $R_f$=1.64 min, m/z 404/414 (M+H)⁺; ¹H-NMR (DMSO, Bruker 400 MHz) δ 12.31 (s, 1H), 8.60-8.57 (m, 1H), 7.87-7.79 (m, 2H), 7.72-7.67 (m, 1H), 7.65-7.62 (m, 1H), 7.50 (d, J=8.1 Hz, 1H), 7.36-7.28 (m, 1H), 5.39-5.33 (m, 1H), 3.84 (s, 3H), 2.46-2.18 (m, 4H), 2.12 (s, 3H).

Step K: methyl 4-(1-(5-chloro-1-methyl-3-(pyridin-2-yl)-1H-pyrazol-4-yl)-4-methoxy-4-oxobutyl)-3-methylbenzoate

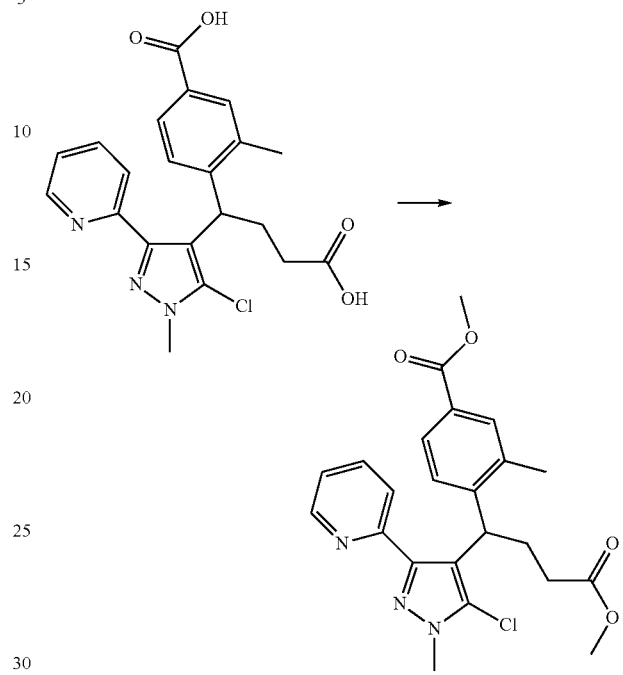

To a mixture of 4-(3-carboxy-1-(5-chloro-1-methyl-3-(pyridin-2-yl)-1H-pyrazol-4-yl)propyl)-3-methylbenzoic acid (1.08 g, 2.61 mmol) and K₂CO₃ (1.44 g, 10.44 mmol) in DMF (20 mL) was added iodomethane (0.82 mL, 13.05 mmol). The mixture was stirred at rt for about 4 h then partitioned between EtOAc (150 mL) and H₂O (150 mL). The organic layer was washed with brine (2×200 mL), dried over Na₂SO₄, filtered and concentrated in vacuo to give methyl 4-(1-(5-chloro-1-methyl-3-(pyridin-2-yl)-1H-pyrazol-4-yl)-4-methoxy-4-oxobutyl)-3-methylbenzoate (1.03 g, 89%): LC-MS (Table 1, Method g) $R_f$=2.50 min, m/z 442 (M+H)⁺; ¹H-NMR (DMSO, Bruker 400 MHz) δ 8.59-8.56 (m, 1H), 7.87-7.80 (m, 2H), 7.75-7.71 (m, 1H), 7.66 (d, J=1.4 Hz, 1H), 7.55 (d, J=8.2 Hz, 1H), 7.37-7.29 (m, 1H), 5.42-5.37 (m, 1H), 3.83 (s, 3H), 3.80 (s, 3H), 3.50 (s, 3H), 2.48-2.22 (m, 4H), 2.12 (s, 3H).

Step L: methyl 4-(1-(5-(2-ethoxy-2-oxoethyl)-1-methyl-3-(pyridin-2-yl)-1H-pyrazol-4-yl)-4-methoxy-4-oxobutyl)-3-methylbenzoate

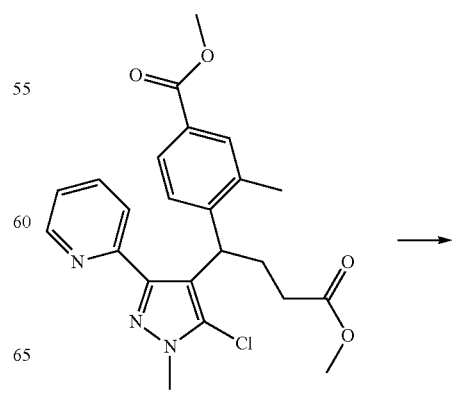

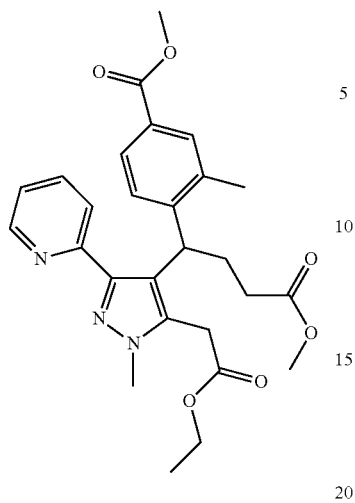

A flask was charged with methyl 4-(1-(5-chloro-1-methyl-3-(pyridin-2-yl)-1H-pyrazol-4-yl)-4-methoxy-4-oxobutyl)-3-methylbenzoate (2.20 g, 4.98 mmol), potassium; ethoxy-carbonyl-acetate (1.70 g, 9.96 mmol), N,N-dimethylpyridin-4-amine (0.608 g, 4.98 mmol), dicyclohexyl-(2',6'-diisopropoxy-biphenyl-2-yl)-phosphane (0.836 g, 1.79 mmol) and allylpalladium(II) chloride (0.219 g, 0.597 mmol). The flask was evacuated and backfilled with Argon. Mesitylene (13.2 mL) was added then the mixture was stirred at rt for about 10 min under Argon. The mixture was heated at about 120° C. for about 16 h, allowed to cool to rt then filtered. The filter cake was rinsed with EtOAc (20 mL). The filtrate was concentrated in vacuo. The residue was semi-purified by column chromatography (SiO$_2$, 10-30% EtOAc/heptane) to give crude methyl 4-(1-(5-(2-ethoxy-2-oxoethyl)-1-methyl-3-(pyridin-2-yl)-1H-pyrazol-4-yl)-4-methoxy-4-oxobutyl)-3-methylbenzoate (1.23 g, 50%). The material was used as such in the next step: LC-MS (Table 1, Method g) R$_t$=2.44 min, m/z 494 (M+H)$^+$.

Step M: 3-methyl-4-(1-methyl-7-oxo-3-(pyridin-2-yl)-1,4,5,6,7,8-hexahydrocyclohepta[c]pyrazol-4-yl)benzoic acid

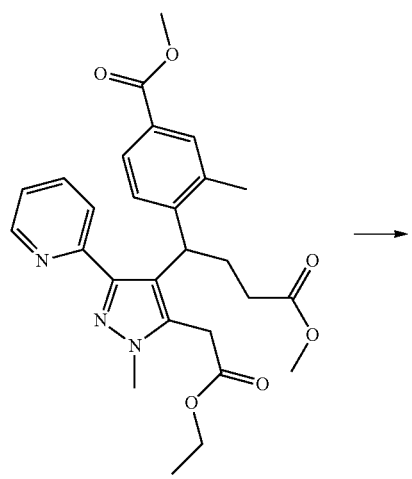

→

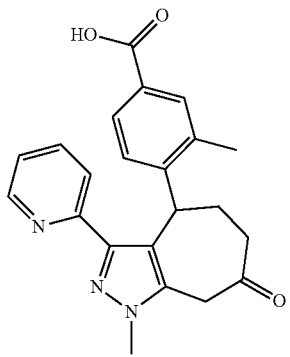

A flask fitted with a Dean-Stark apparatus containing dry molecular sieves was charged with a solution of methyl 4-(1-(5-(2-ethoxy-2-oxoethyl)-1-methyl-3-(pyridin-2-yl)-1H-pyrazol-4-yl)-4-methoxy-4-oxobutyl)-3-methylbenzoate (0.590 g, 1.20 mmol) in toluene (120 mL). The mixture was heated to reflux for about 16 h. The Dean-Stark apparatus was removed and the mixture was cooled to about 0° C. 1 M lithium bis(trimethylsilyl)amide in toluene (1.20 mL, 1.20 mmol) was added in dropwise manner. The mixture was allowed to slowly warm to rt in the cold bath. After about 2 h, 1 M lithium bis(trimethylsilyl)amide in toluene (0.60 mL, 0.60 mmol) was added dropwise. After about 4 h, 1 M lithium bis(trimethylsilyl)amide in toluene (0.30 mL, 0.30 mmol) was added dropwise and the reaction was stirred at rt for about 16 h. The mixture was cooled to about 0° C. then HOAc (10 mL) was added. The mixture was partitioned between EtOAc (100 mL) and brine (100 mL). The organic layer was washed with brine (100 mL), dried over Na$_2$SO$_4$, filtered and concentrated in vacuo. The residue was dissolved in 1,4-dioxane (4 mL) and 6 N aqueous HCl (8.0 mL, 48.0 mmol). The mixture was heated at about 100° C. for about 16 h then cooled to rt and concentrated in vacuo to remove the dioxane. The mixture was neutralized with saturated NaHCO$_3$ then adjusted to pH 5 with HOAc. The mixture was extracted with EtOAc (2×100 mL). The combined organic solutions were dried with Na$_2$SO$_4$, filtered and concentrated in vacuo. The residue was purified by column chromatography (SiO$_2$, O-5% MeOH/DCM) to give 3-methyl-4-(1-methyl-7-oxo-3-(pyridin-2-yl)-1,4,5,6,7,8-hexahydrocyclohepta[c]pyrazol-4-yl)benzoic acid (0.277 g, 58%): LC-MS (Table 1, Method g) R$_t$=1.66 min, m/z 376 (M+H)$^+$; $^1$H-NMR (DMSO, Bruker 400 MHz) δ 12.57 (s, 1H), 8.32-8.25 (m, 1H), 7.72-7.57 (m, 3H), 7.43-7.39 (m, 1H), 7.07-7.03 (m, 1H), 6.68 (d, J=8.0 Hz, 1H), 5.32-5.27 (m, 1H), 4.23 (d, J=15.6 Hz, 1H), 3.97 (d, J=15.6 Hz, 1H), 3.89 (s, 3H), 2.64-2.55 (m, 4H), 2.40-2.27 (m, 2H), 2.18-2.05 (m, 1H).

347

Step N: methyl 3-methyl-4-(1-methyl-7-oxo-3-(pyridin-2-yl)-1,4,5,6,7,8-hexahydrocyclohepta[c]pyrazol-4-yl)benzoate

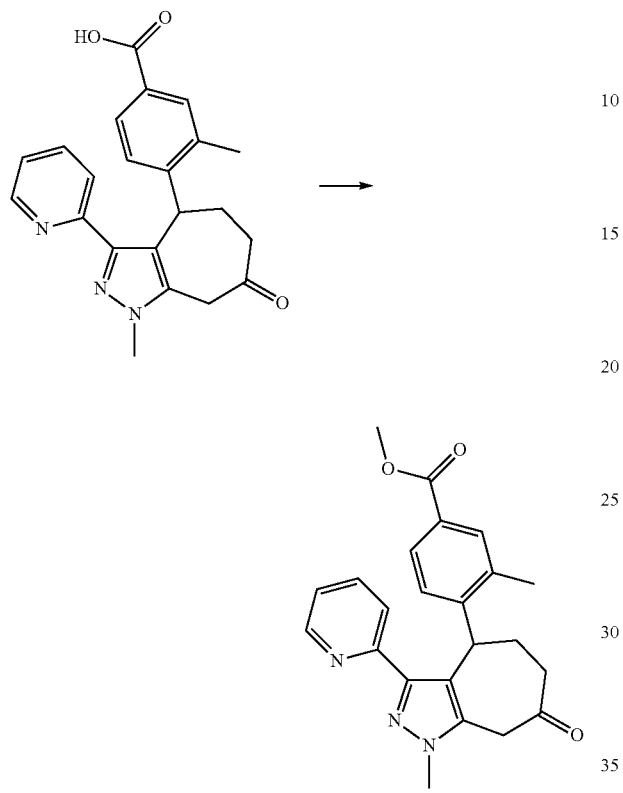

In an Erlenmeyer flask, 1-methyl-3-nitro-1-nitrosoguanidine (1.20 g, 8.16 mmol, TCI) was added portionwise to 45% KOH (10 mL)/H$_2$O (5 mL) and Et$_2$O (24 mL) at 0° C. The mixture was stirred until the yellow color of the ether layer did not change in intensity. The solution was poured into a separatory funnel and the aqueous layer was drained. The ether layer was poured into an Erlenmeyer flask and then decanted into another to remove some residual water. The yellow ether solution was poured slowly into a solution of 3-methyl-4-(1-methyl-7-oxo-3-(pyridin-2-yl)-1,4,5,6,7,8-hexahydrocyclohepta[c]pyrazol-4-yl)benzoic acid (0.240 g, 0.639 mmol) in THF (12 mL) cooled to about 0° C. in an ice bath. The ice bath was allowed to melt. The mixture was diluted with THF (12 mL) and a nitrogen stream was blown over the surface until the solution turned from yellow to colorless. The mixture was concentrated in vacuo to give methyl 3-methyl-4-(1-methyl-7-oxo-3-(pyridin-2-yl)-1,4,5,6,7,8-hexahydrocyclohepta[c]pyrazol-4-yl)benzoate (0.220 g, 88%): LC-MS (Table 1, Method g) R$_t$=2.09 min, m/z 390 (M+H)$^+$; $^1$H-NMR (DMSO, Bruker 400 MHz) δ 8.30-8.24 (m, 1H), 7.71-7.64 (m, 2H), 7.62-7.57 (m, 1H), 7.45-7.41 (m, 1H), 7.08-7.01 (m, 1H), 6.73-6.69 (m, 1H), 5.30-5.26 (m, 1H), 4.28-4.17 (m, 1H), 3.96 (d, J=15.6 Hz, 1H), 3.89 (s, 3H), 3.75 (s, 3H), 2.63-2.56 (m, 4H), 2.39-2.30 (m, 2H), 2.19-2.07 (m, 1H).

348

Step O: rac-methyl 4-((4R,7S)-7-hydroxy-1-methyl-3-(pyridin-2-yl)-7-(trifluoromethyl)-1,4,5,6,7,8-hexahydrocyclohepta[c]pyrazol-4-yl)-3-methylbenzoate and rac-methyl 4-((4R,7R)-7-hydroxy-1-methyl-3-(pyridin-2-yl)-7-(trifluoromethyl)-1,4,5,6,7,8-hexahydrocyclohepta[c]pyrazol-4-yl)-3-methylbenzoate

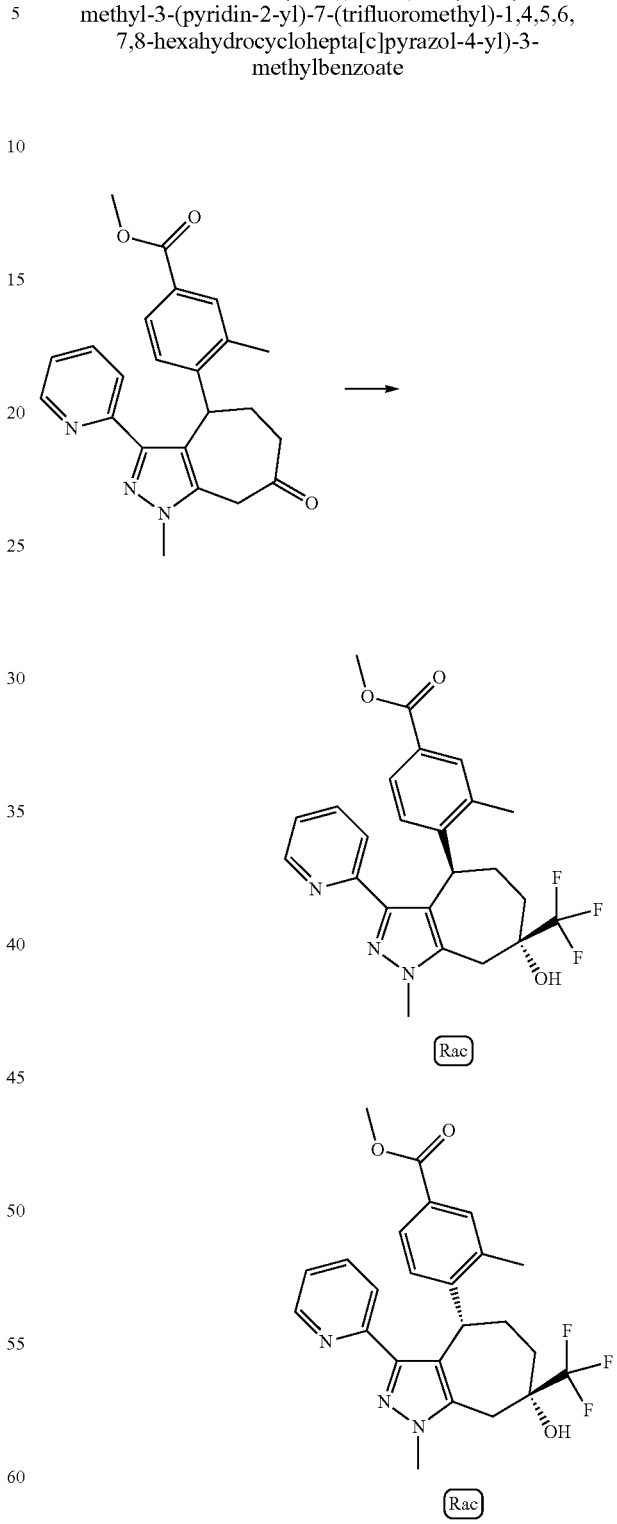

Cesium fluoride (0.037 g, 0.244 mmol) was added to a solution of rac-methyl 3-methyl-4-(1-methyl-7-oxo-3-(pyridin-2-yl)-1,4,5,6,7,8-hexahydrocyclohepta[c]pyrazol-4-yl)

benzoate (0.190 g, 0.488 mmol) in DME (50 mL). The mixture was stirred at rt for about 20 min then it was cooled in an ice bath and (trifluoromethyl)trimethylsilane (1.44 mL, 9.76 mmol) was added in a dropwise manner. After about 30 min, (trifluoromethyl)trimethylsilane (1.44 mL, 9.76 mmol) was added. After about 45 min, the mixture was partitioned between EtOAc (100 mL) and saturated aqueous NH$_4$Cl solution (100 mL). The organic layer was washed with brine (100 mL), dried with Na$_2$SO$_4$, filtered and concentrated in vacuo. The residue was dissolved in EtOAc (20 mL) and 1 M tetrabutylammonium fluoride in THF (0.54 mL, 0.54 mmol) was added. The mixture was stirred at rt for about 1 h then it was washed with saturated NH$_4$Cl (2×50 mL) and brine (50 mL). The organic layer was dried with Na$_2$SO$_4$, filtered and concentrated in vacuo. The residue was purified by column chromatography (SiO$_2$, 25-50% EtOAc/heptane) to give rac-methyl 4-((4R,7S)-7-hydroxy-1-methyl-3-(pyridin-2-yl)-7-(trifluoromethyl)-1,4,5,6,7,8-hexahydrocyclohepta[c]pyrazol-4-yl)-3-methylbenzoate (0.018 g, 8%): LC-MS (Table 1, Method g) R$_t$=2.28 min, m/z 460 (M+H)$^+$; $^1$H-NMR (DMSO, Bruker 400 MHz) δ 8.31-8.27 (m, 1H), 7.75-7.72 (m, 1H), 7.69-7.67 (m, 1H), 7.65-7.60 (m, 1H), 7.53-7.49 (m, 1H), 7.10-7.05 (m, 1H), 6.95 (d, J=8.1 Hz, 1H), 6.30 (s, 1H), 5.22-5.14 (m, 1H), 3.85 (s, 3H), 3.76 (s, 3H), 3.34-3.32 (m, 2H), 2.62 (s, 3H), 2.20-2.08 (m, 1H), 1.98-1.90 (m, 1H), 1.86-1.74 (m, 2H). and rac-methyl 4-((4R,7R)-7-hydroxy-1-methyl-3-(pyridin-2-yl)-7-(trifluoromethyl)-1,4,5,6,7,8-hexahydrocyclohepta[c]pyrazol-4-yl)-3-methylbenzoate (0.034 g, 15%): LC-MS (Table 1, Method g) R$_t$=2.28 min, m/z 460 (M+H)$^+$; $^1$H-NMR (DMSO, Bruker 400 MHz) δ 8.35-8.38 (m, 1H), 7.77-7.74 (m, 1H), 7.71-7.69 (m, 1H), 7.68-7.63 (m, 1H), 7.57-7.52 (m, 1H), 7.14-7.10 (m, 1H), 6.96-6.93 (m, 1H), 6.18 (s, 1H), 5.51-5.45 (m, 1H), 3.90 (s, 3H), 3.76 (s, 3H), 3.36-3.17 (m, 2H), 2.56 (s, 3H), 2.29-2.20 (m, 1H), 1.90-1.79 (m, 1H), 1.76-1.65 (m, 2H).

Step P: rac-4-((4R,7R)-7-hydroxy-1-methyl-3-(pyridin-2-yl)-7-(trifluoromethyl)-1,4,5,6,7,8-hexahydrocyclohepta[c]pyrazol-4-yl)-3-methyl-N-(2-methylpyridin-3-yl)benzamide

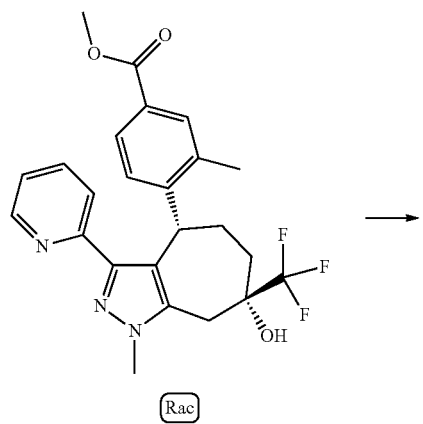

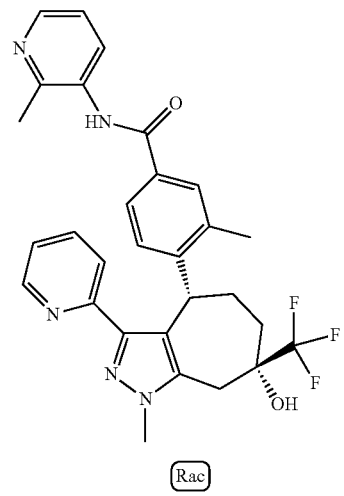

1 M lithium bis(trimethylsilyl)amide in toluene (0.24 mL, 0.24 mmol) was added dropwise to a solution of rac-methyl 4-((4R,7R)-7-hydroxy-1-methyl-3-(pyridin-2-yl)-7-(trifluoromethyl)-1,4,5,6,7,8-hexahydrocyclohepta[c]pyrazol-4-yl)-3-methylbenzoate (0.034 g, 0.07 mmol) and 2-methylpyridin-3-amine (0.012 g, 0.11 mmol, Appollo) in THF (2 mL) at about 0° C. The mixture was allowed to warm to rt. After about 2 h, the mixture was cooled to about 0° C. 2-Methylpyridin-3-amine (0.008 g, 0.07 mmol) and 1 M lithium bis(trimethylsilyl)amide in toluene (0.07 mL, 0.07 mmol) were added then the mixture was allowed to warm to rt. After about 5 h a saturated aqueous NH$_4$ Cl solution (20 mL) was added and then mixture was extracted with EtOAc (2×20 mL). The combined organic extracts were washed with brine (20 mL), dried with Na$_2$SO$_4$, filtered and concentrated in vacuo. The residue was purified by column chromatography (SiO$_2$, 2-6% MeOH/DCM). The appropriate fractions were concentrated in vacuo. The product was recrystallized from Et$_2$O to give rac-4-((4R,7R)-7-hydroxy-1-methyl-3-(pyridin-2-yl)-7-(trifluoromethyl)-1,4,5,6,7,8-hexahydrocyclohepta[c]pyrazol-4-yl)-3-methyl-N-(2-methylpyridin-3-yl)benzamide (0.005 g, 12%): LC-MS (Table 1, Method g) R$_t$=1.86 min, m/z 536 (M+H)$^+$; $^1$H-NMR (DMSO, Bruker 400 MHz) δ 9.85 (s, 1H), 8.44-8.41 (m, 1H), 8.32-8.29 (m, 1H), 7.82-7.78 (m, 1H), 7.75-7.67 (m, 3H), 7.60-7.56 (m, 1H), 7.26-7.22 (m, 1H), 7.18-7.14 (m, 1H), 6.98 (d, J=8.0 Hz, 1H), 6.21 (s, 1H), 5.61-5.55 (m, 1H), 3.93 (s, 3H), 3.40-3.32 (m, 2H), 2.61 (s, 3H), 2.40 (s, 3H), 2.36-2.26 (m, 1H), 1.93-1.83 (m, 1H), 1.80-1.71 (m, 2H).

Step Q: rac-4-((4R,7S)-7-hydroxy-1-methyl-3-(pyridin-2-yl)-7-(trifluoromethyl)-1,4,5,6,7,8-hexahydrocyclohepta[c]pyrazol-4-yl)-3-methyl-N-(2-methylpyridin-3-yl)benzamide

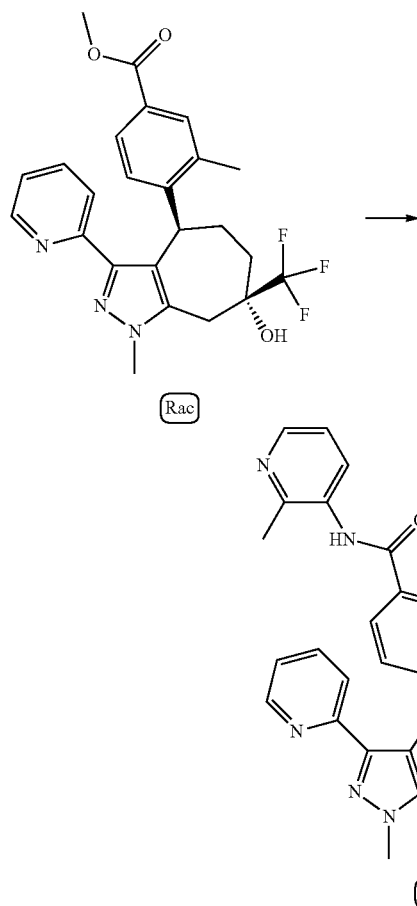

1 M lithium bis(trimethylsilyl)amide in toluene (0.13 mL, 0.13 mmol) was added dropwise to a solution of rac-methyl 4-((4R,7S)-7-hydroxy-1-methyl-3-(pyridin-2-yl)-7-(trifluoromethyl)-1,4,5,6,7,8-hexahydrocyclohepta[c]pyrazol-4-yl)-3-methylbenzoate (0.018 g, 0.04 mmol) and 2-methylpyridin-3-amine (6.4 mg, 0.06 mmol, Appollo) in THF (1 mL) at 0° C. The mixture was allowed to warm to rt. After about 2 h, the mixture was cooled to about 0° C. 2-Methylpyridin-3-amine (4.2 mg, 0.04 mmol) and 1 M lithium bis(trimethylsilyl)amide in toluene (0.04 mL, 0.04 mmol) were added then the mixture was allowed to warm to rt. After about 5 h a saturated aqueous NH$_4$Cl solution (20 mL) was added and then mixture was extracted with EtOAc (2×20 mL). The combined organic extracts were washed with brine (20 mL), dried with Na$_2$SO$_4$, filtered and concentrated in vacuo. The residue was purified by column chromatography (SiO$_2$, 2-6% MeOH/DCM) to give rac-4-((4R,7S)-7-hydroxy-1-methyl-3-(pyridin-2-yl)-7-(trifluoromethyl)-1,4,5,6,7,8-hexahydrocyclohepta[c]pyrazol-4-yl)-3-methyl-N-(2-methylpyridin-3-yl)benzamide (0.001 g, 5%): LC-MS (Table 1, Method g) R$_t$=1.94 min, m/z 536 (M+H)$^+$; $^1$H-NMR (DMSO, Bruker 400 MHz) δ 9.81 (s, 1H), 8.37-8.34 (m, 1H), 8.31-8.27 (m, 1H), 7.79-7.75 (m, 1H), 7.71-7.62 (m, 3H), 7.56-7.51 (m, 1H), 7.26-7.22 (m, 1H), 7.13-7.08 (m, 1H), 6.97 (d, J=8.0 Hz, 1H), 6.32 (s, 1H), 5.28-5.21 (m, 1H), 3.86 (s, 3H), 3.36-3.32 (m, 2H), 2.65 (s, 3H), 2.39 (s, 3H), 2.22-2.12 (m, 1H), 2.00-1.90 (m, 1H), 1.88-1.76 (m, 2H).

Assay Results

Fluorescense polarization binding ranges measured using GR Fluorescence Polarization Assay:

A=a compound with an IC$_{50}$ less than 0.1 μM
B=a compound with an IC$_{50}$ within the range of 0.1 to 1.0 μM
C=a compound with an IC$_{50}$ within the range of 1.0 to 10.0 μM
D=a compound with an IC$_{50}$ greater than 10 μM.

Intrinsic activity cellular assay ranges using A549 Cell Assay to Measure Inflammation Markers A=a compound with E$_{max}$>70%
B=a compound with E$_{max}$>60%
C=a compound with E$_{max}$>50%
D=a compound with E$_{max}$<50%

| Example | GR binding | A549 E$_{max}$ | Example | GR binding | A549 E$_{max}$ |
|---|---|---|---|---|---|
| D.1 | A | B | E.1 | A | D |
| D.2 | C | D | E.2 | C | — |
| D.3 | A | D | E.3 | D | D |
| D.4 | A | D | E.4 | B | — |
| D.5 | A | D | E.5 | C | D |
| D.6 | B | D | E.6 | C | — |
| D.7 | A | D | F.1 | A | A |
| D.8 | A | D | F.2 | C | D |
| D.9 | A | D | F.3 | C | D |
| D.10 | A | D | F.4 | D | D |
| D.11 | A | C | F.5 | D | D |
| D.12 | A | D | F.6 | C | D |
| D.13 | C | D | C.2 | B | D |
| D.14 | A | D | G.1 | B | D |
| D.15 | A | D | G.2 | B | D |
| D.16 | A | D | G.3 | A | D |
| D.17 | B | D | G.4 | A | D |
| D.18 | B | D | G.5 | B | D |
| D.19 | A | D | G.6 | B | D |
| D.20 | A | D | G.7 | A | A |
| D.21 | B | D | G.8 | A | B |
| D.22 | A | D | G.9 | A | D |
| D.23 | B | D | G.10 | A | A |
| D.24 | A | D | G.11 | C | — |
| D.25 | B | D | H.1 | C | D |
| D.26 | A | D | H.2 | D | — |
| D.27 | A | D | H.3 | B | D |
| D.28 | C | D | H.4 | A | A |
| D.29 | A | D | H.5 | C | D |
| D.30 | A | A | I.1 | B | D |
| D.31 | C | D | I.2 | B | — |
| D.32 | A | D | I.3 | C | — |
| D.33 | B | D | I.4 | C | D |
| D.34 | A | D | I.5 | C | — |
| D.35 | C | D | K.2 | C | D |
| D.36 | D | D | K.3 | A | D |
| D.37 | A | C | L.1 | D | D |
| D.38 | A | C | L.2 | C | D |
| D.39 | A | B | L.3 | B | D |
| D.40 | A | D | L.4 | C | D |
| D.41 | A | D | M.1 | B | D |
| D.42 | A | C | M.2 | A | D |
| D.43 | A | D | M.3 | C | D |
| D.44 | A | D | M.4 | A | D |
| D.45 | A | B | M.5 | C | D |
| D.46 | A | D | M.6 | A | D |
| D.47 | B | D | M.7 | C | D |
| D.48 | B | D | M.8 | C | D |
| D.49 | A | D | M.9 | B | D |
| D.50 | B | D | M.10 | C | D |
| D.51 | B | D | M.11 | C | D |
| D.52 | A | D | M.12 | B | D |
| D.53 | A | D | M.13 | A | D |
| D.54 | C | D | M.14 | B | A |

| Example | GR binding | A549 E$_{max}$ | Example | GR binding | A549 E$_{max}$ | Example | GR binding | A549 E$_{max}$ | Example | GR binding | A549 E$_{max}$ |
|---|---|---|---|---|---|---|---|---|---|---|---|
| D.55 | A | D | M.15 | B | A | M.30 | C | — | M.31 | A | A |
| D.56 | A | D | M.16 | C | D | M.32 | A | A | M.33 | B | — |
| D.57 | A | C | M.17 | B | D | M.34 | B | — | M.35 | A | A |
| D.58 | A | C | D.78 | B | — | M.36 | A | B | M.37 | B | — |
| D.59 | B | D | D.79 | A | D | M.38 | B | — | M.39 | A | A |
| D.60 | A | C | D.80 | B | D | M.40 | A | A | M.41 | B | — |
| D.61 | A | D | D.81 | C | — | M.42 | A | B | M.43 | C | — |
| D.62 | B | D | D.82 | B | D | M.44 | A | B | M.45 | C | — |
| D.63 | C | D | D.83 | A | D | M.46 | A | C | M.47 | B | — |
| D.64 | B | D | D.84 | B | D | M.48 | A | C | M.49 | C | — |
| D.65 | A | D | D.85 | B | D | M.50 | C | — | M.51 | A | D |
| D.66 | A | D | D.86 | C | — | M.52 | A | D | M.53 | B | — |
| D.67 | A | D | D.87 | B | — | M.54 | A | D | M.55 | A | D |
| D.68 | A | D | D.88 | C | — | M.56 | B | — | M.57 | A | A |
| D.69 | B | D | D.89 | B | — | M.58 | A | A | M.59 | C | — |
| D.70 | B | D | D.90 | A | D | M.60 | C | — | M.61 | B | — |
| D.71 | C | D | D.91 | C | — | M.62 | A | A | M.63 | B | — |
| D.72 | B | D | D.92 | A | D | M.64 | C | — | M.65 | | — |
| D.73 | D | D | D.100 | A | D | M.66 | B | D | M.67 | B | C |
| D.74 | A | D | D.101 | A | D | M.68 | C | A | M.69 | B | — |
| D.75 | C | — | D.102 | D | — | M.70 | A | D | M.71 | A | D |
| D.76 | D | D | D.103 | A | D | O.1 | C | — | O.2 | B | A |
| D.77 | A | D | D.99 | D | — | Q.1 | B | — | R.1 | A | D |
| D.93 | B | — | D.96 | D | — | S.1 | A | A | S.2 | A | A |
| D.94 | A | D | D.97 | C | — | S.3 | A | D | S.4 | A | D |
| D.95 | C | — | D.98 | D | — | S.5 | A | A | S.6 | B | — |
| D.104 | A | A | D.105 | A | B | S.7 | B | — | S.8 | A | C |
| D.106 | A | D | D.107 | A | D | S.9 | A | D | S.10 | A | A |
| D.108 | A | C | D.109 | A | A | U.1 | C | — | U.2 | C | — |
| E.7 | A | C | F.7 | A | A | U.3 | C | — | U.4 | B | — |
| H.6 | A | A | K.1 | — | — | U.5 | C | — | U.6 | B | — |
| K.4 | A | B | K.5 | — | — | U.7 | C | — | U.8 | C | — |
| K.6 | A | D | K.7 | A | D | U.9 | B | — | U.10 | B | — |
| K.8 | A | D | K.9 | A | D | U.11 | C | — | U.12 | B | — |
| K.10 | A | B | K.11 | A | D | U.13 | B | — | U.14 | C | — |
| M.18 | C | — | M.19 | C | — | U.15 | C | — | U.16 | B | — |
| M.20 | A | A | M.21 | A | A | U.17 | B | — | U.18 | B | — |
| M.22 | A | A | M.23 | A | C | U.19 | C | — | AA.1 | A | D |
| M.24 | A | A | M.25 | C | — | AA.2 | C | — | AA.3 | A | D |
| M.26 | C | — | M.27 | A | B | BB.1 | A | A | | | |
| M.28 | A | B | M.29 | C | — | | | | | | |

| Example | GR binding | A549 Emax |
|---|---|---|
| 4-(4-chloro-2-methyl-phenyl)-1-methyl-3-(1H-pyrazol-5-yl)-4,6,7,8-tetrahydropyrazolo[3,4-e][1,4]thiazepine (Preparation #2) | B | D |
| 3-chloro-4-[1-methyl-3-(2-pyridyl)-4,6,7,8-tetrahydropyrazolo[3,4-e][1,4]thiazepin-4-yl]benzoic acid (Preparation #3) | B | D |
| 6-[4-(2,4-dichlorophenyl)-1-methyl-4,6,7,8-tetrahydropyrazolo[3,4-e][1,4]thiazepin-3-yl]pyridine-3-carboxylic acid (Preparation #3.1) | C | — |
| 1-[4-[1-methyl-3-(2-pyridyl)-4,6,7,8-tetrahydropyrazolo[3,4-e][1,4]thiazepin-4-yl]-1-piperidyl]ethanone (Preparation #4) | D | D |
| (2-methyl-3-pyridyl)-[4-[1-methyl-3-(2-pyridyl)-4,6,7,8-tetrahydropyrazolo[3,4-e][1,4]thiazepin-4-yl]-1-piperidyl]methanone (Preparation #5) | D | — |
| N-(2-methyl-3-pyridyl)-4-[1-methyl-3-(2-pyridyl)-4,6,7,8-tetrahydropyrazolo[3,4-D e][1,4]thiazepin-4-yl]piperidine-1-carboxamide (Preparation #6) | D | — |
| 1-methyl-4-[2-methyl-4-(3-pyridylmethoxy)phenyl]-3-(2-pyridyl)-4,6,7,8-tetrahydropyrazolo[3,4-e][1,4]thiazepine (Preparation #10) | B | D |
| 1-methyl-4-[2-methyl-4-[(2-methyl-3-pyridyl)methoxy]phenyl]-3-(2-pyridyl)-4,6,7,8-tetrahydropyrazolo[3,4-e][1,4]thiazepine (Preparation #11) | A | D |
| 2-[4-(2,4-dichlorophenyl)-1-methyl-3-(2-pyridyl)-6,7-dihydro-4H-pyrazolo[3,4-e][1,4]thiazepin-8-yl]acetic acid (Preparation #12) | C | — |
| 2-[4-(2,4-dichlorophenyl)-1-methyl-3-(2-pyridyl)-6,7-dihydro-4H-pyrazolo[3,4-e][1,4]thiazepin-8-yl]acetamide (Preparation #13) | C | — |
| 4-(4-chloro-2-methyl-phenyl)-1-methyl-3-(6-methyl-2-pyridyl)-4,6,7,8-tetrahydropyrazolo[3,4-e][1,4]thiazepine (Preparation #14) | C | — |
| 4-(4-chloro-2-vinyl-phenyl)-1-methyl-3-(2-pyridyl)-4,6,7,8-tetrahydropyrazolo-[3,4-e][1,4]thiazepine (Preparation #18) | A | B |
| 4-(4-chloro-2-ethyl-phenyl)-1-methyl-3-(2-pyridyl)-4,6,7,8-tetrahydropyrazolo-[3,4-e][1,4]thiazepine (Preparation #19) | A | C |
| 1-methyl-4-(2-methyl-4-methylsulfonyl-phenyl)-3-(2-pyridyl)-4,6,7,8-tetrahydro-pyrazolo[3,4-e][1,4]thiazepine (Preparation #20) | B | D |

-continued

| Example | GR binding | A549 Emax |
|---|---|---|
| 4-(2,4-dichlorophenyl)-1-methyl-3-[(2S)-pyrrolidin-2-yl]-4,6,7,8-tetrahydropyrazolo[3,4-e][1,4]thiazepine (Preparation #23) | D | D |
| 4-(4-chloro-2-methyl-phenyl)-1-methyl-3-[(2S)-pyrrolidin-2-yl]-4,6,7,8-tetrahydropyrazolo[3,4-e][1,4]thiazepine (Preparation #24) | C | D |
| 2-[3-chloro-4-[1-methyl-3-(2-pyridyl)-4,6,7,8-tetrahydropyrazolo[3,4-e][1,4]thiazepin-4-yl]phenyl]propan-2-ol (Preparation #25) | C | — |
| 4-(2-chlorophenyl)-1-methyl-3-(2-pyridyl)-4,6,7,8-tetrahydropyrazolo[3,4-e][1,4]thiazepine (Preparation #25) | A | D |
| 4-(2-chloro-4-methyl-phenyl)-1-methyl-3-(2-pyridyl)-4,6,7,8-tetrahydropyrazolo[3,4-e][1,4]thiazepine (Preparation #26) | A | D |
| 4-(2,4-dichlorophenyl)-1,3,6,6,8-pentamethyl-4H-pyrazolo[3,4-e][1,4]thiazepin-7-one (Preparation #27) | C | D |
| 4-(2,4-dichlorophenyl)-1,3,6,6-tetramethyl-4,7-dihydropyrazolo[3,4-e][1,4]thiazepine-8-carbaldehyde (Preparation #28) | C | D |
| 3-[4-(2,4-dichlorophenyl)-1,3,6,6-tetramethyl-4,7-dihydropyrazolo[3,4-e][1,4]thiazepin-8-yl]-1,1,1-trifluoro-propan-2-ol (Preparation #29) | D | D |
| 3-[4-(2,4-dichlorophenyl)-3,6,6-trimethyl-7,8-dihydro-4H-pyrazolo[3,4-e][1,4]thiazepin-1-yl]-1,1,1-trifluoro-propan-2-ol and 3-[4-(2,4-dichlorophenyl)-3,6,6-trimethyl-7,8-dihydro-4H-pyrazolo[3,4-e][1,4]thiazepin-2-yl]-1,1,1-trifluoro-propan-2-ol (Preparation #30) | C | D |
| 4-(2,4-dichlorophenyl)-1,3,6,6-pentamethyl-4,7-dihydropyrazolo[3,4-e][1,4]thiazepine hydrochloride (Preparation #31) | B | D |
| 4-(4-chloro-2-methyl-phenyl)-3-cyclopropyl-1,6,6-trimethyl-7,8-dihydro-4H-pyrazolo[3,4-e][1,4]thiazepine (Example #1) | A | B |
| (4S)-4-(4-chloro-2-methyl-phenyl)-3-cyclopropyl-1,6,6-trimethyl-7,8-dihydro-4H-pyrazolo[3,4-e][1,4]thiazepine (Example #1) | B | D |
| (4R)-4-(4-chloro-2-methyl-phenyl)-3-cyclopropyl-1,6,6-trimethyl-7,8-dihydro-4H-pyrazolo[3,4-e][1,4]thiazepine (Example #1) | A | B |
| 4-(4-chloro-2-methyl-phenyl)-1-methyl-3-(2-pyridyl)-4,6,7,8-tetrahydropyrazolo[3,4-e][1,4]thiazepine (Example #2) | A | B |
| (4R)-4-(4-chloro-2-methyl-phenyl)-1-methyl-3-(2-pyridyl)-4,6,7,8-tetrahydropyrazolo[3,4-e][1,4]thiazepine (Example #2) | B | D |
| (4S)-4-(4-chloro-2-methyl-phenyl)-1-methyl-3-(2-pyridyl)-4,6,7,8-tetrahydropyrazolo[3,4-e][1,4]thiazepine (Example #2) | A | B |
| 3-chloro-N-(2-methyl-3-pyridyl)-4-[1-methyl-3-(2-pyridyl)-4,6,7,8-tetrahydropyrazolo[3,4-e][1,4]thiazepin-4-yl]benzamide (Example #3) | A | A |
| 3-chloro-N-(2-methyl-3-pyridyl)-4-[(4R)-1-methyl-3-(2-pyridyl)-4,6,7,8-tetrahydropyrazolo[3,4-e][1,4]thiazepin-4-yl]benzamide (Example #3) | C | D |
| 3-chloro-N-(2-methyl-3-pyridyl)-4-[(4S)-1-methyl-3-(2-pyridyl)-4,6,7,8-tetrahydropyrazolo[3,4-e][1,4]thiazepin-4-yl]benzamide (Example #3) | A | A |
| 4-(4-bromo-2-chloro-phenyl)-1-methyl-3-(2-pyridyl)-4,6,7,8-tetrahydropyrazolo[3,4-e]-[1,4]thiazepine (Example #3) | A | D |
| methyl 3-chloro-4-[1-methyl-3-(2-pyridyl)-4,6,7,8-tetrahydropyrazolo[3,4-e][1,4]thiazepin-4-yl]benzoate (Example #3) | A | D |
| 3-methyl-N-(2-methyl-3-pyridyl)-4-[1-methyl-3-(2-pyridyl)-4,6,7,8-tetrahydropyrazolo[3,4-e][1,4]thiazepin-4-yl]benzamide (Example #4) | A | A |
| (R)-3-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide (Example #4) | B | B |
| (S)-3-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide (Example #4) | A | A |
| 4-(4-bromo-2-methyl-phenyl)-1-methyl-3-(2-pyridyl)-4,6,7,8-tetrahydropyrazolo[3,4-e][1,4]thiazepine (Example #4) | A | C |
| 4-(4-chloro-2-methyl-phenyl)-1,7-dimethyl-3-(2-pyridyl)-4,6-dihydropyrazolo[3,4-e][1,4]thiazepine (Example #5) | B | D |
| 4-(4-chloro-2-methyl-phenyl)-1,7-dimethyl-3-(2-pyridyl)-4,6,7,8-tetrahydropyrazolo[3,4-e][1,4]thiazepine | A | A |
| (4R,7S)-4-(4-chloro-2-methylphenyl)-1,7-dimethyl-3-(pyridin-2-yl)-4,6,7,8-tetrahydro-1H-pyrazolo[3,4-e][1,4]thiazepine (Example #5) | C | D |
| (4R,7R)-4-(4-chloro-2-methylphenyl)-1,7-dimethyl-3-(pyridin-2-yl)-4,6,7,8-tetrahydro-1H-pyrazolo[3,4-e][1,4]thiazepine (Example #5) | C | D |
| (4S,7S)-4-(4-chloro-2-methylphenyl)-1,7-dimethyl-3-(pyridin-2-yl)-4,6,7,8-tetrahydro-1H-pyrazolo[3,4-e][1,4]thiazepine (Example #5) | A | D |
| (4S,7R)-4-(4-chloro-2-methylphenyl)-1,7-dimethyl-3-(pyridin-2-yl)-4,6,7,8-tetrahydro-1H-pyrazolo[3,4-e][1,4]thiazepine (Example #5) | A | A |
| (Example #6) 4-(4-bromophenyl)-1-ethyl-3-(pyridin-2-yl)-1,4,5,6,7,8-hexahydropyrazolo[3,4-b]azepine | A | A |
| (Example #7) rac-2-((4S,6S,7R)-4-(4-chloro-2-methylphenyl)-1,3,7-trimethyl-4,6,7,8-tetrahydro-1H-pyrazolo[3,4-e][1,4]thiazepin-6-yl)ethanol | A | A |
| (Example #8) 2-(4R,6R,7S)-4-(4-chloro-2-methylphenyl)-1,3,7-trimethyl-4,6,7,8-tetrahydro-1H-pyrazolo[3,4-e][1,4]thiazepin-6-yl)ethanol | B | A |
| (Example #9) rac-(4R,7R)-4-(4-bromo-2-methylphenyl)-1-methyl-3-(pyridin-2-yl)-7-(trifluoromethyl)-4,6,7,8-tetrahydro-1H-pyrazolo[3,4-e][1,4]thiazepine | A | D |
| (Example #9) rac-(4R,7S)-4-(4-bromo-2-methylphenyl)-1-methyl-3-(pyridin-2-yl)-7-(trifluoromethyl)-4,6,7,8-tetrahydro-1H-pyrazolo[3,4-e][1,4]thiazepine | B | D |
| (Example #10) rac-(4R,7S)-4-(4-bromo-2-methylphenyl)-1-methyl-3-(pyridin-2-yl)-4,6,7,8-tetrahydro-1H-pyrazolo[3,4-e][1,4]thiazepine-7-carboxamide | B | D |

| Example | GR binding | A549 Emax |
|---|---|---|
| (Example #11) rac-(4R,7S)-4-(4-bromo-2-methylphenyl)-1-methyl-3-(pyridin-2-yl)-4,6,7,8-tetrahydro-1H-pyrazolo[3,4-e][1,4]thiazepine-7-carbonitrile | A | B |
| (Example #12) rac-2-((4R,7S)-4-(4-bromo-2-methylphenyl)-1-methyl-3-(pyridin-2-yl)-4,6,7,8-tetrahydro-1H-pyrazolo[3,4-e][1,4]thiazepin-7-yl)acetonitrile | A | C |
| (Example #13) 4-((4S,7R)-7-(hydroxymethyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide | A | A |
| (Example #13) 4-((4R,7S)-7-(hydroxymethyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide | C | — |
| (Example #14) rac-4-(1-(4-fluorophenyl)-6-methyl-1H-indazol-5-yl)-1-methyl-3-(pyridin-2-yl)-6,8-dihydro-1H-pyrazolo[3,4-e][1,4]thiazepin-7(4H)-one | A | A |
| rac-4-((4R,7R)-7-hydroxy-1-methyl-3-(pyridin-2-yl)-7-(trifluoromethyl)-1,4,5,6,7,8-hexahydrocyclohepta[c]pyrazol-4-yl)-3-methyl-N-(2-methylpyridin-3-yl)benzamide (Example #15) | A | A |
| and rac-4-((4R,7S)-7-hydroxy-1-methyl-3-(pyridin-2-yl)-7-(trifluoromethyl)-1,4,5,6,7,8-hexahydrocyclohepta[c]pyrazol-4-yl)-3-methyl-N-(2-methylpyridin-3-yl)benzamide (Example #15) | A | A |

What is claimed:

1. A compound represented by the following formula:

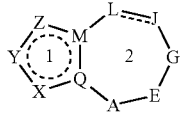

Formula (I)

or a pharmaceutically acceptable salt thereof, wherein:

Ring 1 is heterocyclic or heteroaromatic;

X is N, $N(R^{4'})$, $C(R^4)$, or $C(R^4)(R^4)$;

Y is N, $N(R^{4'})$, or $C(R^4)$;

Z is $N(R^{4'})$, $C(R^4)C(R^4)$ or $C(R^4)$;

A is $N(R^{3'})$ or $C(R^3)(R^3)$;

G and J are independently S, $C(R^1)(R^2)$, or $N(R^3)$, provided that at least one of G and J is $C(R^1)(R^2)$;

E is $N(R^{4'})$, S, or $C(R^1)(R^2)$;

L is $N(R^5)$, $C(R^5)(R^5)$ or $C(R^5)(R^{5'})$; or L is $C(R^5)$ or $C(R^{5'})$ and J is $C(R^1)$ or N;

M and Q are independently N, C or CH;

$R^1$ and $R^2$, for each occurrence, is independently —H, $CF_3$, CN, —C(=O)$NH_2$, OH, an optionally substituted ($C_1$-$C_6$)alkyl, optionally substituted ($C_3$-$C_6$)cycloalkyl, optionally substituted aryl, optionally substituted heteroaryl or optionally substituted heterocyclyl; or $R^1$ and $R^2$, together with the carbon to which they attach, form an optionally substituted ($C_3$-$C_6$)carbocyclic ring spiro to ring 2 or an optionally substituted heterocyclic ring spiro to ring 2;

$R^3$ is independently —H, $CF_3$, CN, OH, —$NR^aR^b$, an optionally substituted ($C_1$-$C_6$)alkyl, optionally substituted ($C_2$-$C_6$)alkenyl, optionally substituted ($C_2$-$C_6$)alkynyl, an optionally substituted aryl, an optionally substituted ($C_3$-$C_6$)cycloalkyl, an optionally substituted heteroaryl, an optionally substituted heterocyclyl, or an optionally substituted benzyl;

$R^{3'}$ is independently —H, an optionally substituted ($C_1$-$C_6$)alkyl, optionally substituted ($C_2$-$C_6$)alkenyl, optionally substituted ($C_2$-$C_6$)alkynyl, an optionally substituted aryl, an optionally substituted ($C_3$-$C_6$)cycloalkyl, an optionally substituted heteroaryl, an optionally substituted heterocyclyl, or an optionally substituted benzyl;

$R^4$ is independently H, —$CF_3$, —CN, —OH, —$NR^aR^b$, an optionally substituted ($C_1$-$C_6$)alkyl, an optionally substituted ($C_2$-$C_6$)alkenyl, an optionally substituted ($C_2$-$C_6$)alkynyl, an optionally substituted ($C_1$-$C_6$) alkoxy, an optionally substituted aryl, an optionally substituted($C_3$-$C_6$)cycloalkyl, an optionally substituted heteroaryl, or an optionally substituted heterocyclyl;

$R^{4'}$ is independently —H, an optionally substituted ($C_1$-$C_8$)alkyl, an optionally substituted ($C_2$-$C_6$)alkenyl, an optionally substituted ($C_2$-$C_6$)alkynyl, an optionally substituted ($C_3$-$C_6$)cycloalkyl, an optionally substituted heterocyclyl, an optionally substituted aryl, or an optionally substituted heteroaryl;

provided that $R^{4'}$ is not an optionally substituted benzisoxazolyl, an optionally substituted isobenzazolyl, an optionally substituted quinazolinyl, an optionally substituted isoquinolinyl or an optionally substituted phthalazinyl;

$R^5$ is independently —H, OH, F, $CF_3$, CN, optionally substituted ($C_1$-$C_6$)alkyl, optionally substituted ($C_2$-$C_6$)alkenyl, optionally substituted ($C_2$-$C_6$)alkynyl, optionally substituted ($C_3$-$C_6$)cycloalkyl, —$(CH_2)_n$-optionally substituted aryl, —$(CH_2)_n$-optionally substituted heterocyclyl, or —$(CH_2)_n$-optionally substituted heteroaryl;

or both $R^5$, together with the carbon to which they are attached, form a carbocyclic spirocyclic ring;

$R^{5'}$ is —$R^{5'a}$—$R^{5'b}$—$R^{5'c}$ wherein $R^{5'a}$ is attached to the ring and $R^{5'a}$ is optionally substituted phenyl or optionally substituted heteroaryl;

$R^{5'b}$ is a bond or —C(=O)N(H) wherein the —C(=O) is attached to $R^{5'a}$; and $R^{5'c}$ is optionally substituted isoxazolyl, optionally substituted oxazolyl, optionally substituted phenyl, optionally substituted pyrazolyl, optionally substituted pyridazinyl, optionally substituted pyridinyl, optionally substituted pyrimidinyl, optionally substituted pyrido[2,3-b]pyrazinyl, tetrazolyl, optionally substituted 1,3,5-thiadiazolyl, or 1,2,4-triazolyl;

$R^a$ and $R^b$ are independently H and optionally substituted ($C_1$-$C_6$)alkyl; and n, for each occurrence, is independently 0, 1, 2 or 3;

provided that when M and Q are both CH or M and Q are both C and Ring 1 contains two nitrogen atoms, Ring 2 is not

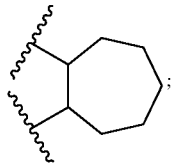 [SMILES: *C1CCCCCC1*]

and, provided that not more than one of X, Y and Z is substituted by phenyl wherein Ring 1 is represented by the following formula and is optionally substituted by one or more R⁴ or R⁴':

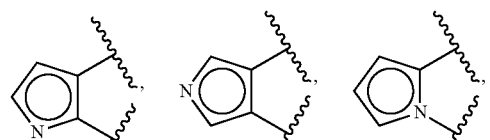

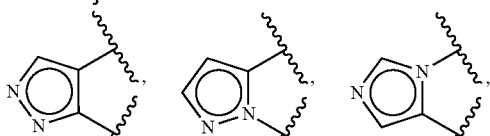

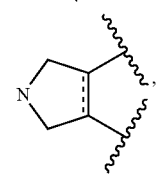 or 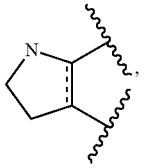

and, wherein Ring 2 is represented by the following formula and is and is optionally substituted by one or more of R¹, R², R³, R³', R⁴, R⁴', R⁵, or R⁵';

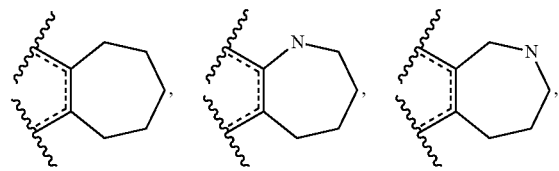

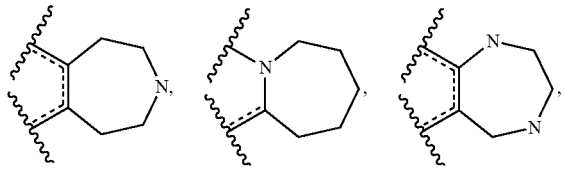

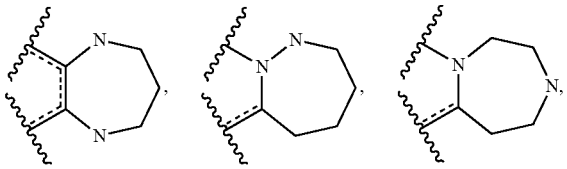

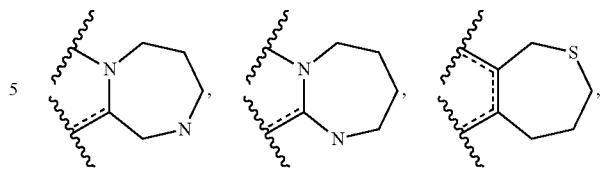

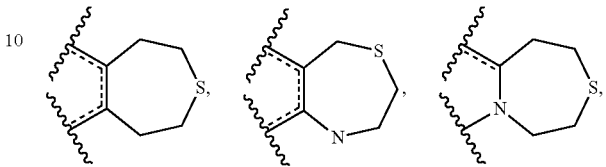

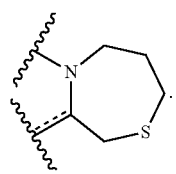

2. The compound of claim 1, wherein Formula (I) is

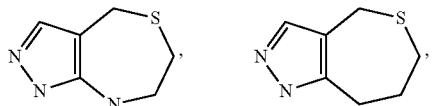

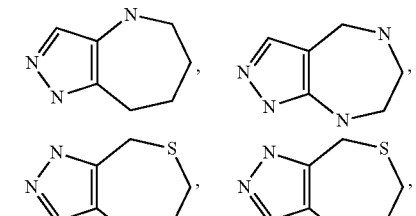

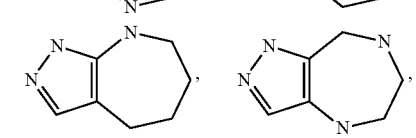

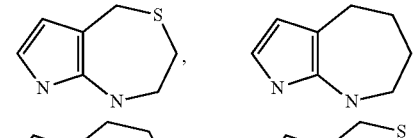

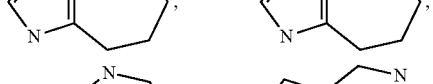

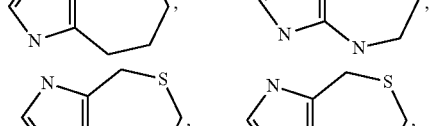

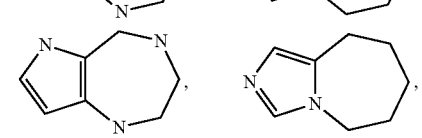

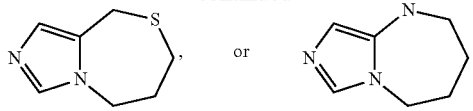 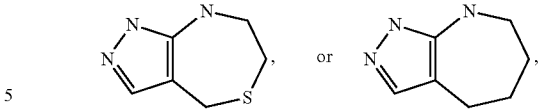

and is optionally substituted by one or more of $R^1$, $R^2$, $R^3$, $R^{3'}$, $R^4$, $R^{4'}$, $R^5$ or $R^{5'}$.

3. The compound according to claim 2 wherein $R^1$ and $R^2$, for each occurrence, is independently —H or optionally substituted $(C_1-C_6)$alkyl; or $R^1$ and $R^2$, together with the carbon to which they attach, form an optionally substituted $(C_3-C_6)$ cycloalkyl spiro to ring 2, or form a tetrahydropyranyl ring 1 spiro to ring 2.

4. The compound according to claim 3 wherein $R^3$ is independently H, optionally substituted phenyl, optionally substituted indazolyl, optionally substituted pyridinyl, optionally substituted pyrazolyl, optionally substituted thiophenyl, optionally substituted piperidinyl, or optionally substituted benzyl.

5. The compound according to claim 4 wherein $R^{3'}$ is H.

6. The compound according to claim 5 wherein
$R^4$ is independently H, optionally substituted methyl, optionally substituted ethyl, optionally substituted isopropyl, optionally substituted tert-butyl, optionally substituted isobutyl, optionally substituted cyclopropyl, optionally substituted cyclopentyl, optionally substituted isothiazolidine, optionally substituted 1,2,4-oxadiazolyl, optionally substituted 1,3,4-oxadiazolyl, optionally substituted tetrahydrofuran, optionally substituted phenyl, optionally substituted pyridinyl, optionally substituted pyrimidinyl, optionally substituted thienyl, optionally substituted thiazolyl, optionally substituted pyrazolyl, optionally substituted isoxazolyl, optionally substituted tetrahydropyranyl, —OH, —CH$_2$CF$_3$, or —CF$_3$.

7. The compound according to claim 6 wherein
$R^{4'}$ is independently H, optionally substituted methyl, optionally substituted ethyl, optionally substituted propyl, optionally substituted cyclopropyl or optionally substituted cyclopentyl, or optionally substituted pyridinyl.

8. The compound according to claim 7 wherein
$R^5$ is independently H, optionally substituted methyl, optionally substituted propyl, optionally substituted benzyl, optionally substituted phenyl, optionally substituted piperidinyl, optionally substituted pyrazolyl, optionally substituted pyridinyl, optionally substituted thienyl.

9. The compound according to claim 8 wherein $R^{5'}$ is $-R^{5'a}-R^{5'b}-R^{5'c}$ wherein $R^{5'a}$ is attached to the ring and
$R^{5'a}$ is optionally substituted phenyl or optionally substituted indazolyl;
$R^{5'b}$ is a bond or —C(=O)N(H) wherein the —C(=O) is attached to $R^{5'a}$; and
$R^{5'c}$ is optionally substituted pyrazolyl or optionally substituted pyridinyl.

10. The compound according to claim 9 wherein n, for each occurrence, is independently 0 or 1.

11. The compound according to claim 10 wherein Formula (I) is and is optionally substituted by one or more $R^1$, $R^2$, $R^3$, $R^{3'}$, $R^4$, $R^{4'}$, $R^5$ or $R^{5'}$.

12. The compound according to claim 11 wherein $R^1$ and $R^2$, for each occurrence, is independently —H, CF$_3$, CH$_3$, CH$_2$OH, CH$_2$CH$_2$OH, OH, optionally substituted phenyl or optionally substituted heteroaryl.

13. The compound according to claim 12 wherein
$R^4$ is H, optionally substituted methyl, optionally substituted 1,3,4-oxadiazolyl, optionally substituted pyridinyl, or optionally substituted pyrimidinyl.

14. The compound of claim 1, wherein the compound is selected from the group consisting of:
4-(2,6-dichlorophenyl)-1-methyl-3-(pyridin-2-yl)-4,6,7,8-tetrahydro-1H-pyrazolo[3,4-e][1,4]thiazepine;
4-(4-chloro-2-(trifluoromethyl)phenyl)-1-methyl-3-(pyridin-2-yl)-4,6,7,8-tetrahydro-1H-pyrazolo[3,4-e][1,4]thiazepine;
4-(2,4-dichlorophenyl)-1,3,6,6-tetramethyl-4,6,7,8-tetrahydro-1H-pyrazolo[3,4-e][1,4]thiazepine;
4-(4-chloro-2-methoxyphenyl)-1-methyl-3-(pyridin-2-yl)-4,6,7,8-tetrahydro-1H-pyrazolo[3,4-e][1,4]thiazepine;
3-chloro-N,N-dimethyl-4-(1-methyl-3-(pyridin-2-yl)-4,6,7,8-tetrahydro-1H-pyrazolo[3,4-e][1,4]thiazepin-4-yl)aniline;
4-(3-chloropyridin-4-yl)-1-methyl-3-(pyridin-2-yl)-4,6,7,8-tetrahydro-1H-pyrazolo[3,4-e][1,4]thiazepine;
4-(2,4-dichlorophenyl)-1-methyl-3-(pyridin-2-yl)-4,6,7,8-tetrahydro-1H-pyrazolo[3,4-e][1,4]thiazepine;
4-(2,4-dimethylphenyl)-1-methyl-3-(pyridin-2-yl)-4,6,7,8-tetrahydro-1H-pyrazolo[3,4-e][1,4]thiazepine;
4-(4-methoxy-2-methylphenyl)-1-methyl-3-(pyridin-2-yl)-4,6,7,8-tetrahydro-1H-pyrazolo[3,4-e][1,4]thiazepine;
4-(4-fluoro-2-methylphenyl)-1-methyl-3-(pyridin-2-yl)-4,6,7,8-tetrahydro-1H-pyrazolo[3,4-e][1,4]thiazepine;
1-methyl-4-(2-methyl-4-(trifluoromethoxy)phenyl)-3-(pyridin-2-yl)-4,6,7,8-tetrahydro-1H-pyrazolo[3,4-e][1,4]thiazepine;
4-(4-chloro-2-methylphenyl)-2-methyl-3-(pyridin-2-yl)-4,6,7,8-tetrahydro-2H-pyrazolo[3,4-e][1,4]thiazepine;
1-methyl-3-(pyridin-2-yl)-4-o-tolyl-4,6,7,8-tetrahydro-1H-pyrazolo[3,4-e][1,4]thiazepine;
3-(5-bromopyridin-2-yl)-4-(2,4-dichlorophenyl)-1-methyl-4,6,7,8-tetrahydro-1H-pyrazolo[3,4-e][1,4]thiazepine;
4-(2,4-dichlorophenyl)-1-methyl-3-(thiazol-2-yl)-4,6,7,8-tetrahydro-1H-pyrazolo[3,4-e][1,4]thiazepine;
4-(2,4-dichlorophenyl)-1,6,6-trimethyl-3-(thiazol-2-yl)-4,6,7,8-tetrahydro-1H-pyrazolo[3,4-e][1,4]thiazepine;
4-(2,4-dichlorophenyl)-1-methyl-3-(pyridin-4-yl)-4,6,7,8-tetrahydro-1H-pyrazolo[3,4-e][1,4]thiazepine;
3-(4-bromopyridin-2-yl)-4-(4-chloro-2-methylphenyl)-1-methyl-4,6,7,8-tetrahydro-1H-pyrazolo[3,4-e][1,4]thiazepine;
4-(2,5-dimethylphenyl)-1-methyl-3-(pyridin-2-yl)-4,6,7,8-tetrahydro-1H-pyrazolo[3,4-e][1,4]thiazepine;
4-(5-chloro-3-methylpyridin-2-yl)-1-methyl-3-(pyridin-2-yl)-4,6,7,8-tetrahydro-1H-pyrazolo[3,4-e][1,4]thiazepine;

4-(4-chloro-2-methylphenyl)-3-(4-methoxypyridin-2-yl)-1-methyl-4,6,7,8-tetrahydro-1H-pyrazolo[3,4-e][1,4]thiazepine;
4-(4-chlorophenyl)-1-methyl-3-(pyridin-2-yl)-4,6,7,8-tetrahydro-1H-pyrazolo[3,4-e][1,4]thiazepine;
4-(4-chloro-2-methylphenyl)-3-(4-chloropyridin-2-yl)-1-methyl-4,6,7,8-tetrahydro-1H-pyrazolo[3,4-e][1,4]thiazepine;
4-(4-bromophenyl)-1-methyl-3-(pyridin-2-yl)-4,6,7,8-tetrahydro-1H-pyrazolo[3,4-e][1,4]thiazepine;
4-(5-bromo-3-methylthiophen-2-yl)-1-methyl-3-(pyridin-2-yl)-4,6,7,8-tetrahydro-1H-pyrazolo[3,4-e][1,4]thiazepine;
4-(5-bromo-2-methylphenyl)-1-methyl-3-(pyridin-2-yl)-4,6,7,8-tetrahydro-1H-pyrazolo[3,4-e][1,4]thiazepine;
4-(5-methoxy-2-methylphenyl)-1-methyl-3-(pyridin-2-yl)-4,6,7,8-tetrahydro-1H-pyrazolo[3,4-e][1,4]thiazepine;
5-(4-(4-bromo-2-methylphenyl)-1-methyl-4,6,7,8-tetrahydro-1H-pyrazolo[3,4-e][1,4]thiazepin-3-yl)-3-methylisoxazole;
4-(4-bromo-2-methylphenyl)-1-ethyl-3-(pyridin-2-yl)-4,6,7,8-tetrahydro-1H-pyrazolo[3,4-e][1,4]thiazepine;
4-(4-(2,4-dichlorophenyl)-1-methyl-4,6,7,8-tetrahydro-1H-pyrazolo[3,4-e][1,4]thiazepin-3-yl)-N,N-dimethylaniline;
4-(2,4-dichlorophenyl)-1,6,6-trimethyl-3-(pyridin-2-yl)-4,6,7,8-tetrahydro-1H-pyrazolo[3,4-e][1,4]thiazepine;
4-(2,3-dimethylphenyl)-1-methyl-3-(pyridin-2-yl)-4,6,7,8-tetrahydro-1H-pyrazolo[3,4-e][1,4]thiazepine;
4-(5-bromo-2-methylthiophen-3-yl)-1-methyl-3-(pyridin-2-yl)-4,6,7,8-tetrahydro-1H-pyrazolo[3,4-e][1,4]thiazepine;
4-(4-chloro-5-methoxy-2-methylphenyl)-1-methyl-3-(pyridin-2-yl)-4,6,7,8-tetrahydro-1H-pyrazolo[3,4-e][1,4]thiazepine;
4-benzyl-1-methyl-3-(pyridin-2-yl)-4,6,7,8-tetrahydro-1H-pyrazolo[3,4-e][1,4]thiazepine hydrochloride;
4-(2-bromo-4-chlorophenyl)-1-methyl-3-(pyridin-2-yl)-4,6,7,8-tetrahydro-1H-pyrazolo[3,4-e][1,4]thiazepine;
4-(4-chloro-2-cyclopropylphenyl)-1-methyl-3-(pyridin-2-yl)-4,6,7,8-tetrahydro-1H-pyrazolo[3,4-e][1,4]thiazepine;
4-(4-chloro-2-(fluoromethyl)phenyl)-1-methyl-3-(pyridin-2-yl)-4,6,7,8-tetrahydro-1H-pyrazolo[3,4-e][1,4]thiazepine;
4-(5-chloro-2-methylphenyl)-1-methyl-3-(pyridin-2-yl)-4,6,7,8-tetrahydro-1H-pyrazolo[3,4-e][1,4]thiazepine;
1-methyl-4-(2-methyl-4-(trifluoromethyl)phenyl)-3-(pyridin-2-yl)-4,6,7,8-tetrahydro-1H-pyrazolo[3,4-e][1,4]thiazepine;
3-methyl-4-(1-methyl-3-(pyridin-2-yl)-4,6,7,8-tetrahydro-1H-pyrazolo[3,4-e][1,4]thiazepin-4-yl)phenol;
3-(4-(4-chloro-2-methylphenyl)-1-methyl-4,6,7,8-tetrahydro-1H-pyrazolo[3,4-e][1,4]thiazepin-3-yl)-5-methylisoxazole;
4-(5-chloro-2-methylphenyl)-3-cyclopropyl-1,6,6-trimethyl-4,6,7,8-tetrahydro-1H-pyrazolo[3,4-e][1,4]thiazepine;
4-(4-chloro-2-methoxyphenyl)-3-cyclopropyl-1,6,6-trimethyl-4,6,7,8-tetrahydro-1H-pyrazolo[3,4-e][1,4]thiazepine hydrochloride;
4-(4-chloro-2-(trifluoromethyl)phenyl)-3-cyclopropyl-1,6,6-trimethyl-4,6,7,8-tetrahydro-1H-pyrazolo[3,4-e][1,4]thiazepine hydrochloride;
3-cyclopropyl-4-(2,5-dimethylphenyl)-1,6,6-trimethyl-4,6,7,8-tetrahydro-1H-pyrazolo[3,4-e][1,4]thiazepine;
4-(5-chloro-3-methylpyridin-2-yl)-3-cyclopropyl-1,6,6-trimethyl-4,6,7,8-tetrahydro-1H-pyrazolo[3,4-e][1,4]thiazepine;
4-(4-bromo-2-methylphenyl)-3-cyclopropyl-1,6-dimethyl-4,6,7,8-tetrahydro-1H-pyrazolo[3,4-e][1,4]thiazepine;
4-(4-bromo-2-methylphenyl)-3-cyclopropyl-1,6-dimethyl-4,6,7,8-tetrahydro-1H-pyrazolo[3,4-e][1,4]thiazepine;
4-(4-chloro-2-fluorophenyl)-3-cyclopropyl-1,6,6-trimethyl-4,6,7,8-tetrahydro-1H-pyrazolo[3,4-e][1,4]thiazepine hydrochloride;
(Z)-4-(5-bromo-2-methylphenyl)-3-cyclopropyl-1,6,6-trimethyl-4,6-dihydro-1H-pyrazolo[3,4-e][1,4]thiazepine;
4-(5-bromo-2-methylphenyl)-3-cyclopropyl-1,6,6-trimethyl-4,6,7,8-tetrahydro-1H-pyrazolo[3,4-e][1,4]thiazepine;
3-cyclopropyl-4-(4-fluoro-2-methylphenyl)-1,6,6-trimethyl-4,6,7,8-tetrahydro-1H-pyrazolo[3,4-e][1,4]thiazepine;
4-(4-chloro-2-methylphenyl)-1,3,6,6-tetramethyl-4,6,7,8-tetrahydro-1H-pyrazolo[3,4-e][1,4]thiazepine;
4-(4-bromo-2-methylphenyl)-1,3,6,6-tetramethyl-4,6,7,8-tetrahydro-1H-pyrazolo[3,4-e][1,4]thiazepine;
4-(4-chloro-2-methylphenyl)-1,3-dimethyl-4,6,7,8-tetrahydro-1H-pyrazolo[3,4-e][1,4]thiazepine;
4-(4-bromo-2-chlorophenyl)-1,3,6,6-tetramethyl-4,6,7,8-tetrahydro-1H-pyrazolo[3,4-e][1,4]thiazepine;
1,3,6,6-tetramethyl-4-(2-methyl-4-(trifluoromethyl)phenyl)-4,6,7,8-tetrahydro-1H-pyrazolo[3,4-e][1,4]thiazepine;
4-(4-bromo-2-methylphenyl)-1,3,6-trimethyl-4,6,7,8-tetrahydro-1H-pyrazolo[3,4-e][1,4]thiazepine;
4-(2,4-dichlorophenyl)-3,6,6-trimethyl-4,6,7,8-tetrahydro-1H-pyrazolo[3,4-e][1,4]thiazepine;
4-(2,4-dichlorophenyl)-3-isopropyl-1,6,6-trimethyl-4,6,7,8-tetrahydro-1H-pyrazolo[3,4-e][1,4]thiazepine hydrochloride;
4'-(2,4-dichlorophenyl)-1',3'-dimethyl-1',4',7',8'-tetrahydrospiro[cyclopentane-1,6'-pyrazolo[3,4-e][1,4]thiazepine];
4'-(2,4-dichlorophenyl)-1',3'-dimethyl-1',4',7',8'-tetrahydrospiro[cyclobutane-1,6'-pyrazolo[3,4-e][1,4]thiazepine];
4'-(2,4-dichlorophenyl)-1', 3'-dimethyl-1',2,3,4',5,6,7',8'-octahydrospiro[pyran-4,6'-pyrazolo[3,4-e][1,4]thiazepine];
4-(2,4-dichlorophenyl)-1,3,6,6-tetramethyl-4,6,7,8-tetrahydro-1H-pyrazolo[3,4-e][1,4]thiazepine;
4-(3-bromo-2-methylphenyl)-3-cyclopropyl-1,6,6-trimethyl-4,6,7,8-tetrahydro-1H-pyrazolo[3,4-e][1,4]thiazepine;
4-(4-chloro-2-methylphenyl)-1-cyclopentyl-3,6,6-trimethyl-4,6,7,8-tetrahydro-1H-pyrazolo[3,4-e][1,4]thiazepine;
1,3,6,6-tetramethyl-4-(2-methyl-4-(methylsulfonyl)phenyl)-4,6,7,8-tetrahydro-1H-pyrazolo[3,4-e][1,4]thiazepine;
4-(4-chloro-2-methylphenyl)-1-methyl-3-(tetrahydrofuran-2-yl)-4,6,7,8-tetrahydro-1H-pyrazolo[3,4-e][1,4]thiazepine;
4-(4-chloro-2-methylphenyl)-1-methyl-4,6,7,8-tetrahydro-1H-pyrazolo[3,4-e][1,4]thiazepin-3-ol;
3-cyclopropyl-4-(2,4-dichlorophenyl)-1,6,6-trimethyl-4,6,7,8-tetrahydro-1H-pyrazolo[3,4-e][1,4]thiazepine;

1,3-dimethyl-4-(4-(p-tolyloxy)phenyl)-4,6,7,8-tetrahydro-1H-pyrazolo[3,4-e][1,4]thiazepine;
4-(1H-indazol-5-yl)-1,3-dimethyl-4,6,7,8-tetrahydro-1H-pyrazolo[3,4-e][1,4]thiazepine;
3-cyclopentyl-4-(2,4-dichlorophenyl)-1-methyl-4,6,7,8-tetrahydro-1H-pyrazolo[3,4-e][1,4]thiazepine;
1,3,6,6-tetramethyl-4-(4-(p-tolyloxy)phenyl)-4,6,7,8-tetrahydro-1H-pyrazolo[3,4-e][1,4]thiazepine;
3-cyclopentyl-4-(2,4-dichlorophenyl)-1,6,6-trimethyl-4,6,7,8-tetrahydro-1H-pyrazolo[3,4-e][1,4]thiazepine;
4-(2,4-dichlorophenyl)-1,3-dimethyl-4,6,7,8-tetrahydro-1H-pyrazolo[3,4-e][1,4]thiazepine;
4-(3-methoxyphenyl)-1,3-dimethyl-4,6,7,8-tetrahydro-1H-pyrazolo[3,4-e][1,4]thiazepine;
3-(4-chlorophenyl)-4-(2,4-dichlorophenyl)-1-methyl-4,6,7,8-tetrahydro-1H-pyrazolo[3,4-e][1,4]thiazepine;
4-(2,4-dichlorophenyl)-1-methyl-3-phenyl-4,6,7,8-tetrahydro-1H-pyrazolo[3,4-e][1,4]thiazepine;
4-(2,4-dichlorophenyl)-3-isopropyl-1-methyl-4,6,7,8-tetrahydro-1H-pyrazolo[3,4-e][1,4]thiazepine;
3-tert-butyl-4-(2,4-dichlorophenyl)-1-methyl-4,6,7,8-tetrahydro-1H-pyrazolo[3,4-e][1,4]thiazepine;
4-(2,4-dichlorophenyl)-1-methyl-3-(pyridin-3-yl)-4,6,7,8-tetrahydro-1H-pyrazolo[3,4-e][1,4]thiazepine;
4-(2,4-dichlorophenyl)-1-methyl-3-p-tolyl-4,6,7,8-tetrahydro-1H-pyrazolo[3,4-e][1,4]thiazepine;
3-(4-tert-butylphenyl)-4-(2,4-dichlorophenyl)-1-methyl-4,6,7,8-tetrahydro-1H-pyrazolo[3,4-e][1,4]thiazepine;
4-(2,4-dichlorophenyl)-3-(3,4-dichlorophenyl)-1-methyl-4,6,7,8-tetrahydro-1H-pyrazolo[3,4-e][1,4]thiazepine;
4-(2,4-dichlorophenyl)-3-(3,5-difluorophenyl)-1-methyl-4,6,7,8-tetrahydro-1H-pyrazolo[3,4-e][1,4]thiazepine;
4-(2,4-dichlorophenyl)-1-methyl-3-(trifluoromethyl)-4,6,7,8-tetrahydro-1H-pyrazolo[3,4-e][1,4]thiazepine;
4-(2,4-dichlorophenyl)-3-isobutyl-1-methyl-4,6,7,8-tetrahydro-1H-pyrazolo[3,4-e][1,4]thiazepine;
4-(2,4-dichlorophenyl)-3-(2,4-difluorophenyl)-1-methyl-4,6,7,8-tetrahydro-1H-pyrazolo[3,4-e][1,4]thiazepine;
4-(2,4-dichlorophenyl)-3-(4-fluorophenyl)-1-methyl-4,6,7,8-tetrahydro-1H-pyrazolo[3,4-e][1,4]thiazepine;
4-(2,4-dichlorophenyl)-1-methyl-3-(4-(trifluoromethoxy)phenyl)-4,6,7,8-tetrahydro-1H-pyrazolo[3,4-e][1,4]thiazepine;
1,3-dimethyl-4-(pyridin-2-yl)-4,6,7,8-tetrahydro-1H-pyrazolo[3,4-e][1,4]thiazepine;
4-(4-methoxyphenyl)-1,3-dimethyl-4,6,7,8-tetrahydro-1H-pyrazolo[3,4-e][1,4]thiazepine;
4-(2-methoxyphenyl)-1,3-dimethyl-4,6,7,8-tetrahydro-1H-pyrazolo[3,4-e][1,4]thiazepine;
1,3-dimethyl-4-(pyridin-3-yl)-4,6,7,8-tetrahydro-1H-pyrazolo[3,4-e][1,4]thiazepine;
2-(4-(4-chlorophenyl)-1,3-dimethyl-4,6,7,8-tetrahydro-1H-pyrazolo[3,4-e][1,4]thiazepin-6-yl)ethanol;
4-(2,4-dichlorophenyl)-1-methyl-3-(thiophen-2-yl)-4,6,7,8-tetrahydro-1H-pyrazolo[3,4-e][1,4]thiazepine;
1,3-dimethyl-4-(1H-pyrazol-3-yl)-4,6,7,8-tetrahydro-1H-pyrazolo[3,4-e][1,4]thiazepine;
4-(4-chloro-2-fluorophenyl)-1-methyl-3-(pyridin-2-yl)-4,6,7,8-tetrahydro-1H-pyrazolo[3,4-e][1,4]thiazepine;
methyl 3-chloro-4-[1-methyl-3-(2-pyridyl)-4,6,7,8-tetrahydropyrazolo[3,4-e][1,4]thiazepin-4-yl]benzoate;
methyl 4-(1-methyl-3-(pyridin-2-yl)-4,6,7,8-tetrahydro-1H-pyrazolo[3,4-e][1,4]thiazepin-4-yl)benzoate;
methyl 3-methyl-4-(1-methyl-3-(pyridin-2-yl)-4,6,7,8-tetrahydro-1H-pyrazolo[3,4-e][1,4]thiazepin-4-yl)benzoate;
methyl 4-(1,3,6,6-tetramethyl-4,6,7,8-tetrahydro-1H-pyrazolo[3,4-e][1,4]thiazepin-4-yl)benzoate;
methyl 5-methyl-4-(1-methyl-3-(pyridin-2-yl)-4,6,7,8-tetrahydro-1H-pyrazolo[3,4-e][1,4]thiazepin-4-yl)thiophene-2-carboxylate;
methyl 6-(4-(2,4-dichlorophenyl)-1-methyl-4,6,7,8-tetrahydro-1H-pyrazolo[3,4-e][1,4]thiazepin-3-yl)nicotinate;
3-chloro-N-(2-methyl-3-pyridyl)-4-[1-methyl-3-(2-pyridyl)-4,6,7,8-tetrahydro-pyrazolo[3,4-e][1,4]thiazepin-4-yl]benzamide;
6-(4-(2,4-dichlorophenyl)-1-methyl-4,6,7,8-tetrahydro-1H-pyrazolo[3,4-e][1,4]thiazepin-3-yl)-N-(2-methylpyridin-3-yl)nicotinamide;
4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide;
4-methyl-5-(1-methyl-3-(pyridin-2-yl)-4,6,7,8-tetrahydro-1H-pyrazolo[3,4-e][1,4]thiazepin-4-yl)-N-(2-methylpyridin-3-yl)thiophene-2-carboxamide;
4-methyl-3-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide;
5-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)thiophene-2-carboxamide;
4-methyl-3-[1-methyl-3-(2-pyridyl)-4,6,7,8-tetrahydro-pyrazolo[3,4-e][1,4]thiazepin-4-yl]benzonitrile;
3-methyl-4-((4S,6S)-1,3,6-trimethyl-4,6,7,8-tetrahydro-1H-pyrazolo[3,4-e][1,4]thiazepin-4-yl)benzonitrile;
3-methyl-4((-4R,6R)-1,3,6-trimethyl-4,6,7,8-tetrahydro-1H-pyrazolo[3,4-e][1,4]thiazepin-4-yl)benzonitrile;
4-((4R,6S)-3-cyclopropyl-1,6-dimethyl-4,6,7,8-tetrahydro-1H-pyrazolo[3,4-e][1,4]thiazepin-4-yl)-3-methylbenzonitrile;
4-((4S,6R)-3-cyclopropyl-1,6-dimethyl-4,6,7,8-tetrahydro-1H-pyrazolo[3,4-e][1,4]thiazepin-4-yl)-3-methylbenzonitrile;
4-((4S,6S)-3-cyclopropyl-1,6-dimethyl-4,6,7,8-tetrahydro-1H-pyrazolo[3,4-e][1,4]thiazepin-4-yl)-3-methylbenzonitrile;
4-((4R,6R)-3-cyclopropyl-1,6-dimethyl-4,6,7,8-tetrahydro-1H-pyrazolo[3,4-e][1,4]thiazepin-4-yl)-3-methylbenzonitrile;
3-(3-cyclopropyl-1,6,6-trimethyl-4,6,7,8-tetrahydro-1H-pyrazolo[3,4-e][1,4]thiazepin-4-yl)-4-methylbenzonitrile;
3-methyl-4-(1,3,6,6-tetramethyl-4,6,7,8-tetrahydro-1H-pyrazolo[3,4-e][1,4]thiazepin-4-yl)benzonitrile;
4-(1,7-dimethyl-3-(pyridin-2-yl)-4,6,7,8-tetrahydro-1H-pyrazolo[3,4-e][1,4]thiazepin-4-yl)-3-methylbenzonitrile;
3-methyl-4-(1-methyl-3-(pyridin-2-yl)-4,6,7,8-tetrahydro-1H-pyrazolo[3,4-e][1,4]thiazepin-4-yl)benzonitrile;
4-(1-ethyl-3-(pyridin-2-yl)-4,6,7,8-tetrahydro-1H-pyrazolo[3,4-e][1,4]thiazepin-4-yl)-3-methylbenzonitrile;
3-methyl-4-((4R,6S)-1,3,6-trimethyl-4,6,7,8-tetrahydro-1H-pyrazolo[3,4-e][1,4]thiazepin-4-yl)benzonitrile;
3-methyl-4-((4S,6R)-1,3,6-trimethyl-4,6,7,8-tetrahydro-1H-pyrazolo[3,4-e][1,4]thiazepin-4-yl)benzonitrile;
3-methyl-N-(3-pyridyl)-4-(1,3,6,6-tetramethyl-7,8-dihydro-4H-pyrazolo[3,4-e][1,4]thiazepin-4-yl)benzamide;
3-(3-cyclopropyl-1,6,6-trimethyl-4,6,7,8-tetrahydro-1H-pyrazolo[3,4-e][1,4]thiazepin-4-yl)-4-methyl-N-(2-methylpyridin-3-yl)benzamide;

3-chloro-4-(1-methyl-3-(pyridin-2-yl)-4,6,7,8-tetrahydro-1H-pyrazolo[3,4-e][1,4]thiazepin-4-yl)-N-(pyridin-3-yl)benzamide;

4-(1-ethyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide;

3-methyl-N-(2-methylpyridin-3-yl)-4-(1,3,6,6-tetramethyl-4,6,7,8-tetrahydro-1H-pyrazolo[3,4-e][1,4]thiazepin-4-yl)benzamide;

3-chloro-4-[1-methyl-3-(2-pyridyl)-4,6,7,8-tetrahydropyrazolo[3,4-e][1,4]thiazepin-4-yl]benzamide;

3-chloro-N-methyl-4-(1-methyl-3-(pyridin-2-yl)-4,6,7,8-tetrahydro-1H-pyrazolo[3,4-e][1,4]thiazepin-4-yl)benzamide;

6-(4-(2,4-dichlorophenyl)-1-methyl-4,6,7,8-tetrahydro-1H-pyrazolo[3,4-e][1,4]thiazepin-3-yl)-N-methylnicotinamide;

3-methyl-4-(1,3,6,6-tetramethyl-4,6,7,8-tetrahydro-1H-pyrazolo[3,4-e][1,4]thiazepin-4-yl)benzamide;

6-(4-(2,4-dichlorophenyl)-1-methyl-4,6,7,8-tetrahydro-1H-pyrazolo[3,4-e][1,4]thiazepin-3-yl)nicotinamide;

4-(4-bromo-2-methyl-phenyl)-1,7-dimethyl-3-(2-pyridyl)-4,6,7,8-tetrahydropyrazolo[3,4-e][1,4]thiazepine;

4-(4-bromo-2-methyl-phenyl)-1,7-dimethyl-3-(2-pyridyl)-4,6,7,8-tetrahydropyrazolo[3,4-e][1,4]thiazepine;

(4R,7R)-4-(4-chloro-2-methylphenyl)-1,3,6,6-tetramethyl-7-phenyl-4,6,7,8-tetrahydro-1H-pyrazolo[3,4-e][1,4]thiazepine;

(4S,7S)-4-(4-chloro-2-methylphenyl)-1,3,6,6-tetramethyl-7-phenyl-4,6,7,8-tetrahydro-1H-pyrazolo[3,4-e][1,4]thiazepine;

4-(4-chloro-2-methylphenyl)-7-isopropyl-1-methyl-3-(pyridin-2-yl)-4,6,7,8-tetrahydro-1H-pyrazolo[3,4-e][1,4]thiazepine;

(R)-4-(4-Chloro-2-methylphenyl)-1,3,6,6-tetramethyl-4,6,7,8-tetrahydro-1H-pyrazolo[3,4-e][1,4]thiazepine;

(S)-4-(4-Chloro-2-methylphenyl)-1,3,6,6-tetramethyl-4,6,7,8-tetrahydro-1H-pyrazolo[3,4-e][1,4]thiazepine;

(S)-4-(4-bromo-2-chlorophenyl)-1-methyl-3-(pyridin-2-yl)-4,6,7,8-tetrahydro-1H-pyrazolo[3,4-e][1,4]thiazepine;

(R)-4-(4-bromo-2-chlorophenyl)-1-methyl-3-(pyridin-2-yl)-4,6,7,8-tetrahydro-1H-pyrazolo[3,4-e][1,4]thiazepine;

(R)-4-(4-chloro-2-fluorophenyl)-3-cyclopropyl-1,6,6-trimethyl-4,6,7,8-tetrahydro-1H-pyrazolo[3,4-e][1,4]thiazepine;

(S)-4-(4-chloro-2-fluorophenyl)-3-cyclopropyl-1,6,6-trimethyl-4,6,7,8-tetrahydro-1H-pyrazolo[3,4-e][1,4]thiazepine;

3-((S)-4-(2,4-dichlorophenyl)-3,6,6-trimethyl-4,6,7,8-tetrahydro-1H-pyrazolo[3,4-e][1,4]thiazepin-1-yl)-1,1,1-trifluoropropan-2-ol;

(R)-4-(4-chloro-2-methylphenyl)-1,3,6,6-tetramethyl-4,6,7,8-tetrahydro-1H-pyrazolo[3,4-e][1,4]thiazepine;

(S)-4-(4-chloro-2-methylphenyl)-1,3,6,6-tetramethyl-4,6,7,8-tetrahydro-1H-pyrazolo[3,4-e][1,4]thiazepine;

(S)-3-chloro-N-(2-methylpyridin-3-yl)-4-(1,3,6,6-tetramethyl-4,6,7,8-tetrahydro-1H-pyrazolo[3,4-e][1,4]thiazepin-4-yl)benzamide;

(R)-3-chloro-N-(2-methylpyridin-3-yl)-4-(1,3,6,6-tetramethyl-4,6,7,8-tetrahydro-1H-pyrazolo[3,4-e][1,4]thiazepin-4-yl)benzamide;

2-((4R,6S)-4-(4-chloro-2-methylphenyl)-1-methyl-3-(pyridin-2-yl)-4,6,7,8-tetrahydro-1H-pyrazolo[3,4-e][1,4]thiazepin-6-yl)ethanol;

2-((4R,6R)-4-(4-chloro-2-methylphenyl)-1-methyl-3-(pyridin-2-yl)-4,6,7,8-tetrahydro-1H-pyrazolo[3,4-e][1,4]thiazepin-6-yl)ethanol;

2-((4S,6R)-4-(4-chloro-2-methylphenyl)-1-methyl-3-(pyridin-2-yl)-4,6,7,8-tetrahydro-1H-pyrazolo[3,4-e][1,4]thiazepin-6-yl)ethanol;

2-((4S,6S)-4-(4-chloro-2-methylphenyl)-1-methyl-3-(pyridin-2-yl)-4,6,7,8-tetrahydro-1H-pyrazolo[3,4-e][1,4]thiazepin-6-yl)ethanol;

2-((4R,6R)-4-(4-chloro-2-methylphenyl)-1,3-dimethyl-4,6,7,8-tetrahydro-1H-pyrazolo[3,4-e][1,4]thiazepin-6-yl)ethanol;

2-((4R,6S)-4-(4-chloro-2-methylphenyl)-1,3-dimethyl-4,6,7,8-tetrahydro-1H-pyrazolo[3,4-e][1,4]thiazepin-6-yl)ethanol;

2-((4S,6S)-4-(4-chloro-2-methylphenyl)-1,3-dimethyl-4,6,7,8-tetrahydro-1H-pyrazolo[3,4-e][1,4]thiazepin-6-yl)ethanol;

2-((4S,6R)-4-(4-chloro-2-methylphenyl)-1,3-dimethyl-4,6,7,8-tetrahydro-1H-pyrazolo[3,4-e][1,4]thiazepin-6-yl)ethanol;

4-(4-chloro-2-methyl-phenyl)-3-cyclopropyl-1,6,6-trimethyl-7,8-dihydro-4H-pyrazolo[3,4-e][1,4]thiazepine;

(4S)-4-(4-chloro-2-methyl-phenyl)-3-cyclopropyl-1,6,6-trimethyl-7,8-dihydro-4H-pyrazolo[3,4-e][1,4]thiazepine;

(4R)-4-(4-chloro-2-methyl-phenyl)-3-cyclopropyl-1,6,6-trimethyl-7,8-dihydro-4H-pyrazolo[3,4-e][1,4]thiazepine;

4-(4-chloro-2-methyl-phenyl)-1-methyl-3-(2-pyridyl)-4,6,7,8-tetrahydropyrazolo[3,4-e][1,4]thiazepine;

(4R)-4-(4-chloro-2-methyl-phenyl)-1-methyl-3-(2-pyridyl)-4,6,7,8-tetrahydropyrazolo[3,4-e][1,4]thiazepine;

(4S)-4-(4-chloro-2-methyl-phenyl)-1-methyl-3-(2-pyridyl)-4,6,7,8-tetrahydropyrazolo[3,4-e][1,4]thiazepine;

3-chloro-N-(2-methyl-3-pyridyl)-4-[1-methyl-3-(2-pyridyl)-4,6,7,8-tetrahydro-pyrazolo[3,4-e][1,4]thiazepin-4-yl]benzamide;

3-chloro-N-(2-methyl-3-pyridyl)-4-[(4R)-1-methyl-3-(2-pyridyl)-4,6,7,8-tetrahydropyrazolo[3,4-e][1,4]thiazepin-4-yl]benzamide;

3-chloro-N-(2-methyl-3-pyridyl)-4-[(4S)-1-methyl-3-(2-pyridyl)-4,6,7,8-tetrahydropyrazolo[3,4-e][1,4]thiazepin-4-yl]benzamide;

3-methyl-N-(2-methyl-3-pyridyl)-4-[1-methyl-3-(2-pyridyl)-4,6,7,8-tetrahydro-pyrazolo[3,4-e][1,4]thiazepin-4-yl]benzamide;

(R)-3-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide;

(S)-3-methyl-4-(1-methyl-3-(pyridin-2-yl)-4,6,7,8-tetrahydro-1H-pyrazolo[3,4-e][1,4]thiazepin-4-yl)-N-(2-methylpyridin-3-yl)benzamide;

(4R,7S)-4-(4-chloro-2-methylphenyl)-1,7-dimethyl-3-(pyridin-2-yl)-4,6,7,8-tetrahydro-1H-pyrazolo[3,4-e][1,4]thiazepine;

(4R,7R)-4-(4-chloro-2-methylphenyl)-1,7-dimethyl-3-(pyridin-2-yl)-4,6,7,8-tetrahydro-1H-pyrazolo[3,4-e][1,4]thiazepine;

(4S,7S)-4-(4-chloro-2-methylphenyl)-1,7-dimethyl-3-(pyridin-2-yl)-4,6,7,8-tetrahydro-1H-pyrazolo[3,4-e][1,4]thiazepine;

(4S,7R)-4-(4-chloro-2-methylphenyl)-1,7-dimethyl-3-(pyridin-2-yl)-4,6,7,8-tetrahydro-1H-pyrazolo[3,4-e][1,4]thiazepine;

4-(4-chloro-2-methyl-phenyl)-1-methyl-3-(1H-pyrazol-5-yl)-4,6,7,8-tetrahydropyrazolo[3,4-e][1,4]thiazepine;

3-chloro-4-[1-methyl-3-(2-pyridyl)-4,6,7,8-tetrahydropyrazolo[3,4-e][1,4]thiazepin-4-yl]benzoic;

6-[4-(2,4-dichlorophenyl)-1-methyl-4,6,7,8-tetrahydropyrazolo[3,4-e][1,4]thiazepin-3-yl]pyridine-3-carboxylic acid;

1-[4-[1-methyl-3-(2-pyridyl)-4,6,7,8-tetrahydropyrazolo[3,4-e][1,4]thiazepin-4-yl]-1-piperidyl]ethanone;

(2-methyl-3-pyridyl)-[4-[1-methyl-3-2-pyridyl)-4,6,7,8-tetrahydropyrazolo[3,4-e][1,4]thiazepin-4-yl]1-piperidyl]methanone;

N-(2-methyl-3-pyridyl)-4-[1-methyl-3-(2-pyridyl)-4,6,7,8-tetrahydropyrazolo[3,4-e][1,4]thiazepin-4-yl]piperidine-1-carboxamide;

1-methyl-4-[2-methyl-4-(3-pyridylmethoxy)phenyl]-3-(2-pyridyl)-4,6,7,8-tetrahydropyrazolo[3,4-e][1,4]thiazepine;

1-methyl-4-[2-methyl-4-[(2-methyl-3-pyridyl)methoxy]phenyl]-3-(2-pyridyl)-4,6,7,8-tetrahydropyrazolo[3,4-e][1,4]thiazepine;

2-[4-(2,4-dichlorophenyl)-1-methyl-3-(2-pyridyl)-6,7-dihydro-4H-pyrazolo[3,4-e][1,4]thiazepin-8-yl]acetic acid;

2-[4-(2,4-dichlorophenyl)-1-methyl-3-(2-pyridyl)-6,7-dihydro-4H-pyrazolo[3,4-e][1,4]thiazepin-8-yl]acetamide;

4-(4-chloro-2-methyl-phenyl)-1-methyl-3-(6-methyl-2-pyridyl)-4,6,7,8-tetrahydropyrazolo[3,4-e][1,4]thiazepine;

[4-(4-chloro-2-methyl-phenyl)-1-methyl-4,6,7,8-tetrahydropyrazolo[3,4-e][1,4]thiazepin-3-yl]trifluoromethanesulfonate;

4-(4-chloro-2-vinyl-phenyl)-1-methyl-3-(2-pyridyl)-4,6,7,8-tetrahydropyrazolo[3,4-e][1,4]thiazepine;

4-(4-chloro-2-ethyl-phenyl)-1-methyl-3-(2-pyridyl)-4,6,7,8-tetrahydropyrazolo[3,4-e][1,4]thiazepine;

1-methyl-4-(2-methyl-4-methylsulfonyl-phenyl)-3-(2-pyridyl)-4,6,7,8-tetrahydropyrazolo[3,4-e][1,4]thiazepine;

4-(2,4-dichlorophenyl)-1-methyl-3-[(2S)-pyrrolidin-2-yl]-4,6,7,8-tetrahydropyrazolo[3,4-e][1,4]thiazepine;

4-(4-chloro-2-methyl-phenyl)-1-methyl-3-[(2S)-pyrrolidin-2-yl]-4,6,7,8-tetrahydropyrazolo[3,4-e][1,4]thiazepine;

2-[3-chloro-4-[1-methyl-3-(2-pyridyl)-4,6,7,8-tetrahydropyrazolo[3,4-e][1,4]thiazepin-4-yl]phenyl]propan-2-ol;

4-(2-chlorophenyl)-1-methyl-3-(2-pyridyl)-4,6,7,8-tetrahydropyrazolo[3,4-e][1,4]thiazepine;

4-(2-chloro-4-methyl-phenyl)-1-methyl-3-(2-pyridyl)-4,6,7,8-tetrahydropyrazolo[3,4-e][1,4]thiazepine;

4-(2,4-dichlorophenyl)-1,3,6,6,8-pentamethyl-4H-pyrazolo[3,4-e][1,4]thiazepin-7-one;

4-(2,4-dichlorophenyl)-1,3,6,6-tetramethyl-4,7-dihydropyrazolo[3,4-e][1,4]thiazepine-8-carbaldehyde;

3-[4-(2,4-dichlorophenyl)-1,3,6,6-tetramethyl-4,7-dihydropyrazolo[3,4-e][1,4]thiazepin-8-yl]-1,1,1-trifluoropropan-2-ol;

3-[4-(2,4-dichlorophenyl)-3,6,6-trimethyl-7,8-dihydro-4H-pyrazolo[3,4-e][1,4]thiazepin-1-yl]-1,1,1-trifluoropropan-2-ol;

3-[4-(2,4-dichlorophenyl)-3,6,6-trimethyl-7,8-dihydro-4H-pyrazolo[3,4-e][1,4]thiazepin-2-yl]-1,1,1-trifluoropropan-2-ol;

4-(2,4-dichlorophenyl)-1,3,6,6,8-pentamethyl-4,7-dihydropyrazolo[3,4-e][1,4]thiazepine hydrochloride;

4-(4-bromo-2-methylphenyl)-1-ethyl-3-(pyrimidin-4-yl)-4,6,7,8-tetrahydro-1H-pyrazolo[3,4-e][1,4]thiazepine;

4-(1-(4-fluorophenyl)-6-methyl-1H-indazol-5-yl)-1-methyl-3-(pyridin-2-yl)-4,6,7,8-tetrahydro-1H-pyrazolo[3,4-e][1,4]thiazepine;

methyl 4-(1,7-dimethyl-3-(pyridin-2-yl)-4,6,7,8-tetrahydro-1H-pyrazolo[3,4-e][1,4]thiazepin-4-yl)-3-methylbenzoate;

3-cyano-4-((4R,7R)-1,7-dimethyl-3-(pyridin-2-yl)-4,6,7,8-tetrahydro-1H-pyrazolo[3,4-e][1,4]thiazepin-4-yl)-N-(2-methylpyridin-3-yl)benzamide;

(R)-3-methyl-4-(1-methyl-3-(pyridin-2-yl)-4,6,7,8-tetrahydro-1H-pyrazolo[3,4-e][1,4]thiazepin-4-yl)benzonitrile;

(S)-3-methyl-4-(1-methyl-3-(pyridin-2-yl)-4,6,7,8-tetrahydro-1H-pyrazolo[3,4-e][1,4]thiazepin-4-yl)benzonitrile;

(S)-4-(1-ethyl-3-(pyridin-2-yl)-4,6,7,8-tetrahydro-1H-pyrazolo[3,4-e][1,4]thiazepin-4-yl)-3-methylbenzonitrile;

2-(4-((4S,7R)-1,7-dimethyl-3-(pyridin-2-yl)-4,6,7,8-tetrahydro-1H-pyrazolo[3,4-e][1,4]thiazepin-4-yl)-3-methylphenoxy)acetonitrile;

2-(4-((4S,7R)-1,7-dimethyl-3-(pyridin-2-yl)-4,6,7,8-tetrahydro-1H-pyrazolo[3,4-e][1,4]thiazepin-4-yl)-3-methylphenoxy)acetamide;

3-(4-((4R,7S)-1-ethyl-7-methyl-3-(pyridin-2-yl)-4,6,7,8-tetrahydro-1H-pyrazolo[3,4-e][1,4]thiazepin-4-yl)-3-methylphenyl)prop-2-yn-1-ol;

3-(4-((4R,7R)-1-ethyl-7-methyl-3-(pyridin-2-yl)-4,6,7,8-tetrahydro-1H-pyrazolo[3,4-e][1,4]thiazepin-4-yl)-3-methylphenyl)prop-2-yn-1-ol;

3-(4-((4S,7R)-1-ethyl-7-methyl-3-(pyridin-2-yl)-4,6,7,8-tetrahydro-1H-pyrazolo[3,4-e][1,4]thiazepin-4-yl)-3-methylphenyl)prop-2-yn-1-ol;

3-(4-((4S,7S)-1-ethyl-7-methyl-3-(pyridin-2-yl)-4,6,7,8-tetrahydro-1H-pyrazolo[3,4-e][1,4]thiazepin-4-yl)-3-methylphenyl)prop-2-yn-1-ol;

4-(4-((4R,7S)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-ol;

4-(4-(4R,7R)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-ol;

4-(4-((4S,7R)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-ol;

4-(4-((4S,7S)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-ol;

3-(4-((4R,7S)-1-ethyl-7-methyl-3-(pyridin-2-yl)-4,6,7,8-tetrahydro-1H-pyrazolo[3,4-e][1,4]thiazepin-4-yl)-3-methylphenyl)propan-1-ol;

3-(4-((4R,7R)-1-ethyl-7-methyl-3-(pyridin-2-yl)-4,6,7,8-tetrahydro-1H-pyrazolo[3,4-e][1,4]thiazepin-4-yl)-3-methylphenyl)propan-1-ol;

3-(4-((4S,7R)-1-ethyl-7-methyl-3-(pyridin-2-yl)-4,6,7,8-tetrahydro-1H-pyrazolo[3,4-e][1,4]thiazepin-4-yl)-3-methylphenyl)propan-1-ol;

3-(4-((4S,7S)-1-ethyl-7-methyl-3-(pyridin-2-yl)-4,6,7,8-tetrahydro-1H-pyrazolo[3,4-e][1,4]thiazepin-4-yl)-3-methylphenyl)propan-1-ol;

4-(4-((4R,7S)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-ol;

4-(4-((4R,7R)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-ol;

4-(4-((4S,7S)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-ol;

4-(4-((4S,7R)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-ol;

4-(4-((4R,7S)-1,7-dimethyl-3-(pyridin-2-yl)-4,6,7,8-tetrahydro-1H-pyrazolo[3,4-e][1,4]thiazepin-4-yl)-3-methylphenyl)-2-methylbutan-2-ol;

4-(4-((4S,7S)-1,7-dimethyl-3-(pyridin-2-yl)-4,6,7,8-tetrahydro-1H-pyrazolo[3,4-e][1,4]thiazepin-4-yl)-3-methylphenyl)-2-methylbutan-2-ol;

4-(4-((4R,7R)-1,7-dimethyl-3-(pyridin-2-yl)-4,6,7,8-tetrahydro-1H-pyrazolo[3,4-e][1,4]thiazepin-4-yl)-3-methylphenyl)-2-methylbutan-2-ol;

4-(4-((4S,7R)-1,7-dimethyl-3-(pyridin-2-yl)-4,6,7,8-tetrahydro-1H-pyrazolo[3,4-e][1,4]thiazepin-4-yl)-3-methylphenyl)-2-methylbutan-2-ol;

4-((4R,7S)-1-ethyl-7-methyl-3-(pyridin-2-yl)-4,6,7,8-tetrahydro-1H-pyrazolo[3,4-e][1,4]thiazepin-4-yl)-3-methylbenzamide;

4-((4S,7R)-1-ethyl-7-methyl-3-(pyridin-2-yl)-4,6,7,8-tetrahydro-1H-pyrazolo[3,4-e][1,4]thiazepin-4-yl)-3-methylbenzamide;

4-((4R,7R)-1-ethyl-7-methyl-3-(pyridin-2-yl)-4,6,7,8-tetrahydro-1H-pyrazolo[3,4-e][1,4]thiazepin-4-yl)-3-methylbenzamide;

4-((4S,7S)-1-ethyl-7-methyl-3-(pyridin-2-yl)-4,6,7,8-tetrahydro-1H-pyrazolo[3,4-e][1,4]thiazepin-4-yl)-3-methylbenzamide;

3-(4-((4R,7S)-1,7-dimethyl-3-(pyridin-2-yl)-4,6,7,8-tetrahydro-1H-pyrazolo[3,4-e][1,4]thiazepin-4-yl)-3-methylphenyl)propan-1-ol;

3-(4-((4R,7R)-1,7-dimethyl-3-(pyridin-2-yl)-4,6,7,8-tetrahydro-1H-pyrazolo[3,4-e][1,4]thiazepin-4-yl)-3-methylphenyl)propan-1-ol;

3-(4-((4S,7R)-1,7-dimethyl-3-(pyridin-2-yl)-4,6,7,8-tetrahydro-1H-pyrazolo[3,4-e][1,4]thiazepin-4-yl)-3-methylphenyl)propan-1-ol;

3-(4-((4S,7S)-1,7-dimethyl-3-(pyridin-2-yl)-4,6,7,8-tetrahydro-1H-pyrazolo[3,4-e][1,4]thiazepin-4-yl)-3-methylphenyl)propan-1-ol;

4-(4-((4R,7S)-1,7-dimethyl-3-(pyridin-2-yl)-4,6,7,8-tetrahydro-1H-pyrazolo[3,4-e][1,4]thiazepin-4-yl)-3-methylphenyl)but-3-yn-1-ol;

4-(4-((4S,7S)-1,7-dimethyl-3-(pyridin-2-yl)-4,6,7,8-tetrahydro-1H-pyrazolo[3,4-e][1,4]thiazepin-4-yl)-3-methylphenyl)but-3-yn-1-ol;

4-(4-((4S,7R)-1,7-dimethyl-3-(pyridin-2-yl)-4,6,7,8-tetrahydro-1H-pyrazolo[3,4-e][1,4]thiazepin-4-yl)-3-methylphenyl)but-3-yn-1-ol;

4-(4-((4R,7R)-1,7-dimethyl-3-(pyridin-2-yl)-4,6,7,8-tetrahydro-1H-pyrazolo[3,4-e][1,4]thiazepin-4-yl)-3-methylphenyl)but-3-yn-1-ol;

4-((4S,7R)-1,7-dimethyl-3-(pyrimidin-4-yl)-4,6,7,8-tetrahydro-1H-pyrazolo[3,4-e][1,4]thiazepin-4-yl)-3-methyl-N-(2-methylpyridin-3-yl)benzamide;

4-((4S,7S)-1,7-dimethyl-3-(pyrimidin-4-yl)-4,6,7,8-tetrahydro-1H-pyrazolo[3,4-e][1,4]thiazepin-4-yl)-3-methyl-N-(2-methylpyridin-3-yl)benzamide;

4-((4R,7S)-1,7-dimethyl-3-(pyrimidin-4-yl)-4,6,7,8-tetrahydro-1H-pyrazolo[3,4-e][1,4]thiazepin-4-yl)-3-methyl-N-(2-methylpyridin-3-yl)benzamide;

4-((4R,7R)-1,7-dimethyl-3-(pyrimidin-4-yl)-4,6,7,8-tetrahydro-1H-pyrazolo[3,4-e][1,4]thiazepin-4-yl)-3-methyl-N-(2-methylpyridin-3-yl)benzamide;

(R)-4-(1-ethyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide;

(S)-4-(1-ethyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide;

2-((4R,7R)-4-(4-bromo-2-methylphenyl)-1,7-dimethyl-4,6,7,8-tetrahydro-1H-pyrazolo[3,4-e][1,4]thiazepin-3-yl)-1,3,4-oxadiazole;

2-((4S,7S)-4-(4-bromo-2-methylphenyl)-1,7-dimethyl-4,6,7,8-tetrahydro-1H-pyrazolo[3,4-e][1,4]thiazepin-3-yl)-1,3,4-oxadiazole;

2-((4R,7R)-4-(4-bromo-2-methylphenyl)-1,7-dimethyl-4,6,7,8-tetrahydro-1H-pyrazolo[3,4-e][1,4]thiazepin-3-yl)-1,3,4-oxadiazole;

2-((4S,7S)-4-(4-bromo-2-methylphenyl)-1,7-dimethyl-4,6,7,8-tetrahydro-1H-pyrazolo[3,4-e][1,4]thiazepin-3-yl)-1,3,4-oxadiazole;

3-(4-((4R,7S)-1-ethyl-7-methyl-3-(pyridin-2-yl)-4,6,7,8-tetrahydro-1H-pyrazolo[3,4-e][1,4]thiazepin-4-yl)-3-methylphenyl)-N,N-dimethylprop-2-yn-1-amine;

3-(4-((4R,7S)-1-ethyl-7-methyl-3-(pyridin-2-yl)-4,6,7,8-tetrahydro-1H-pyrazolo[3,4-e][1,4]thiazepin-4-yl)-3-methylphenyl)-N,N-dimethylprop-2-yn-1-amine;

4-(4-((4S,7S)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-amine;

4-(4-((4S,7R)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbut-3-yn-2-amine;

(R)-4-(1-ethyl-3-(pyridin-2-yl)-4,6,7,8-tetrahydro-1H-pyrazolo[3,4-e][1,4]thiazepin-4-yl)-N-(2-methylpyridin-3-yl)-3-(trifluoromethyl)benzamide;

3-(4-((4R,7R)-1,7-dimethyl-3-(pyridin-2-yl)-4,6,7,8-tetrahydro-1H-pyrazolo[3,4-e][1,4]thiazepin-4-yl)-3-methylphenyl)prop-2-yn-1-ol;

3-(4-((4S,7R)-1,7-dimethyl-3-(pyridin-2-yl)-4,6,7,8-tetrahydro-1H-pyrazolo[3,4-e][1,4]thiazepin-4-yl)-3-methylphenyl)prop-2-yn-1-ol;

3-(4-((4S,7S)-1,7-dimethyl-3-(pyridin-2-yl)-4,6,7,8-tetrahydro-1H-pyrazolo[3,4-e][1,4]thiazepin-4-yl)-3-methylphenyl)prop-2-yn-1-ol;

4-(4-((4R,7R)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-amine;

4-(4-((4S,7S)-1-ethyl-7-methyl-3-(pyridin-2-yl)-4,6,7,8-tetrahydro-1H-pyrazolo[3,4-e][1,4]thiazepin-4-yl)-3-methylphenyl)-2-methylbutan-2-amine;

4-(1-ethyl-3-(pyridin-2-yl)-4,6,7,8-tetrahydro-1H-pyrazolo[3,4-e][1,4]thiazepin-4-yl)-3-methyl-N-(3-methylisoxazol-5-yl)benzamide;

4-(1-ethyl-3-(pyridin-2-yl)-4,6,7,8-tetrahydro-1H-pyrazolo[3,4-e][1,4]thiazepin-4-yl)-3-methyl-N-(1-methyl-1H-pyrazol-5-yl)benzamide;

N-(1,3-dimethyl-1H-pyrazol-5-yl)-4-(1-ethyl-3-(pyridin-2-yl)-4,6,7,8-tetrahydro-1H-pyrazolo[3,4-e][1,4]thiazepin-4-yl)-3-methylbenzamide;

4-(1-ethyl-3-(pyridin-2-yl)-4,6,7,8-tetrahydro-1H-pyrazolo[3,4-e][1,4]thiazepin-4-yl)-3-methyl-N-(1,3,4-thiadiazol-2-yl)benzamide;

4-(1-ethyl-3-(pyridin-2-yl)-4,6,7,8-tetrahydro-1H-pyrazolo[3,4-e][1,4]thiazepin-4-yl)-3-methyl-N-(5-methyl-1,3,4-thiadiaz ol-2-yl)benzamide;
4-(1-ethyl-3-(pyridin-2-yl)-4,6,7,8-tetrahydro-1H-pyrazol[3,4-e][1,4]thiazepin-4-yl)-3-methyl-N-(4H-1,2,4-triazol-3-yl)benzamide;
4-(1-ethyl-3-(pyridin-2-yl)-4,6,7,8-tetrahydro-1H-pyrazol[3,4-e][1,4]thiazepin-4-yl)-3-methyl-N-(1H-tetrazol-5-yl)benzamide;
N-(4-cyano-3-methylisoxazol-5-yl)-4-(1-ethyl-3-(pyridin-2-yl)-4,6,7,8-tetrahydro-1H-pyrazolo[3,4-e][1,4]thiazepin-4-yl)-3-methylbenzamide;
N-(4-cyano-1H-pyrazol-3-yl)-4-(1-ethyl-3-(pyridin-2-yl)-4,6,7,8-tetrahydro-1H-pyrazolo[3,4-e][1,4]thiazepin-4-yl)-3-methylbenzamide;
N-(4-cyano-5-methyl-1H-pyrazol-3-yl)-4-(1-ethyl-3-(pyridin-2-yl)-4,6,7,8-tetrahydro-1H-pyrazol[3,4-e][1,4]thiazepin-4-yl)-3-methylbenzamide;
N-(2-chloropyridin-3-yl)-4-(1-ethyl-3-(pyridin-2-yl)-4,6,7,8-tetrahydro-1H-pyrazol[3,4-e][1,4]thiazepin-4-yl)-3-methylbenzamide;
4-(2-chloro-4-(5-(methylsulfonyl)pyridin-3-yl)phenyl)-1-methyl-3-(pyridin-2-yl)-4,6,7,8-tetrahydro-1H-pyrazolo[3,4-e][1,4]thiazepine;
4-(2-chloro-4-(pyrimidin-5-yl)phenyl)-1-methyl-3-(pyridin-2-yl)-4,6,7,8-tetrahydro-1H-pyrazolo[3,4-e][1,4]thiazepine;
4-(2-chloro-4-(pyridazin-4-yl)phenyl)-1-methyl-3-(pyridin-2-yl)-4,6,7,8-tetrahydro-1H-pyrazolo[3,4-e][1,4]thiazepine;
5-(3-chloro-4-(1-methyl-3-(pyridin-2-yl)-4,6,7,8-tetrahydro-1H-pyrazolo[3,4-e][1,4]thiazepin-4-yl)phenyl)nicotinonitrile;
(2-(4-(3-chloro-4-(1-methyl-3-(pyridin-2-yl)-4,6,7,8-tetrahydro-1H-pyrazolo[3,4-e][1,4]thiazepin-4-yl)phenyl)-1H-pyrazol-1-yl)ethyl)morpholine;
4-(2-chloro-4-(1-(tetrahydro-2H-pyran-2-yl)-1H-pyrazol-4-yl)phenyl)-1-methyl-3-(pyridin-2-yl)-4,6,7,8-tetrahydro-1H-pyrazolo[3,4-e][1,4]thiazepine;
5-(3-chloro-4-(1-methyl-3-(pyridin-2-yl)-4,6,7,8-tetrahydro-1H-pyrazolo[3,4-e][1,4]thiazepin-4-yl)phenyl)nicotinamide;
5-(3-chloro-4-(1-methyl-3-(pyridin-2-yl)-4,6,7,8-tetrahydro-1H-pyrazolo[3,4-e][1,4]thiazepin-4-yl)phenyl)-N-methylnicotinamide;
4-(3-chloro-4-(1-methyl-3-(pyridin-2-yl)-4,6,7,8-tetrahydro-1H-pyrazolo[3,4-e][1,4]thiazepin-4-yl)phenyl)nicotinonitrile;
3-(3-chloro-4-(1-methyl-3-(pyridin-2-yl)-4,6,7,8-tetrahydro-1H-pyrazolo[3,4-e][1,4]thiazepin-4-yl)phenyl)isonicotinonitrile;
4-(2-chloro-4-(pyrido[2,3-b]pyrazin-7-yl)phenyl)-1-methyl-3-(pyridin-2-yl)-4,6,7,8-tetrahydro-1H-pyrazolo[3,4-e][1,4]thiazepine;
(5-(3-chloro-4-(1-methyl-3-(pyridin-2-yl)-4,6,7,8-tetrahydro-1H-pyrazolo[3,4-e][1,4]thiazepin-4-yl)phenyl)pyridin-3-yl)(morpholino)methanone;
4-(2-chloro-4-(6-(methylsulfonyl)pyridin-3-yl)phenyl)-1-methyl-3-(pyridin-2-yl)-4,6,7,8-tetrahydro-1H-pyrazolo[3,4-e][1,4]thiazepine;
1-(4-(5-(3-chloro-4-(1-methyl-3-(pyridin-2-yl)-4,6,7,8-tetrahydro-1H-pyrazolo[3,4-e][1,4]thiazepin-4-yl)phenyl)pyridin-2-yl)piperazin-1-yl)ethanone;
4-(2-chloro-4-(1-(2-methoxyethyl)-1H-pyrazol-4-yl)phenyl)-1-methyl-3-(pyridin-2-yl)-4,6,7,8-tetrahydro-1H-pyrazolo[3,4-e][1,4]thiazepine;
3-(4-(3-chloro-4-(1-methyl-3-(pyridin-2-yl)-46,7,8-tetrahydro-1H-pyrazolo[3,4-e][1,4]thiazepin-4-yl)phenyl)-1H-pyrazol-1-yl)propanenitrile;
2-(4-(3-chloro-4-(1-methyl-3-(pyridin-2-yl)-4,6,7,8-tetrahydro-1H-pyrazolo[3,4-e][1,4]thiazepin-4-yl)phenyl)-1H-pyrazol-1-yl)acetamide;
3-(4-(3-chloro-4-(1-methyl-3-(pyridin-2-yl)-4,6,7,8-tetrahydro-1H-pyrazolo[3,4-e][1,4]thiazepin-4-yl)phenyl)-1H-pyrazol-1-yl)propanamide;
4-(5-(3-chloro-4-(1-methyl-3-(pyridin-2-yl)-4,6,7,8-tetrahydro-1H-pyrazolo[3,4-e][1,4]thiazepin-4-yl)phenyl)pyrimidin-2-yl)morpholine;
4-(4-bromo-2-methylphenyl)-1-ethyl-3-(pyridin-2-yl)-1,4,5,6,7,8-hexahydropyrazolo[3,4-b]azepine;
4-(4-bromophenyl)-1-ethyl-3-(pyridin-2-yl)-1,4,5,6,7,8-hexahydropyrazolo[3,4-b]azepine;
rac-2-((4S,6S,7R)-4-(4-chloro-2-methylphenyl)-1,3,7-trimethyl-4,6,7,8-tetrahydro-1H-pyrazolo[3,4-e][1,4]thiazepin-6-yl)ethanol;
2-((4R,6R,7S)-4-(4-chloro-2-methylphenyl)-1,3,7-trimethyl-4,6,7,8-tetrahydro-1H-pyrazolo[3,4-e][1,4]thiazepin-6-yl)ethanol;
rac-(4R,7 R)-4-(4-bromo-2-methylphenyl)-1-methyl-3-(pyridin-2-yl)-7-(trifluoromethyl)-4,6,7,8-tetrahydro-1H-pyrazolo[3,4-e][1,4]thiazepine;
rac-(4R,7S)-4-(4-bromo-2-methylphenyl)-1-methyl-3-(pyridin-2-yl)-7-(trifluoromethyl)-4,6,7,8-tetrahydro-1H-pyrazolo[3,4-e][1,4]thiazepine;
rac-(4R,7S)-4-(4-bromo-2-methylphenyl)-1-methyl-3-(pyridin-2-yl)-4,6,7,8-tetrahydro-1H-pyrazolo[3,4-e][1,4]thiazepine-7-carboxamide;
rac-(4R,7 S)-4-(4-bromo-2-methylphenyl)-1-methyl-3-(pyridin-2-yl)-4,6,7,8-tetrahydro-1H-pyrazolo[3,4-e][1,4]thiazepine-7-carbonitrile;
rac-2-((4R,7 S)-4-(4-bromo-2-methylphenyl)-1-methyl-3-(pyridin-2-yl)-4,6,7,8-tetrahydro-1H-pyrazolo[3,4-e][1,4]thiazepin-7-yl)acetonitrile;
4-((4S,7R)-7-(hydroxymethyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide;
4-((4R,7S)-7-(hydroxymethyl)-1-methyl-3-(pyridin-2-yl)-4,6,7,8-tetrahydro-1H-pyrazolo[3,4-e][1,4]thiazepin-4-yl)-3-methyl-N-(2-methylpyridin-3-yl)benzamide;
rac-4-(1-(4-fluorophenyl)-6-methyl-1H-indazol-5-yl)-1-methyl-3-(pyridin-2-yl)-6,8-dihydro-1H-pyrazolo[3,4-e][1,4]thiazepin-7(4H)-one;
1-methyl-4-(6-methyl-1-(2-methylpyridin-4-yl)-1H-indazol-5-yl)-3-(pyridin-2-yl)-6,8-dihydro-1H-pyrazolo[3,4-e][1,4]thiazepin-7(4H)-one;
4-(1-(4-fluorophenyl)-6-methyl-1H-indazol-5-yl)-1-methyl-3-(pyridin-2-yl)-6,8-dihydro-1H-pyrazolo[3,4-e][1,4]thiazepin-7(4H)-one;
4-(6-chloro-1-(2-methylpyridin-4-yl)-1H-indazol-5-yl)-1-methyl-3-(pyridin-2-yl)-6,8-dihydro-1H-pyrazolo[3,4-e][1,4]thiazepin-7(4H)-one;
1-methyl-4-(1-(2-methylpyridin-4-yl)-1H-indazol-5-yl)-3-(pyridin-2-yl)-6,8-dihydro-1H-pyrazolo[3,4-e][1,4]thiazepin-7(4H)-one;
4-(6-chloro-1-(4-fluorophenyl)-1H-indazol-5-yl)-1-methyl-3-(pyridin-2-yl)-6,8-dihydro-1H-pyrazolo[3,4-e][1,4]thiazepin-7(4H)-one;
4-(1-(4-fluorophenyl)-1H-indazol-5-yl)-1-methyl-3-(pyridin-2-yl)-6,8-dihydro-1H-pyrazolo[3,4-e][1,4]thiazepin-7(4H)-one;

4-(6-fluoro-1-(2-methylpyridin-4-yl)-1H-indazol-5-yl)-1-methyl-3-(pyridin-2-yl)-6,8-dihydro-1H-pyrazolo[3,4-e][1,4]thiazepin-7(4H)-one;

4-(6-fluoro-1-(4-fluorophenyl)-1H-indazol-5-yl)-1-methyl-3-(pyridin-2-yl)-6,8-dihydro-1H-pyrazolo[3,4-e][1,4]thiazepin-7(4H)-one;

1-methyl-4-(1-(2-methylpyridin-4-yl)-6-(trifluoromethyl)-1H-indazol-5-yl)-3-(pyridin-2-yl)-6,8-dihydro-1H-pyrazolo[3,4-e][1,4]thiazepin-7(4H)-one;

4-(1-(4-fluorophenyl)-6-(trifluoromethyl)-1H-indazol-5-yl)-1-methyl-3-(pyridin-2-yl)-6,8-dihydro-1H-pyrazolo[3,4-e][1,4]thiazepin-7(4H)-one;

1-ethyl-4-(6-methyl-1-(2-methylpyridin-4-yl)-1H-indazol-5-yl)-3-(pyridin-2-yl)-6,8-dihydro-1H-pyrazolo[3,4-e][1,4]thiazepin-7(4H)-one;

4-(6-chloro-1-(2-methylpyridin-4-yl)-1H-indazol-5-yl)-1-ethyl-3-(pyridin-2-yl)-6,8-dihydro-1H-pyrazolo[3,4-e][1,4]thiazepin-7(4H)-one;

1-ethyl-4-(1-(2-methylpyridin-4-yl)-1H-indazol-5-yl)-3-(pyridin-2-yl)-6,8-dihydro-1H-pyrazolo[3,4-e][1,4]thiazepin-7(4H)-one;

1-ethyl-4-(6-fluoro-1-(2-methylpyridin-4-yl)-1H-indazol-5-yl)-3-(pyridin-2-yl)-6,8-dihydro-1H-pyrazolo[3,4-e][1,4]thiazepin-7(4H)-one;

1-ethyl-4-(1-(2-methylpyridin-4-yl)-6-(trifluoromethyl)-1H-indazol-5-yl)-3-(pyridin-2-yl)-6,8-dihydro-1H-pyrazolo[3,4-e][1,4]thiazepin-7(4H)-one;

1-ethyl-4-(1-(4-fluorophenyl)-6-methyl-1H-indazol-5-yl)-3-(pyridin-2-yl)-6,8-dihydro-1H-pyrazolo[3,4-e][1,4]thiazepin-7(4H)-one;

(Z)-3-(1-aminobuta-1,3-dien-1-yl)-4-(6-chloro-1-(4-fluorophenyl)-1H-indazol-5-yl)-1-ethyl-6,8-dihydro-1H-pyrazolo[3,4-e][1,4]thiazepin-7(4H)-one;

(Z)-3-(1-aminobuta-1,3-dien-1-yl)-1-ethyl-4-(1-(4-fluorophenyl)-1H-indazol-5-yl)-6,8-dihydro-1H-pyrazolo[3,4-e][1,4]thiazepin-7(4H)-one;

1-ethyl-4-(6-fluoro-1-(4-fluorophenyl)-1H-indazol-5-yl)-3-(pyridin-2-yl)-6,8-dihydro-1H-pyrazolo[3,4-e][1,4]thiazepin-7(4H)-one;

1-ethyl-4-(1-(4-fluorophenyl)-6-(trifluoromethyl)-1H-indazol-5-yl)-3-(pyridin-2-yl)-6,8-dihydro-1H-pyrazolo[3,4-e][1,4]thiazepin-7(4H)-one;

15. A pharmaceutical composition comprising a compound of claim 1 or claim 14, and a pharmaceutically acceptable carrier or excipient.

16. A method of treating a disease or condition comprising administering a pharmaceutical composition of claim 15, wherein the disease or condition to be treated is age-related macular degeneration, ankylosing spondylitis, atopic dermatitis, Crohn's disease, dry eye syndrome, giant cell arteritis, inflammatory bowel disease, juvenile idiopathic arthritis, juvenile rheumatoid arthritis, lupus, macular edema, plaque psoriasis, psoriasis, polymyalgia rheumatica, psoriatic arthritis, rheumatoid arthritis, ulcerative colitis, or uveitis.

* * * * *